United States Patent [19]

Fujita et al.

[11] Patent Number: 5,604,229

[45] Date of Patent: Feb. 18, 1997

[54] 2-AMINO-1,3-PROPANEDIOL COMPOUND AND IMMUNOSUPPRESSANT

[75] Inventors: Tetsuro Fujita, Muko; Shigeo Sasaki; Masahiko Yoneta, both of Kobe; Tadashi Mishina, Iruma; Kunitomo Adachi, Iruma; Kenji Chiba, Iruma, all of Japan

[73] Assignees: Yoshitomi Pharmaceutical Industries, Ltd., Osaka; Taito Co., Ltd., Tokyo, both of Japan

[21] Appl. No.: 244,942

[22] PCT Filed: Oct. 18, 1993

[86] PCT No.: PCT/JP93/01515

§ 371 Date: Jun. 17, 1994

§ 102(e) Date: Jun. 17, 1994

[87] PCT Pub. No.: WO94/08943

PCT Pub. Date: Apr. 28, 1994

[30] Foreign Application Priority Data

Oct. 21, 1992 [JP] Japan ................................. 4-283281
Jul. 20, 1993 [JP] Japan ................................. 5-179427

[51] Int. Cl.[6] ..................... C07C 211/00; C07D 333/20; A01N 43/40; A01N 33/02

[52] U.S. Cl. ..................... 514/255; 514/357; 514/372; 514/403; 514/427; 514/438; 514/459; 514/471; 544/401; 546/246; 546/247; 546/334; 548/214; 548/373.1; 548/516; 549/75; 549/426; 549/495; 549/472; 564/336; 564/340; 564/342; 564/346; 564/374; 564/383; 564/454; 564/123

[58] Field of Search ....................... 546/210, 246, 546/247, 334; 560/172; 562/11; 558/169; 514/114, 119, 357, 255, 372, 403, 427, 438, 459, 471; 564/336, 340, 342, 346, 374, 383, 454, 123; 549/75, 426, 495; 548/214, 373.1, 516; 544/401

[56] References Cited

U.S. PATENT DOCUMENTS

| 3,062,839 | 11/1962 | Shetty et al. | 260/347.7 |
|---|---|---|---|
| 3,324,043 | 1/1967 | Krum | 252/401 |
| 3,426,042 | 2/1969 | Hostettler et al. | 260/340.2 |
| 3,432,603 | 3/1969 | Zenitz | 424/325 |
| 3,660,488 | 5/1972 | Cobb | 260/584 |
| 3,928,572 | 11/1975 | Kluepfel et al. | 424/122 |
| 4,499,221 | 2/1985 | Saitoh et al. | 524/109 |
| 4,910,218 | 3/1990 | Bair | 514/443 |
| 5,068,247 | 11/1991 | Fujita et al. | 514/440 |

FOREIGN PATENT DOCUMENTS

| 0044203A2 | 1/1982 | European Pat. Off. . |
|---|---|---|
| 0410176 | 1/1991 | European Pat. Off. . |
| 0450527A2 | 10/1991 | European Pat. Off. . |
| 51-54565 | 5/1976 | Japan . |
| 57-21366 | 2/1982 | Japan . |
| 57-156459 | 9/1982 | Japan . |
| 58-101108 | 6/1983 | Japan . |
| 63-2904 | 1/1988 | Japan . |
| 63-43140 | 2/1988 | Japan . |
| 9309 | 1/1992 | Japan . |
| 69320 | 3/1992 | Japan . |
| 173723 | 6/1992 | Japan . |
| 224548 | 8/1992 | Japan . |
| 78294 | 3/1993 | Japan . |
| 92/16236A2 | 10/1982 | WIPO . |

OTHER PUBLICATIONS

Merck Index, No. 460 (2–Amino–2–methyl–1,3–propane diol) p. 73 1989.

Bair et al., J. Med.Chem., "1–Pyrenylmethyl)amino alcohols, a New Class Antitumor DNA Intercalators. Discovery and Initial Amine Side Chain Structure–Activity Studies", 1990, 33, pp. 2385–2393.

Shetty et al., J. Org. Chem. Nov. 1960, pp. 2057–2059.

Rembarz et al., J. Prakt. Chem., 68; vol. 37 (1–2); pp. 59–63. 1968.

Chemical Abstracts, vol. 85, No. 23, Dec. 6, 1976, Columbus, Ohio, U.S. abstract No. 177498z, 2,4–Di–1–aziridinyl–6–amino–s–triazines & Otkrytiya, Izobret., Prom. Obraztsy, Tovarnye znaki,vol. 53, No. 26, 1976, pp. 78–79, Malyugina, L. L. et al., & Chemical Abstracts 9th coll. Index page 8505cs, 1,4–Butanediol, 2–amino–2–(hydroxymethyl)–.

Derwent Abstract of Japan Patent Unexamined Pub. No. 416/1987 published Jan. 1986.

Derwent abstract of Japan Patent Unexamined Pub. No. 192962/1984 published Nov. 1984.

Merck Index, 11th Edition, No. 9684 (Tromethamine), pp. 1536–1537 (1989).

Derwent abstract of Japan Patent Unexamined Pub. 104087/1989 published Apr., 1989.

Merck Index, No. 451 (2–Amino–2–ethyl–1,3–propanediol) 1989.

*Primary Examiner*—C. Warren Ivy
*Assistant Examiner*—Raymond Covington
*Attorney, Agent, or Firm*—Wenderoth, Lind & Ponack

[57] ABSTRACT

2-Amino-1,3-propanediol compounds of the formula (I)

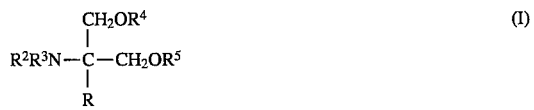

wherein R is an optionally substituted straight- or branched carbon chain, an optionally substituted aryl, an optionally substituted cycloalkyl or the like, and $R^2$, $R^3$, $R^4$ and $R^5$ are the same or different and each is a hydrogen, an alkyl, an aralkyl, an acyl or an alkoxycarbonyl, pharmaceutically acceptable salts thereof and immunosuppressants comprising these compounds as active ingredients.

The 2-amino-1,3-propanediol compounds of the present invention show immunosuppressive action and are useful for suppressing rejection in organ or bone marrow tranplantation, prevention and treatment of autoimmune diseases or as reagents for use in medicinal and pharmaceutical fields.

52 Claims, No Drawings

2-AMINO-1,3-PROPANEDIOL COMPOUND AND IMMUNOSUPPRESSANT

This application is a 371 of PCT/JP93/01515 filed Oct. 18, 1993 and published as WO94/08943 Apr. 28, 1994.

TECHNICAL FIELD

The present invention relates to 2-amino-1,3-propanediol compounds useful as pharmaceuticals, particularly as an immunosuppressant.

BACKGROUND ART

In recent years, cyclosporin is in use for suppressing rejection developed in transplanting organs. Inclusive of the compounds currently under development, the so-called immunosuppressants are expected to be useful as therapeutic agents for articular rheumatism and so on. Said cyclosporin, however, also poses problems of side effects such as renal disorders.

Meanwhile, Japanese Patent Unexamined Publication No. 104087/1989 discloses that an immunosuppressive substance is obtained from a liquid culture of *Isaria sinclairii* and said substance has been confirmed to be (2S,3R,4R)-(E)-2-amino-3,4-dihydroxy-2-hydroxymethyl-14-oxoicosa-6-enoic acid of the formula

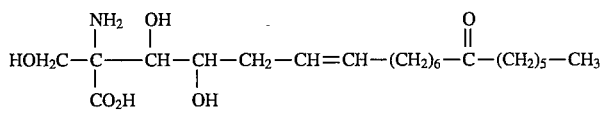

disclosed in U.S. Pat. No. 3928572. In addition, Japanese Patent Unexamined Publication No. 128347/1991 states that a series of said compound has an immunosuppressive action.

Referring to Merck Index, 11th edition, it is described that 2-amino-2-methyl-1,3-propanediol (Index No. 460), 2-amino-2-ethyl-1,3-propanediol (Index No. 451) and 2-amino-2-hydroxymethyl-1,3-propanediol (also called tromethamine, Index No. 9684) can be used as surfactants, intermediates for pharmaceuticals, emulsifiers or gas adsorbents and that tromethamine is medically usable as an alkalization agent. In Japanese Patent Unexamined Publication No. 416/1987, a hair dye containing 2-amino-2-(C1–C5 alkyl)-1,3-propanediol is disclosed. U.S. Pat. No. 4,910,218 and J. Med. Chem., vol. 33, 2385–2393 (1990) teach 2-amino-2-(methyl or ethyl)-1,3-propanediol as an intermediate for an antitumor agent. Also, Japanese Patent Unexamined Publication No. 192962/1984 teaches that the aforementioned 2-amino-2-(C1–C5 alkyl)-1,3-propanediol or 2-amino-1,3-propanediol can be used as a stabilizer for an antigen or antibody-sensitized latex reagent. Moreover, U.S. Pat. No. 3,062,839 teaches 2-methyl- or ethyl-amino-2-(furylmethyl, phenylmethyl or phenylmethyl substituted by lower alkyl, lower alkoxy, chloro, hydroxy or unsubstituted amine)-1,3-propanediol having a tranquilizer action and J. Org. Chem., vol. 25, 2057–2059 (1960) teaches 2-methylamino-2-(phenylmethyl or phenylmethyl substituted by 2-methyl, 3-methyl, 4-methyl, 4-methoxy or 4-hydroxy)-1,3-propanediol. It is not known, however, that these compounds have immunosuppressive actions such as suppression of rejection developed in organ transplantation, prevention and treatment of autoimmune diseases and the like.

An object of the present invention is to provide novel 2-amino-1,3-propanediol compounds having superior immunosuppressive action with less side effects.

DISCLOSURE OF THE INVENTION

The present invention relates to
(1) a 2-amino-1,3-propanediol compound of the formula

wherein
R is an optionally substituted straight- or branched carbon chain which may have, in the chain, a bond, a hetero atom or a group selected from the group consisting of a double bond, a triple bond, oxygen, sulfur, sulfinyl, sulfonyl, —N($R^6$)— where $R^6$ is hydrogen, alkyl, aralkyl, acyl or alkoxycarbonyl, carbonyl, optionally substituted arylene, optionally substituted cycloalkylene, optionally substituted heteroarylene and an alicycle thereof, and which may be substituted, at the chain end thereof, by a double bond, a triple bond, optionally substituted aryl, optionally substituted cycloalkyl, optionally substituted heteroaryl or an alicycle thereof; an optionally substituted aryl, an optionally substituted cycloalkyl, an optionally substituted heteroaryl or an alicycle thereof; and $R^2$, $R^3$, $R^4$ and $R^5$ are the same or different and each is a hydrogen, an alkyl, an aralkyl, an acyl or an alkoxycarbonyl, or $R^4$ and $R^5$ may be bonded to form an alkylene chain which may be substituted by alkyl, aryl or aralkyl;

wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxyimino, hydroxy, carboxy, optionally substituted aryl, optionally substituted aryloxy, optionally substituted cycloalkyl, optionally substituted heteroaryl and an alicycle thereof; the aforementioned optionally substituted arylene, optionally substituted cycloalkylene, optionally substituted heteroarylene and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy; and the optionally substituted aryl, optionally substituted aryloxy, optionally substituted cycloalkyl, optionally substituted heteroaryl and an alicycle thereof may have a substituent selected from the group consisting of alkyl, alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy;
provided that when R is C1–C5 alkyl, the alkyl should be substituted and when R is furylmethyl, phenylmethyl or phenylmethyl substituted by lower alkyl, lower alkoxy, chloro, hydroxy or amino, one of $R^2$ and $R^3$ is not methyl or ethyl, and a pharmaceutically acceptable salt thereof;
(2) a 2-amino-1,3-propanediol compound according to the above-mentioned (1), having the formula

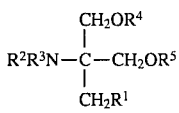

(I-1)

wherein
- $R^1$ is an optionally substituted straight- or branched carbon chain which may have, in the chain, a bond, a hereto atom or a group selected from the group consisting of a double bond, a triple bond, oxygen, sulfur, sulfinyl, sulfonyl, —$N(R^6)$— where $R^6$ is hydrogen, alkyl, aralkyl, acyl or alkoxycarbonyl, carbonyl, optionally substituted arylene, optionally substituted cycloalkylene, optionally substituted heteroarylene and an alicycle thereof; and which may be substituted, at the chain end (ω-position) thereof, by a double bond, a triple bond, optionally substituted aryl, optionally substituted cycloalkyl, optionally substituted heteroaryl or an alicycle thereof; an optionally substituted aryl, an optionally substituted cycloalkyl, an optionally substituted heteroaryl or an alicycle thereof; and
- $R^2$, $R^3$, $R^4$ and $R^5$ are the same or different and each is a hydrogen, an alkyl, an aralkyl, an acyl or an alkoxycarbonyl, or $R^4$ and $R^5$ may be bonded to form an alkylene chain which may be substituted by alkyl, aryl or aralkyl;

wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxyimino, hydroxy, carboxy, optionally substituted aryl, optionally substituted aryloxy, optionally substituted cycloalkyl, optionally substituted heteroaryl and an alicycle thereof; and the aforementioned optionally substituted arylene, optionally substituted cycloalkylene, optionally substituted heteroarylene, an alicycle thereof, optionally substituted aryl, optionally substituted aryloxy, optionally substituted cycloalkyl, optionally substituted heteroaryl and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy;

provided that when $R^1$ is C1–C4 alkyl, the alkyl should be substituted and when $R^1$ is furyl, phenyl or phenyl substituted by lower alkyl, lower alkoxy, chloro, hydroxy or amino, one of $R^2$ and $R^3$ is not methyl or ethyl, and a pharmaceutically acceptable salt thereof;

(3) a 2-amino-1,3-propanediol compound according to the above-mentioned (1) or (2), having the formula

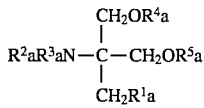

(I-2)

wherein
- $R^1a$ is an optionally substituted straight- or branched carbon chain which may have, in the chain, a bond, a hetero atom or a group selected from the group consisting of a double bond, a triple bond, oxygen, sulfur, sulfinyl, sulfonyl, —$N(R^6)$— where $R^6$ is hydrogen, alkyl, aralkyl, acyl or alkoxycarbonyl, carbonyl, optionally substituted phenylene and optionally substituted cycloalkylene; an optionally substituted phenyl or an optionally substituted cycloalkyl; and

- $R^2a$, $R^3a$, $R^4a$ and $R^5a$ are the same or different and each is a hydrogen, an alkyl, an acyl or an alkoxycarbonyl;

wherein the optionally substituted phenyl and optionally substituted cycloalkyl may have a substituent selected from the group consisting of optionally substituted straight- or branched carbon chain which may have, in the chain, a bond, a hetero atom or a group selected from the group consisting of a double bond, a triple bond, oxygen, sulfur, sulfinyl, sulfonyl, —$(R^6)$— where $R^6$ is hydrogen, alkyl, aralkyl, acyl or alkoxycarbonyl, carbonyl, optionally substituted phenylene and optionally substituted cycloalkylene; alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, nitro, halogen, amino, hydroxy, carboxy, optionally substituted phenyl, optionally substituted phenoxy and optionally substituted cycloalkyl; the optionally substituted carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, nitro, halogen, amino, hydroxy, carboxy, optionally substituted phenyl, optionally substituted phenoxy and optionally substituted cycloalkyl; and the aforementioned optionally substituted phenylene, optionally substituted cycloalkylene, optionally substituted phenyl, optionally substituted phenoxy and optionally substituted cycloalkyl may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, nitro, halogen, amino, hydroxy and carboxy; provided that when $R^1a$ is C1–C4 alkyl, the alkyl should be substituted and when $R^1a$ is furyl, phenyl or phenyl substituted by lower alkyl, lower alkoxy, chloro, hydroxy or amino, one of $R^2a$ and $R^3a$ is not methyl or ethyl, and a pharmaceutically acceptable salt thereof;

(4) a 2-amino-1,3-propanediol compound according to the above-mentioned (3), having the formula

(I-3)

wherein
- $R^1b$ is an optionally substituted alkyl, an optionally substituted alkenyl, an optionally substituted alkynyl, an optionally substituted phenyl or an optionally substituted cycloalkyl, and

- $R^2b$, $R^3b$, $R^4b$ and $R^5b$ are the same or different and each is a hydrogen, an alkyl or an acyl;

wherein the optionally substituted alkyl, optionally substituted alkenyl and optionally substituted alkynyl may have a substituent selected from the group consisting of alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy, carboxy, optionally substituted phenyl and optionally substituted cycloalkyl; and the aforementioned optionally substituted phenyl and optionally substituted cycloalkyl may have 1 to 3 substituents selected from the group consisting of alkyl, alkenyl, alkynyl, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, haloalkyl, nitro, halogen, amino, hydroxy and carboxy; provided that when $R^1b$ is C1–C4 alkyl, the alkyl should be substituted and when $R^1b$ is furyl, phenyl or phenyl substituted by lower alkyl, lower alkoxy, chloro, hydroxy or amino, one of $R^2b$ and $R^3b$ is not methyl or ethyl, and a pharmaceutically acceptable salt thereof;

(5) a 2-amino-1,3-propanediol compound according to the above-mentioned (1), (2), (3) or (4), having the formula

 (I-4)

wherein

Ra is a straight- or branched chain alkyl having 12 to 22 carbon atoms, which may have, in the chain, a bond or a hetero atom selected from the group consisting of a double bond, a triple bond, oxygen, sulfur, sulfinyl, sulfonyl, —($R^6$)— where $R^6$ is hydrogen, alkyl, aralkyl, acyl or alkoxycarbonyl, and carbonyl, and which may have, as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxyimino, hydroxy or carboxy, and $R^2b$, $R^3b$, $R^4b$ and $R^5b$ are the same or different and each is a hydrogen, an alkyl or an acyl, and a pharmaceutically acceptable salt thereof;

(6) a 2-amino-1,3-propanediol compound according to the above-mentioned (5), having the formula

 (I-5)

wherein

Rb is a straight- or branched chain alkyl having 13 to 20 carbon atoms, which may have, in the chain, an oxygen atom and which may have, as a substituent, nitro, halogen, amino, hydroxy or carboxy, and $R^2c$ and $R^3c$ are the same or different and each is a hydrogen or an alkyl, and a pharmaceutically acceptable salt thereof;

(7) a 2-amino-1,3-propanediol compound according to the above-mentioned (5) or (6), having the formula

 (I-6)

wherein

Rc is a straight- or branched chain alkyl having 13 to 20 carbon atoms or a straight- or branched chain alkyl having 13 to 20 carbon atoms which is substituted by halogen, and a pharmaceutically acceptable salt thereof;

(8) a 2-amino-1,3-propanediol compound according to the above-mentioned (5), (6) or (7), which is selected from 2-amino-2-tridecyl-1,3-propanediol, 2-amino-2-tetradecyl-1,3-propanediol, 2-amino-2-pentadecyl-1,3-propanediol, 2-amino-2-hexadecyl-1,3-propanediol, 2-amino-2-heptadecyl-1,3-propanediol, 2-amino-2-octadecyl-1,3-propanediol, 2-amino-2-nonadecyl-1,3-propanediol, 2-amino-2-icosyl-1,3-propanediol, 2-amino-2-(12-fluorododecyl)-1,3-propanediol and 2-amino-2-(14-fluorotetradecyl)-1,3-propanediol, and a pharmaceutically acceptable salt thereof;

(9) a 2-amino-1,3-propanediol compound according to the above-mentioned (1), (2), (3) or (4), having the formula

 (I-7)

wherein

Rd is a phenylalkyl, a substituted phenylalkyl, a cycloalkylalkyl, a substituted cycloalkylalkyl, a heteroarylalkyl, a substituted heteroaryl alkyl, a heterocyclic alkyl or a substituted heterocyclic alkyl, wherein the alkyl moiety may have, in the carbon chain, a bond or a hetero atom selected from the group consisting of a double bond, a triple bond, oxygen, sulfur, sulfinyl, sulfonyl, —($R^6$)— where $R^6$ is hydrogen, alkyl, aralkyl, acyl or alkoxycarbonyl, and carbonyl, and may have, as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy; and the substituted phenylalkyl, substituted cycloalkylalkyl, substituted heteroarylalkyl and substituted heterocyclic alkyl may have a substituent selected from the group consisting of alkyl, alkoxy, alkenyloxy, alkynyloxy, aralkyloxy, haloaralkyloxy, aralkyloxyalkyl, phenoxyalkyl, phenoxyalkoxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy, and a pharmaceutically acceptable salt thereof;

(10) a 2-amino-1,3-propanediol compound according to the above-mentioned (9), having the formula

 (I-8)

wherein

Re is a phenylalkyl wherein the alkyl moiety is a straight- or branched chain having 6 to 20 carbon atoms; a phenylalkyl which may be substituted by a straight- or branched chain C6–C20 alkyl optionally substituted by halogen, a straight- or branched chain C6–C20 alkoxy optionally substituted by halogen, a straight- or branched chain C6–C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms, or a heterocyclic alkyl substituted by a straight- or branched chain alkyl having 6 to 20 carbon atoms; wherein the alkyl moiety may have, in the carbon chain, a bond or a hetero atom selected from the group consisting of a double bond, a triple bond, oxygen, sulfur, sulfinyl, sulfonyl, —($R^6$)— where $R^6$ is hydrogen, alkyl, aralkyl, acyl or alkoxycarbonyl, and carbonyl, and may have, as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and a pharmaceutically acceptable salt thereof;

(11) a 2-amino-1,3-propanediol compound according to the above-mentioned (9) or (10), having the formula

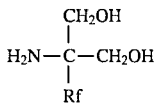

(I-9)

wherein

Rf is a phenylalkyl wherein the alkyl moiety is a straight- or branched chain having 6 to 20 carbon atoms which may have, in the carbon chain, one or two oxygen atoms; a phenylalkyl which may be substituted by a straight- or branched chain C6–C20 alkyl optionally substituted by halogen, a straight- or branched chain C6–C20 alkoxy optionally substituted by halogen, a straight- or branched chain C6–C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms which may have, in the carbon chain, one or two oxygen atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms which may have, in the carbon chain, one or two oxygen atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms which may have, in the carbon chain, one or two oxygen atoms, or a heterocyclic alkyl substituted by a straight- or branched chain alkyl having 6 to 20 carbon atoms;

wherein the alkyl moiety may have, in the carbon chain, a substituent selected from the group consisting of alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy and carboxy, and a pharmaceutically acceptable salt thereof;

(12) a 2-amino-1,3-propanediol compound according to the above-mentioned (9), (10) or (11), having the formula

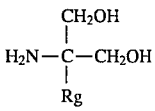

(I-10)

wherein

Rg is a phenylalkyl wherein the alkyl moiety is a straight- or branched chain having 6 to 20 carbon atoms which may have, in the carbon chain, one or two oxygen atoms, a phenylalkyl which may be substituted by a straight- or branched chain C6–C14 alkyl optionally substituted by halogen, a straight- or branched chain C6–C14 alkoxy optionally substituted by halogen, a straight- or branched chain C6–C14 alkenyloxy, phenylalkoxy, halophenylalkoxy, phenylalkoxyalkyl, phenoxyalkoxy or phenoxyalkyl; a cycloalkylalkyl wherein the alkyl moiety has 6 to 20 carbon atoms; a cycloalkylalkyl substituted by a straight- or branched chain alkyl having 6 to 14 carbon atoms; a heteroarylalkyl wherein the alkyl moiety has 6 to 20 carbon atoms; a heteroarylalkyl substituted by a straight- or branched chain alkyl having 6 to 14 carbon atoms; a heterocyclic alkyl wherein the alkyl moiety has 6 to 20 carbon atoms, or a heterocyclic alkyl substituted by a straight- or branched chain alkyl having 6 to 14 carbon atoms, and a pharmaceutically acceptable salt thereof;

(13) a 2-amino-1,3-propanediol compound according to the above-mentioned (12), having the formula

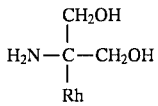

(I-11)

wherein

Rh is a phenylalkyl wherein the alkyl moiety has 6 to 20 carbon atoms, a phenylalkoxyalkyl wherein the alkyl moiety and alkoxy moiety have 6 to 20 carbon atoms in total, a phenoxyalkyl wherein the alkyl moiety has 6 to 20 carbon atoms or a phenoxyalkoxyalkyl wherein the alkyl moiety and alkoxy moiety have 6 to 20 carbon atoms in total, and a pharmaceutically acceptable salt thereof;

(14) a 2-amino-1,3-propanediol compound according to the above-mentioned (13), which is selected from the group consisting of 2-amino-2-(8-phenyloctyl)-1,3-propanediol, 2-amino-2-(9-phenylnonyl)-1,3-propanediol, 2-amino-2-(10-phenyldecyl)-1,3-propanediol, 2-amino-2-(11-phenylundecyl)-1,3-propanediol, 2-amino-2-(12-phenyldodecyl)-1,3-propanediol, 2-amino-2-(13-phenyltridecyl)-1,3-propanediol, 2-amino-2-(14-phenyltetradecyl)-1,3-propanediol, 2-amino-2-(15-phenylpentadecyl)-1,3-propanediol, 2-amino-2-(16-phenylhexadecyl)-1,3-propanediol, 2-amino-2-[6-(8-phenyloctyloxy)hexyl]-1,3-propanediol, 2-amino-2-(8-phenylmethyloxyoctyl)-1,3-propanediol, 2-amino-2-(9-phenoxynonyl)-1,3-propanediol, 2-amino-2-(12-phenoxydodecyl)-1,3-propanediol and 2-amino-2-[6-(2-phenoxyethyloxy)hexyl]-1,3-propanediol, and a pharmaceutically acceptable salt thereof;

(15) a 2-amino-1,3-propanediol compound according to the above-mentioned (13) which is selected from the group consisting of 2-amino-2-(10-phenyldecyl)-1,3-propanediol, 2-amino-2-(13-phenyltridecyl)-1,3-propanediol, 2-amino-2-[6-(8-phenyloctyloxy)hexyl]-1,3-propanediol, 2-amino-2-(8-phenylmethyloxyoctyl)-1,3-propanediol, 2-amino-2-(9-phenoxynonyl)-1,3-propanediol, 2-amino-2-(12-phenoxydodecyl)-1,3-propanediol and 2-amino-2-[6-(2-phenoxyethyloxy)hexyl]-1,3-propanediol, and a pharmaceutically acceptable salt thereof;

(16) a 2-amino-1,3-propanediol compound according to the above-mentioned (12), having the formula

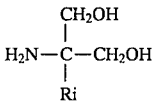

(I-12)

wherein

Ri is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy;

wherein the alkyl moiety of phenylalkyl may be substituted by hydroxy, and a pharmaceutically acceptable salt thereof;

(17) a 2-amino-1,3-propanediol compound according to the above-mentioned (16), having the formula

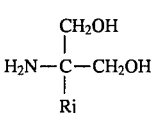

(I-13)

wherein

Rj is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy, wherein the alkyl moiety is a C2–C6 alkyl optionally substituted by hydroxy, and a pharmaceutically acceptable salt thereof;

(18) a 2-amino-1,3-propanediol compound according to the above-mentioned (16) or (17), which is selected from the group consisting of 2-amino-2-[2-(4-heptylphenyl)ethyl]-1,3-propanediol, 2-amino-2-[2-(4-octylphenyl)ethyl]-1,3-propanediol, 2-amino-2-[2-(4-nonylphenyl)ethyl]-1,3-propanediol, 2-amino-2-[2-(4-decylphenyl)ethyl]-1,3-propanediol, 2-amino-2-[2-(4-undecylphenyl)ethyl]-1,3-propanediol, 2-amino-2-[2-(4-dodecylphenyl)ethyl]-1,3-propanediol, 2-amino-2-[2-(4-tridecylphenyl)ethyl]-1,3-propanediol, 2-amino-2-[2-(4-tetradecylphenyl)ethyl]-1,3-propanediol, 2-amino-2-[2-(4-hexyloxyphenyl)ethyl]-1,3-propanediol, 2-amino-2-[2-(4-heptyloxyphenyl)ethyl]-1,3-propanediol, 2-amino-2-[2-(4-octyloxyphenyl)ethyl]-1,3-propanediol, 2-amino-2-[2-(4-nonyloxyphenyl)ethyl]-1,3-propanediol, 2-amino-2-[2-(4-decyloxyphenyl)ethyl]-1,3-propanediol, 2-amino-2-[2-(4-undecyloxyphenyl)ethyl]-1,3-propanediol, 2-amino-2-[2-(4-dodecyloxyphenyl)ethyl]-1,3-propanediol, 2-amino-2-[2-(4-tridecyloxyphenyl)ethyl]-1,3-propanediol, 2-amino-2-[2-(4-(8-fluorooctyl)phenyl)ethyl]-1,3-propanediol, 2-amino-2-[2-(4-(12-fluorododecyl)phenyl)ethyl]-1,3-propanediol, 2-amino-2-[2-(4-(7-fluoroheptyloxy)phenyl)ethyl]-1,3-propanediol, 2-amino-2-[2-(4-(11-fluoroundecyloxy)phenyl)ethyl]-1,3-propanediol and 2-amino-2-[2-(4-(7-octenyloxy)phenyl)ethyl]-1,3-propanediol, and a pharmaceutically acceptable salt thereof;

(19) a 2-amino-1,3-propanediol compound according to the above-mentioned (16) or (17), which is selected from the group consisting of 2-amino-2-[2-(4-heptylphenyl)ethyl]-1,3-propanediol, 2-amino-2-[2-(4-octylphenyl)ethyl]-1,3-propanediol, 2-amino-2-[2-(4-nonylphenyl)ethyl]-1,3-propanediol, 2-amino-2 -[2-(4-decylphenyl)ethyl]-1,3-propanediol, 2-amino-2-[2-(4-undecylphenyl)ethyl]-1,3-propanediol, 2-amino-2-[2-(4-dodecylphenyl)ethyl]-1,3-propanediol, 2-amino-2-[2-(4-heptyloxyphenyl)ethyl]-1,3-propanediol, 2-amino-2-[2-(4-octyloxyphenyl)ethyl]-1,3-propanediol, 2-amino-2-[2-(4-nonyloxyphenyl)ethyl]-1,3-propanediol, 2-amino-2-[2-(4-undecyloxyphenyl)ethyl]-1,3-propanediol and 2-amino-2-[2-(4-(7-octenyloxy)phenyl)ethyl]-1,3-propanediol, and a pharmaceutically acceptable salt thereof;

(20) a 2-amino-1,3-propanediol compound according to the above-mentioned (12), having the formula

(I-14)

wherein

Rk is a phenylalkyl substituted by phenylalkoxy, halophenylalkoxy, phenylalkoxyalkyl, phenoxyalkoxy or phenoxyalkyl, and a pharmaceutically acceptable salt thereof;

(21) a 2-amino-1,3-propanediol compound according to the above-mentioned (20), having the formula

(I-15)

wherein

Rl is a phenylalkyl substituted by phenylalkoxy wherein the alkoxy moiety has 2 to 8 carbon atoms, halophenylalkoxy wherein the alkoxy moiety has 2 to 8 carbon atoms, phenylalkoxyalkyl wherein the alkoxy moiety and alkyl moiety have 2 to 8 carbon atoms in total, phenoxyalkoxy wherein the alkoxy moiety has 2 to 8 carbon atoms or phenoxyalkyl wherein the alkyl moiety has 2 to 8 carbon atoms, where the alkyl moiety has 2 to 6 carbon atoms, and a pharmaceutically acceptable salt thereof;

(22) a 2-amino-1,3-propanediol compound according to the above-mentioned (20) or (21), which is selected from the group consisting of 2-amino-2-[2-(4-phenylmethyloxyphenyl)ethyl]-1,3-propanediol, 2-amino-2-[2-(4-(2-phenylethyloxy)phenyl)ethyl]-1,3-propanediol, 2-amino-2-[2-(4-(3-phenylpropyloxy)phenyl)ethyl]-1,3-propanediol, 2-amino-2-[2-(4-(4-phenylbutyloxy)phenyl)ethyl]-1,3-propanediol, 2-amino-2-[2-(4-(5-phenylpentyloxy)phenyl)ethyl]-1,3-propanediol, 2-amino-2-[2-(4-(6-phenylhexyloxy)phenyl)ethyl]-1,3-propanediol, 2-amino-2-[2-(4-(7phenylheptyloxy) phenyl)ethyl]-1,3-propanediol, 2-amino-2-[2-(4-(8-phenyloctyloxy)phenyl)ethyl]-1,3-propanediol, 2-amino-2-[4-(6-(4-fluorophenyl)hexyloxy)phenyl)ethyl]-1,3-propanediol, 2-amino-2-[2-(4-(5-phenylpentyloxymethyl)phenyl)ethyl]-1,3-propanediol, 2-amino-2-[2-(4-(4-phenoxybutyloxy)phenyl)ethyl]-1,3-propanediol, 2-amino-2-[2-(4-(5-phenoxypentyloxy)phenyl)ethyl]-1,3-propanediol, 2-amino-2-[2-(4-(6-phenoxyhexyloxy)phenyl)ethyl]-1,3-propanediol, 2-amino-2-[2-(4-(7-phenoxyheptyloxy)phenyl)ethyl]-1,3-propanediol, 2-amino-2-[2-(4-(4-phenoxybutyl)phenyl)ethyl]-1,3-propanediol, 2-amino-2-[2-(4 -(5-phenoxypentyl)phenyl)ethyl]-1,3-propanediol, 2-amino-2-[2-(4-(6-phenoxyhexyl)phenyl)ethyl]-1,3-propanediol and 2-amino-2-[2-(4-(7-phenoxyheptyl)phenyl)ethyl]-1,3-propanediol, and a pharmaceutically acceptable salt thereof;

(23) a 2-amino-1,3-propanediol compound according to the above-mentioned (20) or (21) which is selected from the group consisting of 2-amino-2-[2-(4-(6-phenylhexyloxy)phenyl)ethyl]-1,3-propanediol and 2-amino-2-[2-(4-(5-phenylpentyloxymethyl)phenyl)ethyl]-1,3-propanediol, and a pharmaceutically acceptable salt thereof;

(24) a 2-amino-1,3-propanediol compound according to the above-mentioned (12), having the formula

(I-16)

wherein

Rm is an alkyl-substituted cycloalkylalkyl wherein the alkyl moiety has 6 to 20 carbon atoms in total, and a pharmaceutically acceptable salt thereof;

(25) a 2-amino-1,3-propanediol compound according to the above-mentioned (24), which is selected from the group consisting of 2-amino-2-[3-(4-heptylcyclohexyl)propyl]-1,3-propanediol, 2-amino-2-[4-(4-butylcyclohexyl)butyl]-1,3-propanediol, 2-amino-2-[2-(4-octylcyclohexyl)ethyl]-1,3-propanediol, 2-amino-2-[2-(4-nonylcyclohexyl)ethyl]-1,3-propanediol and 2-amino-2-[2-(4-dodecylcyclohexyl)ethyl]-1,3-propanediol, and a pharmaceutically acceptable salt thereof;

(26) a 2-amino-1,3-propanediol compound according to the above-mentioned (12), having the formula

(I-17)

wherein

Rn is a 1-alkyl-substituted piperidin-4-ylalkyl wherein the alkyl moiety has 6 to 20 carbon atoms in total, and a pharmaceutically acceptable salt thereof;

(27) a 2-amino-1,3-propanediol compound according to the above-mentioned (26), which is selected from the group consisting of 2-amino-2-[2-(1-octylpiperidin-4-yl)ethyl]-1,3-propanediol and 2-amino-2-[2-(1-dodecylpiperidin-4-yl)ethyl]-1,3-propanediol, and a pharmaceutically acceptable salt thereof;

(28) a 2-amino-1,3-propanediol compound according to the above-mentioned (12), having the formula

wherein

Ro is a thienylalkyl wherein the alkyl moiety has 6 to 20 carbon atoms, an alkyl-substituted thienylalkyl wherein the alkyl moiety has 6 to 20 carbon atoms in total, pyridylalkyl wherein the alkyl moiety has 6 to 20 carbon atoms or an alkyl-substituted pyridylalkyl wherein the alkyl moiety has 6 to 20 carbon atoms in total, and a pharmaceutically acceptable salt thereof;

(29) a 2-amino-1,3-propanediol compound according to the above-mentioned (28), which is selected from the group consisting of 2-amino-2-[2-(5-octyl-2-thienyl)ethyl]-1,3-propanediol, 2-amino-2-[2-(5-nonyl-2-thienyl)ethyl]-1,3-propanediol, 2-amino-2-[2-(5-decyl-2-thienyl)ethyl]-1,3-propanediol, 2-amino-2-[2-(5-dodecyl-2-thienyl)ethyl]-1,3-propanediol, 2-amino-2-[13-(2-thienyl)tridecyl]-1,3-propanediol, 2-amino-2-[2-(5-octyl-2-pyridyl)ethyl]-1,3-propanediol, 2-amino-2-[2-(5-decyl-2-pyridyl)ethyl]1,3-propanediol, 2-amino-2-[13-(2-pyridyl)tridecyl]-1,3-propanediol, 2-amino-2-[2-(2-octyl-5-pyridyl)ethyl]-1,3-propanediol, 2-amino-2-[2-(2-decyl-5-pyridyl)ethyl]-1,3-propanediol and 2-amino-2-[13-(3-pyridyl)tridecyl]-1,3-propanediol, and a pharmaceutically acceptable salt thereof;

(30) a 2-amino-1,3-propanediol compound according to the above-mentioned (1) or (2), having the formula

wherein

Rp is a phenyl substituted by C6–C18 alkyl, a cycloalkyl, a heteroaryl or a heterocycle, and a pharmaceutically acceptable salt thereof;

(31) a 2-amino-1,3-propanediol compound according to the above-mentioned (30), having the formula

wherein

Rq is a phenyl substituted by C6–C18 alkyl, and a pharmaceutically acceptable salt thereof;

(32) a 2-amino-1,3-propanediol compound according to the above-mentioned (30) or (31), which is selected from the group consisting of 2-amino-2-(4-decylphenyl)-1,3-propanediol, 2-amino-2-(4-dodecylphenyl)-1,3-propanediol, 2-amino-2-(4-tetradecylphenyl)-1,3-propanediol and 2-amino-2-(4-hexadecylphenyl)-1,3-propanediol, and a pharmaceutically acceptable salt thereof;

(33) a 2-amino-1,3-propanediol compound according to the above-mentioned (1) or (2), having the formula

wherein $R^1$ is an optionally substituted straight- or branched carbon chain which may have, in the chain, a bond, a hetero atom or a group selected from the group consisting of a double bond, a triple bond, oxygen, sulfur, sulfinyl, sulfonyl, —N($R^6$)— where $R^6$ is hydrogen, alkyl, aralkyl, acyl or alkoxycarbonyl, and carbonyl, optionally substituted arylene, optionally substituted cycloalkylene, optionally substituted heteroarylene and an alicycle thereof, and which may be substituted, at the chain end (ω-position) thereof, by a double bond, a triple bond, optionally substituted aryl, optionally substituted cycloalkyl, optionally substituted heteroaryl or an alicycle thereof, an optionally substituted aryl, an optionally substituted cycloalkyl, an optionally substituted heteroaryl or an alicycle thereof, and $R^2$a, $R^3$a, $R^4$a and $R^5$a are the same or different and each is a hydrogen, an alkyl, an acyl or an alkoxycarbonyl; wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxyimino, hydroxy, carboxy, optionally substituted aryl, optionally substituted aryloxy, optionally substituted cycloalkyl, optionally substituted heteroaryl and an alicycle thereof; and the aforementioned optionally substituted arylene, optionally substituted cycloalkylene, optionally substituted heteroarylene, an alicycle thereof, optionally substituted aryl, optionally substituted aryloxy, optionally substituted cycloalkyl, optionally substituted heteroaryl and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy, and a pharmaceutically acceptable salt thereof;

(34) a 2-amino-1,3-propanediol compound according to the above-mentioned (33), having the formula

wherein

Rr is an alkyl optionally substituted by hydroxy and/or hydroxyimino which may have, in the chain, a double bond or carbonyl, and a pharmaceutically acceptable salt thereof;

(35) a 2-amino-1,3-propanediol compound according to the above-mentioned (33) or (34), which is selected from the group consisting of 2-amino-2-(1,2,12-trihydroxy-4-octadecenyl)-1,3-propanediol, 2-amino-2-(1,2-dihydroxy-4-octadecenyl)-1,3-propanediol, 2-amino-2-(1,2-dihydroxyoctadecyl)-1,3-propanediol, 2-amino-2-(1,12-dihydroxy-4-octadecenyl)-1,3-propanediol, 2-amino-2-(1,2,4-trihydroxybutyl)-1,3-propanediol, 2-amino-2-(1,2,12-trihydroxyoctadecyl)-1,3-propanediol and 2-amino-2-(1,12-dihydroxyoctadecyl)-1,3-propanediol, and a pharmaceutically acceptable salt thereof;

(36) a 2-amino-1,3-propanediol compound according to the above-mentioned (33), having the formula

 (I-23)

wherein

Rs is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy, and a pharmaceutically acceptable salt thereof;

(37) a 2-amino-1,3-propanediol compound according to the above-mentioned (36), which is selected from the group consisting of 2-amino-2-[1-hydroxy-2-(4-octylphenyl)ethyl]-1,3-propanediol, 2-amino-2-[2-(4-dodecylphenyl)-1-hydroxyethyl]-1,3-propanediol, 2-amino-2-[2-(4-heptyloxyphenyl)-1-hydroxyethyl]-1,3-propanediol, 2-amino-2-[1-hydroxy-2-(4-undecyloxyphenyl)ethyl]-1,3-propanediol, 2-amino-2-[2-(4-(8-fluorooctyl)phenyl)-1-hydroxyethyl]-1,3-propanediol, 2-amino-2-[2-(4-(12-fluorododecyl)phenyl)-1-hydroxyethyl]-1,3-propanediol, 2-amino-2-[2-(4-(7-fluoroheptyloxy)phenyl)-1-hydroxyethyl]-1,3-propanediol and 2-amino-2-[1-hydroxy-2-(4-(11-fluoroundecyloxy)phenyl)ethyl]-1,3-propanediol, and a pharmaceutically acceptable salt thereof;

(38) a 2-amino-1,3-propanediol compound according to the above-mentioned (1) or (2), having the formula

 (I-24)

wherein

Rt is an optionally substituted straight- or branched carbon chain which may have, in the chain, a bond, a hetero atom or a group selected from the group consisting of a double bond, a triple bond, oxygen, sulfur, sulfinyl, sulfonyl, —(R$^6$)— where R$^6$ is hydrogen, alkyl, aralkyl, acyl or alkoxycarbonyl, carbonyl, optionally substituted arylene, optionally substituted cycloalkylene, optionally substituted heteroarylene and an alicycle thereof, an optionally substituted aryl, an optionally substituted cycloalkyl, an optionally substituted heteroaryl or an alicycle thereof, and R$^2$a, R$^3$a, R$^4$a and R$^5$a are the same or different and each is a hydrogen, an alkyl, an acyl or an alkoxycarbonyl; wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy, carboxy, optionally substituted aryl, optionally substituted aryloxy, optionally substituted cycloalkyl, optionally substituted heteroaryl and an alicycle thereof; and the aforementioned optionally substituted arylene, optionally substituted cycloalkylene, optionally substituted heteroarylene, an alicycle thereof, optionally substituted aryl, optionally substituted aryloxy, optionally substituted cycloalkyl, optionally substituted heteroaryl and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy, and a pharmaceutically acceptable salt thereof;

(39) a 2-amino-1,3-propanediol compound according to the above-mentioned (38), having the formula

 (I-25)

wherein

Ru is a phenyl substituted by alkyl having 4 to 16 carbon atoms, and a pharmaceutically acceptable salt thereof;

(40) a 2-amino-1,3-propanediol compound according to the above-mentioned (38) or (39), which is selected from the group consisting of 2-amino-2-[2-(4-octylphenyl)ethenyl]-1,3-propanediol, 2-amino-2-[2-(4-decylphenyl)ethenyl]-1,3-propanediol, 2-amino-2-[2-(4-dodecylphenyl)ethenyl]-1,3-propanediol and 2-amino-2-[2-(4-tetradecylphenyl)ethenyl]-1,3-propanediol, and a pharmaceutically acceptable salt thereof;

(41) a 2-amino-1,3-propanediol compound according to the above-mentioned (1) or (2), having the formula

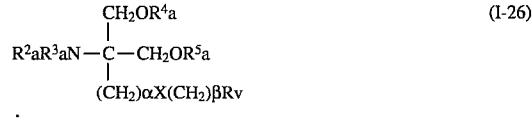 (I-26)

wherein

Rv is an optionally substituted aryl, an optionally substituted cycloalkyl, an optionally substituted heteroaryl or an alicycle thereof;

R$^2$a, R$^3$a, R$^4$a and R$^5$a are the same or different and each is a hydrogen, an alkyl, an acyl or an alkoxycarbonyl;

X is an oxygen, a sulfur, a sulfinyl, a sulfonyl, —N(R$^6$)— where R$^6$ is hydrogen, alkyl, aralkyl, acyl or alkoxycarbonyl; and α and β are 0 or an integer of 1–20 provided that α+β=5–20, wherein the optionally substituted aryl, optionally substituted cycloalkyl, optionally substituted heteroaryl and an alicycle thereof may have a substituent selected from the group consisting of alkyl, alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy, and a pharmaceutically acceptable salt thereof;

(42) a 2-amino-1,3-propanediol compound according to the above-mentioned (41), having the formula

 (I-27)

wherein

Rw is a phenyl substituted by C4–C16 alkyl, and a pharmaceutically acceptable salt thereof;

(43) a 2-amino-1,3-propanediol compound according to the above-mentioned (41) or (42), which is selected from the group consisting of 2-amino-2-(4-octylphenoxymethyl)-1,3-propanediol, 2-amino-2-(4-decylphenoxymethyl)-1,3-propanediol, 2-amino-2-(4-dodecylphenoxymethyl)-1,3-propanediol and 2-amino-2-(4-tetradecylphenoxymethyl)-1,3-propanediol, and a pharmaceutically acceptable salt thereof;

(44) a pharmaceutical composition comprising either one of the above-mentioned compounds (1) through (4);

(45) an immunosuppressant comprising a 2-amino-1,3-propanediol compound of the formula

 (I-28)

wherein

R is an optionally substituted straight- or branched carbon chain which may have, in the chain, a bond, a hetero atom or a group selected from the group consisting of a double bond, a triple bond, oxygen, sulfur, sulfinyl, sulfonyl, —($R^6$)— where $R^6$ is hydrogen, alkyl, aralkyl, acyl or alkoxycarbonyl, carbonyl, optionally substituted arylene, optionally substituted cycloalkylene, optionally substituted heteroarylene and an alicycle thereof, and which may be substituted, at the chain end thereof, by a double bond, a triple bond, optionally substituted aryl, optionally substituted cycloalkyl, optionally substituted heteroaryl or an alicycle thereof, an optionally substituted aryl, an optionally substituted cycloalkyl, an optionally substituted heteroaryl or an alicycle thereof, and $R^2$, $R^3$, $R^4$ and $R^5$ are the same or different and each is a hydrogen, an alkyl, an aralkyl, an acyl or an alkoxycarbonyl, or $R^4$ and $R^5$ may be bonded by an alkylene chain which may be substituted by alkyl, aryl or aralkyl;

wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxyimino, hydroxy, carboxy, optionally substituted aryl, optionally substituted aryloxy, optionally substituted cycloalkyl, optionally substituted heteroaryl and an alicycle thereof; the aforementioned optionally substituted arylene, optionally substituted cycloalkylene, optionally substituted heteroarylene and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy; and the optionally substituted aryl, optionally substituted aryloxy, optionally substituted cycloalkyl, optionally substituted heteroaryl and an alicycle thereof may have a substituent selected from the group consisting of alkyl, alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy, and a pharmaceutically acceptable salt thereof;

(46) an immunosuppressant comprising a 2-amino-1,3-propanediol compound or a pharmaceutically acceptable salt thereof according to either one of the aforementioned (1) through (43);

(47) a pharmaceutical agent according to the aforementioned (45) or (46), wherein the immunosuppressant is an agent for suppressing rejection;

(48) a pharmaceutical agent according to the aforementioned (45) or (46), wherein the immunosuppressant is an agent for the prevention and treatment of autoimmune diseases; and

(49) a pharmaceutical agent according to the aforementioned (48), wherein the agent for the prevention and treatment of autoimmune diseases is an agent for the prevention and treatment of rheumatism.

The groups represented by respective symbols in the present specification are explained in the following.

The carbon chain at R, $R^1$, $R^1a$ or Rt is a straight- or branched carbon chain having 1 to 30 carbon atoms and is exemplified by methyl, ethyl, propyl, isopropyl, butyl, isobutyl, tert-butyl, pentyl, isopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl and triacontyl.

The arylene at R, $R^1$ or Rt is exemplified by phenylene and naphthylene, with preference given to phenylene.

The cycloalkylene at R, $R^1$, $R^1a$ or Rt is that having 3 to 10 carbon atoms and is exemplified by cyclopropylene, cyclobutylene, cyclopentylene, cyclohexylene, cycloheptylene, cyclooctylene, cyclononylene and cyclodecylene, with preference given to cyclohexylene.

The heteroarylene at R, $R^1$ or Rt is a 5- or 6-membered heteroarylene optionally having, in the ring, 1 or 2 hetero atoms selected from nitrogen atom, oxygen atom and sulfur atom and is exemplified by thiophen-(2,4-, 2,5- or 3,4-)ylene, furan-(2,4-, 2,5- or 3,4-)ylene, pyrrol-(1,3-, 2,4-, 2,5- or 3,4-)ylene, imidazol-(1,4-, 2,4- or 2,5-)ylene, thiazol-(2,4- or 2,5-)ylene, isothiazol-(3,4- or 3,5-)ylene, oxazol-(2,4- or 2,5-)ylene, isoxazol-(3,4- or 3,5-)ylene, pyridin-(2,4-, 2,5-, 2,6- or 3,5-)ylene, pyrimidin-(2,4- or 2,5-)ylene, pyrazin-2,5-ylene, pyridazin-(3,5- or 3,6-)ylene and pyran-(2,4-, 2,5- or 2,6-)ylene, with preference given to thiophen-2,5-ylene and pyridin-2,5-ylene.

The alicycle of the aforementioned heteroarylene at R, $R^1$ or Rt is the aforementioned heteroarylene when saturated and is exemplified by pyrrolidine-(1,3-, 2,4-, 2,5- or 3,4-)ylene, piperidine-(1,4-, 2,4-, 2,5-, 2,6- or 3,5-)ylene, piperazine-1,4-ylene, morpholine-2,4 or 3,4-ylene and thiomorpholine-2,4 or 3,4-ylene.

The aryl at R, $R^1$, Rt or Rv is exemplified by phenyl and naphthyl, with preference given to phenyl.

The cycloalkyl at R, $R^1$, $R^1a$, $R^1b$, Rp, Rt or Rv is cycloalkyl having 3 to 10 carbon atoms and includes, for example, cyclopropyl, cyclobutyl, cyclopentyl, cyclohexyl, cycloheptyl, cyclooctyl, cyclononyl and cyclodecyl, with preference given to cyclohexyl.

The heteroaryl at R, $R^1$, Rp, Rt or Rv is a 5- or 6-membered heteroaryl optionally having, in the ring, 1 to 4 hetero atoms selected from nitrogen atom, oxygen atom and sulfur atom and includes, for example, monocyclic heteroaryl such as thienyl(2-thienyl, 3-thienyl), furyl(2-furyl, 3-furyl), pyrrolyl(1-pyrrolyl, 2-pyrrolyl, 3-pyrrolyl), imidazolyl (2-imidazolyl, 4-imidazolyl ), pyrazolyl (3-pyrazolyl, 4-pyrazolyl), triazolyl, tetrazolyl, thiazolyl(2-thiazolyl, 4-thiazolyl), isothiazolyl(3-isothiazolyl, 4-isothiazolyl), oxazolyl(2-oxazolyl, 4-oxazolyl), isooxazolyl(3-isooxazolyl, 4-isooxazolyl), pyridyl(2-pyridyl, 3-pyridyl, 4-pyridyl), pyrazinyl, pyrimidinyl(2-pyrimidinyl, 4-pyrimidinyl), pyridazinyl(3-pyridazinyl, 4-pyridazinyl) or pyranyl(2-pyranyl, 3-pyranyl, 4-pyranyl), and bicyclic heteroaryl such as indolyl(2-indolyl, 3-indolyl), quinolyl(2-quinolyl, 3-quinolyl), isoquinolyl(1-isoquinolyl, 3-isoquinolyl), benzofuranyl(2-benzofuranyl, 3-benzofuranyl), benzothienyl(2-benzothienyl, 3-benzothienyl), 1H-benzimidazol2-yl or chromenyl(2-chromenyl, 3-chromenyl, 4-chromenyl).

The alicycle of the aforementioned heteroaryl at R, $R^1$, Rt or Rv is the above-mentioned monocyclic heteroaryl when saturated and includes, for example, pyrrolidinyl(1-pyrrolidinyl, 2-pyrrolidinyl, 3-pyrrolidinyl), piperidyl(2-piperidyl, 3-piperidyl, 4-piperidyl), piperidino, piperazinyl, morpholinyl and thiomorpholinyl.

The heterocycle at Rp means an alicycle of heteroaryl.

The alkyl at $R^1b$ or Rr is a straight- or branched chain alkyl having 1 to 30 carbon atoms and is exemplified by methyl, ethyl, propyl, isopropyl, butyl, isobutyl, tert-butyl, pentyl, isopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl and triacontyl.

The straight- or branched chain alkyl having 12 to 22 carbon atoms at Ra and the straight- or branched chain alkyl having 13 to 20 carbon atoms at Rb or Rc are the above-mentioned alkyl having the specified numbers of carbon atoms.

The alkenyl at $R^1b$ is a straight- or branched chain alkenyl having 2 to 30 carbon atoms and includes, for example, ethenyl, propenyl, isopropenyl, butenyl, isobutenyl, pentenyl, isopentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl, nonacosenyl and triacontenyl.

The alkynyl at $R^1b$ is a straight- or branched chain alkynyl having 2 to 30 carbon atoms and includes, for example, ethynyl, propynyl, isopropynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl and triacontynyl.

The phenylalkyl at Rd, Re, Rf, Rg, Ri, Rk or Rs is that where the alkyl moiety is a straight- or branched chain alkyl having 1 to 30 carbon atoms and includes, for example, benzyl, 1-phenylethyl, 2-phenylethyl, 1-phenylpropyl, 2-phenylpropyl, 3-phenylpropyl, 4-phenylbutyl, 5-phenylpentyl, 6-phenylhexyl, 7-phenylheptyl, 8-phenyloctyl, 9-phenylnonyl, 10-phenyldecyl, 11-phenylundecyl, 12-phenyldodecyl, 13-phenyltridecyl, 14-phenyltetradecyl, 15-phenylpentadecyl, 16-phenylhexadecyl, 17-phenylheptadecyl, 18-phenyloctadecyl, 19-phenylnonadecyl, 20-phenylicosyl, 21-phenylhenicosyl, 22-phenyldocosyl, 23-phenyltricosyl, 24-phenyltetracosyl, 25-phenylpentacosyl, 26-phenylhexacosyl, 27-phenylheptacosyl, 28-phenyloctacosyl, 29-phenylnonacosyl and 30-phenyltriacontyl.

The phenylalkyl at Re, Rf, Rg or Rh where the alkyl moiety has 6 to 20 carbon atoms and that at Rj or Rl where the alkyl moiety has 2 to 6 carbon atoms are the above-mentioned phenylalkyl having the specified numbers of carbon atoms.

The phenylalkoxyalkyl at Rh where the alkyl moiety and alkoxy moiety have 6 to 20 carbon atoms in total is exemplified by 5-phenylmethyloxypentyl, 6-phenylmethyloxyhexyl, 7-phenylmethyloxyheptyl, 8-phenylmethyloxyoctyl, 9-phenylmethyloxynonyl, 10-phenylmethyloxydecyl, 12-phenylmethyloxydodecyl, 14-phenylmethyloxytetradecyl, 16-phenylmethyloxyhexadecyl, 18-phenylmethyloxyoctadecyl, 2-(8-phenyloctyloxy)ethyl, 3-(8-phenyloctyloxy)propyl, 4-(8-phenyloctyloxy)butyl, 5-(8-phenyloctyloxy)pentyl, 6-(8-phenyloctyloxy)hexyl and 7-(8-phenyloctyloxy)heptyl.

The phenoxyalkyl at Rh where the alkyl moiety has 6 to 20 carbon atoms is exemplified by 6-phenoxyhexyl, 7-phenoxyheptyl, 8-phenoxyoctyl, 9-phenoxynonyl, 10-phenoxydecyl, 11-phenoxyundecyl, 12-phenoxydodecyl, 13-phenoxytridecyl, 14-phenoxytetradecyl, 15-phenoxypentadecyl, 16-phenoxyhexadecyl, 17-phenoxyheptadecyl, 18-phenoxyoctadecyl, 19-phenoxynonadecyl and 20-phenoxyicosyl.

The phenoxyalkoxyalkyl at Rh where the alkyl moiety and alkoxy moiety have 6 to 20 carbon atoms in total is exemplified by 5-(2-phenoxyethyloxy)pentyl, 6-(2-phenoxyethyloxy)hexyl, 7-(2-phenoxyethyloxy)heptyl, 8-(2-phenoxyethyloxy)octyl, 5-(3-phenoxypropyloxy)pentyl, 6-(3-phenoxypropyloxy)hexyl, 7-(3-phenoxypropyloxy)heptyl, 8-(3-phenoxypropyloxy)octyl, 5-(4-phenoxybutyloxy)pentyl, 6-(4-phenoxybutyloxy)hexyl, 7-(4-phenoxybutyloxy)heptyl, 8-(4-phenoxybutyloxy)octyl, 5-(6-phenoxyhexyloxy)pentyl, 6-(6-phenoxyhexyloxy)hexyl, 7-(6-phenoxyhexyloxy)heptyl and 8-(6-phenoxyhexyloxy) octyl.

The cycloalkylalkyl at Rd, Re, Rf or Rg is that where the alkyl moiety is a straight- or branched chain alkyl having 1 to 30 carbon atoms and the cycloalkyl moiety is a cycloalkyl having 3 to 10 carbon atoms, and is exemplified by cyclohexylmethyl, 1-cyclohexylethyl, 2-cyclohexylethyl, 1-cyclohexylpropyl, 2-cyclohexylpropyl, 3-cyclohexylpropyl, 4-cyclohexylbutyl, 5-cyclohexylpentyl, 6-cyclohexylhexyl, 7-cyclohexylheptyl, 8-cyclohexyloctyl, 9-cyclohexylnonyl, 10-cyclohexyldecyl, 11-cyclohexylundecyl, 12-cyclohexyldodecyl, 13-cyclohexyltridecyl, 14-cyclohexyltetradecyl, 15-cyclohexylpentadecyl, 16-cyclohexylhexadecyl, 17-cyclohexylheptadecyl, 18-cyclohexyloctadecyl, 19-cyclohexylnonadecyl, 20-cyclohexylicosyl, 21-cyclohexylhenicosyl, 22-cyclohexyldocosyl, 23-cyclohexyltricosyl, 24-cyclohexyltetracosyl, 25-cyclohexylpentacosyl, 26-cyclohexylhexacosyl, 27-cyclohexylheptacosyl, 28-cyclohexyloctacosyl, 29-cyclohexylnonacosyl and 30-cyclohexyltriacontyl.

The cycloalkylalkyl at Re, Rf or Rg where the alkyl moiety has 6 to 20 carbon atoms is the above-mentioned cycloalkylalkyl having the specified numbers of carbon atoms.

The alkyl-substituted cycloalkylalkyl at Rm where the alkyl moiety has 6 to 20 carbon atoms is exemplified by 3-(4-heptylcyclohexyl)propyl, 4-(4-butylcyclohexyl)butyl, 2-(4-octylcyclohexyl)ethyl, 2-(4-nonylcyclohexyl)ethyl and 2-(4-dodecylcyclohexyl)ethyl.

The heteroarylalkyl at Rd, Re, Rf or Rg is that where the alkyl moiety is a straight- or branched chain alkyl having 1 to 30 carbon atoms and is exemplified by thienylalkyl and pyridylalkyl such as (thienyl or pyridyl)methyl, 1-(thienyl or pyridyl)ethyl, 2-(thienyl or pyridyl)ethyl, 1-(thienyl or pyridyl)propyl, 2-(thienyl or pyridyl)propyl, 3-(thienyl or pyridyl)propyl, 4-(thienyl or pyridyl)butyl, 5-(thienyl or pyridyl)pentyl, 6-(thienyl or pyridyl)hexyl, 7-(thienyl or pyridyl)heptyl, 8-(thienyl or pyridyl)octyl, 9-(thienyl or pyridyl)nonyl, 10-(thienyl or pyridyl)decyl, 11-(thienyl or pyridyl)undecyl, 12-(thienyl or pyridyl)dodecyl, 13-(thienyl or pyridyl)tridecyl, 14-(thienyl or pyridyl)tetradecyl, 15-(thienyl or pyridyl)pentadecyl, 16-(thienyl or pyridyl) hexadecyl, 17-(thienyl or pyridyl)heptadecyl, 18-(thienyl or pyridyl)octadecyl, 19-(thienyl or pyridyl)nonadecyl, 20-(thienyl or pyridyl)icosyl, 21-(thienyl or pyridyl)henicosyl, 22-(thienyl or pyridyl)docosyl, 23-(thienyl or pyridyl) tricosyl, 24-(thienyl or pyridyl)tetracosyl, 25-(thienyl or pyridyl)pentacosyl, 26-(thienyl or pyridyl)hexacosyl, 27-(thienyl or pyridyl)heptacosyl, 28-(thienyl or pyridyl)octacosyl, 29-(thienyl or pyridyl)nonacosyl and 30-(thienyl or pyridyl)triacontyl.

The heteroarylalkyl at Re, Rf or Rg where the alkyl moiety has 6 to 20 carbon atoms is the above-mentioned heteroarylalkyl having the specified numbers of carbon atoms.

The alkyl-substituted thienylalkyl at Ro where the alkyl moiety has 6 to 20 carbon atoms in total is exemplified by 2-(5-octyl-2-thienyl)ethyl, 2-(5-nonyl-2-thienyl)ethyl, 2-(5-decyl-2-thienyl)ethyl and 2-(5-dodecyl-2-thienyl)ethyl.

The thienylalkyl at Ro where the alkyl moiety has 6 to 20 carbon atoms is thienylalkyl from among the above-mentioned heteroarylalkyls. Preferred is 13-(2-thienyl)tridecyl.

The alkyl-substituted pyridylalkyl at Ro where the alkyl moiety has 6 to 20 carbon atoms in total is exemplified by 2-(5-octyl-2-pyridyl)ethyl, 2-(5-decyl-2-pyridyl)ethyl, 2-(2-octyl-5-pyridyl)ethyl and 2-(2-decyl-5-pyridyl)ethyl.

The pyridylalkyl at Ro where the alkyl moiety has 6 to 20 carbon atoms is pyridylalkyl from among the above-mentioned heteroarylalkyls. Preferred are 13-(2-pyridyl)tridecyl and 13(3-pyridyl)tridecyl.

The heterocyclic alkyl at Rd, Re, Rf or Rg where the alkyl moiety is a straight- or branched chain alkyl having 1 to 30 carbon atoms and heterocyclic means an alicycle of heteroaryl, is exemplified by 4-piperidylmethyl, 1-(4-piperidyl)ethyl, 2-(4-piperidyl)ethyl, 1-(4-piperidyl)propyl, 2-(4-piperidyl)propyl, 3-(4-piperidyl)propyl, 4-(4-piperidyl)butyl, 5-(4-piperidyl)pentyl, 6-(4-piperidyl)hexyl, 7-(4-piperidyl)heptyl, 8-(4-piperidyl)octyl, 9-(4-piperidyl)nonyl, 10-(4-piperidyl)decyl, 11-(4-piperidyl)undecyl, 12-(4-piperidyl)dodecyl, 13-(4piperidyl)tridecyl, 14-(4-piperidyl)tetradecyl, 15-(4-piperidyl)pentadecyl, 16-(4-piperidyl)hexadecyl, 17-(4-piperidyl)heptadecyl, 18-(4-piperidyl)octadecyl, 19-(4-piperidyl)nonadecyl, 20-(4-piperidyl)icosyl, 21-(4-piperidyl)henicosyl, 22-(4-piperidyl)docosyl, 23-(4-piperidyl)tricosyl, 24-(4-piperidyl)tetracosyl, 25-(4-piperidyl)pentacosyl, 26-(4-piperidyl)hexacosyl, 27-(4-piperidyl)heptacosyl, 28-(4piperidyl)octacosyl, 29-(4-piperidyl)nonacosyl and 30-(4-piperidyl)triacontyl.

The heterocyclic alkyl at Re, Rf or Rg where the alkyl moiety has 6 to 20 carbon atoms is the above-mentioned heterocyclic alkyl having the specified numbers of carbon atoms.

The 1-alkyl-substituted piperidin-4-ylalkyl at Rn where the alkyl moiety has 6 to 20 carbon atoms in total is, for example, 2-(1-octylpiperidin-4-yl)ethyl and 2-(1-dodecylpiperidin-4-yl)ethyl.

The alkyl as a substitutent at R, $R^1b$, Rd, Rm, Rn, Ro or Rv is a straight- or branched chain alkyl having 1 to 20 carbon atoms and is exemplified by methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl.

The straight- or branched chain alkyl having 6 to 20 carbon atoms as a substituent at Re or Rf, the straight- or branched chain alkyl having 6 to 14 carbon atoms as a substituent at Rg, Ri, Rj or Rs, the alkyl having 6 to 18 carbon atoms as a substituent at Rp or Rq and the alkyl having 4 to 16 carbon atoms as a substituent at Ru or Rw are the above-mentioned alkyls having the specified numbers of carbon atoms.

The alkoxy as a substituent at R, $R^1$, $R^1a$, $R^1b$, Ra, Rd, Re, Rf, Rt or Rv is a straight- or branched chain alkoxy having 1 to 20 carbon atoms and is exemplified by methoxy, ethoxy, propoxy, isopropoxy, butoxy, isobutoxy, sec-butoxy, tert-butoxy, pentyloxy, isopentyloxy, tert-pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy and icosyloxy.

The straight- or branched chain alkoxy having 6 to 20 carbon atoms as a substituent at Re or Rf and the straight- or branched chain alkoxy having 6 to 14 carbon atoms as a substituent at Rg, Ri, Rj or Rs are the above-mentioned alkoxys having the specified numbers of carbon atoms.

The alkenyloxy as a substituent at R, $R^1$, $R^1a$, $R^1b$, Ra, Rd, Re, Rf, Rt or Rv is that where the alkenyl moiety is a straight- or branched chain alkenyl having 2 to 20 carbon atoms and is exemplified by vinyloxy, propenyloxy, isopropenyloxy, butenyloxy, isobutenyloxy, pentenyloxy, isopentenyloxy, hexenyloxy, heptenyloxy, octenyloxy, nonenyloxy, decenyloxy, undecenyloxy, dodecenyloxy, tridecenyloxy, tetradecenyloxy, pentadecenyloxy, hexadecenyloxy, heptadecenyloxy, octadecenyloxy, nonadecenyloxy and icosenyloxy.

The straight- or branched chain alkenyloxy having 6 to 20 carbon atoms as a substituent at Re or Rf and the straight- or branched chain alkenyloxy having 6 to 14 carbon atoms as a substituent at Rg, Ri, Rj or Rs are the above-mentioned alkenyloxys having the specified numbers of carbon atoms.

The alkynyloxy as a substituent at R, $R^1$, $R^1a$, $R^1b$, Ra, Rd, Re, Rf, Rt or Rv is that where the alkynyl moiety is a straight- or branched chain alkynyl having 2 to 20 carbon atoms and is exemplified by ethynyloxy, propynyloxy, butynyloxy, pentynyloxy, hexynyloxy, heptynyloxy, octynyloxy, nonynyloxy, deeynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy and icosynyloxy.

The aralkyloxy as a substituent at R, $R^1$, $R^1a$, $R^1b$, Ra, Rd, Re, Rf, Rt or Rv is that wherein the aralkyl is that where the alkyl moiety is a straight- or branched chain alkyl having 1 to 20 carbon atoms and the aralkyloxy is exemplified by phenylalkoxy such as benzyloxy, 2-phenethyloxy, 1-phenylethyloxy, 1-phenylpropyloxy, 2-phenylpropyloxy, 3-phenylpropyloxy, 4-phenylbutyloxy, 5-phenylpentyloxy, 6-phenylhexyloxy, 7-phenylheptyloxy, 8-phenyloctyloxy, 9-phenylnonyloxy, 10-phenyldecyloxy, 11-phenylundecyloxy, 12-phenyldodecyloxy, 13-phenyltridecyloxy or 14-phenyltetradecyloxy, and naphthylalkoxy such as naphthylmethyl or 2-naphthylethyl, with preference given to phenylalkoxy.

The phenylalkoxy as a substituent at Re, Rf, Rg or Rk is phenylalkoxy of the aforementioned aralkyloxy.

The phenylalkoxy as a substituent at $R^1$ where the alkoxy moiety has 2 to 8 carbon atoms is phenylalkoxy of the aforementioned aralkyloxy, having the specified numbers of carbon atoms.

The alkylenedioxy as a substituent at R, $R^1$, $R^1a$, Rd, Rt or Rv is alkylenedioxy where the alkylene moiety is a straight- or branched chain alkylene having 1 to 20 carbon atoms and is exemplified by methylenedioxy, ethylenedioxy, propylenedioxy, trimethylenedioxy, butylenedioxy, 1,2-dimethylethylenedioxy, pentamethylenedioxy, hexamethylenedioxy, heptamethylenedioxy, octamethylenedioxy, nonamethylenedioxy, decamethylenedioxy, undecamethylenedioxy, dodecamethylenedioxy, tridecamethylenedioxy, tetradecamethylenedioxy, pentadecamethylenedioxy, hexadecamethylenedioxy, heptadecamethylenedioxy, octadecamethylenedioxy, nonadecamethylenedioxy and icosamethylenedioxy, with preference given to methylenedioxy and ethylenedioxy.

The acyl as a substituent at R, $R^1$, $R^1a$, $R^1b$, Ra, Rd, Re, Rf, Rt or Rv is optionally substituted alkanoyl or aroyl, in which alkanoyl is a straight- or branched chain alkanoyl having 1 to 20 carbon atoms, and is exemplified by formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl, where alkanoyl may be substituted by phenyl. Examples of the alkanoyl optionally substituted by phenyl include phenylacetyl and phenylpropionyl. Examples of aroyl include benzoyl.

The alkylamino as a substituent at R, $R^1$, $R^1a$, $R^1b$, Ra, Rd, Re, Rf, Rt or Rv is that where the alkyl moiety is a straight- or branched chain alkyl having 1 to 20 carbon atoms, and is exemplified by methylamino, ethylamino, propylamino, isopropylamino, butylamino, isobutylamino, sec-butylamino, tert-butylamino, pentylamino, isopentylamino, tert-pentylamino, hexylamino, heptylamino, octylamino, nonylamino, decylamino, undecylamino, dodecylamino, tridecylamino, tetradecylamino, pentadecylamino, hexadecylamino, heptadecylamino, octadecylamino, nonadecylamino and icosylamino.

The alkylthio as a substituent at R, $R^1$, $R^1a$, $R^1b$, Ra, Rd, Re, Rf, Rt or Rv is that where the alkyl moiety is a straight- or branched chain alkyl having 1 to 20 carbon atoms, and is exemplified by methylthio, ethylthio, propylthio, isopropylthio, butylthio, isobutylthio, sec-butylthio, tert-butylthio, pentylthio, isopentylthio, tert-pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio and icosylthio.

The acylamino as a substituent at R, $R^1$, $R^1a$, $R^1b$, Ra, Rd, Re, Rf, Rt or Rv is that where the acyl moiety is a straight- or branched chain alkanoyl having 1 to 20 carbon atoms, and is exemplified by formylamino, acetylamino, propionylamino, butyrylamino, isobutyrylamino, pentanoylamino, pivaloylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, nonadecanoylamino and icosanoylamino.

The alkoxycarbonyl as a substituent at R, $R^1$, $R^1a$, $R^1b$, Ra, Rd, Re, Rf, Rt or Rv is that where the alkoxy moiety is an optionally substituted straight- or branched chain alkoxy having 1 to 20 carbon atoms, and is exemplified by methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl and icosyloxycarbonyl, which may be substituted by phenyl. Examples thereof include benzyloxycarbonyl.

The alkoxycarbonylamino as a substituent at R, $R^1$, $R^1a$, $R^1b$, Ra, Rd, Re, Rf, Rt or Rv is that where the alkoxy moiety is an optionally substituted straight- or branched chain alkoxy having 1 to 20 carbon atoms, and is exemplified by methoxycarbonylamino, ethoxycarbonylamino, propoxycarbonylamino, isopropoxycarbonylamino, butoxycarbonylamino, isobutoxycarbonylamino, tert-butoxycarbonylamino, pentyloxycarbonylamino, isopentyloxycarbonylamino, tert-pentyloxycarbonylamino, hexyloxycarbonylamino, heptyloxycarbonylamino, octyloxycarbonylamino, nonyloxycarbonylamino, decyloxycarbonylamino, undecyloxycarbonylamino, dodecyloxycarbonylamino, tridecyloxycarbonylamino, tetradecyloxycarbonylamino, pentadecyloxycarbonylamino, hexadecyloxycarbonylamino, heptadecyloxycarbonylamino, octadecyloxycarbonylamino, nonadecyloxycarbonylamino and icosyloxycarbonylamino, which may be substituted by phenyl. Examples thereof include benzyloxycarbonylamino.

The acyloxy as a substituent at R, $R^1$, $R^1a$, $R^1b$, Ra, Rd, Re, Rf, Rt or Rv is that where the acyl moiety is a straight- or branched chain alkanoyl having 2 to 20 carbon atoms, and is exemplified by acetoxy, propionyloxy, butyryloxy, isobutyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy and icosanoyloxy.

The alkylcarbamoyl as a substituent at R, $R^1$, $R^1a$, $R^1b$, Ra, Rd, Re, Rf, Rt or Rv is that where the alkyl moiety is a straight- or branched chain alkyl having 1 to 20 carbon atoms, and is exemplified by methylcarbamoyl, ethylcarbamoyl, propylcarbamoyl, butylcarbamoyl, pentylcarbamoyl, hexylcarbamoyl, heptylcarbamoyl, octylcarbamoyl, nonylcarbamoyl, decylcarbamoyl, undecylcarbamoyl, dodecylcarbamoyl, tridecylcarbamoyl, tetradecylcarbamoyl, pentadecylcarbamoyl, hexadecylcarbamoyl, heptadecylcarbamoyl, octadecylcarbamoyl, nonadecylcarbamoyl and icosylcarbamoyl.

The haloalkyl as a substituent at R, $R^1$, $R^1a$, $R^1b$, Rd, Rt or Rv is that where the alkyl moiety is a straight- or branched chain alkyl having 1 to 20 carbon atoms, and is exemplified by fluoromethyl, trifluoromethyl, chloromethyl, 2,2,2-trifluoroethyl, perfluoroethyl, 3-chloropropyl, 3-fluoropropyl, 4-chlorobutyl, 4-fluorobutyl, 5-chloropentyl, 6-chlorohexyl, 6-fluorohexyl, 7-chloroheptyl, 7-fluoroheptyl, 8-fluorooctyl, 9-fluorononyl, 10-fluorodecyl, 11-fluoroundecyl, 12-fluorododecyl, 13-fluorotridecyl, 14-fluorotetradecyl, 15-fluoropentadecyl, 16-fluorohexadecyl, 17-fluoroheptadecyl, 18-fluorooctadecyl, 19-fluorononadecyl and 20-fluoroicosyl.

The haloalkoxy as a substituent at R, $R^1$, Rd, Rt or Rv has 1 to 20 carbon atoms, and is exemplified by chloromethoxy, bromomethoxy, fluoromethoxy, dichloromethoxy, dibromomethoxy, difluoromethoxy, 2-chloroethoxy, 2-fluoroethoxy, 2,2,2-trifluoroethoxy, 3-chloropropoxy, 3-fluoropropoxy, 2,2,3,3-tetrafluoropropoxy, 4-chlorobutoxy, 4-fluorobutoxy, 5-chloropentyloxy, 5-fluoropentyloxy, 6-chlorohexyloxy, 6-fluorohexyloxy, 7-chloroheptyloxy, 7-fluoroheptyloxy, 8-fluorooctyloxy, 9-fluorononyloxy, 10-fluorodecyloxy, 11-fluoroundecyloxy, 12-fluorododecyloxy, 13-fluorotridecyloxy, 14-fluorotetradecyloxy, 15-fluoropentadecyloxy, 16-fluorohexadecyloxy, 17-fluoroheptadecyloxy, 18-fluorooctadecyloxy, 19-fluorononadecyloxy and 20-fluoroicosyloxy.

The halogen as a substituent at R, $R^1$, $R^1a$, $R^1b$, Ra, Rb, Rc, Rd, Re, Rf, Rg, Ri, Rj, Rs, Rt or Rv is exemplified by fluorine, chlorine, bromine and iodine.

The aryl as a substituent at R, $R^1$ or Rt is exemplified by phenyl and naphthyl, with preference given to phenyl.

The aryloxy as a substituent at R, $R^1$ or Rt is exemplified by phenoxy and naphthyloxy, with preference given to phenoxy.

The cycloalkyl as a substituent at R, $R^1$, $R^1a$, $R^1b$ or Rt is that having 3 to 10 carbon atoms and is exemplified by cyclopropyl, cyclobutyl, cyclopentyl, cyclohexyl, cycloheptyl, cyclooctyl, cyclononyl and cyclodecyl, with preference given to cyclohexyl.

The heteroaryl as a substituent at R, $R^1$ or Rt is a 5- or 6-membered heteroaryl optionally having, in the ring, 1 to 4 hetero atoms selected from nitrogen atom, oxygen atom and sulfur atom and includes, for example, monocyclic heteroaryl such as thienyl(2-thienyl, 3-thienyl), furyl(2-furyl, 3-furyl), pyrrolyl(1-pyrrolyl, 2-pyrrolyl, 3-pyrrolyl), imidazolyl(2-imidazolyl, 4-imidazolyl etc.), pyrazolyl(3-pyrazolyl, 4-pyrazolyl etc.), triazolyl, tetrazolyl, thiazolyl(2-thiazolyl, 4-thiazolyl), isothiazolyl(3-isothiazolyl, 4-isothiazolyl), oxazolyl(2-oxazolyl, 4-oxazolyl), isoxazolyl(3-isooxazolyl, 4-isooxazolyl), pyridyl(2-pyridyl, 3-pyridyl, 4-pyridyl), pyrazinyl, pyrimidinyl(2-pyrimidinyl, 4-pyrimidinyl), pyridazinyl(3-pyridazinyl, 4-pyridazinyl) and pyranyl(2-pyranyl, 3-pyranyl, 4-pyranyl), and bicyclic heteroaryl such as indolyl(2-indolyl, 3-indolyl), quinolyl(2-quinolyl, 3-quinolyl), isoquinolyl(1-isoquinolyl, 3-isoquinolyl), benzofuranyl(2-benzofuranyl, 3-benzofuranyl), benzothienyl(2-benzothienyl, 3-benzothienyl), 1H-benzimidazol-2-yl or chromenyl(2-chromenyl, 3-chromenyl, 4-chromenyl).

The alicycle of the aforementioned heteroaryl as a substituent at R, $R^1$ or Rt is the above-mentioned monocyclic heteroaryl when saturated such as pyrrolidinyl(1-pyrrolidinyl, 2-pyrrolidinyl, 3-pyrrolidinyl), piperidyl(2-piperidyl, 3-piperidyl, 4-piperidyl), piperidino, piperazinyl, morpholinyl or thiomorpholinyl.

The carbon chain as a substituent at $R^1a$ is a straight- or branched carbon chain having 1 to 30 carbon atoms such as methyl, ethyl, propyl, isopropyl, butyl, isobutyl, tert-butyl, pentyl, isopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl or triacontyl.

The alkenyl as a substituent at $R^1b$ is a straight- or branched chain alkenyl having 2 to 20 carbon atoms such as ethenyl, propenyl, isopropenyl, butenyl, isobutenyl, pentenyl, isopentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl or icosenyl.

The alkynyl as a substituent at $R^1b$ is a straight- or branched chain alkynyl having 2 to 20 carbon atoms such as ethynyl, propynyl, isopropynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl or icosynyl.

The haloaralkyloxy as a substituent at Rd is that including aralkyl where the alkyl moiety is a straight- or branched chain alkyl having 1 to 20 carbon atoms, and is exemplified by halophenylalkoxy such as 4-fluorobenzyloxy, 2-(4-fluorophenyl)ethyloxy, 1-(4-fluorophenyl)ethyloxy, 1-(4-fluorophenyl)propyloxy, 2-(4-fluorophenyl)propyloxy, 3-(4-fluorophenyl)propyloxy, 4-(4-fluorophenyl)butyloxy, 5-(4-fluorophenyl)pentyloxy, 6-(4-fluorophenyl)hexyloxy, 7-(4-fluorophenyl)heptyloxy, 8-(4-fluorophenyl)octyloxy, 9-(4-fluorophenyl)nonyloxy, 10-(4-fluorophenyl)decyloxy, 11-(4-fluorophenyl)undecyloxy, 12-(4-fluorophenyl)dodecyloxy, 13-(4-fluorophenyl)tridecyloxy or 14-(4-fluorophenyl)tetradecyloxy, and halonaphthylalkoxy such as (7-fluoro-2-naphthyl)methyloxy or 2-(7-fluoro-2-naphthyl) ethyloxy, with preference given to halophenylalkoxy.

The halophenylalkoxy as a substituent at Re, Rf, Rg or Rk is that of the aforementioned haloaralkyloxy.

The halophenylalkoxy as a substituent at Rl, where the alkoxy moiety has 2 to 8 carbon atoms, is halophenylalkoxy of the aforementioned haloaralkyloxy, having the specified numbers of carbon atoms.

The aralkyloxyalkyl as a substituent at Rd is that where the alkyl moiety and the alkyl moiety of the aralkyl are straight- or branched chain alkyls having 1 to 20 carbon atoms and have 2 to 20 carbon atoms in total, and is exemplified by phenylalkoxyalkyl such as phenylmethyloxymethyl, 2-phenylethyloxymethyl, 3-phenylpropyloxymethyl, 4-phenylbutyloxymethyl, 5-phenylpentyloxymethyl, 6-phenylhexyloxymethyl, 7-phenylheptyloxymethyl, 8-phenyloctyloxymethyl, 9-phenylnonyloxymethyl, 10-phenyldecyloxymethyl, 12-phenyldodecyloxymethyl, 14-phenyltetradecyloxymethyl, 16-phenylhexadecyloxymethyl or 18-phenyloctadecyloxymethyl, and naphthylalkoxyalkyl such as 4-(2 -naphthyl)butyloxymethyl, 5-(2-naphthyl)pentyloxymethyl or 6-(2-naphthyl) hexyloxymethyl, with preference given to phenylalkoxyalkyl.

The phenylalkoxyalkyl as a substituent at Re, Rf, Rg or Rk is that of the aforementioned aralkyloxyalkyl.

The phenylalkoxyalkyl as a substituent at Rl, where the alkoxy moiety and the alkyl moiety have 2 to 8 carbon atoms in total, is phenylalkoxyalkyl of the aforementioned aralkyloxyalkyl, having the specified numbers of carbon atoms, in which the carbon number of the alkoxy moiety and the alkyl moiety is respectively 1 to 7, with total being 2 to 8.

The phenoxyalkyl as a substituent at Rd, Re, Rf, Rg or Rk is that where the alkyl moiety is a straight- or branched chain alkyl having 1 to 20 carbon atoms and is exemplified by phenoxymethyl, 1-phenoxyethyl, 2-phenoxyethyl, 1-phenoxypropyl, 2-phenoxypropyl, 3-phenoxypropyl, 4-phenoxybutyl, 5-phenoxypentyl, 6-phenoxyhexyl, 7-phenoxyheptyl, 8-phenoxyoctyl, 9-phenoxynonyl, 10-phenoxydecyl, 11-phenoxyundecyl, 12-phenoxydodecyl, 13-phenoxytridecyl, 14-phenoxytetradecyl, 15-phenoxypentadecyl, 16-phenoxyhexadecyl, 17-phenoxyheptadecyl, 18-phenoxyoctadecyl, 19-phenoxynonadecyl and 20-phenoxyicosyl.

The phenoxyalkyl as a substituent at Rl, where the alkyl moiety has 2 to 8 carbon atoms, is the aforementioned phenoxyalkyl having the specified numbers of carbon atoms.

The phenoxyalkoxy as a substituent at Rd, Re, Rf, Rg or Rk is that where the alkoxy moiety is a straight- or branched chain alkoxy having 1 to 20 carbon atoms and is exemplified by phenoxymethoxy, 1-phenoxyethyloxy, 2-phenoxyethyloxy, 1-phenoxypropyloxy, 2-phenoxypropyloxy, 3-phenoxypropyloxy, 4-phenoxybutyloxy, 5-phenoxypentyloxy, 6-phenoxyhexyloxy, 7-phenoxyheptyloxy, 8-phenoxyoctyloxy, 9-phenoxynonyloxy, 10-phenoxydecyloxy, 11-phenoxyundecyloxy, 12-phenoxydodecyloxy, 13-phenoxytridecyloxy, 14-phenoxytetradecyloxy, 15-phenoxypentadecyloxy, 16-phenoxyhexadecyloxy, 17-phenoxyheptadecyloxy, 18-phenoxyoctadecyloxy, 19-phenoxynonadecyloxy and 20-phenoxyicosyloxy.

The phenoxyalkoxy as a substituent at $R^{1.}$ where the alkoxy moiety has 2 to 8 carbon atoms, is the aforementioned phenoxyalkoxy having the specified numbers of carbon atoms.

The alkyl at $R^2$, $R^2a$, $R^2b$, $R^2c$, $R^3$, $R^3a$, $R^3b$, $R^3c$, $R^4$, $R^4a$, $R^4b$, $R^5$, $R^5a$, $R^5b$ or $R^6$ is that having 1 to 20 carbon atoms and is exemplified by methyl, ethyl, propyl, isopropyl, butyl, isobutyl, tert-butyl, pentyl, isopentyl, tert-pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl.

The aralkyl at $R^2$, $R^3$, $R^4$, $R^5$ or $R^6$ is that where the alkyl moiety is a straight- or branched chain alkyl having 1 to 20 carbon atoms and is exemplified by benzyl, 1-phenylethyl, 2-phenylethyl, 1-phenylpropyl, 2-phenylpropyl, 3-phenylpropyl, 4-phenylbutyl, 5-phenylpentyl, 6-phenylhexyl, 7-phenylheptyl, 8-phenyloctyl, 9-phenylnonyl, 10-phenyldecyl, 11-phenylundecyl, 12-phenyldodecyl, 13-phenyltridecyl, 14-phenyltetradecyl, 15-phenylpentadecyl, 16-phenylhexadecyl, 17-phenylheptadecyl, 18-phenyloctadecyl, 19-phenylnonadecyl and 20-phenylicosyl.

The acyl at $R^2$, $R^2a$, $R^2b$, $R^3$, $R^3a$, $R^3b$, $R^4$, $R^4a$, $R^4b$, $R^5$, $R^5a$, $R^5b$ or $R^6$ is optionally substituted alkanoyl or aroyl where the alkanoyl is a straight- or branched chain alkanoyl having 1 to 20 carbon atoms, and alkoanoyl is exemplified by formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl, which may be substituted by phenyl. Examples thereof include phenylacetyl and phenylpropionyl. Examples of aroyl include benzoyl.

The alkoxycarbonyl at $R^2$, $R^2a$, $R^3$, $R^3a$, $R^4$, $R^4a$, $R^5$, $R^5a$ or $R^6$ is that where the alkoxy moiety is an optionally substituted straight- or branched chain alkoxy having 1 to 20 carbon atoms and is exemplified by methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl and icosyloxycarbonyl, which may be substituted by phenyl. Examples thereof include benzyloxycarbonyl.

The alkylene chain formed by $R^4$ and $R^5$ is a straight- or branched chain alkylene having 1 to 5 carbon atoms and is exemplified by methylene, ethylene, trimethylene, propylene, butylene, 1,2-dimethylethylene and pentamethylene.

The alkyl as a substituent at $R^4$ or $R^5$ is a straight- or branched chain alkyl having 1 to 5 carbon atoms and is exemplified by methyl, ethyl, propyl, isopropyl, butyl, isobutyl, sec-butyl, tert-butyl and pentyl.

The aryl as a substituent at $R^4$ or $R^5$ is, for example, phenyl or naphthyl.

The aralkyl as a substituent at $R^4$ or $R^5$ is that where the alkyl moiety is a straight- or branched chain alkyl having 1 to 5 carbon atoms and is exemplified by benzyl, 2-phenethyl, 1-phenylethyl, 1-phenylpropyl, 2-phenylpropyl, 3-phenylpropyl, 4-phenylbutyl and 5-phenylpentyl.

The alkylene chain formed by $R^4$ and $R^5$, which is substituted by alkyl, aryl or aralkyl, is preferably ethylidene, isopropylidene, benzylidene or 2-phenylethylidene.

The preferable compounds of the present invention are shown in the following tables.

$$R^2R^3N-\underset{\underset{CH_2R^1}{|}}{\overset{\overset{CH_2OR^4}{|}}{C}}-CH_2OR^5$$

| $R^1$ | $R^2$ | $R^3$ | $R^4$ | $R^5$ |
|---|---|---|---|---|
| $CH(CH_3)_2$ | H | H | H | H |
| $CH(CH_3)C_2H_5$ | H | H | H | H |
| $CH(CH_3)C_3H_7$ | H | H | H | H |
| $C(CH_3)_3$ | H | H | H | H |
| $CH(CH_3)_2C_2H_5$ | H | H | H | H |
| $CH(CH_3)_2C_3H_7$ | H | H | H | H |
| $C_5H_{11}$ | H | H | H | H |
| $C_5H_{11}$ | $COCH_3$ | H | $COCH_3$ | $COCH_3$ |
| $C_6H_{13}$ | H | H | H | H |
| $C_7H_{15}$ | H | H | H | H |
| $C_7H_{15}$ | $COCH_3$ | H | $COCH_3$ | $COCH_3$ |
| $C_8H_{17}$ | H | H | H | H |
| $C_9H_{19}$ | H | H | H | H |
| $C_9H_{19}$ | $COCH_3$ | H | $COCH_3$ | $COCH_3$ |
| $C_{10}H_{21}$ | H | H | H | H |
| $C_{11}H_{23}$ | H | H | H | H |
| $C_{11}H_{23}$ | $COCH_3$ | H | $COCH_3$ | $COCH_3$ |
| $[CH_2CH(CH_3)(CH_2)_2]_2CH_2CH(CH_3)_2$ | H | H | H | H |
| $[CH_2CH(CH_3)(CH_2)_2]_2CH_2CH(CH_3)_2$ | $COCH_3$ | H | $COCH_3$ | $COCH_3$ |
| $C_{12}H_{25}$ | H | H | H | H |
| $C_{12}H_{25}$ | $COCH_3$ | H | $COCH_3$ | $COCH_3$ |
| $C_{13}H_{27}$ | H | H | H | H |
| $C_{13}H_{27}$ | $CH_3$ | $CH_3$ | H | H |
| $(CH_2)_3CH(CH_3)C_{10}H_{12}$ | H | H | H | H |
| $C_{14}H_{29}$ | H | H | H | H |
| $C_{14}H_{29}$ | $COCH_3$ | H | $COCH_3$ | $COCH_3$ |
| $C_{15}H_{31}$ | H | H | H | H |
| $C_{16}H_{33}$ | H | H | H | H |
| $C_{17}H_{35}$ | H | H | H | H |
| $C_{17}H_{35}$ | $C_2H_5$ | H | H | H |
| $C_{17}H_{35}$ | H | H | $COCH_3$ | $COCH_3$ |
| $C_{17}H_{35}$ | $COC_4H_9$ | H | $COCH_3$ | $COCH_3$ |
| $C_{17}H_{35}$ | $COC_4H_9$ | H | H | H |
| $C_{17}H_{35}$ | $C_5H_{11}$ | H | H | H |
| $C_{17}H_{35}$ | $COC_9H_{19}$ | H | $COCH_3$ | $COCH_3$ |
| $C_{17}H_{35}$ | $COC_9H_{19}$ | H | H | H |
| $C_{17}H_{35}$ | $C_{10}H_{21}$ | H | H | H |
| $C_{17}H_{35}$ | $CH_3$ | $CH_3$ | $COCH_3$ | $COCH_3$ |
| $C_{17}H_{35}$ | $CH_3$ | $CH_3$ | H | H |
| $C_{18}H_{37}$ | H | H | H | H |
| $C_{19}H_{39}$ | H | H | H | H |
| $C_{20}H_{41}$ | H | H | H | H |

-continued $$R^2R^3N-\overset{\overset{\displaystyle CH_2OR^4}{|}}{\underset{\underset{\displaystyle CH_2R^1}{|}}{C}}-CH_2OR^5$$

| $R^1$ | $R^2$ | $R^3$ | $R^4$ | $R^5$ |
|---|---|---|---|---|
| $C_{21}H_{43}$ | H | H | H | H |
| $C_{22}H_{45}$ | H | H | H | H |
| $C_{23}H_{47}$ | H | H | H | H |
| $C_{24}H_{49}$ | H | H | H | H |
| $C_{25}H_{51}$ | H | H | H | H |
| $C_{26}H_{53}$ | H | H | H | H |
| $C_{27}H_{55}$ | H | H | H | H |
| $C_{28}H_{57}$ | H | H | H | H |
| $C_{29}H_{59}$ | H | H | H | H |
| $CH=CH_2$ | H | H | H | H |
| $CH=CHCH_3$ | H | H | H | H |
| $CH=CHC_2H_5$ | H | H | H | H |
| $CH=CHC_3H_7$ | H | H | H | H |
| $CH=CHC_4H_9$ | H | H | H | H |
| $CH=CHC_5H_{11}$ | H | H | H | H |
| $CH=CHC_6H_{13}$ | H | H | H | H |
| $CH=CHC_7H_{15}$ | H | H | H | H |
| $CH=CHC_9H_{19}$ | H | H | H | H |
| $CH=CHC_{11}H_{23}$ | H | H | H | H |
| $CH=CHC_{13}H_{27}$ | H | H | H | H |
| $CH=CHC_{15}H_{31}$ | H | H | H | H |
| $CH=CHC_{17}H_{35}$ | H | H | H | H |
| $CH=CHC_{27}H_{55}$ | H | H | H | H |
| $CH_2CH=CH_2$ | H | H | H | H |
| $CH_2CH=CHCH_3$ | H | H | H | H |
| $CH_2CH=CHC_2H_5$ | H | H | H | H |
| $CH_2CH=CHC_3H_7$ | H | H | H | H |
| $CH_2CH=CHC_4H_9$ | H | H | H | H |
| $CH_2CH=CHC_5H_{11}$ | H | H | H | H |
| $CH_2CH=CHC_6H_{13}$ | H | H | H | H |
| $CH_2CH=CHC_8H_{17}$ | H | H | H | H |
| $CH_2CH=CHC_{10}H_{21}$ | H | H | H | H |
| $CH_2CH=CHC_{12}H_{25}$ | H | H | H | H |
| $CH_2CH=CHC_{14}H_{29}$ | H | H | H | H |
| $CH_2CH=CHC_{16}H_{33}$ | H | H | H | H |
| $CH_2CH=CHC_{26}H_{53}$ | H | H | H | H |
| $(CH_2)_2CH=CH_2$ | H | H | H | H |
| $(CH_2)_2CH=CHCH_3$ | H | H | H | H |
| $(CH_2)_2CH=CHC_2H_5$ | H | H | H | H |
| $(CH_2)_2CH=CHC_3H_7$ | H | H | H | H |
| $(CH_2)_2C(CH_3)=CHC_4H_9$ | H | H | H | H |
| $(CH_2)_2CH=CHC_4H_9$ | H | H | H | H |
| $(CH_2)_2CH=CHC_5H_{11}$ | H | H | H | H |
| $(CH_2)_2CH=CHC_7H_{15}$ | H | H | H | H |
| $(CH_2)_2CH=CHC_9H_{19}$ | H | H | H | H |
| trans: $(CH_2)_2CH=CHC_9H_{19}$ | H | H | H | H |
| cis: $(CH_2)_2CH=CHC_9H_{19}$ | H | H | H | H |
| $(CH_2)_2CH=CHC_{11}H_{23}$ | H | H | H | H |
| $(CH_2)_2CH=CHC_{13}H_{27}$ | H | H | H | H |
| $(CH_2)_2CH=CHC_{15}H_{31}$ | H | H | H | H |
| $(CH_2)_2CH=CHC_{25}H_{51}$ | H | H | H | H |
| $(CH_2)_3CH=CH_2$ | H | H | H | H |
| $(CH_2)_3CH=CHCH_3$ | H | H | H | H |
| $(CH_2)_3CH=CHC_2H_5$ | H | H | H | H |
| $(CH_2)_3C(CH_3)=CHC_3H_7$ | H | H | H | H |
| $(CH_2)_3CH=CHC_3H_7$ | H | H | H | H |
| $(CH_2)_3CH=CHC_4H_9$ | H | H | H | H |
| $(CH_2)_3CH=CHC_6H_{13}$ | H | H | H | H |
| $(CH_2)_3CH=CHC_8H_{17}$ | H | H | H | H |
| $(CH_2)_3CH=CHC_{10}H_{21}$ | H | H | H | H |
| $(CH_2)_3CH=CHC_{12}H_{25}$ | H | H | H | H |
| $(CH_2)_3CH=CHC_{14}H_{29}$ | H | H | H | H |
| $(CH_2)_3CH=CHC_{24}H_{49}$ | H | H | H | H |
| $(CH_2)_4CH=CH_2$ | H | H | H | H |
| $(CH_2)_4CH=CHCH_3$ | H | H | H | H |
| $(CH_2)_4CH=CHC_2H_5$ | H | H | H | H |
| $(CH_2)_4CH=CHC_3H_7$ | H | H | H | H |
| $(CH_2)_4CH=CHC_5H_{11}$ | H | H | H | H |
| $(CH_2)_4CH=CHC_7H_{15}$ | H | H | H | H |
| $(CH_2)_4CH=CHC_9H_{19}$ | H | H | H | H |
| $(CH_2)_4CH=CHC_{11}H_{23}$ | H | H | H | H |
| $(CH_2)_4CH=CHC_{13}H_{27}$ | H | H | H | H |
| $(CH_2)_4CH=CHC_{23}H_{47}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_5CH=CH_2$ | H | H | H | H |
| $(CH_2)_5CH=CHCH_3$ | H | H | H | H |
| $(CH_2)_5CH=CHC_2H_5$ | H | H | H | H |
| $(CH_2)_5CH=CHC_4H_9$ | H | H | H | H |
| $(CH_2)_5CH=CHC_6H_{13}$ | H | H | H | H |
| $(CH_2)_5CH=CHC_8H_{17}$ | H | H | H | H |
| $(CH_2)_5CH=CHC_{10}H_{21}$ | H | H | H | H |
| $(CH_2)_5CH=CHC_{12}H_{25}$ | H | H | H | H |
| $(CH_2)_5CH=CHC_{22}H_{45}$ | H | H | H | H |
| $(CH_2)_6CH=CH_2$ | H | H | H | H |
| $(CH_2)_6CH=CHCH_3$ | H | H | H | H |
| $(CH_2)_6CH=CHC_3H_7$ | H | H | H | H |
| $(CH_2)_6CH=CHC_5H_{11}$ | H | H | H | H |
| $(CH_2)_6CH=CHC_7H_{15}$ | H | H | H | H |
| $(CH_2)_2CH(C_2H_5)(CH_2)_3CH=CHC_9H_{19}$ | H | H | H | H |
| $(CH_2)_6CH=CHC_9H_{19}$ | H | H | H | H |
| $(CH_2)_6CH=CHC_{11}H_{23}$ | H | H | H | H |
| $(CH_2)_6CH=CHC_{21}H_{43}$ | H | H | H | H |
| $(CH_2)_7CH=CH_2$ | H | H | H | H |
| $(CH_2)_7CH=CHC_2H_5$ | H | H | H | H |
| $(CH_2)_7CH=CHC_4H_9$ | H | H | H | H |
| $(CH_2)_7CH=CHC_6H_{13}$ | H | H | H | H |
| $(CH_2)_7CH=CHC_8H_{17}$ | H | H | H | H |
| $(CH_2)_7CH=CHC_{10}H_{21}$ | H | H | H | H |
| $(CH_2)_7CH=CHC_{20}H_{41}$ | H | H | H | H |
| $(CH_2)_8CH=CHCH_3$ | H | H | H | H |
| $(CH_2)_8CH=CHC_3H_7$ | H | H | H | H |
| $(CH_2)_8CH=CHC_5H_{11}$ | H | H | H | H |
| $(CH_2)_8CH=CHC_7H_{15}$ | H | H | H | H |
| $(CH_2)_8CH=CHC_9H_{19}$ | H | H | H | H |
| $(CH_2)_8CH=CHC_{19}H_{39}$ | H | H | H | H |
| $(CH_2)_{10}CH=CHCH_3$ | H | H | H | H |
| $(CH_2)_{10}CH=CHC_3H_7$ | H | H | H | H |
| $(CH_2)_3CH(C_3H_7)(CH_2)_6CH=CHC_5H_{11}$ | H | H | H | H |
| $(CH_2)_{10}CH=CHC_5H_{11}$ | H | H | H | H |
| $(CH_2)_{10}CH=CHC_7H_{15}$ | H | H | H | H |
| $(CH_2)_{10}CH=CHC_{17}H_{35}$ | H | H | H | H |
| $(CH_2)_{12}CH=CHCH_3$ | H | H | H | H |
| $(CH_2)_{12}CH=CHC_3H_7$ | H | H | H | H |
| $(CH_2)_{12}CH=CHC_5H_{11}$ | H | H | H | H |
| $(CH_2)_{12}CH=CHC_{15}H_{31}$ | H | H | H | H |
| $(CH_2)_{14}CH=CHCH_3$ | H | H | H | H |
| $(CH_2)_{14}C(CH_3)=CHC_3H_7$ | H | H | H | H |
| $(CH_2)_{14}CH=CHC_3H_7$ | H | H | H | H |
| $(CH_2)_{14}CH=CHC_{13}H_{27}$ | H | H | H | H |
| $(CH_2)_{16}CH=CHCH_3$ | H | H | H | H |
| $(CH_2)_{16}CH=CHC_{11}H_{23}$ | H | H | H | H |
| $(CH_2)_{19}CH=CHC_8H_{17}$ | H | H | H | H |
| $(CH_2)_{20}CH=CHC_7H_{15}$ | H | H | H | H |
| $(CH_2)_{22}CH=CHC_5H_{11}$ | H | H | H | H |
| $(CH_2)_{24}CH=CHC_3H_7$ | H | H | H | H |
| $(CH_2)_{26}CH=CHCH_3$ | H | H | H | H |
| $[CH=C(CH_3)CH_2CH_2]_3-H$ | H | H | H | H |
| $[CH=C(CH_3)CH_2CH_2]_3-H$ | $COCH_3$ | H | $COCH_3$ | $COCH_3$ |
| $C\equiv CH$ | H | H | H | H |
| $C\equiv CCH_3$ | H | H | H | H |
| $C\equiv CC_2H_5$ | H | H | H | H |
| $C\equiv CC_3H_7$ | H | H | H | H |
| $C\equiv CC_4H_9$ | H | H | H | H |
| $C\equiv CC_5H_{11}$ | H | H | H | H |
| $C\equiv CC_6H_{13}$ | H | H | H | H |
| $C\equiv CC_7H_{15}$ | H | H | H | H |
| $C\equiv CC_9H_{19}$ | H | H | H | H |
| $C\equiv CC_{11}H_{23}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| C≡CC₁₂H₂₅ | H | H | H | H |
| C≡CC₁₂H₂₅ | COCH₃ | H | COCH₃ | COCH₃ |
| C≡CC₁₃H₂₇ | H | H | H | H |
| C≡CC₁₅H₃₁ | H | H | H | H |
| C≡CC₁₇H₃₅ | H | H | H | H |
| C≡CC₂₇H₅₅ | H | H | H | H |
| CH₂C≡CH | H | H | H | H |
| CH₂C≡CCH₃ | H | H | H | H |
| CH₂C≡CC₂H₅ | H | H | H | H |
| CH₂C≡CC₃H₇ | H | H | H | H |
| CH₂C≡CC₄H₉ | H | H | H | H |
| CH₂C≡CC₅H₁₁ | H | H | H | H |
| CH₂C≡CC₆H₁₃ | H | H | H | H |
| CH₂C≡CC₈H₁₇ | H | H | H | H |
| CH₂C≡CC₁₀H₂₁ | H | H | H | H |
| CH₂C≡CC₁₂H₂₅ | H | H | H | H |
| CH₂C≡CC₁₄H₂₉ | H | H | H | H |
| CH₂C≡CC₁₆H₃₃ | H | H | H | H |
| CH₂C≡CC₂₆H₅₃ | H | H | H | H |
| (CH₂)₂C≡CH | H | H | H | H |
| (CH₂)₂C≡CCH₃ | H | H | H | H |
| (CH₂)₂C≡CC₂H₅ | H | H | H | H |
| (CH₂)₂C≡CC₃H₇ | H | H | H | H |
| (CH₂)₂C≡CC₄H₉ | H | H | H | H |
| (CH₂)₂C≡CC₅H₁₁ | H | H | H | H |
| (CH₂)₂C≡CC₇H₁₅ | H | H | H | H |
| (CH₂)₂C≡CC₉H₁₉ | H | H | H | H |
| (CH₂)₂C≡CC₁₁H₂₃ | H | H | H | H |
| (CH₂)₂C≡CC₁₃H₂₇ | H | H | H | H |
| (CH₂)₂C≡CC₁₅H₃₁ | H | H | H | H |
| (CH₂)₂C≡CC₂₅H₅₁ | H | H | H | H |
| (CH₂)₃C≡CH | H | H | H | H |
| (CH₂)₃C≡CCH₃ | H | H | H | H |
| (CH₂)₃C≡CC₂H₅ | H | H | H | H |
| (CH₂)₃C≡CC₃H₇ | H | H | H | H |
| (CH₂)₃C≡CC₄H₉ | H | H | H | H |
| (CH₂)₃C≡CC₆H₁₃ | H | H | H | H |
| (CH₂)₃C≡CC₈H₁₇ | H | H | H | H |
| (CH₂)₂CH(CH₃)C≡CC₁₀H₂₁ | H | H | H | H |

-continued $$\begin{array}{c} CH_2OR^4 \\ | \\ R^2R^3N-C-CH_2OR^5 \\ | \\ CH_2R^1 \end{array}$$

| R¹ | R² | R³ | R⁴ | R⁵ |
|---|---|---|---|---|
| $(CH_2)_3C\equiv CC_{10}H_{21}$ | H | H | H | H |
| $(CH_2)_3C\equiv CC_{12}H_{25}$ | H | H | H | H |
| $(CH_2)_3C\equiv CC_{14}H_{29}$ | H | H | H | H |
| $(CH_2)_3C\equiv CC_{24}H_{49}$ | H | H | H | H |
| $(CH_2)_4C\equiv CH$ | H | H | H | H |
| $(CH_2)_4C\equiv CCH_3$ | H | H | H | H |
| $(CH_2)_4C\equiv CC_2H_5$ | H | H | H | H |
| $(CH_2)_4C\equiv CC_3H_7$ | H | H | H | H |
| $(CH_2)_4C\equiv CC_5H_{11}$ | H | H | H | H |
| $(CH_2)_4C\equiv CC_7H_{15}$ | H | H | H | H |
| $(CH_2)_4C\equiv CC_9H_{19}$ | H | H | H | H |
| $(CH_2)_4C\equiv CC_{11}H_{23}$ | H | H | H | H |
| $(CH_2)_4C\equiv CC_{13}H_{27}$ | H | H | H | H |
| $(CH_2)_4C\equiv CC_{23}H_{47}$ | H | H | H | H |
| $(CH_2)_5C\equiv CH$ | H | H | H | H |
| $(CH_2)_5C\equiv CCH_3$ | H | H | H | H |
| $(CH_2)_5C\equiv CC_2H_5$ | H | H | H | H |
| $(CH_2)_5C\equiv CC_4H_9$ | H | H | H | H |
| $(CH_2)_5C\equiv CC_6H_{13}$ | H | H | H | H |
| $(CH_2)_5C\equiv CC_8H_{17}$ | H | H | H | H |
| $(CH_2)_5C\equiv CC_{10}H_{21}$ | H | H | H | H |
| $(CH_2)_5C\equiv CC_{12}H_{25}$ | H | H | H | H |
| $(CH_2)_5C\equiv CC_{22}H_{45}$ | H | H | H | H |
| $(CH_2)_6C\equiv CH$ | H | H | H | H |
| $(CH_2)_6\equiv CCH_3$ | H | H | H | H |
| $(CH_2)_6C\equiv CC_3H_7$ | H | H | H | H |
| $(CH_2)_6C\equiv CC_5H_{11}$ | H | H | H | H |
| $(CH_2)_6C\equiv CC_7H_{15}$ | H | H | H | H |
| $(CH_2)_6C\equiv CC_9H_{19}$ | H | H | H | H |
| $(CH_2)_6C\equiv CC_{11}H_{23}$ | H | H | H | H |
| $(CH_2)_6C\equiv CC_{21}H_{43}$ | H | H | H | H |
| $(CH_2)_7C\equiv CH$ | H | H | H | H |
| $(CH_2)_7C\equiv CC_2H_5$ | H | H | H | H |
| $(CH_2)_7C\equiv CC_4H_9$ | H | H | H | H |
| $(CH_2)_7C\equiv CC_6H_{13}$ | H | H | H | H |
| $(CH_2)_2CH(CH_3)(CH_2)_4C\equiv CC_8H_{17}$ | H | H | H | H |
| $(CH_2)_7C\equiv CC_8H_{17}$ | H | H | H | H |
| $(CH_2)_7C\equiv CC_{10}H_{21}$ | H | H | H | H |
| $(CH_2)_7C\equiv CC_{20}H_{41}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₈C≡CCH₃ | H | H | H | H |
| (CH₂)₈C≡CC₃H₇ | H | H | H | H |
| (CH₂)₈C≡CC₅H₁₁ | H | H | H | H |
| (CH₂)₈C≡CC₇H₁₅ | H | H | H | H |
| (CH₂)₈C≡CC₉H₁₉ | H | H | H | H |
| (CH₂)₈C≡CC₁₉H₃₉ | H | H | H | H |
| (CH₂)₁₀C≡CCH₃ | H | H | H | H |
| (CH₂)₁₀C≡CC₃H₇ | H | H | H | H |
| (CH₂)₁₀C≡CC₅H₁₁ | H | H | H | H |
| (CH₂)₃CH(CH₃)(CH₂)₆C≡CC₇H₁₅ | H | H | H | H |
| (CH₂)₁₀C≡CC₇H₁₅ | H | H | H | H |
| (CH₂)₁₀C≡CC₁₇H₃₅ | H | H | H | H |
| (CH₂)₁₂C≡CCH₃ | H | H | H | H |
| (CH₂)₁₂C≡CC₃H₇ | H | H | H | H |
| (CH₂)₁₂C≡CC₅H₁₁ | H | H | H | H |
| (CH₂)₁₂C≡CC₁₅H₃₁ | H | H | H | H |
| (CH₂)₁₄C≡CCH₃ | H | H | H | H |
| (CH₂)₁₄C≡CC₃H₇ | H | H | H | H |
| (CH₂)₁₄C≡CC₁₃H₂₇ | H | H | H | H |
| (CH₂)₁₆C≡CCH₃ | H | H | H | H |
| (CH₂)₁₆C≡CC₁₁H₂₃ | H | H | H | H |
| (CH₂)₁₈C≡CC₉H₁₉ | H | H | H | H |
| (CH₂)₂₀C≡CC₇H₁₅ | H | H | H | H |
| (CH₂)₂₂C≡CC₅H₁₁ | H | H | H | H |
| (CH₂)₂₄C≡CC₃H₇ | H | H | H | H |
| (CH₂)₂₆C≡CCH₃ | H | H | H | H |
| CH₂OH | H | H | H | H |
| (CH₂)₂OH | H | H | H | H |
| CH₂(OH)CH₃ | H | H | H | H |
| (CH₂)₃OH | H | H | H | H |
| (CH₂)₄OH | H | H | H | H |
| (CH₂)₅OH | H | H | H | H |
| (CH₂)₆OH | H | H | H | H |
| (CH₂)₇OH | H | H | H | H |
| (CH₂)₈OH | H | H | H | H |
| (CH₂)₉OH | H | H | H | H |
| (CH₂)₁₀OH | H | H | H | H |
| (CH₂)₁₁OH | H | H | H | H |
| (CH₂)₆CH(C₆H₁₃)OH | H | H | H | H |
| (CH₂)₆CH(C₆H₁₃)OH | COCH₃ | H | COCH₃ | COCH₃ |
| (CH₂)₁₇OH | H | H | H | H |
| (CH₂)₁₉OH | H | H | H | H |
| (CH₂)₂₉OH | H | H | H | H |
| COOH | H | H | H | H |
| CH₂COOH | H | H | H | H |
| (CH₂)₂COOH | H | H | H | H |
| (CH₂)₃COOH | H | H | H | H |
| (CH₂)₄COOH | H | H | H | H |
| (CH₂)₅COOH | H | H | H | H |
| (CH₂)₆COOH | H | H | H | H |
| (CH₂)₇COOH | H | H | H | H |

-continued $$R^2R^3N-\underset{\underset{CH_2R^1}{|}}{\overset{\overset{CH_2OR^4}{|}}{C}}-CH_2OR^5$$

| $R^1$ | $R^2$ | $R^3$ | $R^4$ | $R^5$ |
|---|---|---|---|---|
| $(CH_2)_8COOH$ | H | H | H | H |
| $(CH_2)_9COOH$ | H | H | H | H |
| $(CH_2)_{10}COOH$ | H | H | H | H |
| $(CH_2)_{11}COOH$ | H | H | H | H |
| $(CH_2)_{17}COOH$ | H | H | H | H |
| $(CH_2)_{19}COOH$ | H | H | H | H |
| $(CH_2)_{29}COOH$ | H | H | H | H |
| $CH_2COOCH_3$ | H | H | H | H |
| $CH_2COOC_2H_5$ | H | H | H | H |
| $CH_2COOC_{10}H_{21}$ | H | H | H | H |
| $CH_2COOC_{14}H_{29}$ | H | H | H | H |
| $(CH_2)_2COOCH_3$ | H | H | H | H |
| $(CH_2)_2COOC_2H_5$ | H | H | H | H |
| $(CH_2)_2COOC_{10}H_{21}$ | H | H | H | H |
| $(CH_2)_2COOC_{13}H_{27}$ | H | H | H | H |
| $(CH_2)_3COOCH_3$ | H | H | H | H |
| $(CH_2)_3COOC_2H_5$ | H | H | H | H |
| $(CH_2)_3COOC_{10}H_{21}$ | H | H | H | H |
| $(CH_2)_3COOC_{12}H_{25}$ | H | H | H | H |
| $(CH_2)_4COOCH_3$ | H | H | H | H |
| $(CH_2)_4COOC_2H_5$ | H | H | H | H |
| $(CH_2)_4COOC_{10}H_{21}$ | H | H | H | H |
| $(CH_2)_4COOC_{11}H_{23}$ | H | H | H | H |
| $(CH_2)_5COOCH_3$ | H | H | H | H |
| $(CH_2)_5COOC_2H_5$ | H | H | H | H |
| $(CH_2)_5COOC_{10}H_{21}$ | H | H | H | H |
| $(CH_2)_6COOCH_3$ | H | H | H | H |
| $(CH_2)_6COOC_2H_5$ | H | H | H | H |
| $(CH_2)_6COOC_9H_{19}$ | H | H | H | H |
| $(CH_2)_7COOCH_3$ | H | H | H | H |
| $(CH_2)_7COOC_2H_5$ | H | H | H | H |
| $(CH_2)_7COOC_8H_{17}$ | H | H | H | H |
| $(CH_2)_8COOCH_3$ | H | H | H | H |
| $(CH_2)_3CH(C_4H_9)COOC_2H_5$ | H | H | H | H |
| $(CH_2)_8COOC_7H_{15}$ | H | H | H | H |
| $(CH_2)_9COOCH_3$ | H | H | H | H |
| $(CH_2)_9COOC_2H_5$ | H | H | H | H |
| $(CH_2)_9COOC_6H_{13}$ | H | H | H | H |
| $(CH_2)_{10}COOCH_3$ | H | H | H | H |
| $(CH_2)_{10}COOCH_3$ | $COCH_3$ | H | $COCH_3$ | $COCH_3$ |
| $(CH_2)_{10}COOC_2H_5$ | H | H | H | H |
| $(CH_2)_{10}COOC_5H_{11}$ | H | H | H | H |
| $(CH_2)_{11}COOCH_3$ | H | H | H | H |
| $(CH_2)_{11}COOC_2H_5$ | H | H | H | H |
| $(CH_2)_{11}COOC_4H_9$ | H | H | H | H |
| $(CH_2)_{17}COOCH_3$ | H | H | H | H |
| $(CH_2)_{17}COOC_2H_5$ | H | H | H | H |
| $(CH_2)_{17}COOC_{10}H_{21}$ | H | H | H | H |
| $(CH_2)_{19}COOCH_3$ | H | H | H | H |
| $(CH_2)_{19}COOC_2H_5$ | H | H | H | H |
| $(CH_2)_{19}COOC_{10}H_{21}$ | H | H | H | H |
| $(CH_2)_{29}COOCH_3$ | H | H | H | H |
| $(CH_2)_{29}COOC_2H_5$ | H | H | H | H |
| $(CH_2)_{29}COOC_{10}H_{21}$ | H | H | H | H |
| $CH_2OCOCH_3$ | H | H | H | H |
| $CH_2OCOC_2H_5$ | H | H | H | H |
| $CH_2OCOC_3H_7$ | H | H | H | H |
| $CH_2OCOC_{14}H_{29}$ | H | H | H | H |
| $(CH_2)_2OCOCH_3$ | H | H | H | H |
| $(CH_2)_2OCOC_2H_5$ | H | H | H | H |
| $(CH_2)_2OCOC_3H_7$ | H | H | H | H |
| $(CH_2)_2OCOC_{13}H_{27}$ | H | H | H | H |
| $(CH_2)_3OCOCH_3$ | H | H | H | H |
| $(CH_2)_3OCOC_2H_5$ | H | H | H | H |
| $(CH_2)_3OCOC_3H_7$ | H | H | H | H |
| $(CH_2)_3OCOC_{12}H_{25}$ | H | H | H | H |
| $(CH_2)_4OCOCH_3$ | H | H | H | H |
| $(CH_2)_4OCOC_2H_5$ | H | H | H | H |
| $(CH_2)_4OCOC_3H_7$ | H | H | H | H |
| $(CH_2)_4OCOC_{11}H_{23}$ | H | H | H | H |
| $(CH_2)_5OCOCH_3$ | H | H | H | H |
| $(CH_2)_5OCOC_2H_5$ | H | H | H | H |
| $(CH_2)_5OCOC_3H_7$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_5OCOC_{10}H_{21}$ | H | H | H | H |
| $(CH_2)_6OCOCH_3$ | H | H | H | H |
| $(CH_2)_6OCOC_2H_5$ | H | H | H | H |
| $(CH_2)_6OCOC_3H_7$ | H | H | H | H |
| $(CH_2)_6OCOC_9H_{19}$ | H | H | H | H |
| $(CH_2)_7OCOCH_3$ | H | H | H | H |
| $(CH_2)_7OCOC_2H_5$ | H | H | H | H |
| $(CH_2)_7OCOC_3H_7$ | H | H | H | H |
| $(CH_2)_7OCOC_8H_{17}$ | H | H | H | H |
| $(CH_2)_8OCOCH_3$ | H | H | H | H |
| $(CH_2)_8OCOC_2H_5$ | H | H | H | H |
| $(CH_2)_8OCOC_3H_7$ | H | H | H | H |
| $(CH_2)_8OCOC_7H_{15}$ | H | H | H | H |
| $(CH_2)_9OCOCH_3$ | H | H | H | H |
| $(CH_2)_9OCOC_2H_5$ | H | H | H | H |
| $(CH_2)_2CH(C_6H_{13})OCOC_3H_7$ | H | H | H | H |
| $(CH_2)_9OCOC_6H_{13}$ | H | H | H | H |
| $(CH_2)_{10}OCOCH_3$ | H | H | H | H |
| $(CH_2)_{10}OCOC_2H_5$ | H | H | H | H |
| $(CH_2)_{10}OCOC_3H_7$ | H | H | H | H |
| $(CH_2)_{10}OCOC_5H_{11}$ | H | H | H | H |
| $(CH_2)_{11}OCOCH_3$ | H | H | H | H |
| $(CH_2)_{11}OCOC_2H_5$ | H | H | H | H |
| $(CH_2)_{11}OCOC_3H_7$ | H | H | H | H |
| $(CH_2)_{11}OCOC_4H_9$ | H | H | H | H |
| $(CH_2)_{17}OCOCH_3$ | H | H | H | H |
| $(CH_2)_{17}OCOC_2H_5$ | H | H | H | H |
| $(CH_2)_{17}OCOC_3H_7$ | H | H | H | H |
| $(CH_2)_{17}OCOC_9H_{19}$ | H | H | H | H |
| $(CH_2)_{19}OCOCH_3$ | H | H | H | H |
| $(CH_2)_{19}OCOC_2H_5$ | H | H | H | H |
| $(CH_2)_{19}OCOC_3H_7$ | H | H | H | H |
| $(CH_2)_{19}OCOC_9H_{19}$ | H | H | H | H |
| $(CH_2)_{29}OCOCH_3$ | H | H | H | H |
| $(CH_2)_{29}OCOC_2H_5$ | H | H | H | H |
| $(CH_2)_{29}OCOC_3H_7$ | H | H | H | H |
| $(CH_2)_{29}OCOC_9H_{19}$ | H | H | H | H |
| $CH(CH_3)OCOCH_3$ | H | H | H | H |
| $CH(CH_3)OCOC_2H_5$ | H | H | H | H |
| $CH(CH_3)OCOC_3H_7$ | H | H | H | H |
| $CH(CH_3)OCOC_{14}H_{29}$ | H | H | H | H |
| $CH_2COC_7H_{15}$ | H | H | H | H |
| $CH_2COC_9H_{19}$ | H | H | H | H |
| $CH_2COC_{11}H_{23}$ | H | H | H | H |
| $(CH_2)_6COC_6H_{13}$ | H | H | H | H |
| $(CH_2)_6COC_6H_{13}$ | $COCH_3$ | H | $COCH_3$ | $COCH_3$ |
| $CH_2COC_{15}H_{31}$ | H | H | H | H |
| $CH_2COC_{17}H_{35}$ | H | H | H | H |
| $(CH_2)_2SC_{12}H_{25}$ | H | H | H | H |
| $(CH_2)_2SC_{12}H_{25}$ | $COCH_3$ | H | $COCH_3$ | $COCH_3$ |
| $CH_2CH(C_7H_{15})SCH_3$ | H | H | H | H |
| $CH_2CH(C_7H_{15})SC_2H_5$ | H | H | H | H |
| $CH_2CH(C_7H_{15})SC_7H_{15}$ | H | H | H | H |
| $(CH_2)_9SCH_3$ | H | H | H | H |
| $(CH_2)_9SC_2H_5$ | H | H | H | H |
| $(CH_2)_9SC_7H_{15}$ | H | H | H | H |
| $CH_2CH(C_9H_{19})SCH_3$ | H | H | H | H |
| $CH_2CH(C_9H_{19})SC_2H_5$ | H | H | H | H |
| $CH_2CH(C_9H_{19})SC_7H_{15}$ | H | H | H | H |
| $(CH_2)_{11}SCH_3$ | H | H | H | H |
| $(CH_2)_{11}SC_2H_5$ | H | H | H | H |
| $(CH_2)_{11}SC_7H_{15}$ | H | H | H | H |
| $CH_2CH(C_{11}H_{23})SCH_3$ | H | H | H | H |
| $CH_2CH(C_{11}H_{23})SC_2H_5$ | H | H | H | H |
| $CH_2CH(C_{11}H_{23})SC_3H_7$ | H | H | H | H |
| $(CH_2)_{13}SCH_3$ | H | H | H | H |
| $(CH_2)_{13}SC_2H_5$ | H | H | H | H |
| $(CH_2)_{13}SC_7H_{15}$ | H | H | H | H |
| $CH_2CH(C_{15}H_{31})SCH_3$ | H | H | H | H |
| $CH_2CH(C_{15}H_{31})SC_2H_5$ | H | H | H | H |
| $CH_2CH(C_{15}H_{31})SC_{10}H_{21}$ | H | H | H | H |
| $CH_2CH(C_{17}H_{35})SCH_3$ | H | H | H | H |
| $CH_2CH(C_{17}H_{35})SC_2H_5$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $CH_2CH(C_{17}H_{35})SC_{10}H_{21}$ | H | H | H | H |
| $CH_2NH_2$ | H | H | H | H |
| $(CH_2)_2NH_2$ | H | H | H | H |
| $(CH_2)_3NH_2$ | H | H | H | H |
| $(CH_2)_4NH_2$ | H | H | H | H |
| $(CH_2)_5NH_2$ | H | H | H | H |
| $(CH_2)_6NH_2$ | H | H | H | H |
| $(CH_2)_3CH(C_3H_7)NH_2$ | H | H | H | H |
| $(CH_2)_8NH_2$ | H | H | H | H |
| $(CH_2)_9NH_2$ | H | H | H | H |
| $(CH_2)_{10}NH_2$ | H | H | H | H |
| $(CH_2)_{11}NH_2$ | H | H | H | H |
| $(CH_2)_{17}NH_2$ | H | H | H | H |
| $(CH_2)_{19}NH_2$ | H | H | H | H |
| $(CH_2)_{29}NH_2$ | H | H | H | H |
| $CH_2NHCOOCH_3$ | H | H | H | H |
| $CH_2NHCOOC_2H_5$ | H | H | H | H |
| $CH_2NHCOOC_{10}H_{21}$ | H | H | H | H |
| $CH_2NHCOOC_{14}H_{29}$ | H | H | H | H |
| $(CH_2)_2NHCOOCH_3$ | H | H | H | H |
| $(CH_2)_2NHCOOC_2H_5$ | H | H | H | H |
| $(CH_2)_2NHCOOC_{10}H_{21}$ | H | H | H | H |
| $(CH_2)_2NHCOOC_{13}H_{27}$ | H | H | H | H |
| $(CH_2)_3NHCOOCH_3$ | H | H | H | H |
| $(CH_2)_3NHCOOC_2H_5$ | H | H | H | H |
| $(CH_2)_3NHCOOC_{10}H_{21}$ | H | H | H | H |
| $(CH_2)_3NHCOOC_{12}H_{25}$ | H | H | H | H |
| $(CH_2)_4NHCOOCH_3$ | H | H | H | H |
| $(CH_2)_4NHCOOC_2H_5$ | H | H | H | H |
| $(CH_2)_4NHCOOC_{10}H_{21}$ | H | H | H | H |
| $(CH_2)_4NHCOOC_{11}H_{23}$ | H | H | H | H |
| $(CH_2)_5NHCOOCH_3$ | H | H | H | H |
| $(CH_2)_5NHCOOC_2H_5$ | H | H | H | H |
| $(CH_2)_5NHCOOC_{10}H_{21}$ | H | H | H | H |
| $(CH_2)_6NHCOOCH_3$ | H | H | H | H |
| $(CH_2)_6NHCOOC_2H_5$ | H | H | H | H |
| $(CH_2)_6NHCOOC_9H_{19}$ | H | H | H | H |
| $(CH_2)_7NHCOOCH_3$ | H | H | H | H |
| $(CH_2)_7NHCOOC_2H_5$ | H | H | H | H |
| $(CH_2)_7NHCOOC_8H_{17}$ | H | H | H | H |
| $(CH_2)_8NHCOOCH_3$ | H | H | H | H |
| $(CH_2)_8NHCOOC_2H_5$ | H | H | H | H |
| $(CH_2)_8NHCOOC_7H_{15}$ | H | H | H | H |
| $(CH_2)_9NHCOOCH_3$ | H | H | H | H |
| $(CH_2)_9NHCOOC_2H_5$ | H | H | H | H |
| $(CH_2)_9NHCOOC_6H_{13}$ | H | H | H | H |
| $(CH_2)_{10}NHCOOCH_3$ | H | H | H | H |
| $(CH_2)_{10}NHCOOC_2H_5$ | H | H | H | H |
| $(CH_2)_{10}NHCOOC_5H_{11}$ | H | H | H | H |
| $(CH_2)_{11}NHCOOCH_3$ | H | H | H | H |
| $(CH_2)_{11}NHCOOC_2H_5$ | H | H | H | H |
| $(CH_2)_{11}NHCOOC_4H_9$ | H | H | H | H |
| $(CH_2)_{17}NHCOOCH_3$ | H | H | H | H |
| $(CH_2)_{17}NHCOOC_2H_5$ | H | H | H | H |
| $(CH_2)_{17}NHCOOC_{10}H_{21}$ | H | H | H | H |
| $(CH_2)_8CH(C_{10}H_{21})NHCOOCH_3$ | H | H | H | H |
| $(CH_2)_{19}NHCOOC_2H_5$ | H | H | H | H |
| $(CH_2)_{19}NHCOOC_{10}H_{21}$ | H | H | H | H |
| $(CH_2)_{29}NHCOOCH_3$ | H | H | H | H |
| $(CH_2)_{29}NHCOOC_2H_5$ | H | H | H | H |
| $(CH_2)_{29}NHCOOC_{10}H_{21}$ | H | H | H | H |
| $CH_2NHCOCH_3$ | H | H | H | H |
| $CH_2NHCOC_2H_5$ | H | H | H | H |
| $CH_2NHCOC_3H_7$ | H | H | H | H |
| $CH_2NHCOC_{11}H_{23}$ | H | H | H | H |
| $CH_2NHCOC_{14}H_{29}$ | H | H | H | H |
| $(CH_2)_2NHCOCH_3$ | H | H | H | H |
| $(CH_2)_2NHCOC_2H_5$ | H | H | H | H |
| $(CH_2)_2NHCOC_3H_7$ | H | H | H | H |
| $(CH_2)_2NHCOC_{13}H_{27}$ | H | H | H | H |
| $(CH_2)_3NHCOCH_3$ | H | H | H | H |
| $(CH_2)_3NHCOC_2H_5$ | H | H | H | H |
| $(CH_2)_3NHCOC_3H_7$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_3NHCOC_{12}H_{25}$ | H | H | H | H |
| $(CH_2)_4NHCOCH_3$ | H | H | H | H |
| $(CH_2)_4NHCOC_2H_5$ | H | H | H | H |
| $(CH_2)_4NHCOC_3H_7$ | H | H | H | H |
| $(CH_2)_4NHCOC_{11}H_{23}$ | H | H | H | H |
| $(CH_2)_5NHCOCH_3$ | H | H | H | H |
| $(CH_2)_5NHCOC_2H_5$ | H | H | H | H |
| $(CH_2)_5NHCOC_3H_7$ | H | H | H | H |
| $(CH_2)_5NHCOC_{10}H_{21}$ | H | H | H | H |
| $(CH_2)_6NHCOCH_3$ | H | H | H | H |
| $(CH_2)_6NHCOC_2H_5$ | H | H | H | H |
| $(CH_2)_6NHCOC_3H_7$ | H | H | H | H |
| $(CH_2)_6NHCOC_9H_{19}$ | H | H | H | H |
| $(CH_2)_7NHCOCH_3$ | H | H | H | H |
| $(CH_2)_7NHCOC_2H_5$ | H | H | H | H |
| $(CH_2)_7NHCOC_3H_7$ | H | H | H | H |
| $(CH_2)_7NHCOC_8H_{17}$ | H | H | H | H |
| $(CH_2)_8NHCOCH_3$ | H | H | H | H |
| $(CH_2)_8NHCOC_2H_5$ | H | H | H | H |
| $(CH_2)_8NHCOC_3H_7$ | H | H | H | H |
| $(CH_2)_8NHCOC_7H_{15}$ | H | H | H | H |
| $(CH_2)_9NHCOCH_3$ | H | H | H | H |
| $(CH_2)_9NHCOC_2H_5$ | H | H | H | H |
| $(CH_2)_4CH(C_4H_9)NHCOC_3H_7$ | H | H | H | H |
| $(CH_2)_9NHCOC_6H_{13}$ | H | H | H | H |
| $(CH_2)_{10}NHCOCH_3$ | H | H | H | H |
| $(CH_2)_{10}NHCOC_2H_5$ | H | H | H | H |
| $(CH_2)_{10}NHCOC_3H_7$ | H | H | H | H |
| $(CH_2)_{10}NHCOC_5H_{11}$ | H | H | H | H |
| $(CH_2)_{11}NHCOCH_3$ | H | H | H | H |
| $(CH_2)_{11}NHCOC_2H_5$ | H | H | H | H |
| $(CH_2)_{11}NHCOC_3H_7$ | H | H | H | H |
| $(CH_2)_{11}NHCOC_4H_9$ | H | H | H | H |
| $(CH_2)_{17}NHCOCH_3$ | H | H | H | H |
| $(CH_2)_{17}NHCOC_2H_5$ | H | H | H | H |
| $(CH_2)_{17}NHCOC_3H_7$ | H | H | H | H |
| $(CH_2)_{17}NHCOC_9H_{19}$ | H | H | H | H |
| $(CH_2)_{19}NHCOCH_3$ | H | H | H | H |
| $(CH_2)_{19}NHCOC_2H_5$ | H | H | H | H |
| $(CH_2)_{19}NHCOC_3H_7$ | H | H | H | H |
| $(CH_2)_{19}NHCOC_9H_{19}$ | H | H | H | H |
| $(CH_2)_{29}NHCOCH_3$ | H | H | H | H |
| $(CH_2)_{29}NHCOC_2H_5$ | H | H | H | H |
| $(CH_2)_{29}NHCOC_3H_7$ | H | H | H | H |
| $(CH_2)_{29}NHCOC_9H_{19}$ | H | H | H | H |
| $CH(CH_3)NHCOCH_3$ | H | H | H | H |
| $CH(CH_3)NHCOC_2H_5$ | H | H | H | H |
| $CH(CH_3)NHCOC_3H_7$ | H | H | H | H |
| $CH(CH_3)NHCOC_{14}H_{29}$ | H | H | H | H |
| $CH_2NHCH_3$ | H | H | H | H |
| $CH_2NHC_2H_5$ | H | H | H | H |
| $CH_2NHC_3H_7$ | H | H | H | H |
| $CH_2NHC_{12}H_{25}$ | H | H | H | H |
| $CH_2NHC_{15}H_{31}$ | H | H | H | H |
| $(CH_2)_2NHCH_3$ | H | H | H | H |
| $(CH_2)_2NHC_2H_5$ | H | H | H | H |
| $(CH_2)_2NHC_3H_7$ | H | H | H | H |
| $(CH_2)_2NHC_{14}H_{29}$ | H | H | H | H |
| $(CH_2)_3NHCH_3$ | H | H | H | H |
| $(CH_2)_3NHC_2H_5$ | H | H | H | H |
| $(CH_2)_3NHC_3H_7$ | H | H | H | H |
| $(CH_2)_3NHC_{13}H_{27}$ | H | H | H | H |
| $(CH_2)_4NHCH_3$ | H | H | H | H |
| $(CH_2)_4NHC_2H_5$ | H | H | H | H |
| $(CH_2)_4NHC_3H_7$ | H | H | H | H |
| $(CH_2)_4NHC_{12}H_{25}$ | H | H | H | H |
| $(CH_2)_5NHCH_3$ | H | H | H | H |
| $(CH_2)_5NHC_2H_5$ | H | H | H | H |
| $(CH_2)_5NHC_3H_7$ | H | H | H | H |
| $(CH_2)_5NHC_{11}H_{23}$ | H | H | H | H |
| $(CH_2)_6NHCH_3$ | H | H | H | H |
| $(CH_2)_6NHC_2H_5$ | H | H | H | H |
| $(CH_2)_6NHC_3H_7$ | H | H | H | H |

-continued $$\begin{array}{c} CH_2OR^4 \\ | \\ R^2R^3N-C-CH_2OR^5 \\ | \\ CH_2R^1 \end{array}$$

| $R^1$ | $R^2$ | $R^3$ | $R^4$ | $R^5$ |
|---|---|---|---|---|
| $(CH_2)_6NHC_{10}H_{21}$ | H | H | H | H |
| $(CH_2)_7NHCH_3$ | H | H | H | H |
| $(CH_2)_7NHC_2H_5$ | H | H | H | H |
| $(CH_2)_7NHC_3H_7$ | H | H | H | H |
| $(CH_2)_7NHC_9H_{19}$ | H | H | H | H |
| $(CH_2)_8NHCH_3$ | H | H | H | H |
| $(CH_2)_8NHC_2H_5$ | H | H | H | H |
| $(CH_2)_8NHC_3H_7$ | H | H | H | H |
| $(CH_2)_8NHC_8H_{17}$ | H | H | H | H |
| $(CH_2)_9NHCH_3$ | H | H | H | H |
| $(CH_2)_9NHC_2H_5$ | H | H | H | H |
| $(CH_2)_9NHC_3H_7$ | H | H | H | H |
| $(CH_2)_9NHC_7H_{15}$ | H | H | H | H |
| $(CH_2)_{10}NHCH_3$ | H | H | H | H |
| $(CH_2)_{10}NHC_2H_5$ | H | H | H | H |
| $(CH_2)_{10}NHC_3H_7$ | H | H | H | H |
| $(CH_2)_{10}NHC_6H_{13}$ | H | H | H | H |
| $(CH_2)_{11}NHCH_3$ | H | H | H | H |
| $(CH_2)_{11}NHC_2H_5$ | H | H | H | H |
| $(CH_2)_{11}NHC_3H_7$ | H | H | H | H |
| $(CH_2)_4CH(C_6H_{13})NHC_5H_{11}$ | H | H | H | H |
| $(CH_2)_{17}NHCH_3$ | H | H | H | H |
| $(CH_2)_{17}NHC_2H_5$ | H | H | H | H |
| $(CH_2)_{17}NHC_3H_7$ | H | H | H | H |
| $(CH_2)_{17}NHC_{10}H_{21}$ | H | H | H | H |
| $(CH_2)_{19}NHCH_3$ | H | H | H | H |
| $(CH_2)_{19}NHC_2H_5$ | H | H | H | H |
| $(CH_2)_{19}NHC_3H_7$ | H | H | H | H |
| $(CH_2)_{19}NHC_{10}H_{21}$ | H | H | H | H |
| $(CH_2)_{29}NHCH_3$ | H | H | H | H |
| $(CH_2)_{29}NHC_2H_5$ | H | H | H | H |
| $(CH_2)_{29}NHC_3H_7$ | H | H | H | H |
| $(CH_2)_{29}NHC_{10}H_{21}$ | H | H | H | H |
| $CONHCH_3$ | H | H | H | H |
| $CONHC_2H_5$ | H | H | H | H |
| $CONHC_{10}H_{21}$ | H | H | H | H |
| $COOC_{15}H_{31}$ | H | H | H | H |
| $CH_2CONHCH_3$ | H | H | H | H |
| $CH_2CONHC_2H_5$ | H | H | H | H |
| $CH_2CONHC_{10}H_{21}$ | H | H | H | H |
| $CH_2CONHC_{14}H_{29}$ | H | H | H | H |
| $(CH_2)_3CONHCH_3$ | H | H | H | H |
| $(CH_2)_3CONHC_2H_5$ | H | H | H | H |
| $(CH_2)_3CONHC_{10}H_{21}$ | H | H | H | H |
| $(CH_2)_3CONHC_{12}H_{25}$ | H | H | H | H |
| $(CH_2)_4CONHCH_3$ | H | H | H | H |
| $(CH_2)_4CONHC_2H_5$ | H | H | H | H |
| $(CH_2)_4CONHC_{10}H_{21}$ | H | H | H | H |
| $(CH_2)_4CONHC_{11}H_{23}$ | H | H | H | H |
| $(CH_2)_5CONHCH_3$ | H | H | H | H |
| $(CH_2)_5CONHC_2H_5$ | H | H | H | H |
| $(CH_2)_5CONHC_{10}H_{21}$ | H | H | H | H |
| $(CH_2)_6CONHCH_3$ | H | H | H | H |
| $(CH_2)_6CONHC_2H_5$ | H | H | H | H |
| $(CH_2)_6CONHC_{10}H_{21}$ | H | H | H | H |
| $(CH_2)_7CONHCH_3$ | H | H | H | H |
| $(CH_2)_7CONHC_2H_5$ | H | H | H | H |
| $(CH_2)_7CONHC_8H_{17}$ | H | H | H | H |
| $(CH_2)_8CONHCH_3$ | H | H | H | H |
| $(CH_2)_8CONHC_2H_5$ | H | H | H | H |
| $(CH_2)_8CONHC_7H_{15}$ | H | H | H | H |
| $(CH_2)_9CONHCH_3$ | H | H | H | H |
| $(CH_2)_9CONHC_2H_5$ | H | H | H | H |
| $(CH_2)_9CONHC_6H_{13}$ | H | H | H | H |
| $(CH_2)_{10}CONHCH_3$ | H | H | H | H |
| $(CH_2)_{10}CONHC_2H_5$ | H | H | H | H |
| $(CH_2)_{10}CONHC_5H_{11}$ | H | H | H | H |
| $(CH_2)_{11}CONHCH_3$ | H | H | H | H |
| $(CH_2)_{11}CONHC_2H_5$ | H | H | H | H |
| $(CH_2)_{11}CONHC_4H_9$ | H | H | H | H |
| $(CH_2)_{17}CONHCH_3$ | H | H | H | H |
| $(CH_2)_8CH(C_8H_{17})CONHC_2H_5$ | H | H | H | H |
| $(CH_2)_{17}CONHC_{10}H_{21}$ | H | H | H | H |

-continued $$R^2R^3N-\underset{\underset{CH_2R^1}{|}}{\overset{\overset{CH_2OR^4}{|}}{C}}-CH_2OR^5$$

| R$^1$ | R$^2$ | R$^3$ | R$^4$ | R$^5$ |
|---|---|---|---|---|
| (CH$_2$)$_{19}$CONHCH$_3$ | H | H | H | H |
| (CH$_2$)$_{19}$CONHC$_2$H$_5$ | H | H | H | H |
| (CH$_2$)$_{19}$CONHC$_{10}$H$_{21}$ | H | H | H | H |
| (CH$_2$)$_{29}$CONHCH$_3$ | H | H | H | H |
| (CH$_2$)$_{29}$CONHC$_2$H$_5$ | H | H | H | H |
| (CH$_2$)$_{29}$CONHC$_{10}$H$_{21}$ | H | H | H | H |
| CH$_2$NO$_2$ | H | H | H | H |
| (CH$_2$)$_2$NO$_2$ | H | H | H | H |
| (CH$_2$)$_3$NO$_2$ | H | H | H | H |
| (CH$_2$)$_4$NO$_2$ | H | H | H | H |
| (CH$_2$)$_5$NO$_2$ | H | H | H | H |
| (CH$_2$)$_6$NO$_2$ | H | H | H | H |
| (CH$_2$)$_7$NO$_2$ | H | H | H | H |
| (CH$_2$)$_8$NO$_2$ | H | H | H | H |
| (CH$_2$)$_9$NO$_2$ | H | H | H | H |
| (CH$_2$)$_{10}$NO$_2$ | H | H | H | H |
| (CH$_2$)$_4$CH(C$_6$H$_{13}$)NO$_2$ | H | H | H | H |
| (CH$_2$)$_{17}$NO$_2$ | H | H | H | H |
| (CH$_2$)$_{19}$NO$_2$ | H | H | H | H |
| (CH$_2$)$_{29}$NO$_2$ | H | H | H | H |
| CH$_2$Cl | H | H | H | H |
| (CH$_2$)$_2$Cl | H | H | H | H |
| (CH$_2$)$_3$Cl | H | H | H | H |
| (CH$_2$)$_4$Cl | H | H | H | H |
| (CH$_2$)$_5$Cl | H | H | H | H |
| (CH$_2$)$_6$Cl | H | H | H | H |
| (CH$_2$)$_7$Cl | H | H | H | H |
| (CH$_2$)$_8$Cl | H | H | H | H |
| (CH$_2$)$_9$Cl | H | H | H | H |
| (CH$_2$)$_{10}$Cl | H | H | H | H |
| (CH$_2$)$_{11}$Cl | H | H | H | H |
| (CH$_2$)$_{17}$Cl | H | H | H | H |
| (CH$_2$)$_{19}$Cl | H | H | H | H |
| (CH$_2$)$_{29}$Cl | H | H | H | H |
| CH$_2$Br | H | H | H | H |
| (CH$_2$)$_2$Br | H | H | H | H |
| (CH$_2$)$_3$Br | H | H | H | H |
| (CH$_2$)$_4$Br | H | H | H | H |
| (CH$_2$)$_5$Br | H | H | H | H |
| (CH$_2$)$_6$Br | H | H | H | H |
| (CH$_2$)$_7$Br | H | H | H | H |
| (CH$_2$)$_8$Br | H | H | H | H |
| (CH$_2$)$_2$CHBrC$_6$H$_{13}$ | H | H | H | H |
| (CH$_2$)$_{10}$Br | H | H | H | H |
| (CH$_2$)$_{11}$Br | H | H | H | H |
| (CH$_2$)$_{17}$Br | H | H | H | H |
| (CH$_2$)$_{19}$Br | H | H | H | H |
| (CH$_2$)$_{29}$Br | H | H | H | H |
| CH$_2$F | H | H | H | H |
| (CH$_2$)$_2$F | H | H | H | H |
| (CH$_2$)$_3$F | H | H | H | H |
| (CH$_2$)$_4$F | H | H | H | H |
| (CH$_2$)$_5$F | H | H | H | H |
| (CH$_2$)$_6$F | H | H | H | H |
| (CH$_2$)$_7$F | H | H | H | H |
| (CH$_2$)$_8$F | H | H | H | H |
| (CH$_2$)$_9$F | H | H | H | H |
| (CH$_2$)$_{10}$F | H | H | H | H |
| (CH$_2$)$_{11}$F | H | H | H | H |
| (CH$_2$)$_{11}$F | COCH$_3$ | H | COCH$_3$ | COCH$_3$ |
| (CH$_2$)$_{12}$F | H | H | H | H |
| (CH$_2$)$_{12}$F | COCH$_3$ | H | COCH$_3$ | COCH$_3$ |
| (CH$_2$)$_3$CHFC$_7$H$_{15}$ | H | H | H | H |
| (CH$_2$)$_{13}$F | H | H | H | H |
| (CH$_2$)$_{13}$F | COCH$_3$ | H | COCH$_3$ | COCH$_3$ |
| (CH$_2$)$_{12}$CHF$_2$ | H | H | H | H |
| (CH$_2$)$_{12}$CHF$_2$ | COCH$_3$ | H | COCH$_3$ | COCH$_3$ |
| (CH$_2$)$_{12}$CF$_3$ | H | H | H | H |
| (CH$_2$)$_{12}$CF$_3$ | COCH$_3$ | H | COCH$_3$ | COCH$_3$ |
| (CH$_2$)$_{14}$F | H | H | H | H |
| (CH$_2$)$_{14}$F | COCH$_3$ | H | COCH$_3$ | COCH$_3$ |
| (CH$_2$)$_{17}$F | H | H | H | H |
| (CH$_2$)$_{19}$F | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_{29}F$ | H | H | H | H |
| $CH_2OCH_3$ | H | H | H | H |
| $CH_2OC_2H_5$ | H | H | H | H |
| $CH_2OC_{15}H_{31}$ | H | H | H | H |
| $(CH_2)_2OCH_3$ | H | H | H | H |
| $(CH_2)_2OC_2H_5$ | H | H | H | H |
| $(CH_2)_2OC_{15}H_{31}$ | H | H | H | H |
| $(CH_2)_3OCH_3$ | H | H | H | H |
| $(CH_2)_3OC_2H_5$ | H | H | H | H |
| $(CH_2)_3OC_{13}H_{27}$ | H | H | H | H |
| $(CH_2)_4OCH_3$ | H | H | H | H |
| $(CH_2)_4OC_2H_5$ | H | H | H | H |
| $(CH_2)_4OC_{12}H_{25}$ | H | H | H | H |
| $(CH_2)_5OC_8H_{17}$ | H | H | H | H |
| $(CH_2)_5OC_8H_{17}$ | $COCH_3$ | H | $COCH_3$ | $COCH_3$ |
| $(CH_2)_5OC_{11}H_{23}$ | H | H | H | H |
| $(CH_2)_6OC_7H_{15}$ | H | H | H | H |
| $(CH_2)_6OC_7H_{15}$ | H | H | H | H |
| $(CH_2)_6OC_{10}H_{21}$ | H | H | H | H |
| $(CH_2)_7OC_6H_{13}$ | H | H | H | H |
| $(CH_2)_7OC_6H_{13}$ | $COCH_3$ | H | $COCH_3$ | $COCH_3$ |
| $(CH_2)_7OC_9H_{19}$ | H | H | H | H |
| $(CH_2)_8OC_5H_{11}$ | H | H | H | H |
| $(CH_2)_8OC_5H_{11}$ | $COCH_3$ | H | $COCH_3$ | $COCH_3$ |
| $(CH_2)_8OC_8H_{17}$ | H | H | H | H |
| $(CH_2)_9OC_7H_{15}$ | H | H | H | H |
| $(CH_2)_{10}OC_6H_{13}$ | H | H | H | H |
| $(CH_2)_{11}OC_5H_{11}$ | H | H | H | H |
| $(CH_2)_{12}OC_4H_9$ | H | H | H | H |
| $(CH_2)_{13}OC_3H_7$ | H | H | H | H |
| $(CH_2)_{14}OC_2H_5$ | H | H | H | H |
| $(CH_2)_{15}OCH_3$ | H | H | H | H |
| $CH_2OCH_2CH=CH_2$ | H | H | H | H |
| $(CH_2)_2OCH_2CH=CH_2$ | H | H | H | H |
| $(CH_2)_3OCH_2CH=CH_2$ | H | H | H | H |
| $(CH_2)_9OCH_2CH=CH_2$ | H | H | H | H |
| $(CH_2)_{13}OCH_2CH=CH_2$ | H | H | H | H |
| $CH_2OCH_2CH=CHCH_3$ | H | H | H | H |
| $(CH_2)_2OCH_2CH=CHCH_3$ | H | H | H | H |
| $(CH_2)_3OCH_2CH=CHCH_3$ | H | H | H | H |
| $(CH_2)_9OCH_2CH=CHCH_3$ | H | H | H | H |
| $(CH_2)_{12}OCH_2CH=CHCH_3$ | H | H | H | H |
| $CH_2OCH_2CH=CHC_7H_{15}$ | H | H | H | H |
| $(CH_2)_2OCH_2CH=CHC_7H_{15}$ | H | H | H | H |
| $(CH_2)_3OCH_2CH=CHC_7H_{15}$ | H | H | H | H |
| $(CH_2)_6OCH_2CH=CHC_7H_{15}$ | H | H | H | H |
| $(CH_2)_9OCH_2CH=CHC_7H_{15}$ | H | H | H | H |
| $CH_2OCH_2C\equiv CH$ | H | H | H | H |
| $(CH_2)_2OCH_2C\equiv CH$ | H | H | H | H |
| $(CH_2)_3OCH_2C\equiv CH$ | H | H | H | H |
| $(CH_2)_9OCH_2C\equiv CH$ | H | H | H | H |
| $(CH_2)_{11}CH(CH_3)OCH_2C\equiv CH$ | H | H | H | H |
| $CH_2OCH_2C\equiv CCH_3$ | H | H | H | H |
| $(CH_2)_2OCH_2C\equiv CCH_3$ | H | H | H | H |
| $(CH_2)_3OCH_2C\equiv CCH_3$ | H | H | H | H |
| $(CH_2)_9OCH_2C\equiv CCH_3$ | H | H | H | H |
| $(CH_2)_{12}OCH_2C\equiv CCH_3$ | H | H | H | H |
| $CH_2OCH_2C\equiv CC_7H_{15}$ | H | H | H | H |
| $(CH_2)_2OCH_2C\equiv CC_7H_{15}$ | H | H | H | H |
| $(CH_2)_3OCH_2C\equiv CC_7H_{15}$ | H | H | H | H |
| $(CH_2)_6OCH_2C\equiv CC_7H_{15}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₉OCH₂C≡CC₇H₁₅ | H | H | H | H |
| CH₂OCH₂C₆H₅ | H | H | H | H |
| CH₂O(CH₂)₂C₆H₅ | H | H | H | H |
| CH₂O(CH₂)₃C₆H₅ | H | H | H | H |
| (CH₂)₂OCH₂C₆H₅ | H | H | H | H |
| (CH₂)₂O(CH₂)₂C₆H₅ | H | H | H | H |
| (CH₂)₂O(CH₂)₃C₆H₅ | H | H | H | H |
| (CH₂)₃OCH₂C₆H₅ | H | H | H | H |
| (CH₂)₃O(CH₂)₂C₆H₅ | H | H | H | H |
| (CH₂)₃O(CH₂)₃C₆H₅ | H | H | H | H |
| (CH₂)₄OCH₂C₆H₅ | H | H | H | H |
| (CH₂)₄O(CH₂)₂C₆H₅ | H | H | H | H |
| (CH₂)₄O(CH₂)₃C₆H₅ | H | H | H | H |
| (CH₂)₅O(CH₂)₂C₆H₅ | H | H | H | H |
| (CH₂)₅O(CH₂)₃C₆H₅ | H | H | H | H |
| (CH₂)₅O(CH₂)₃C₆H₅ | COCH₃ | H | COCH₃ | COCH₃ |
| (CH₂)₆O(CH₂)₂C₆H₅ | H | H | H | H |
| (CH₂)₇OCH₂C₆H₅ | H | H | H | H |
| (CH₂)₇OCH₂C₆H₅ | COCH₃ | H | COCH₃ | COCH₃ |
| (CH₂)₇O(CH₂)₂C₆H₅ | H | H | H | H |
| (CH₂)₈O(CH₂)₂C₆H₅ | H | H | H | H |
| (CH₂)₉O(CH₂)₂C₆H₅ | H | H | H | H |
| (CH₂)₁₀O(CH₂)₂C₆H₅ | H | H | H | H |
| (CH₂)₁₁O(CH₂)₂C₆H₅ | H | H | H | H |
| (CH₂)₁₂O(CH₂)₂C₆H₅ | H | H | H | H |
| (CH₂)₈CH(C₄H₉)O(CH₂)₂C₆H₅ | H | H | H | H |
| (CH₂)₁₄O(CH₂)₂C₆H₅ | H | H | H | H |
| (CH₂)₁₅O(CH₂)₂C₆H₅ | H | H | H | H |
| C₁₇H₃₅ | CH₃ | H | H | H |
| C₁₇H₃₅ | CH₃ | CH₃ | H | H |
| C₁₇H₃₅ | C₁₈H₃₇ | H | H | H |
| C₁₇H₃₅ | C₁₈H₃₇ | C₁₈H₃₇ | H | H |
| C₁₇H₃₅ | COCH₃ | H | H | H |
| C₁₇H₃₅ | COC₁₇H₃₅ | H | H | H |
| CH₂C₆H₅ | H | H | H | H |
| CH₂C₆H₅ | COCH₃ | H | COCH₃ | COCH₃ |
| CH(CH₃)C₆H₅ | H | H | H | H |
| CH=CHC₆H₅ | H | H | H | H |
| CH=CHC₆H₅ | COCH₃ | H | COCH₃ | COCH₃ |
| C≡CC₆H₅ | H | H | H | H |
| C≡CC₆H₅ | COCH₃ | H | COCH₃ | COCH₃ |
| (CH₂)₃C₆H₅ | H | H | H | H |
| CH₂CH(CH₃)C₆H₅ | H | H | H | H |
| CH₂CH(CH₃)C₆H₅ | COCH₃ | H | COCH₃ | COCH₃ |
| (CH₂)₄C₆H₅ | H | H | H | H |
| (CH₂)₅C₆H₅ | H | H | H | H |
| (CH₂)₅C₆H₅ | COCH₃ | H | COCH₃ | COCH₃ |
| (CH₂)₆C₆H₅ | H | H | H | H |
| (CH₂)₇C₆H₅ | H | H | H | H |
| (CH₂)₈C₆H₅ | H | H | H | H |
| (CH₂)₉C₆H₅ | H | H | H | H |
| (CH₂)₉C₆H₅ | COCH₃ | H | COCH₃ | COCH₃ |
| (CH₂)₉C₆H₁₁ | H | H | H | H |
| (CH₂)₁₁C₆H₅ | H | H | H | H |
| (CH₂)₁₂C₆H₅ | H | H | H | H |
| (CH₂)₁₂C₆H₅ | COCH₃ | H | COCH₃ | COCH₃ |
| (CH₂)₁₃C₆H₅ | H | H | H | H |
| (CH₂)₁₅C₆H₅ | H | H | H | H |
| (CH₂)₁₇C₆H₅ | H | H | H | H |
| (CH₂)₁₉C₆H₅ | H | H | H | H |
| (CH₂)₂₉C₆H₅ | H | H | H | H |
| C₆H₄-3-CH₃ | H | H | H | H |
| C₆H₄-4-CH₃ | H | H | H | H |
| C₆H₄-3-C₂H₅ | H | H | H | H |
| C₆H₄-4-C₂H₅ | H | H | H | H |
| C₆H₄-3-C₃H₇ | H | H | H | H |
| C₆H₄-2-C₃H₇ | H | H | H | H |
| C₆H₄-4-C₃H₇ | H | H | H | H |
| C₆H₄-3-C₄H₉ | H | H | H | H |
| C₆H₄-4-C₄H₉ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| C₆H₄-3-C₆H₁₃ | H | H | H | H |
| C₆H₄-4-C₉H₁₉ | H | H | H | H |
| C₆H₄-4-C₉H₁₉ | COCH₃ | H | COCH₃ | COCH₃ |
| C₆H₁₀-3-C₆H₁₃ | H | H | H | H |
| C₆H₄-4-C₆H₁₃ | H | H | H | H |
| C₆H₄-3-C₁₀H₂₁ | H | H | H | H |
| C₆H₄-4-C₁₀H₂₁ | H | H | H | H |
| C₆H₄-3-C₁₂H₂₅ | H | H | H | H |
| C₆H₄-4-C₁₂H₂₅ | H | H | H | H |
| C₆H₄-3-C₂₀H₄₁ | H | H | H | H |
| C₆H₄-4-C₂₀H₄₁ | H | H | H | H |
| CH₂C₆H₄-3-CH₃ | H | H | H | H |
| CH₂C₆H₄-4-CH₃ | H | H | H | H |
| CH₂C₆H₄-3-C₂H₅ | H | H | H | H |
| CH₂C₆H₄-4-C₂H₅ | H | H | H | H |
| CH₂C₆H₄-3-C₃H₇ | H | H | H | H |
| CH₂C₆H₄-4-C₃H₇ | H | H | H | H |
| CH₂C₆H₄-3-C₄H₉ | H | H | H | H |
| CH₂C₆H₄-4-C₄H₉ | H | H | H | H |
| CH₂C₆H₄-3-C₆H₁₃ | H | H | H | H |
| CH₂C₆H₄-2-C₄H₉ | H | H | H | H |
| CH₂C₆H₄-2-C₆H₁₃ | H | H | H | H |
| CH₂C₆H₄-4-C₆H₁₃ | H | H | H | H |
| CH₂C₆H₄-4-(CH₂)₃CH(CH₃)₂ | H | H | H | H |
| CH₂C₆H₄-4-(CH₂)₃CH(CH₃)₂ | COCH₃ | H | COCH₃ | COCH₃ |
| CH₂C₆H₄-4-C₇H₁₅ | H | H | H | H |
| CH₂C₆H₄-4-C₇H₁₅ | COCH₃ | H | COCH₃ | COCH₃ |
| CH₂C₆H₄-4-C₈H₁₇ | H | H | H | H |
| CH₂C₆H₄-4-C₈H₁₇ | COCH₃ | H | H | H |
| CH₂C₆H₄-4-C₈H₁₇ | COCH₃ | H | COCH₃ | COCH₃ |
| CH₂C₆H₄-4-C₈H₁₇ | CH₃ | CH₃ | H | H |
| CH₂C₆H₄-2-C₈H₁₇ | H | H | H | H |
| CH₂C₆H₄-2-C₈H₁₇ | COCH₃ | H | COCH₃ | COCH₃ |
| CH₂C₆H₄-3-C₈H₁₇ | H | H | H | H |
| CH₂C₆H₄-3-C₈H₁₇ | COCH₃ | H | COCH₃ | COCH₃ |
| CH₂C₆H₄-3-C₁₀H₂₁ | H | H | H | H |
| CH₂C₆H₄-4-C₁₀H₂₁ | H | H | H | H |
| CH₂C₆H₄-3-C₁₂H₂₅ | H | H | H | H |
| CH₂C₆H₄-4-C₁₂H₂₅ | H | H | H | H |
| CH₂C₆H₄-4-C₁₂H₂₅ | COCH₃ | H | COCH₃ | COCH₃ |
| CH₂C₆H₄-3-C₂₀H₄₁ | H | H | H | H |
| CH₂C₆H₄-4-C₂₀H₄₁ | H | H | H | H |
| (CH₂)₂C₆H₄-3-CH₃ | H | H | H | H |
| (CH₂)₂C₆H₄-4-CH₃ | H | H | H | H |
| (CH₂)₂C₆H₄-3-C₂H₅ | H | H | H | H |
| (CH₂)₂C₇H₁₂-3-C₂H₅ | H | H | H | H |
| (CH₂)₂C₆H₄-4-C₂H₅ | H | H | H | H |
| (CH₂)₂C₆H₄-3-C₃H₇ | H | H | H | H |
| (CH₂)₂C₆H₄-4-C₃H₇ | H | H | H | H |
| (CH₂)₂C₆H₄-3-C₄H₉ | H | H | H | H |
| (CH₂)₂C₆H₄-4-C₄H₉ | H | H | H | H |
| (CH₂)₂C₆H₄-3-C₆H₁₃ | H | H | H | H |
| (CH₂)₂C₆H₄-4-C₆H₁₃ | H | H | H | H |
| (CH₂)₂C₆H₁₀-4-C₇H₁₅ | H | H | H | H |
| (CH₂)₂C₆H₁₀-4-C₇H₁₅ | COCH₃ | H | COCH₃ | COCH₃ |
| (CH₂)₂C₆H₄-4-C₇H₁₅ | H | H | H | H |
| (CH₂)₂C₆H₄-4-C₇H₁₅ | COCH₃ | H | COCH₃ | COCH₃ |
| (CH₂)₂C₆H₄-3-C₁₀H₂₁ | H | H | H | H |
| (CH₂)₂C₆H₄-4-C₁₀H₂₁ | H | H | H | H |
| (CH₂)₂C₆H₄-4-C₁₁H₂₃ | H | H | H | H |
| (CH₂)₂C₆H₄-4-C₁₁H₂₃ | COCH₃ | H | COCH₃ | COCH₃ |
| (CH₂)₂C₆H₄-3-C₁₂H₂₅ | H | H | H | H |
| (CH₂)₂C₆H₄-4-C₁₂H₂₅ | H | H | H | H |
| (CH₂)₂C₆H₄-3-C₂₀H₄₁ | H | H | H | H |
| (CH₂)₂C₆H₄-4-C₂₀H₄₁ | H | H | H | H |
| (CH₂)₃C₆H₄-3-CH₃ | H | H | H | H |
| (CH₂)₃C₆H₄-4-CH₃ | H | H | H | H |
| (CH₂)₃C₆H₄-3-C₂H₅ | H | H | H | H |
| (CH₂)₃C₆H₄-4-C₂H₅ | H | H | H | H |
| (CH₂)₃C₆H₄-3-C₃H₇ | H | H | H | H |
| (CH₂)₃C₆H₄-4-C₃H₇ | H | H | H | H |
| (CH₂)₃C₆H₄-3-C₄H₉ | H | H | H | H |
| (CH₂)₃C₆H₁₀-4-C₄H₉ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_3C_6H_{10}$-4-$C_4H_9$ | $COCH_3$ | H | $COCH_3$ | $COCH_3$ |
| $(CH_2)_3C_6H_4$-4-$C_4H_9$ | H | H | H | H |
| $(CH_2)_3C_6H_4$-4-$C_4H_9$ | $COCH_3$ | H | $COCH_3$ | $COCH_3$ |
| $(CH_2)_3C_6H_4$-3-$C_6H_{13}$ | H | H | H | H |
| $(CH_2)_3C_6H_4$-4-$C_6H_{13}$ | H | H | H | H |
| $(CH_2)_3C_6H_4$-4-$C_6H_{13}$ | $COCH_3$ | H | $COCH_3$ | $COCH_3$ |
| $(CH_2)_3C_6H_4$-4-$C_8H_{17}$ | H | H | H | H |
| $(CH_2)_3C_6H_4$-4-$C_8H_{17}$ | $COCH_3$ | H | $COCH_3$ | $COCH_3$ |
| $(CH_2)_3C_6H_4$-3-$C_{10}H_{21}$ | H | H | H | H |
| $(CH_2)_3C_6H_4$-4-$C_{10}H_{21}$ | H | H | H | H |
| $(CH_2)_3C_6H_4$-2-$C_{10}H_{21}$ | H | H | H | H |
| $(CH_2)_3C_6H_4$-3-$C_{12}H_{25}$ | H | H | H | H |
| $(CH_2)_3C_6H_4$-4-$C_{12}H_{25}$ | H | H | H | H |
| $(CH_2)_3C_6H_4$-3-$C_{20}H_{41}$ | H | H | H | H |
| $(CH_2)_3C_6H_4$-4-$C_{20}H_{41}$ | H | H | H | H |
| $(CH_2)_4C_6H_4$-3-$CH_3$ | H | H | H | H |
| $(CH_2)_4C_6H_4$-4-$CH_3$ | H | H | H | H |
| $(CH_2)_4C_6H_4$-3-$C_2H_5$ | H | H | H | H |
| $(CH_2)_4C_6H_4$-4-$C_2H_5$ | H | H | H | H |
| $(CH_2)_4C_6H_4$-3-$C_3H_7$ | H | H | H | H |
| $CH_2CH=CHCH_2C_6H_4$-3-$C_3H_7$ | H | H | H | H |
| $(CH_2)_4C_6H_4$-4-$C_3H_7$ | H | H | H | H |
| $(CH_2)_4C_6H_4$-3-$C_4H_9$ | H | H | H | H |
| $(CH_2)_4C_6H_4$-4-$C_4H_9$ | H | H | H | H |
| $(CH_2)_4C_6H_4$-3-$C_6H_{13}$ | H | H | H | H |
| $(CH_2)_4C_6H_4$-4-$C_6H_{13}$ | H | H | H | H |
| $(CH_2)_4C_6H_4$-3-$C_{10}H_{21}$ | H | H | H | H |
| $(CH_2)_4C_6H_4$-4-$C_{10}H_{21}$ | H | H | H | H |
| $(CH_2)_4C_6H_4$-2-$C_{12}H_{25}$ | H | H | H | H |
| $(CH_2)_4C_6H_4$-3-$C_{12}H_{25}$ | H | H | H | H |
| $(CH_2)_4C_6H_4$-4-$C_{12}H_{25}$ | H | H | H | H |
| $(CH_2)_4C_6H_{10}$-4-$C_{12}H_{25}$ | H | H | H | H |
| $(CH_2)_4C_6H_4$-3-$C_{20}H_{41}$ | H | H | H | H |
| $(CH_2)_4C_6H_4$-4-$C_{20}H_{41}$ | H | H | H | H |
| $(CH_2)_5C_6H_4$-3-$CH_3$ | H | H | H | H |
| $(CH_2)_5C_6H_4$-4-$CH_3$ | H | H | H | H |
| $(CH_2)_5C_6H_4$-3-$C_2H_5$ | H | H | H | H |
| $(CH_2)_5C_6H_4$-4-$C_2H_5$ | H | H | H | H |
| $(CH_2)_5C_6H_4$-3-$C_3H_7$ | H | H | H | H |
| $(CH_2)_5C_6H_4$-4-$C_3H_7$ | H | H | H | H |
| $(CH_2)_5C_6H_4$-3-$C_4H_9$ | H | H | H | H |
| $(CH_2)_5C_6H_4$-4-$C_4H_9$ | H | H | H | H |
| $(CH_2)_5C_6H_4$-4-$C_4H_9$ | $COCH_3$ | H | $COCH_3$ | $COCH_3$ |
| $(CH_2)_5C_6H_4$-2-$C_6H_{13}$ | H | H | H | H |
| $(CH_2)_5C_6H_4$-3-$C_6H_{13}$ | H | H | H | H |
| $(CH_2)_5C_6H_4$-4-$C_6H_{13}$ | H | H | H | H |
| $(CH_2)_5C_6H_4$-3-$C_{10}H_{21}$ | H | H | H | H |
| $(CH_2)_5C_6H_4$-4-$C_{10}H_{21}$ | H | H | H | H |
| $(CH_2)_5C_6H_{10}$-4-$C_{10}H_{21}$ | H | H | H | H |
| $(CH_2)_5C_6H_4$-3-$C_{12}H_{25}$ | H | H | H | H |
| $(CH_2)_5C_6H_4$-4-$C_{12}H_{25}$ | H | H | H | H |
| $(CH_2)_5C_6H_4$-3-$C_{20}H_{41}$ | H | H | H | H |
| $(CH_2)_5C_6H_4$-4-$C_{20}H_{41}$ | H | H | H | H |
| $(CH_2)_7C_6H_4$-3-$C_7H_{15}$ | H | H | H | H |
| $(CH_2)_7C_6H_4$-4-$C_6H_{13}$ | H | H | H | H |
| $(CH_2)_7C_6H_4$-4-$C_2H_5$ | H | H | H | H |
| $(CH_2)_7C_6H_4$-4-$C_2H_5$ | $COCH_3$ | H | $COCH_3$ | $COCH_3$ |
| $(CH_2)_7C_6H_4$-4-$C_6H_{13}$ | H | H | H | H |
| $(CH_2)_7C_6H_4$-4-$C_6H_{13}$ | $COCH_3$ | H | $COCH_3$ | $COCH_3$ |
| $(CH_2)_2CH=C(C_3H_7)C_6H_{10}$-4-$C_6H_{13}$ | H | H | H | H |
| $(CH_2)_9C_6H_4$-3-$C_5H_{11}$ | H | H | H | H |
| $(CH_2)_9C_6H_4$-4-$C_4H_9$ | H | H | H | H |
| $(CH_2)_{11}C_6H_4$-3-$C_3H_7$ | H | H | H | H |
| $(CH_2)_{11}C_6H_4$-4-$C_2H_5$ | H | H | H | H |
| $(CH_2)_{13}C_6H_4$-3-$CH_3$ | H | H | H | H |
| $C_6H_4$-3-$CH=CH_2$ | H | H | H | H |
| $C_6H_4$-4-$CH=CH_2$ | H | H | H | H |
| $CH_2C_6H_4$-3-$CH=CH_2$ | H | H | H | H |
| $CH_2C_6H_4$-4-$CH=CH_2$ | H | H | H | H |
| $CH_2C_6H_4$-3-$CH=CHCH_3$ | H | H | H | H |
| $CH_2C_6H_4$-4-$CH=CHCH_3$ | H | H | H | H |
| $CH_2C_6H_4$-2-$CH=CHCH_3$ | H | H | H | H |
| $CH_2C_6H_4$-3-$CH=CHC_8H_{17}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| CH₂C₆H₄-4-CH=CHC₈H₁₇ | H | H | H | H |
| (CH₂)₂C₆H₄-3-CH=CH₂ | H | H | H | H |
| (CH₂)₂C₆H₄-4-CH=CH₂ | H | H | H | H |
| (CH₂)₂C₆H₄-3-CH=CHCH₃ | H | H | H | H |
| (CH₂)₂C₆H₄-4-CH=CHCH₃ | H | H | H | H |
| (CH₂)₂C₆H₁₀-4-CH=CHCH₃ | H | H | H | H |
| (CH₂)₂C₆H₄-3-CH=CHC₈H₁₇ | H | H | H | H |
| (CH₂)₂C₆H₄-4-CH=CHC₈H₁₇ | H | H | H | H |
| (CH₂)₃C₆H₄-3-CH=CH₂ | H | H | H | H |
| (CH₂)₃C₆H₄-4-CH=CH₂ | H | H | H | H |
| (CH₂)₃C₆H₄-3-CH=CHCH₃ | H | H | H | H |
| (CH₂)₃C₆H₄-4-CH=CHCH₃ | H | H | H | H |
| (CH₂)₃C₆H₄-3-CH=CHC₈H₁₇ | H | H | H | H |
| (CH₂)₃C₆H₄-4-CH=CHC₈H₁₇ | H | H | H | H |
| CH₂CH(CH₃)C₆H₄-4-CH=CHC₈H₁₇ | H | H | H | H |
| (CH₂)₄C₆H₄-3-CH=CH₂ | H | H | H | H |
| (CH₂)₄C₆H₄-4-CH=CH₂ | H | H | H | H |
| (CH₂)₄C₆H₄-3-CH=CHCH₃ | H | H | H | H |
| (CH₂)₄C₆H₄-4-CH=CHCH₃ | H | H | H | H |
| (CH₂)₄C₆H₄-2-CH=CHC₈H₁₇ | H | H | H | H |
| (CH₂)₄C₆H₄-3-CH=CHC₈H₁₇ | H | H | H | H |
| CH₂CH(C₂H₅)-C₅H₈-3-CH=CHC₈H₁₇ | H | H | H | H |
| (CH₂)₄C₆H₄-4-CH=CHC₈H₁₇ | H | H | H | H |
| CH=CH(CH₂)₂C₆H₄-4-CH=CHC₈H₁₇ | H | H | H | H |
| (CH₂)₅C₆H₄-3-CH=CH₂ | H | H | H | H |
| (CH₂)₅C₆H₄-4-CH=CH₂ | H | H | H | H |
| (CH₂)₅C₆H₄-3-CH=CHCH₃ | H | H | H | H |
| (CH₂)₅C₆H₄-4-CH=CHCH₃ | H | H | H | H |
| (CH₂)₅C₆H₄-3-CH=CHC₈H₁₇ | H | H | H | H |
| (CH₂)₅C₆H₄-4-(CH₂)₄CH=CHC₄H₉ | H | H | H | H |
| (CH₂)₇C₆H₄-3-CH=CH₂ | H | H | H | H |
| (CH₂)₇C₆H₄-4-CH=CH₂ | H | H | H | H |
| (CH₂)₇C₆H₁₀-3-CH=CHCH₃ | H | H | H | H |
| (CH₂)₇C₆H₄-3-CH₂CH=CH₂ | H | H | H | H |
| (CH₂)₇C₆H₄-4-CH=CHCH₃ | H | H | H | H |
| (CH₂)₇C₆H₄-3-(CH₂)₄CH=CHC₄H₉ | H | H | H | H |
| (CH₂)₇C₆H₄-4-(CH₂)₆CH=CHC₂H₅ | H | H | H | H |
| C₆H₄-3-C≡CH | H | H | H | H |
| C₆H₄-4-C≡CH | H | H | H | H |
| C₆H₁₀-4-C≡CH | H | H | H | H |
| CH₂C₆H₄-3-C≡CH | H | H | H | H |
| CH₂C₆H₄-4-C≡CH | H | H | H | H |
| CH₂C₆H₄-3-C≡CCH₃ | H | H | H | H |
| CH₂C₆H₄-4-C≡CCH₃ | H | H | H | H |
| CH₂C₆H₄-3-(CH₂)₆C≡CC₂H₅ | H | H | H | H |
| CH₂C₆H₄-4-(CH₂)₃C≡CC₅H₁₁ | H | H | H | H |
| CH₂C₆H₄-2-(CH₂)₃C≡CC₅H₁₁ | H | H | H | H |
| CH₂C₆H₁₀-4-(CH₂)₃C≡CC₅H₁₁ | H | H | H | H |
| (CH₂)₂C₆H₄-3-C≡CH | H | H | H | H |
| (CH₂)₂C₆H₄-4-C≡CH | H | H | H | H |
| (CH₂)₂C₆H₄-3-C≡CCH₃ | H | H | H | H |
| (CH₂)₂C₆H₄-4-C≡CCH₃ | H | H | H | H |
| (CH₂)₂C₆H₄-4-(CH₂)₂C≡CCH₃ | H | H | H | H |
| (CH₂)₂C₆H₄-3-(CH₂)₃C≡CC₅H₁₁ | H | H | H | H |
| (CH₂)₂C₆H₄-3-C≡CC₈H₁₇ | H | H | H | H |
| (CH₂)₃C₆H₄-3-C≡CH | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_3C_6H_4$-4-C≡CH | H | H | H | H |
| $(CH_2)_3C_6H_4$-3-C≡$CCH_3$ | H | H | H | H |
| $CH(C_2H_5)C_6H_4$-4-C≡$CCH_3$ | H | H | H | H |
| $(CH_2)_3C_6H_4$-3-$(CH_2)_4$C≡$CC_4H_9$ | H | H | H | H |
| $(CH_2)_3C_6H_4$-2-C≡$CC_8H_{17}$ | H | H | H | H |
| $CH_2CH(CH_3)C_6H_{10}$-2-$(CH_2)_3$C≡$CC_5H_{11}$ | H | H | H | H |
| $(CH_2)_3C_6H_4$-4-C≡$CC_8H_{17}$ | H | H | H | H |
| $CH_2CH(CH_3)C_6H_{10}$-4-$(CH_2)_3$C≡$CC_5H_{11}$ | H | H | H | H |
| $(CH_2)_4C_6H_4$-3-C≡CH | H | H | H | H |
| $(CH_2)_4C_6H_4$-4-C≡CH | H | H | H | H |
| $(CH_2)_4C_6H_4$-3-C≡$CCH_3$ | H | H | H | H |
| $(CH_2)_4C_6H_4$-4-$CH_2$C≡CH | H | H | H | H |
| $(CH_2)_4C_6H_4$-3-C≡$CC_8H_{17}$ | H | H | H | H |
| $(CH_2)_4C_6H_4$-4-$(CH_2)_8$C≡CH | H | H | H | H |
| $(CH_2)_4C_5H_8$-4-$(CH_2)_8$C≡CH | H | H | H | H |
| $CH_2CH=CHCH_2C_5H_8$-4-$(CH_2)_8$C≡CH | H | H | H | H |
| $(CH_2)_5C_6H_4$-3-C≡CH | H | H | H | H |
| $(CH_2)_5C_6H_4$-4-C≡CH | H | H | H | H |
| $(CH_2)_5C_6H_4$-2-C≡CH | H | H | H | H |
| $(CH_2)_5C_6H_4$-2-C≡CH | $COCH_3$ | H | $COCH_3$ | $COCH_3$ |
| $(CH_2)_5C_6H_4$-3-$CH_2$C≡CH | H | H | H | H |
| $(CH_2)_5C_6H_4$-4-C≡$CCH_3$ | H | H | H | H |
| $(CH_2)_2CH(C_2H_5)C_6H_4$-3-$(CH_2)_2$C≡$CC_6H_{13}$ | H | H | H | H |
| $(CH_2)_5C_6H_4$-4-C≡$CC_8H_{17}$ | H | H | H | H |
| $(CH_2)_7C_6H_4$-3-C≡CH | H | H | H | H |
| $(CH_2)_7C_6H_4$-4-C≡CH | H | H | H | H |
| $(CH_2)_7C_6H_4$-3-$CH_2$C≡CH | H | H | H | H |
| $(CH_2)_7C_6H_4$-3-C≡$CCH_3$ | H | H | H | H |
| $(CH_2)_3CH(C_3H_7)C_6H_4$-3-$(CH_2)_5$C≡$CC_3H_7$ | H | H | H | H |
| $(CH_2)_7C_6H_4$-4-C≡$CC_8H_{17}$ | H | H | H | H |
| $(CH_2)_7C_8H_{12}$-4-$(CH_2)_4$C≡$CC_4H_9$ | H | H | H | H |
| C≡$C(CH_2)_3CH(CH_3)C_6H_4$-4-C≡$CC_8H_{17}$ | H | H | H | H |
| $C_6H_4$-3-$OCH_3$ | H | H | H | H |
| $C_6H_4$-4-$OCH_3$ | H | H | H | H |
| $C_6H_4$-3-$OC_2H_5$ | H | H | H | H |
| $C_6H_4$-4-$OC_2H_5$ | H | H | H | H |
| $C_6H_4$-3-$OC_3H_7$ | H | H | H | H |
| $C_6H_4$-4-$OC_3H_7$ | H | H | H | H |
| $C_6H_4$-3-$OC_4H_9$ | H | H | H | H |
| $C_6H_4$-2-$OC_4H_9$ | H | H | H | H |
| $C_6H_{10}$-3-$OC_4H_9$ | H | H | H | H |
| $C_6H_4$-4-$OC_4H_9$ | H | H | H | H |
| $C_6H_4$-3-$OC_6H_{13}$ | H | H | H | H |
| $C_6H_4$-4-$OC_6H_{13}$ | H | H | H | H |
| $C_6H_4$-4-$OC_8H_{17}$ | H | H | H | H |
| $C_6H_4$-4-$OC_8H_{17}$ | $COCH_3$ | H | $COCH_3$ | $COCH_3$ |

-continued $$R^2R^3N-\underset{\underset{CH_2R^1}{|}}{\overset{\overset{CH_2OR^4}{|}}{C}}-CH_2OR^5$$

| R$^1$ | R$^2$ | R$^3$ | R$^4$ | R$^5$ |
|---|---|---|---|---|
| C$_6$H$_4$-3-OC$_{10}$H$_{21}$ | H | H | H | H |
| C$_6$H$_4$-4-OC$_{10}$H$_{21}$ | H | H | H | H |
| C$_6$H$_4$-4-OC$_{10}$H$_{21}$ | COCH$_3$ | H | COCH$_3$ | COCH$_3$ |
| C$_6$H$_4$-3-OC$_{12}$H$_{25}$ | H | H | H | H |
| C$_6$H$_4$-4-OC$_{12}$H$_{25}$ | H | H | H | H |
| C$_6$H$_4$-3-OC$_{20}$H$_{41}$ | H | H | H | H |
| C$_6$H$_4$-4-OC$_{20}$H$_{41}$ | H | H | H | H |
| CH$_2$C$_6$H$_4$-3-OCH$_3$ | H | H | H | H |
| CH$_2$C$_6$H$_4$-4-OCH$_3$ | H | H | H | H |
| CH$_2$C$_6$H$_4$-3-OC$_2$H$_5$ | H | H | H | H |
| CH$_2$C$_6$H$_4$-4-OC$_2$H$_5$ | H | H | H | H |
| CH$_2$C$_6$H$_4$-3-OC$_3$H$_7$ | H | H | H | H |
| CH$_2$C$_6$H$_4$-4-OC$_3$H$_7$ | H | H | H | H |
| CH$_2$C$_6$H$_4$-2-OC$_4$H$_9$ | H | H | H | H |
| CH$_2$C$_6$H$_4$-3-OC$_4$H$_9$ | H | H | H | H |
| CH$_2$C$_6$H$_4$-4-OC$_4$H$_9$ | H | H | H | H |
| CH$_2$C$_6$H$_4$-4-OC$_5$H$_{11}$ | H | H | H | H |
| CH$_2$C$_6$H$_4$-4-OC$_5$H$_{11}$ | COCH$_3$ | H | COCH$_3$ | COCH$_3$ |
| CH$_2$C$_6$H$_4$-4-OC$_6$H$_{13}$ | H | H | H | H |
| CH$_2$C$_6$H$_4$-4-OC$_6$H$_{13}$ | COCH$_3$ | H | COCH$_3$ | COCH$_3$ |
| CH$_2$C$_6$H$_4$-4-OC$_7$H$_{15}$ | H | H | H | H |
| CH$_2$C$_6$H$_4$-4-OC$_7$H$_{15}$ | COCH$_3$ | H | COCH$_3$ | COCH$_3$ |
| CH$_2$C$_6$H$_4$-4-O(CH$_2$)$_6$CH=CH$_2$ | H | H | H | H |
| CH$_2$C$_6$H$_4$-4-O(CH$_2$)$_6$CH=CH$_2$ | COCH$_3$ | H | COCH$_3$ | COCH$_3$ |
| CH$_2$C$_6$H$_4$-4-OC$_8$H$_{17}$ | H | H | H | H |
| CH$_2$C$_6$H$_4$-4-OC$_8$H$_{17}$ | COCH$_3$ | H | COCH$_3$ | COCH$_3$ |
| CH$_2$C$_6$H$_4$-4-OC$_9$H$_{19}$ | H | H | H | H |
| CH$_2$C$_6$H$_4$-4-OC$_9$H$_{19}$ | COCH$_3$ | H | COCH$_3$ | COCH$_3$ |
| CH$_2$C$_6$H$_4$-3-OC$_6$H$_{13}$ | H | H | H | H |
| CH$_2$C$_6$H$_4$-4-OC$_6$H$_{13}$ | H | H | H | H |
| CH$_2$C$_6$H$_4$-3-OC$_{10}$H$_{21}$ | H | H | H | H |
| CH$_2$C$_6$H$_4$-4-OC$_{10}$H$_{21}$ | H | H | H | H |
| CH$_2$C$_6$H$_4$-4-OC$_{11}$H$_{23}$ | H | H | H | H |
| CH$_2$C$_6$H$_4$-4-OC$_{11}$H$_{23}$ | COCH$_3$ | H | COCH$_3$ | COCH$_3$ |
| (CH$_2$)$_2$C$_6$H$_4$-3-OCH$_3$ | H | H | H | H |
| (CH$_2$)$_2$C$_6$H$_4$-4-OCH$_3$ | H | H | H | H |
| (CH$_2$)$_2$C$_6$H$_4$-3-OC$_2$H$_5$ | H | H | H | H |
| (CH$_2$)$_2$C$_6$H$_4$-4-OC$_2$H$_5$ | H | H | H | H |
| (CH$_2$)$_2$C$_6$H$_4$-3-OC$_3$H$_7$ | H | H | H | H |
| (CH$_2$)$_2$C$_6$H$_4$-4-OC$_3$H$_7$ | H | H | H | H |
| (CH$_2$)$_2$C$_6$H$_4$-3-OC$_4$H$_9$ | H | H | H | H |
| (CH$_2$)$_2$C$_5$H$_8$-3-OC$_4$H$_9$ | H | H | H | H |
| (CH$_2$)$_2$C$_6$H$_4$-4-OC$_4$H$_9$ | H | H | H | H |
| (CH$_2$)$_2$C$_6$H$_4$-3-OC$_6$H$_{13}$ | H | H | H | H |
| (CH$_2$)$_2$C$_6$H$_4$-4-OC$_6$H$_{13}$ | H | H | H | H |
| (CH$_2$)$_2$C$_6$H$_4$-4-OC$_6$H$_{13}$ | COCH$_3$ | H | COCH$_3$ | COCH$_3$ |
| (CH$_2$)$_2$C$_6$H$_4$-4-OC$_7$H$_{15}$ | H | H | H | H |
| (CH$_2$)$_2$C$_6$H$_4$-4-OC$_7$H$_{15}$ | COCH$_3$ | H | COCH$_3$ | H |
| (CH$_2$)$_2$C$_6$H$_4$-3-OC$_7$H$_{15}$ | H | H | H | H |
| (CH$_2$)$_2$C$_6$H$_4$-3-OC$_7$H$_{15}$ | COCH$_3$ | H | H | H |
| (CH$_2$)$_2$C$_6$H$_4$-4-OC$_8$H$_{17}$ | H | H | H | H |
| (CH$_2$)$_2$C$_6$H$_4$-4-OC$_8$H$_{17}$ | COCH$_3$ | H | COCH$_3$ | COCH$_3$ |
| (CH$_2$)$_2$C$_6$H$_4$-3-OC$_{10}$H$_{21}$ | H | H | H | H |
| (CH$_2$)$_2$C$_6$H$_4$-4-OC$_{10}$H$_{21}$ | H | H | H | H |
| CH=CHC$_6$H$_4$-4-OC$_{10}$H$_{21}$ | COCH$_3$ | H | COCH$_3$ | COCH$_3$ |
| (CH$_2$)$_2$C$_6$H$_4$-3-OC$_{11}$H$_{23}$ | COCH$_3$ | H | H | H |
| (CH$_2$)$_2$C$_6$H$_4$-3-OC$_{11}$H$_{23}$ | H | H | H | H |
| (CH$_2$)$_2$C$_6$H$_4$-3-OC$_{11}$H$_{23}$ | COCH$_3$ | H | COCH$_3$ | COCH$_3$ |
| (CH$_2$)$_2$C$_6$H$_4$-2-OC$_{12}$H$_{25}$ | H | H | H | H |
| (CH$_2$)$_2$C$_6$H$_4$-3-OC$_{12}$H$_{25}$ | H | H | H | H |
| (CH$_2$)$_2$C$_6$H$_4$-4-OC$_{12}$H$_{25}$ | H | H | H | H |
| (CH$_2$)$_2$C$_6$H$_4$-3-OC$_{20}$H$_{41}$ | H | H | H | H |
| (CH$_2$)$_2$C$_6$H$_4$-4-OC$_{20}$H$_{41}$ | H | H | H | H |
| (CH$_2$)$_3$C$_6$H$_4$-3-OCH$_3$ | H | H | H | H |
| (CH$_2$)$_3$C$_6$H$_4$-4-OCH$_3$ | H | H | H | H |
| (CH$_2$)$_3$C$_6$H$_4$-3-OC$_2$H$_5$ | H | H | H | H |
| (CH$_2$)$_3$C$_6$H$_4$-4-OC$_2$H$_5$ | H | H | H | H |
| (CH$_2$)$_3$C$_6$H$_4$-3-OC$_3$H$_7$ | H | H | H | H |
| (CH$_2$)$_3$C$_6$H$_4$-4-OC$_3$H$_7$ | H | H | H | H |
| (CH$_2$)$_3$C$_6$H$_4$-3-OC$_4$H$_9$ | H | H | H | H |
| (CH$_2$)$_3$C$_6$H$_4$-4-OC$_4$H$_9$ | H | H | H | H |
| (CH$_2$)$_3$C$_6$H$_4$-4-OC$_5$H$_{11}$ | H | H | H | H |
| (CH$_2$)$_3$C$_6$H$_4$-4-OC$_5$H$_{11}$ | COCH$_3$ | H | COCH$_3$ | COCH$_3$ |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_3C_6H_4$-3-$OC_6H_{13}$ | H | H | H | H |
| $(CH_2)_3C_6H_4$-4-$OC_6H_{13}$ | H | H | H | H |
| $(CH_2)_3C_6H_4$-4-$OC_6H_{13}$ | $COCH_3$ | H | $COCH_3$ | $COCH_3$ |
| $(CH_2)_3C_6H_4$-3-$OC_{10}H_{21}$ | H | H | H | H |
| $(CH_2)_3C_6H_4$-2-$OC_{10}H_{21}$ | H | H | H | H |
| $(CH_2)_3C_6H_4$-4-$OC_{10}H_{21}$ | H | H | H | H |
| $(CH_2)_3C_6H_4$-3-$OC_{11}H_{23}$ | H | H | H | H |
| $(CH_2)_3C_6H_4$-3-$OC_{11}H_{23}$ | $COCH_3$ | H | $COCH_3$ | $COCH_3$ |
| $(CH_2)_3C_6H_4$-3-$OC_{12}H_{25}$ | H | H | H | H |
| $(CH_2)_3C_6H_4$-4-$OC_{12}H_{25}$ | H | H | H | H |
| $(CH_2)_3C_6H_4$-3-$OC_{20}H_{41}$ | H | H | H | H |
| $(CH_2)_3C_6H_4$-4-$OC_{20}H_{41}$ | H | H | H | H |
| $(CH_2)_3C_8H_{14}$-5-$OC_{20}H_{41}$ | H | H | H | H |
| $(CH_2)_4C_6H_4$-3-$OCH_3$ | H | H | H | H |
| $(CH_2)_4C_6H_4$-4-$OCH_3$ | H | H | H | H |
| $(CH_2)_4C_6H_4$-3-$OC_2H_5$ | H | H | H | H |
| $(CH_2)_4C_6H_4$-4-$OC_2H_5$ | H | H | H | H |
| $(CH_2)_4C_6H_4$-3-$OC_3H_7$ | H | H | H | H |
| $(CH_2)_4C_6H_4$-4-$OC_3H_7$ | H | H | H | H |
| $(CH_2)_4C_6H_4$-4-$OC_4H_9$ | H | H | H | H |
| $(CH_2)_4C_6H_4$-4-$OC_4H_9$ | $COCH_3$ | H | $COCH_3$ | $COCH_3$ |
| $(CH_2)_4C_6H_4$-3-$OC_4H_9$ | H | H | H | H |
| $(CH_2)_4C_6H_4$-4-$OC_4H_9$ | H | H | H | H |
| $(CH_2)_4C_6H_4$-3-$OC_6H_{13}$ | H | H | H | H |
| $(CH_2)_4C_6H_{10}$-3-$OC_6H_{13}$ | H | H | H | H |
| $(CH_2)_4C_6H_4$-4-$OC_6H_{13}$ | H | H | H | H |
| $(CH_2)_4C_6H_4$-3-$OC_{10}H_{21}$ | H | H | H | H |
| $CH_2CH=CHCH_2C_6H_4$-4-$OC_{10}H_{21}$ | H | H | H | H |
| $(CH_2)_4C_6H_4$-3-$OC_{12}H_{25}$ | H | H | H | H |
| $(CH_2)_4C_6H_4$-4-$OC_{12}H_{25}$ | H | H | H | H |
| $(CH_2)_4C_6H_4$-3-$OC_{20}H_{41}$ | H | H | H | H |
| $(CH_2)_4C_6H_4$-4-$OC_{20}H_{41}$ | H | H | H | H |
| $(CH_2)_5C_6H_4$-2-$OCH_3$ | H | H | H | H |
| $(CH_2)_5C_6H_4$-3-$OCH_3$ | H | H | H | H |
| $(CH_2)_5C_6H_4$-4-$OCH_3$ | H | H | H | H |
| $(CH_2)_5C_6H_4$-3-$OC_2H_5$ | H | H | H | H |
| $(CH_2)_5C_6H_4$-4-$OC_2H_5$ | H | H | H | H |
| $(CH_2)_5C_6H_4$-3-$OC_3H_7$ | H | H | H | H |
| $(CH_2)_5C_6H_4$-4-$OC_3H_7$ | H | H | H | H |
| $(CH_2)_5C_6H_4$-3-$OC_4H_9$ | H | H | H | H |
| $(CH_2)_5C_6H_4$-4-$OC_4H_9$ | H | H | H | H |
| $(CH_2)_5C_6H_4$-3-$OC_6H_{13}$ | H | H | H | H |
| $(CH_2)_5C_6H_4$-4-$OC_6H_{13}$ | H | H | H | H |
| $C\equiv C(CH_2)_3C_6H_4$-3-$OC_{10}H_{21}$ | H | H | H | H |
| $C\equiv C(CH_2)_3C_6H_{10}$-3-$OC_{10}H_{21}$ | H | H | H | H |
| $(CH_2)_5C_6H_4$-4-$OC_{10}H_{21}$ | H | H | H | H |
| $(CH_2)_5C_6H_4$-3-$OC_{12}H_{25}$ | H | H | H | H |
| $(CH_2)_5C_6H_4$-4-$OC_{12}H_{25}$ | H | H | H | H |
| $(CH_2)_5C_6H_4$-3-$OC_{20}H_{41}$ | H | H | H | H |
| $(CH_2)_5C_6H_4$-4-$OC_{20}H_{41}$ | H | H | H | H |
| $(CH_2)_7C_6H_4$-4-$OCH_3$ | H | H | H | H |
| $(CH_2)_7C_6H_4$-4-$OCH_3$ | $COCH_3$ | H | $COCH_3$ | $COCH_3$ |
| $(CH_2)_7C_6H_4$-3-$OC_7H_{15}$ | H | H | H | H |
| $(CH_2)_7C_6H_4$-4-$OC_6H_{13}$ | H | H | H | H |
| $(CH_2)_9C_6H_4$-2-$OC_5H_{11}$ | H | H | H | H |
| $(CH_2)_9C_6H_4$-3-$OC_5H_{11}$ | H | H | H | H |
| $(CH_2)_9C_6H_4$-4-$OC_4H_9$ | H | H | H | H |
| $(CH_2)_{11}C_6H_4$-3-$OC_3H_7$ | H | H | H | H |
| $(CH_2)_{11}C_6H_4$-3-$OC_2H_5$ | H | H | H | H |
| $(CH_2)_{13}C_6H_4$-3-$OCH_3$ | H | H | H | H |
| $C_6H_4$-3-$OCH=CH_2$ | H | H | H | H |
| $C_6H_4$-4-$OCH=CH_2$ | H | H | H | H |
| $CH_2C_6H_4$-3-$OCH=CH_2$ | H | H | H | H |
| $CH_2C_6H_4$-4-$OCH=CH_2$ | H | H | H | H |
| $CH_2C_6H_4$-3-$OCH_2CH=CH_2$ | H | H | H | H |
| $CH_2C_6H_4$-4-$OCH_2CH=CH_2$ | H | H | H | H |
| $CH_2C_6H_4$-3-$O(CH_2)_4CH=CHC_4H_9$ | H | H | H | H |
| $CH_2C_6H_4$-4-$O(CH_2)_7CH=CHCH_3$ | H | H | H | H |
| $(CH_2)_2C_6H_4$-3-$OCH_2CH=CH_2$ | H | H | H | H |
| $(CH_2)_2C_6H_4$-4-$OCH_2CH=CH_2$ | H | H | H | H |
| $(CH_2)_2C_6H_{10}$-4-$OCH_2CH=CH_2$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_2C_6H_4$-3-$O(CH_2)_4CH=CHC_4H_9$ | H | H | H | H |
| $(CH_2)_2C_6H_4$-4-$O(CH_2)_4CH=CHC_4H_9$ | H | H | H | H |
| $(CH_2)_3C_6H_4$-3-$OCH_2CH=CH_2$ | H | H | H | H |
| $(CH_2)_3C_6H_4$-4-$OCH_2CH=CH_2$ | H | H | H | H |
| $(CH_2)_3C_6H_4$-3-$O(CH_2)_4CH=CHC_4H_9$ | H | H | H | H |
| $(CH_2)_3C_6H_4$-4-$O(CH_2)_6CH=CHC_2H_5$ | H | H | H | H |
| $(CH_2)_9C_6H_4$-3-$OCH_2CH=CH_2$ | H | H | H | H |
| $(CH_2)_9C_6H_4$-4-$OCH_2CH=CH_2$ | H | H | H | H |
| $(CH_2)_9C_6H_4$-3-$O(CH_2)_4CH=CHC_4H_9$ | H | H | H | H |
| $(CH_2)_9C_6H_4$-4-$O(CH_2)_4CH=CHC_4H_9$ | H | H | H | H |
| $C_6H_4$-3-$OC\equiv CH$ | H | H | H | H |
| $C_6H_4$-4-$OC\equiv CH$ | H | H | H | H |
| $CH_2C_6H_4$-3-$OC\equiv CH$ | H | H | H | H |
| $CH_2C_6H_4$-4-$OC\equiv CH$ | H | H | H | H |
| $CH_2C_6H_4$-3-$OCH_2C\equiv CH$ | H | H | H | H |
| $CH_2C_6H_4$-4-$OCH_2C\equiv CH$ | H | H | H | H |
| $CH_2C_6H_4$-3-$O(CH_2)_4C\equiv CC_4H_9$ | H | H | H | H |
| $CH_2C_6H_4$-4-$O(CH_2)_4C\equiv CC_4H_9$ | H | H | H | H |
| $(CH_2)_2C_6H_4$-3-$OCH_2C\equiv CH$ | H | H | H | H |
| $(CH_2)_2C_6H_4$-4-$OCH_2C\equiv CH$ | H | H | H | H |
| $(CH_2)_2C_5H_8$-2-$OCH_2C\equiv CH$ | H | H | H | H |
| $(CH_2)_2C_6H_4$-3-$O(CH_2)_6C\equiv CC_2H_5$ | H | H | H | H |
| $(CH_2)_2C_6H_4$-4-$O(CH_2)_4C\equiv CC_4H_9$ | H | H | H | H |
| $(CH_2)_3C_6H_4$-3-$OCH_2C\equiv CH$ | H | H | H | H |
| $(CH_2)_3C_6H_4$-4-$OCH_2C\equiv CH$ | H | H | H | H |
| $(CH_2)_3C_6H_4$-3-$O(CH_2)_2C\equiv CC_6H_{13}$ | H | H | H | H |
| $(CH_2)_3C_6H_4$-4-$O(CH_2)_7C\equiv CCH_3$ | H | H | H | H |
| $(CH_2)_4C_6H_4$-2-$OCH_2C\equiv CH$ | H | H | H | H |
| $(CH_2)_4C_6H_4$-3-$OCH_2C\equiv CH$ | H | H | H | H |
| $(CH_2)_4C_6H_4$-4-$OCH_2C\equiv CH$ | H | H | H | H |
| $(CH_2)_4C_6H_4$-3-$O(CH_2)_2C\equiv CC_6H_{13}$ | H | H | H | H |
| $CH_2CH=CHCH_2C_6H_4$-4-$O(CH_2)_4C\equiv CC_4H_9$ | H | H | H | H |
| $(CH_2)_5C_6H_4$-3-$OCH_2C\equiv CH$ | H | H | H | H |
| $(CH_2)_2CH(C_2H_5)C_6H_4$-4-$OCH_2C\equiv CH$ | H | H | H | H |
| $(CH_2)_2CH(C_2H_5)C_6H_{10}$-4-$OCH_2C\equiv CH$ | H | H | H | H |
| $(CH_2)_5C_6H_4$-3-$O(CH_2)_5C\equiv CC_3H_7$ | H | H | H | H |
| $(CH_2)_5C_6H_4$-4-$O(CH_2)_5C\equiv CC_4H_9$ | H | H | H | H |
| $(CH_2)_7C_6H_4$-3-$OCH_2C\equiv CH$ | H | H | H | H |
| $(CH_2)_7C_6H_4$-4-$OCH_2C\equiv CH$ | H | H | H | H |
| $(CH_2)_7C_6H_4$-3-$O(CH_2)_5C\equiv CC_3H_7$ | H | H | H | H |
| $(CH_2)_2C\equiv C(CH_2)_3C_6H_4$-4-$O(CH_2)_7C\equiv CCH_3$ | H | H | H | H |
| $(CH_2)_9C_6H_4$-3-$OCH_2C\equiv CH$ | H | H | H | H |
| $(CH_2)_9C_6H_4$-4-$O(CH_2)_2C\equiv CCH_3$ | H | H | H | H |
| $(CH_2)_5CH(C_3H_7)C_6H_4$-3-$O(CH_2)_3C\equiv CC_5H_{11}$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| $(CH_2)_9C_6H_4$-4-$O(CH_2)_6C\equiv CC_2H_5$ | H | H | H | H |
| $(CH_2)_{11}C_6H_4$-3-$OCH_2C\equiv CH$ | H | H | H | H |
| $(CH_2)_3C\equiv C(CH_2)_6C_6H_4$-4-$O(CH_2)_2C\equiv CCH_3$ | H | H | H | H |
| $(CH_2)_{11}C_6H_4$-2-$O(CH_2)_2C\equiv CC_6H_{13}$ | H | H | H | H |
| $(CH_2)_{11}C_6H_4$-3-$O(CH_2)_2C\equiv CC_6H_{13}$ | H | H | H | H |
| $(CH_2)_{11}C_6H_4$-4-$O(CH_2)_8C\equiv CH$ | H | H | H | H |
| $(CH_2)_{13}C_6H_4$-3-$O(CH_2)_2C\equiv CC_2H_5$ | H | H | H | H |
| $(CH_2)_{13}C_6H_4$-4-$O(CH_2)_2C\equiv CCH_3$ | H | H | H | H |
| $(CH_2)_4CH=CH(CH_2)_3C_6H_4$-3-$O(CH_2)_2C\equiv CC_6H_{13}$ | H | H | H | H |
| $(CH_2)_{13}C_6H_4$-4-$O(CH_2)_8C\equiv CH$ | H | H | H | H |
| $C_6H_4$-4-$OCH_2C_6H_5$ | H | H | H | H |
| $C_6H_{10}$-4-$OCH_2C_6H_5$ | H | H | H | H |
| $C_6H_4$-4-$O(CH_2)_2C_6H_5$ | H | H | H | H |
| $C_6H_{10}$-4-$O(CH_2)_2C_6H_5$ | H | H | H | H |
| $C_6H_4$-2-$O(CH_2)_4C_6H_5$ | H | H | H | H |
| $C_6H_4$-4-$O(CH_2)_4C_6H_5$ | H | H | H | H |
| $C_6H_{10}$-4-$O(CH_2)_4C_6H_5$ | H | H | H | H |
| $C_6H_4$-4-$O(CH_2)_8C_6H_5$ | H | H | H | H |
| $C_6H_{10}$-4-$O(CH_2)_{10}C_6H_5$ | H | H | H | H |
| $C_6H_4$-4-$O(CH_2)_{12}C_6H_5$ | H | H | H | H |
| $C_6H_{10}$-4-$O(CH_2)_{14}C_6H_5$ | H | H | H | H |
| $(CH_2)_2C_6H_4$-2-$O(CH_2)_4C_6H_5$ | H | H | H | H |
| $(CH_2)_2C_6H_4$-3-$O(CH_2)_4C_6H_5$ | H | H | H | H |
| $(CH_2)_2C_6H_4$-4-$O(CH_2)_4C_6H_5$ | H | H | H | H |
| $(CH_2)_2C_6H_{10}$-4-$O(CH_2)_4C_6H_5$ | H | H | H | H |
| $(CH_2)_4C_6H_4$-4-$O(CH_2)_4C_6H_5$ | H | H | H | H |
| $(CH_2)_5CH(CH_3)C_6H_4$-4-$O(CH_2)_4C_6H_5$ | H | H | H | H |
| $CH_2CH=CHCH_2CH(C_2H_5)C_6H_4$-4-$O(CH_2)_4C_6H_5$ | H | H | H | H |
| $CH_2CH=CHCH_2CH(C_2H_5)C_6H_{10}$-4-$O(CH_2)_4C_6H_5$ | H | H | H | H |
| $(CH_2)_3C\equiv C(CH_2)_2C_6H_{10}$-4-$O(CH_2)_4C_6H_5$ | H | H | H | H |
| $(CH_2)_{11}C_6H_4$-4-$O(CH_2)_4C_6H_5$ | H | H | H | H |
| $(CH_2)_2C_6H_4$-4-$O(CH_2)_5C_6H_5$ | H | H | H | H |
| $(CH_2)_2C_{10}H_4$-4-$O(CH_2)_6C_6H_5$ | H | H | H | H |
| $(CH_2)_4C_6H_4$-4-$O(CH_2)_8C_6H_5$ | H | H | H | H |
| $(CH_2)_5CH(CH_3)C_6H_4$-4-$O(CH_2)_{10}C_6H_5$ | H | H | H | H |
| $CH_2CH=CHCH_2CH(C_2H_5)C_6H_4$-4-$O(CH_2)_{12}C_6H_5$ | H | H | H | H |
| $CH_2CH=CHCH_2CH(C_2H_5)C_6H_{10}$-4-$O(CH_2)_{13}C_6H_5$ | H | H | H | H |
| $(CH_2)_3C\equiv C(CH_2)_2C_6H_{10}$-4-$(CH_2)_3C_6H_5$ | H | H | H | H |
| $(CH_2)_{11}C_6H_4$-4-$(CH_2)_5C_6H_5$ | H | H | H | H |
| $C_6H_4$-4-$COCH_3$ | H | H | H | H |
| $C_6H_{10}$-4-$COCH_3$ | H | H | H | H |
| $C_6H_4$-4-$COC_2H_5$ | H | H | H | H |
| $C_6H_4$-4-$COC_5H_{11}$ | H | H | H | H |
| $C_6H_{10}$-4-$COC_7H_{15}$ | H | H | H | H |
| $C_6H_4$-4-$COC_{13}H_{27}$ | H | H | H | H |
| $CH_2C_6H_4$-2-$COCH_3$ | H | H | H | H |
| $CH_2C_6H_{10}$-2-$COCH_3$ | H | H | H | H |
| $CH_2C_6H_4$-3-$COCH_3$ | H | H | H | H |
| $CH_2C_6H_{10}$-3-$COCH_3$ | H | H | H | H |
| $CH_2C_6H_4$-4-$COCH_3$ | H | H | H | H |
| $CH_2C_6H_{10}$-4-$COCH_3$ | H | H | H | H |
| $(CH_2)_2C_6H_4$-4-$COCH_3$ | H | H | H | H |
| $(CH_2)_2C_6H_4$-4-$COC_6H_{13}$ | H | H | H | H |
| $(CH_2)_2C_6H_4$-4-$COC_9H_{19}$ | H | H | H | H |
| $(CH_2)_2C_6H_4$-4-$COC_{10}H_{21}$ | H | H | H | H |
| $(CH_2)_3C_6H_4$-4-$COC_3H_7$ | H | H | H | H |
| $(CH_2)_3C_6H_4$-4-$COC_9H_{19}$ | H | H | H | H |
| $(CH_2)_3C_6H_{10}$-4-$COC_3H_7$ | H | H | H | H |
| $(CH_2)_4C_6H_4$-4-$COCH_3$ | H | H | H | H |
| $(CH_2)_3CH(CH_3)C_6H_4$-3-$COC_5H_{11}$ | H | H | H | H |
| $CH=CHCH_2CH(CH_3)C_6H_4$-3-$COC_5H_{11}$ | | | | |
| $(CH_2)_7C_6H_4$-4-$COCH_3$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₇C₆H₁₀-4-COCH₃ | H | H | H | H |
| CH₂C≡C(CH₂)₄C₆H₁₀-4-COCH₃ | H | H | H | H |
| CH₂C₆H₄-4-COC₇H₁₅ | H | H | H | H |
| (CH₂)₉C₆H₄-2-COC₇H₁₅ | H | H | H | H |
| (CH₂)₉C₆H₄-3-COC₇H₁₅ | H | H | H | H |
| (CH₂)₉C₆H₄-4-COC₇H₁₅ | H | H | H | H |
| (CH₂)₉C₈H₁₄-4-COC₇H₁₅ | H | H | H | H |
| (CH₂)₁₁C₆H₄-4-COC₃H₇ | H | H | H | H |
| (CH₂)₆CH(C₄H₉)C₆H₄-4-COC₂H₅ | H | H | H | H |
| (CH₂)₁₃C₆H₄-4-COCH₃ | H | H | H | H |
| (CH₂)₁₀C≡CCH(CH₃)C₆H₄-4-COCH₃ | H | H | H | H |
| (CH₂)₁₀C≡CCH(CH₃)C₆H₄-4-COC₇H₁₅ | H | H | H | H |
| (CH₂)₁₄CH(CH₃)C₆H₄-4-COCH₃ | H | H | H | H |
| (CH₂)₁₇C₆H₄-4-COC₄H₉ | H | H | H | H |
| (CH₂)₉C₆H₄-4-COC₉H₁₉ | H | H | H | H |
| (CH₂)₉C₆H₁₀-4-COC₉H₁₉ | H | H | H | H |
| (CH₂)₈CH(CH₃)C₆H₁₀-4-COC₁₃H₂₇ | H | H | H | H |
| (CH₂)₂C₆H₄-4-COC₁₇H₃₅ | H | H | H | H |
| (CH₂)₃C₆H₄-4-COC₁₈H₃₇ | H | H | H | H |
| C₆H₄-4-NHCOCH₃ | H | H | H | H |
| C₆H₁₀-4-NHCOCH₃ | H | H | H | H |
| C₆H₄-4-NHCOC₂H₅ | H | H | H | H |
| C₆H₄-4-NHCOC₅H₁₁ | H | H | H | H |
| C₆H₁₀-4-NHCOC₇H₁₅ | H | H | H | H |
| C₆H₄-4-NHCOC₁₃H₂₇ | H | H | H | H |
| CH₂C₆H₄-4-NHCOCH₃ | H | H | H | H |
| CH₂C₆H₁₀-4-NHCOCH₃ | H | H | H | H |
| CH₂C₆H₄-2-NHCOCH₃ | H | H | H | H |
| CH₂C₆H₄-3-NHCOCH₃ | H | H | H | H |
| (CH₂)₂C₆H₄-4-NHCOCH₃ | H | H | H | H |
| (CH₂)₂C₆H₄-4-NHCOC₉H₁₉ | H | H | H | H |
| (CH₂)₂C₆H₄-4-NHCOC₉H₁₉ | COOC(CH₃)₃ | H | H | H |
| (CH₂)₃C₆H₄-4-NHCOC₃H₇ | H | H | H | H |
| (CH₂)₃C₆H₁₀-4-NHCOC₃H₇ | H | H | H | H |
| (CH₂)₄C₆H₄-4-NHCOCH₃ | H | H | H | H |
| (CH₂)₃CH(CH₃)C₆H₄-3-NHCOC₅H₁₁ | H | H | H | H |
| CH=CHCH₂CH(CH₃)C₆H₄-3-NHCOC₅H₁₁ | H | H | H | H |
| (CH₂)₇C₆H₄-4-NHCOCH₃ | H | H | H | H |
| (CH₂)₇C₆H₁₀-4-NHCOCH₃ | H | H | H | H |
| CH₂C≡C(CH₂)₄C₆H₁₀-4-NHCOCH₃ | H | H | H | H |
| CH₂C₆H₄-4-NHCOC₇H₁₅ | H | H | H | H |
| (CH₂)₉C₆H₄-4-NHCOC₇H₁₅ | H | H | H | H |
| (CH₂)₉C₈H₁₄-4-NHCOC₇H₁₅ | H | H | H | H |
| (CH₂)₁₁C₆H₄-4-NHCOC₃H₇ | H | H | H | H |
| (CH₂)₆CH(C₄H₉)C₆H₄-4-NHCOC₂H₅ | H | H | H | H |
| (CH₂)₁₃C₆H₄-4-NHCOCH₃ | H | H | H | H |
| (CH₂)₁₀C≡CCH(CH₃)C₆H₄-4-NHCOCH₃ | H | H | H | H |
| (CH₂)₁₀C≡CCH(CH₃)C₆H₄-4-NHCOC₇H₁₅ | H | H | H | H |
| (CH₂)₁₄CH(CH₃)C₆H₄-4-NHCOCH₃ | H | H | H | H |
| (CH₂)₁₇C₆H₄-4-NHCOC₄H₉ | H | H | H | H |
| (CH₂)₉C₆H₄-4-NHCOC₉H₁₉ | H | H | H | H |
| (CH₂)₉C₆H₁₀-4-NHCOC₉H₁₉ | H | H | H | H |
| (CH₂)₈CH(CH₃)C₆H₁₀-4-NHCOC₁₃H₂₇ | H | H | H | H |
| (CH₂)₂C₆H₄-4-NHCOC₁₇H₃₅ | H | H | H | H |
| (CH₂)₃C₆H₄-4-NHCOC₁₈H₃₇ | H | H | H | H |
| C₆H₄-4-OCOCH₃ | H | H | H | H |
| C₆H₁₀-4-OCOCH₃ | H | H | H | H |
| C₆H₄-4-OCOC₂H₅ | H | H | H | H |
| C₆H₄-2-OCOC₅H₁₁ | H | H | H | H |
| C₆H₄-4-OCOC₅H₁₁ | H | H | H | H |
| C₆H₁₀-4-OCOC₇H₁₅ | H | H | H | H |
| C₆H₄-4-OCOC₁₃H₂₇ | H | H | H | H |
| CH₂C₆H₄-4-OCOCH₃ | H | H | H | H |
| CH₂C₆H₁₀-4-OCOCH₃ | H | H | H | H |
| CH₂C₆H₄-3-OCOCH₃ | H | H | H | H |
| (CH₂)₂C₆-4-OCOCH₃ | H | H | H | H |
| (CH₂)₃C₆H₄-4-OCOC₃H₇ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₃C₆H₁₀-4-OCOC₃H₇ | H | H | H | H |
| (CH₂)₄C₆H₄-4-OCOCH₃ | H | H | H | H |
| (CH₂)₃CH(CH₃)C₆H₄-3-OCOC₅H₁₁ | H | H | H | H |
| CH=CHCH₂CH(CH₃)C₆H₄-3-OCOC₅H₁₁ | H | H | H | H |
| (CH₂)₇C₆H₄-4-OCOCH₃ | H | H | H | H |
| (CH₂)₇C₆H₁₀-4-OCOCH₃ | H | H | H | H |
| CH₂C≡C(CH₂)₄C₆H₁₀-4-OCOCH₃ | H | H | H | H |
| CH₂C₆H₄-2-OCOC₇H₁₅ | H | H | H | H |
| CH₂C₆H₄-3-OCOC₇H₁₅ | H | H | H | H |
| CH₂C₆H₄-4-OCOC₇H₁₅ | H | H | H | H |
| (CH₂)₉C₆H₄-4-OCOC₇H₁₅ | H | H | H | H |
| (CH₂)₉C₈H₁₄-4-OCOC₇H₁₅ | H | H | H | H |
| (CH₂)₁₁C₆H₄-4-OCOC₃H₇ | H | H | H | H |
| (CH₂)₆CH(C₄H₉)C₆H₄-4-OCOC₂H₅ | H | H | H | H |
| (CH₂)₁₃C₆H₄-2-OCOCH₃ | H | H | H | H |
| (CH₂)₁₃C₆H₄-3-OCOCH₃ | H | H | H | H |
| (CH₂)₁₃C₆H₄-4-OCOCH₃ | H | H | H | H |
| (CH₂)₁₀C≡CCH(CH₃)C₆H₄-4-OCOCH₃ | H | H | H | H |
| (CH₂)₁₀C≡CCH(CH₃)C₆H₄-4-OCOC₇H₁₅ | H | H | H | H |
| (CH₂)₁₄CH(CH₃)C₆H₄-4-OCOCH₃ | H | H | H | H |
| (CH₂)₁₇C₆H₄-4-OCOC₄H₉ | H | H | H | H |
| (CH₂)₉C₆H₄-4-OCOC₉H₁₉ | H | H | H | H |
| (CH₂)₉C₆H₁₀-4-OCOC₉H₁₉ | H | H | H | H |
| (CH₂)₈CH(CH₃)C₆H₁₀-4-OCOC₁₃H₂₇ | H | H | H | H |
| (CH₂)₂C₆H₄-4-OCOC₁₇H₃₅ | H | H | H | H |
| (CH₂)₃C₆H₄-4-OCOC₁₈H₃₇ | H | H | H | H |
| C₆H₄-4-COOCH₃ | H | H | H | H |
| C₆H₁₀-4-COOCH₃ | H | H | H | H |
| C₆H₄-4-COOC₂H₅ | H | H | H | H |
| C₆H₄-4-COOC₄H₉ | H | H | H | H |
| C₆H₁₀-2-COOC₈H₁₇ | H | H | H | H |
| C₆H₁₀-3-COOC₈H₁₇ | H | H | H | H |
| C₆H₁₀-4-COOC₈H₁₇ | H | H | H | H |
| C₆H₄-4-COOC₁₄H₂₉ | H | H | H | H |
| CH₂C₆H₄-4-COOCH₃ | H | H | H | H |
| CH₂C₆H₁₀-4-COOCH₃ | H | H | H | H |
| CH₂C₆H₄-3-COOCH₃ | H | H | H | H |
| (CH₂)₂C₆H₄-4-COOCH₃ | H | H | H | H |
| (CH₂)₃C₆H₄-4-COOC₄H₉ | H | H | H | H |
| (CH₂)₃C₆H₁₀-4-COOC₄H₉ | H | H | H | H |
| (CH₂)₄C₆H₄-4-COOCH₃ | H | H | H | H |
| (CH₂)₃CH(CH₃)C₆H₄-3-COOC₆H₁₃ | H | H | H | H |
| CH=CHCH₂CH(CH₃)C₆H₄-3-COOC₆H₁₃ | H | H | H | H |
| (CH₂)₇C₆H₄-2-COOCH₃ | H | H | H | H |
| (CH₂)₇C₆H₄-3-COOCH₃ | H | H | H | H |
| (CH₂)₇C₆H₄-4-COOCH₃ | H | H | H | H |
| (CH₂)₇C₆H₁₀-4-COOCH₃ | H | H | H | H |
| CH₂C≡C(CH₂)₄C₆H₁₀-4-COOCH₃ | H | H | H | H |
| CH₂C₆H₄-4-COOC₈H₁₇ | H | H | H | H |
| (CH₂)₉C₆H₄-4-COOC₈H₁₇ | H | H | H | H |
| (CH₂)₉C₈H₁₄-4-COOC₈H₁₇ | H | H | H | H |
| (CH₂)₁₁C₆H₄-4-COOC₄H₉ | H | H | H | H |
| (CH₂)₆CH(C₄H₉)C₆H₄-4-COOC₃H₇ | H | H | H | H |
| (CH₂)₁₃C₆H₄-4-COOCH₃ | H | H | H | H |
| (CH₂)₁₀C≡CCH(CH₃)C₆H₄-4-COOCH₃ | H | H | H | H |
| (CH₂)₁₀C≡CCH(CH₃)C₆H₄-4-COOC₈H₁₇ | H | H | H | H |
| (CH₂)₁₄CH(CH₃)C₆H₄-4-COOCH₃ | H | H | H | H |
| (CH₂)₁₇C₆H₄-4-COOC₅H₁₁ | H | H | H | H |
| (CH₂)₉C₆H₄-4-COOC₁₀H₂₁ | H | H | H | H |
| (CH₂)₉C₆H₁₀-4-COOC₁₀H₂₁ | H | H | H | H |
| (CH₂)₈CH(CH₃)C₆H₁₀-4-COOC₁₄H₂₉ | H | H | H | H |
| (CH₂)₂C₆H₄-4-COOC₁₈H₃₆ | H | H | H | H |
| (CH₂)₃C₆H₄-2-COOC₁₉H₃₉ | H | H | H | H |
| (CH₂)₃C₆H₄-3-COOC₁₉H₃₉ | H | H | H | H |
| (CH₂)₃C₆H₄-4-COOC₁₉H₃₉ | H | H | H | H |
| C₆H₄-4-NHCOOCH₃ | H | H | H | H |
| C₆H₁₀-4-NHCOOCH₃ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| C₆H₄-2-NHCOOC₂H₅ | H | H | H | H |
| C₆H₄-3-NHCOOC₂H₅ | H | H | H | H |
| C₆H₄-4-NHCOOC₂H₅ | H | H | H | H |
| C₆H₄-4-NHCOOC₄H₉ | H | H | H | H |
| C₆H₁₀-4-NHCOOC₈H₁₇ | H | H | H | H |
| C₆H₄-4-NHCOOC₁₄H₂₉ | H | H | H | H |
| CH₂C₆H₄-4-NHCOOCH₃ | H | H | H | H |
| CH₂C₆H₁₀-4-NHCOOCH₃ | H | H | H | H |
| CH₂C₆H₄-3-NHCOOCH₃ | H | H | H | H |
| (CH₂)₂C₆H₄-2-NHCOOCH₃ | H | H | H | H |
| (CH₂)₂C₆H₄-4-NHCOOCH₃ | H | H | H | H |
| (CH₂)₃C₆H₄-4-NHCOOC₄H₉ | H | H | H | H |
| (CH₂)₃C₆H₁₀-4-NHCOOC₄H₉ | H | H | H | H |
| (CH₂)₄C₆H₄-4-NHCOOCH₃ | H | H | H | H |
| (CH₂)₃CH(CH₃)C₆H₄-3-NHCOOC₆H₁₃ | H | H | H | H |
| CH=CHCH₂CH(CH₃)C₆H₄-3-NHCOOC₆H₁₃ | H | H | H | H |
| (CH₂)₇C₆H₄-4-NHCOOCH₃ | H | H | H | H |
| (CH₂)₇C₆H₁₀-4-NHCOOCH₃ | H | H | H | H |
| CH₂C≡C(CH₂)₄C₆H₁₀-4-NHCOOCH₃ | H | H | H | H |
| CH₂C₆H₄-4-NHCOOC₈H₁₇ | H | H | H | H |
| (CH₂)₉C₆H₄-4-NHCOOC₈H₁₇ | H | H | H | H |
| (CH₂)₉C₈H₁₇-4-NHCOOC₈H₁₇ | H | H | H | H |
| (CH₂)₁₁C₆H₄-4-NHCOOC₄H₉ | H | H | H | H |
| (CH₂)₆CH(C₄H₉)C₆H₄-4-NHCOOC₃H₇ | H | H | H | H |
| (CH₂)₁₃C₆H₄-4-NHCOOCH₃ | H | H | H | H |
| (CH₂)₁₀C≡CCH(CH₃)C₆H₄-4-NHCOOCH₃ | H | H | H | H |
| (CH₂)₁₀C≡CCH(CH₃)C₆H₄-4-NHCOOC₈H₁₇ | H | H | H | H |
| (CH₂)₁₄CH(CH₃)C₆H₄-4-NHCOOCH₃ | H | H | H | H |
| (CH₂)₁₇C₆H₄-4-NHCOOC₅H₁₁ | H | H | H | H |
| (CH₂)₉C₆H₄-4-NHCOOC₁₀H₂₁ | H | H | H | H |
| (CH₂)₉C₆H₁₀-4-NHCOOC₁₀H₂₁ | H | H | H | H |
| (CH₂)₈CH(CH₃)C₆H₁₀-4-NHCOOC₁₄H₂₉ | H | H | H | H |
| (CH₂)₂C₆H₄-4-NHCOOC₁₈H₃₇ | H | H | H | H |
| (CH₂)₃C₆H₄-4-NHCOOC₁₉H₃₉ | H | H | H | H |
| C₆H₄-4-NHCH₃ | H | H | H | H |
| C₆H₁₀-4-NHCH₃ | H | H | H | H |
| C₆H₄-4-NHC₂H₅ | H | H | H | H |
| C₆H₄-4-NHC₄H₉ | H | H | H | H |
| C₆H₁₀-4-NHC₈H₁₇ | H | H | H | H |
| C₆H₄-4-NHC₁₄H₂₉ | H | H | H | H |
| CH₂C₆H₄-4-NHCH₃ | H | H | H | H |
| CH₂C₆H₁₀-4-NHCH₃ | H | H | H | H |
| CH₂C₆H₄-3-NHCH₃ | H | H | H | H |
| CH₂C₆H₄-4-N(CH₃)C₁₀H₂₁ | H | H | H | H |
| CH₂C₆H₄-4-N(CH₃)C₁₀H₂₁ | COCH₃ | H | COCH₃ | COCH₃ |
| (CH₂)₂C₆H₄-4-NHCH₃ | H | H | H | H |
| (CH₂)₂C₆H₄-4-NHC₁₀H₂₁ | H | H | H | H |
| (CH₂)₃C₆H₄-4-NHC₄H₉ | H | H | H | H |
| (CH₂)₃C₆H₁₀-4-NHC₄H₉ | H | H | H | H |
| (CH₂)₄C₆H₄-4-NHCH₃ | H | H | H | H |
| (CH₂)₃CH(CH₃)C₆H₄-2-NHC₆H₁₃ | H | H | H | H |
| (CH₂)₃CH(CH₃)C₆H₄-3-NHC₆H₁₃ | H | H | H | H |
| CH=CHCH₂CH(CH₃)C₆H₄-3-NHC₆H₁₃ | H | H | H | H |
| (CH₂)₇C₆H₄-4-NHCH₃ | H | H | H | H |
| (CH₂)₇C₆H₁₀-4-NHCH₃ | H | H | H | H |
| CH₂C≡C(CH₂)₄C₆H₁₀-4-NHCH₃ | H | H | H | H |
| CH₂C₆H₄-4-NHC₈H₁₇ | H | H | H | H |
| (CH₂)₉C₆H₄-4-NHC₈H₁₇ | H | H | H | H |
| (CH₂)₉C₈H₁₄-4-NHC₈H₁₇ | H | H | H | H |
| (CH₂)₁₁C₆H₄-4-NHC₄H₉ | H | H | H | H |
| (CH₂)₆CH(C₄H₉)C₆H₄-4-NHC₃H₇ | H | H | H | H |
| (CH₂)₁₃C₆H₄-4-NHCH₃ | H | H | H | H |
| (CH₂)₁₀C≡CCH(CH₃)C₆H₄-4-NHCH₃ | H | H | H | H |
| (CH₂)₁₀C≡CCH(CH₃)C₆H₄-4-NHC₈H₁₇ | H | H | H | H |
| (CH₂)₁₄CH(CH₃)C₆H₄-4-NHCH₃ | H | H | H | H |
| (CH₂)₁₇C₆H₄-4-NHC₅H₁₁ | H | H | H | H |
| (CH₂)₉C₆H₄-4-NHC₁₀H₂₁ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₉C₆H₁₀-4-NHC₁₀H₂₁ | H | H | H | H |
| (CH₂)₈CH(CH₃)C₆H₁₀-4-NHC₁₄H₂₉ | H | H | H | H |
| (CH₂)₂C₆H₄-4-NHC₁₈H₃₇ | H | H | H | H |
| (CH₂)₃C₆H₄-4-NHC₁₉H₃₉ | H | H | H | H |
| C₆H₄-4-SCH₃ | H | H | H | H |
| C₆H₁₀-4-SCH₃ | H | H | H | H |
| C₆H₄-4-SC₂H₅ | H | H | H | H |
| C₆H₄-4-SC₄H₉ | H | H | H | H |
| C₆H₁₀-4-SC₈H₁₇ | H | H | H | H |
| C₆H₄-4-SC₈H₁₇ | H | H | H | H |
| C₆H₄-4-SC₈H₁₇ | COCH₃ | H | H | H |
| C₆H₄-4-SC₁₄H₂₉ | H | H | H | H |
| CH₂C₆H₄-2-SCH₃ | H | H | H | H |
| CH₂C₆H₄-3-SCH₃ | H | H | H | H |
| CH₂C₆H₄-4-SCH₃ | H | H | H | H |
| CH₂C₆H₁₀-2-SCH₃ | H | H | H | H |
| CH₂C₆H₄-2-SC₇H₁₅ | H | H | H | H |
| CH₂C₆H₄-2-SC₇H₁₅ | COCH₃ | H | COCH₃ | COCH₃ |
| (CH₂)₂C₆H₄-4-SCH₃ | H | H | H | H |
| (CH₂)₃C₆H₄-4-SC₄H₉ | H | H | H | H |
| (CH₂)₃C₆H₁₀-4-SC₄H₉ | H | H | H | H |
| (CH₂)₄C₆H₄-4-SCH₃ | H | H | H | H |
| (CH₂)₃CH(CH₃)C₆H₄-3-SC₆H₁₃ | H | H | H | H |
| CH=CHCH₂CH(CH₃)C₆H₄-3-SC₆H₁₃ | H | H | H | H |
| (CH₂)₇C₆H₄-4-SCH₃ | H | H | H | H |
| (CH₂)₇C₆H₁₀-4-SCH₃ | H | H | H | H |
| CH₂C≡C(CH₂)₄C₆H₁₀-4-SCH₃ | H | H | H | H |
| CH₂C₆H₄-4-SC₈H₁₇ | H | H | H | H |
| (CH₂)₉C₆H₄-4-SC₈H₁₇ | H | H | H | H |
| (CH₂)₉C₈H₁₄-4-SC₈H₁₇ | H | H | H | H |
| (CH₂)₁₁C₆H₄-4-SC₄H₉ | H | H | H | H |
| (CH₂)₆CH(C₄H₉)C₆H₄-4-SC₃H₇ | | | | |
| (CH₂)₁₃C₆H₄-4-SCH₃ | H | H | H | H |
| (CH₂)₁₀C≡CCH(CH₃)C₆H₄-4-SCH₃ | H | H | H | H |
| (CH₂)₁₀C≡CCH(CH₃)C₆H₄-4-SC₈H₁₇ | H | H | H | H |
| (CH₂)₁₄CH(CH₃)C₆H₄-4-SCH₃ | H | H | H | H |
| (CH₂)₁₇C₆H₄-4-SC₅H₁₁ | H | H | H | H |
| (CH₂)₉C₆H₄-4-SC₁₀H₂₁ | H | H | H | H |
| (CH₂)₉C₆H₁₀-4-SC₁₀H₂₁ | H | H | H | H |
| (CH₂)₈CH(CH₃)C₆H₁₀-4-SC₁₄H₂₉ | H | H | H | H |
| (CH₂)₂C₆H₄-4-SC₁₈H₃₇ | H | H | H | H |
| (CH₂)₃C₆H₄-4-SC₁₉H₃₉ | H | H | H | H |
| C₆H₄-4-CONHCH₃ | H | H | H | H |
| C₆H₁₀-4-CONHCH₃ | H | H | H | H |
| C₆H₄-4-CONHC₂H₅ | H | H | H | H |
| C₆H₄-4-CONHC₄H₉ | H | H | H | H |
| C₆H₁₀-4-CONHC₈H₁₇ | H | H | H | H |
| C₆H₄-4-CONHC₁₄H₂₉ | H | H | H | H |
| CH₂C₆H₄-4-CONHCH₃ | H | H | H | H |
| CH₂C₆H₁₀-4-CONHCH₃ | H | H | H | H |
| CH₂C₆H₄-2-CONHCH₃ | H | H | H | H |
| CH₂C₆H₄-3-CONHCH₃ | H | H | H | H |
| (CH₂)₂C₆H₄-4-CONHCH₃ | H | H | H | H |
| (CH₂)₃C₆H₄-4-CONHC₄H₉ | H | H | H | H |
| (CH₂)₃C₆H₁₀-4-CONHC₄H₉ | H | H | H | H |
| (CH₂)₄C₆H₄-4-CONHCH₃ | H | H | H | H |
| (CH₂)₃CH(CH₃)C₆H₄-3-CONHC₆H₁₃ | H | H | H | H |
| CH=CHCH₂CH(CH₃)C₆H₄-3-CONHC₆H₁₃ | H | H | H | H |
| (CH₂)₇C₆H₄-4-CONHCH₃ | H | H | H | H |
| (CH₂)₇C₆H₁₀-4-CONHCH₃ | H | H | H | H |
| CH₂C≡C(CH₂)₄C₆H₁₀-4-CONHCH₃ | H | H | H | H |
| CH₂C₆H₄-4-CONHC₈H₁₇ | H | H | H | H |
| (CH₂)₉C₆H₄-4-CONHC₈H₁₇ | H | H | H | H |
| (CH₂)₉C₈H₁₄-4-CONHC₈H₁₇ | H | H | H | H |
| (CH₂)₁₁C₆H₄-4-CONHC₄H₉ | H | H | H | H |
| (CH₂)₆CH(C₄H₉)C₆H₄-4-CONHC₃H₇ | H | H | H | H |
| (CH₂)₁₃C₆H₄-4-CONHCH₃ | H | H | H | H |
| (CH₂)₁₀C≡CCH(CH₃)C₆H₄-4-CONHCH₃ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH$_2$)$_{10}$C≡CCH(CH$_3$)C$_6$H$_4$-4-CONHC$_{18}$H$_{17}$ | H | H | H | H |
| (CH$_2$)$_{14}$CH(CH$_3$)C$_6$H$_4$-4-CONHCH$_3$ | H | H | H | H |
| (CH$_2$)$_{17}$C$_6$H$_4$-4-CONHC$_5$H$_{11}$ | H | H | H | H |
| (CH$_2$)$_9$C$_6$H$_4$-4-CONHC$_{10}$H$_{21}$ | H | H | H | H |
| (CH$_2$)$_9$C$_6$H$_{10}$-4-CONHC$_{10}$H$_{21}$ | H | H | H | H |
| (CH$_2$)$_8$CH(CH$_3$)C$_6$H$_{10}$-4-CONHC$_{14}$H$_{29}$ | H | H | H | H |
| (CH$_2$)$_2$C$_6$H$_4$-4-CONHC$_{18}$H$_{37}$ | H | H | H | H |
| (CH$_2$)$_3$C$_6$H$_4$-4-CONHC$_{19}$H$_{39}$ | H | H | H | H |
| C$_6$H$_4$-4-CH$_2$Br | H | H | H | H |
| C$_6$H$_{10}$-4-CH$_2$Br | H | H | H | H |
| C$_6$H$_4$-2-CH$_2$Br | H | H | H | H |
| C$_6$H$_{10}$-3-CH$_2$Br | H | H | H | H |
| C$_6$H$_4$-4-(CH$_2$)$_2$F | H | H | H | H |
| C$_6$H$_4$-3-(CH$_2$)$_4$Cl | H | H | H | H |
| C$_6$H$_{10}$-4-(CH$_2$)$_2$CHFC$_3$H$_7$ | H | H | H | H |
| C$_6$H$_4$-4-(CH$_2$)$_7$CHBrC$_6$H$_{13}$ | H | H | H | H |
| CH$_2$C$_6$H$_4$-4-CH$_2$Br | H | H | H | H |
| CH$_2$C$_6$H$_{10}$-2-CF$_3$ | H | H | H | H |
| CH$_2$C$_6$H$_{10}$-3-CF$_3$ | H | H | H | H |
| CH$_2$C$_6$H$_{10}$-4-CF$_3$ | H | H | H | H |
| CH$_2$C$_6$H$_4$-4-CH$_2$Cl | H | H | H | H |
| CH$_2$C$_6$H$_4$-3-CH$_2$Br | H | H | H | H |
| CH$_2$C$_6$H$_4$-4-(CH$_2$)$_8$F | H | H | H | H |
| CH$_2$C$_6$H$_4$-4-(CH$_2$)$_8$F | COCH$_3$ | H | COCH$_3$ | COCH$_3$ |
| CH$_2$C$_6$H$_4$-4-CF$_2$C$_7$H$_{15}$ | H | H | H | H |
| CH$_2$C$_6$H$_4$-4-CF$_2$C$_7$H$_{15}$ | COCH$_3$ | H | COCH$_3$ | COCH$_3$ |
| (CH$_2$)$_2$C$_6$H$_4$-4-CH$_2$Br | H | H | H | H |
| (CH$_2$)$_3$C$_6$H$_4$-4-(CH$_2$)$_4$Br | H | H | H | H |
| (CH$_2$)$_3$C$_6$H$_{10}$-4-(CH$_2$)Br | H | H | H | H |
| (CH$_2$)$_4$C$_6$H$_4$-4-CH$_2$Cl | H | H | H | H |
| (CH$_2$)$_5$C$_6$H$_4$-3-CH$_2$Br | H | H | H | H |
| CH=CHCH$_2$CH(CH$_3$)C$_6$H$_4$-3-(CH$_2$)$_2$CHClC$_3$H$_7$ | H | H | H | H |
| (CH$_2$)$_7$C$_6$H$_4$-4-CH$_2$F | H | H | H | H |
| (CH$_2$)$_7$C$_6$H$_{10}$-4-CH$_2$Br | H | H | H | H |
| CH$_2$C≡C(CH$_2$)$_4$C$_6$H$_{10}$-4-CH$_2$Br | H | H | H | H |
| CH$_2$C$_6$H$_4$-4-(CH$_2$)$_3$CHFC$_4$H$_9$ | H | H | H | H |
| (CH$_2$)$_9$C$_6$H$_4$-4-(CH$_2$)$_5$CHClC$_2$H$_5$ | H | H | H | H |
| (CH$_2$)$_9$C$_8$H$_{14}$-4-(CH$_2$)$_5$CHClC$_2$H$_5$ | H | H | H | H |
| (CH$_2$)$_{11}$C$_6$H$_4$-3-(CH$_2$)$_4$Cl | H | H | H | H |
| (CH$_2$)$_6$CH(C$_4$H$_9$)C$_6$H$_4$-2-CH$_2$CHBrCH$_3$ | H | H | H | H |
| (CH$_2$)$_{13}$C$_6$H$_4$-4-CH$_2$Br | H | H | H | H |
| (CH$_2$)$_{10}$C≡CCH(CH$_3$)C$_6$H$_4$-4-CH$_2$Br | H | H | H | H |
| (CH$_2$)$_{10}$C≡CCH(CH$_3$)C$_6$H$_4$-3-(CH$_2$)$_3$CHFC$_4$H$_9$ | H | H | H | H |
| (CH$_2$)$_{14}$CH(CH$_3$)C$_6$H$_4$-4-CH$_2$Br | H | H | H | H |
| (CH$_2$)$_{17}$C$_6$H$_4$-4-(CH$_2$)$_2$CHClC$_2$H$_5$ | H | H | H | H |
| (CH$_2$)$_9$C$_6$H$_4$-3-(CH$_2$)$_{10}$Cl | H | H | H | H |
| (CH$_2$)$_9$C$_6$H$_{10}$-4-(CH$_2$)$_7$CHClC$_2$H$_5$ | H | H | H | H |
| (CH$_2$)$_8$CH(CH$_3$)C$_6$H$_{10}$-3-(CH$_2$)$_3$CHFC$_{10}$H$_{21}$ | H | H | H | H |
| (CH$_2$)$_2$C$_6$H$_4$-3-(CH$_2$)$_9$CBr$_2$C$_8$H$_{17}$ | H | H | H | H |
| (CH$_2$)$_3$C$_6$H$_4$-4-(CH$_2$)$_{18}$CF$_3$ | H | H | H | H |
| C$_6$H$_4$-4-NH$_2$ | H | H | H | H |
| C$_6$H$_{10}$-4-NH$_2$ | H | H | H | H |
| CH$_2$C$_6$H$_4$-4-NH$_2$ | H | H | H | H |
| CH$_2$C$_6$H$_{10}$-4-NH$_2$ | H | H | H | H |
| CH$_2$C$_6$H$_4$-3-NH$_2$ | H | H | H | H |
| (CH$_2$)$_2$C$_6$H$_4$-4-NH$_2$ | H | H | H | H |
| (CH$_2$)$_3$C$_6$H$_4$-4-NH$_2$ | H | H | H | H |
| (CH$_2$)$_3$C$_6$H$_{10}$-2-NH$_2$ | H | H | H | H |
| (CH$_2$)$_3$C$_6$H$_{10}$-4-NH$_2$ | H | H | H | H |
| (CH$_2$)$_4$C$_6$H$_4$-4-NH$_2$ | H | H | H | H |
| (CH$_2$)$_5$C$_6$H$_4$-3-NH$_2$ | H | H | H | H |
| CH=CHCH$_2$CH(CH$_3$)C$_6$H$_4$-3-NH$_2$ | H | H | H | H |
| (CH$_2$)$_7$C$_6$H$_4$-4-NH$_2$ | H | H | H | H |
| (CH$_2$)$_7$C$_6$H$_{10}$-2-NH$_2$ | H | H | H | H |
| (CH$_2$)$_7$C$_6$H$_{10}$-4-NH$_2$ | H | H | H | H |
| CH$_2$C≡C(CH$_2$)$_4$C$_6$H$_{10}$-4-NH$_2$ | H | H | H | H |
| (CH$_2$)$_9$C$_6$H$_4$-4-NH$_2$ | H | H | H | H |
| (CH$_2$)$_9$C$_8$H$_{14}$-4-NH$_2$ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| (CH₂)₁₁C₆H₄-4-NH₂ | H | H | H | H |
| (CH₂)₆CH(C₄H₉)C₆H₄-4-NH₂ | H | H | H | H |
| (CH₂)₁₃C₆H₄-4-NH₂ | H | H | H | H |
| (CH₂)₁₀C≡CCH(CH₃)C₆H₄-4-NH₂ | H | H | H | H |
| (CH₂)₃CH[(CH₂)₆C≡CC₂H₅]C₆H₄-4-NH₂ | H | H | H | H |
| (CH₂)₁₄CH(CH₃)C₆H₄-3-NH₂ | H | H | H | H |
| (CH₂)₁₇C₆H₄-4-NH₂ | H | H | H | H |
| CH₂CH(C₇H₁₅)C₆H₁₀-4-NH₂ | H | H | H | H |
| (CH₂)₈CH(CH₃)C₆H₁₀-4-NH₂ | H | H | H | H |
| C₆H₄-4-NO₂ | H | H | H | H |
| C₆H₁₀-4-NO₂ | H | H | H | H |
| CH₂C₆H₄-4-NO₂ | H | H | H | H |
| CH₂C₆H₁₀-4-NO₂ | H | H | H | H |
| CH₂C₆H₄-3-NO₂ | H | H | H | H |
| (CH₂)₂C₆H₄-4-NO₂ | H | H | H | H |
| (CH₂)₂C₆H₄-4-NO₂ | COCH₃ | H | H | H |
| (CH₂)₃C₆H₄-4-NO₂ | H | H | H | H |
| (CH₂)₃C₆H₁₀-4-NO₂ | H | H | H | H |
| (CH₂)₄C₆H₄-4-NO₂ | H | H | H | H |
| (CH₂)₃CH(CH₃)C₆H₄-3-NO₂ | H | H | H | H |
| CH=CHCH₂CH(CH₃)C₆H₄-3-NO₂ | H | H | H | H |
| (CH₂)₇C₆H₄-4-NO₂ | H | H | H | H |
| (CH₂)₇C₆H₁₀-4-NO₂ | H | H | H | H |
| CH₂C≡C(CH₂)₄C₆H₁₀-4-NO₂ | H | H | H | H |
| (CH₂)₉C₆H₄-4-NO₂ | H | H | H | H |
| (CH₂)₉C₈H₁₄-4-NO₂ | H | H | H | H |
| (CH₂)₁₁C₆H₄-4-NO₂ | H | H | H | H |
| (CH₂)₆CH(C₄H₉)C₆H₄-4-NO₂ | H | H | H | H |
| (CH₂)₁₃C₆H₄-4-NO₂ | H | H | H | H |
| (CH₂)₁₀C≡CCH(CH₃)C₆H₄-4-NO₂ | H | H | H | H |
| (CH₂)₃CH[(CH₂)₆C≡CC₂H₅]C₆H₄-4-NO₂ | H | H | H | H |
| (CH₂)₁₄C≡CC₆H₄-3-NO₂ | H | H | H | H |
| (CH₂)₁₇C₆H₄-4-NO₂ | H | H | H | H |
| CH₂CH(C₇H₁₅)C₆H₁₀-4-NO₂ | H | H | H | H |
| (CH₂)₈CH(CH₃)C₆H₁₀-4-NO₂ | H | H | H | H |
| C₆H₄-4-OH | H | H | H | H |
| C₆H₁₀-4-OH | H | H | H | H |
| CH₂C₆H₄-4-OH | H | H | H | H |
| CH₂C₆H₄-4-OH | COCH₃ | H | COCH₃ | COCH₃ |
| CH₂C₆H₁₀-4-OH | H | H | H | H |
| CH₂C₆H₄-3-OH | H | H | H | H |
| (CH₂)₂C₆H₄-4-OH | H | H | H | H |
| (CH₂)₃C₆H₄-4-OH | H | H | H | H |
| (CH₂)₃C₆H₁₀-4-OH | H | H | H | H |
| (CH₂)₄C₆H₄-4-OH | H | H | H | H |
| (CH₂)₃CH(CH₃)C₆H₄-3-OH | H | H | H | H |
| CH=CHCH₂CH(CH₃)C₆H₄-3-OH | H | H | H | H |
| (CH₂)₇C₆H₄-4-OH | H | H | H | H |
| (CH₂)₇C₆H₁₀-4-OH | H | H | H | H |
| CH₂C≡C(CH₂)₄C₆H₁₀-4-OH | H | H | H | H |
| (CH₂)₉C₆H₄-2-OH | H | H | H | H |
| (CH₂)₉C₆H₄-4-OH | H | H | H | H |
| (CH₂)₉C₈H₁₄-4-OH | H | H | H | H |
| (CH₂)₁₁C₆H₄-4-OH | H | H | H | H |
| (CH₂)₆CH(C₄H₉)C₆H₄-4-OH | H | H | H | H |
| (CH₂)₁₃C₆H₄-4-OH | H | H | H | H |
| (CH₂)₁₀C≡CCH(CH₃)C₆H₄-4-OH | H | H | H | H |
| (CH₂)₃CH[(CH₂)₆C≡CC₂H₅]C₆H₄-4-OH | H | H | H | H |
| (CH₂)₁₄CH(CH₃)C₆H₄-3-OH | H | H | H | H |
| (CH₂)₁₇C₆H₄-4-OH | H | H | H | H |
| CH₂CH(C₇H₁₅)C₆H₁₀-4-OH | H | H | H | H |
| (CH₂)₈CH(CH₃)C₆H₁₀-4-OH | H | H | H | H |
| C₆H₄-4-COOH | H | H | H | H |
| C₆H₁₀-4-COOH | H | H | H | H |
| CH₂C₆H₄-4-COOH | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| CH₂C₆H₁₀-4-COOH | H | H | H | H |
| CH₂C₆H₄-3-COOH | H | H | H | H |
| (CH₂)₂C₆H₄-4-COOH | H | H | H | H |
| (CH₂)₃C₆H₄-4-COOH | H | H | H | H |
| (CH₂)₃C₆H₁₀-4-COOH | H | H | H | H |
| (CH₂)₄C₆H₄-4-COOH | H | H | H | H |
| (CH₂)₃CH(CH₃)C₆H₄-3-COOH | H | H | H | H |
| CH=CHCH₂CH(CH₃)C₆H₄-2-COOH | H | H | H | H |
| CH=CHCH₂CH(CH₃)C₆H₄-3-COOH | H | H | H | H |
| (CH₂)₇C₆H₄-4-COOH | H | H | H | H |
| (CH₂)₇C₆H₁₀-2-COOH | H | H | H | H |
| (CH₂)₇C₆H₁₀-3-COOH | H | H | H | H |
| (CH₂)₇C₆H₁₀-4-COOH | H | H | H | H |
| CH₂C≡C(CH₂)₄C₆H₁₀-4-COOH | H | H | H | H |
| (CH₂)₉C₆H₄-4-COOH | H | H | H | H |
| (CH₂)₉C₈H₁₄-4-COOH | H | H | H | H |
| (CH₂)₁₁C₆H₄-4-COOH | H | H | H | H |
| (CH₂)₆CH(C₄H₉)C₆H₄-4-COOH | H | H | H | H |
| (CH₂)₁₃C₆H₄-4-COOH | H | H | H | H |
| (CH₂)₁₀C≡CCH(CH₃)C₆H₄-4-COOH | H | H | H | H |
| (CH₂)₃CH[(CH₂)₆C≡CC₂H₅]C₆H₄-4-COOH | H | H | H | H |
| (CH₂)₁₄CH(CH₃)C₆H₄-3-COOH | H | H | H | H |
| (CH₂)₁₇C₆H₄-4-COOH | H | H | H | H |
| CH₂CH(C₇H₁₅)C₆H₁₀-4-COOH | H | H | H | H |
| (CH₂)₈CH(CH₃)C₆H₁₀-4-COOH | H | H | H | H |
| C₆H₄-4-Br | H | H | H | H |
| C₆H₁₀-4-Cl | H | H | H | H |
| CH₂C₆H₄-4-Br | H | H | H | H |
| CH₂C₆H₁₀-4-Cl | H | H | H | H |
| CH₂C₆H₄-4-Cl | H | H | H | H |
| CH₂C₆H₄-4-F | H | H | H | H |
| CH₂C₆H₄-4-F | COCH₃ | H | COCH₃ | COCH₃ |
| CH₂C₆H₄-3-F | H | H | H | H |
| (CH₂)₂C₆H₄-4-Br | H | H | H | H |
| (CH₂)₃C₆H₄-4-F | H | H | H | H |
| (CH₂)₃C₆H₄-4-Cl | H | H | H | H |
| (CH₂)₃C₆H₄-4-Cl | COCH₃ | H | COCH₃ | COCH₃ |
| (CH₂)₃C₆H₄-4-Br | H | H | H | H |
| (CH₂)₃C₆H₄-4-Br | COCH₃ | H | COCH₃ | COCH₃ |
| (CH₂)₃C₆H₄-4-I | H | H | H | H |
| (CH₂)₃C₆H₁₀-2-Br | H | H | H | H |
| (CH₂)₃C₆H₁₀-4-Br | H | H | H | H |
| (CH₂)₄C₆H₄-4-F | H | H | H | H |
| (CH₂)₃CH(CH₃)C₆H₄-2-Br | H | H | H | H |
| (CH₂)₃CH(CH₃)C₆H₄-3-Br | H | H | H | H |
| CH=CHCH₂CH(CH₃)C₆H₄-3-Br | H | H | H | H |
| (CH₂)₇C₆H₄-4-F | H | H | H | H |
| (CH₂)₇C₆H₁₀-4-Br | H | H | H | H |
| CH₂C≡C(CH₂)₄C₆H₁₀-4-Br | H | H | H | H |
| (CH₂)₉C₆H₄-4-F | H | H | H | H |
| (CH₂)₉C₈H₁₄-4-F | H | H | H | H |
| (CH₂)₁₁C₆H₄-4-Br | H | H | H | H |
| (CH₂)₆CH(C₄H₉)C₆H₄-4-F | H | H | H | H |
| (CH₂)₁₃C₆H₄-2-Br | H | H | H | H |
| (CH₂)₁₃C₆H₄-4-Br | H | H | H | H |
| (CH₂)₁₀C≡CCH(CH₃)C₆H₄-4-Cl | H | H | H | H |
| (CH₂)₃CH[(CH₂)₆C≡CC₂H₅]C₆H₄-4-Br | H | H | H | H |
| (CH₂)₁₄CH(CH₃)C₆H₄-3-Cl | H | H | H | H |
| (CH₂)₁₇C₆H₄-4-Br | H | H | H | H |
| CH₂CH(C₇H₁₅)C₆H₁₀-4-F | H | H | H | H |
| (CH₂)₈CH(CH₃)C₆H₁₀-4-Cl | H | H | H | H |
| CH₂C₆H₃(-4-NH₂)-3-Cl | H | H | H | H |
| CH₂C₆H₉(-4-NH₂)-2-CH₃ | H | H | H | H |
| CH₂C₆H₃(-2-NHCOCH₃)-4-OCH₃ | H | H | H | H |
| (CH₂)₃C₆H₉(-4-COOC₂H₅)-3-C₁₀H₂₁ | H | H | H | H |
| (CH₂)₄C₆H₂(-4-Br)(-3-C₂H₅)-2-COOH | H | H | H | H |
| (CH₂)₃CH(CH₃)C₆H₂(-3-C₄H₉)(-2-F)-4-NO₂ | H | H | H | H |

-continued $$\begin{array}{c} \text{CH}_2\text{OR}^4 \\ | \\ R^2R^3N-C-\text{CH}_2\text{OR}^5 \\ | \\ \text{CH}_2R^1 \end{array}$$

| R¹ | R² | R³ | R⁴ | R⁵ |
|---|---|---|---|---|
| CH₂C₆H₃(-3-F)-4-C₈H₁₇ | H | H | H | H |
| CH₂C₆H₃(-3-F)-4-C₈H₁₇ | COCH₃ | H | COCH₃ | COCH₃ |
| CH₂C₆H₃(-2-C₂H₅)-4-C₈H₁₇ | H | H | H | H |
| CH₂C₆H₃(-2-C₂H₅)-4-C₈H₁₇ | COCH₃ | H | COCH₃ | COCH₃ |
| CH₂C₆H₃(-3-CH₃)-4-C₈H₁₇ | H | H | H | H |
| CH₂C₆H₃(-3-CH₃)-4-C₈H₁₇ | COCH₃ | H | COCH₃ | COCH₃ |
| CH₂C₆H₃(-4-OC₇H₁₅)-3-OCH₃ | H | H | H | H |
| CH₂C₆H₃(-4-OC₇H₁₅)-3-OCH₃ | COCH₃ | H | COCH₃ | COCH₃ |
| CH₂C₆H₃(-4-OC₇H₁₅)-3-CH₃ | H | H | H | H |
| CH₂C₆H₃(-4-OC₇H₁₅)-3-CH₃ | COCH₃ | H | COCH₃ | COCH₃ |
| 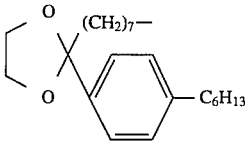 | H | H | H | H |
| 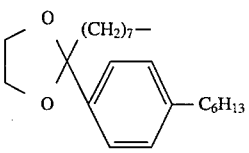 | COCH₃ | H | COCH₃ | COCH₃ |
| 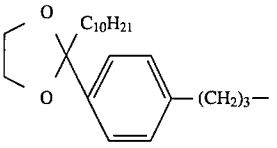 | H | H | H | H |
| 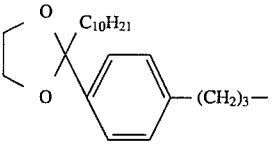 | COCH₃ | H | COCH₃ | COCH₃ |
| 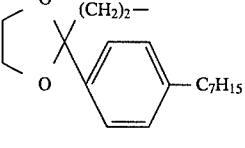 | H | H | H | H |
| 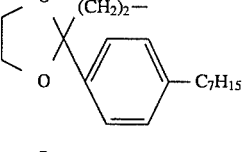 | COCH₃ | H | COCH₃ | COCH₃ |
| 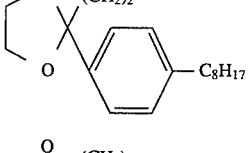 | H | H | H | H |
| 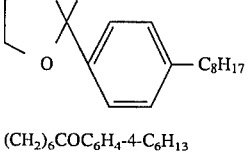 | COCH₃ | H | COCH₃ | COCH₃ |
| (CH₂)₆COC₆H₄-4-C₆H₁₃ | H | H | H | H |

-continued $$R^2R^3N-\underset{\underset{CH_2R^1}{|}}{\overset{\overset{CH_2OR^4}{|}}{C}}-CH_2OR^5$$

| R¹ | R² | R³ | R⁴ | R⁵ |
|---|---|---|---|---|
| COC₆H₄-4-C₇H₁₅ | H | H | H | H |
| COC₆H₄-4-C₇H₁₅ | COCH₃ | H | COCH₃ | COCH₃ |
| COC₆H₄-4-C₈H₁₅ | H | H | H | H |
| COC₆H₄-4-C₈H₁₅ | COCH₃ | H | COCH₃ | COCH₃ |
| CH(OH)C₆H₄-4-C₇H₁₅ | H | H | H | H |
| CH(OH)C₆H₄-4-C₇H₁₅ | COCH₃ | H | COCH₃ | COCH₃ |
| CH(OH)C₆H₄-4-C₈H₁₇ | H | H | H | H |
| CH(OH)C₆H₄-4-C₈H₁₇ | COCH₃ | H | COCH₃ | COCH₃ |
| (CH₂)₅OC₆H₄-4-OC₆H₁₃ | H | H | H | H |
| (CH₂)₅OC₆H₄-4-OC₆H₁₃ | COCH₃ | H | H | H |
| CH₂C₆H₄-4-O(CH₂)₇F | H | H | H | H |
| CH₂C₆H₄-4-O(CH₂)₇F | COCH₃ | H | COCH₃ | COCH₃ |
| CH₂C₆H₄-4-OCF₂C₆H₁₃ | H | H | H | H |
| CH₂C₆H₄-4-OCF₂C₆H₁₃ | COCH₃ | H | COCH₃ | COCH₃ |
| (CH₂)₈OC₆H₅ | H | H | H | H |
| (CH₂)₈OC₆H₅ | COCH₃ | H | COCH₃ | COCH₃ |
| (CH₂)₁₁OC₆H₅ | COCH₃ | H | H | H |
| (CH₂)₁₁OC₆H₅ | H | H | H | H |
| (CH₂)₅O(CH₂)₂OC₆H₅ | H | H | H | H |
| (CH₂)₅O(CH₂)₂OC₆H₅ | COCH₃ | H | COCH₃ | COCH₃ |
| CH₂C₆H₄OCH₂C₆H₅ | H | H | H | H |
| CH₂C₆H₄OCH₂C₆H₅ | COCH₃ | H | COCH₃ | COCH₃ |
| CH₂C₆H₄O(CH₂)₆C₆H₅ | H | H | H | H |
| CH₂C₆H₄O(CH₂)₆C₆H₅ | COCH₃ | H | COCH₃ | COCH₃ |
| CH₂C₆H₄CH₂O(CH₂)₅C₆H₅ | H | H | H | H |
| CH₂C₆H₄CH₂O(CH₂)₅C₆H₅ | COCH₃ | H | COCH₃ | COCH₃ |

$$R^2R^3N-\underset{\underset{R}{|}}{\overset{\overset{CH_2OR^4}{|}}{C}}-CH_2OR^5$$

| R | R² | R³ | R⁴ | R⁵ |
|---|---|---|---|---|
| [structure: chain with OH, OH, CH=CH, NH₂, CH₃] | H | H | H | H |
| [structure: chain with OH, OH, NH₂, CH₃] | H | H | H | H |
| [structure: chain with OH, CH=CH, NH₂, CH₃] | H | H | H | H |
| [structure: chain with OH, NH₂, CH₃] | H | H | H | H |
| [structure: chain with OH, OH, CH=CH, CH=CH, OH, CH₃] | H | H | H | H |
| [structure: chain with OH, CH₃] | H | H | H | H |

-continued

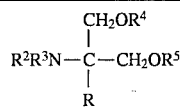

| R | R² | R³ | R⁴ | R⁵ |
|---|---|---|---|---|
| (structure: CH₃-CH(OH)-CH(OH)-CH₂-CH(OH)-CH(OH)-(CH₂)₁₂-CH₃) | H | H | H | H |
| (structure: CH₃-CH(OH)-CH₂-CH(OH)-CH₂-CH(OH)-CH(OH)-(CH₂)₁₂-CH₃) | H | H | H | H |
| (structure with 6 OH groups on long chain) | H | H | H | H |
| (structure: CH₃-CH(OH)-(CH₂)₁₂-C(=O)-(CH₂)₆-CH₃) | H | H | H | H |
| (structure: CH₃-CH(OH)-CH(OH)-CH₂-CH₂-OH) | H | H | H | H |
| (structure: CH₃-CH(OH)-(CH₂)₃-OH) | H | H | H | H |
| (structure: CH₃-CH(OH)-(CH₂)₁₂-C(=N-OH)-(CH₂)₆-CH₃) | H | H | H | H |

-continued

   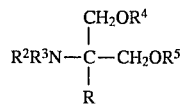

| R | R² | R³ | R⁴ | R⁵ | R | R² | R³ | R⁴ | R⁵ |
|---|---|---|---|---|---|---|---|---|---|
| C₆H₄-4-(CH₂)₃CH₃ | H | H | H | H | C₆H₄-4-O—(CH₂)₁₀CH₃ | H | H | H | H |
| C₆H₄-4-(CH₂)₄CH₃ | H | H | H | H | C₆H₄-4-O—(CH₂)₁₁CH₃ | H | H | H | H |
| C₆H₄-4-(CH₂)₅CH₃ | H | H | H | H | C₆H₄-4-O—(CH₂)₁₂CH₃ | H | H | H | H |
| C₆H₄-4-(CH₂)₆CH₃ | H | H | H | H | C₆H₄-4-O—(CH₂)₁₃CH₃ | H | H | H | H |
| C₆H₄-4-(CH₂)₇CH₃ | H | H | H | H | C₆H₄-4-O—(CH₂)₁₄CH₃ | H | H | H | H |
| C₆H₄-4-(CH₂)₈CH₃ | H | H | H | H | C₆H₄-4-O—(CH₂)₁₄CH₃ | H | H | H | H |
| C₆H₄-4-(CH₂)₉CH₃ | H | H | H | H | C₆H₄-4-O—(CH₂)₉F | H | H | H | H |
| C₆H₄-4-(CH₂)₁₀CH₃ | H | H | H | H | C₆H₄-4-O—(CH₂)₁₃F | H | H | H | H |
| C₆H₄-4-(CH₂)₁₁CH₃ | H | H | H | H | CH₂C₆H₄-4-S—(CH₂)₅CH₃ | H | H | H | H |
| C₆H₄-4-(CH₂)₁₂CH₃ | H | H | H | H | CH₂C₆H₄-4-S—(CH₂)₆CH₃ | H | H | H | H |
| C₆H₄-4-(CH₂)₁₃CH₃ | H | H | H | H | CH₂C₆H₄-4-S—(CH₂)₈CH₃ | H | H | H | H |
| C₆H₄-4-(CH₂)₁₄CH₃ | H | H | H | H | CH₂C₆H₄-4-S—(CH₂)₉CH₃ | H | H | H | H |
| C₆H₄-4-(CH₂)₁₅CH₃ | H | H | H | H | CH₂C₆H₄-4-S—(CH₂)₁₀CH₃ | H | H | H | H |
| C₆H₄-2-(CH₂)₉CH₃ | H | H | H | H | CH₂C₆H₄-4-S—(CH₂)₁₁CH₃ | H | H | H | H |
| C₆H₄-3-(CH₂)₉CH₃ | H | H | H | H | CH₂C₆H₄-4-S—(CH₂)₁₂CH₃ | H | H | H | H |
| C₆H₄-4-O—(CH₂)₃CH₃ | H | H | H | H | CH₂C₆H₄-4-S—(CH₂)₁₃CH₃ | H | H | H | H |
| C₆H₄-4-O—(CH₂)₄CH₃ | H | H | H | H | CH₂C₆H₄-4-S(=O)(CH₂)₅CH₃ | H | H | H | H |
| C₆H₄-4-O—(CH₂)₅CH₃ | H | H | H | H | CH₂C₆H₄-4-S(=O)(CH₂)₆CH₃ | H | H | H | H |
| C₆H₄-4-O—(CH₂)₆CH₃ | H | H | H | H | CH₂C₆H₄-4-S(=O)(CH₂)₇CH₃ | H | H | H | H |
| C₆H₄-4-O—(CH₂)₇CH₃ | H | H | H | H | CH₂C₆H₄-4-S(=O)(CH₂)₇CH₃ | COCH₃ | H | COCH₃ | COCH₃ |
| C₆H₄-4-O—(CH₂)₈CH₃ | H | H | H | H | CH₂C₆H₄-4-S(=O)(CH₂)₈CH₃ | H | H | H | H |
| C₆H₄-4-O—(CH₂)₉CH₃ | H | H | H | H | CH₂C₆H₄-4-S(=O)(CH₂)₉CH₃ | H | H | H | H |

89 -continued $$\begin{array}{c} CH_2OR^4 \\ | \\ R^2R^3N-C-CH_2OR^5 \\ | \\ R \end{array}$$

| R | $R^2$ | $R^3$ | $R^4$ | $R^5$ |
|---|---|---|---|---|
| $CH_2C_6H_4$-4-S(=O)$(CH_2)_{10}CH_3$ | H | H | H | H |
| $CH_2C_6H_4$-4-S(=O)$(CH_2)_{11}CH_3$ | H | H | H | H |
| $CH_2C_6H_4$-4-S(=O)$(CH_2)_{12}CH_3$ | H | H | H | H |
| $CH_2C_6H_4$-4-S(=O)$(CH_2)_{13}CH_3$ | H | H | H | H |
| $CH_2C_6H_4$-4-S(=O)$(CH_2)_5CH_3$ | H | H | H | H |
| $CH_2C_6H_4$-4-S(=O)$_2(CH_2)_6CH_3$ | H | H | H | H |
| $CH_2C_6H_4$-4-S(=O)$_2(CH_2)_7CH_3$ | H | H | H | H |
| $CH_2C_6H_4$-4-S(=O)$_2(CH_2)_7CH_3$ | $COCH_3$ | H | $COCH_3$ | $COCH_3$ |
| $CH_2C_6H_4$-4-S(=O)$_2(CH_2)_8CH_3$ | H | H | H | H |
| $CH_2C_6H_4$-4-S(=O)$_2(CH_2)_9CH_3$ | H | H | H | H |
| $CH_2C_6H_4$-4-S(=O)$_2(CH_2)_{10}CH_3$ | H | H | H | H |
| $CH_2C_6H_4$-4-S(=O)$_2(CH_2)_{11}CH_3$ | H | H | H | H |
| $CH_2C_6H_4$-4-S(=O)$_2(CH_2)_{12}CH_3$ | H | H | H | H |
| $CH_2C_6H_4$-4-S(=O)$_2(CH_2)_{13}CH_3$ | H | H | H | H |
| $(CH_2)_2C_6H_4$-4-S(=O)$(CH_2)_6CH_3$ | H | H | H | H |
| $(CH_2)_2C_6H_4$-4-S(=O)$(CH_2)_{10}CH_3$ | H | H | H | H |
| $(CH_2)_2C_6H_4$-4-S(=O)$_2(CH_2)_6CH_3$ | H | H | H | H |
| $(CH_2)_2C_6H_4$-4-S(=O)$_2(CH_2)_{10}CH_3$ | H | H | H | H |
| $(CH_2)_2C_6H_4$-4-$(CH_2)_8CH_3$ | H | H | H | H |
| $(CH_2)_2C_6H_4$-4-$(CH_2)_8CH_3$ | $COCH_3$ | H | $COCH_3$ | $COCH_3$ |
| $(CH_2)_2C_6H_4$-4-$(CH_2)_9CH_3$ | $COCH_3$ | H | $COCH_3$ | $COCH_3$ |
| $(CH_2)_2C_6H_4$-4-$(CH_2)_{10}CH_3$ | H | H | H | H |
| $(CH_2)_2C_6H_4$-4-$(CH_2)_{10}CH_3$ | $COCH_3$ | H | $COCH_3$ | $COCH_3$ |
| $(CH_2)_2C_6H_4$-4-$(CH_2)_{11}CH_3$ | $COCH_3$ | H | $COCH_3$ | $COCH_3$ |
| $(CH_2)_2C_6H_4$-4-$(CH_2)_{12}CH_3$ | H | H | H | H |
| $(CH_2)_2C_6H_4$-4-$(CH_2)_{12}CH_3$ | $COCH_3$ | H | $COCH_3$ | $COCH_3$ |
| $(CH_2)_2C_6H_4$-4-$(CH_2)_{13}CH_3$ | H | H | H | H |
| $(CH_2)_2C_6H_4$-4-$(CH_2)_{14}CH_3$ | $COCH_3$ | H | $COCH_3$ | $COCH_3$ |
| $(CH_2)_2C_6H_4$-4-O-$(CH_2)_{12}CH_3$ | H | H | H | H |
| $(CH_2)_2C_6H_4$-4-O-$(CH_2)_{12}CH_3$ | $COCH_3$ | H | $COCH_3$ | $COCH_3$ |
| $(CH_2)_2C_6H_4$-4-O-$(CH_2)_{13}CH_3$ | H | H | H | H |
| $(CH_2)_2C_6H_4$-4-O-$(CH_2)_{13}CH_3$ | $COCH_3$ | H | $COCH_3$ | $COCH_3$ |
| $(CH_2)_2C_6H_4$-4-$(CH_2)_7F$ | H | H | H | H |
| $(CH_2)_2C_6H_4$-4-$(CH_2)_7F$ | $COCH_3$ | H | $COCH_3$ | $COCH_3$ |
| $(CH_2)_2C_6H_4$-4-$(CH_2)_{12}F$ | H | H | H | H |
| $(CH_2)_2C_6H_4$-4-$(CH_2)_{12}F$ | $COCH_3$ | H | $COCH_3$ | $COCH_3$ |
| $(CH_2)_2C_6H_4$-4-O-$(CH_2)_7F$ | H | H | H | H |
| $(CH_2)_2C_6H_4$-4-O-$(CH_2)_7F$ | $COCH_3$ | H | $COCH_3$ | $COCH_3$ |
| $(CH_2)_2C_6H_4$-4-O-$(CH_2)_8F$ | H | H | H | H |
| $(CH_2)_2C_6H_4$-4-O-$(CH_2)_8F$ | $COCH_3$ | H | $COCH_3$ | $COCH_3$ |
| $(CH_2)_2C_6H_4$-4-O-$(CH_2)_{11}F$ | H | H | H | H |
| $(CH_2)_2C_6H_4$-4-O-$(CH_2)_{11}F$ | $COCH_3$ | H | $COCH_3$ | $COCH_3$ |
| $(CH_2)_2C_6H_{10}$-4-$(CH_2)_4CH_3$ | H | H | H | H |
| $(CH_2)_2C_6H_{10}$-4-$(CH_2)_5CH_3$ | H | H | H | H |
| $(CH_2)_2C_6H_{10}$-4-$(CH_2)_6CH_3$ | H | H | H | H |
| $(CH_2)_2C_6H_{10}$-4-$(CH_2)_7CH_3$ | H | H | H | H |
| $(CH_2)_2C_6H_{10}$-4-$(CH_2)_7CH_3$ | $COCH_3$ | H | $COCH_3$ | $COCH_3$ |
| $(CH_2)_2C_6H_{10}$-4-$(CH_2)_9CH_3$ | H | H | H | H |
| $(CH_2)_2C_6H_{10}$-4-$(CH_2)_{10}CH_3$ | H | H | H | H |
| $(CH_2)_2C_6H_{10}$-4-$(CH_2)_{11}CH_3$ | H | H | H | H |
| $(CH_2)_2C_6H_{10}$-4-$(CH_2)_{11}CH_3$ | $COCH_3$ | H | $COCH_3$ | $COCH_3$ |
| $(CH_2)_2C_6H_{10}$-4-$(CH_2)_{12}CH_3$ | H | H | H | H |
| $(CH_2)_2C_6H_{10}$-4-$(CH_2)_{13}CH_3$ | H | H | H | H |
| $(CH_2)_{11}C_6H_5$ | H | H | H | H |
| $(CH_2)_{15}C_6H_5$ | H | H | H | H |
| $(CH_2)_{17}C_6H_5$ | H | H | H | H |
| $(CH_2)_{19}C_6H_5$ | H | H | H | H |
| $(CH_2)_8C_6H_4$-4-F | H | H | H | H |
| $(CH_2)_9C_6H_4$-4-F | H | H | H | H |
| $(CH_2)_{10}C_6H_4$-3-F | H | H | H | H |
| $(CH_2)_{10}C_6H_4$-3-F | $COCH_3$ | H | $COCH_3$ | $COCH_3$ |
| $(CH_2)_{11}C_6H_4$-4-F | H | H | H | H |
| $(CH_2)_{12}C_6H_4$-4-F | H | H | H | H |
| $(CH_2)_{13}C_6H_4$-4-F | H | H | H | H |
| $(CH_2)_{10}C_6H_4$-4-F | $COCH_3$ | H | $COCH_3$ | $COCH_3$ |
| $(CH_2)_{14}C_6H_4$-4-F | H | H | H | H |
| $(CH_2)_{15}C_6H_4$-4-F | H | H | H | H |
| $(CH_2)_{16}C_6H_4$-4-F | H | H | H | H |
| $(CH_2)_{17}C_6H_4$-4-F | H | H | H | H |
| $(CH_2)_{18}C_6H_4$-4-F | H | H | H | H |
| $(CH_2)_{19}C_6H_4$-4-F | H | H | H | H |
| $(CH_2)_{20}C_6H_4$-4-F | H | H | H | H |
| $(CH_2)_6O(CH_2)_2C_6H_5$ | H | H | H | H |

90 -continued $$\begin{array}{c} CH_2OR^4 \\ | \\ R^2R^3N-C-CH_2OR^5 \\ | \\ R \end{array}$$

| R | $R^2$ | $R^3$ | $R^4$ | $R^5$ |
|---|---|---|---|---|
| $(CH_2)_6O(CH_2)_2C_6H_5$ | $COCH_3$ | H | $COCH_3$ | $COCH_3$ |
| $(CH_2)_8OCH_2C_6H_5$ | H | H | H | H |
| $(CH_2)_8OCH_2C_6H_5$ | $COCH_3$ | H | $COCH_3$ | $COCH_3$ |
| $(CH_2)_2C_6H_4$-4-$OCH_2C_6H_5$ | H | H | H | H |
| $(CH_2)_2C_6H_4$-4-$OCH_2C_6H_5$ | $COCH_3$ | H | $COCH_3$ | $COCH_3$ |
| $(CH_2)_2C_6H_4$-4-O-$(CH_2)_2C_6H_5$ | H | H | H | H |
| $(CH_2)_2C_6H_4$-4-O-$(CH_2)_3C_6H_5$ | H | H | H | H |
| $(CH_2)_2C_6H_4$-4-O-$(CH_2)_4C_6H_5$ | H | H | H | H |
| $(CH_2)_2C_6H_4$-4-O-$(CH_2)_5C_6H_5$ | H | H | H | H |
| $(CH_2)_2C_6H_4$-4-O-$(CH_2)_7C_6H_5$ | H | H | H | H |
| $(CH_2)_2C_6H_4$-4-O-$(CH_2)_8C_6H_5$ | H | H | H | H |
| $(CH_2)_2C_6H_4$-4-O-$(CH_2)_3OC_6H_5$ | H | H | H | H |
| $(CH_2)_2C_6H_4$-4-O-$(CH_2)_4OC_6H_5$ | H | H | H | H |
| $(CH_2)_2C_6H_4$-4-O-$(CH_2)_5OC_6H_5$ | H | H | H | H |
| $(CH_2)_2C_6H_4$-4-O-$(CH_2)_6OC_6H_5$ | H | H | H | H |
| $(CH_2)_2C_6H_4$-4-O-$(CH_2)_7OC_6H_5$ | H | H | H | H |
| $(CH_2)_2C_6H_4$-4-O-$(CH_2)_8OC_6H_5$ | H | H | H | H |
| $(CH_2)_2C_6H_4$-4-$(CH_2)_3OC_6H_5$ | H | H | H | H |
| $(CH_2)_2C_6H_4$-4-$(CH_2)_4OC_6H_5$ | H | H | H | H |
| $(CH_2)_2C_6H_4$-4-$(CH_2)_5OC_6H_5$ | H | H | H | H |
| $(CH_2)_2C_6H_4$-4-$(CH_2)_6OC_6H_5$ | H | H | H | H |
| $(CH_2)_2C_6H_4$-4-$(CH_2)_7OC_6H_5$ | H | H | H | H |
| $(CH_2)_2C_6H_4$-4-$(CH_2)_8OC_6H_5$ | H | H | H | H |
| $(CH_2)_2C_6H_4$-4-O-$(CH_2)_2C_6H_4$-4-F | H | H | H | H |
| $(CH_2)_2C_6H_4$-4-O-$(CH_2)_3C_6H_4$-4-F | H | H | H | H |
| $(CH_2)_2C_6H_4$-4-O-$(CH_2)_4C_6H_4$-4-F | H | H | H | H |
| $(CH_2)_2C_6H_4$-4-O-$(CH_2)_5C_6H_4$-4-F | H | H | H | H |
| $(CH_2)_2C_6H_4$-4-O-$(CH_2)_5C_6H_4$-4-F | $COCH_3$ | H | $COCH_3$ | $COCH_3$ |
| $(CH_2)_2C_6H_4$-4-O-$(CH_2)_6C_6H_4$-4-F | H | H | H | H |
| $(CH_2)_2C_6H_4$-4-O-$(CH_2)_6C_6H_4$-4-F | $COCH_3$ | H | $COCH_3$ | $COCH_3$ |
| $(CH_2)_2C_6H_4$-4-O-$(CH_2)_7C_6H_4$-4-F | H | H | H | H |
| $(CH_2)_2C_6H_4$-4-O-$(CH_2)_8C_6H_4$-4-F | H | H | H | H |
| $(CH_2)_2C_6H_4$-4-$OCH_2C_6H_4$-4-F | H | H | H | H |
| $(CH_2)_2C_6H_4$-4-O-$(CH_2)_2C_6H_4$-4-F | H | H | H | H |
| $(CH_2)_2C_6H_4$-4-O-$(CH_2)_3C_6H_4$-4-F | H | H | H | H |
| $(CH_2)_2C_6H_4$-4-O-$(CH_2)_4C_6H_4$-4-F | H | H | H | H |
| $(CH_2)_2C_6H_4$-4-O-$(CH_2)_5C_6H_4$-4-F | H | H | H | H |
| $(CH_2)_2C_6H_4$-4-O-$(CH_2)_7C_6H_4$-4-F | H | H | H | H |
| $(CH_2)_2C_6H_4$-4-O-$(CH_2)_8C_6H_4$-4-F | H | H | H | H |
| $(CH_2)_2C_6H_4$-4-O-$(CH_2)_3OC_6H_4$-4-F | H | H | H | H |
| $(CH_2)_2C_6H_4$-4-O-$(CH_2)_4OC_6H_4$-4-F | H | H | H | H |
| $(CH_2)_2C_6H_4$-4-O-$(CH_2)_5OC_6H_4$-4-F | H | H | H | H |
| $(CH_2)_2C_6H_4$-4-O-$(CH_2)_6OC_6H_4$-4-F | H | H | H | H |
| $(CH_2)_2C_6H_4$-4-O-$(CH_2)_7OC_6H_4$-4-F | H | H | H | H |
| $(CH_2)_2C_6H_4$-4-O-$(CH_2)_8OC_6H_4$-4-F | H | H | H | H |
| $(CH_2)_2C_6H_4$-4-$(CH_2)_3OC_6H_4$-4-F | H | H | H | H |
| $(CH_2)_2C_6H_4$-4-$(CH_2)_4OC_6H_4$-4-F | H | H | H | H |
| $(CH_2)_2C_6H_4$-4-$(CH_2)_5OC_6H_4$-4-F | H | H | H | H |
| $(CH_2)_2C_6H_4$-4-$(CH_2)_6OC_6H_4$-4-F | H | H | H | H |
| $(CH_2)_2C_6H_4$-4-$(CH_2)_7OC_6H_4$-4-F | H | H | H | H |
| $(CH_2)_2C_6H_4$-4-$(CH_2)_8OC_6H_4$-4-F | H | H | H | H |
| $CH_2CH(OH)C_6H_4$-4-$(CH_2)_5CH_3$ | H | H | H | H |
| $CH_2CH(OH)C_6H_4$-4-$(CH_2)_6CH_3$ | H | H | H | H |
| $CH_2CHFC_6H_4$-4-$(CH_2)_7CH_3$ | H | H | H | H |
| $CH_2CHFC_6H_4$-4-$(CH_2)_7CH_3$ | $COCH_3$ | H | $COCH_3$ | $COCH_3$ |
| $CH_2CHFC_6H_4$-4-$(CH_2)_8CH_3$ | H | H | H | H |
| $CH_2CH(OH)C_6H_4$-4-$(CH_2)_9CH_3$ | H | H | H | H |
| $CH_2CH(OH)C_6H_4$-4-$(CH_2)_{10}CH_3$ | H | H | H | H |
| $CH_2CH(OH)C_6H_4$-4-$(CH_2)_{11}CH_3$ | H | H | H | H |
| $CH_2CH(OH)C_6H_4$-4-$(CH_2)_{11}CH_3$ | $COCH_3$ | H | $COCH_3$ | $COCH_3$ |
| $CH_2CH(OH)C_6H_4$-4-$(CH_2)_{12}CH_3$ | H | H | H | H |
| $CH_2CH(OH)C_6H_4$-4-$(CH_2)_{13}CH_3$ | H | H | H | H |
| $CH(OH)CH(OH)C_6H_4$-4-$(CH_2)_5CH_3$ | H | H | H | H |
| $CH(OH)CH(OH)C_6H_4$-4-$(CH_2)_6CH_3$ | H | H | H | H |
| $CH(OH)CH(OH)C_6H_4$-4-$(CH_2)_7CH_3$ | H | H | H | H |
| $CH(OH)CH(OH)C_6H_4$-4-$(CH_2)_7CH_3$ | $COCH_3$ | H | $COCH_3$ | $COCH_3$ |
| $CH(OH)CH(OH)C_6H_4$-4-$(CH_2)_8CH_3$ | H | H | H | H |
| $CH(OH)CH(OH)C_6H_4$-4-$(CH_2)_9CH_3$ | H | H | H | H |
| $CH(OH)CH(OH)C_6H_4$-4-$(CH_2)_{10}CH_3$ | H | H | H | H |
| $CH(OH)CH(OH)C_6H_4$-4-$(CH_2)_{11}CH_3$ | H | H | H | H |
| $CH(OH)CH(OH)C_6H_4$-4-$(CH_2)_{11}CH_3$ | $COCH_3$ | H | $COCH_3$ | $COCH_3$ |
| $CH(OH)CH(OH)C_6H_4$-4-$(CH_2)_{12}CH_3$ | H | H | H | H |
| $CH(OH)CH_2C_6H_5$ | H | H | H | H |

91 -continued $$R^2R^3N-\underset{R}{\underset{|}{C}}(CH_2OR^4)(CH_2OR^5)$$

| R | $R^2$ | $R^3$ | $R^4$ | $R^5$ |
|---|---|---|---|---|
| CH(OH)CH$_2$C$_6$H$_4$-4-(CH$_2$)$_5$CH$_3$ | H | H | H | H |
| CH(OH)CH$_2$C$_6$H$_4$-4-(CH$_2$)$_6$CH$_3$ | H | H | H | H |
| CH(OH)CH$_2$C$_6$H$_4$-4-(CH$_2$)$_6$CH$_3$ | COCH$_3$ | H | H | H |
| CH(OH)CH$_2$C$_6$H$_4$-4-(CH$_2$)$_7$CH$_3$ | H | H | H | H |
| CH(OH)CH$_2$C$_6$H$_4$-4-(CH$_2$)$_7$CH$_3$ | COCH$_3$ | H | H | H |
| CH(OH)CH$_2$C$_6$H$_4$-4-(CH$_2$)$_8$CH$_3$ | H | H | H | H |
| CH(OH)CH$_2$C$_6$H$_4$-4-(CH$_2$)$_9$CH$_3$ | H | H | H | H |
| CH(OH)CH$_2$C$_6$H$_4$-4-(CH$_2$)$_{10}$CH$_3$ | H | H | H | H |
| CH(OH)CH$_2$C$_6$H$_4$-4-(CH$_2$)$_{11}$CH$_3$ | H | H | H | H |
| CH(OH)CH$_2$C$_6$H$_4$-4-(CH$_2$)$_{11}$CH$_3$ | COCH$_3$ | H | COCH$_3$ | COCH$_3$ |
| CH(OH)CH$_2$C$_6$H$_4$-4-(CH$_2$)$_{12}$CH$_3$ | H | H | H | H |
| CH(OH)CH$_2$C$_6$H$_4$-4-(CH$_2$)$_{13}$CH$_3$ | H | H | H | H |
| CH(OH)CH$_2$C$_6$H$_4$-4-O—(CH$_2$)$_6$CH$_3$ | H | H | H | H |
| [CH(OH)]$_2$C$_6$H$_4$-4-O—(CH$_2$)$_6$C$_6$H$_5$ | H | H | H | H |
| CH$_2$CH(OH)C$_6$H$_4$-4-O—(CH$_2$)$_6$C$_6$H$_5$ | H | H | H | H |
| CH(OH)CH$_2$C$_6$H$_4$-4-O—(CH$_2$)$_6$C$_6$H$_5$ | COCH$_3$ | H | COCH$_3$ | COCH$_3$ |
| [CH(OH)]$_2$C$_6$H$_4$-4-O—(CH$_2$)$_6$C$_6$H$_5$ | COCH$_3$ | H | COCH$_3$ | COCH$_3$ |
| CH$_2$CH(OH)C$_6$H$_4$-4-O—(CH$_2$)$_6$C$_6$H$_5$ | COCH$_2$ | H | COCH$_3$ | COCH$_3$ |
| CH=CHC$_6$H$_4$-4-(CH$_2$)$_5$CH$_3$ | H | H | H | H |
| CH=CHC$_6$H$_4$-4-(CH$_2$)$_6$CH$_3$ | H | H | H | H |
| CH=CHC$_6$H$_4$-4-(CH$_2$)$_7$CH$_3$ | H | H | H | H |
| CH=CHC$_6$H$_4$-4-(CH$_2$)$_7$CH$_3$ | COCH$_3$ | H | COCH$_3$ | COCH$_3$ |
| CH=CHC$_6$H$_4$-4-(CH$_2$)$_8$CH$_3$ | H | H | H | H |
| CH=CHC$_6$H$_4$-4-(CH$_2$)$_9$CH$_3$ | H | H | H | H |
| CH=CHC$_6$H$_4$-4-(CH$_2$)$_{10}$CH$_3$ | H | H | H | H |
| CH=CHC$_6$H$_4$-4-(CH$_2$)$_{11}$CH$_3$ | H | H | H | H |
| CH=CHC$_6$H$_4$-4-(CH$_2$)$_{11}$CH$_3$ | COCH$_3$ | H | COCH$_3$ | COCH$_3$ |
| CH=CHC$_6$H$_4$-4-(CH$_2$)$_{12}$CH$_3$ | H | H | H | H |
| CH=CHC$_6$H$_4$-4-(CH$_2$)$_{13}$CH$_3$ | H | H | H | H |
| CH$_2$CH=CHCH$_2$C$_6$H$_4$-4-(CH$_2$)$_4$CH$_3$ | H | H | H | H |
| CH$_2$CH=CHCH$_2$C$_6$H$_4$-4-(CH$_2$)$_5$CH$_3$ | H | H | H | H |
| CH$_2$CH=CHCH$_2$C$_6$H$_4$-4-(CH$_2$)$_5$CH$_3$ | COCH$_3$ | H | COCH$_3$ | COCH$_3$ |
| CH$_2$CH=CHCH$_2$C$_6$H$_4$-4-(CH$_2$)$_6$CH$_3$ | H | H | H | H |
| CH$_2$CH=CHCH$_2$C$_6$H$_4$-4-(CH$_2$)$_7$CH$_3$ | H | H | H | H |
| CH$_2$CH=CHCH$_2$C$_6$H$_4$-4-(CH$_2$)$_8$CH$_3$ | H | H | H | H |
| CH$_2$CH=CHCH$_2$C$_6$H$_4$-4-(CH$_2$)$_9$CH$_3$ | H | H | H | H |
| CH$_2$CH=CHCH$_2$C$_6$H$_4$-4-(CH$_2$)$_9$CH$_3$ | COCH$_3$ | H | COCH$_3$ | COCH$_3$ |
| CH$_2$CH=CHCH$_2$C$_6$H$_4$-4-(CH$_2$)$_{10}$CH$_3$ | H | H | H | H |
| CH$_2$CH=CHCH$_2$C$_6$H$_4$-4-(CH$_2$)$_{11}$CH$_3$ | H | H | H | H |
| CH$_2$OC$_6$H$_4$-4-(CH$_2$)$_5$CH$_3$ | H | H | H | H |
| CH$_2$OC$_6$H$_4$-4-(CH$_2$)$_6$CH$_3$ | H | H | H | H |
| CH$_2$OC$_6$H$_4$-4-(CH$_2$)$_7$CH$_3$ | H | H | H | H |
| CH$_2$OC$_6$H$_4$-4-(CH$_2$)$_7$CH$_3$ | COCH$_3$ | H | COCH$_3$ | COCH$_3$ |
| CH$_2$OC$_6$H$_4$-4-(CH$_2$)$_8$CH$_3$ | H | H | H | H |
| CH$_2$OC$_6$H$_4$-4-(CH$_2$)$_9$CH$_3$ | H | H | H | H |
| CH$_2$OC$_6$H$_4$-4-(CH$_2$)$_{10}$CH$_3$ | H | H | H | H |

92 -continued $$R^2R^3N-\underset{R}{\underset{|}{C}}(CH_2OR^4)(CH_2OR^5)$$

| R | $R^2$ | $R^3$ | $R^4$ | $R^5$ |
|---|---|---|---|---|
| CH$_2$OC$_6$H$_4$-4-(CH$_2$)$_{11}$CH$_3$ | H | H | H | H |
| CH$_2$OC$_6$H$_4$-4-(CH$_2$)$_{11}$CH$_3$ | COCH$_3$ | H | COCH$_3$ | COCH$_3$ |
| CH$_2$OC$_6$H$_4$-4-(CH$_2$)$_{12}$CH$_3$ | H | H | H | H |
| CH$_2$OC$_6$H$_4$-4-(CH$_2$)$_{13}$CH$_3$ | H | H | H | H |
| CH$_2$OCH$_2$C$_6$H$_5$ | H | H | H | H |
| CH$_2$OCH$_2$C$_6$H$_5$ | COCH$_3$ | H | COCH$_3$ | COCH$_3$ |
| CH$_2$OCH$_2$C$_6$H$_4$-4-(CH$_2$)$_6$CH$_3$ | H | H | H | H |
| CH$_2$O(CH$_2$)$_2$C$_6$H$_4$-4-(CH$_2$)$_5$CH$_3$ | H | H | H | H |
| CH$_2$O(CH$_2$)$_3$C$_6$H$_4$-4-(CH$_2$)$_4$CH$_3$ | H | H | H | H |
| CH$_2$O(CH$_2$)$_4$C$_6$H$_4$-4-(CH$_2$)$_3$CH$_3$ | H | H | H | H |
| CH$_2$O(CH$_2$)$_5$C$_6$H$_4$-4-(CH$_2$)$_2$CH$_3$ | H | H | H | H |
| CH$_2$O(CH$_2$)$_6$C$_6$H$_4$-4-CH$_2$CH$_3$ | H | H | H | H |
| CH$_2$O(CH$_2$)$_7$C$_6$H$_4$-4-CH$_3$ | H | H | H | H |
| CH$_2$O(CH$_2$)$_8$C$_6$H$_5$ | H | H | H | H |
| CH$_2$O(CH$_2$)$_{11}$C$_6$H$_5$ | H | H | H | H |
| CH$_2$OC$_6$H$_4$-4-O(CH$_2$)$_4$C$_6$H$_5$ | H | H | H | H |
| CH$_2$OC$_6$H$_4$-4-O(CH$_2$)$_5$C$_6$H$_5$ | H | H | H | H |
| CH$_2$OC$_6$H$_4$-4-O(CH$_2$)$_6$C$_6$H$_5$ | H | H | H | H |
| CH$_2$OC$_6$H$_4$-4-O(CH$_2$)$_6$C$_6$H$_5$ | COCH$_3$ | H | COCH$_3$ | COCH$_3$ |
| CH$_2$OC$_6$H$_4$-4-O(CH$_2$)$_6$C$_6$H$_4$-4-F | H | H | H | H |
| CH$_2$OC$_6$H$_4$-4-O(CH$_2$)$_7$C$_6$H$_5$ | H | H | H | H |
| CH$_2$OC$_6$H$_4$-4-O(CH$_2$)$_8$C$_6$H$_5$ | H | H | H | H |
| CH$_2$OC$_6$H$_4$-4-O(CH$_2$)$_9$C$_6$H$_5$ | H | H | H | H |
| (CH$_2$)$_2$C$_6$H$_3$(3-OCH$_3$)-4-OC$_{11}$H$_{23}$ | H | H | H | H |
| (CH$_2$)$_2$C$_6$H$_3$(3-OCH$_3$)-4-OC$_{11}$H$_{23}$ | COCH$_3$ | H | COCH$_3$ | COCH$_3$ |
| (CH$_2$)$_2$C$_6$H$_3$(2-F)-4-(CH$_2$)$_7$CH$_3$ | H | H | H | H |
| (CH$_2$)$_2$C$_6$H$_3$(2-F)-4-(CH$_2$)$_7$CH$_3$ | COCH$_3$ | H | COCH$_3$ | COCH$_3$ |
| (CH$_2$)$_2$C$_6$H$_3$(2-F)-4-(CH$_2$)$_{11}$CH$_3$ | H | H | H | H |
| (CH$_2$)$_2$C$_6$H$_3$(2-F)-4-(CH$_2$)$_{11}$CH$_3$ | COCH$_3$ | H | COCH$_3$ | COCH$_3$ |
| (CH$_2$)$_2$C$_6$H$_3$(3-F)-4-O(CH$_2$)$_6$CH$_3$ | H | H | H | H |
| (CH$_2$)$_2$C$_6$H$_3$(3-F)-4-O(CH$_2$)$_6$CH$_3$ | COCH$_3$ | H | COCH$_3$ | COCH$_3$ |
| (CH$_2$)$_2$C$_6$H$_3$(3-F)-4-O(CH$_2$)$_{10}$CH$_3$ | H | H | H | H |
| (CH$_2$)$_2$C$_6$H$_3$(3-F)-4-O(CH$_2$)$_{10}$CH$_3$ | COCH$_3$ | H | COCH$_3$ | COCH$_3$ |
| (CH$_2$)$_2$C$_6$H$_3$(2-F)-4-O(CH$_2$)$_6$CH$_3$ | H | H | H | H |
| (CH$_2$)$_2$C$_6$H$_3$(2-F)-4-O(CH$_2$)$_6$CH$_3$ | COCH$_3$ | H | COCH$_3$ | COCH$_3$ |
| (CH$_2$)$_2$C$_6$H$_3$(2-F)-4-O(CH$_2$)$_{10}$CH$_3$ | H | H | H | H |
| (CH$_2$)$_2$C$_6$H$_3$(2-F)-4-O(CH$_2$)$_{10}$CH$_3$ | COCH$_3$ | H | COCH$_3$ | COCH$_3$ |
| (CH$_2$)$_2$C$_6$H$_4$-4-N(CH$_3$)C$_7$H$_{15}$ | H | H | H | H |
| (CH$_2$)$_2$C$_6$H$_4$-4-N(CH$_3$)C$_7$H$_{15}$ | COCH$_3$ | H | COCH$_3$ | COCH$_3$ |
| (CH$_2$)$_2$C$_6$H$_4$-4-N(CH$_3$)C$_{11}$H$_{23}$ | H | H | H | H |
| (CH$_2$)$_2$C$_6$H$_4$-4-N(CH$_3$)C$_{11}$H$_{23}$ | COCH$_3$ | H | COCH$_3$ | COCH$_3$ |
| (CH$_2$)$_2$C$_6$H$_4$-4-NHCOC$_6$H$_{13}$ | H | H | H | H |
| (CH$_2$)$_2$C$_6$H$_4$-4-NHCOC$_6$H$_{13}$ | COCH$_3$ | H | COCH$_3$ | COCH$_3$ |
| (CH$_2$)$_2$C$_6$H$_4$-4-NHCOC$_{10}$H$_{21}$ | H | H | H | H |
| (CH$_2$)$_2$C$_6$H$_4$-4-NHCOC$_{10}$H$_{21}$ | COCH$_3$ | H | COCH$_3$ | COCH$_3$ |

$$R^2R^3N-\underset{R}{\underset{|}{C}}(CH_2OR^4)(CH_2OR^5)$$

| R | $R^2$ | $R^3$ | $R^4$ | $R^5$ |
|---|---|---|---|---|
| 2-C$_4$H$_2$S-4-(CH$_2$)$_{10}$CH$_3$ | H | H | H | H |
| CH$_2$-2-C$_4$H$_2$S-4-(CH$_2$)$_9$CH$_3$ | H | H | H | H |
| CH$_2$-2-C$_4$H$_2$S-4-(CH$_2$)$_9$CH$_3$ | COCH$_3$ | H | COCH$_3$ | COCH$_3$ |
| (CH$_2$)$_2$-2-C$_4$H$_2$S-4-(CH$_2$)$_8$CH$_3$ | H | H | H | H |
| (CH$_2$)$_2$-2-C$_4$H$_2$S-4-(CH$_2$)$_8$CH$_3$ | COCH$_3$ | H | COCH$_3$ | COCH$_3$ |
| (CH$_2$)$_3$-2-C$_4$H$_2$S-4-(CH$_2$)$_7$CH$_3$ | H | H | H | H |
| (CH$_2$)$_4$-2-C$_4$H$_2$S-4-(CH$_2$)$_6$CH$_3$ | H | H | H | H |
| (CH$_2$)$_4$-2-C$_4$H$_2$S-4-(CH$_2$)$_6$CH$_3$ | COCH$_3$ | H | COCH$_3$ | COCH$_3$ |
| (CH$_2$)$_5$-2-C$_4$H$_2$S-4-(CH$_2$)$_5$CH$_3$ | H | H | H | H |
| (CH$_2$)$_5$-2-C$_4$H$_2$S-4-(CH$_2$)$_5$CH$_3$ | COCH$_3$ | H | COCH$_3$ | COCH$_3$ |
| (CH$_2$)$_6$-2-C$_4$H$_2$S-4-(CH$_2$)$_4$CH$_3$ | H | H | H | H |
| (CH$_2$)$_6$-2-C$_4$H$_2$S-4-(CH$_2$)$_4$CH$_3$ | COCH$_3$ | H | COCH$_3$ | COCH$_3$ |
| (CH$_2$)$_7$-2-C$_4$H$_2$S-4-(CH$_2$)$_3$CH$_3$ | H | H | H | H |
| (CH$_2$)$_7$-2-C$_4$H$_2$S-4-(CH$_2$)$_3$CH$_3$ | COCH$_3$ | H | COCH$_3$ | COCH$_3$ |
| (CH$_2$)$_8$-2-C$_4$H$_2$S-4-(CH$_2$)$_2$CH$_3$ | H | H | H | H |

-continued $$R^2R^3N-\underset{\underset{R}{|}}{\overset{\overset{CH_2OR^4}{|}}{C}}-CH_2OR^5$$

| R | $R^2$ | $R^3$ | $R^4$ | $R^5$ |
|---|---|---|---|---|
| $(CH_2)_9$-2-$C_4H_2$S-4-$CH_2CH_3$ | H | H | H | H |
| $(CH_2)_9$-2-$C_4H_2$S-4-$CH_2CH_3$ | $COCH_3$ | H | $COCH_3$ | $COCH_3$ |
| $(CH_2)_{10}$-2-$C_4H_2$S-4-$CH_3$ | H | H | H | H |
| $(CH_2)_{10}$-2-$C_4H_2$S-4-$CH_3$ | $COCH_3$ | H | $COCH_3$ | $COCH_3$ |
| $(CH_2)_{11}$-2-$C_4H_3$S | H | H | H | H |
| $(CH_2)_{12}$-2-$C_4H_3$S | H | H | H | H |
| $(CH_2)_{13}$-2-$C_4H_3$S | H | H | H | H |
| $(CH_2)_{13}$-2-$C_4H_3$S | $COCH_3$ | H | $COCH_3$ | $COCH_3$ |
| $(CH_2)_{14}$-2-$C_4H_3$S | H | H | H | H |
| $(CH_2)_{15}$-2-$C_4H_3$S | H | H | H | H |
| $(CH_2)_{15}$-2-$C_4H_3$S | $COCH_3$ | H | $COCH_3$ | $COCH_3$ |
| $(CH_2)_{16}$-2-$C_4H_3$S | H | H | H | H |
| $(CH_2)_{17}$-2-$C_4H_3$S | H | H | H | H |
| $(CH_2)_{18}$-2-$C_4H_3$S | H | H | H | H |
| $(CH_2)_{18}$-2-$C_4H_3$S | $COCH_3$ | H | $COCH_3$ | $COCH_3$ |
| $(CH_2)_2$-2-$C_4H_2$S-4-$(CH_2)_7CH_3$ | H | H | H | H |
| $(CH_2)_2$-2-$C_4H_2$S-4-$(CH_2)_9CH_3$ | H | H | H | H |
| $(CH_2)_2$-2-$C_4H_2$S-4-$(CH_2)_9CH_3$ | $COCH_3$ | H | $COCH_3$ | $COCH_3$ |
| $(CH_2)_2$-2-$C_4H_2$S-4-$(CH_2)_{10}CH_3$ | H | H | H | H |
| $(CH_2)_2$-2-$C_4H_2$S-4-$(CH_2)_{10}CH_3$ | $COCH_3$ | H | $COCH_3$ | $COCH_3$ |
| $(CH_2)_2$-2-$C_4H_2$S-4-$(CH_2)_{11}CH_3$ | H | H | H | H |
| $(CH_2)_2$-2-$C_4H_2$S-4-$(CH_2)_{11}CH_3$ | $COCH_3$ | H | $COCH_3$ | $COCH_3$ |
| $(CH_2)_2$-2-$C_4H_2$S-4-$(CH_2)_{12}CH_3$ | H | H | H | H |
| $(CH_2)_2$-2-$C_4H_2$S-4-$(CH_2)_{12}CH_3$ | $COCH_3$ | H | $COCH_3$ | $COCH_3$ |
| $(CH_2)_2$-2-$C_4H_2$S-4-$CH_2C_6H_5$ | H | H | H | H |
| $(CH_2)_2$-2-$C_4H_2$S-4-$(CH_2)_2C_6H_5$ | H | H | H | H |
| $(CH_2)_2$-2-$C_4H_2$S-4-$(CH_2)_3C_6H_5$ | H | H | H | H |
| $(CH_2)_2$-2-$C_4H_2$S-4-$(CH_2)_4C_6H_5$ | H | H | H | H |
| $(CH_2)_2$-2-$C_4H_2$S-4-$(CH_2)_5C_6H_5$ | H | H | H | H |
| $(CH_2)_2$-2-$C_4H_2$S-4-$(CH_2)_6C_6H_5$ | H | H | H | H |
| $(CH_2)_2$-2-$C_4H_2$S-4-$(CH_2)_6C_6H_5$ | $COCH_3$ | H | $COCH_3$ | $COCH_3$ |
| $(CH_2)_2$-2-$C_4H_2$S-4-$(CH_2)_7C_6H_5$ | H | H | H | H |
| $(CH_2)_2$-2-$C_4H_2$S-4-$(CH_2)_7C_6H_5$ | $COCH_3$ | H | $COCH_3$ | $COCH_3$ |
| $(CH_2)_2$-2-$C_4H_2$S-4-$(CH_2)_8C_6H_5$ | H | H | H | H |
| $(CH_2)_2$-2-$C_4H_2$S-4-$(CH_2)_8C_6H_5$ | $COCH_3$ | H | $COCH_3$ | $COCH_3$ |
| $(CH_2)_2$-2-$C_4H_2$S-4-$(CH_2)_9C_6H_5$ | H | H | H | H |
| $(CH_2)_2$-2-$C_4H_2$S-4-$(CH_2)_9C_6H_5$ | $COCH_3$ | H | $COCH_3$ | $COCH_3$ |
| $(CH_2)_2$-2-$C_4H_2$S-4-$(CH_2)_{10}C_6H_5$ | H | H | H | H |
| $(CH_2)_2$-2-$C_4H_2$S-4-$(CH_2)_{10}C_6H_5$ | $COCH_3$ | H | $COCH_3$ | $COCH_3$ |
| $(CH_2)_2-C_6H_4$-4-$CH_2$-2-$C_4H_3$S | H | H | H | H |
| $(CH_2)_2-C_6H_4$-4-$(CH_2)_2$-2-$C_4H_3$S | H | H | H | H |
| $(CH_2)_2-C_6H_4$-4-$(CH_2)_3$-2-$C_4H_3$S | H | H | H | H |
| $(CH_2)_2-C_6H_4$-4-$(CH_2)_4$-2-$C_4H_3$S | H | H | H | H |
| $(CH_2)_2-C_6H_4$-4-$(CH_2)_5$-2-$C_4H_3$S | H | H | H | H |
| $(CH_2)_2-C_6H_4$-4-$(CH_2)_6$-2-$C_4H_3$S | H | H | H | H |
| $(CH_2)_2-C_6H_4$-4-$(CH_2)_6$-2-$C_4H_3$S | $COCH_3$ | H | $COCH_3$ | $COCH_3$ |
| $(CH_2)_2-C_6H_4$-4-$(CH_2)_7$-2-$C_4H_3$S | H | H | H | H |
| $(CH_2)_2-C_6H_4$-4-$(CH_2)_7$-2-$C_4H_3$S | $COCH_3$ | H | $COCH_3$ | $COCH_3$ |
| $(CH_2)_2-C_6H_4$-4-$(CH_2)_8$-2-$C_4H_3$S | H | H | H | H |
| $(CH_2)_2-C_6H_4$-4-$(CH_2)_8$-2-$C_4H_3$S | $COCH_3$ | H | $COCH_3$ | $COCH_3$ |
| $(CH_2)_2-C_6H_4$-4-$(CH_2)_9$-2-$C_4H_3$S | H | H | H | H |
| $(CH_2)_2-C_6H_4$-4-$(CH_2)_9$-2-$C_4H_3$S | $COCH_3$ | H | $COCH_3$ | $COCH_3$ |
| $(CH_2)_2-C_6H_4$-4-$(CH_2)_{10}$-2-$C_4H_3$S | H | H | H | H |
| $(CH_2)_2-C_6H_4$-4-$(CH_2)_{10}$-2-$C_4H_3$S | $COCH_3$ | H | $COCH_3$ | $COCH_3$ |
| $(CH_2)_2-C_6H_4$-4-$CH_2$-3-$C_4H_3$S | H | H | H | H |
| $(CH_2)_2-C_6H_4$-4-$(CH_2)_2$-3-$C_4H_3$S | H | H | H | H |
| $(CH_2)_2-C_6H_4$-4-$(CH_2)_3$-3-$C_4H_3$S | H | H | H | H |
| $(CH_2)_2-C_6H_4$-4-$(CH_2)_4$-3-$C_4H_3$S | H | H | H | H |
| $(CH_2)_2-C_6H_4$-4-$(CH_2)_5$-3-$C_4H_3$S | H | H | H | H |
| $(CH_2)_2-C_6H_4$-4-$(CH_2)_6$-3-$C_4H_3$S | H | H | H | H |
| $(CH_2)_2-C_6H_4$-4-$(CH_2)_6$-3-$C_4H_3$S | $COCH_3$ | H | $COCH_3$ | $COCH_3$ |
| $(CH_2)_2-C_6H_4$-4-$(CH_2)_7$-3-$C_4H_3$S | H | H | H | H |
| $(CH_2)_2-C_6H_4$-4-$(CH_2)_7$-3-$C_4H_3$S | $COCH_3$ | H | $COCH_3$ | $COCH_3$ |
| $(CH_2)_2-C_6H_4$-4-$(CH_2)_8$-3-$C_4H_3$S | H | H | H | H |
| $(CH_2)_2-C_6H_4$-4-$(CH_2)_8$-3-$C_4H_3$S | $COCH_3$ | H | $COCH_3$ | $COCH_3$ |
| $(CH_2)_2-C_6H_4$-4-$(CH_2)_9$-3-$C_4H_3$S | H | H | H | H |
| $(CH_2)_2-C_6H_4$-4-$(CH_2)_9$-3-$C_4H_3$S | $COCH_3$ | H | $COCH_3$ | $COCH_3$ |
| $(CH_2)_2-C_6H_4$-4-$(CH_2)_{10}$-3-$C_4H_3$S | H | H | H | H |
| $(CH_2)_2-C_6H_4$-4-$(CH_2)_{10}$-3-$C_4H_3$S | $COCH_3$ | H | $COCH_3$ | $COCH_3$ |
| 2-$C_4H_2$S-5-$(CH_2)_9CH_3$ | H | H | H | H |
| $CH_2$-2-$C_4H_2$S-5-$(CH_2)_8CH_3$ | H | H | H | H |
| $CH_2$-2-$C_4H_2$S-5-$(CH_2)_8CH_3$ | $COCH_3$ | H | H | H |
| $CH_2$-2-$C_4H_2$S-5-$(CH_2)_8CH_3$ | $COCH_3$ | H | $COCH_3$ | $COCH_3$ |

-continued $$R^2R^3N-\underset{\underset{R}{|}}{\overset{\overset{CH_2OR^4}{|}}{C}}-CH_2OR^5$$

| R | R² | R³ | R⁴ | R⁵ |
|---|---|---|---|---|
| (CH₂)₂-2-C₄H₂S-5-(CH₂)₇CH₃ | H | H | H | H |
| (CH₂)₂-2-C₄H₂S-5-(CH₂)₇CH₃ | COCH₃ | H | COCH₃ | COCH₃ |
| (CH₂)₃-2-C₄H₂S-5-(CH₂)₆CH₃ | H | H | H | H |
| (CH₂)₃-2-C₄H₂S-5-(CH₂)₆CH₃ | COCH₃ | H | COCH₃ | COCH₃ |
| (CH₂)₄-2-C₄H₂S-5-(CH₂)₄CH₃ | H | H | H | H |
| (CH₂)₄-2-C₄H₂S-5-(CH₂)₄CH₃ | COCH₃ | H | COCH₃ | COCH₃ |
| (CH₂)₅-2-C₄H₂S-5-(CH₂)₄CH₃ | H | H | H | H |
| (CH₂)₅-2-C₄H₂S-5-(CH₂)₄CH₃ | COCH₃ | H | COCH₃ | COCH₃ |
| (CH₂)₆-2-C₄H₂S-5-(CH₂)₃CH₃ | H | H | H | H |
| (CH₂)₆-2-C₄H₂S-5-(CH₂)₃CH₃ | COCH₃ | H | COCH₃ | COCH₃ |
| (CH₂)₇-2-C₄H₂S-5-(CH₂)₂CH₃ | H | H | H | H |
| (CH₂)₇-2-C₄H₂S-5-CH₂CH₃ | COCH₃ | H | H | H |
| (CH₂)₇-2-C₄H₂S-5-CH₂CH₃ | COCH₃ | H | COCH₃ | COCH₃ |
| (CH₂)₈-2-C₄H₂S-5-CH₃ | H | H | H | H |
| (CH₂)₈-2-C₄H₂S-5-CH₃ | COCH₃ | H | COCH₃ | COCH₃ |
| (CH₂)₈-3-C₄H₃S | H | H | H | H |
| (CH₂)₉-3-C₄H₃S | H | H | H | H |
| (CH₂)₁₀-3-C₄H₃S | H | H | H | H |
| (CH₂)₁₁-3-C₄H₃S | H | H | H | H |
| (CH₂)₁₂-3-C₄H₃S | H | H | H | H |
| (CH₂)₁₃-3-C₄H₃S | H | H | H | H |
| (CH₂)₁₄-3-C₄H₃S | H | H | H | H |
| (CH₂)₁₅-3-C₄H₃S | H | H | H | H |
| (CH₂)₁₆-3-C₄H₃S | H | H | H | H |
| (CH₂)₁₇-3-C₄H₃S | H | H | H | H |
| (CH₂)₁₈-3-C₄H₃S | H | H | H | H |
| (CH₂)₂-2-C₄H₂S-5-(CH₂)₇CH₃ | H | H | H | H |
| (CH₂)₂-2-C₄H₂S-5-(CH₂)₈CH₃ | H | H | H | H |
| (CH₂)₂-2-C₄H₂S-5-(CH₂)₈CH₃ | COCH₃ | H | COCH₃ | COCH₃ |
| (CH₂)₂-2-C₄H₂S-5-(CH₂)₉CH₃ | H | H | H | H |
| (CH₂)₂-2-C₄H₂S-5-(CH₂)₉CH₃ | COCH₃ | H | COCH₃ | COCH₃ |
| (CH₂)₂-2-C₄H₂S-5-(CH₂)₁₀CH₃ | H | H | H | H |
| (CH₂)₂-2-C₄H₂S-5-(CH₂)₁₀CH₃ | COCH₃ | H | COCH₃ | COCH₃ |
| (CH₂)₂-2-C₄H₂S-5-(CH₂)₁₂CH₃ | H | H | H | H |
| (CH₂)₂-2-C₄H₂S-5-(CH₂)₁₂CH₃ | COCH₃ | H | COCH₃ | COCH₃ |
| (CH₂)₂-2-C₄H₂S-5-CH₂C₆H₅ | H | H | H | H |
| (CH₂)₂-2-C₄H₂S-5-(CH₂)₂C₆H₅ | H | H | H | H |
| (CH₂)₂-2-C₄H₂S-5-(CH₂)₃C₆H₅ | H | H | H | H |
| (CH₂)₂-2-C₄H₂S-5-(CH₂)₄C₆H₅ | H | H | H | H |
| (CH₂)₂-2-C₄H₂S-5-(CH₂)₅C₆H₅ | H | H | H | H |
| (CH₂)₂-2-C₄H₂S-5-(CH₂)₆C₆H₅ | H | H | H | H |
| (CH₂)₂-2-C₄H₂S-5-(CH₂)₆C₆H₅ | COCH₃ | H | COCH₃ | COCH₃ |
| (CH₂)₂-2-C₄H₂S-5-(CH₂)₇C₆H₅ | H | H | H | H |
| (CH₂)₂-2-C₄H₂S-5-(CH₂)₇C₆H₅ | COCH₃ | H | COCH₃ | COCH₃ |
| (CH₂)₂-2-C₄H₂S-5-(CH₂)₈C₆H₅ | H | H | H | H |
| (CH₂)₂-2-C₄H₂S-5-(CH₂)₈C₆H₅ | COCH₃ | H | COCH₃ | COCH₃ |
| (CH₂)₂-2-C₄H₂S-5-(CH₂)₉C₆H₅ | H | H | H | H |
| (CH₂)₂-2-C₄H₂S-5-(CH₂)₉C₆H₅ | COCH₃ | H | COCH₃ | COCH₃ |
| (CH₂)₂-2-C₄H₂S-5-(CH₂)₁₀C₆H₅ | H | H | H | H |
| (CH₂)₂-2-C₄H₂S-5-(CH₂)₁₀C₆H₅ | COCH₃ | H | COCH₃ | COCH₃ |
| 3-C₄H₂S-4-(CH₂)₁₁CH₃ | H | H | H | H |
| CH₂-3-C₄H₂S-4-(CH₂)₁₀CH₃ | H | H | H | H |
| CH₂-3-C₄H₂S-4-(CH₂)₁₀CH₃ | COCH₃ | H | H | H |
| CH₂-3-C₄H₂S-4-(CH₂)₁₀CH₃ | COCH₃ | H | COCH₃ | COCH₃ |
| (CH₂)₂-3-C₄H₂S-4-(CH₂)₉CH₃ | H | H | H | H |
| (CH₂)₂-3-C₄H₂S-4-(CH₂)₉CH₃ | COCH₃ | H | H | H |
| (CH₂)₂-3-C₄H₂S-4-(CH₂)₉CH₃ | COCH₃ | H | COCH₃ | COCH₃ |
| (CH₂)₃-3-C₄H₂S-4-(CH₂)₈CH₃ | H | H | H | H |
| (CH₂)₃-3-C₄H₂S-4-(CH₂)₈CH₃ | COCH₃ | H | COCH₃ | COCH₃ |
| (CH₂)₄-3-C₄H₂S-4-(CH₂)₇CH₃ | H | H | H | H |
| (CH₂)₄-3-C₄H₂S-4-(CH₂)₇CH₃ | COCH₃ | H | COCH₃ | COCH₃ |
| (CH₂)₅-3-C₄H₂S-4-(CH₂)₆CH₃ | H | H | H | H |
| (CH₂)₅-3-C₄H₂S-4-(CH₂)₆CH₃ | COCH₃ | H | COCH₃ | COCH₃ |
| (CH₂)₆-3-C₄H₂S-4-(CH₂)₅CH₃ | H | H | H | H |
| (CH₂)₆-3-C₄H₂S-4-(CH₂)₅CH₃ | COCH₃ | H | COCH₃ | COCH₃ |
| (CH₂)₇-3-C₄H₂S-4-(CH₂)₄CH₃ | H | H | H | H |
| (CH₂)₇-3-C₄H₂S-4-(CH₂)₄CH₃ | COCH₃ | H | COCH₃ | COCH₃ |
| (CH₂)₈-3-C₄H₂S-4-(CH₂)₃CH₃ | H | H | H | H |
| (CH₂)₈-3-C₄H₂S-4-(CH₂)₃CH₃ | COCH₃ | H | COCH₃ | COCH₃ |
| (CH₂)₉-3-C₄H₂S-4-(CH₂)₂CH₃ | H | H | H | H |
| (CH₂)₁₀-3-C₄H₂S-4-CH₂CH₃ | COCH₃ | H | H | H |
| (CH₂)₁₀-3-C₄H₂S-4-CH₂CH₃ | COCH₃ | H | COCH₃ | COCH₃ |
| (CH₂)₁₁-3-C₄H₂S-4-CH₃ | H | H | H | H |

-continued $$R^2R^3N-\underset{\underset{R}{|}}{\overset{\overset{CH_2OR^4}{|}}{C}}-CH_2OR^5$$

| R | $R^2$ | $R^3$ | $R^4$ | $R^5$ |
|---|---|---|---|---|
| $(CH_2)_{11}$-3-$C_4H_2S$-4-$CH_3$ | $COCH_3$ | H | $COCH_3$ | $COCH_3$ |
| $(CH_2)_2$-3-$C_4H_2S$-4-$(CH_2)_8CH_3$ | H | H | H | H |
| $(CH_2)_2$-3-$C_4H_2S$-4-$(CH_2)_9CH_3$ | H | H | H | H |
| $(CH_2)_2$-3-$C_4H_2S$-4-$(CH_2)_9CH_3$ | $COCH_3$ | H | $COCH_3$ | $COCH_3$ |
| $(CH_2)_2$-3-$C_4H_2S$-4-$(CH_2)_{10}CH_3$ | H | H | H | H |
| $(CH_2)_2$-3-$C_4H_2S$-4-$(CH_2)_{10}CH_3$ | $COCH_3$ | H | $COCH_3$ | $COCH_3$ |
| $(CH_2)_2$-3-$C_4H_2S$-4-$(CH_2)_{11}CH_3$ | H | H | H | H |
| $(CH_2)_2$-3-$C_4H_2S$-4-$(CH_2)_{11}CH_3$ | $COCH_3$ | H | $COCH_3$ | $COCH_3$ |
| $(CH_2)_2$-3-$C_4H_2S$-4-$(CH_2)_{12}CH_3$ | H | H | H | H |
| $(CH_2)_2$-3-$C_4H_2S$-4-$(CH_2)_{12}CH_3$ | $COCH_3$ | H | $COCH_3$ | $COCH_3$ |
| $(CH_2)_2$-3-$C_4H_2S$-4-$CH_2C_6H_5$ | H | H | H | H |
| $(CH_2)_2$-3-$C_4H_2S$-4-$(CH_2)_2C_6H_5$ | H | H | H | H |
| $(CH_2)_2$-3-$C_4H_2S$-4-$(CH_2)_3C_6H_5$ | H | H | H | H |
| $(CH_2)_2$-3-$C_4H_2S$-4-$(CH_2)_4C_6H_5$ | H | H | H | H |
| $(CH_2)_2$-3-$C_4H_2S$-4-$(CH_2)_5C_6H_5$ | H | H | H | H |
| $(CH_2)_2$-3-$C_4H_2S$-4-$(CH_2)_6C_6H_5$ | H | H | H | H |
| $(CH_2)_2$-3-$C_4H_2S$-4-$(CH_2)_6C_6H_5$ | $COCH_3$ | H | $COCH_3$ | $COCH_3$ |
| $(CH_2)_2$-3-$C_4H_2S$-4-$(CH_2)_7C_6H_5$ | H | H | H | H |
| $(CH_2)_2$-3-$C_4H_2S$-4-$(CH_2)_7C_6H_5$ | $COCH_3$ | H | $COCH_3$ | $COCH_3$ |
| $(CH_2)_2$-3-$C_4H_2S$-4-$(CH_2)_8C_6H_5$ | H | H | H | H |
| $(CH_2)_2$-3-$C_4H_2S$-4-$(CH_2)_8C_6H_5$ | $COCH_3$ | H | $COCH_3$ | $COCH_3$ |
| $(CH_2)_2$-3-$C_4H_2S$-4-$(CH_2)_9C_6H_5$ | H | H | H | H |
| $(CH_2)_2$-3-$C_4H_2S$-4-$(CH_2)_9C_6H_5$ | $COCH_3$ | H | $COCH_3$ | $COCH_3$ |
| $(CH_2)_2$-3-$C_4H_2S$-4-$(CH_2)_{10}C_6H_5$ | H | H | H | H |
| $(CH_2)_2$-3-$C_4H_2S$-4-$(CH_2)_{10}C_6H_5$ | $COCH_3$ | H | $COCH_3$ | $COCH_3$ |
| 3-$C_4H_2S$-5-$(CH_2)_{10}CH_3$ | H | H | H | H |
| $CH_2$-3-$C_4H_2S$-5-$(CH_2)_9CH_3$ | H | H | H | H |
| $CH_2$-3-$C_4H_2S$-5-$(CH_2)_9CH_3$ | $COCH_3$ | H | $COCH_3$ | $COCH_3$ |
| $(CH_2)_2$-3-$C_4H_2S$-5-$(CH_2)_8CH_3$ | H | H | H | H |
| $(CH_2)_2$-3-$C_4H_2S$-5-$(CH_2)_8CH_3$ | $COCH_3$ | H | $COCH_3$ | $COCH_3$ |
| $(CH_2)_3$-3-$C_4H_2S$-5-$(CH_2)_7CH_3$ | H | H | H | H |
| $(CH_2)_4$-3-$C_4H_2S$-5-$(CH_2)_6CH_3$ | H | H | H | H |
| $(CH_2)_4$-3-$C_4H_2S$-5-$(CH_2)_6CH_3$ | $COCH_3$ | H | $COCH_3$ | $COCH_3$ |
| $(CH_2)_5$-3-$C_4H_2S$-5-$(CH_2)_5CH_3$ | H | H | H | H |
| $(CH_2)_5$-3-$C_4H_2S$-5-$(CH_2)_5CH_3$ | $COCH_3$ | H | $COCH_3$ | $COCH_3$ |
| $(CH_2)_6$-3-$C_4H_2S$-5-$(CH_2)_4CH_3$ | H | H | H | H |
| $(CH_2)_6$-3-$C_4H_2S$-5-$(CH_2)_4CH_3$ | $COCH_3$ | H | $COCH_3$ | $COCH_3$ |
| $(CH_2)_7$-3-$C_4H_2S$-5-$(CH_2)_3CH_3$ | H | H | H | H |
| $(CH_2)_7$-3-$C_4H_2S$-5-$(CH_2)_3CH_3$ | $COCH_3$ | H | $COCH_3$ | $COCH_3$ |
| $(CH_2)_8$-3-$C_4H_2S$-5-$(CH_2)_2CH_3$ | H | H | H | H |
| $(CH_2)_9$-3-$C_4H_2S$-5-$CH_2CH_3$ | H | H | H | H |
| $(CH_2)_9$-3-$C_4H_2S$-5-$CH_2CH_3$ | $COCH_3$ | H | $COCH_3$ | $COCH_3$ |
| $(CH_2)_{10}$-3-$C_4H_2S$-5-$CH_3$ | H | H | H | H |
| $(CH_2)_{10}$-3-$C_4H_2S$-5-$CH_3$ | $COCH_3$ | H | $COCH_3$ | $COCH_3$ |
| $(CH_2)_2$-3-$C_4H_2S$-5-$(CH_2)_7CH_3$ | H | H | H | H |
| $(CH_2)_2$-3-$C_4H_2S$-5-$(CH_2)_9CH_3$ | H | H | H | H |
| $(CH_2)_2$-3-$C_4H_2S$-5-$(CH_2)_9CH_3$ | $COCH_3$ | H | $COCH_3$ | $COCH_3$ |
| $(CH_2)_2$-3-$C_4H_2S$-5-$(CH_2)_{10}CH_3$ | H | H | H | H |
| $(CH_2)_2$-3-$C_4H_2S$-5-$(CH_2)_{10}CH_3$ | $COCH_3$ | H | $COCH_3$ | $COCH_3$ |
| $(CH_2)_2$-3-$C_4H_2S$-5-$(CH_2)_{11}CH_3$ | H | H | H | H |
| $(CH_2)_2$-3-$C_4H_2S$-5-$(CH_2)_{11}CH_3$ | $COCH_3$ | H | $COCH_3$ | $COCH_3$ |
| $(CH_2)_2$-3-$C_4H_2S$-5-$(CH_2)_{12}CH_3$ | H | H | H | H |
| $(CH_2)_2$-3-$C_4H_2S$-5-$(CH_2)_{12}CH_3$ | $COCH_3$ | H | $COCH_3$ | $COCH_3$ |
| $(CH_2)_2$-3-$C_4H_2S$-5-$CH_2C_6H_5$ | H | H | H | H |
| $(CH_2)_2$-3-$C_4H_2S$-5-$(CH_2)_2C_6H_5$ | H | H | H | H |
| $(CH_2)_2$-3-$C_4H_2S$-5-$(CH_2)_3C_6H_5$ | H | H | H | H |
| $(CH_2)_2$-3-$C_4H_2S$-5-$(CH_2)_4C_6H_5$ | H | H | H | H |
| $(CH_2)_2$-3-$C_4H_2S$-5-$(CH_2)_5C_6H_5$ | H | H | H | H |
| $(CH_2)_2$-3-$C_4H_2S$-5-$(CH_2)_6C_6H_5$ | H | H | H | H |
| $(CH_2)_2$-3-$C_4H_2S$-5-$(CH_2)_6C_6H_5$ | $COCH_3$ | H | $COCH_3$ | $COCH_3$ |
| $(CH_2)_2$-3-$C_4H_2S$-5-$(CH_2)_7C_6H_5$ | H | H | H | H |
| $(CH_2)_2$-3-$C_4H_2S$-5-$(CH_2)_7C_6H_5$ | $COCH_3$ | H | $COCH_3$ | $COCH_3$ |
| $(CH_2)_2$-3-$C_4H_2S$-5-$(CH_2)_8C_6H_5$ | H | H | H | H |
| $(CH_2)_2$-3-$C_4H_2S$-5-$(CH_2)_8C_6H_5$ | $COCH_3$ | H | $COCH_3$ | $COCH_3$ |
| $(CH_2)_2$-3-$C_4H_2S$-5-$(CH_2)_9C_6H_5$ | H | H | H | H |
| $(CH_2)_2$-3-$C_4H_2S$-5-$(CH_2)_9C_6H_5$ | $COCH_3$ | H | $COCH_3$ | $COCH_3$ |
| $(CH_2)_2$-3-$C_4H_2S$-5-$(CH_2)_{10}C_6H_5$ | H | H | H | H |
| $(CH_2)_2$-3-$C_4H_2S$-5-$(CH_2)_{10}C_6H_5$ | $COCH_3$ | H | $COCH_3$ | $COCH_3$ |

$$R^2R^3N-\underset{\underset{R}{|}}{\overset{\overset{CH_2OR^4}{|}}{C}}-CH_2OR^5$$

| R | $R^2$ | $R^3$ | $R^4$ | $R^5$ |
|---|---|---|---|---|
| 2-$C_5H_3$N-4-$(CH_2)_{10}CH_3$ | H | H | H | H |
| $CH_2$-2-$C_5H_3$N-4-$(CH_2)_9CH_3$ | H | H | H | H |
| $(CH_2)_3$-2-$C_5H_3$N-4-$(CH_2)_7CH_3$ | H | H | H | H |
| $(CH_2)_4$-2-$C_5H_3$N-4-$(CH_2)_6CH_3$ | H | H | H | H |
| $(CH_2)_5$-2-$C_5H_3$N-4-$(CH_2)_5CH_3$ | H | H | H | H |
| $(CH_2)_6$-2-$C_5H_3$N-4-$(CH_2)_4CH_3$ | H | H | H | H |
| $(CH_2)_7$-2-$C_5H_3$N-4-$(CH_2)_3CH_3$ | H | H | H | H |
| $(CH_2)_8$-2-$C_5H_3$N-4-$(CH_2)_2CH_2$ | H | H | H | H |
| $(CH_2)_9C_5H_3$N-4-$CH_2CH_3$ | H | H | H | H |
| $(CH_2)_{10}$-2-$C_5H_3$N-4-$CH_3$ | H | H | H | H |
| $CH_2$-2-$C_5H_4$N | H | H | H | H |
| $CH_2$-2-$C_5H_4$N | $CH_3CO$ | H | $CH_3CO$ | $CH_3CO$ |
| $(CH_2)_{11}$-2-$C_5H_4$N | H | H | H | H |
| $(CH_2)_{11}$-2-$C_5H_4$N | $CH_3CO$ | H | $CH_3CO$ | $CH_3CO$ |
| $(CH_2)_9$-2-$C_5H_4$N | H | H | H | H |
| $(CH_2)_9$-2-$C_5H_4$N | $CH_3CO$ | H | $CH_3CO$ | $CH_3CO$ |
| $(CH_2)_{10}$-2-$C_5H_4$N | H | H | H | H |
| $(CH_2)_{10}$-2-$C_5H_4$N | $CH_3CO$ | H | $CH_3CO$ | $CH_3CO$ |
| $(CH_2)_{12}$-2-$C_5H_4$N | H | H | H | H |
| $(CH_2)_{12}$-2-$C_5H_4$N | $CH_3CO$ | H | $CH_3CO$ | $CH_3CO$ |
| $(CH_2)_{13}$-2-$C_5H_4$N | H | H | H | H |
| $(CH_2)_{13}$-2-$C_5H_4$N | $CH_3CO$ | H | $CH_3CO$ | $CH_3CO$ |
| $(CH_2)_{14}$-2-$C_5H_4$N | H | H | H | H |
| $(CH_2)_{14}$-2-$C_5H_4$N | $CH_3CO$ | H | $CH_3CO$ | $CH_3CO$ |
| $(CH_2)_{15}$-2-$C_5H_4$N | H | H | H | H |
| $(CH_2)_{15}$-2-$C_5H_4$N | $CH_3CO$ | H | $CH_3CO$ | $CH_3CO$ |
| $(CH_2)_{16}$-2-$C_5H_4$N | H | H | H | H |
| $(CH_2)_{16}$-2-$C_5H_4$N | $CH_3CO$ | H | $CH_3CO$ | $CH_3CO$ |
| $(CH_2)_{17}$-2-$C_5H_4$N | H | H | H | H |
| $(CH_2)_{17}$-2-$C_5H_4$N | $CH_3CO$ | H | $CH_3CO$ | $CH_3CO$ |
| $(CH_2)_2$-2-$C_5H_3$N-4-$(CH_2)_8CH_3$ | H | H | H | H |
| $(CH_2)_2$-2-$C_5H_3$N-4-$(CH_2)_8CH_3$ | $CH_3CO$ | H | $CH_3CO$ | $CH_3CO$ |
| $(CH_2)_2$-2-$C_5H_3$N-4-$(CH_2)_{12}CH_3$ | H | H | H | H |
| $(CH_2)_2$-2-$C_5H_3$N-4-$(CH_2)_{12}CH_3$ | $CH_3CO$ | H | $CH_3CO$ | $CH_3CO$ |
| $(CH_2)_2$-2-$C_5H_3$N-4-$CH_2-C_6H_5$ | H | H | H | H |
| $(CH_2)_2$-2-$C_5H_3$N-4-$CH_2-C_6H_5$ | $CH_3CO$ | H | $CH_3CO$ | $CH_3CO$ |
| $(CH_2)_2$-2-$C_5H_3$N-4-$(CH_2)_2-C_6H_5$ | H | H | H | H |
| $(CH_2)_2$-2-$C_5H_3$N-4-$(CH_2)_2-C_6H_5$ | $CH_3CO$ | H | $CH_3CO$ | $CH_3CO$ |
| $(CH_2)_2$-2-$C_5H_3$N-4-$(CH_2)_3-C_6H_5$ | H | H | H | H |
| $(CH_2)_2$-2-$C_5H_3$N-4-$(CH_2)_3-C_6H_5$ | $CH_3CO$ | H | $CH_3CO$ | $CH_3CO$ |
| $(CH_2)_2$-2-$C_5H_3$N-4-$(CH_2)_4-C_6H_5$ | H | H | H | H |
| $(CH_2)_2$-2-$C_5H_3$N-4-$(CH_2)_4-C_6H_5$ | $CH_3CO$ | H | $CH_3CO$ | $CH_3CO$ |
| $(CH_2)_2$-2-$C_5H_3$N-4-$(CH_2)_5-C_6H_5$ | H | H | H | H |
| $(CH_2)_2$-2-$C_5H_3$N-4-$(CH_2)_5-C_6H_5$ | $CH_3CO$ | H | $CH_3CO$ | $CH_3CO$ |
| $(CH_2)_2$-2-$C_5H_3$N-4-$(CH_2)_6-C_6H_5$ | H | H | H | H |
| $(CH_2)_2$-2-$C_5H_3$N-4-$(CH_2)_6-C_6H_5$ | $CH_3CO$ | H | $CH_3CO$ | $CH_3CO$ |
| $(CH_2)_2$-2-$C_5H_3$N-4-$(CH_2)_7-C_6H_5$ | H | H | H | H |
| $(CH_2)_2$-2-$C_5H_3$N-4-$(CH_2)_7-C_6H_5$ | $CH_3CO$ | H | $CH_3CO$ | $CH_3CO$ |
| $(CH_2)_2$-2-$C_5H_3$N-4-$(CH_2)_8-C_6H_5$ | H | H | H | H |
| $(CH_2)_2$-2-$C_5H_3$N-4-$(CH_2)_8-C_6H_5$ | $CH_3CO$ | H | $CH_3CO$ | $CH_3CO$ |
| $(CH_2)_2$-2-$C_5H_3$N-4-$(CH_2)_9-C_6H_5$ | H | H | H | H |
| $(CH_2)_2$-2-$C_5H_3$N-4-$(CH_2)_9-C_6H_5$ | $CH_3CO$ | H | $CH_3CO$ | $CH_3CO$ |
| $(CH_2)_2$-2-$C_5H_3$N-4-$(CH_2)_{10}-C_6H_5$ | H | H | H | H |
| $(CH_2)_2$-2-$C_5H_3$N-4-$(CH_2)_{10}-C_6H_5$ | $CH_3CO$ | H | $CH_3CO$ | $CH_3CO$ |
| $(CH_2)_2-C_6H_4$-4-$CH_2$-2-$C_5H_4$N | H | H | H | H |
| $(CH_2)_2-C_6H_4$-4-$CH_2$-2-$C_5H_4$N | $CH_3CO$ | H | $CH_3CO$ | $CH_3CO$ |
| $(CH_2)_2-C_6H_4$-4-$(CH_2)_2$-2-$C_5H_4$N | H | H | H | H |
| $(CH_2)_2-C_6H_4$-4-$(CH_2)_2$-2-$C_5H_4$N | $CH_3CO$ | H | $CH_3CO$ | $CH_3CO$ |
| $(CH_2)_2-C_6H_4$-4-$(CH_2)_3$-2-$C_5H_4$N | H | H | H | H |
| $(CH_2)_2-C_6H_4$-4-$(CH_2)_3$-2-$C_5H_4$N | $CH_3CO$ | H | $CH_3CO$ | $CH_3CO$ |
| $(CH_2)_2-C_6H_4$-4-$(CH_2)_4$-2-$C_5H_4$N | H | H | H | H |
| $(CH_2)_2-C_6H_4$-4-$(CH_2)_4$-2-$C_5H_4$N | $CH_3CO$ | H | $CH_3CO$ | $CH_3CO$ |
| $(CH_2)_2-C_6H_4$-4-$(CH_2)_5$-2-$C_5H_4$N | H | H | H | H |
| $(CH_2)_2-C_6H_4$-4-$(CH_2)_5$-2-$C_5H_4$N | $CH_3CO$ | H | $CH_3CO$ | $CH_3CO$ |
| $(CH_2)_2-C_6H_4$-4-$(CH_2)_6$-2-$C_5H_4$N | H | H | H | H |
| $(CH_2)_2-C_6H_4$-4-$(CH_2)_6$-2-$C_5H_4$N | $CH_3CO$ | H | $CH_3CO$ | $CH_3CO$ |
| $(CH_2)_2-C_6H_4$-4-$(CH_2)_7$-2-$C_5H_4$N | H | H | H | H |
| $(CH_2)_2-C_6H_4$-4-$(CH_2)_7$-2-$C_5H_4$N | $CH_3CO$ | H | $CH_3CO$ | $CH_3CO$ |
| $(CH_2)_2-C_6H_4$-4-$(CH_2)_8$-2-$C_5H_4$N | H | H | H | H |
| $(CH_2)_2-C_6H_4$-4-$(CH_2)_8$-2-$C_5H_4$N | $CH_3CO$ | H | $CH_3CO$ | $CH_3CO$ |
| $(CH_2)_2-C_6H_4$-4-$(CH_2)_9$-2-$C_5H_4$N | H | H | H | H |
| $(CH_2)_2-C_6H_4$-4-$(CH_2)_9$-2-$C_5H_4$N | $CH_3CO$ | H | $CH_3CO$ | $CH_3CO$ |
| $(CH_2)_2-C_6H_4$-4-$(CH_2)_{10}$-2-$C_5H_4$N | H | H | H | H |

-continued $$R^2R^3N-\underset{\underset{R}{|}}{\overset{\overset{CH_2OR^4}{|}}{C}}-CH_2OR^5$$

| R | R² | R³ | R⁴ | R⁵ |
|---|---|---|---|---|
| (CH₂)₂-C₆H₄-4-(CH₂)₁₀-2-C₅H₄N | CH₃CO | H | CH₃CO | CH₃CO |
| 4-C₅H₃N-2-(CH₂)₁₀CH₃ | H | H | H | H |
| CH₂-4-C₅H₃N-2-(CH₂)₉CH₃ | H | H | H | H |
| (CH₂)₃-4-C₅H₃N-2-(CH₂)₇CH₃ | H | H | H | H |
| (CH₂)₄-4-C₅H₃N-2-(CH₂)₆CH₃ | H | H | H | H |
| (CH₂)₅-4-C₅H₃N-2-(CH₂)₅CH₃ | H | H | H | H |
| (CH₂)₆-4-C₅H₃N-2-(CH₂)₄CH₃ | H | H | H | H |
| (CH₂)₇-4-C₅H₃N-2-(CH₂)₃CH₃ | H | H | H | H |
| (CH₂)₈-4-C₅H₃N-2-(CH₂)₂CH₃ | H | H | H | H |
| (CH₂)₉-4-C₅H₃N-2-CH₂CH₃ | H | H | H | H |
| (CH₂)₁₀-4-C₅H₃N-2-CH₃ | H | H | H | H |
| CH₂-4-C₅H₄N | H | H | H | H |
| CH₂-4-C₅H₄N | CH₃CO | H | CH₃CO | CH₃CO |
| (CH₂)₁₁-4-C₅H₄N | H | H | H | H |
| (CH₂)₁₁-4-C₅H₄N | CH₃CO | H | CH₃CO | CH₃CO |
| (CH₂)₉-4-C₅H₄N | H | H | H | H |
| (CH₂)₉-4-C₅H₄N | CH₃CO | H | CH₃CO | CH₃CO |
| (CH₂)₁₀-4-C₅H₄N | H | H | H | H |
| (CH₂)₁₀-4-C₅H₄N | CH₃CO | H | CH₃CO | CH₃CO |
| (CH₂)₁₂-4-C₅H₄N | H | H | H | H |
| (CH₂)₁₂-4-C₅H₄N | CH₃CO | H | CH₃CO | CH₃CO |
| (CH₂)₁₃-4-C₅H₄N | H | H | H | H |
| (CH₂)₁₃-4-C₅H₄N | CH₃CO | H | CH₃CO | CH₃CO |
| (CH₂)₁₄-4-C₅H₄N | H | H | H | H |
| (CH₂)₁₄-4-C₅H₄N | CH₃CO | H | CH₃CO | CH₃CO |
| (CH₂)₁₅-4-C₅H₄N | H | H | H | H |
| (CH₂)₁₅-4-C₅H₄N | CH₃CO | H | CH₃CO | CH₃CO |
| (CH₂)₁₆-4-C₅H₄N | H | H | H | H |
| (CH₂)₁₆-4-C₅H₄N | CH₃CO | H | CH₃CO | CH₃CO |
| (CH₂)₁₇-4-C₅H₄N | H | H | H | H |
| (CH₂)₁₇-4-C₅H₄N | CH₃CO | H | CH₃CO | CH₃CO |
| (CH₂)₂-4-C₅H₃N-2-(CH₂)₈CH₃ | H | H | H | H |
| (CH₂)₂-4-C₅H₃N-2-(CH₂)₈CH₃ | CH₃CO | H | CH₃CO | CH₃CO |
| (CH₂)₂-4-C₅H₃N-2-(CH₂)₁₂CH₃ | H | H | H | H |
| (CH₂)₂-4-C₅H₃N-2-(CH₂)₁₂CH₃ | CH₃CO | H | CH₃CO | CH₃CO |
| (CH₂)₂-4-C₅H₃N-2-CH₂—C₆H₅ | H | H | H | H |
| (CH₂)₂-4-C₅H₃N-2-CH₂—C₆H₅ | CH₃CO | H | CH₃CO | CH₃CO |
| (CH₂)₂-4-C₅H₃N-2-(CH₂)₂—C₆H₅ | H | H | H | H |
| (CH₂)₂-4-C₅H₃N-2-(CH₂)₂—C₆H₅ | CH₃CO | H | CH₃CO | CH₃CO |
| (CH₂)₂-4-C₅H₃N-2-(CH₂)₃—C₆H₅ | H | H | H | H |
| (CH₂)₂-4-C₅H₃N-2-(CH₂)₃—C₆H₅ | CH₃CO | H | CH₃CO | CH₃CO |
| (CH₂)₂-4-C₅H₃N-2-(CH₂)₄—C₆H₅ | H | H | H | H |
| (CH₂)₂-4-C₅H₃N-2-(CH₂)₄—C₆H₅ | CH₃CO | H | CH₃CO | CH₃CO |
| (CH₂)₂-4-C₅H₃N-2-(CH₂)₅—C₆H₅ | H | H | H | H |
| (CH₂)₂-4-C₅H₃N-2-(CH₂)₅—C₆H₅ | CH₃CO | H | CH₃CO | CH₃CO |
| (CH₂)₂-4-C₅H₃N-2-(CH₂)₆—C₆H₅ | H | H | H | H |
| (CH₂)₂-4-C₅H₃N-2-(CH₂)₆—C₆H₅ | CH₃CO | H | CH₃CO | CH₃CO |
| (CH₂)₂-4-C₅H₃N-2-(CH₂)₇—C₆H₅ | H | H | H | H |
| (CH₂)₂-4-C₅H₃N-2-(CH₂)₇—C₆H₅ | CH₃CO | H | CH₃CO | CH₃CO |
| (CH₂)₂-4-C₅H₃N-2-(CH₂)₈—C₆H₅ | H | H | H | H |
| (CH₂)₂-4-C₅H₃N-2-(CH₂)₈—C₆H₅ | CH₃CO | H | CH₃CO | CH₃CO |
| (CH₂)₂-4-C₅H₃N-2-(CH₂)₉—C₆H₅ | H | H | H | H |
| (CH₂)₂-4-C₅H₃N-2-(CH₂)₉—C₆H₅ | CH₃CO | H | CH₃CO | CH₃CO |
| (CH₂)₂-4-C₅H₃N-2-(CH₂)₁₀—C₆H₅ | H | H | H | H |
| (CH₂)₂-4-C₅H₃N-2-(CH₂)₁₀—C₆H₅ | CH₃CO | H | CH₃CO | CH₃CO |
| (CH₂)₂—C₆H₄-4-CH₂-4-C₅H₄N | H | H | H | H |
| (CH₂)₂—C₆H₄-4-CH₂-4-C₅H₄N | CH₃CO | H | CH₃CO | CH₃CO |
| (CH₂)₂—C₆H₄-4-(CH₂)₂-4-C₅H₄N | H | H | H | H |
| (CH₂)₂—C₆H₄-4-(CH₂)₂-4-C₅H₄N | CH₃CO | H | CH₃CO | CH₃CO |
| (CH₂)₂—C₆H₄-4-(CH₂)₃-4-C₅H₄N | H | H | H | H |
| (CH₂)₂—C₆H₄-4-(CH₂)₃-4-C₅H₄N | CH₃CO | H | CH₃CO | CH₃CO |
| (CH₂)₂—C₆H₄-4-(CH₂)₄-4-C₅H₄N | H | H | H | H |
| (CH₂)₂—C₆H₄-4-(CH₂)₄-4-C₅H₄N | CH₃CO | H | CH₃CO | CH₃CO |
| (CH₂)₂—C₆H₄-4-(CH₂)₅-4-C₅H₄N | H | H | H | H |
| (CH₂)₂—C₆H₄-4-(CH₂)₅-4-C₅H₄N | CH₃CO | H | CH₃CO | CH₃CO |
| (CH₂)₂—C₆H₄-4-(CH₂)₆-4-C₅H₄N | H | H | H | H |
| (CH₂)₂—C₆H₄-4-(CH₂)₆-4-C₅H₄N | CH₃CO | H | CH₃CO | CH₃CO |
| (CH₂)₂—C₆H₄-4-(CH₂)₇-4-C₅H₄N | H | H | H | H |
| (CH₂)₂—C₆H₄-4-(CH₂)₇-4-C₅H₄N | CH₃CO | H | CH₃CO | CH₃CO |
| (CH₂)₂—C₆H₄-4-(CH₂)₈-4-C₅H₄N | H | H | H | H |
| (CH₂)₂—C₆H₄-4-(CH₂)₈-4-C₅H₄N | CH₃CO | H | CH₃CO | CH₃CO |
| (CH₂)₂—C₆H₄-4-(CH₂)₉-4-C₅H₄N | H | H | H | H |
| (CH₂)₂—C₆H₄-4-(CH₂)₉-4-C₅H₄N | CH₃CO | H | CH₃CO | CH₃CO |

-continued $$R^2R^3N-\underset{\underset{R}{|}}{\overset{\overset{CH_2OR^4}{|}}{C}}-CH_2OR^5$$

| R | $R^2$ | $R^3$ | $R^4$ | $R^5$ |
|---|---|---|---|---|
| $(CH_2)_2-C_6H_4-4-(CH_2)_{10}-4-C_5H_4N$ | H | H | H | H |
| $(CH_2)_2-C_6H_4-4-(CH_2)_{10}-4-C_5H_4N$ | $CH_3CO$ | H | $CH_3CO$ | $CH_3CO$ |
| $2-C_5H_3N-5-(CH_2)_9CH_3$ | H | H | H | H |
| $CH_2-2-C_5H_3N-5-(CH_2)_3CH_3$ | H | H | H | H |
| $CH_2-2-C_5H_3N-5-(CH_2)_8CH_3$ | H | H | H | H |
| $(CH_2)_3-2-C_5H_3N-5-(CH_2)_6CH_3$ | H | H | H | H |
| $(CH_2)_4-2-C_5H_3N-5-(CH_2)_5CH_3$ | H | H | H | H |
| $(CH_2)_5-2-C_5H_3N-5-(CH_2)_4CH_3$ | H | H | H | H |
| $(CH_2)_6-2-C_5H_3N-5-(CH_2)_3CH_3$ | H | H | H | H |
| $(CH_2)_7-2-C_5H_3N-5-(CH_2)_2CH_3$ | H | H | H | H |
| $(CH_2)_8-2-C_5H_3N-5-CH_2CH_3$ | H | H | H | H |
| $(CH_2)_9-2-C_5H_3N-5-CH_3$ | H | H | H | H |
| $(CH_2)_2-2-C_5H_3N-5-(CH_2)_7CH_3$ | H | H | H | H |
| $(CH_2)_2-2-C_5H_3N-5-(CH_2)_7CH_3$ | $CH_3CO$ | H | $CH_3CO$ | $CH_3CO$ |
| $(CH_2)_2-2-C_5H_3N-5-(CH_2)_{11}CH_3$ | H | H | H | H |
| $(CH_2)_2-2-C_5H_3N-5-(CH_2)_{11}CH_3$ | $CH_3CO$ | H | $CH_3CO$ | $CH_3CO$ |
| $(CH_2)_2-2-C_5H_3N-5-CH_2-C_6H_5$ | H | H | H | H |
| $(CH_2)_2-2-C_5H_3N-5-CH_2-C_6H_5$ | $CH_3CO$ | H | $CH_3CO$ | $CH_3CO$ |
| $(CH_2)_2-2-C_5H_3N-5-(CH_2)_2-C_6H_5$ | H | H | H | H |
| $(CH_2)_2-2-C_5H_3N-5-(CH_2)_2-C_6H_5$ | $CH_3CO$ | H | $CH_3CO$ | $CH_3CO$ |
| $(CH_2)_2-2-C_5H_3N-5-(CH_2)_3-C_6H_5$ | H | H | H | H |
| $(CH_2)_2-2-C_5H_3N-5-(CH_2)_3-C_6H_5$ | $CH_3CO$ | H | $CH_3CO$ | $CH_3CO$ |
| $(CH_2)_2-2-C_5H_3N-5-(CH_2)_4-C_6H_5$ | H | H | H | H |
| $(CH_2)_2-2-C_5H_3N-5-(CH_2)_4-C_6H_5$ | $CH_3CO$ | H | $CH_3CO$ | $CH_3CO$ |
| $(CH_2)_2-2-C_5H_3N-5-(CH_2)_5-C_6H_5$ | H | H | H | H |
| $(CH_2)_2-2-C_5H_3N-5-(CH_2)_5-C_6H_5$ | $CH_3CO$ | H | $CH_3CO$ | $CH_3CO$ |
| $(CH_2)_2-2-C_5H_3N-5-(CH_2)_6-C_6H_5$ | H | H | H | H |
| $(CH_2)_2-2-C_5H_3N-5-(CH_2)_6-C_6H_5$ | $CH_3CO$ | H | $CH_3CO$ | $CH_3CO$ |
| $(CH_2)_2-2-C_5H_3N-5-(CH_2)_7-C_6H_5$ | H | H | H | H |
| $(CH_2)_2-2-C_5H_3N-5-(CH_2)_7-C_6H_5$ | $CH_3CO$ | H | $CH_3CO$ | $CH_3CO$ |
| $(CH_2)_2-2-C_5H_3N-5-(CH_2)_8-C_6H_5$ | H | H | H | H |
| $(CH_2)_2-2-C_5H_3N-5-(CH_2)_8-C_6H_5$ | $CH_3CO$ | H | $CH_3CO$ | $CH_3CO$ |
| $(CH_2)_2-2-C_5H_3N-5-(CH_2)_9-C_6H_5$ | H | H | H | H |
| $(CH_2)_2-2-C_5H_3N-5-(CH_2)_9-C_6H_5$ | $CH_3CO$ | H | $CH_3CO$ | $CH_3CO$ |
| $(CH_2)_2-2-C_5H_3N-5-(CH_2)_{10}-C_6H_5$ | H | H | H | H |
| $(CH_2)_2-2-C_5H_3N-5-(CH_2)_{10}-C_6H_5$ | $CH_3CO$ | H | $CH_3CO$ | $CH_3CO$ |
| $5-C_5H_3N-2-(CH_2)_9CH_3$ | H | H | H | H |
| $CH_2-5-C_5H_3N-2-(CH_2)_3CH_3$ | H | H | H | H |
| $CH_2-5-C_5H_3N-2-(CH_2)_8CH_3$ | H | H | H | H |
| $(CH_2)_3-5-C_5H_3N-2-(CH_2)_6CH_3$ | H | H | H | H |
| $(CH_2)_4-5-C_5H_3N-25-(CH_2)_5CH_3$ | H | H | H | H |
| $(CH_2)_5-5-C_5H_3N-2-(CH_2)_4CH_3$ | H | H | H | H |
| $(CH_2)_6-5-C_5H_3N-2-(CH_2)_3CH_3$ | H | H | H | H |
| $(CH_2)_7-5-C_5H_3N-2-(CH_2)_2CH_3$ | H | H | H | H |
| $(CH_2)_8-5-C_5H_3N-2-CH_2CH_3$ | H | H | H | H |
| $(CH_2)_9-5-C_5H_3N-2-CH_3$ | H | H | H | H |
| $(CH_2)_2-5-C_5H_3N-2-(CH_2)_7CH_3$ | H | H | H | H |
| $(CH_2)_2-5-C_5H_3N-2-(CH_2)_7CH_3$ | $CH_3CO$ | H | $CH_3CO$ | $CH_3CO$ |
| $(CH_2)_2-5-C_5H_3N-2-(CH_2)_{11}CH_3$ | H | H | H | H |
| $(CH_2)_2-5-C_5H_3N-2-(CH_2)_{11}CH_3$ | $CH_3CO$ | H | $CH_3CO$ | $CH_3CO$ |
| $(CH_2)_2-5-C_5H_3N-2-CH_2-C_6H_5$ | H | H | H | H |
| $(CH_2)_2-5-C_5H_3N-2-CH_2-C_6H_5$ | $CH_3CO$ | H | $CH_3CO$ | $CH_3CO$ |
| $(CH_2)_2-5-C_5H_3N-2-(CH_2)_2-C_6H_5$ | H | H | H | H |
| $(CH_2)_2-5-C_5H_3N-2-(CH_2)_2-C_6H_5$ | $CH_3CO$ | H | $CH_3CO$ | $CH_3CO$ |
| $(CH_2)_2-5-C_5H_3N-2-(CH_2)_3-C_6H_5$ | H | H | H | H |
| $(CH_2)_2-5-C_5H_3N-2-(CH_2)_3-C_6H_5$ | $CH_3CO$ | H | $CH_3CO$ | $CH_3CO$ |
| $(CH_2)_2-5-C_5H_3N-2-(CH_2)_4-C_6H_5$ | H | H | H | H |
| $(CH_2)_2-5-C_5H_3N-2-(CH_2)_4-C_6H_5$ | $CH_3CO$ | H | $CH_3CO$ | $CH_3CO$ |
| $(CH_2)_2-5-C_5H_3N-2-(CH_2)_5-C_6H_5$ | H | H | H | H |
| $(CH_2)_2-5-C_5H_3N-2-(CH_2)_5-C_6H_5$ | $CH_3CO$ | H | $CH_3CO$ | $CH_3CO$ |
| $(CH_2)_2-5-C_5H_3N-2-(CH_2)_6-C_6H_5$ | H | H | H | H |
| $(CH_2)_2-5-C_5H_3N-2-(CH_2)_6-C_6H_5$ | $CH_3CO$ | H | $CH_3CO$ | $CH_3CO$ |
| $(CH_2)_2-5-C_5H_3N-2-(CH_2)_7-C_6H_5$ | H | H | H | H |
| $(CH_2)_2-5-C_5H_3N-2-(CH_2)_7-C_6H_5$ | $CH_3CO$ | H | $CH_3CO$ | $CH_3CO$ |
| $(CH_2)_2-5-C_5H_3N-2-(CH_2)_8-C_6H_5$ | H | H | H | H |
| $(CH_2)_2-5-C_5H_3N-2-(CH_2)_8-C_6H_5$ | $CH_3CO$ | H | $CH_3CO$ | $CH_3CO$ |
| $(CH_2)_2-5-C_5H_3N-2-(CH_2)_9-C_6H_5$ | H | H | H | H |
| $(CH_2)_2-5-C_5H_3N-2-(CH_2)_9-C_6H_5$ | $CH_3CO$ | H | $CH_3CO$ | $CH_3CO$ |
| $(CH_2)_2-5-C_5H_3N-2-(CH_2)_{10}-C_6H_5$ | H | H | H | H |
| $(CH_2)_2-5-C_5H_3N-2-(CH_2)_{10}-C_6H_5$ | $CH_3CO$ | H | $CH_3CO$ | $CH_3CO$ |
| $2-C_5H_3N-6-(CH_2)_{10}CH_3$ | H | H | H | H |
| $CH_2-2-C_5H_3N-6-(CH_2)_9CH_3$ | H | H | H | H |
| $(CH_2)_3-2-C_5H_3N-6-(CH_2)_7CH_3$ | H | H | H | H |

-continued $$R^2R^3N-\underset{\underset{R}{|}}{\overset{\overset{CH_2OR^4}{|}}{C}}-CH_2OR^5$$

| R | R² | R³ | R⁴ | R⁵ |
|---|---|---|---|---|
| (CH₂)₄-2-C₅H₃N-6-(CH₂)₆CH₃ | H | H | H | H |
| (CH₂)₅-2-C₅H₃N-6-(CH₂)₅CH₃ | H | H | H | H |
| (CH₂)₆-2-C₅H₃N-6-(CH₂)₄CH₃ | H | H | H | H |
| (CH₂)₇-2-C₅H₃N-6-(CH₂)₃CH₃ | H | H | H | H |
| (CH₂)₈-2-C₅H₃N-6-(CH₂)₂CH₃ | H | H | H | H |
| (CH₂)₉-2-C₅H₃N-6-CH₂CH₃ | H | H | H | H |
| (CH₂)₁₀-2-C₅H₃N-6-CH₃ | H | H | H | H |
| (CH₂)₂-2-C₅H₃N-6-(CH₂)₈CH₃ | H | H | H | H |
| (CH₂)₂-2-C₅H₃N-6-(CH₂)₈CH₃ | CH₃CO | H | CH₃CO | CH₃CO |
| (CH₂)₂-2-C₅H₃N-6-(CH₂)₁₂CH₃ | H | H | H | H |
| (CH₂)₂-2-C₅H₃N-6-(CH₂)₁₂CH₃ | CH₃CO | H | CH₃CO | CH₃CO |
| (CH₂)₂-2-C₅H₃N-6-CH₂—C₆H₅ | H | H | H | H |
| (CH₂)₂-2-C₅H₃N-6-CH₂—C₆H₅ | CH₃CO | H | CH₃CO | CH₃CO |
| (CH₂)₂-2-C₅H₃N-6-(CH₂)₂—C₆H₅ | H | H | H | H |
| (CH₂)₂-2-C₅H₃N-6-(CH₂)₂—C₆H₅ | CH₃CO | H | CH₃CO | CH₃CO |
| (CH₂)₂-2-C₅H₃N-6-(CH₂)₃—C₆H₅ | H | H | H | H |
| (CH₂)₂-2-C₅H₃N-6-(CH₂)₃—C₆H₅ | CH₃CO | H | CH₃CO | CH₃CO |
| (CH₂)₂-2-C₅H₃N-6-(CH₂)₄—C₆H₅ | H | H | H | H |
| (CH₂)₂-2-C₅H₃N-6-(CH₂)₄—C₆H₅ | CH₃CO | H | CH₃CO | CH₃CO |
| (CH₂)₂-2-C₅H₃N-6-(CH₂)₅—C₆H₅ | H | H | H | H |
| (CH₂)₂-2-C₅H₃N-6-(CH₂)₅—C₆H₅ | CH₃CO | H | CH₃CO | CH₃CO |
| (CH₂)₂-2-C₅H₃N-6-(CH₂)₆—C₆H₅ | H | H | H | H |
| (CH₂)₂-2-C₅H₃N-6-(CH₂)₆—C₆H₅ | CH₃CO | H | CH₃CO | CH₃CO |
| (CH₂)₂-2-C₅H₃N-6-(CH₂)₇—C₆H₅ | H | H | H | H |
| (CH₂)₂-2-C₅H₃N-6-(CH₂)₇—C₆H₅ | CH₃CO | H | CH₃CO | CH₃CO |
| (CH₂)₂-2-C₅H₃N-6-(CH₂)₈—C₆H₅ | H | H | H | H |
| (CH₂)₂-2-C₅H₃N-6-(CH₂)₈—C₆H₅ | CH₃CO | H | CH₃CO | CH₃CO |
| (CH₂)₂-2-C₅H₃N-6-(CH₂)₉—C₆H₅ | H | H | H | H |
| (CH₂)₂-2-C₅H₃N-6-(CH₂)₉—C₆H₅ | CH₃CO | H | CH₃CO | CH₃CO |
| (CH₂)₂-2-C₅H₃N-6-(CH₂)₁₀—C₆H₅ | H | H | H | H |
| (CH₂)₂-2-C₅H₃N-6-(CH₂)₁₀—C₆H₅ | CH₃CO | H | CH₃CO | CH₃CO |
| 3-C₅H₃N-5-(CH₂)₁₀CH₃ | H | H | H | H |
| CH₂-3-C₅H₃N-5-(CH₂)₉CH₃ | H | H | H | H |
| (CH₂)₃-3-C₅H₃N-5-(CH₂)₇CH₃ | H | H | H | H |
| (CH₂)₄-3-C₅H₃N-5-(CH₂)₆CH₃ | H | H | H | H |
| (CH₂)₅-3-C₅H₃N-5-(CH₂)₅CH₃ | H | H | H | H |
| (CH₂)₆-3-C₅H₃N-5-(CH₂)₄CH₃ | H | H | H | H |
| (CH₂)₇-3-C₅H₃N-5-(CH₂)₃CH₃ | H | H | H | H |
| (CH₂)₈-3-C₅H₃N-5-(CH₂)₂CH₃ | H | H | H | H |
| (CH₂)₉-3-C₅H₃N-5-CH₂CH₃ | H | H | H | H |
| (CH₂)₁₀-3-C₅H₃N-5-CH₃ | H | H | H | H |
| (CH₂)₁₁-3-C₅H₄N | H | H | H | H |
| (CH₂)₁₁-3-C₅H₄N | CH₃CO | H | CH₃CO | CH₃CO |
| (CH₂)₉-3-C₅H₄N | H | H | H | H |
| (CH₂)₉-3-C₅H₄N | CH₃CO | H | CH₃CO | CH₃CO |
| (CH₂)₁₀-3-C₅H₄N | H | H | H | H |
| (CH₂)₁₀-3-C₅H₄N | CH₃CO | H | CH₃CO | CH₃CO |
| (CH₂)₁₂-3-C₅H₄N | H | H | H | H |
| (CH₂)₁₂-3-C₅H₄N | CH₃CO | H | CH₃CO | CH₃CO |
| (CH₂)₁₃-3-C₅H₄N | H | H | H | H |
| (CH₂)₁₃-3-C₅H₄N | CH₃CO | H | CH₃CO | CH₃CO |
| (CH₂)₁₄-3-C₅H₄N | H | H | H | H |
| (CH₂)₁₄-3-C₅H₄N | CH₃CO | H | CH₃CO | CH₃CO |
| (CH₂)₁₅-3-C₅H₄N | H | H | H | H |
| (CH₂)₁₅-3-C₅H₄N | CH₃CO | H | CH₃CO | CH₃CO |
| (CH₂)₁₆-3-C₅H₄N | H | H | H | H |
| (CH₂)₁₆-3-C₅H₄N | CH₃CO | H | CH₃CO | CH₃CO |
| (CH₂)₁₇-3-C₅H₄N | H | H | H | H |
| (CH₂)₁₇-3-C₅H₄N | CH₃CO | H | CH₃CO | CH₃CO |
| (CH₂)₂-3-C₅H₃N-5-(CH₂)₈CH₃ | H | H | H | H |
| (CH₂)₂-3-C₅H₃N-5-(CH₂)₈CH₃ | CH₃CO | H | CH₃CO | CH₃CO |
| (CH₂)₂-3-C₅H₃N-5-(CH₂)₁₂CH₃ | H | H | H | H |
| (CH₂)₂-3-C₅H₃N-5-(CH₂)₁₂CH₃ | CH₃CO | H | CH₃CO | CH₃CO |
| (CH₂)₂-3-C₅H₃N-5-CH₂—C₆H₅ | H | H | H | H |
| (CH₂)₂-3-C₅H₃N-5-CH₂—C₆H₅ | CH₃CO | H | CH₃CO | CH₃CO |
| (CH₂)₂-3-C₅H₃N-5-(CH₂)₇CH₃ | H | H | H | H |
| (CH₂)₂-3-C₅H₃N-5-(CH₂)₇CH₃ | CH₃CO | H | CH₃CO | CH₃CO |
| (CH₂)₂-3-C₅H₃N-5-(CH₂)₁₁CH₃ | CH₃CO | H | CH₃CO | CH₃CO |
| (CH₂)₂-3-C₅H₃N-5-(CH₂)₁₁CH₃ | H | H | H | H |
| (CH₂)₂-3-C₅H₃N-5-CH₂—C₆H₅ | CH₃CO | H | CH₃CO | CH₃CO |
| (CH₂)₂-3-C₅H₃N-5-(CH₂)₂—C₆H₅ | H | H | H | H |
| (CH₂)₂-3-C₅H₃N-5-(CH₂)₂—C₆H₅ | CH₃CO | H | CH₃CO | CH₃CO |
| (CH₂)₂-3-C₅H₃N-5-(CH₂)₃—C₆H₅ | H | H | H | H |
| (CH₂)₂-3-C₅H₃N-5-(CH₂)₃—C₆H₅ | CH₃CO | H | CH₃CO | CH₃CO |

-continued $$R^2R^3N-\underset{R}{\underset{|}{C}}-\overset{CH_2OR^4}{\overset{|}{\phantom{C}}}CH_2OR^5$$

| R | R² | R³ | R⁴ | R⁵ |
|---|---|---|---|---|
| (CH₂)₂-3-C₅H₃N-5-(CH₂)₄—C₆H₅ | H | H | H | H |
| (CH₂)₂-3-C₅H₃N-5-(CH₂)₄—C₆H₅ | CH₃CO | H | CH₃CO | CH₃CO |
| (CH₂)₂-3-C₅H₃N-5-(CH₂)₅—C₆H₅ | H | H | H | H |
| (CH₂)₂-3-C₅H₃N-5-(CH₂)₅—C₆H₅ | CH₃CO | H | CH₃CO | CH₃CO |
| (CH₂)₂-3-C₅H₃N-5-(CH₂)₆—C₆H₅ | H | H | H | H |
| (CH₂)₂-3-C₅H₃N-5-(CH₂)₆—C₆H₅ | CH₃CO | H | CH₃CO | CH₃CO |
| (CH₂)₂-3-C₅H₃N-5-(CH₂)₇—C₆H₅ | H | H | H | H |
| (CH₂)₂-3-C₅H₃N-5-(CH₂)₇—C₆H₅ | CH₃CO | H | CH₃CO | CH₃CO |
| (CH₂)₂-3-C₅H₃N-5-(CH₂)₈—C₆H₅ | H | H | H | H |
| (CH₂)₂-3-C₅H₃N-5-(CH₂)₈—C₆H₅ | CH₃CO | H | CH₃CO | CH₃CO |
| (CH₂)₂-3-C₅H₃N-5-(CH₂)₉—C₆H₅ | H | H | H | H |
| (CH₂)₂-3-C₅H₃N-5-(CH₂)₉—C₆H₅ | CH₃CO | H | CH₃CO | CH₃CO |
| (CH₂)₂-3-C₅H₃N-5-(CH₂)₁₀—C₆H₅ | H | H | H | H |
| (CH₂)₂-3-C₅H₃N-5-(CH₂)₁₀—C₆H₅ | CH₃CO | H | CH₃CO | CH₃CO |
| (CH₂)₂—C₆H₄-4-CH₂-3-C₅H₄N | H | H | H | H |
| (CH₂)₂—C₆H₄-4-CH₂-3-C₅H₄N | CH₃CO | H | CH₃CO | CH₃CO |
| (CH₂)₂—C₆H₄-4-(CH₂)₂-3-C₅H₄N | H | H | H | H |
| (CH₂)₂—C₆H₄-4-(CH₂)₂-3-C₅H₄N | CH₃CO | H | CH₃CO | CH₃CO |
| (CH₂)₂—C₆H₄-4-(CH₂)₃-3-C₅H₄N | H | H | H | H |
| (CH₂)₂—C₆H₄-4-(CH₂)₃-3-C₅H₄N | CH₃CO | H | CH₃CO | CH₃CO |
| (CH₂)₂—C₆H₄-4-(CH₂)₄-3-C₅H₄N | H | H | H | H |
| (CH₂)₂—C₆H₄-4-(CH₂)₄-3-C₅H₄N | CH₃CO | H | CH₃CO | CH₃CO |
| (CH₂)₂—C₆H₄-4-(CH₂)₅-3-C₅H₄N | H | H | H | H |
| (CH₂)₂—C₆H₄-4-(CH₂)₅-3-C₅H₄N | CH₃CO | H | CHCO | CH₃CO |
| (CH₂)₂—C₆H₄-4-(CH₂)₆-3-C₅H₄N | H | H | H | H |
| (CH₂)₂—C₆H₄-4-(CH₂)₆-3-C₅H₄N | CH₃CO | H | CH₃CO | CH₃CO |
| (CH₂)₂—C₆H₄-4-(CH₂)₇-3-C₅H₄N | H | H | H | H |
| (CH₂)₂—C₆H₄-4-(CH₂)₇-3-C₅H₄N | CH₃CO | H | CH₃CO | CH₃CO |
| (CH₂)₂—C₆H₄-4-(CH₂)₈-3-C₅H₄N | H | H | H | H |
| (CH₂)₂—C₆H₄-4-(CH₂)₈-3-C₅H₄N | CH₃CO | H | CH₃CO | CH₃CO |
| (CH₂)₂—C₆H₄-4-(CH₂)₉-3-C₅H₄N | H | H | H | H |
| (CH₂)₂—C₆H₄-4-(CH₂)₉-3-C₅H₄N | CH₃CO | H | CH₃CO | CH₃CO |
| (CH₂)₂—C₆H₄-4-(CH₂)₁₀-3-C₅H₄N | H | H | H | H |
| (CH₂)₂—C₆H₄-4-(CH₂)₁₀-3-C₅H₄N | CH₃CO | H | CH₃CO | CH₃CO |

$$R^2R^3N-\underset{R}{\underset{|}{C}}-\overset{CH_2OR^4}{\overset{|}{\phantom{C}}}CH_2OR^5$$

| R | R² | R³ | R⁴ | R⁵ |
|---|---|---|---|---|
| —⟨piperidine⟩N—(CH₂)₉CH₃ | H | H | H | H |
| CH₂—⟨piperidine⟩N—(CH₂)₈CH₃ | H | H | H | H |
| (CH₂)₂—⟨piperidine⟩N—(CH₂)₇CH₃ | H | H | H | H |
| (CH₂)₃—⟨piperidine⟩N—(CH₂)₆CH₃ | H | H | H | H |
| (CH₂)₄—⟨piperidine⟩N—(CH₂)₅CH₃ | H | H | H | H |

-continued $$R^2R^3N-\underset{\underset{R}{|}}{\overset{\overset{CH_2OR^4}{|}}{C}}-CH_2OR^5$$

| R | R² | R³ | R⁴ | R⁵ |
|---|----|----|----|----|
| (CH₂)₅—⟨N—(CH₂)₄CH₃⟩ | H | H | H | H |
| (CH₂)₆—⟨N—(CH₂)₃CH₃⟩ | CH₃CO | H | CH₃CO | CH₃CO |
| (CH₂)₇—⟨N—(CH₂)₂CH₃⟩ | H | H | H | H |
| (CH₂)₈—⟨N—CH₂CH₃⟩ | H | H | H | H |
| (CH₂)₉—⟨N—CH₃⟩ | H | H | H | H |
| (CH₂)₁₀—⟨NH⟩ | H | H | H | H |
| (CH₂)₁₁—⟨NH⟩ | H | H | H | H |
| CH₂—N⟨⟩—(CH₂)₈CH₃ | H | H | H | H |
| (CH₂)₂—N⟨⟩—(CH₂)₇CH₃ | H | H | H | H |
| (CH₂)₃—N⟨⟩—(CH₂)₆CH₃H | H | H | H | H |
| (CH₂)₄—N⟨⟩—(CH₂)₅CH₃ | H | H | H | H |
| (CH₂)₅—N⟨⟩—(CH₂)₄CH₃ | H | H | H | H |
| (CH₂)₆—N⟨⟩—(CH₂)₃CH₃ | H | H | H | H |
| (CH₂)₇—N⟨⟩—(CH₂)₂CH₃ | H | H | H | H |

-continued $$R^2R^3N-\underset{R}{\underset{|}{\overset{CH_2OR^4}{\overset{|}{C}}}}-CH_2OR^5$$

| R | $R^2$ | $R^3$ | $R^4$ | $R^5$ |
|---|---|---|---|---|
| $(CH_2)_8-N\underset{}{\diagdown}\diagup-CH_2CH_3$ | H | H | H | H |
| $(CH_2)_9-N\underset{}{\diagdown}\diagup-CH_3$ | H | H | H | H |
| $(CH_2)_{10}-N\underset{}{\diagdown}\diagup$ | H | H | H | H |
| $(CH_2)_2-N\underset{}{\diagdown}\diagup-(CH_2)_8CH_3$ | H | H | H | H |
| $(CH_2)_2-N\underset{}{\diagdown}\diagup-(CH_2)_9CH_3$ | CH$_3$CO | H | CH$_3$CO | CH$_3$CO |
| $(CH_2)_2-N\underset{}{\diagdown}\diagup-(CH_2)_{10}CH_3$ | H | H | H | H |
| $(CH_2)_2-N\underset{}{\diagdown}\diagup-(CH_2)_{11}CH_3$ | H | H | H | H |
| $(CH_2)_{11}-N\underset{}{\diagdown}\diagup$ | H | H | H | H |
| $(CH_2)_{12}-N\underset{}{\diagdown}\diagup$ | CH$_3$CO | H | CH$_3$CO | CH$_3$CO |
| $(CH_2)_{13}-N\underset{}{\diagdown}\diagup$ | H | H | H | H |
| $(CH_2)_{14}-N\underset{}{\diagdown}\diagup$ | H | H | H | H |
| $(CH_2)_{15}-N\underset{}{\diagdown}\diagup$ | H | H | H | H |
| $(CH_2)_{16}-N\underset{}{\diagdown}\diagup$ | H | H | H | H |

-continued $$R^2R^3N-\underset{R}{\underset{|}{\overset{CH_2OR^4}{\overset{|}{C}}}}-CH_2OR^5$$

| R | $R^2$ | $R^3$ | $R^4$ | $R^5$ |
|---|---|---|---|---|
| (CH$_2$)$_{11}$–piperidine | H | H | H | H |
| (CH$_2$)$_{12}$–piperidine | H | H | H | H |
| (CH$_2$)$_{13}$–piperidine | H | H | H | H |
| (CH$_2$)$_{14}$–piperidine | H | H | H | H |
| (CH$_2$)$_{15}$–piperidine | H | H | H | H |
| (CH$_2$)$_{16}$–piperidine | H | H | H | H |
| (CH$_2$)$_2$–C$_6$H$_4$–CH$_2$–N(piperidinyl) | H | H | H | H |
| (CH$_2$)$_2$–C$_6$H$_4$–(CH$_2$)$_2$–N(piperidinyl) | H | H | H | H |
| (CH$_2$)$_2$–C$_6$H$_4$–(CH$_2$)$_3$–N(piperidinyl) | H | H | H | H |
| (CH$_2$)$_2$–C$_6$H$_4$–(CH$_2$)$_4$–N(piperidinyl) | H | H | H | H |
| (CH$_2$)$_2$–C$_6$H$_4$–(CH$_2$)$_5$–N(piperidinyl) | H | H | H | H |
| (CH$_2$)$_2$–C$_6$H$_4$–(CH$_2$)$_6$–N(piperidinyl) | H | H | H | H |
| (CH$_2$)$_2$–C$_6$H$_4$–(CH$_2$)$_7$–N(piperidinyl) | H | H | H | H |
| (CH$_2$)$_2$–C$_6$H$_4$–(CH$_2$)$_8$–N(piperidinyl) | H | H | H | H |

-continued
$$R^2R^3N-\underset{R}{\overset{CH_2OR^4}{\underset{|}{C}}}-CH_2OR^5$$
| R | R² | R³ | R⁴ | R⁵ |
|---|----|----|----|----|
|  | H | H | H | H |
| 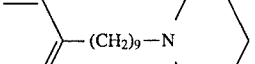 | H | H | H | H |
|  | H | H | H | H |
|  | H | H | H | H |
| 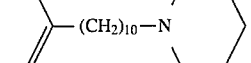 | H | H | H | H |
|  | H | H | H | H |
|  | H | H | H | H |
| 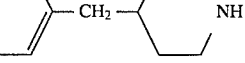 | H | H | H | H |
|  | H | H | H | H |
| 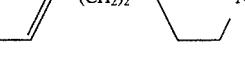 | H | H | H | H |
|  | H | H | H | H |
|  | H | H | H | H |

-continued $$R^2R^3N-\underset{R}{\overset{CH_2OR^4}{\underset{|}{C}}}-CH_2OR^5$$

| R | R² | R³ | R⁴ | R⁵ |
|---|----|----|----|----|
| (CH₂)₂—⟨piperidine⟩N—(CH₂)₂—⟨phenyl⟩ | H | H | H | H |
| (CH₂)₂—⟨piperidine⟩N—(CH₂)₃—⟨phenyl⟩ | H | H | H | H |
| (CH₂)₂—⟨piperidine⟩N—(CH₂)₄—⟨phenyl⟩ | H | H | H | H |
| (CH₂)₂—⟨piperidine⟩N—(CH₂)₅—⟨phenyl⟩ | H | H | H | H |
| (CH₂)₂—⟨piperidine⟩N—(CH₂)₆—⟨phenyl⟩ | H | H | H | H |
| (CH₂)₂—⟨piperidine⟩N—(CH₂)₇—⟨phenyl⟩ | H | H | H | H |
| (CH₂)₂—⟨piperidine⟩N—(CH₂)₈—⟨phenyl⟩ | H | H | H | H |
| (CH₂)₂—⟨piperidine⟩N—(CH₂)₉—⟨phenyl⟩ | H | H | H | H |
| (CH₂)₂—⟨piperidine⟩N—(CH₂)₁₀—⟨phenyl⟩ | H | H | H | H |
| (CH₂)₂—N⟨piperidine⟩—CH₂—⟨phenyl⟩ | H | H | H | H |
| (CH₂)₂—N⟨piperidine⟩—(CH₂)₂—⟨phenyl⟩ | H | H | H | H |
| (CH₂)₂—N⟨piperidine⟩—(CH₂)₃—⟨phenyl⟩ | H | H | H | H |
| (CH₂)₂—N⟨piperidine⟩—(CH₂)₄—⟨phenyl⟩ | H | H | H | H |
| (CH₂)₂—N⟨piperidine⟩—(CH₂)₅—⟨phenyl⟩ | H | H | H | H |

-continued
$$R^2R^3N-\underset{R}{\overset{CH_2OR^4}{\underset{|}{C}}}-CH_2OR^5$$
| R | $R^2$ | $R^3$ | $R^4$ | $R^5$ |
|---|---|---|---|---|
| 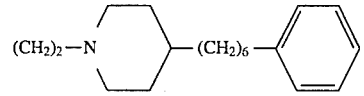 | H | H | H | H |
| 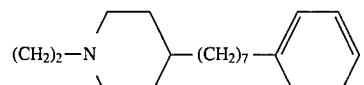 | H | H | H | H |
| 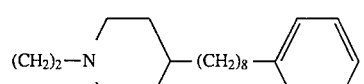 | H | H | H | H |
| 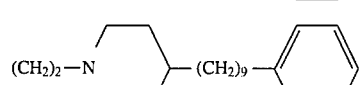 | H | H | H | H |
| 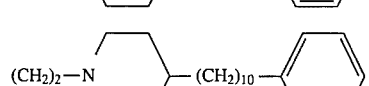 | H | H | H | H |
| 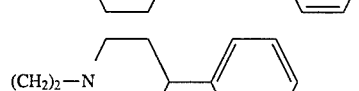 | H | H | H | H |
| 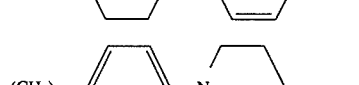 | H | H | H | H |
| 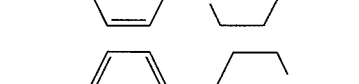 | H | H | H | H |
| 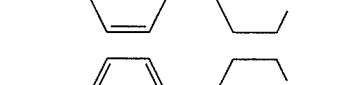 | H | H | H | H |
| 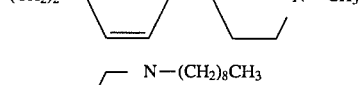 | H | H | H | H |
| 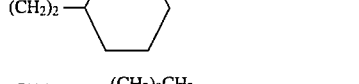 | H | H | H | H |
|  | H | H | H | H |

-continued $$R^2R^3N-\underset{R}{\underset{|}{C}}-CH_2OR^5 \quad \text{with} \quad CH_2OR^4 \text{ above}$$

| R | $R^2$ | $R^3$ | $R^4$ | $R^5$ |
|---|---|---|---|---|
| 4-(CH₂)₂, 3-(CH₂)₈CH₃ piperidine (NH) | H | H | H | H |
| 2-(CH₂)₂, 6-(CH₂)₈CH₃ piperidine (N) | H | H | H | H |
| (CH₂)₂N[piperazine]N(CH₂)₉CH₃ | H | H | H | H |
| CH₂—N[piperazine]N—(CH₂)₈CH₃ | H | H | H | H |
| (CH₂)₂—N[piperazine]N—(CH₂)₇CH₃ | H | H | H | H |
| (CH₂)₃—N[piperazine]N—(CH₂)₆CH₃ | H | H | H | H |
| (CH₂)₄—N[piperazine]N—(CH₂)₅CH₃ | H | H | H | H |
| (CH₂)₅—N[piperazine]N—(CH₂)₄CH₃ | H | H | H | H |
| (CH₂)₆—N[piperazine]N—(CH₂)₃CH₃ | H | H | H | H |
| (CH₂)₇—N[piperazine]N—(CH₂)₂CH₃ | H | H | H | H |
| (CH₂)₈—N[piperazine]N—CH₂CH₃ | H | H | H | H |
| (CH₂)₉—N[piperazine]N—CH₃ | H | H | H | H |
| (CH₂)₁₀—N[piperazine]NH | H | H | H | H |

-continued $$R^2R^3N-\underset{R}{\underset{|}{C}}\overset{CH_2OR^4}{\overset{|}{-}}CH_2OR^5$$

| R | R² | R³ | R⁴ | R⁵ |
|---|---|---|---|---|
| (CH₂)₂—N(piperazine)N—(CH₂)₂—C₆H₅ | CH₃CO | H | CH₃CO | CH₃CO |
| (CH₂)₂—N(piperazine)N—(CH₂)₃—C₆H₅ | H | H | H | H |
| (CH₂)₂—N(piperazine)N—(CH₂)₄—C₆H₅ | H | H | H | H |
| (CH₂)₂—N(piperazine)N—(CH₂)₅—C₆H₅ | H | H | H | H |
| (CH₂)₂—N(piperazine)N—(CH₂)₆—C₆H₅ | H | H | H | H |
| (CH₂)₂—N(piperazine)N—(CH₂)₇—C₆H₅ | H | H | H | H |
| (CH₂)₂—N(piperazine)N—(CH₂)₈—C₆H₅ | H | H | H | H |
| (CH₂)₂—N(piperazine)N—(CH₂)₉—C₆H₅ | H | H | H | H |
| (CH₂)₂—N(piperazine)N—(CH₂)₁₀—C₆H₅ | H | H | H | H |
| (CH₂)₂—C₆H₄—CH₂—N(piperazine)NH | H | H | H | H |
| (CH₂)₂—C₆H₄—(CH₂)₂—N(piperazine)NH | H | H | H | H |
| (CH₂)₂—C₆H₄—(CH₂)₃—N(piperazine)NH | H | H | H | H |
| (CH₂)₂—C₆H₄—(CH₂)₄—N(piperazine)NH | H | H | H | H |
| (CH₂)₂—C₆H₄—(CH₂)₅—N(piperazine)NH | H | H | H | H |

-continued $$\begin{array}{c} \text{CH}_2\text{OR}^4 \\ | \\ \text{R}^2\text{R}^3\text{N} - \text{C} - \text{CH}_2\text{OR}^5 \\ | \\ \text{R} \end{array}$$

| R | R² | R³ | R⁴ | R⁵ |
|---|---|---|---|---|
| (CH₂)₂—C₆H₄—(CH₂)₆—N(piperazine)NH | H | H | H | H |
| (CH₂)₂—C₆H₄—(CH₂)₇—N(piperazine)NH | H | H | H | H |
| (CH₂)₂—C₆H₄—(CH₂)₈—N(piperazine)NH | H | H | H | H |
| (CH₂)₂—C₆H₄—(CH₂)₉—N(piperazine)NH | H | H | H | H |
| (CH₂)₂—C₆H₄—(CH₂)₁₀—N(piperazine)NH | H | H | H | H |
| (CH₂)₂—N(piperazine)N—(CH₂)₁₁CH₃ | H | H | H | H |
| (CH₂)₂—(morpholine with N—(CH₂)₈CH₃, O) | H | H | H | H |
| (CH₂)₂—(thiomorpholine with N—(CH₂)₈CH₃, S) | H | H | H | H |
| CH₂—(pyrrolidine)N—(CH₂)₉CH₃ | H | H | H | H |
| (CH₂)₂—(pyrrolidine)N—(CH₂)₈CH₃ | H | H | H | H |
| (CH₂)₃—(pyrrolidine)N—(CH₂)₇CH₃ | H | H | H | H |
| (CH₂)₄—(pyrrolidine)N—(CH₂)₆CH₃ | H | H | H | H |
| (CH₂)₅—(pyrrolidine)N—(CH₂)₅CH₃ | H | H | H | H |
| (CH₂)₆—(pyrrolidine)N—(CH₂)₄CH₃ | H | H | H | H |
| (CH₂)₇—(pyrrolidine)N—(CH₂)₃CH₃ | H | H | H | H |

-continued $$R^2R^3N-\underset{R}{\overset{CH_2OR^4}{\underset{|}{C}}}-CH_2OR^5$$

| R | R² | R³ | R⁴ | R⁵ |
|---|---|---|---|---|
| (CH₂)₈—[3-(N-propyl)pyrrolidinyl] | H | H | H | H |
| (CH₂)₉—[3-(N-ethyl)pyrrolidinyl] | H | H | H | H |
| (CH₂)₁₀—[3-(N-methyl)pyrrolidinyl] | H | H | H | H |
| CH₂—[1-N,3-(CH₂)₉CH₃-pyrrolidinyl] | H | H | H | H |
| (CH₂)₂—[1-N,3-(CH₂)₈CH₃-pyrrolidinyl] | H | H | H | H |
| (CH₂)₃—[1-N,3-(CH₂)₇CH₃-pyrrolidinyl] | H | H | H | H |
| (CH₂)₄—[1-N,3-(CH₂)₆CH₃-pyrrolidinyl] | H | H | H | H |
| (CH₂)₅—[1-N,3-(CH₂)₅CH₃-pyrrolidinyl] | H | H | H | H |
| (CH₂)₆—[1-N,3-(CH₂)₄CH₃-pyrrolidinyl] | H | H | H | H |
| (CH₂)₇—[1-N,3-(CH₂)₃CH₃-pyrrolidinyl] | H | H | H | H |
| (CH₂)₈—[1-N,3-(CH₂)₂CH₃-pyrrolidinyl] | H | H | H | H |
| (CH₂)₉—[1-N,3-CH₂CH₃-pyrrolidinyl] | H | H | H | H |
| (CH₂)₁₀—[1-N,3-CH₃-pyrrolidinyl] | H | H | H | H |
| (CH₂)₂—[1-N,3-(CH₂)₁₂CH₃-pyrrolidinyl] | H | H | H | H |
| (CH₂)₂—C₆H₄—CH₂—N(pyrrolidinyl) | H | H | H | H |
| (CH₂)₂—C₆H₄—(CH₂)₂—N(pyrrolidinyl) | H | H | H | H |

-continued
$$R^2R^3N-\underset{\underset{R}{|}}{\overset{\overset{CH_2OR^4}{|}}{C}}-CH_2OR^5$$
| R | $R^2$ | $R^3$ | $R^4$ | $R^5$ |
|---|---|---|---|---|
| 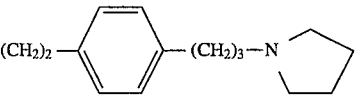 | H | H | H | H |
| 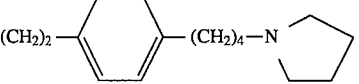 | CH₃CO | H | CH₃CO | CH₃CO |
| 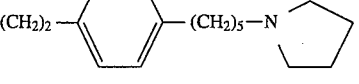 | H | H | H | H |
| 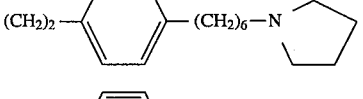 | H | H | H | H |
| 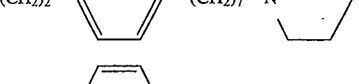 | H | H | H | H |
|  | H | H | H | H |
| 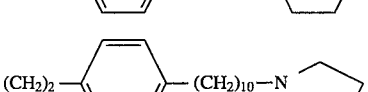 | H | H | H | H |
| 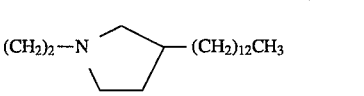 | H | H | H | H |
| 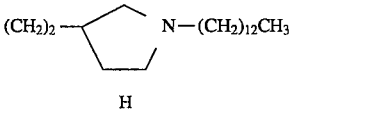 | CH₃CO | H | CH₃CO | CH₃CO |
| 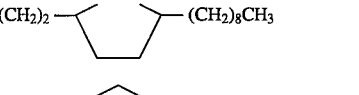 | H | H | H | H |
| 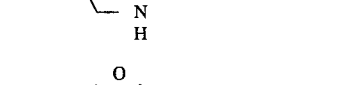 | H | H | H | H |
| 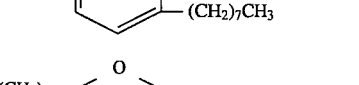 | H | H | H | H |
| 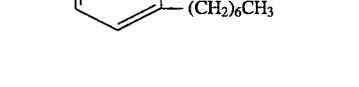 | H | H | H | H |

-continued $$R^2R^3N-\underset{R}{\underset{|}{C}}-\overset{CH_2OR^4}{\underset{CH_2OR^5}{|}}$$

| R | R² | R³ | R⁴ | R⁵ |
|---|----|----|----|----|
| (CH₂)₄—[dihydropyran]—(CH₂)₅CH₃ | H | H | H | H |
| (CH₂)₅—[dihydropyran]—(CH₂)₄CH₃ | H | H | H | H |
| (CH₂)₆—[dihydropyran]—(CH₂)₃CH₃ | H | H | H | H |
| (CH₂)₇—[dihydropyran]—(CH₂)₂CH₃ | H | H | H | H |
| (CH₂)₈—[dihydropyran]—CH₂CH₃ | H | H | H | H |
| (CH₂)₉—[dihydropyran]—CH₃ | CH₃CO | H | CH₃CO | CH₃CO |
| (CH₂)₂—[dihydropyran]—(CH₂)₁₁CH₃ | H | H | H | H |
| (CH₂)₂—[dihydropyran]—(CH₂)₁₂CH₃ | H | H | H | H |
| (CH₂)₂—[dihydropyran]—CH₂—Ph | CH₃CO | H | CH₃CO | CH₃CO |
| (CH₂)₂—[dihydropyran]—(CH₂)₂—Ph | H | H | H | H |
| (CH₂)₂—[dihydropyran]—(CH₂)₃—Ph | H | H | H | H |
| (CH₂)₂—[dihydropyran]—(CH₂)₄—Ph | H | H | H | H |
| (CH₂)₂—[dihydropyran]—(CH₂)₅—Ph | H | H | H | H |

-continued $$R^2R^3N-\underset{\underset{R}{|}}{\overset{\overset{CH_2OR^4}{|}}{C}}-CH_2OR^5$$

| R | R² | R³ | R⁴ | R⁵ |
|---|---|---|---|---|
| (CH₂)₂—[dihydropyran]—(CH₂)₆—[phenyl] | H | H | H | H |
| (CH₂)₂—[dihydropyran]—(CH₂)₇—[phenyl] | H | H | H | H |
| (CH₂)₂—[dihydropyran]—(CH₂)₈—[phenyl] | H | H | H | H |
| (CH₂)₂—[dihydropyran]—(CH₂)₉—[phenyl] | H | H | H | H |
| (CH₂)₂—[dihydropyran]—(CH₂)₁₀—[phenyl] | CH₃CO | H | CH₃CO | CH₃CO |
| (CH₂)₂—[phenyl]—CH₂—[dihydropyran] | H | H | H | H |
| (CH₂)₂—[phenyl]—(CH₂)₂—[dihydropyran] | H | H | H | H |
| (CH₂)₂—[phenyl]—(CH₂)₃—[dihydropyran] | H | H | H | H |
| (CH₂)₂—[phenyl]—(CH₂)₄—[dihydropyran] | H | H | H | H |
| (CH₂)₂—[phenyl]—(CH₂)₅—[dihydropyran] | CH₃CO | H | CH₃CO | CH₃CO |
| (CH₂)₂—[phenyl]—(CH₂)₆—[dihydropyran] | H | H | H | H |
| (CH₂)₂—[phenyl]—(CH₂)₇—[dihydropyran] | H | H | H | H |
| (CH₂)₂—[phenyl]—(CH₂)₈—[dihydropyran] | H | H | H | H |

-continued $$R^2R^3N-\underset{R}{\underset{|}{C}}\begin{matrix}CH_2OR^4\\-CH_2OR^5\end{matrix}$$

| R | R² | R³ | R⁴ | R⁵ |
|---|---|---|---|---|
| (CH₂)₂—C₆H₄—(CH₂)₉—(3,6-dihydro-2H-pyran-2-yl) | H | H | H | H |
| (CH₂)₂—C₆H₄—(CH₂)₁₀—(3,6-dihydro-2H-pyran-2-yl) | CH₃CO | H | CH₃CO | CH₃CO |
| (CH₂)₂—C₆H₄—(CH₂)₁₁—(3,6-dihydro-2H-pyran-2-yl) | H | H | H | H |
| (CH₂)₂—(3,6-dihydro-2H-pyran-2-yl)—(CH₂)₈CH₃ | H | H | H | H |
| (CH₂)₂—(3,6-dihydro-2H-pyran-4-yl)—(CH₂)₈CH₃ | H | H | H | H |

$$R^2R^3N-\underset{R}{\underset{|}{C}}\begin{matrix}CH_2OR^4\\-CH_2OR^5\end{matrix}$$

| R | R² | R³ | R⁴ | R⁵ |
|---|---|---|---|---|
| (CH₂)₁₀—(fur-2-yl) | H | H | H | H |
| (CH₂)₁₄—(fur-2-yl) | H | H | H | H |
| (CH₂)₁₁—(fur-2-yl) | H | H | H | H |
| (CH₂)₁₅—(fur-2-yl) | H | H | H | H |
| (CH₂)₂—(fur-2,5-diyl)—(CH₂)₇CH₃ | H | H | H | H |
| (CH₂)₂—(fur-2,5-diyl)—(CH₂)₁₁CH₃ | H | H | H | H |
| (CH₂)₂—(fur-2,5-diyl)—(CH₂)₉CH₃ | H | H | H | H |
| (CH₂)₂—(fur-2,5-diyl)—(CH₂)₁₃CH₃ | H | H | H | H |
| (CH₂)₂—(fur-2,4-diyl)—(CH₂)₈CH₃ | H | H | H | H |
| (CH₂)₂—(fur-2,4-diyl)—(CH₂)₁₂CH₃ | H | H | H | H |
| (CH₂)₂—(fur-2,5-diyl)—(CH₂)₈CH₃ | H | H | H | H |
| (CH₂)₂—(fur-2,5-diyl)—(CH₂)₁₂CH₃ | H | H | H | H |
| (CH₂)₂—C₆H₄—(CH₂)₄—(fur-2-yl) | H | H | H | H |

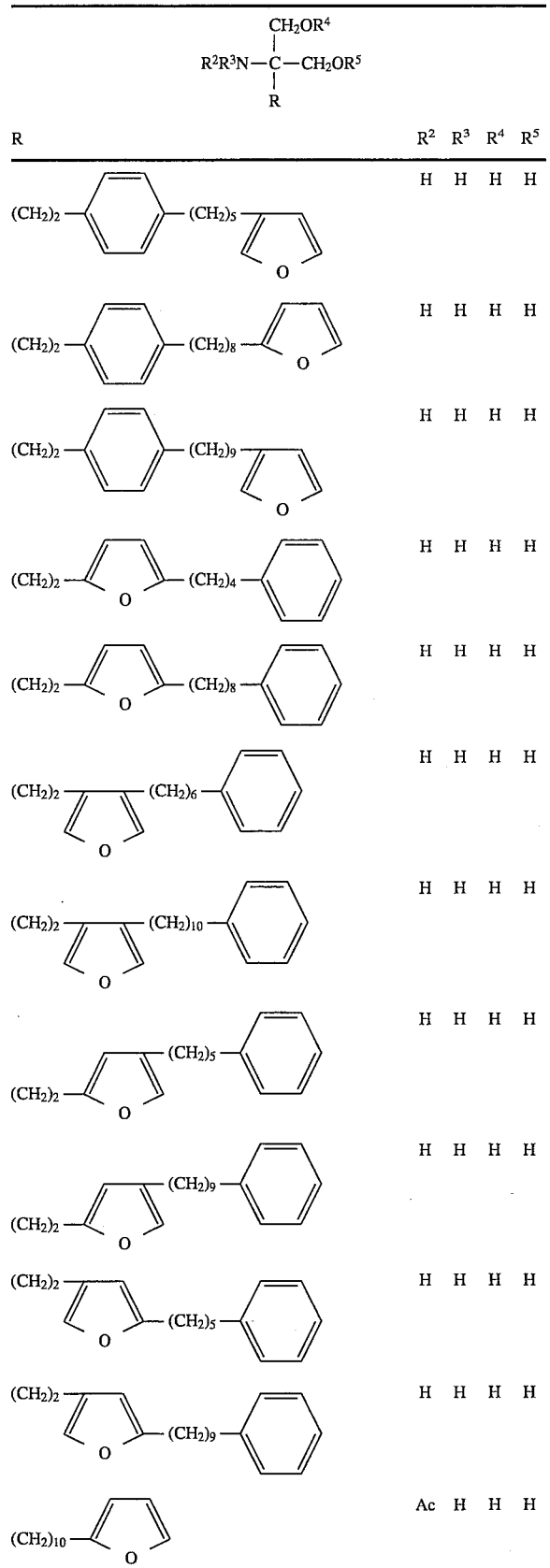
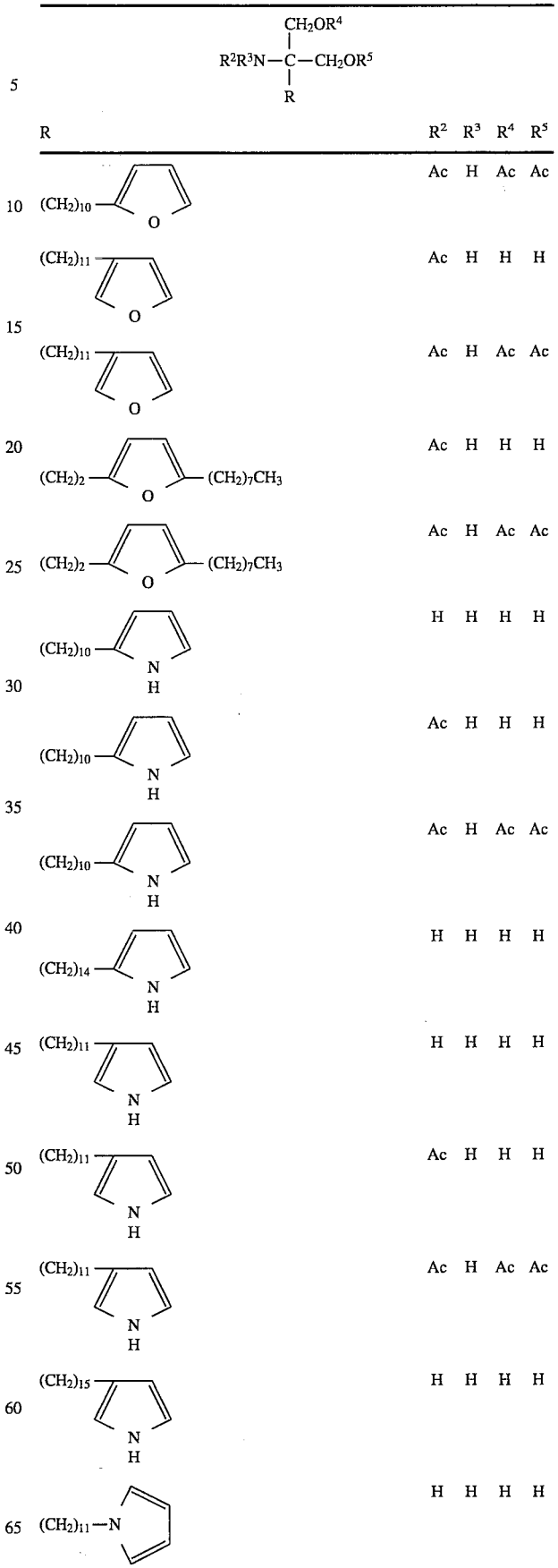

139
-continued $$R^2R^3N-\underset{R}{\underset{|}{C}}\genfrac{}{}{0pt}{}{CH_2OR^4}{CH_2OR^5}$$

| R | $R^2$ | $R^3$ | $R^4$ | $R^5$ |
|---|---|---|---|---|
| 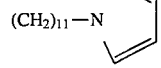 | Ac | H | H | H |
| 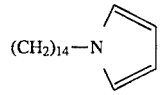 | H | H | H | H |
| 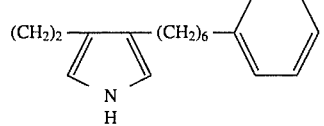 | H | H | H | H |
| 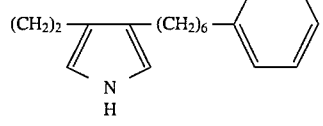 | Ac | H | H | H |
| 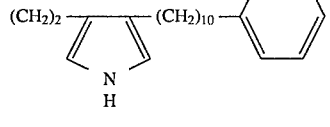 | H | H | H | H |
| 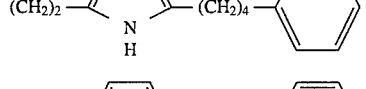 | H | H | H | H |
| 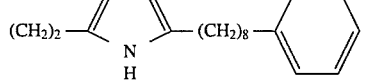 | Ac | H | H | H |
| 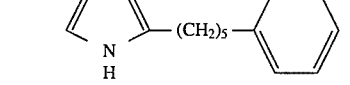 | H | H | H | H |
| 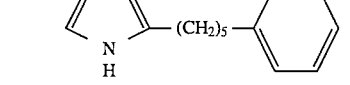 | H | H | H | H |
| 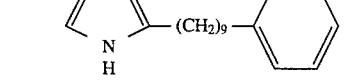 | Ac | H | H | H |
| 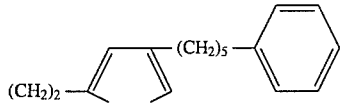 | H | H | H | H |

140
-continued $$R^2R^3N-\underset{R}{\underset{|}{C}}\genfrac{}{}{0pt}{}{CH_2OR^4}{CH_2OR^5}$$

| R | $R^2$ | $R^3$ | $R^4$ | $R^5$ |
|---|---|---|---|---|
| 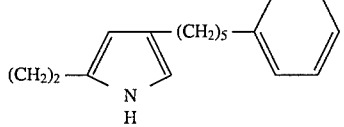 | H | H | H | H |
| 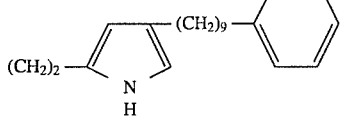 | Ac | H | H | H |
| 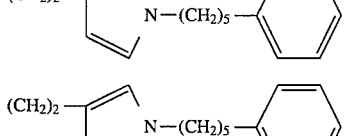 | H | H | H | H |
| 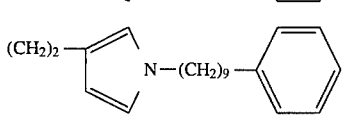 | H | H | H | H |
| 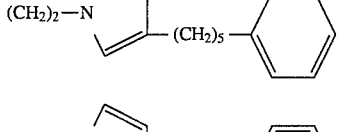 | Ac | H | H | H |
| 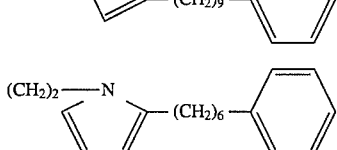 | H | H | H | H |
| 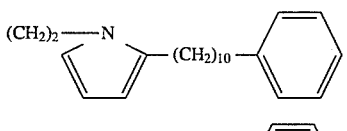 | H | H | H | H |
| 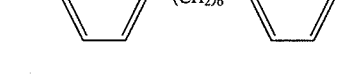 | H | H | H | H |
| (CH₂)₂—N⟨pyrrole⟩—(CH₂)₆—C₆H₅ | H | H | H | H |
| (CH₂)₂—N⟨pyrrole⟩—(CH₂)₁₀—C₆H₅ | H | H | H | H |
| (CH₂)₂—N⟨pyrrole⟩—(CH₂)₆—C₆H₅ | Ac | H | H | H |

141
-continued $$R^2R^3N-\underset{R}{\underset{|}{C}}\overset{CH_2OR^4}{\overset{|}{-}}CH_2OR^5$$

| R | R² | R³ | R⁴ | R⁵ |
|---|---|---|---|---|
| (CH₂)₂–C₆H₄–(CH₂)₅–pyrrole(NH) | H | H | H | H |
| (CH₂)₂–C₆H₄–(CH₂)₅–pyrrole(NH) | Ac | H | H | H |
| (CH₂)₂–C₆H₄–(CH₂)₉–pyrrole(NH) | H | H | H | H |
| (CH₂)₂–C₆H₄–(CH₂)₄–pyrrole(NH) | H | H | H | H |
| (CH₂)₂–C₆H₄–(CH₂)₄–pyrrole(NH) | Ac | H | H | H |
| (CH₂)₂–C₆H₄–(CH₂)₈–pyrrole(NH) | H | H | H | H |
| (CH₂)₂–C₆H₄–(CH₂)₅–N-pyrrole | H | H | H | H |
| (CH₂)₂–C₆H₄–(CH₂)₅–N-pyrrole | Ac | H | H | H |
| (CH₂)₂–C₆H₄–(CH₂)₉–N-pyrrole | H | H | H | H |
| (CH₂)₁₁–N-imidazole | H | H | H | H |
| (CH₂)₁₅–N-imidazole | H | H | H | H |
| (CH₂)₁₁–2-imidazole | H | H | H | H |

142
-continued $$R^2R^3N-\underset{R}{\underset{|}{C}}\overset{CH_2OR^4}{\overset{|}{-}}CH_2OR^5$$

| R | R² | R³ | R⁴ | R⁵ |
|---|---|---|---|---|
| (CH₂)₁₅–2-imidazole | H | H | H | H |
| (CH₂)₁₁–4-imidazole | H | H | H | H |
| (CH₂)₁₅–4-imidazole | H | H | H | H |
| (CH₂)₂–C₆H₄–(CH₂)₅–N-imidazole | H | H | H | H |
| (CH₂)₂–C₆H₄–(CH₂)₉–N-imidazole | H | H | H | H |
| (CH₂)₂–C₆H₄–(CH₂)₅–2-imidazole | H | H | H | H |
| (CH₂)₂–C₆H₄–(CH₂)₉–2-imidazole | H | H | H | H |
| (CH₂)₂–C₆H₄–(CH₂)₅–4-imidazole | H | H | H | H |
| (CH₂)₂–C₆H₄–(CH₂)₉–4-imidazole | H | H | H | H |
| (CH₂)₂–N-imidazole-(CH₂)₅–C₆H₅ | H | H | H | H |
| (CH₂)₂–N-imidazole-(CH₂)₉–C₆H₅ | H | H | H | H |
| (CH₂)₂–2-imidazole-(CH₂)₅–C₆H₅ | H | H | H | H |
| (CH₂)₂–2-imidazole-(CH₂)₉–C₆H₅ | H | H | H | H |

| R | R² | R³ | R⁴ | R⁵ |
|---|---|---|---|---|
| (CH₂)₂-[imidazole]-(CH₂)₅-phenyl | Ac | H | H | H |
| (CH₂)₂-N[imidazole]-(CH₂)₅-phenyl via other N | Ac | H | H | H |
| (CH₂)₂-[imidazole]-(CH₂)₅-phenyl | H | H | H | H |
| (CH₂)₂-[imidazole]-(CH₂)₉-phenyl | H | H | H | H |
| (CH₂)₂-[imidazole]-(CH₂)₅-phenyl | Ac | H | H | H |
| (CH₂)₂-phenyl-(CH₂)₅-N[imidazole] | H | H | H | H |
| (CH₂)₂-phenyl-(CH₂)₉-N[imidazole] | H | H | H | H |
| (CH₂)₂-phenyl-(CH₂)₅-[imidazole] | H | H | H | H |
| (CH₂)₂-phenyl-(CH₂)₉-[imidazole] | H | H | H | H |
| (CH₂)₂-phenyl-(CH₂)₅-[imidazole] | H | H | H | H |
| (CH₂)₂-phenyl-(CH₂)₉-[imidazole] | H | H | H | H |
| (CH₂)₂-phenyl-(CH₂)₅-[imidazole] | Ac | H | H | H |
| (CH₂)₁₁-[thiazole] | H | H | H | H |

| R | R² | R³ | R⁴ | R⁵ |
|---|---|---|---|---|
| (CH₂)₁₅-[thiazole] | H | H | H | H |
| (CH₂)₁₁-[thiazole] | H | H | H | H |
| (CH₂)₁₅-[thiazole] | H | H | H | H |
| (CH₂)₂-phenyl-(CH₂)₅-[thiazole] | H | H | H | H |
| (CH₂)₂-phenyl-(CH₂)₉-[thiazole] | H | H | H | H |
| (CH₂)₂-phenyl-(CH₂)₅-[thiazole] | H | H | H | H |
| (CH₂)₂-phenyl-(CH₂)₉-[thiazole] | H | H | H | H |
| (CH₂)₂-[thiazole]-(CH₂)₅-phenyl | H | H | H | H |
| (CH₂)₂-[thiazole]-(CH₂)₉-phenyl | H | H | H | H |
| (CH₂)₂-[thiazole]-(CH₂)₅-phenyl | H | H | H | H |
| (CH₂)₂-[thiazole]-(CH₂)₉-phenyl | H | H | H | H |
| (CH₂)₂-[thiazole]-(CH₂)₅-phenyl | Ac | H | H | H |
| (CH₂)₂-[thiazole]-(CH₂)₅-phenyl | H | H | H | H |

145 -continued $$R^2R^3N-\underset{R}{\overset{CH_2OR^4}{\underset{|}{C}}}-CH_2OR^5$$

| R | R² | R³ | R⁴ | R⁵ |
|---|----|----|----|----|
| (CH₂)₂-[thiazole]-(CH₂)₉-Ph | H | H | H | H |
| (CH₂)₂-[thiazole]-(CH₂)₅-Ph | Ac | H | H | H |
| (CH₂)₂-[thiazole]-(CH₂)₅-Ph | H | H | H | H |
| (CH₂)₂-[thiazole]-(CH₂)₉-Ph | H | H | H | H |
| (CH₂)₂-[thiazole]-(CH₂)₅-Ph | Ac | H | H | H |
| (CH₂)₂-[thiazole]-(CH₂)₉-Ph | Ac | H | H | H |
| (CH₂)₂-[isothiazole]-(CH₂)₉CH₃ | H | H | H | H |
| (CH₂)₂-[isothiazole]-(CH₂)₁₃CH₃ | H | H | H | H |
| (CH₂)₂-[isothiazole]-(CH₂)₈CH₃ | H | H | H | H |
| (CH₂)₂-[isothiazole]-(CH₂)₁₂CH₃ | H | H | H | H |
| (CH₂)₂-[isoxazole]-(CH₂)₉CH₃ | H | H | H | H |
| (CH₂)₂-[isoxazole]-(CH₂)₁₃CH₃ | H | H | H | H |
| (CH₂)₂-[isoxazole]-(CH₂)₈CH₃ | H | H | H | H |
| (CH₂)₂-[isoxazole]-(CH₂)₁₂CH₃ | H | H | H | H |

146 -continued $$R^2R^3N-\underset{R}{\overset{CH_2OR^4}{\underset{|}{C}}}-CH_2OR^5$$

| R | R² | R³ | R⁴ | R⁵ |
|---|----|----|----|----|
| (CH₂)₂-[oxazole]-(CH₂)₈CH₃ | H | H | H | H |
| (CH₂)₂-[oxazole]-(CH₂)₁₂CH₃ | H | H | H | H |
| (CH₂)₂-[oxazole]-(CH₂)₇CH₃ | H | H | H | H |
| (CH₂)₂-[oxazole]-(CH₂)₁₁CH₃ | H | H | H | H |
| (CH₂)₂-[imidazole]-(CH₂)₇CH₃ | H | H | H | H |
| (CH₂)₂-[imidazole]-(CH₂)₁₁CH₃ | H | H | H | H |
| (CH₂)₂-[imidazole]-(CH₂)₆CH₃ | H | H | H | H |
| (CH₂)₂-[imidazole]-(CH₂)₁₀CH₃ | H | H | H | H |
| (CH₂)₂-[pyrazine]-(CH₂)₆CH₃ | H | H | H | H |
| (CH₂)₂-[pyrazine]-(CH₂)₁₀CH₃ | H | H | H | H |
| (CH₂)₂-[pyrazine]-(CH₂)₇CH₃ | H | H | H | H |
| (CH₂)₂-[pyrazine]-(CH₂)₁₁CH₃ | H | H | H | H |
| (CH₂)₂-[pyridazine]-(CH₂)₇CH₃ | H | H | H | H |

-continued $$R^2R^3N-\underset{\underset{R}{|}}{\overset{\overset{CH_2OR^4}{|}}{C}}-CH_2OR^5$$

| R | | | | $R^2$ | $R^3$ | $R^4$ | $R^5$ |
|---|---|---|---|---|---|---|---|
| $(CH_2)_2-\underset{N=N}{\underset{||}{\diagdown}}\!\!\diagup\!\!\diagdown\!\!\underset{}{\diagup}-(CH_2)_{11}CH_3$ | | | | H | H | H | H |
| $(CH_2)_2-\underset{N=N}{\underset{||}{\diagdown}}\!\!\diagup\!\!\diagdown\!\!\underset{}{\diagup}-(CH_2)_6CH_3$ | | | | H | H | H | H |
| $(CH_2)_2-\underset{N=N}{\underset{||}{\diagdown}}\!\!\diagup\!\!\diagdown\!\!\underset{}{\diagup}-(CH_2)_{10}CH_3$ | | | | H | H | H | H |

Examples of the pharmaceutically acceptable salts of the compounds of the formula (I) [hereinafter referred to as Compound (I)] include salts with inorganic acids, such as hydrochloride, hydrobromide and sulfate, salts with organic acids, such as acetate, fumarate, maleate, benzoate, citrate, malate, methanesulfonate and benzenesulfonate, and when carboxyl group is included, salts with metals such as sodium salt, potassium salt, calcium salt and aluminum salt, salts with amines, such as triethylamine and salts with dibasic amino acids, such as lysine. The compounds of the present invention encompass hydrates and solvates.

When the compounds of the present invention include geometric isomers, the present invention encompasses cis- compounds, trans- compounds and mixtures thereof. When the compounds of the present invention have one or more asymmetric centers in the molecule, various optical isomers are obtained. The present invention also encompasses optical isomers, racemates, diastereomers and mixtures thereof.

The compounds of the present invention can be produced by the following methods.

(Method A)

A compound of the formula (II)

$$R^1CH_2-G \qquad (II)$$

wherein $R^1CH_2$ is the same as the aforementioned $R^1CH_2$, $R^1CH_2$, $R^1bCH_2$, Ra, Rb, Rc, Rd, Re, Rf, Rg, Rh, Ri, Rj, Rk, Rl, Rm, Rn or Ro which are encompassed in R, and G is a leaving group in wide use in the field of organic synthetic chemistry, such as halogen (fluorine, chlorine, bromine, iodine), methane-sulfonyloxy, p-toluenesulfonyloxy or trifluoromethanesulfonyloxy [hereinafter referred to as Compound (II)], or when $R^1$ has a functional group (e.g. amino, hydroxyl group, mercapto, ketone, carboxyl), a compound with protection of the functional group as necessary [hereinafter referred to as Compound B-(II)] is condensed, in the presence of a base, with a compound of the formula (III)

$$QHN-\underset{\underset{H}{|}}{\overset{\overset{COOY}{|}}{C}}-COOY \qquad (III)$$

wherein Y is lower alkyl (e.g. methyl, ethyl, propyl, isopropyl, butyl, tert-butyl) or aralkyl (e.g. benzyl, nitrobenzyl, methoxybenzyl, methylbenzyl), and Q is an amino-protecting group widely used in the field of organic synthetic chemistry, such as acetyl, benzoyl, tert-butoxycarbonyl or benzyloxycarbonyl, where the two Ys in the molecule in the formula may together form a ring such as dioxane and Q and Y in the molecule may together form a ring such as oxazolidine or oxazine [hereinafter referred to as Compound (III)] to give a compound of the formula (IV)

$$QHN-\underset{\underset{CH_2R^1}{|}}{\overset{\overset{COOY}{|}}{C}}-COOY \qquad (IV)$$

wherein $R^1$, Q and Y are as defined above [hereinafter referred to as Compound (IV)], which is subjected to reduction of carboxyl with a suitable reducing agent and deprotection as necessary to give a compound of the formula (1-29)

$$H_2N-\underset{\underset{CH_2R^1}{|}}{\overset{\overset{CH_2OH}{|}}{C}}-CH_2OH \qquad (I-29)$$

wherein $R^1$ is as defined above [hereinafter referred to as Compound (I-29)] or an N- and/or O-protected compound thereof.

Examples of the base to be used in the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo [5.4.0]undeca-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (IV) can be purified by a method known in the field of organic synthetic chemistry, such as solvent extraction, recrystallization, chromatography and a method using an ion exchange resin.

Examples of the reducing agent to be used in the reduction of carboxyl include metallic reducing reagent such as sodium borohydride, lithium borohydride or lithium aluminum hydride, and diborane.

Examples of the organic solvent to be used in the reduction of carboxyl include methanol, ethanol, tert-butyl alcohol, tetrahydrofuran, diethyl ether and ethylene glycol dimethyl ether.

The temperature for the reduction of carboxyl is generally from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the objective compound can be purified by a method known in the field of organic synthetic chemistry, such as solvent extraction, recrystallization, chromatography and a method using an ion exchange resin.

(Method B)

A Compound (II) or a Compound B-(II) is condensed, in the presence of a base, with a compound of the formula (V)

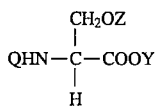
$$\begin{array}{c} CH_2OZ \\ | \\ QHN-C-COOY \\ | \\ H \end{array} \quad (V)$$

wherein Y and Q are as defined above, and Z is a hydroxy-protecting group widely used in the field of organic synthetic chemistry, such as acetyl, benzoyl, benzyl, trimethylsilyl, tert-butyldimethylsilyl, methoxymethyl, methoxyethoxymethyl or tetrahydropyranyl [hereinafter referred to as Compound (V)] to give a Compound of the formula (VI)

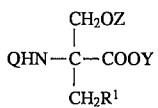
$$\begin{array}{c} CH_2OZ \\ | \\ QHN-C-COOY \\ | \\ CH_2R^1 \end{array} \quad (VI)$$

wherein $R^1$, Q, Y and Z are as defined above [hereinafter referred to as Compound (VI)]. The obtained compound is then subjected to reduction of carboxyl with a suitable reducing agent and deprotection as necessary to give a compound (I-29) or an N- and/or O-protected compound thereof.

Examples of the base to be used in the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (VI) can be purified by a method known in the field of organic synthetic chemistry, such as solvent extraction, recrystallization, chromatography and a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The temperature of the reduction of carboxyl is generally from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the objective compound can be purified by a method known in the field of organic synthetic chemistry, such as solvent extraction, recrystallization, chromatography and a method using an ion exchange resin.

(Method C)

A Compound (II) or a Compound B-(II) is condensed, in the presence of a base, with a compound of the formula (VII)

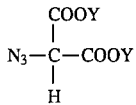
$$\begin{array}{c} COOY \\ | \\ N_3-C-COOY \\ | \\ H \end{array} \quad (VII)$$

wherein Y is as defined above [hereinafter referred to as Compound (VII)] to give a compound of the formula (VIII)

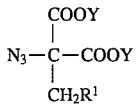
$$\begin{array}{c} COOY \\ | \\ N_3-C-COOY \\ | \\ CH_2R^1 \end{array} \quad (VIII)$$

wherein $R^1$ and Y are as defined above [hereinafter referred to as Compound (VIII)]. The obtained compound is then subjected to reduction of carboxyl and azide with a suitable reducing agent and deprotection as necessary to give a Compound (I-29) or an O-protected compound thereof.

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the organic solvent to be used for the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (VIII) can be purified by a method known in the field of organic synthetic chemistry, such as solvent extraction, recrystallization, chromatography and a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The temperature of the reduction of carboxyl is generally from −20° C. to 80° C. and a temperature lower or higher than this temperature range may be selected on demand.

The reduction is generally carried out for 30 minutes to 10 hours and the reaction period longer or shorter than the indicated period may be used as necessary.

Examples of the reducing agent to be used for the reduction of azide include metallic reducing reagent such as sodium borohydride, lithium borohydride or lithium aluminum hydride, and transition metal such as palladium-carbon, platinum oxide, Raney nickel, rhodium or ruthenium for catalytic reduction.

Examples of the organic solvent to be used for the reduction of azide include methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The temperature of the reduction of azide is generally from −20° C. to 80° C. and a temperature lower or higher than this temperature range may be selected on demand.

After the reduction is carried out under the abovementioned conditions or after removing the protecting group on demand, the objective compound can be purified by a method known in the field of organic synthetic chemistry, such as solvent extraction, recrystallization, chromatography and a method using an ion exchange resin.

(Method D)

A Compound (II) or a Compound B-(II) is condensed, in the presence of a base, with a compound of the formula (IX)

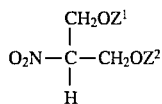  (IX)

wherein $Z^1$ and $Z^2$ are the same or different and each is hydroxyl-protecting group widely used in the field of organic synthetic chemistry, such as acetyl, benzoyl, benzyl, trimethylsilyl, tert-butyldimethylsilyl, methoxymethyl, methoxyethoxymethyl or tetrahydropyranyl and $Z^1$ and $Z^2$ may together form a ring such as dioxane [hereinafter referred to as Compound (IX)] to give a compound of the formula (X)

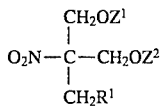  (X)

wherein $R^1$, $Z^1$ and $Z^2$ are as defined above [hereinafter referred to as Compound (X)]. The obtained compound is then subjected to reduction of nitro with a suitable reducing agent and deprotection as necessary to give a Compound (I-29) or an O-protected compound thereof.

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the organic solvent to be used for the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (X) can be purified by a method known in the field of organic synthetic chemistry, such as solvent extraction, recrystallization, chromatography and a method using an ion exchange resin.

Examples of the reducing agent to be used for the reduction of nitro include metallic reducing reagent such as sodium borohydride, lithium borohydride or lithium aluminum hydride, transition metal such as palladium-carbon, platinum oxide, Raney nickel, rhodium or ruthenium for catalytic reduction, and metal such as iron, zinc or tin.

Examples of the solvent to be used for the reduction of nitro include water, methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction of nitro generally proceeds at a temperature of from −20° C. to 80° C. and a temperature lower or higher than this temperature range may be selected on demand.

After the reduction is carried out under the abovementioned conditions or after removing the protecting group on demand, the objective compound can be purified by a method known in the field of organic synthetic chemistry, such as solvent extraction, recrystallization, chromatography and a method using an ion exchange resin.

The above-mentioned methods A through D can be used for the synthesis of the compounds of the formulas (I-1) to (I-18).

(Method E)

A compound of the formula (XI)

  (XI)

wherein R" is the same as the aforementioned $CH_2R^1$, $CH_2R^1a$, $CH_2R^1b$, Ra, Rb, Rc, Rd, Re, Rf, Rg, Rh, Ri, Rj, Rk, Rl, Rm, Rn, Ro, Rp, Rq, $CH=CHRt$, $CH=CHRu$, $(CH_2)\alpha-X-(CH=)\beta Rv$ (when $\alpha \geq 1$) or $CH_2ORw$ which are encompassed in R, M is a metal in wide use in the field of organic synthetic chemistry, such as lithium, magnesium chloride, magnesium bromide, magnesium iodide, copper, lithium copper or nickel, and n is an integer of 1 to 3 [hereinafter referred to as Compound (XI)], or when R" has a functional group (e.g. amino, hydroxyl group, mercapto, ketone, carboxyl), a compound with protection of the functional group as necessary [hereinafter referred to as Compound B-(XI)] is subjected to nucleophilic addition to a compound of the formula (XII)

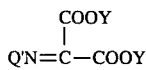  (XII)

wherein Y is as defined above and Q' is an imino-protecting group in wide use in the field of organic synthetic chemistry, such as acetyl, benzoyl, tert-butoxycarbonyl or benzyloxycarbonyl [hereinafter referred to as Compound (XII)] to give a compound of the formula (IV-a)

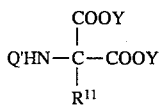  (IV-a)

wherein R", Q' and Y are as defined above [hereinafter referred to as Compound (IV-a)]. The obtained compound is then subjected to reduction of carboxyl with a suitable reducing agent and deprotection as necessary to give a compound of the formula (I-30)

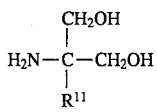
(I-30)

wherein R" is as defined above [hereinafter referred to as Compound (I-30)] or an N- and/or O-protected compound thereof.

Examples of the organic solvent to be used for the addition include tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The addition generally proceeds at a temperature of from −100° C. to 80° C. and a temperature lower or higher than this temperature range may be selected on demand.

The addition is generally carried out for 30 minutes to 2 days and the reaction period longer or shorter than the indicated period may be used as necessary.

After the addition is carried out under the above-mentioned conditions or after removing the protecting group on demand, the compound (IV-a) can be purified by a method known in the field of organic synthetic chemistry, such as solvent extraction, recrystallization, chromatography and a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The reduction of carboxyl generally proceeds at a temperature of from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the objective compound can be purified by a method known in the field of organic synthetic chemistry, such as solvent extraction, recrystallization, chromatography and a method using an ion exchange resin.

The instant method can be used for the synthesis of the compounds of the formulas (I-1) to (I-20), (I-24), (I-25), (I-26) when $\alpha \geq 1$ and (I-27).

(Method F)

A compound of the formula (XIII)

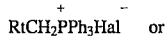 or (XIII-1)

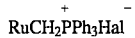 (XIII-2)

wherein Hal is halogen such as chlorine, bromine or iodine and Rt and Ru are as defined above [hereinafter referred to as Compound (XIII-1) or Compound (XIII-2)], or when Rt and Ru have a functional group (e.g. amino, hydroxyl, mercapto, ketone, carboxyl), a compound with protection of the functional group as necessary [hereinafter referred to as Compound B-(XIII-1) or Compound B-(XIII-2)] is condensed, in the presence of a base, with a compound of the formula (XIV)

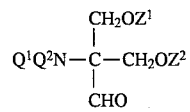
(XIV)

wherein $Q^1$ and $Q^2$ are amino-protecting groups widely used in the field of organic synthetic chemistry, such as acetyl, benzoyl, tert-butoxycarbonyl, benzyloxycarbonyl or benzyl and one of them may be hydrogen, and $Z^1$ and $Z^2$ are as defined above [hereinafter referred to as Compound (XIV)] to give a compound of the formula (XV)

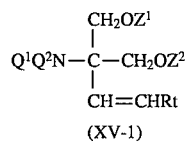 or 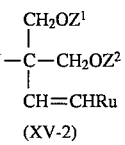

(XV-1)          (XV-2)

wherein Rt, Ru, $Q^1$, $Q^2$, $Z^1$ and $Z^2$ are as defined above [hereinafter referred to as Compound (XV-1) or Compound (XV-2)]. The obtained compound is then subjected to deprotection as necessary to give a compound (I-24) or (I-25).

Examples of the base to be used in the condensation include sodium hydroxide, sodium methoxide, sodium ethoxide, potassium tert-butoxide, sodium hydride, potassium hydride, lithium diisopropylamide, butyl lithium, lithium hexamethyldisilazane, triethylamine, diisopropylethylamine, pyridine and 1,8-diazabicyclo[5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XV-1) or (XV-2) can be purified by a method known in the field of organic synthetic chemistry, such as solvent extraction, recrystallization, chromatography or a method using an ion exchange resin.

The instant method can be used for the synthesis of the compounds of the formulas (I-24) and (I-25). By reducing the double bond of the compounds of the formulas (I-24) and (I-25), or an N- and/or O-protected compound thereof, the compounds of the formulas (I-1) through (I-18) and (I-26) when $\alpha \geq 2$ can be obtained.

Examples of the reducing agent to be used for the reduction of the double bond include metal reducing reagent such as sodium borohydride, lithium borohydride or lithium aluminum hydride, and transition metal such as palladium-carbon, platinum oxide, Raney nickel, rhodium or ruthenium for catalytic reduction.

Examples of the organic solvent to be used for the reduction of the double bond include methanol, ethanol, tertbutyl alcohol, tetrahydrofuran, diethyl ether, dioxane, acetone, ethyl acetate, acetic acid, benzene, toluene, xylene, dimethylformamide and dimethyl sulfoxide.

The reduction of the double bond generally proceeds at a temperature of from −20° C. to 80° C. and a temperature lower or higher than this temperature range may be selected on demand.

After the reduction is carried out under the abovementioned conditions or after removing the protecting group on demand, the objective compounds of the formulas (I-1) through (I-18) and (I-26) when α≧2 can be purified by a method known in the field of organic synthetic chemistry, such as solvent extraction, recrystallization, chromatography or a method using an ion exchange resin.

(Method G)

A compound of the formula (XVI)

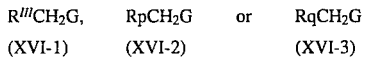

| $R'''CH_2G$, | $RpCH_2G$ | or | $RqCH_2G$ |
|---|---|---|---|
| (XVI-1) | (XVI-2) |  | (XVI-3) | wherein R''' is the aforementioned $CH_2R^1$, $CH_2R^1a$, $CH_2R^1b$, Ra, Rb, Rc, Rd, Re, Rf, Rg, Rh, Ri, Rj, Rk, Rl, Rm, Rn or Ro which are encompassed in R, and Rp, Rq and G are as defined above [hereinafter referred to as Compound (XVI-1), Compound (XVI-2) or Compound (XVI-3)], or when R''', Rp and Rq have a functional group (e.g. amino, hydroxyl, mercapto, ketone, carboxyl), a compound with protection thereof as necessary [hereinafter referred to as Compound B-(XVI-1), Compound B-(XVI-2) or Compound B-(XVI-3)] is reacted with a compound of the formula (XVII)

$$M^{n+}(NO_2^-)_n \qquad (XVII)$$

wherein M is a metal such as sodium, potassium, magenesium, silver, calcium or lithium and n is an integer of 1 or 2 [hereinafter referred to as Compound (XVII)] to give a compound of the formula (XVIII)

| $R'''CH_2NO_2$, | $RpCH_2NO_2$ | or | $RqCH_2NO_2$ |
|---|---|---|---|
| (XVIII-1) | (XVIII-2) |  | (XVIII-3) | wherein R''', Rp and Rq are as defined above [hereinafter referred to as Compound (XVIII-1), Compound (XVIII-2) or Compound (XVIII-3)]. The obtained compound is condensed with formalin in the presence of a base, and then subjected to protection of hydroxyl as necessary to give a compound of the formula (XIX)

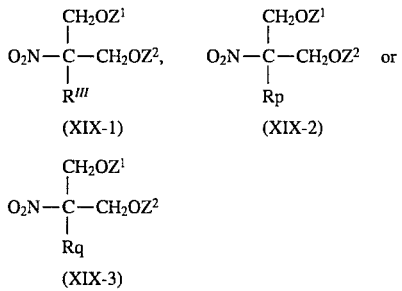

$$\begin{array}{ccc}
CH_2OZ^1 & CH_2OZ^1 & \\
| & | & \\
O_2N-C-CH_2OZ^2, & O_2N-C-CH_2OZ^2 & \text{or} \\
| & | & \\
R''' & Rp & \\
(XIX-1) & (XIX-2) & \\
\end{array}$$

$$\begin{array}{c}
CH_2OZ^1 \\
| \\
O_2N-C-CH_2OZ^2 \\
| \\
Rq \\
(XIX-3)
\end{array}$$

wherein R''', Rp, Rq, $Z^1$ and $Z^2$ are as defined above [hereinafter referred to as Compound (XIX-1), Compound (XIX-2) or Compound (XIX-3)]. The obtained compound is then subjected to reduction of nitro with a suitable reducing agent and deprotection as necessary to give a desired compound inclusive of the compounds (I-19) and (I-20).

Examples of the solvent to be used for the condensation of nitrite (XVII) and the Compound (XVI-1), (XVI-2) or (XVI-3) include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XVIII-1), (XVIII-2) or (XVIII-3) can be purified by a method known in the field of organic synthetic chemistry, such as solvent extraction, recrystallization, chromatography or a method using an ion exchange resin.

Examples of the solvent to be used for the condensation of the Compound (XVIII-1), (XVIII-2) or (XVIII-3) and formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XIX-1), (XIX-2) or (XIX-3) can be purified by a method known in the field of organic synthetic chemistry, such as solvent extraction, recrystallization, chromatography or a method using an ion exchange resin.

Examples of the reducing agent to be used for the reduction of nitro include metallic reducing reagent such as sodium borohydride, lithium borohydride or lithium aluminum hydride, transition metal such as palladium-carbon, platinum oxide, Raney nickel, rhodium or ruthenium for catalytic reduction, and metal such as iron, zinc or tin.

Examples of the solvent to be used for the reduction of nitro include water, methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction of nitro generally proceeds at a temperature of from −20° C. to 80° C. and a temperature lower or higher than this temperature range may be selected on demand.

After the reduction is carried out under the abovementioned conditions or after removing the protecting group on demand, the objective compound can be purified by a method known in the field of organic synthetic chemistry, such as solvent extraction, recrystallization, chromatography or a method using an ion exchange resin.

The instant method is suitable for the synthesis of the compounds (I-19) and (I-20), as well as for the synthesis of the compounds of the formulas (I-1) through (I-18).

(Method H)

A compound of the formula (XX)

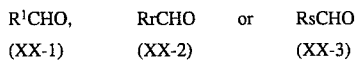

| $R^1CHO$, | RrCHO | or | RsCHO |
|---|---|---|---|
| (XX-1) | (XX-2) | | (XX-3) | wherein $R^1$, Rr and Rs are as defined above [hereinafter referred to as Compound (XX-1), Compound (XX-2) or Compound (XX-3)] is condensed, in the presence of a base, with a Compound (IX) and subjected to protection of hydroxyl as necessary to give a compound of the formula (XXI)

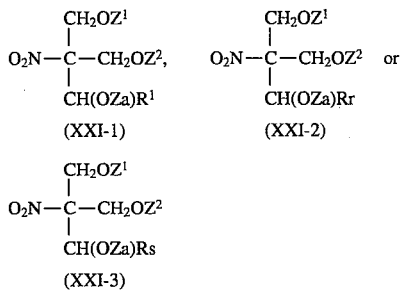

wherein $R^1$, Rr, Rs, $Z^1$ and $Z^2$ are as defined above and Za is hydrogen or a hydroxyl-protecting group in wide use in the field of organic synthetic chemistry, such as acetyl, benzoyl, benzyl, trimethylsilyl, tert-butyldimethylsilyl, methoxymethyl, methoxyethoxymethyl or tetrahydropyranyl [hereinafter referred to as Compound (XXI-1), Compound (XXI-2) or Compound (XXI-3)]. The obtained compound is then subjected to reduction of nitro with a suitable reducing agent and deprotection as necessary to give a compound of the formula (XXII)

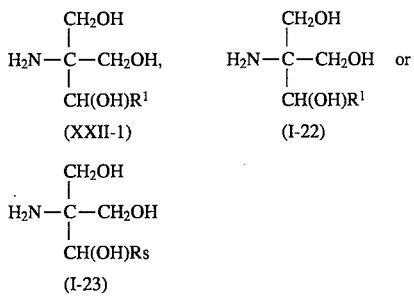

wherein $R^1$, Rr and Rs are as defined above [hereinafter referred to as Compound (XXII-1), Compound (I-22) or Compound (I-23)].

Examples of the base to be used for the condensation with aldehyde include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo-[5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XXI-1), (XXI-2) or (XXI-3) can be purified by a method known in the field of organic synthetic chemistry, such as solvent extraction, recrystallization, chromatography or a method using an ion exchange resin.

Examples of the reducing agent to be used for the reduction of nitro include metal reducing reagent such as sodium borohydride, lithium borohydride or lithium aluminum hydride, transition metal such as palladium-carbon, platinum oxide, Raney nickel, rhodium or ruthenium for catalytic reduction, and metal such as iron, zinc or tin.

Examples of the solvent to be used for the reduction of nitro include water, methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction of nitro generally proceeds at a temperature of from −20° C. to 80° C. and a temperature lower or higher than this temperature range may be selected on demand.

After the reduction is carried out under the abovementioned conditions or after removing the protecting group on demand, the Compound (XXII-1), (I-22) or (I-23) can be purified by a method known in the field of organic synthetic chemistry, such as solvent extraction, recrystallization, chromatography or a method using an ion exchange resin.

Accordingly, the instant method can be used for the synthesis of the compounds of the formulas (I-21) through (I23).

(Method I)

Compound (XVIII-1) can be also produced by the following method.

A compound of the formula (XX')

| $R^ACHO$ | (XX') |
|---|---| wherein $R^A$ is a straight- or branched carbon chain optionally having a substituent having a carbon number less i from that of the substituent at R''' [hereinafter referred to as Compound (XX')] is condensed with nitromethane in the presence of a base to give a compound of the formula (XXIII)

| $R^ACH=CHNO_2$ | (XXIII) |
|---|---| wherein $R^A$ is as defined above [hereinafter referred to as Compound (XXIII)]. The obtained compound is then subjected to reduction of the double bond with a suitable reducing agent to give a compound (XVIII-1).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XXIII) can be purified by a method known in the field of organic synthetic chemistry, such as solvent extraction, recrystallization, chromatography or a method using an ion exchange resin.

Examples of the reducing agent to be used for the reduction of the double bond include metallic reducing reagent such as lithium borohydride or lithium aluminum hydride, and transition metal such as palladium-carbon, platinum oxide, Raney nickel, rhodium or ruthenium for catalytic reduction.

Examples of the organic solvent to be used for the reduction of the double bond include methanol, ethanol, tertbutyl alcohol, tetrahydrofuran, diethyl ether, dioxane, acetone, ethyl acetate, acetic acid, benzene, toluene, xylene, dimethylformamide and dimethyl sulfoxide.

The reduction of the double bond generally proceeds at a temperature of from $-20°$ C. to $80°$ C. and a temperature lower or higher than this temperature range may be selected on demand.

After the reduction is carried out under the abovementioned conditions or after removing the protecting group on demand, the Compound (XVIII-1) can be purified by a method known in the field of organic synthetic chemistry, such as solvent extraction, recrystallization, chromatography or a method using an ion exchange resin.

(Method J)

Compound (XXI-1), Compound (XXI-2) and Compound (XXI-3) can be also produced by the following method.

A Compound (XX-1), (XX-2) or (XX-3) is condensed with nitromethane in the presence of a base and subjected to protection of hydroxyl as necessary to give a compound of the formula (XXIV)

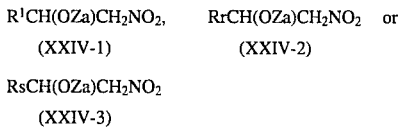

wherein $R^1$, Rr, Rs and Za are as defined above [hereinafter referred to as Compound (XXIV-1), Compound (XXIV-2) or Compound (XXIV-3)]. The obtained compound is condensed with formalin in the presence of a base and then subjected to protection of hydroxyl as necessary to give a Compound (XXI-1), (XXI-2) or (XXI-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from $-20°$ C. to $150°$ C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XXIV-1), (XXIV-2) or (XXIV-3) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from $-20°$ C. to $150°$ C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XXI-1), (XXI-2) or (XXI-3) can be purified by a method known in the field of organic synthetic chemistry, such as solvent extraction, recrystallization, chromatography or a method using an ion exchange resin.

(Method K)

Compound (XXI-1), Compound (XXI-2) and Compound (XXI-3) can be also produced by the following method.

A compound (XXV)

$$ZOCH_2CH_2NO_2 \quad (XXV)$$

wherein Z is as defined above [hereinafter referred to as Compound (XXV)] is condensed with a Compound (XX-1), (XX-2) or (XX-3) in the presence of a base and subjected to protection of hydroxyl as necessary, to give a compound of the formula (XXVI)

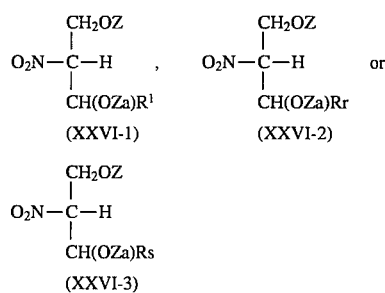

wherein $R^1$, Rr, Rs, Z and Za are as defined above [hereinafter referred to as Compound (XXVI-1), Compound (XXVI-2) or Compound (XXVI-3)]. The obtained compound is condensed with formalin in the presence of a base and then subjected to protection of hydroxyl as necessary to give a Compound (XXI-1), (XXI-2) or (XXI-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXVI-1), (XXVI-2) or (XXVI-3) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXI-1), (XXI-2) or (XXI-3) can be purified by a method known in the field of organic synthetic chemistry, such as solvent extraction, recrystallization, chromatography or a method using an ion exchange resin.

(Method L)

A compound of the formula (XXVII)

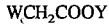

$$W{CH_2}COOY \qquad (XXVII)$$

wherein W is azide, nitro or amino protected by a suitable protecting group and Y is as defined above [hereinafter referred to as Compound (XXVII)] is condensed, in the presence of a base, with a compound of the formula (XXVIII)

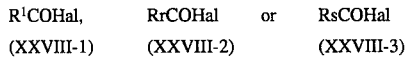

R¹COHal,     RrCOHal     or     RsCOHal
(XXVIII-1)     (XXVIII-2)          (XXVIII-3)

wherein R¹, Rr, Rs and Hal are as defined above [hereinafter referred to as Compound (XXVIII-1), Compound (XXVIII-2) or Compound (XXVIII-3)] to give a compound of the formula (XXIX)

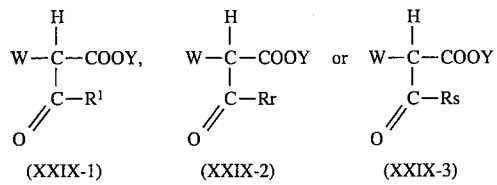

(XXIX-1)     (XXIX-2)     (XXIX-3)

wherein $R^1$, Rr, Rs, W and Y are as defined above [hereinafter referred to as Compound (XXIX-1), Compound (XXIX-2) or Compound (XXIX-3)]. The obtained compound is condensed with formalin in the presence of a base and subjected to protection of hydroxyl as necessary to give a compound of the formula (XXX)

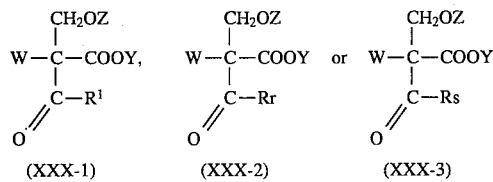

(XXX-1)     (XXX-2)     (XXX-3)

wherein $R^1$, Rr, Rs, W, Y and Z are as defined above [hereinafter referred to as Compound (XXX-1), Compound (XXX-2) or Compound (XXX-3)]. The obtained compound is subjected to reduction of carboxyl with a suitable reducing agent and protection of hydroxyl as necessary to give a compound of the formula (XXXI)

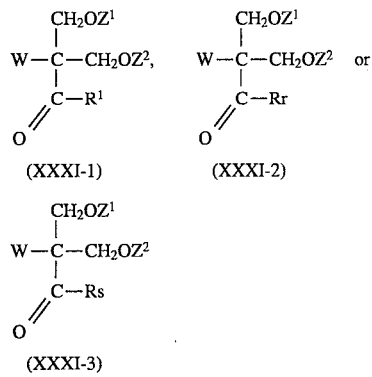

(XXXI-1)     (XXXI-2)

(XXXI-3)

wherein $R^1$, Rr, Rs, W, $Z^1$ and $Z^2$ are as defined above [hereinafter referred to as Compound (XXXI-1), Compound (XXXI-2) or Compound (XXXI-3)] and the obtained compound is subjected to reduction of carbonyl with a suitable reducing agent, and reduction and deprotection as necessary, to give a Compound (XXII-1), (I-22) or (I-23).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXIX-1), (XXIX-2) or (XXIX-3) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXX-1), (XXX-2) or (XXX-3) can be purified by a method known in the field of organic synthetic chemistry, such as solvent extraction, recrystallization, chromatography or a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The reduction of carboxyl generally proceeds at a temperature of from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the Compound (XXXI-1), (XXXI-2) or (XXXI-3) can be purified by a method known in the field of organic synthetic chemistry, such as solvent extraction, recrystallization, chromatography or a method using an ion exchange resin.

Examples of the reducing agent to be used for the reduction of carbonyl include metallic reducing reagent such as sodium borohydride, lithium borohydride or lithium aluminum hydride, and diborane.

Examples of the organic solvent to be used for the reduction of carbonyl include methanol, ethanol, tert-butyl alcohol, tetrahydrofuran, diethyl ether and ethylene glycol dimethyl ether.

The reduction of carbonyl generally proceeds at a temperature of from −20° C. to 80° C. and a temperature lower or higher than this temperature range may be selected on demand.

The reduction of carbonyl is generally carried out for 30 minutes to 10 hours and the reaction period longer or shorter than the indicated period may be used as necessary.

When (i) W=azide, examples of the reducing agent to be used for the reduction of azide include metallic reducing agent such as sodium borohydride, lithium borohydride or lithium aluminum hydride, and transition metal such as palladium-carbon, platinum oxide, Raney nickel, rhodium or ruthenium for catalytic reduction.

Examples of the organic solvent to be used for the reduction of azide include methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction of azide generally proceeds at a temperature of from −20° C. to 80° C. and a temperature lower or higher than this temperature range may be selected on demand.

When (ii) W=nitro, examples of the reducing agent to be used for the reduction of nitro include metallic reducing reagent such as sodium borohydride, lithium borohydride or lithium aluminum hydride, transition metal such as palladium-carbon, platinum oxide, Raney nickel, rhodium or ruthenium for catalytic reduction, and metal such as iron, zinc or tin.

Examples of the solvent to be used for the reduction of nitro include water, methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction of nitro generally proceeds at a temperature of from −20° C. to 80° C. and a temperature lower or higher than this temperature range may be selected on demand.

After the reduction is carried out under the abovementioned conditions or after removing the protecting group on demand, the Compound (XXII-1), (I-22) or (I-23) can be purified by a method known in the field of organic synthetic chemistry, such as solvent extraction, recrystallization, chromatography or a method using an ion exchange resin.

Accordingly, the instant method is applicable to the synthesis of the compounds of the formulas (I-21) through (I-23).

(Method M)

Compound (XXX-1), Compound (XXX-2) and Compound (XXX-3) can be also produced by the following method.

A compound (XXVIII) and a compound of the formula (XXXII)

wherein W, Y and Z are as defined above [hereinafter referred to as Compound (XXXII)] are condensed in the presence of a base to give a Compound (XXX-1), (XXX-2) or (XXX-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXX-1), (XXX-2) or (XXX-3) can be purified by a method known in the field of organic synthetic chemistry, such as solvent extraction, recrystallization, chromatography or a method using an ion exchange resin.

(Method N)

When W=nitro, Compound (XXX-1), (XXX-2) and (XXX-3) can be also produced by the following method.

A compound (XXVIII-1), (XXVIII-2) or (XXVIII-3) and a compound (XXXIII)

$CH_3NO_2$            (XXXIII)

[hereinafter referred to as Compound (XXXIII)] are condensed in the presence of a base to give a compound of the formula (XXXIV)

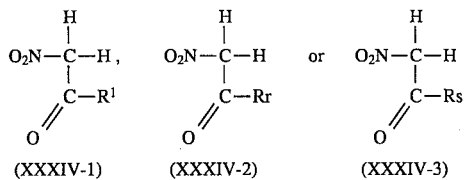

(XXXIV-1)    (XXXIV-2)    (XXXIV-3)

wherein $R^1$, Rr and Rs are as defined above [hereinafter referred to as Compound (XXXIV-I), Compound (XXXIV-2) or Compound (XXXIV-3)] and the obtained compound is condensed with formalin in the presence of a base and subjected to protection of hydroxyl as necessary to give a Compound (XXXI-1), (XXXI-2) or (XXXI-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXIV-1), (XXXIV-2) or (XXXIV-3) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXI-1), (XXXI-2) or (XXXI-3) can be purified by a method known in the field of organic synthetic chemistry, such as solvent extraction, recrystallization, chromatography or a method using an ion exchange resin.

(Method O)

Compound (XXXIV-1), Compound (XXXIV-2) and Compound (XXXIV-3) can be also produced by the following method.

A Compound (XVII) and a compound of the formula (XXXV)

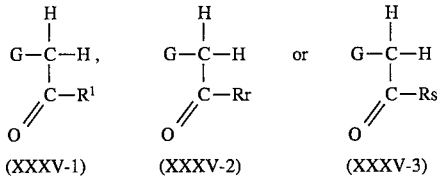

(XXXV-1)    (XXXV-2)    (XXXV-3)

wherein $R^1$, Rr, Rs and G are as defined above [hereinafter referred to as Compound (XXXV-1), Compound (XXXV-2) or Compound (XXXV-3)] are condensed in the presence of a base to give a Compound (XXXIV-1), (XXXIV-2) or (XXXIV-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXIV-1), (XXXIV-2) or (XXXIV-3) can be purified by a method known in the field of organic synthetic chemistry, such as solvent extraction, recrystallization, chromatography or a method using an ion exchange resin.

(Method P)

When W=nitro, Compound (XXXI-1), Compound (XXXI-2) and Compound (XXXI-3) can be also produced by the following method.

A Compound (XXV) and a Compound (XXVIII-1), (XXVIII-2) or (XXVIII-3) are condensed in the presence of a base to give a compound of the formula (XXXVI)

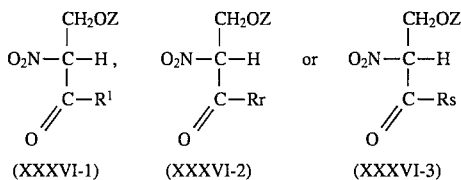

(XXXVI-1)  (XXXVI-2)  (XXXVI-3)

wherein $R^1$, Rr, Rs and Z are as defined above [hereinafter referred to as Compound (XXXVI-1), Compound (XXXVI-2) or Compound (XXXVI-3)]. The obtained compound is condensed with formalin in the presence of a base and subjected to protection of hydroxyl as necessary to give a Compound (XXXI-1), (XXXI-2) or (XXXI-3).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXVI-1), (XXXVI-2) or (XXXVI-3) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXI-1), (XXXI-2) or (XXXI-3) can be purified by a method known in the field of organic synthetic chemistry, such as solvent extraction, recrystallization, chromatography or a method using an ion exchange resin.

(Method Q)

Compound (X) can be also produced by the following method.

A Compound (II) and a Compound (XXVII) (W=nitro) are condensed in the presence of a base to give a compound of the formula (XXXVII)

wherein $R^1$ and Y are as defined above [hereinafter referred to as Compound (XXXVII)]. The obtained compound is condensed with formalin in the presence of a base and subjected to protection of hydroxyl as necessary to give a compound of the formula (XXXVIII)

wherein $R^1$, Y and Z are as defined above [hereinafter referred to as Compound (XXXVIII)] and the obtained compound is subjected to reduction of carboxyl with a suitable reducing agent and protection of hydroxyl as necessary to give a Compound (X).

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXVII) can be purified by a method known in the field of organic synthetic chemistry, such as solvent extraction, recrystallization, chromatography or a method using an ion exchange resin.

Examples of the solvent to be used for the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

Examples of the base to be used for the condensation include sodium hydroxide, sodium methoxide, sodium ethoxide, sodium hydride, potassium hydride, triethylamine, diisopropylethylamine and 1,8-diazabicyclo[5.4.0]undeca-7-ene.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXVIII) can be purified by a method known in the field of organic synthetic chemistry, such as solvent extraction, recrystallization, chromatography or a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The reduction of carboxyl generally proceeds at a temperature of from $-20°$ C. to $80°$ C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the Compound (X) can be purified by a method known in the field of organic synthetic chemistry, such as solvent extraction, recrystallization, chromatography or a method using an ion exchange resin.

(Method R)

A compound of the formula (XXXIX)

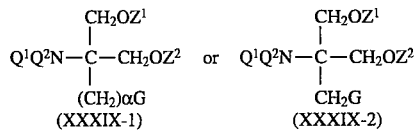

wherein $Q^1$, $Q^2$, $Z^1$, $Z^2$, G and a are as defined above [hereinafter referred to as Compound (XXXIX-1) or Compound (XXXIX-2)] and a compound of the formula (XXXX)

Rv(CH₂)β—XH    or    Rw—OH
(XXXX-1)              (XXXX-2)

wherein Rv, Rw, X and B are as defined above [hereinafter referred to as Compound (XXXX-1) or Compound (XXXX-2)] are condensed in the presence of a base to give a compound of the formula (XXXXI)

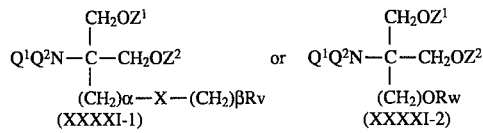

wherein Rv, Rw, X, $Q^1$, $Q^2$, $Z^1$, $Z^2$, α and β are as defined above [hereinafter referred to as Compound (XXXXI-1) or Compound (XXXXI-2)] and the obtained compound is subjected to deprotection as necessary to give a compound (I-26) or (I-27).

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo [5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from $-20°$ C. to $150°$ C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXXI-1) or (XXXXI-2) can be purified by a method known in the field of organic synthetic chemistry, such as solvent extraction, recrystallization, chromatography or a method using an ion exchange resin.

In the instant method, a compound wherein X is sulfinyl or sulfonyl can be obtained by oxidation of a compound wherein X is sulfur.

Accordingly, the instant method can be used for the synthesis of the compounds of the formulas (I-26) and (I-27). It is also applicable to the synthesis of the compounds (I-1), (I-2), (I-4), (I-5) and (I-7) through (I-11).

(Method S)

Compound (XXXXI-1) and Compound (XXXXI-2) can be also produced by the following method.

A compound of the formula (XXXXII)

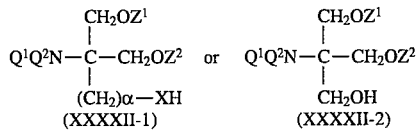

wherein $Q^1$, $Q^2$, $Z^1$, $Z^2$, X and α are as defined above [hereinafter referred to as Compound (XXXXII-1) or Compound (XXXXII-2)] and a compound of the formula (XXXXIII)

Rv(CH₂)β—G    or    Rw—G (XXXXIII-1)         (XXXXIII-2)

wherein Rv, Rw, G and β are as defined above [hereinafter referred to as Compound (XXXXIII-1) or Compound (XXXXIII-2)] are condensed in the presence of a base and the obtained compound is subjected to deprotection on demand to give a Compound (XXXXI-1) or (XXXXI-2).

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo [5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXXI-1) or (XXXXI-2) can be purified by a method known in the field of organic synthetic chemistry, such as solvent extraction, recrystallization, chromatography or a method using all ion exchange resin.

(Method T)

Compound (XXXXI-1) and Compound (XXXXI-2) can be also produced by the following method.

A compound of the formula (XXXIV)

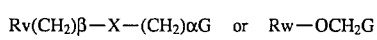

(XXXXIV-1)            (XXXXIV-2)

wherein Rv, Rw, G, X, α and β are as defined above [hereinafter referred to as Compound (XXXXIV-1) or Compound (XXXXIV-2)] and a Compound (III) are condensed in the presence of a base to give a compound of the formula (XXXXV)

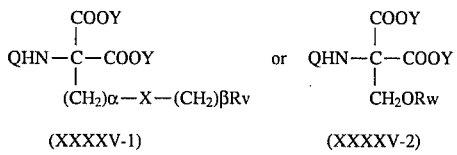

(XXXXV-1)            (XXXXV-2)

wherein Rv, Rw, X, Q, Y, α and β are as defined above [hereinafter referred to as Compound (XXXXV-1) or Compound (XXXXV-2)]. The obtained compound is subjected to reduction with a suitable reducing agent and protection of hydroxyl and amino as necessary to give a compound (XXXXI-1) or (XXXXI-2).

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the above-mentioned conditions or after removing the protecting group on demand, the Compound (XXXXV-1) or (XXXXV-2) can be purified by a method known in the field of organic synthetic chemistry, such as solvent extraction, recrystallization, chromatography or a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The reduction of carboxyl generally proceeds at a temperature of from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the Compound (XXXXI-1) or (XXXXI-2) can be purified by a method known in the field of organic synthetic chemistry, such as solvent extraction, recrystallization, chromatography or a method using an ion exchange resin.

(Method U)

A Compound (XIV) is added with a compound of the formula (XXXXVI)

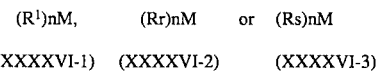

(XXXXVI-1)   (XXXXVI-2)   (XXXXVI-3)

wherein $R^1$, Rr, Rs, M and n are as defined above [hereinafter referred to as Compound (XXXXVI-1), Compound (XXXXVI-2) or Compound (XXXXVI-3)] and the mixture is subjected to protection of hydroxyl as necessary to give a compound of the formula (XXXXVII)

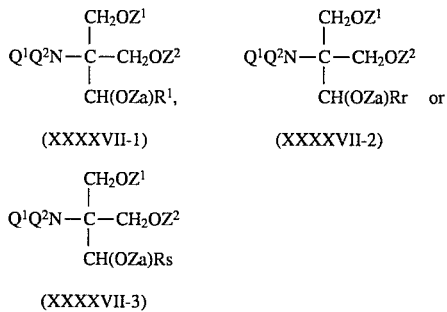

(XXXXVII-3)

wherein $R^1$, Rr, Rs, $Q^1$, $Q^2$, $Z^1$, $Z^2$ and Za are as defined above [hereinafter referred to as Compound (XXXXVII-1), Compound (XXXXVII-2) or Compound (XXXXVII-3)]. The obtained compound is subjected to deprotection on demand to give a Compound (XXII-1), (I-22) or (I-23).

Examples of the solvent to be used for the addition include tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The addition generally proceeds at a temperature of from −100° C. to 80° C. and a temperature lower or higher than this temperature range may be selected on demand.

The addition is generally carried out for 30 minutes to 2 days and the reaction period longer or shorter than the indicated period may be used as necessary.

After the addition is carried out under the above-mentioned conditions or after removing the protecting group on demand, the Compound (XXXXVII-1), (XXXXVII-2) or (XXXXVII-3) can be purified by a method known in the field of organic synthetic chemistry, such as solvent extraction, recrystallization, chromatography or a method using an ion exchange resin.

Accordingly, the instant method can be used for the synthesis of the compounds of the formulas (I-21) through (I-23).

(Method V)

A compound of the formula (XXXXVIII)

wherein Y is as defined above [hereinafter referred to as Compound (XXXXVIII)] and a Compound (II) are condensed in the presence of a base to give a compound of the formula (XXXXIX)

wherein $R^1$ and Y are as defined above [hereinafter referred to as Compound (XXXXIX)] and the obtained compound is reacted with an amination agent of the formula (XXXXX)

wherein Le means a leaving group such as 2,4-dinitrophenoxy, in the presence of a base to give a compound of the formula (XXXXXI)

wherein $R^1$ and Y are as defined above [hereinafter referred to as Compound (XXXXXI)]. The obtained compound is subjected to reduction of carboxyl with a suitable reducing agent and deprotection as necessary to give a Compound (I-29).

Examples of the base to be used for the condensation include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the solvent to be used for the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a temperature lower or higher than this temperature range may be selected on demand.

The condensation is generally carried out for 30 minutes to 2 days and the reaction period longer or shorter than the indicated period may be used as necessary.

After the condensation is carried out under the abovementioned conditions or after removing the protecting group on demand, the Compound (XXXXIX) can be purified by a method known in the field of organic synthetic chemistry, such as solvent extraction, recrystallization, chromatography or a method using an ion exchange resin.

Examples of the base to be used for the amination include sodium hydroxide, sodium methoxide, sodium ethoxide, sodium hydride, potassium hydride, lithium diisopropylamide, butyl lithium, lithium hexamethyldisilazane, triethylamine, diisopropylethylamine and 1,8-diazabicyclo[5.4.0]undeca-7-ene.

Examples of the solvent to be used for the amination include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The amination generally proceeds at a temperature of from −20° C. to 150° C. and a temperature lower or higher than this temperature range may be selected on demand.

The amination is generally carried out for 30 minutes to 2 days and the reaction period longer or shorter than the indicated period may be used as necessary.

After the amination is carried out under the abovementioned conditions or after removing the protecting group on demand, the Compound (XXXXXI) can be purified by a method known in the field of organic synthetic chemistry, such as solvent extraction, recrystallization, chromatography or a method using an ion exchange resin.

Examples of the reducing agent to be used for the reduction of carboxyl include metallic reducing reagent such as sodium borohydride, lithium borohydride or lithium aluminum hydride, and diborane.

Examples of the organic solvent to be used for the reduction of carboxyl include methanol, ethanol, tert-butyl alcohol, tetrahydrofuran, diethyl ether and ethylene glycol dimethyl ether.

The reduction of carboxyl generally proceeds at a temperature of from −20° C. to 80° C. and a temperature lower or higher than this temperature range may be selected on demand.

The reduction of carboxyl is generally carried out for 30 minutes to 10 hours and the reaction period longer or shorter than the indicated period may be used as necessary.

After the reduction is carried out under the abovementioned conditions or after removing the protecting group on demand, the Compound (I-29) can be purified by a method known in the field of organic synthetic chemistry, such as solvent extraction, recrystallization, chromatography or a method using an ion exchange resin.

The instant method can be used for the synthesis of the compounds of the formulas (I-1) through (I-18), preferably for the synthesis of the compounds of the formulas (I-12) and (I13).

(Method W)

Of the compounds of the formula (I) of the present invention, a compound wherein R is —CH(OH)Rr when it is a compound of the formula

wherein Rr is as defined above [hereinafter referred to as Compound (XXXXXII)] or a derivative at carboxyl group thereof or a compound (XXXXXII) wherein the α-position of alkyl at Rr, which may have a double bond or carbonyl in the chain, is substituted by hydroxyl, can be produced by reduction, hydrogenation, ozonolysis or oxidation known per se, which may be used solely or in combination, of a corresponding lactone compound or a compound wherein amino or hydroxy of a Compound (XXXXXII) or lactone compound is protected by a protecting group.

Examples of the derivative at the carboxyl group of the Compound (XXXXXII) include ester (e.g. methyl ester, ethyl ester, benzyl ester, p-nitrobenzyl ester, trimethylsilyl ester, tert-butyldimethylsilyl ester), acid halide (e.g. acid chloride), acid anhydride and mixed acid anhydride.

A Compound (I) wherein Rr is an α-position hydroxyl-substituted alkyl is preferably produced by using the aforementioned lactone compound as a starting material.

Reduction proceeds in a solvent inert to the reaction and in the presence of a metal hydride complex at a temperature from under cooling to under refluxing. Examples of the metal hydride complex include aluminum hydride, lithium aluminum hydride, lithium aluminum hydride-aluminum chloride, lithium trimethoxy aluminum hydride, sodium bis(2-methoxyethoxy)-aluminum hydride, diisobutyl aluminum hydride, sodium borohydride, sodium hydride, lithium borohydride and borohydride, and examples of the solvent include alcohol solvents such as methanol, ethanol, isopropanol and diethylene glycol, hydrocarbon solvents such as benzene, toluene and xylene, halohydrocarbon solvents such as methylene chloride, dichloroethane and chloroform, ether solvents such as diethyl ether, dipropyl ether, tetrahydrofuran and dioxane, dimethylformamide, and dimethyl sulfoxide, which may be used solely or in combination.

The reduction may be catalytic reduction using zinc-hydrochloric acid saturated acetic anhydride, copper-chromite catalyst, palladium-carbon, Raney nickel or rhenium oxide, or electroreduction. These reactions proceed in a manner similar to the reaction known per se.

The hydrogenation generally proceeds according to a method known per se using a conventional catalyst such as a palladium, nickel or platinum catalyst. In the reaction, a solvent inert to the reaction may be used and examples thereof are as mentioned above.

In the present invention, the compound obtained by the above-mentioned reactions can be used as a starting material.

Of the Compounds (XXXXXII), a compound wherein Rr is an α-position hydroxyl-substituted alkyl which may have a double bond or carbonyl in the chain and lactone compound thereof are known compounds reported in Japanese Patent Unexamined Publication Nos. 104087/1989 and 128347/1991 mentioned above and are produced according to the method described therein. Of the Compounds (XXXXXII), a compound wherein Rr is an alkyl which may have a double bond or carbonyl in the chain, such as heptadecyl, is produced, for example, by fermentation or by using a compound (XXXXXIII) produced by the fermentation and having the formula

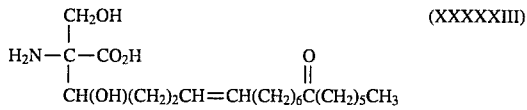

(XXXXXIII)

as a starting meterial. Examples of the microorganism capable of producing the compound (XXXXXIII) include those belonging to Ascomycetes or *Fungi Imperfecti*, particularly the genera Isaria and Mycetia belonging to the *Fungi Imperfecti* and the genus Myriococcum (the genus Thietavia) belonging to Ascomycetes, which are respectively deposited at American Type Culture Collection as *Isaria sinctairii* ATCC No. 24400, *Myriococcum albomyces* ATCC No. 16425 and *Mycetia steritia* ATCC No. 20349. Also, *Myriococcum albomyces* ATCC No. 16425 has been deposited at the Institute of Fermentation, Osaka as IFO32292.

Compound (XXXXXIII) can be produced, for example, by a mutant strain obtained by mutating the above-mentioned strain by a conventional artificial mutating method using ultraviolet rays, high frequency radiation, drug or the like.

The Compound (XXXXXIII)-producing cell may be cultured in various culture media containing conventional nutrition sources for mold. For example, a medium may contain glucose, starch, glycerin, sugar syrup, dextrin, molasses, maltose, xylose or the like as a carbon source and an inorganic or organic nitrogen compound such as corn steep liquor, peptone, yeast extract, potato brew, meat broth, soybean powder, wheat germ, potassium nitrate, sodium nitrate, ammonium sulfate, casein, gluten meal, cottonseed powder or feather powder as a nitrogen source. Besides these, there may be contained additives conventionally used for culture such as conventional inorganic salt, organic or inorganic substance which promotes the growth of cell and enhances production of the Compound (XXXXXIII), and antifoaming agent.

While the culture method is subject to no particular limitation, aerobic submerged culture is desirable. The temperature appropriate for the culture is 20°–35° C., preferably 25°–30° C. for the microorganisms belonging to the genus Isaria and 30°–50° C., preferably 35°–45° C. for the microorganisms belonging to the genus Myriococcum or Mycelia.

The Compound (XXXXXIII) produced in the culture medium is isolated therefrom by conventional steps such as extraction and adsorption which may be used in combination as necessary. For example, in the ease of a microorganism belonging to the genus Isaria such as *Isaria sinclairii*, the Compound (XXXXXIII) is taken out from the culture by filtering off the insoluble matters such as cells from the culture, isolation by centrifugation, passing the culture filtrate through Amberlite XAD-2 (trade mark) and adsorbing Compound (XXXXXIII). The Compound (XXXXXIII) thus obtained is eluted with, for example, methanol and the eluate is fractionated by reversed phase chromatography, whereby a highly purified product of Compound (XXXXXIII) can be obtained. In the ease of a microorganism belonging to the genus Myriococcum or the genus Mycelia, such as *Myriococcum albomyces, Mycelia sterilia* or the like, cells are separated from the culture by filtration, centrifugation and the like and the culture filtrate is treated in the same manner as in the case of the microorganisms belonging to the genus Isaria. The Compound (XXXXXIII) is extracted from the separated cells by the use of methanol and the extract is treated with Amberlite XAD-2 in the same manner as with the filtrate above and purified by chromatography and recrystallization.

The 2-amino-1,3-propanediol compounds, isomers thereof and salts thereof of the present invention show superior immunosuppressive effect and are useful as a suppressant of rejection in organ or bone marrow transplantation in mammals inclusive of human, cow, horse, dog, mouse, rat etc., an agent for the prevention and treatment of autoimmune diseases such as rheumatoid arthritis, atopic eczema (atopic dermatitis), Behçet's disease, uvea diseases, systemic lupus erythematosus, Sjögren's syndrome, polysclerosis, myasthenia gravis, diabetes type I, endocrine eye disorders, primary biliary cirrhosis, Crohn's disease, glomerulonephritis, sarcoidosis, psoriasis, pemphigus, aplastic anemia, idiopathic thrombocytopenic purpura, allergy, polyarteritis nodosa, progressive systemic sclerosis, mixed connective-tissue disease, aortitis syndrome, polymyositis, dermatomyositis, Wegener's granulomatosis, ulcerative colitis, active chronic hepatitis, autoimmune hemolytic anemia, Evans syndrome, bronchial asthma, pollinosis and so on, and a reagent for use in medicine and pharmacy. Also, the compounds protected with a protecting group are useful as intermediates for the synthesis of the compounds having superior pharmacological actions as recited above.

When these compounds are used as pharmaceuticals, an effective amount thereof is generally admixed with carrier, excipient, diluent and so on and formulated into powder, capsule, tablet, injection or the like for the administration to patients. A lyophilized preparation may be produced by a method known per se.

While the dose of these compounds varies depending on disease, symptom, body weight, sex, age and so on, they are administered, for example, to an adult daily by 0.01–10 mg (potency) in a single to several times divided doses when suppressing rejection in kidney transplantation.

Moreover, the compounds of the present invention can be used in combination with other immunosuppressant such as cyclosporin, azathioprine, steroids or FK-506 (EP-A184162).

The present invention is hereinafter explained in detail by illustrating examples, to which the present invention is not limited.

EXAMPLE 1

(1) Diethyl 2-acetamidomalonate (3.0 g) was dissolved in 50 ml of dry ethanol and 1.13 g of sodium ethoxide was added thereto. A solution of 4.7 g of tetradecyl bromide in 20 ml of ethanol was added to the mixed solution while stirring at room temperature. The inside of the reaction vessel was displaced with nitrogen and the mixture was refluxed for about 15 hours. Then, the mixture was neutralized with a 1N aqueous hydrochloric acid solution and concentrated. The concentrate was purified by silica gel column chromatography to give 3.5 g of diethyl 2-acetamido-2-tetradecylmalonate.
melting point=58.5°–60.5° C.
IR(KBr): 3280, 2970, 2930, 2860, 1750, 1655, 1525, 1480, 1220, 1030 cm$^{-1}$ (2) Diethyl 2-acetamido-2-tetradecylmalonate (3.40 g) was dissolved in 200 ml of dry tetrahydrofuran. The reaction vessel was equipped with a calcium chloride tube and 1.58 g of lithium aluminum hydride was added thereto in an ice water bath, followed by stirring. After stirring the mixture at room temperature for 30 minutes, 3.0 ml of water was added thereto to stop the reaction. The reaction mixture was concentrated under reduced pressure and 100 ml of acetic anhydride and 80 ml of pyridine were added to the concentrate. The mixture was stirred at room temperature overnight. The reaction mixture was poured into ice water to make the total amount 1600 ml and extracted three times with 500 ml of ethyl acetate. The ethyl acetate layers were combined and washed with a 1N aqueous hydrochloric acid solution, a saturated aqueous sodium hydrogencarbonate solution and a saturated aqueous sodium chloride solution in order. The mixture was dried over anhydrous magnesium sulfate and concentrated. The concentrate was purified by silica gel column chromatography to give 1.35 g of 2-acetamido-1,3-diacetoxy-2-tetradecylpropane.
melting point=84.0°–85.5° C.
IR(KBr): 3310, 2950, 2920, 2840, 1750, 1655, 1550, 1470, 1375, 1255, 1230, 1035, 900 cm$^{-1}$

EXAMPLE 2

2-Acetamido-1,3-diacetoxy-2-tetradecylpropane (1.25 g) was dissolved in 100 ml of methanol and 19.4 ml of a 1N aqueous sodium hydroxide solution was added thereto. The mixture was refluxed under heating for 6 hours. The mixture was neutralized with a 1N aqueous hydrochloric acid solution and concentrated under reduced pressure. The concentrate was washed with water and ethyl acetate:hexane =1:1 in order to give 791 mg of 2-amino-2-tetradecyl-1,3-propanediol hydrochloride.
melting point=96.5°–98.5° C.
Rf: 0.55 (chloroform:methanol:water =65:35:5)
IR(KBr): 3520, 3450, 3300, 3050, 2920, 2850, 1630, 1530, 1470, 1290, 1070, 1050 cm$^{-1}$

EXAMPLE 3

(1) Diethyl 2-acetamidomalonate (3.0 g) was dissolved in 50 ml of dry ethanol and 1.13 g of sodium ethoxide was added thereto. A solution of 5.5 g of hexadecyl bromide in 20 ml of ethanol was added thereto at room temperature with stirring. The inside of the reaction vessel was displaced with nitrogen and the mixture was refluxed for about 15 hours. The mixture was neutralized with a 1N aqueous hydrochloric acid solution and concentrated. The concentrate was purified by silica gel column chromatography to give 4.37 g of diethyl 2-acetamido-2-hexadecylmalonate.
melting point=65.0°–67.0° C.
IR(KBr): 3300, 2920, 2850, 1745, 1650, 1515, 1210, 1020 cm$^{-1}$ (2) Diethyl 2-acetamido-2-hexadecylmalonate (4.30 g) was dissolved in 200 ml of dry tetrahydrofuran and the reaction vessel was equipped with a calcium chloride tube. Thereto was added 1.90 g of lithium aluminum hydride in an ice water bath and the mixture was stirred. After stirring the mixture at room temperature for 30 minutes, 3.6 ml of water was added thereto to stop the reaction. The reaction mixture was concentrated under reduced pressure and 100 ml of acetic anhydride and 80 ml of pyridine were added to the residue. The mixture was stirred at room temperature overnight. The reaction mixture was poured into ice water to make the total amount 1600 ml and extracted three times with 500 ml of ethyl acetate. The ethyl acetate layers were combined and washed with a 1N aqueous hydrochloric acid solution, a saturated aqueous sodium hydrogencarbonate solution and a saturated aqueous sodium chloride solution in order. The resultant mixture was dried over anhydrous magnesium sulfate and concentrated. The concentrate was purified by silica gel column chromatography to give 1.83 g of 2-acetamido-1,3-diacetoxy-2-hexadecylpropane.
melting point=84°–86° C.
IR(KBr): 3300, 2920, 2850, 1740, 1655, 1560, 1390, 1270, 1240, 1055 cm$^{-1}$

EXAMPLE 4

2-Acetamido-1,3-diacetoxy-2-hexadecylpropane (1.75 g) was dissolved in 100 ml of methanol and 23.8 ml of a 1N aqueous sodium hydroxide solution was added thereto. The mixture was refluxed under heating for 6 hours. The mixture was neutralized with a 1N aqueous hydrochloric acid solution and concentrated under reduced pressure. The concentrate was washed with water and ethyl acetate:hexane =1:1 in order to give 892 mg of 2-amino-2-hexadecyl-1,3-propanediol hydrochloride.
melting point=100.5°–104.0° C.

Rf: 0.55 (chloroform:methanol:water=65:35:5)
IR(KBr): 3350, 2920, 2850, 1590, 1470, 1050 cm$^{-1}$

EXAMPLE 5

(1) Diethyl 2-acetamidomalonate (5.0 g) was dissolved in 64 ml of dry ethanol and 1.71 g of sodium ethoxide was added thereto. A solution of 8.4 g of octadecyl bromide in 20 ml of dry ethanol was added thereto while stirring at room temperature. The inside of the reaction vessel was displaced with nitrogen and the mixture was refluxed for about 15 hours. The mixture was neutralized with a 1N aqueous hydrochloric acid solution and concentrated. The concentrate was purified by silica gel column chromatography to give 6.4 g of diethyl 2-acetamido-2-octadecylmalonate.
melting point=70°–71° C.
$^1$H-NMR (200 MHz, CDCl$_3$) δ:
  6.77 (1H, br.s, —NH—), 4.24 (4H, q, J=7.16 Hz, —OCH$_2$—×2), 2.35–2.26 (2H, m, C$_3$Ha, Hb), 2.03 (3H, s, CH$_3$ CONH—), 1.25 (38H, m, O—CH$_2$ —C H$_3$×2, CH$_2$×16), 0.88 (3H, t, J=6.47 Hz, CH$_3$)
IR: 3260, 2910, 2850, 1745, 1640, 1515, 1210, 1020 cm$^{-1}$ (2) Diethyl 2-acetamido-2-octadecylmalonate (3.0 g) was dissolved in dry tetrahydrofuran and the reaction vessel was equipped with a calcium chloride tube. In an ice water bath, 1.2 g of lithium aluminum hydride was added thereto and the mixture was stirred. Then, the mixture was stirred at room temperature for 30 minutes and 2.31 g of water was added thereto to stop the reaction. The reaction mixture was concentrated under reduced pressure and 130 ml of acetic anhydride and 120 ml of pyridine were added to the concentrate. The mixture was stirred at room temperature overnight. The resultant mixture was poured into ice water to make the total amount 2200 ml and extracted three times with 700 ml of ethyl acetate. The ethyl acetate layers were combined and washed with a 1N aqueous hydrochloric acid solution, an aqueous sodium hydrogencarbonate solution and an aqueous sodium chloride solution in order. The mixture was dehydrated over anhydrous magnesium sulfate and concentrated. The concentrate was purified by silica gel column chromatography to give 1.7 g of 2-acetamido-1,3-diacetoxy-2-octadecylpropane.
melting point=90°–91° C
$^1$H-NMR (200 MHz, CDCl$_3$) δ:
  5.64 (1H, br.s, —NH—), 4.30 (4H, s, —CH$_2$O—×2), 2.09 (6H, s, OCOCH$_3$×2), 1.97 (3H, s, NHCOCH3), 1.25 (34H, br.s, CH$_2$×17), 0.88 (3H, t, J=6.47 Hz, CH$_3$)
IR: 3280, 2920, 2850, 1750, 1735, 1645, 1565, 1385, 1270, 1240, 1045 cm$^{-1}$

EXAMPLE 6

2-Acetamido-1,3-diacetoxy-2-octadecylpropane (1.00 g) was dissolved in 26 ml of methanol and 6.4 ml of a 1N aqueous sodium hydroxide solution was added thereto. The mixture was refluxed under heating for 6 hours. The mixture was neutralized with a 1N aqueous hydrochloric acid solution and concentrated under reduced pressure. The concentrate was washed with water and ethyl acetate:hexane=1:1 in order to give 639 mg of 2-amino-2-octadecyl-1,3-propanediol hydrochloride.
melting point=108.5°–109.5° C.
$^1$H-NMR (200MHz, CD$_3$OD) δ:
  3.64 (2H, d, J=11.48 Hz, —CHa—O—), 3.57 (2H, d, J=11.47 Hz, —CHb—O—), 1.28 (34H, br.s, CH$_2$×17), 0.90 (3H, t, J=6.35 Hz, —CH$_3$)
IR: 3275, 2900, 2840, 1630, 1600, 1530, 1465, 1290, 1050 cm$^{-1}$

EXAMPLE 7

2-Amino-2-octadecyl-1,3-propanediol hydrochloride (100 mg) as obtained in Example 6 was dissolved in 200 ml of methanol and the mixture was dropwise added to 50 ml of Diaion WA-10 (trade mark, anion exchange resin). The solvent of the eluate was distilled away to give 64 mg of 2-amino-2-octadecyl-1,3-propanediol.
melting point=76.0°–80.0° C.
IR: 3290, 3175, 2910, 2850, 1590, 1580, 1480, 1065, 1050, 1000 cm$^{-1}$

EXAMPLE 8

(1) Diethyl 2-acetamidomalonate (3.0 g) was dissolved in 50 ml of dry ethanol and 1.3 g of sodium ethoxide was added thereto. A solution of 6.5 g of docosyl bromide in 20 ml of dry ethanol was added thereto while stirring at room temperature. The inside of the reaction vessel was displaced with nitrogen and the mixture was refluxed for about 15 hours. The mixture was neutralized with a 1N aqueous hydrochloric acid solution and concentrated. The concentrate was purified by silica gel column chromatography to give 4.2 g of diethyl 2-acetamido-2-docosylmalonate.
melting point=79°–80° C.
IR(KBr): 3300, 2925, 2860, 1750, 1655, 1520, 1220 cm$^{-1}$ (2) Diethyl 2-acetamido-2-docosylmalonate (4.15 g) was dissolved in dry tetrahydrofuran and the reaction vessel was equipped with a calcium chloride tube. In an ice water bath, 1.4 g of lithium aluminum hydride was added thereto and the mixture was stirred. The mixture was stirred at room temperature for 30 minutes and 2.31 g of water was added thereto to stop the reaction. The reaction mixture was concentrated under reduced pressure and 130 ml of acetic anhydride and 120 ml of pyridine were added thereto. The mixture was stirred at room temperature overnight. The reaction mixture was poured into ice water to make the total amount 2200 ml and extracted three times with 700 ml of ethyl acetate. The ethyl acetate layers were combined and washed with a 1N aqueous hydrochloric acid solution, a saturated aqueous sodium hydrogencarbonate solution and a saturated aqueous sodium chloride solution in order. The mixture was dried over anhydrous magnesium sulfate and concentrated. The concentrate was purified by silica gel column chromatography to give 1.8 g of 2-acetamido-1,3-diacetoxy-2-docosylpropane.
melting point=94°–95° C.
IR(KBr): 3280, 2920, 2850, 1750, 1655, 1520, 1480, 1220 cm$^{-1}$

EXAMPLE 9

2-Acetamido-1,3-diacetoxy-2-docosylpropane (1.5 g) was dissolved in 40 ml of methanol and 9.6 ml of a 1N aqueous sodium hydroxide solution was added thereto. The mixture was refluxed under heating for 6 hours. The mixture was neutralized with a 1N aqueous hydrochloric acid solution and concentrated under reduced pressure. The concentrate was washed with water and ethyl acetate:hexane =1:1 in order to give 846 mg of 2-amino-2-docosyl-1,3-propanediol hydrochloride.
melting point=109.0°–110.5° C.
Rf: 0.55 (chloroform:methanol:water =65:35:5) IR(KBr): 3500, 3450, 3290, 2920, 2850, 1640, 1530, 1470, 1060 cm$^{-1}$

EXAMPLE 10

(1) Diethyl 2-acetamidomalonate (3.0 g) was dissolved in 50 ml of dry ethanol and 1.3 g of sodium ethoxide was added thereto. A solution of 6.0 g of icosyl bromide in 20 ml of dry ethanol was added thereto while stirring at room temperature. The inside of the reaction vessel was displaced with nitrogen and the mixture was refluxed for about 15 hours. The mixture was neutralized with a 1N aqueous hydrochloric acid solution and concentrated. The concentrate was purified by silica gel column chromatography to give 4 g of diethyl 2-acetamido-2-icosylmalonate.
melting point=76.5°–77.5° C.
IR(KBr): 2920, 2850, 1750, 1655, 1520, 1480, 1220 $cm^{-1}$ (2) Diethyl 2-acetamido-2-icosylmalonate (3.7 g) was dissolved in dry tetrahydrofuran. The reaction vessel was equipped with a calcium chloride tube and the mixture was cooled to 0° C. Lithium aluminum hydride (1.4 g) was added thereto and the mixture was stirred. The mixture was stirred at room temperature for 30 minutes and 2.31 g of water was added thereto to stop the reaction. The reaction mixture was concentrated under reduced pressure and 130 ml of acetic anhydride and 120 ml of pyridine were added thereto. The mixture was stirred at room temperature overnight. The reaction mixture was poured into ice water to make the total amount 2200 ml and extracted three times with 700 ml of ethyl acetate. The ethyl acetate layers were combined and washed with a 1N aqueous hydrochloric acid solution, a saturated aqueous sodium hydrogencarbonate solution and a saturated aqueous sodium chloride solution in order. The mixture was dried over anhydrous magnesium sulfate and concentrated. The concentrate was purified by silica gel column chromatography to give 1.7 g of 2-acetamido-1,3-diacetoxy-2-icosylpropane.
melting point=93°–94° C.
IR(KBr): 3280, 2920, 2855, 1775, 1755, 1650, 1565, 1480, 1385, 1270, 1245, 1045 $cm^{-1}$

EXAMPLE 11

2-Acetamido-1,3-diacetoxy-2-icosylpropane (1.5 g) was dissolved in 40 ml of methanol and 9.6 ml of a 1N aqueous sodium hydroxide solution was added thereto. The mixture was refluxed under heating for 6 hours. The mixture was neutralized with a 1N aqueous hydrochloric acid solution and the reaction mixture was concentrated under reduced pressure. The concentrate was washed with water and ethyl acetate:hexane =1:1 in order to give 817 mg of 2-amino-2-icosyl-1,3-propanediol hydrochloride.
melting point=109.5°–111.0° C.
Rf: 0.55 (chloroform:methanol:water=65:35:5)
IR(KBr): 3300, 2910, 2850, 1640, 1600, 1480, 1065, 1050 $cm^{-1}$

EXAMPLE 12

(1) Diethyl 2-acetamidomalonate (15 g) was dissolved in 200 ml of dry ethanol and 5.6 g of sodium ethoxide was added thereto. To the reaction mixture, 22 g of 9-octadecenyl chloride was added while stirring at room temperature. The inside of the reaction vessel was displaced with nitrogen and the mixture was refluxed for about 15 hours. The mixture was neutralized with ethanol-concentrated hydrochloric acid (11:1) and concentrated. The concentrate was purified by silica gel column chromatography to give 1.3 g of diethyl 2-acetamido-2-(9-octadecenyl)malonate as a colorless, oily and viscous substance.
$^1$H-NMR (200 MHz, CDCl$_3$) δ:

6.765 (1H, br.s, —NH—), 5.340–5.310 (2H, m, CH=CH), 4.240 (4H, q, J=7.4Hz, —OCH$_2$—×2), 2.032 (3H, s, CH$_3$ CON), 1.990 (4H, m, CH$_2$CH=2), 1.252 (26H, m, CH$_2$×13), 1.252 (6H, t, J=7.2Hz, OCH$_2$ —CH$_3$×2), 0.880 (3H, t, J=6.5Hz, CH$_3$)

(2) Diethyl 2-acetamido-2-(9-octadecenyl)malonate (1.3 g) was dissolved in 30 ml of dry tetrahydrofuran and 450 mg of lithium aluminum hydride was added thereto under ice-cooling. The inside of the reaction vessel was displaced with dry nitrogen and the mixture was stirred. Then, the mixture was stirred at room temperature for 2 hours and 1 ml of water was added thereto to stop the reaction. The reaction mixture was concentrated under reduced pressure and 10 ml of acetic anhydride and 5 ml of pyridine were added thereto. The mixture was stirred at room temperature overnight. Water was added to the reaction mixture under ice-cooling to make the total amount about 100 ml and the mixture was extracted twice with 50 ml of ethyl acetate. The ethyl acetate layers were combined and washed with a 1N aqueous hydrochloric acid solution, a saturated aqueous sodium hydrogencarbonate solution and a saturated aqueous sodium chloride solution in order. The mixture was dried over anhydrous magnesium sulfate and concentrated to give 430 mg of 2-acetamido-1,3-diacetoxy-2-(9-octadecenyl)propane as a colorless, oily and viscous substance.
IR(CHCl$_3$): 3460, 3420, 3010, 2940, 2860, 1750, 1690, 1520, 1475, 1390, 1380, 1240 (br), 1045, 990 $cm^{-1}$

EXAMPLE 13

2-Acetamido-1,3-diacetoxy-2-(9-octadecenyl)propane (332 mg) was dissolved in 30 ml of methanol and 7.8 ml of a 1N aqueous sodium hydroxide solution was added thereto. The mixture was refluxed under heating overnight. The mixture was neutralized with methanol-concentrated hydrochloric acid (11:1) and concentrated under reduced pressure. The concentrate was dissolved in methanol-water (1:1) and subjected to reversed phase column chromatography [packing: Sep-Pak(C$_{18}$)]. After washing, the mixture was eluted with methanol. The eluate was concentrated to give 209 mg of 2-amino-2-(9-octadecenyl)-1,3-propanediol hydrochloride as a colorless, oily and viscous substance.
$^1$H-NMR (200 MHz, CD$_3$ OD) δ:

5.385–5.315 (2H, m, CH=CH), 3.616 (2H, d, J=11.4 Hz, OCH$_{2a}$×2), 3.548 (2H, d, J=11.4 Hz, OCH$_{2b}$×2), 2.071–1.957 (4H, m, CH$_2$CH=×2), 1.665–1.580 (2H, m, CCH$_2$), 1.39–1.28 (24H, m, CH$_2$×12), 0.896 (3H, t, J=6 Hz, CH$_3$)
IR: 3300(br), 2920, 2850, 1600, 1500, 1465, 1050, 965 $cm^{-1}$

EXAMPLE 14

(1) Sodium (0.23 g) was added to 15 ml of absolute ethanol and the mixture was stirred at room temperature for 30 minutes in a nitrogen flow to give a 10 mmol solution of sodium ethoxide in ethanol. To this solution, 1.98 g of diethyl 2-acetamidomalonate was added and the mixture was heated at 50° C. for 30 minutes in a stream of nitrogen. 3-Phenylpropyl bromide was added thereto at room temperature and the mixture was refluxed under heating for 24 hours. The mixture was neutralized with dilute hydrochloric acid and ethanol was distilled away. The resultant residue was extracted with ethyl acetate. The ethyl acetate layer was washed with water and dried over anhydrous magnesium sulfate. The solvent was distilled away and the residue was purified by silica gel column chromatography (ethyl acetate:hexane=1:4–1:1) and recrystallized from diisopropyl ether-hexane to give 800 mg of diethyl 2-acetamido-2-(3-phenylpropyl)malonate as white crystals.

melting point=76°–77° C. Rf: 0.58 (ethyl acetate:hexane= 1:1) $^1$H-NMR (90 MHz, CDCl$_3$) δ: 1.22 (3H, t, J=7 Hz), 1.10–1.56 (4H, m), 2.02 (3H, s), 2.28–2.75 (2H, m), 4.21 (4H, q, J=7 Hz), 6.75 (1H, br.s), 7.02–7.42 (5H, m) IRv: 3259, 2980, 2863, 1738, 1648 cm$^{-1}$ MS(EI): 335(M$^+$)

(2) A solution (50 ml) of 1.0 g of the above-mentioned compound and 136 mg of lithium borohydride in tetrahydrofuran was refluxed under heating for 1 hour in a nitrogen flow. The reaction mixture was poured into 100 ml of ice water and extracted with ethyl acetate. The extract was washed and dried, and the solvent was distilled away. The residue was purified by silica gel column chromatography (methanol:chloroform=1:20) to give 720 mg of 2-acetamido-2-(3-phenylpropyl)-1,3-propanediol as a colorless, oily substance.

Rf: 0.30 (ethyl acetate) $^{-1}$H-NMR (90 MHz, CDCl$_3$) δ: 1.47–1.89 (4H, m), 2.00 (3H, s), 2.44–2.84 (2H, m), 3.73 (4H, dd, J=7 Hz, 15 Hz), 3.37–4.17 (2H, m), 5.51–5.97 (1H, m), 7.00–7.45 (5H, m) IRv: 3294, 2938, 1652 cm$^{-1}$ MS(EI): 251(M$^+$)

EXAMPLE 15

2-Acetamido-2-(3-phenylpropyl)-1,3-propanediol (600 mg) was dissolved in 25 ml of methanol and 11.9 ml of a 1N aqueous sodium hydroxide solution was added thereto. The mixture was refluxed under heating for 6 hours. The mixture was poured into 30 ml of ice water and neutralized with dilute hydrochloric acid. The solvent was distilled away. Chloroform was added to the residue for extraction and the chloroform layer was washed and dried. The solvent was distilled away and the residue was purified by column chromatography (chloroform:methanol=9:1–4:1) to give 250 mg of 2-amino-2-(3-phenylpropyl)-1,3-propanediol as a pale yellow, oily substance.

Rf: 0.22 (methanol:chloroform =1:4) $^1$H-NMR (90 MHz, CDCl$_3$) δ: 1.11–1.98 (4H, m), 2.43–2.75 (2H, m), 3.15–4.03 (4H, m), 3.62 (4H, br.s), 7.19 (5H, s) IRv: 3347, 3023, 2937, 1583 cm$^{-1}$ MS(EI): 209(M$^+$)

EXAMPLE 16

(1) A solution of 5.42 g of cinnamyl bromide, 5.43 g of diethyl 2-acetamidomalonate and 1.87 g of sodium ethoxide in 70 ml of ethanol was refluxed under heating for 2 hours under a nitrogen atmosphere. The mixture was poured into 200 ml of ice water and extracted with ethyl acetate. The extract was dried over anhydrous sodium sulfate and the solvent was distilled away. The residue was purified by silica gel chromatography (ethyl acetate:hexane=1:10–1:3) to give 2.68 g of diethyl 2-acetamido-2-(3-phenyl-2-propenyl)malonate as white crystals.

melting point=70°–75° C. Rf: 0.38 (ethyl acetate:hexane= 1:5) $^1$H-NMR (CDCl$_3$/TMS) δ: 1.31 (6H, t, J=7.5 Hz), 1.56 (2H, s), 2.09 (3H, s), 4.28 (4H, q, J=7.5 Hz), 6.30–6.80 (2H, m), 7.27 (5H, s) IR(KBr): 3280, 2990, 1740, 1640 cm$^{-1}$ (2) A solution (80 ml) of 2.50 g of the above-mentioned compound and 1.63 g of lithium borohydride in tetrahydrofuran was refluxed under heating for 2 hours under a nitrogen atmosphere. After the reaction, the solvent was distilled away and the residue was evaporated to dryness. Acetic anhydride (14 ml) and 50 ml of pyridine were added to the residue and the mixture was stirred at room temperature overnight. The mixture was poured into ice water and extracted with ethyl acetate. The extract was washed with 2N hydrochloric acid, a saturated aqueous sodium bicarbonate solution and saturated brine in order and dried. The solvent was distilled away and the residue was purified by silica gel column chromatography (ethyl acetate:hexane= 3:1) to give 200 mg of 2-acetamido-1,3-diacetoxy-2-(3-phenyl-2-propenyl)propane as white crystals.

melting point:=88°–90° C. Rf: 0.70 (ethyl acetate) $^1$H-NMR (CDCl$_3$/TMS) δ: 1.96 (3H, s), 2.07 (6H, s), 2.82 (2H, d, J=7.5 Hz), 4.36 (4H, s) IR(KBr): 3311, 3084, 1750, 1655, 1560 cm$^{-1}$ MS(EI): 333(M$^+$) elemental analysis: calculated C 64.85, H 6.95, N 4.20 found C 64.85, H 6.88, N 4.15

EXAMPLE 17

2-Acetamido-1,3-diacetoxy-2-(3-phenyl-2-propenyl)propane (170 mg) was dissolved in 6 ml of methanol and 6 ml of a 1N aqueous sodium hydroxide solution was added thereto. The mixture was refluxed under heating for 3 hours. After the reaction, the solvent was distilled away and the residue was purified by silica gel column chromatography (methanol:chloroform=1:30–1:6) to give 70 mg of 2-amino-2-(3-phenyl-2-propenyl)-1,3-propanediol as pale brown crystals.

Rf: 0.14 (methanol:chloroform=1:10) IR(KBr): 3367, 2935, 1556 cm$^{-1}$

EXAMPLE 18

(1) 1-Phenyl-1-propyn-3-ol (5 g), 5.1 g of tosyl chloride and 20 ml of pyridine were stirred at room temperature for 1 hour. The reaction mixture was poured into 100 ml of ice water and extracted with ethyl acetate. The oil layer was washed with 1N hydrochloric acid and saturated brine and dried over anhydrous sodium sulfate. The solvent was distilled away. The residue was purified by silica gel column chromatography (ethyl acetate:hexane=1:5) to give 2.54 g of 3-phenyl-2-propynyl chloride as a pale yellow, oily substance.

Rf: 0.81 (ethyl acetate:hexane=1:2) $^1$H-NMR (CDCl$_3$/ TMS) δ: 4.37 (2H, s), 7.23–7.60 (5H, m) IR(neat): 2222, 758, 690 cm$^{-1}$ MS(70 eV): 150(M$^+$)

(2) A solution of 2.5 g of the above-mentioned compound, 3.79 g of dimethyl 2-acetamidomalonate and 1.43 g of sodium ethoxide in 50 ml of ethanol was refluxed under heating for 3 hours under a nitrogen atmosphere. Water (20 ml) was added thereto to stop the reaction and the mixture was extracted with ethyl acetate. The extract was dried over anhydrous sodium sulfate and the solvent was distilled away. The residue was purified by silica gel column chromatography (ethyl acetate:hexane=1:7–1:2) to give 2.5 g of diethyl 2-acetamido-2-(3-phenyl-2-propynyl)malonate as white crystals.

melting point=94°–96.5° C. Rf: 0.38 (ethyl acetate:hexane=1:2) $^1$H-NMR (CDCl$_3$/TMS) δ: 1.28 (6H, t, J=7.5 Hz), 2.08 (3H, s), 3.49 (2H, s), 4.30 (4H, q, J=7.5 Hz), 6.98 (1H, br.s), 7.16–7.49 (5H, m) IR(KBr): 3260, 1747, 1643, 1197 cm$^{-1}$ MS(70 eV): 331(M$^+$)

(3) A solution (50 ml) of 1.8 g of the above-mentioned compound and 0.47 g of lithium borohydride in tetrahydrofuran was refluxed under heating for 1.5 hours under a nitrogen atmosphere. After cooling, the mixture was neutralized with 8 ml of a 1N aqueous hydrochloric acid solution and evaporated to dryness. Acetic anhydride (4 ml) and 30 ml of pyridine were added to the residue and the mixture was stirred at room temperature for 2.5 hours. The reaction mixture was poured into ice water and extracted with chloroform. The extract was washed with 1N hydrochloric acid and saturated brine in order and dried. The solvent was distilled away and the residue was purified by silica gel column chromatography (ethyl acetate:hexane= 2:1) to give 430 mg of 2-acetamido-1,3-diacetoxy-2-(3-phenyl-2-propynyl)propane as a colorless, oily substance.

Rf: 0.64 (ethyl acetate) $^1$H-NMR (CDCl$_3$/TMS) δ: 1.98 (3H, s), 2.07 (6H, s), 3.09 (2H, s), 4.47 (4H, s), 5.95 (1H, br.s), 7.18–7.48 (5H, m ) IR(neat): 3293, 2135, 1745, 1662 cm$^{-1}$ MS(70 eV): 331(M$^+$)

EXAMPLE 19

2-Acetamido-1,3-diacetoxy-2-(3-phenyl-2-propynyl)propane (430 mg) was dissolved in 8 ml of methanol and 8 ml of a 1N aqueous sodium hydroxide solution was added thereto. The mixture was refluxed under heating for 2 hours. The solvent was distilled away and the residue was purified by silica gel column chromatography (methanol:chloroform=1:50–1:7) to give 230 mg of 2-amino-2-(3-phenyl-2-propynyl)-1,3-propanediol as a pale yellow, amorphous-like solid.

Rf: 0.20 (methanol:chloroform=1:5) IR(KBr): 3281, 2932, 1558, 1049 cm$^{-1}$

EXAMPLE 20

(1) A solution of 1.1 g of 4-(4-butylphenyl)butanol, 1.05 g of tosyl chloride, 0.48 ml of pyridine and a catalytic amount of dimethylaminopyridine in dichloromethane was allowed to stand at room temperature overnight. The reaction mixture was poured into 50 ml of ice water and extracted with chloroform. The extract was dried over anhydrous sodium sulfate and the solvent was distilled away. The residue was purified by silica gel column chromatography (ethyl acetate:hexane=1:6) to give 1.2814 g of 4-(4-butylphenyl)butyl p-toluenesulfonate as a colorless, oily substance.

$^1$H-NMR (CDCl$_3$/TMS) δ: 0.96 (3H, t, J=7 Hz), 1.50–2.00 (8H, m), 2.48 (3H, s), 2.40–2.75 (4H, m), 4.08 (2H, t, J=6 Hz), 7.07 (4H, m), 7.36 (2H, d, J=8 Hz), 7.83 (2H, d, J=8 Hz) IR: 2956, 2929, 2858, 1361 cm$^{-1}$ MS: 360(M$^+$)

(2) The above-mentioned compound (1.2138 g) and 0.606 g of sodium iodide were dissolved in 34 ml of 2-butanone and the mixture was refluxed under heating for 4 hours. The mixture was poured into 100 ml of ice water and extracted with ethyl acetate. The extract was dried over anhydrous sodium sulfate and the solvent was distilled away. The residue was purified by silica gel column chromatography (ethyl acetate:hexane=1:9) to give 0.953 g of 4-(4-butylphenyl)-1-iodobutane as a red, oily substance.

Rf: 0.75 (ethyl acetate:hexane=1:5) $^1$H-NMR (CDCl$_3$/TMS) δ: 0.92 (3H, t, J=7 Hz), 1.10–2.05 (8H, m), 2.59 (4H, t, J=7.5 Hz), 3.20 (2H, t, J=7 Hz), 7.07 (5H, s)

(3) A solution of 953.4 mg of the above-mentioned compound, 687.7 mg of diethyl 2-acetamidomalonate and 280 mg of sodium ethoxide in 10 ml of ethanol was refluxed under heating for 3 hours under a nitrogen atmosphere. The mixture was poured into 100 ml of ice water and extracted with ethyl acetate. The extract was dried over anhydrous sodium sulfate and the solvent was distilled away. The residue was purified by silica gel column chromatography (ethyl acetate:hexane=1:3–1:2) to give 480 mg of diethyl 2-acetamido-2-[4-(4-butylphenyl)butyl]malonate as white crystals.

melting point=60°–61° C. Rf: 0.38 (ethyl acetate:hexane= 1:2) $^1$H-NMR (CDCl$_3$/TMS) δ: 0.93 (3H, t, J=6 Hz), 1.24 (3H, t, J=7 Hz), 1.09–1.85 (8H, m), 2.02 (3H, s), 2.35 (2H, m), 2.58 (4H, t, J=7.5 Hz), 4.25 (2H, q, J=6 Hz), 6.75 (1H, br.s), 7.07 (4H, s) IR: 3270, 2930, 2880, 1740, 1640 cm$^{-1}$ MS: 405(M$^+$), 290 elemental analysis: calculated C 68.12, H 8.70, N 3.45 found C 68.25, H 8.69, N 3.55

(4) A solution (15 ml) of 450 mg of the above-mentioned compound and 100 mg of lithium borohydride in tetrahydrofuran was refluxed under heating for 2 hours under a nitrogen atmosphere. The mixture was neutralized with 2.5 ml of a 2N aqueous hydrochloric acid solution and dried to solidness. Acetic anhydride (2 ml) and 4 ml of pyridine were added to the residue and the mixture was stirred at room temperature overnight. The reaction mixture was poured into ice water and extracted with ethyl acetate. The extract was washed with 2N hydrochloric acid, a saturated sodium bicarbonate solution and saturated brine in order and dried. The solvent was distilled away and the residue was purified by silica gel column chromatography (ethyl acetate:hexane= 3:1) to give 72.4 mg of 2-acetamido-1,3-diacetoxy-2-[4-(4-butylphenyl)butyl]propane as white crystals.

melting point=68°–71° C. Rf: 0.63 (ethyl acetate) $^1$H-NMR (CDCl$_3$/TMS) δ: 0.91 (3H, t, J=7 Hz), 1.10–2.40 (10H, m), 1.93 (3H, s), 2.06 (6H, s), 2.58 (4H, t, J=7.5 Hz), 4.28 (4H, s), 5.62 (1H, br.s), 7.07 (4H, s) IR: 3298, 3090, 2931, 2859, 1739, 1652, 1557 cm$^{-1}$ MS: 405(M$^+$) elemental analysis: calculated C 68.12, H 8.70, N 3.45 found C 67.95, H 8.52, N 3.44

EXAMPLE 21

2-Acetamido-1,3-diacetoxy-2-[4-(4-butylphenyl)butyl] propane (66.2 mg) was dissolved in 2 ml of methanol and 2 ml of a 1N aqueous sodium hydroxide solution was added thereto. The mixture was refluxed under heating for 4 hours. The solvent was distilled away and the residue was purified by silica gel thin layer chromatography (methanol:chloroform=1:4) to give 24.9 mg of 2-amino-2-[4-(4-butylphenyl)butyl]-1,3-propanediol as white crystals.

melting point=92°–94° C. Rf: 0.15 (methanol:chloroform=1:4) IR: 3276, 2928, 2858, 1560 cm$^{-1}$

EXAMPLE 22

(1) 4-(4-Hexylphenyl)butanol (5.0 g) was dissolved in 20 ml of pyridine and 4.88 g of tosyl chloride was added thereto. The reaction mixture was left standing at room temperature overnight. The reaction mixture was poured into ice water and extracted with ethyl acetate. The extract was washed with 2N hydrochloric acid, a saturated aqueous sodium bicarbonate solution and saturated brine in order and concentrated. The residue was purified by silica gel column chromatography (ethyl acetate:hexane=1:7) to give 2.21 g of 4-(4-hexylphenyl)butyl p-toluenesulfonate as a colorless, oily substance.

Rf: 0.35 (ethyl acetate:hexane=1:5) $^1$H-NMR (CDCl$_3$/TMS) δ: 0.90 (3H, t, J=6 Hz), 1.09–1.85 (12H, m), 2.46 (3H, s), 2.53 (4H, m), 4.06 (2H, t, J=6 Hz), 7.06 (4H, s), 7.34 (2H, d, J=8 Hz), 7.81 (2H, d, J=8 Hz) IR: 2927, 2856, 1599 cm$^{-1}$ MS: 388(M$^+$), 216 elemental analysis: calculated C 71.10, H 8.30 found C 71.35, H 8.34

(2) The above-mentioned compound (2.21 g) and 1.02 g of sodium iodide were dissolved in 57 ml of 2-butanone and the mixture was refluxed under heating for 2 hours. The reaction mixture was poured into ice water and extracted with ethyl acetate. The extract was washed with saturated brine, and dried and concentrated. The residue was purified by silica gel column chromatography (ethyl acetate:hexane= 1:9) to give 1.765 g of 4-(4-hexylphenyl)-1-iodobutane as a colorless, oily substance.

Rf: 0.43 (ethyl acetate:hexane=1:5) $^1$H-NMR (CDCl$_3$/TMS) δ: 0.90 (3H, t, J=6 Hz), 1.05–2.05 (12H, m), 2.60 (4H, m), 3.21 (2H, t, J=7 Hz), 7.10 (4H, s) MS: 344(M$^+$), 273, 175 elemental analysis: calculated C 55.82, H 7.32 found C 55.81, H 7.32

(3) A solution of 1.6806 g of the above-mentioned compound, 1.1133 g of diethyl 2-acetamidomalonate and 523 mg of sodium ethoxide in 20 ml of ethanol was refluxed under heating for 4.5 hours under a nitrogen atmosphere. The reaction mixture was poured into ice water and extracted with ethyl acetate. The extract was dried and concentrated. The residue was purified by silica gel column chromatography (ethyl acetate:hexane=1:3) to give 870 mg of diethyl 2-acetamido-2-[4-(4-hexylphenyl)butyl]malonate as white crystals.

melting point=57°–58° C. Rf: 0.42 (ethyl acetate:hexane= 1:2) $^1$H-NMR (CDCl$_3$/TMS) δ: 0.91 (3H, t, J=6 Hz), 1.24 (6H, t, J=7 Hz), 1.08–1.90 (12H, m), 2.02 (3H, s), 2.35 (2H, m), 2.58 (4H, t, J=7 Hz), 4.23 (4H, q, J=7 Hz), 6.74 (1H, br.s), 7.07 (4H, s) IR: 3270, 2927, 2858, 1746, 1644, 1514 cm$^{-1}$ MS: 433(M$^+$), 360, 318 elemental analysis: calculated C 69.25, H 9.07, N 3.23 found C 69.44, H 8.97, N 3.26

(4) A solution (20 ml) of 840 mg of the above-mentioned compound and 211 mg of lithium borohydride in tetrahydrofuran was refluxed under heating for 4 hours under a nitrogen atmosphere. The mixture was neutralized with 2N hydrochloric acid and the solvent was evaporated to dryness. Acetic anhydride (5.5 ml) and 16 ml of pyridine were added to the residue and the mixture was stirred at room temperature overnight. The reaction mixture was treated conventionally and the residue obtained was purified by silica gel column chromatography (ethyl acetate:hexane=3:1) to give 244.5 mg of 2-acetamido-1,3-diacetoxy-2-[4-(4-hexylphenyl)butyl]propane as white crystals.

melting point=61°–64° C. Rf: 0.71 (ethyl acetate) $^1$H-NMR (CDCl$_3$/TMS) δ: 0.88 (3H, t, J=6 Hz), 1.10–1.90 (14H, m), 1.92 (3H, s), 2.04 (6H, s), 2.58 (4H, t, J=7 Hz), 4.28 (4H, s), 5.58 (1H, br.s), 7.06 (4H, s) IR: 3313, 2928, 2856, 1750, 1656 cm$^{-1}$ MS: 433(M$^+$), 389, 373 elemental analysis: calculated C 69.25, H 9.07, N 3.23 found C 69.26, H 9.01, N 3.22

EXAMPLE 23

2-Acetamido-1,3-diacetoxy-2-[4-(4-hexylphenyl)butyl] propane (200.2 mg) was dissolved in 7 ml of methanol and 1N sodium hydroxide was added thereto. The mixture was refluxed under heating for 5 hours. The solvent was distilled away and the residue obtained was purified by silica gel thin layer chromatography (methanol:chloroform=1:3) to give 79.7 mg of 2-amino-2-[4-(4-hexylphenyl)butyl]-1,3-propanediol as white crystals.

melting point=99°–102° C. Rf: 0.14 (methanol:chloroform=1:4) IR: 3286, 2927, 2858, 1562, 1514 cm$^{-1}$

EXAMPLE 24

(1) Concentrated sulfuric acid (18.3 g) was gradually added dropwise to 13.94 g of concentrated nitric acid and the mixture was vigorously shaken for 10 minutes. To the mixed solution, 10 g of 3 phenylpropyl bromide was gradually added dropwise at −20° C. and the mixture was stirred at −20° C. for 1 hour. The reaction mixture was poured into 500 ml of ice water and extracted with ether. The extract was washed and dried, and the solvent was distilled away. The residue was purified by silica gel column chromatography (ethyl acetate:hexane=1:9) to give 4.5 g of 3-(4-nitrophenyl)propyl bromide as a colorless, oily substance.

Rf: 0.33 (ethyl acetate:hexane=1:15)

(2) Sodium (0.68 g) was added to 40 ml of absolute ethanol under ice-cooling. The mixture was stirred at room temperature for 30 minutes in a stream of nitrogen to give a sodium ethoxide solution. To this solution, 1.98 g of diethyl 2-acetamidomalonate was added and 4.8 g of the compound of (1) above was dropwise added thereto. The mixture was refluxed under heating for 6 hours. The reaction mixture was poured into 100 ml of ice water and extracted with ethyl acetate. The extract was washed and dried, and the solvent was distilled away. The residue was purified by silica gel column chromatography (ethyl acetate:hexane=1:3–1:1) to give 3.0 g of diethyl 2-acetamido-2-[3-(4-nitrophenyl)propyl]malonate as a yellow, oily substance.

Rf: 0.51 (ethyl acetate:hexane=1:1)

(3) A solution (50 ml) of 1.0 g of the compound of (2) above and 228 mg of lithium borohydride in tetrahydrofuran was refluxed under heating for 2 hours in a stream of nitrogen. The reaction mixture was poured into 100 ml of ice water and extracted with ethyl acetate. The extract was washed and dried, and the solvent was distilled away. The residue was purified by silica gel column chromatography (methanol:chloroform=1:9) to give 400 mg of 2-acetamido-2-[3-(4-nitrophenyl)propyl]-1,3-propanediol as a yellow, oily substance.

Rf: 0.22 (ethyl acetate) $^1$H-NMR (90 MHz, CDCl$_3$) δ: 1.38–1.80 (4H, m), 2.00 (3H, s), 2.57–3.04 (2H, m), 3.39–4.28 (4H, m), 3.93 (2H, br.s), 6.23–6.58 (1H, m), 7.17–7.63 (2H, m), 7.75–8.20 (2H, m) IRv: 3301, 2944, 1652, 1519 cm$^{-1}$ MS(EI): 296(M$^+$)

EXAMPLE 25

2-Acetamido-2-[3-(4-nitrophenyl)propyl]-1,3-propanediol (400 mg) was dissolved in 50 ml of methanol and 6.7 ml of a 1N aqueous-sodium hydroxide solution was added thereto. The mixture was refluxed under heating for 3 hours and neutralized with dilute hydrochloric acid. The solvent was distilled away and chloroform was added to the residue for extraction. The chloroform layer was washed and dried, and the solvent was distilled away. The residue was purified by silica gel column chromatography (methanol:chloroform=1:4) to give 100 mg of 2-amino-2-[3-(4-nitrophenyl)propyl]-1,3-propanediol as a red, oily substance.

Rf: 0.13 (chloroform:methanol=4:1) $^1$H-NMR (90 MHz, CDCl$_3$) δ: 1.10–2.05 (4H, m), 2.52–3.11 (2H, m), 3.19–3.86 (4H, m), 4.65 (4H, br.s), 7.08–7.65 (3H, m), 7.70–8.18 (1H, m) IRv: 3359, 2936, 2866, 1524 cm$^{-1}$

EXAMPLE 26

(1) A 15N aqueous sodium hydroxide solution (2 ml) and a solution (10 ml) of 8.0 g of undecyl bromide in ethanol was added to a solution (30 ml) of 4.56 g of 3-(3-hydroxyphenyl)propanol in ethanol and the mixture was stirred at 70° C. for 12 hours. The solvent was distilled away and the residue was extracted with ethyl acetate. The extract was washed with saturated sodium hydrogencarbonate and brine, and dried over magnesium sulfate. The solvent was distilled away and the residue was purified by silica gel column chromatography (ethyl acetate:hexane=1:20–1:3) to give 7.37 g of 3-(3-undecyloxyphenyl)propanol as a colorless, oily substance.

$^1$H-NMR (90 MHz, CDCl$_3$) δ: 0.87 (3H, t, J=6 Hz), 1.10–2.08 (20H, m), 1.60 (1H, br.s), 2.69 (2H, t, J=6 Hz), 3.55–3.81 (2H, m), 3.94 (3H, t, J=6 Hz), 6.62–6.87 (3H, m), 7.06–7.23 (1H, m)

(2) Carbon tetrabromide (5.68 g) and 4.49 g of triphenylphosphine were added to a solution (100 ml) of 5 g of the above-mentioned compound in methylene chloride and the mixture was stirred at room temperature overnight. The reaction mixture was poured into ice water and extracted with methylene chloride. The organic layer was washed and dried, and the solvent was distilled away. Petroleum ether was added to the residue and insoluble matters were filtered off. The petroleum ether layer was distilled away and the residue was purified by silica gel column chromatography (ethyl acetate:hexane=1:20) to give 4.6 g of 3-(3-undecyloxyphenyl)propyl bromide as a colorless, oily substance.

$^1$H-NMR (90 MHz, CDCl$_3$) δ: 0.83 (3H, t, J=7 Hz), 1.04–1.53 (16H, m), 1.55–1.86 (2H, m), 2.14 (2H, m, J=7 Hz), 2.70 (2H, t, J=7 Hz), 3.34 (2H, t, J=7 Hz), 3.90 (2H, t, J=7 Hz), 6.73–6.85 (3H, m), 7.14–7.42 (1H, m) IR: 2925, 2553, 1583, 1451, 1261 cm$^{-1}$ (3) Sodium (0.43 g) was added to absolute ethanol (40 ml) under ice-cooling and the mixture was stirred at room temperature for 30 minutes in a stream of nitrogen to give a 19 mmol solution of sodium ethoxide in ethanol. To this solution, 4.0 g of diethyl 2-acetamidomalonate was added and the mixture was stirred at 50° C. for 30 minutes in a stream of nitrogen. The compound (4.6 g) of (2) above was added thereto at room temperature and the mixture was refluxed under heating for 6 hours. After cooling to room temperature, the mixture was neutralized with dilute hydrochloric acid and ethanol was distilled away. The residue was extracted with ethyl acetate. The ethyl acetate layer was washed and dried, and the solvent was distilled away. The residue was purified by silica gel column chromatography (ethyl acetate:hexane=1:5–1:1) to give 4.2 g of diethyl 2-acetamido-2-[3-(3-undecyloxyphenyl)propyl]malonate as white crystals.

melting point=38°–39° C. $^1$H-NMR (90 MHz, CDCl$_3$) δ: 0.88 (3H, t, J=7 Hz), 1.12–1.90 (27H, m), 2.03 (3H, s), 2.27–2.73 (4H, m), 3.93 (3H, t, J=7 Hz), 4.22 (4H, q, J=7 Hz), 6.61–6.87 (3H, m), 7.04–7.22 (1H, m) IR: 3251, 2917, 1741, 1680 cm$^{-1}$ MS(EI): 505(M$^+$)

(4) A solution (20 ml) of 3.5 g of the compound of (3) above in anhydrous tetrahydrofuran was dropwise added to a solution (50 ml) of 1.08 g of lithium aluminum hydride in anhydrous tetrahydrofuran under ice-cooling and the mixture was stirred under ice-cooling for 1 hour. The excess lithium aluminum hydride was decomposed and filtered off. The filtrate was extracted with ethyl acetate. The ethyl acetate layer was washed and dried. The solvent was distilled away and the residue was purified by silica gel column chromatography (ethyl acetate, chloroform:methanol:=9:1) to give 1.6 g of 2-acetamido-2-[3-(3-undecyloxyphenyl)propyl]-1,3-propanediol as a colorless, oily substance.

$^1$H-NMR (90 MHz, CDCl$_3$) δ: 0.86 (3H, t, J=6 Hz), 1.05–1.45 (16H, m), 1.45–1.87 (6H, m), 1.99 (3H, s), 2.47–2.70 (2H, m), 3.64 (4H, dd, J=12 Hz, 21 Hz), 3.82 (2H, t, J=6 Hz), 3.79–4.10 (2H, m), 5.89 (1H, br.s), 6.60–6.82 (3H, m), 7.03–7.31 (1H, m) IR: 3307, 2926, 2857, 1652 cm$^{-1}$ MS(EI): 421 (M$^+$)

EXAMPLE 27

2-Acetamido-2-[3-(3-undecyloxyphenyl)propyl]-1,3-propanediol (1.4 g) was dissolved in 50 ml of methanol and 16.6 ml of a 1N aqueous sodium hydroxide solution was added thereto. The mixture was refluxed under heating for 3 hours. The mixture was poured into ice water and neutralized with dilute hydrochloric acid. The solvent was distilled away and chloroform was added to the residue for extraction. The chloroform layer was washed and dried. The solvent was distilled away and the residue was recrystallized from diisopropyl ether-hexane to give 0.9 g of 2-amino-2-[3-(3-undecyloxyphenyl)propyl]-1,3-propanediol as white crystals.

melting point=71°–72° C. $^1$H-NMR (90 MHz, CDCl$_3$) δ: 0.86 (3H, t, J=6 Hz), 1.14–1.91 (22H, m), 2.20 (4H, br.s), 2.60 (2H, t, J=6 Hz), 3.49 (4H, dd, J=10 Hz, 13 Hz), 3.94 (2H, t, J=6 Hz), 6.62–6.86 (3H, m), 7.05–7.21 (1H, m) IR: 3344, 3289, 3179, 2919, 1610 cm$^{-1}$ MS(EI): 379(M$^+$)

EXAMPLE 28

2-Amino-2-[2-(4-octylphenyl)ethyl]-1,3-propanediol (1) 2-(4-Octanoylphenyl)ethyl acetate Aluminum chloride (111.8 g) was added to dichloroethane (500 ml) in a stream of nitrogen and the mixture was stirred at room temperature. Then, phenethyl acetate (91.8 g) and decanoyl chloride (100 g) were dropwise added thereto under ice-cooling and the mixture was stirred at room temperature overnight. The reaction mixture was poured into ice water and extracted with diethyl ether. The ether layer was washed with saturated brine and dried over anhydrous magnesium sulfate. The solvent was distilled away and the residue was purified by silica gel column chromatography (eluent; ethyl acetate:hexane=1:20) to give 61.3 g of the subject compound (yield 38%) as an oily substance.

IRv Neat max: 2929, 1740, 1685, 1236 cm$^{-1}$ (2) 2-(4-Octylphenyl)ethyl acetate Triethylsilane (28.8 ml) was added to a solution (86ml) of the above-mentioned compound (24.9 g) in trifluoroacetic acid under ice-cooling and the mixture was stirred at room temperature for 2 hours. The solvent was distilled away and thereto was added ice water and then a cool, saturated sodium hydrogencarbonate solution gradually. The mixture was extracted with ethyl acetate and the ethyl acetate layer was washed and dried over magnesium sulfate. The solvent was distilled away and the residue obtained was purified by silica gel column chromatography (eluent; ethyl acetate:hexane=1:20) to give 20.5 g of the subject compound as an oily substance (yield 87%).

IRv Neat max: 2927, 2855, 1742, 1237 cm$^{-1}$ (3) 2-(4-Octylphenyl)ethyl alcohol Sodium methoxide (11.9 g) was added to a solution of the above-mentioned compound (30.3 g) in methanol (300 ml) and the mixture was refluxed under heating for 3 hours. The reaction mixture was concentrated and ice water was added thereto. The mixture was extracted with ethyl acetate and the ethyl acetate layer was washed with a 5% aqueous HCl solution and saturated brine. The resultant mixture was dried over magnesium sulfate. The solvent was distilled away and the residue obtained was purified by silica gel column chromatography (eluent; ethyl acetate:hexane=1:15, ethyl acetate) to give 25.0 g of the subject compound as an oily substance (yield 97%).

IRv Neat max: 3357, 2927, 2855, 1467 cm$^{-1}$ (4) 2-(4-Octylphenyl)ethyl methanesulfonate Triethylamine (16.4 ml) was added to a solution (500 ml) of the above-mentioned compound (25 g) in dichloromethane and the mixture was ice-cooled. Methanesulfonyl chloride (13.4 g) was dropwise added thereto and the mixture was stirred at room temperature for 1 hour. The reaction mixture was poured into ice water and extracted with dichloromethane. The dichloromethane layer was washed with a saturated potassium hydrogencarbonate solution, a 1% saturated aqueous hydrochloric acid solution and saturated brine and dried over anhydrous magnesium sulfate. The solvent was distilled away and the residue was purified by silica gel column chromatography (eluent; ethyl acetate:hexane=1:19) to give 31.6 g of the subject compound as an oily substance (yield 95%).

$^1$H-NMR (CDCl$_3$) δ: 0.86 (3H, t, J=6 Hz), 1.13–1.79 (12H, m), 2.58 (2H, t, J=6 Hz), 2.82 (3H, s), 3.01 (2H, t, J=6 Hz), 4.39 (2H, t, J=6 Hz), 7.12 (4H, s) IRv Neat max: 2926, 1356, 1174 cm$^{-1}$ (5) 2-(4-Octylphenyl)ethyl iodide Sodium iodide (18.13 g) was added to a solution (500 ml) of the above-mentioned compound (31.5 g) in 2-butanone and the mixture was refluxed under heating for 4 hours. The reaction mixture was concentrated and poured into ice water. The resultant mixture was extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate: hexane= 1:20) to give 27.5 g of the subject compound as an oily substance (yield 80%).

$^1$H-NMR (CDCl$_3$) δ: 0.86 (3H, t, J=6 Hz), 1.07–1.79 (12H, m), 2.58 (2H, t, J=6 Hz), 3.01–3.57 (4H, m), 7.11 (4H, s) IRv p Neat max: 2925, 2853, 1168 cm$^{-1}$ (6) Diethyl 2-acetamido-2-(4-octylphenyl)ethyl malonate A solution (80 ml) of sodium ethoxide (8.2 g) in absolute ethanol was dropwise added to diethyl acetamidomalonate (26 g) in a stream of nitrogen and the mixture was stirred at 65° C. for 30 minutes. Then, a solution of the above-mentioned compound (13.8 g) in anhydrous tetrahydrofuran was dropwise added thereto and the mixture was stirred at 65° C. for 30 minutes. The reaction mixture was concentrated and poured into ice water. The resultant mixture was extracted with ethyl acetate. The extract was washed with saturated brine and dried over anhydrous magnesium sulfate. The solvent was distilled away and the residue was purified by silica gel column chromatography (eluent; ethyl acetate:hexane=1:3) to give 10.6 g of the subject compound (yield 61%).

melting point=49°–51° C. $^1$H-NMR (CDCl$_3$) δ: 0.86 (3H, t, J=6 Hz), 1.14 (6H, t, J=6 Hz), 1.20–1.73 (12H, m), 2.95 (3H, s), 2.30–2.83 (6H, m), 4.21 (4H, q, J=6 Hz), 6.74 (1H, s), 7.05 (4H, s) IRv max: 3257, 2924, 1747, 1643 cm$^{-1}$ (7) 2-Amino-2-[2-(4-octylphenyl)ethyl]-1,3-propanediol (a) A solution (100 ml) of the above-mentioned compound (11.55 g) in anhydrous tetrahydrofuran was dropwise added to a solution (260 ml) of lithium aluminum hydride (3.03 g) in anhydrous tetrahydrofuran under ice-cooling in a stream of nitrogen and the mixture was stirred at room temperature for 2 hours. A saturated aqueous sodium sulfate solution was added to the reaction mixture under ice-cooling. The resultant aluminum hydroxide was filtered off and the resultant mixture was dried over anhydrous sodium sulfate. The solvent was distilled away and pyridine (40 ml) was added to the residue. Acetic anhydride (30 ml) was added thereto under ice-cooling and the mixture was left standing at room temperature overnight. The reaction mixture was poured into water-cooled 5% hydrochloric acid and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=2:1) to give 8.25 g of 1,3-propanediyl-2-acetamido-2-[2-(4-octylphenyl)ethyl]ylidenediacetate as white crystals.

(b) An aqueous solution (100 ml) of lithium hydroxide (7.2 g) was added to a solution (100 ml) of the above-mentioned diacetate (8.25 g) in methanol and the mixture was refluxed under heating for 2 hours. The reaction mixture was concentrated and extracted with ethyl acetate. The extract was washed with saturated brine and dried over anhydrous magnesium sulfate. The solvent was distilled away and the residue was recrystallized from ethyl acetate to give 4 g of the subject compound, melting point 103°–105° C.

$^1$H-NMR (DMSO) δ: 0.86 (3H, t, J=6 Hz), 1.10–1.85 (14H, m), 2.38–2.79 (6H, m), 3.39 (4H, s), 7.06 (4H, s), 7.84 (2H, brs) IRv: 3354, 2925, 1019 cm$^{-1}$

EXAMPLE 29

2-Amino-2-[2-(4-octylphenyl)ethyl]-1,3-propanediol hydrochloride

2-Amino-2-[2-(4-octylphenyl)ethyl]-1,3-propanediol (7 g) was dissolved in ethanol (50 ml) and a 1N hydrochloric acid/ether solution (50 ml) was added thereto. The solvent was distilled away and the resultant crystals were recrystallized from ethanol to give 4.2 g of the subject compound.

melting point=118°–120° C. $^1$H-NMR (DMSO) δ: 0.89 (3H, t, J=6 Hz), 1.07–1.77 (12H, m), 1.82–2.17 (2H, m), 2.42–2.95 (4H, m), 3.80 (4H, s), 5.03 (2H, brs), 7.11 (4H, s), 8.07 (3H, brs) IRv: 3371, 3265, 2924, 1069 cm$^{-1}$

EXAMPLE 30

2-Acetamido-1,3-diacetoxy-2-[2-(4-octylphenyl) ethyl]-1,3 propane

A solution (100 ml) of diethyl 2-acetamido-2-[2-(4-octylphenyl)ethyl]malonate (11.55 g) in anhydrous tetrahydrofuran was dropwise added to a solution (260 ml) of lithium aluminum hydride (3.0 g) in anhydrous tetrahydrofuran under ice-cooling. The mixture was stirred for 1 hour under ice-cooling and then at room temperature for 2 hours. A saturated aqueous solution of sodium sulfate was dropwise added under ice-cooling to decompose lithium aluminum hydride, which was then filtered off. The resultant mixture was extracted with ethyl acetate and the ethyl acetate layer was washed and dried. The solvent was distilled away and the residue was purified by silica gel column chromatography (chloroform/methanol=9/1) to give crystals of 2-acetamido-2-[2-(4-octylphenyl)ethyl]-1,3-propanediol, melting point 66°–68° C. The obtained compound was dissolved in pyridine (40 ml) and acetic anhydride (30 ml) was added thereto under ice-cooling. The mixture was left standing at room temperature overnight. The reaction mixture was poured into a 10% aqueous hydrochloric acid solution (500 ml) and extracted with ethyl acetate. The ethyl acetate layer was washed with an aqueous potassium hydrogencarbonate solution and saturated brine, and dried over anhydrous magnesium sulfate. The solvent was distilled away and the residue was purified by silica gel column chromatography (ethyl acetate/hexane=2/1) to give 8.25 g of the subject compound.

yield 71% melting point=105°–107° C. $^1$H-NMR (CDCl$_3$) δ: 0.85 (3H, t), 1.22–1.29 (10H, m), 1.51–1.61 (2H, m), 1.93 (3H, s), 2.07 (6H, s), 2.17 (2H, t), 2.54 (2H, t), 2.55 (2H, t), 4.35 (4H, s), 5.61 (1H, brs), 7.07 (4H, s) IR (Nujol)v: 3310, 2920, 1738, 1652, 1556 cm$^{-1}$ In the same manner as in the above-mentioned Examples, the following compounds can be produced.

EXAMPLE 31

2-Amino-2-hexyl-1,3-propanediol hydrochloride

Rf value: 0.47 (CHCl$_3$:MeOH:CH$_3$COOH:H$_2$O= 70:20:6:4) IR(KBr): 3950, 1560, 1420, 1050 cm$^{-1}$

EXAMPLE 32

2-Amino-2-octyl-1,3-propanediol hydrochloride

Rf value: 0.48 (CHCl$_3$:MeOH:CH$_3$COOH:H$_2$O= 70:20:6:4) IR(KBr): 3190, 2930, 2850, 1630, 1560, 1410, 1100, 1060, 1020 cm$^{-1}$

EXAMPLE 33

2-Amino-2-decyl-1,3-propanediol hydrochloride

Rf value: 0.49 (CHCl$_3$:MeOH:CH$_3$COOH:H$_2$O= 70:20:6:4) IR(KBr): 3350, 2920, 2850, 1560, 1470, 1420, 1060 cm$^{-1}$

EXAMPLE 34

2-Amino-2-dodecyl-1,3-propanediol hydrochloride

IR(KBr): 3260, 3050, 2920, 2850, 1590, 1520, 1470, 1260, 1070, 1050 cm$^{-1}$ melting point=94.0°–95.5° C.

EXAMPLE 35

2-Amino-2-tridecyl-1,3-propanediol hydrochloride

IR(KBr): 3420, 3320, 2400, 2350, 1620, 1590, 1510, 1465, 1085, 1045, 1030, 1000 cm$^{-1}$ melting point= 103.0°–104.0° C.

EXAMPLE 36

2-Amino-2-pentadecyl-1,3-propanediol hydrochloride

IR(KBr): 3430, 3350, 3030, 2920, 2850, 1620, 1590, 1510, 1475, 1080, 1055, 1040 cm$^{-1}$ elemental analysis: calculated C 63.97, H 11.93, N 4.14, O 9.47, Cl 10.49 found C 63.91, H 11.96, N 4.17, O 9.45, Cl 10.51 melting point=106.5°–108.0° C.

EXAMPLE 37

2-Amino-2-(2-pentadecynyl)-1,3-propanediol hydrochloride

IR(KBr): 3400, 2920, 2850, 1500, 1470, 1060 cm$^{-1}$ elemental analysis: calculated C 64.74, H 10.87, N 4.19, O 9.58, Cl 10.62 found C 64.34, H 10.95, N 4.13, O 9.57, Cl 10.66 melting point=100.0°–101.0° C.

The instant compound is produced according to the following steps (1) through (6).

(1) Propargyl alcohol (3.00 g) was portionwise added to a mixed solution of 2.256 g of sodium hydride and 30 ml of dry dimethylformamide under ice-cooling under a nitrogen atmosphere. The mixture was stirred at room temperature for 30 minutes. The mixture was ice-cooled again and 5.175 g of chloro methyl methyl ether was portionwise added thereto. The mixture was stirred at room temperature overnight. Then, 4.284 g of sodium hydride was added thereto under ice-cooling and the mixture was heated to room temperature, followed by stirring for 30 minutes. The reaction mixture was ice-cooled again and a solution of 26.68 g of lauryl bromide in 20 ml of dry dimethylformamide was portionwise added thereto. The mixture was stirred at room temperature overnight. The reaction mixture was poured into ice water and extracted three times with ethyl acetate. The ethyl acetate layer was washed with saturated brine and dried over magnesium sulfate anhydride. The solvent was distilled away under reduced pressure and the residue was purified by silica gel column chromatography to give 12.374 g of 15-methoxymethoxy-13-pentadecyne.

IR(cm$^{-1}$): 2940, 2850, 1470, 1150, 1005, 1400, 1000, 930 $^1$H-NMR (CDCl$_3$) δ: 0.879 (3H, t, J=6.74 Hz, CH$_2$CH$_3$), 1.257 (20H, br.s, CH$_2$×10), 2.213 (2H, tt, J=6.96, 2.20 Hz, C≡C—CH$_2$CH$_2$), 3.380 (3H, s, OCH$_3$), 4.204 (2H, t, J=2.20 Hz, OCH$_2$C≡C), 4.711 (2H, s, OCH$_2$O)

(2) The compound (12.374 g) of (1) above was dissolved in a 1N solution (230 ml) of hydrochloric acid in methanol and the mixture was heated at 65° C. for 1.5 hours. The reaction mixture was concentrated under reduced pressure and the residue was purified by silica gel column chromatography to give 8.465 g of 2-pentadecynyl alcohol.

melting point=41.5°–42.5° C. IR(cm$^{-1}$): 3300, 3200, 2960, 2930, 2850, 1480, 1030 $^1$H-NMR (CDCl$_3$) δ: 0.880 (3H, t, J=6.74 Hz, CH$_3$), 1.260 (20H, br.s, CH$_2$×10), 2.209 (2H, tt, J=6.96, 2.12 Hz, C≡CCH$_2$), 4.255 (2H, dd, J=2.69, 2.44 Hz, OCH$_2$)

(3) In a reaction vessel equipped with a calcium chloride tube, 8.465 g of the compound of (2) above was dissolved in 85 ml of dichloromethane and 15.683 g of carbon tetrabromide and 14.867 g of triphenylphosphine were added thereto under ice-cooling. The mixture was stirred at 0° C. for 5 minutes. The reaction mixture was concentrated under reduced pressure and the residue was extracted with hexane. The hexane extract obtained was concentrated under reduced pressure and the residue was purified by silica gel column chromatography to give 7.964 g of 2-pentadecynyl bromide.

IR(cm$^{-1}$): 2930, 2850, 1470, 1420 $^1$H-NMR (CDCl$_3$) δ: 0.880 (3H, t, J=6.43 Hz, CH$_3$), 1.261 (20H, br.s, CH$_2$×10), 2.232 (2H, tt, J=6.96 Hz, 2.36 Hz, C≡C—CH$_2$), 3.932 (2H, t, J=2.32 Hz, BrCH$_2$C≡C)

(4) Diethyl acetamidomalonate (3.327 g) and 1.137 g of sodium ethylate were dissolved in 50 ml of dry ethanol and the mixture was stirred at room temperature for 30 minutes under a nitrogen atmosphere. A solution of 4.000 g of the compound of (3) above in 30 ml of dry ethanol was added thereto and the mixture was refluxed for 15 hours. Methanol (50 ml) was added to the reaction mixture and the insoluble matters were removed. The solvent was distilled away under reduced pressure and the residue was purified by silica gel column chromatography to give 3.236 g of diethyl 2-acetamido-2-(2-pentadecynyl)malonate.

melting point=43.0°–43.5° C. IR(cm$^{-1}$): 3250, 2920, 2850, 1750, 1650, 1540, 1470, 1380, 1300, 1240, 1200, 1100, 1080, 1060, 1020, 865 $^1$H-NMR (CDCl$_3$) δ: 0.879 (3H, t, J=6.35 Hz, CH$_3$), 1.261 (20H, s, CH$_2$×10), 1.261 (6H, t, J=7.21 Hz, OCH$_2$CH$_3$), 2.057 (3H, s, Ac), 2.123–2.077 (2H, m, C≡CCH$_2$CH$_2$), 3.211 (2H, t, J=2.32 Hz, CCH$_2$—C≡C), 4.253 (2H, q, J=7.08 Hz, OCH$_2$CH$_3$), 4.257 (2H, q, J=7.08 Hz, OCH$_2$CH$_3$), 6.896 (1H, br.s, NH)

(5) In a reaction vessel equipped with a calcium chloride tube, 2.437 g of diethyl 2-acetamido-2-(pentadecynyl)malonate was dissolved in 80 ml of dry tetrahydrofuran and 0.898 g of lithium aluminum hydride was added thereto under ice-cooling. After heating to a room temperature, the mixture was stirred for 30 minutes. Water (3 ml) was added thereto under ice-cooling to stop the reaction and the solvent was distilled away under reduced pressure. Pyridine (70 ml) and 130 ml of acetic anhydride were added to the residue and the mixture was stirred at room temperature overnight. The reaction mixture was poured into ice water and extracted three times with ethyl acetate. The ethyl acetate layer was washed with 1N hydrochloric acid, a saturated aqueous sodium hydrogencarbonate solution and saturated brine in order and dried over anhydrous magnesium sulfate. The solvent was distilled away under reduced pressure and the residue was purified by silica gel column chromatography and recrystallized from hexane to give 808 mg of 2-acetamido-1,3-diacetoxy-2-(2-pentadecynyl)propane.

melting point=95.5°–96.5° C. IR(cm$^{-1}$): 3300, 2930, 2850, 1740, 1650, 1580, 1400, 1380, 1260, 1040 $^1$H-NMR (CDCl$_3$) δ: 0.879 (3H, t, J=6.47 Hz, CH$_3$), 1.225 (24H, br.s, CH$_2$×12), 1.980 (3H, s, NAc), 2.089 (6H, s, OAc×2), 2.140 (2H, m, CH$_2$C≡C—CH$_2$CH$_2$), 2.790 (2H, t, J=2.32 Hz, CH$_2$C≡C—CH$_2$CH$_2$), 4.422 (4H, s, CH$_2$O×2), 5.829 (1H, br.s, NH)

(6) 2-Acetamido-1,3-diacetoxy-2-(2-pentadecynyl)propane (600 mg) was dissolved in 28 ml of methanol and 7.09 ml of a 1N aqueous sodium hydroxide solution was added thereto. The mixture was refluxed for 6 hours. The reaction mixture was concentrated under reduced pressure and the residue was dissolved in 20 ml of a solvent (methanol:water=3:7). After adsorption onto Sep-Pak, the residue was eluted with methanol:water=8:2 and the eluate was concentrated. The residue was dissolved in methanol and the mixture was acidified with hydrochloric acid. The solvent was distilled away under reduced pressure to give 343 mg of 2-amino-2-(2-pentadecynyl)-1,3-propanediol hydrochloride.

EXAMPLE 38

2-Amino-2-(12-hydroxydodecyl)-1,3-propanediol hydrochloride

IR(KBr): 3350, 2920, 2850, 1500, 1470, 1080, 1050, 1040 cm$^{-1}$ melting point=138.0°–142.0° C.

The instant compound is produced according to the following steps (1) through (5).

(1) Dodecanediol (23.000 g) was dissolved in 230 ml of dry tetrahydrofuran and 40 ml of dichloromethane, and 10 mg of p-toluenesulfonic acid and 9.578 g of dihydropyran were added thereto. The mixture was stirred at room temperature for a day. Triethylamine (1.0 ml) was added thereto to stop the reaction and the reaction mixture was concentrated under reduced pressure. The residue was purified by silica gel column chromatography to give 8.132 g of dodecanediol monotetrahydropyranyl ether.

IR(cm$^{-1}$): 3620, 3450, 2930, 2850, 1460, 1360, 1140, 1125, 1080, 1030

(2) The above-mentioned dodecanediol monotetrahydropyranyl ether (7.882 g) and 11.437 g of carbon tetrabromide were dissolved in 78 ml of dichloromethane. Triphenylphosphine (10.843 g) was added thereto under ice-cooling and the mixture was stirred at 0° C. for 5 minutes. The solvent was distilled away under reduced pressure and the residue was purified by silica gel column chromatography to give 4.029 g of 1-bromo-12-tetrahydropyranyloxydodecane.

IR(cm$^{-1}$): 2930, 2850, 1460, 1445, 1360, 1140, 1120, 1080, 1020, 980 $^1$H-NMR (CDCl$_3$) δ: 1.274 (16H, br.s), 1.611–1.554 (6H, m), 1.750–1.689 (1H, m), 1.888–1.802 (1H, m), 1.852 (2H, qui, J=7.1 Hz), 3.381 (1H, dt, J=9.5, 6.9 Hz), 3.407 (2H, t, J=6.9 Hz), 3.526–3.472 (1H, m), 3.728 (1H, dt, J=9.5, 7.0 Hz), 3.900–3.845 (1H, m), 4.574 (1H, dd, J=4.4, 2.7 Hz)

(3) Diethyl acetamidomalonate (6.996 g) and 3.189 g of sodium ethoxide were dissolved in 130 ml of dry ethanol and a solution of 10.698 g of 1-bromo-12-tetrahydropyranyloxydodecane in 200 ml of dry ethanol was added thereto. The mixture was refluxed under heating for 8 hours. The solvent was distilled away under reduced pressure and the residue was purified by silica gel column chromatography to give 5.837 g of diethyl 2-acetamido-2-(12-tetrahydropyranyloxydodecyl)malonate.

IR(cm$^{-1}$): 3450, 2930, 2850, 1740, 1680, 1500, 1380, 1285, 1020 $^1$H-NMR (CDCl$_3$) δ: 1.25 (6H, t, J=7.1 Hz), 1.25 (20H, br.s), 1.61–1.52 (6H, m), 1.83–1.71 (2H, m), 2.03 (3H, s), 3.87–3.35 (4H, m), 4.24 (4H, q, J=7.1 Hz), 4.58 (1H, d,d, J=4.4, 2.4 Hz), 6.77 (1H, br.s)

(4) Diethyl 2-acetamido-2-(12-tetrahydropyranyloxydodecyl)malonate (5.837 g) was dissolved in 13.0 ml of methanol and 2.202 g of sodium borohydride was gradually added thereto under ice-cooling. The entire amount of sodium hydride was added thereto and the mixture was left standing at room temperature for 2 hours. Methanol (30 ml) was added thereto and the mixture was made to assume weak acidity with 2N hydrochloric acid. The solvent was distilled away under reduced pressure. Pyridine (100 ml) and acetic anhydride (200 ml) were added to the residue and the mixture was stirred at room temperature for day and night. The reaction mixture was poured into ice water and extracted with ethyl acetate. The ethyl acetate layer was washed with 1N hydrochloric acid, a saturated aqueous sodium hydrogencarbonate solution and a saturated aqueous sodium chloride solution in order. The mixture was dried over anhydrous magnesium sulfate and concentrated under reduced pressure. The concentrate was dissolved in 100 ml of methanol and 30 mg of p-toluenesulfonic acid was added thereto. The mixture was stirred at room temperature for 1 hour. Triethylamine (0.5 ml) was added thereto and the mixture was stirred for 10 minutes, followed by concentration under reduced pressure. The concentrate was purified by silica gel column chromatography to give 1.180 g of 2-acetamido-1,3-diacetoxy-2-(12-hydroxydodecyl)propane.

melting point=75.0°–76.5° C. IR(cm$^{-1}$): 3350, 2930, 2850, 1740, 1630, 1550, 1375, 1270, 1240, 1040 $^1$H-NMR (CDCl$_3$) δ: 1.236 (22H, br.s, CH$_2$×11), 1.843–1.821 (2H, m, CH$_2$), 1.937 (3H, s, NAc), 2.056 (6H, s, OAc×2), 3.608 (2H, br.s, CH$_2$OH), 4.269 (4H, d,d, J=14.0, 11.5 Hz, CH$_2$OAc×2), 5.607 (1H, br.s, NH)

(5) 2-Acetamido-1,3-diacetoxy-2-(12-hydroxydodecyl) propane (500 mg) was dissolved in 24 ml of methanol and 6.0 ml of a 1N aqueous sodium hydroxide solution was added thereto. The mixture was refluxed under heating for 6 hours. The reaction mixture was concentrated under reduced pressure and methanol was distilled away. The residue was extracted with ethyl acetate, and the extract was washed with water and dried over anydrous magnesium sulfate. The solvent was distilled away under reduced pressure and the residue was dissolved in methanol. The mixture was acidified with hydrochloric acid and the solvent was distilled away by concentration under reduced pressure. The residue was dried in vacuo to give 103 mg of 2-amino-2-(12-hydroxydodecyl)-1,3-propanediol hydrochloride.

$^1$H-NMR (DMSO) δ: 1.23 (22H, s, $CH_2\times 11$), 3.49–3.40 (6H, m, $CH_2O\times 3$), 5.26 (3H, br.s, $OH\times 3$) elemental analysis: calculated C 56.94, H 10.99, N 4.43, O 16.43, Cl 11.21 found C 56.73, H 10.95, N 4.32, O 16.49, Cl 11.51

EXAMPLE 39

2-Acetamido-1,3-diacetoxy-2-hexylpropane melting point=55°–56° C.

EXAMPLE 40

2-Acetamido-1,3-diacetoxy-2-octylpropane melting point=79.5°–82° C.

EXAMPLE 41

2-Acetamido-1,3-diacetoxy-2-decylpropane melting point=70°–72° C.

EXAMPLE 42

2-Acetamido-1,3-diacetoxy-2-dodecylpropane melting point=75.5°–76.5° C.

EXAMPLE 43

2-Acetamido-1,3-diacetoxy-2-tridecylpropane melting point=77.0°–78.0° C.

EXAMPLE 44

2-Acetamido-1,3-diacetoxy-2-pentadecylpropane melting point=82.0°–83.0° C.

EXAMPLE 45

2-Acetamido-1,3-diacetoxy-2-(2-pentadecynyl)propane

IR(KBr ): 3300, 2930, 2850, 1740, 1650, 1580, 1400, 1380, 1260, 1040 $cm^{-1}$ melting point=95.5°–96.5° C.

EXAMPLE 46

2-Amino-2-tetradecyl-1,3-propanediol

IR(KBr):3300, 3260, 3200, 2930, 2860, 1580, 1480, 1070, 105 $cm^{-1}$ melting point=68.5°–69.5° C.

EXAMPLE 47

2-(N-Ethylamino)-2-octadecyl-1,3-propanediol

IR(KBr): 3360(br), 2920, 2850, 1470, 1070 $cm^{-1}$
$^1$H-NMR ($CDCl_3$/TMS) δ: 3.530 (2H, d, J=11.4 Hz), 3.472 (2H, d, J=11.4 Hz), 2.545 (2H, q, J=7.2 Hz), 2.5 (2H, br.s), 1.252 (34H, m), 1.121 (3H, t, J=7.0 Hz), 0.879 (3H, t, J=6.6 Hz) melting point=65.0°–67.0° C.

EXAMPLE 48

2-(N,N-Dimethylamino)-2-tetradecyl-1,3-propanediol

IR(KBr): 3530, 3050(br), 2920, 2850, 1470, 1060, 1040, 1030 $cm^{-1}$ melting point=51°–52° C.

EXAMPLE 49

2-Amino-2-(4-tetradecenyl)-1,3-propanediol hydrochloride

The instant compound is produced by the following steps (1) through (6).

(1) Diethyl acetamidomalonate (6.0 g) was dissolved in 50 ml of dehydrated ethanol and 2.26 g of sodium ethoxide and 5.22 g of 5-bromo-1-pentene were added thereto. The mixture was refluxed under a nitrogen atmosphere overnight. The reaction mixture was neutralized and concentrated. The concentrate was purified by silica gel column chromatography using hexane-ethyl acetate (5:1→2:1) as an eluent to give 4.871 g of colorless, oily diethyl 2-acetamido-2-pentenylmalonate.

IRv max ($CHCl_3$): 3450, 3000, 2950, 1740, 1680, 1500, 1480, 1280, 1200, 1100, 1020, 920, 860 $cm^{-1}$ $^1$H-NMR ($CDCl_3$/TMS) δ: 1.25 (2H, m), 1.255 (6H, t, J=7.2 Hz), 2.044 (2H, m), 2.040 (3H, s), 2.336 (2H, m), 4.246 (4H, q, J=7.2 Hz), 4.990 (1H, dd, J=1.8, 17.2 Hz), 5.013 (1H, dd, J=1.8, 10.6 Hz), 5.758 (1H, ddt, J=6.2, 10.6, 17.2 Hz), 6.789 (1H, s)

(2) Diethyl 2-acetamido-2-pentenylmalonate (4.0 g) was dissolved in 210 ml of acetone and 3.3 g of N-methylmorpholine-N-oxide and 36 ml of a 1% aqueous osmium tetraoxide solution were added thereto. The mixture was stirred at room temperature for 2 hours. A solution of 700 mg of sodium sulfite in 20 ml of water was added thereto and the mixture was stirred for 15 minutes. The reaction mixture was concentrated and subjected to silica gel column chromatography using chloroform/methanol (10:1) as an eluent and a fraction having an Rf value: 0.3 (chloroform:methanol=10:1) was concentrated. The residue was dissolved in 630 ml of 1,4-dioxane and 70 ml of a 0.2M aqueous meta-sodium periodate solution was added thereto. The mixture was stirred at room temperature for 2 hours. The reaction mixture was filtrated, concentrated, extracted with ethyl acetate and washed with water. The hexane layer was dried and concentrated to give 4.17 g of colorless, oily diethyl 2-acetamido-2-(4-formylbutyl)malonate.

Rf value=0.4 (chloroform:methanol=10:1)

(3) Decane bromide (7.0 g) and 10 g of triphenylphosphine were stirred at 120° C. under a nitrogen atmosphere for 8 hours. The mixture was recrystallized from acetone-ether to give 14.4 g of colorless, crystalline decyltriphenylphosphonium bromide. IRv max ($CHCl_3$): 2920, 2850, 1440, 1120, 1000, 680 $cm^{-1}$ (4) Decyltriphenylphosphonium bromide (10.85 g) was dissolved in 100 ml of dry tetrahydrofuran. Under an argon atmosphere, 13 ml of a 1.6 M n-butyl lithium/hexane solution was dropwise added thereto and the mixture was stirred for 15 minutes. The mixture was cooled to −78° C. and a solution of diethyl 2-acetamido-2-(4-formylbutyl)malonate (4.17 g)/dry tetrahydrofuran (50 ml) was dropwise added thereto and the mixture was stirred at 78° C. for 40 minutes under an argon atmosphere. Under the same conditions, a solution of t-butanol (3.3 ml)/tetrahydrofuran (15 ml) was dropwise added thereto and the mixture was stirred at room temperature under an argon atmosphere for 1.5 hours. The reaction mixture was diluted with ether and washed with water. The organic layer was dried and concentrated. The concentrate was purified by silica gel column chromatography using hexane-acetic acid (5:1→5:2) as an eluent to give 2.1 g of colorless, oily diethyl 2-acetamido-2-(4-tetradecenyl)malonate.

IRν max (CHCl$_3$): 3450, 2940, 2850, 1740, 1680, 1500, 1380, 1280, 1200, 1100, 1020, 860 cm$^{-1}$ $^1$H-NMR (CDCl$_3$/TMS) δ: 0.88 (3H, t, J=6.6 Hz), 1.257 (16H, m), 1.255 (6H, t, J=7.08 Hz), 2.010 (4H, m), 2.066 (3H, s), 2.334 (2H, m), 4.243 (4H, q, J=7.08 Hz), 5.273 (1H, dt, J=5.4, 10.8 Hz), 5.376 (1H, dt, J=5.4, 10.8 Hz), 6.775 (1H, s)

(5) Diethyl 2-acetamido-2-(4-tetradecenyl)malonate (807 mg) was dissolved in 25 ml of dry tetrahydrofuran and 297 mg of lithium aluminum hydride was added thereto under ice-cooling. The mixture was stirred at room temperature for 1.5 hours. Water (0.544 ml) was added thereto under ice-cooling and the mixture was stirred at room temperature for 30 minutes. The reaction mixture was concentrated and an appropriate amount of pyridine-acetic anhydride was added to the residue. The mixture was stirred at room temperature overnight. The reaction mixture was added to ice, extracted with ethyl acetate and washed with 1N hydrochloric acid, a saturated aqueous sodium hydrogencarbonate solution and a saturated aqueous sodium chloride solution. The ethyl acetate layer was dried, concentrated and purified by silica gel column chromatography using hexane-ethyl acetate (3:1→2:1) as an eluent to give 537 mg of colorless, powdery 2-acetamido-1,3-diacetoxy-2-(4-tetradecenyl)propane.

IRν max (CHCl$_3$): 3430, 2920, 2850, 1740, 1680, 1500, 1370, 1280, 1180, 1090, 1010, 855 cm$^{-1}$ (6) 2-Acetamido-1,3-diacetoxy-2-(4-tetradecenyl)propane (450 mg) was dissolved in 27 ml of methanol and 9 ml of a 1N aqueous sodium hydroxide solution was added thereto. The mixture was refluxed under a nitrogen atmosphere for 8 hours. The reaction mixture was neutralized with hydrochloric acid and concentrated. Water was added to the concentrate and the mixture was subjected to chromatography using Sep-Pak(C$_{18}$) (trade mark) and elution with methanol. The methanol eluate was concentrated to give 332 mg of pale yellow, oily 2-amino-2-(4-tetradecenyl)1,3-propanediol hydrochloride.

IRν max (KBr): 3400(br), 2920, 2850, 1590, 1500, 1470, 1050, 1040 cm$^{-1}$ Rf value: 0.6 (chloroform:methanol:acetic acid:water=70:20:6:4)

EXAMPLE 50

2-Amino-1,3-diacetoxy-2-octadecylpropane

IR(CHCl$_3$): 3400(br), 2930, 2850, 1740, 1470, 1380, 1240, 1040 cm$^{-1}$ $^1$H-NMR (CDCl$_3$/TMS) δ: 4.014 (2H, d, J=11.0 Hz), 3.938 (2H, d, J=11.0 Hz), 2.089 (6H, s), 1.255 (34H, m), 0.879 (3H, t, J=6.6 Hz)

The instant compound is produced as follows.

(1) 2-Amino-1,3-propanediol hydrochloride (7 g) was suspended in 150 ml of N,N-dimethylformamide, and 3.8 g of triethylamine and 5.4 g of di-t-butyldicarbonate were added thereto. The mixture was stirred at 50° C. for 5 hours. Under ice-cooling, water was added to the reaction mixture and the mixture was stirred. The resultant precipitate was collected by filtration. The precipitate was recrystallized from hexane-ethyl acetate (5:1) to give 6.79 g of colorless, crystalline 2-octadecyl-2-(N-t-butoxycarbonylamino)-1,3-propanediol.

IRν max (KBr): 3400(br), 3300, 2920, 2850, 1680, 1560, 1300, 1180, 1020 cm$^{-1}$ (2) The compound (4 g) of (1) above was dissolved in 15 ml of pyridine and 50 ml of acetic anhydride and the mixture was refluxed at room temperature overnight. The reaction mixture was poured into ice water, extracted with ethyl acetate and washed with 1N hydrochloric acid, a saturated aqueous sodium hydrogencarbonate solution and a saturated aqueous sodium chloride solution. After dehydration, the reaction mixture was concentrated to give 4.8 g of colorless, oily 1,3-diacetoxy-2-(N-t-butoxycarbonylamino)propane.

IRν max (CHCl$_3$): 3460, 2930, 2850, 1740, 1690(sh), 1510, 1470, 1380, 1240, 1160, 1040 cm$^{-1}$ (3) The compound (4.8 g) of (2) above was dissolved in 10 ml of trifluoroacetic acid and the mixture was left standing at room temperature for 15 minutes. The reaction mixture was diluted with ethyl acetate and washed with a saturated aqueous sodium hydrogencarbonate solution and saturated sodium chloride. The ethyl acetate layer was dried and concentrated to give 3.83 g of colorless, oily 2-amino-1,3-diacetoxy-2-octadecylpropane.

EXAMPLE 51

1,3-Diacetoxy-2-octadecyl-2-(N-pentanoylamino)propane

IR(CHCl$_3$): 3450, 3400, 2920, 2850, 1740, 1680, 1520, 1460, 1380, 1240, 1020 cm$^{-1}$ $^1$H-NMR (CDCl$_3$/TMS) δ: 5.599 (1H, s), 4.330 (2H, d, J=11.6 Hz), 4.271 (2H, d, J=11.6 Hz), 2.150 (2H, t, J=7.2 Hz), 2.078 (6H, s), 1.6 (4H, m), 1.251 (34H, m), 0.918 (3H, t, J=7.4 Hz), 0.879 (3H, t, J=6.8 Hz)

EXAMPLE 52

2-Octadecyl-2-(N-pentanoylamino)-1,3-propanediol

IR(KBr): 3420, 3350(br), 2920, 2850, 1650, 1520, 1460, 1030 cm$^{-1}$ $^1$H-NMR (CDCl$_3$/TMS) δ: 5.840 (1H, s), 4.021 (2H, br.s), 3.803 (2H, d, J=11.4 Hz), 3.559 (2H, t, J=11.4 Hz), 2.231 (2H, t, J=7.8 Hz), 1.6 (4H, m), 1.251 (34H, m), 0.928 (3H, t, J=7.4 Hz), 0.878 (3H, t, J=6.6 Hz) melting point=73.0°–73.5° C.

The instant compound is produced as follows.

(1) 2-Amino-1,3-diacetoxy-2-octadecylpropane (1.0 g) was dissolved in 50 ml of dry ether and 425 mg of N,N-dimethylaniline and 500 mg of pentanoyl chloride were added thereto. The mixture was stirred at room temperature under a nitrogen atmosphere for 6 hours. The reaction mixture was diluted with ethyl acetate and washed with 1N hydrochloric acid, a saturated aqueous sodium hydrogencarbonate solution and a saturated aqueous sodium chloride solution. The organic layer was dried and the resultant mixture was concentrated. The concentrate was purified by silica gel column chromatography using hexane-ethyl acetate (5:1→2:1) as an eluent to give 1.036 g of colorless, oily 1,3-diacetoxy-2-octadecyl-2-(N-pentanoylamino)propane. IRν max (CHCl$_3$): 3450, 3400, 2920, 2850, 1740, 1680, 1520, 1460, 1380, 1240, 1020 cm$^{-1}$ $^1$H-NMR (CDCl$_3$/TMS) δ: 0.879 (3H, t, J=6.8 Hz), 0.918 (3H, t, J=7.4 Hz), 1.251 (34H, m), 1.6 (4H, m), 2.078 (6H, s), 2.150 (2H, t, J=7.2 Hz), 4.271 (2H, d, J=11.6 Hz), 4.330 (2H, d, J=11.6 Hz), 5.599 (1H, s)

(2) 1,3-Diacetoxy-2-octadecyl-2-(N-pentanoylamino)propane (400 mg) was dissolved in 8 ml of methanol and 17 mg of a 28% sodium methoxide-methanol solution was added thereto. The mixture was stirred at room temperature for 1 hour. Concentrated hydrochloric acid-methanol (1:11, 0.088 ml) was added thereto and the mixture was concentrated. The concentrate was subjected to silica gel column chromatography using chloroform-methanol (30:1) as an eluent. The resultant crystals were recrystallized from chloroform-hexane to give 312 mg of colorless, crystalline 2-octadecyl-2-(N-pentanoylamino)-1,3-propanediol.

EXAMPLE 53

2-Octadecyl-2-(N-pentylamino)-1,3-propanediol

IR(KBr): 3470(br), 2930, 2850, 1480, 1060 cm$^{-1}$ $^1$H-NMR (CDCl$_3$/TMS) δ: 3.990 (3H, br.s), 3.707 (2H, d, J=12.8 Hz), 3.643 (2H, d, J=12.8 Hz), 2.686 (2H, t, J=7.8 Hz), 1.252 (40H, m), 0.908 (3H, t, J=7.0 Hz), 0.879 (3H, t, J=6.6 Hz) melting point=53.0°–54.0° C.

The instant compound is produced as follows.

1,3-Diacetoxy-2-octadecyl-2-(N-pentanoylamino)propane (400 mg) was dissolved in 30 ml of dry ether and 150 mg of lithium aluminum hydride was added thereto under ice-cooling. The mixture was stirred at room temperature for 3 hours. The reaction mixture was concentrated and 20 ml of dry tetrahydrofuran was added thereto. Under ice-cooling, 0.15 ml of water, 0.15 ml of a 15% aqueous sodium hydroxide solution and 0.45 ml of water were added in order and the reaction mixture was filtered. The filtrate was concentrated and purified by silica gel column chromatography using chloroform-methanol-acetic acid (19:1:0.1→10:1:0.05) as an eluent to give 153 mg of colorless, powdery 2-octadecyl-2-(N-pentylamino)-1,3-propanediol.

EXAMPLE 54

2-(N-Decanoylamino)-1,3-diacetoxy-2-octadecylpropane $^1$H-NMR (CDCl$_3$/TMS) δ: 5.594 (1H, s), 4.828 (2H, d, J=12.0 Hz), 4.269 (2H, d, J=12.0 Hz), 2.140 (2H, t, J=7.2 Hz), 1.6 (2H, m), 1.252 (46H, m), 0.878 (6H, t, J=6.8 Hz) Rf value: 0.5 (EtOAc:C$_6$H$_{14}$=1:2)

EXAMPLE 55

2-(N-Decanoylamino)-2-octadecyl-1,3-propanediol

IR(KBr): 3350, 3100, 2920, 2850, 1640, 1560, 1480, 1080 cm$^{-1}$ melting point=71.5°–72.5° C.

EXAMPLE 56

2-(N-Decylamino)-2-octadecyl-1,3-propanediol

IR(KBr): 3350(br), 2920, 2850, 1470, 1060 cm$^{-1}$ $^1$H-NMR (CDCl$_3$/TMS) δ: 3.562 (2H, d, J=12.8 Hz), 3.498 (2H, d, J=12.8 Hz), 2.741 (3H, br.s), 2.536 (2H, t, J=7.2 Hz), 1.525 (2H, m), 1.251 (48H, m), 0.879 (6H, t, J=6.8 Hz) melting point=48.0°–49.5° C.

EXAMPLE 57

1,3-Diacetoxy-2-(N,N-dimethylamino)-2-octadecylpropane $^1$H-NMR (CDCl$_3$/TMS) δ: 4.208 (2H, d, J=11.4 Hz), 4.071 (2H, d, J=11.4 Hz), 2.359 (6H, s), 2.070 (6H, s), 1.252 (34H, m), 0.878 (3H, t, J=6.8 Hz) Rf value: 0.4 (EtOAc:C$_6$H$_{14}$=3:2)

EXAMPLE 58

2-(N,N-Dimethylamino)-2-octadecyl-1,3-propanediol

IR(KBr): 3540, 3100(br), 2920, 2850, 1470, 1060, 1040 cm$^{-1}$ $^1$H-NMR (CDCl$_3$/TMS) δ: 3.715 (2H, d, J=10.8 Hz), 3.632 (2H, d, J=10.8 Hz), 3.040 (2H, br.s), 2.412 (6H, s), 1.253 (34H, m), 0.880 (3H, t, J=6.8 Hz) melting point=63.5°–64.5° C.

The instant compound is produced as follows.

(1) 2-Amino-1,3-diacetoxy-2-octadecylpropane (700 mg) was dissolved in 35 ml of acetonitrile and 1.38 g of 37% formaldehyde and 330 mg of sodium cyanoborohydride were added thereto. The mixture was stirred at room temperature for 1 hour. Acetic acid (0.265 ml) was added thereto and the mixture was stirred at room temperature for 1 hour. The reaction mixture was concentrated and purified by silica gel column chromatography using hexane-ethyl acetate (4:1→3:1) as an eluent to give 436 mg of colorless, oily 1,3-diacetoxy-2-(N,N-dimethylamino)-2-octadecylpropane.

$^1$H-NMR (CDCl$_3$/TMS) δ: 0.878 (3H, t, J=6.8 Hz), 1.252 (34H, m), 2.070 (6H, s) 2.359 (6H, s), 4.071 (2H, d, J=11.4 Hz), 4.208 (2H, d, J=11.4 Hz) Rf value: 0.4 (ethyl acetate-:hexane=3:2)

(2) The compound (436 mg) of (1) above was dissolved in 15 ml of methanol and 37 mg of a 28% sodium methoxide methanol solution was added thereto. The mixture was stirred at room temperature for 6 hours. The reaction mixture was concentrated and water was added thereto. The resultant precipitate was collected by filtration and recrystallized from chloroformhexane to give 295 mg of colorless, crystalline 2-(N,N-dimethylamino)-2-octadecyl-1,3-propanediol.

EXAMPLE 59

2-Amino-2-(cis- or trans-4-tetradecenyl)-1,3-propanediol hydrochloride

EXAMPLE 60

2-Amino-2-(3-dodecylthiopropyl)-1,3-propanediol hydrochloride

IR(KBr): 3510, 3450, 3380, 3020, 2920, 2850, 1630, 1530, 1460, 1070, 1050 cm$^{-1}$ $^1$H-NMR (CDCl$_3$-DMSO$_6$/TMS) δ: 3.78 (2H, d, J=11.8 Hz), 3.68 (2H, d, J=11.8 Hz), 2.5 (4H, m), 1.26 (24H, m), 0.88 (3H, t, J=7.1 Hz) melting point=76°–78° C.

The subject compound was prepared as follows:

(1) Dodecylthiol (5 g) was dissolved in 50 ml of dry N,N-dimethylformamide and 1 g of 60% sodium hydride was added thereto under ice-cooling. The mixture was stirred at room temperature for 1 hour. Further, a solution of 3.45 g of 3-bromopropanol in 10 ml of dry N,N-dimethylformamide was dropwise added thereto under ice-cooling and the mixture was stirred at room temperature for 3 hours. The reaction mixture was poured into ice, extracted with ether and washed with 1N hydrochloric acid, a saturated aqueous sodium hydrogencarbonate solution and a saturated aqueous sodium chloride solution. The ether layer was dehydrated and concentrated. The resultant mixture was purified by silica gel column chromatography using hexane-ethyl acetate (10:1→3:1) as an eluent to give 6.071 g of 3-dodecylthiopropanol as a colorless powder.

IRν max (CHCl$_3$): 3450(br), 2930, 2850, 1460, 1050 cm$^{-1}$ (2) 3-Dodecylthiopropanol (3.0 g) was dissolved in 60 ml of dichloromethane and 7.66 g of carbon tetrabromide and 5.44 g of triphenylphosphine were added thereto under ice-cooling. The mixture was stirred under ice-cooling for 15 minutes. The reaction mixture was concentrated, and the residue was extracted with hexane. The extract was concentrated and purified by silica gel column chromatography using hexane as an eluent to give 3.255 g of pale yellow, oily 3-bromopropyldodecyl sulfide.

Rf value=0.4 (hexane)

(3) Diethyl acetamidomalonate (1.6 g) was dissolved in 30 ml of dehydrated ethanol and 505 mg of sodium ethoxide and 2 g of 3-bromopropyldodecyl sulfide were added thereto. The mixture was refluxed under a nitrogen atmosphere overnight. The reaction mixture was neutralized with concentrated hydrochloric acid-ethanol (1:11) and concentrated. The concentrate was purified by silica gel column chromatography using hexane-ethyl acetate (5:1→5:2) as an eluent to give 1.722 g of colorless, powdery diethyl 2-acetamido-2-(3-dodecylthiopropyl)malonate. IRv max (CHCl$_3$): 3440, 2930, 2850, 1740, 1680, 1500, 1380, 1260, 1100, 1020, 860 cm$^{-1}$ $^1$H-NMR (CDCl$_3$/TMS) δ: 0.88 (3H, t, J=7.4 Hz), 1.26 (18H, m), 1.26 (6H, t, J=7.3 Hz), 1.57 (4H, m), 2.04 (3H, s), 2.42 (2H, m), 2.47 (2H, t, J=7.3 Hz), 2.48 (2H, t, J=7.3 Hz), 4.25 (4H, q, J=7.4 Hz), 6.78 (1H, s)

(4) Diethyl 2-acetamido-2-(3-dodecylthiopropyl)malonate (1.5 g) was dissolved in 30 ml of dry tetrahydrofuran and 500 mg of lithium aluminum hydride was added thereto under ice-cooling. The mixture was stirred under ice-cooling for 30 minutes and at room temperature for 1 hour. To the reaction mixture was added 1.0 ml of water under ice-cooling and the mixture was stirred for 1 hour and concentrated. Pyridine (5 ml) and 10 ml of acetic anhydride were added to the residue, and the mixture was stirred at room temperature overnight. The reaction mixture was poured to ice, extracted with ethyl acetate and washed with 1N hydrochloric acid, a saturated aqueous sodium hydrogencarbonate solution and a saturated aqueous sodium chloride solution. The ethyl acetate layer was dried and concentrated. The concentrate was subjected to silica gel column chromatography using hexane-ethyl acetate (3:1→1:1) as an eluent and recrystallized from hexane to give 852 mg of 2-acetamido-1,3-diacetoxy-2-(3-dodecylthiopropyl)propane.

$^1$H-NMR (CDCl$_3$/TMS) δ: 0.88 (3H, t, J=6.8 Hz), 1.26 (24H, m), 1.96 (3H, s), 2.09 (6H, s), 2.5 (4H, m), 4.30 (4H, s), 5.67 (1H, s) Rf value=0.4 (ethyl acetate:hexane=7:3)

(5) 2-Acetamido-1,3-diacetoxy-2-(3-dodecylthiopropyl)propane (750 mg) was dissolved in 30 ml of methanol and 10 ml of a 1N aqueous sodium hydroxide solution was added thereto. The mixture was refluxed under a nitrogen atmosphere for 6 hours. The reaction mixture was cooled with ice and the resultant precipitate was collected by filtration. The precipitate was dissolved in methanol and 3 ml of concentrated hydrochloric acid-methanol (1:11) was added thereto. The mixture was concentrated and recrystallized from ethyl acetate-hexane to give 449 mg of colorless, crystalline 2-amino-2-(3-dodecylthiopropyl)-1,3-propanediol hydrochloride.

EXAMPLE 61

2-Acetamido-1,3-diacetoxy-2-(3-dodecylthiopropyl)propane $^1$H-NMR (CDCl$_3$/TMS) δ: 5.67 (1H, s), 4.30 (4H, s), 2.5 (4H, m), 2.09 (6H, s), 1.96 (3H, s), 1.26 (24H, m), 0.88 (3H, t, J=6.8 Hz) Rf value: 0.4 (EtOAc:C$_6$H$_{14}$=7:3)

EXAMPLE 62

2-Amino-2-(3,7,11-trimethyldodecyl)-1,3-propanediol hydrochloride

EXAMPLE 63

2-Amino-2-(3,7,11-trimethyl-2,6,10-tridecenyl)-1,3-propanediol hydrochloride

EXAMPLE 64

2-Amino-2-(8-oxotetradecyl)-1,3-propanediol hydrochloride

EXAMPLE 65

2-Amino-2-(8-hydroxytetradecyl)-1,3-propanediol hydrochloride

EXAMPLE 66

2-Amino-2-(2-dodecylaminoethyl)-1,3-propanediol hydrochloride

EXAMPLE 67

2-Amino-2-(2-dodecanoylaminoethyl)-1,3-propanediol hydrochloride

EXAMPLE 68

2-Amino-2-(11-carboxyundecyl)-1,3-propanediol hydrochloride

EXAMPLE 69

2-Amino-2-(11-methoxycarbonylundecyl)-1,3-propanediol hydrochloride

EXAMPLE 70

2-Amino-2-(12-acetoxydodecyl)-1,3-propanediol hydrochloride

EXAMPLE 71

2-Acetamido-1,3-diacetoxy-2-(3,7,11-trimethyldodecyl)propane

EXAMPLE 72

2-Acetamido-1,3-diacetoxy-2-(3,7,11-trimethyl-2,6,10-tridecenyl)propane

EXAMPLE 73

2-Acetamido-1,3-diacetoxy-2-(8-oxotetradecyl)propane

EXAMPLE 74

2-Acetamido-1,3-diacetoxy-2-(8-hydroxytetradecyl)propane

EXAMPLE 75

2-Acetamido-1,3-diacetoxy-2-(11-methoxycarbonylundecyl)propane

EXAMPLE 76

2-Amino-2-(2-propynyl)-1,3-propanediol

EXAMPLE 77

2-Amino-2-(2-propenyl)-1,3-propanediol

EXAMPLE 78

2-(N-Methylamino)-2-octadecyl-1,3-propanediol

EXAMPLE 79

2-(N,N-Dimethylamino)-2-octadecyl-1,3-propanediol

EXAMPLE 80

2-(N-Octadecylamino)-2-octadecyl-1,3-propanediol

EXAMPLE 81

2-(N,N-Dioctadecylamino)-2-octadecyl-1,3-propanediol

EXAMPLE 82

2-(N-Octadecanoylamino)-2-octadecyl-1,3-propanediol

EXAMPLE 83

2-Amino-2-decyl-1,3-propanediol

EXAMPLE 84

2-Amino-2-dodecyl-1,3-propanediol

EXAMPLE 85

2-Acetamido-2-octadecyl-1,3-propanediol

EXAMPLE 86

2-Amino-2-(2-octadecynyl)-1,3-propanediol

EXAMPLE 87

2-Amino-2-(2-octadecenyl)-1,3-propanediol

EXAMPLE 88

2-Amino-2-(4-phenylbutyl)-1,3-propanediol

EXAMPLE 89

2-Amino-2-(5-phenylpentyl)-1,3-propanediol

EXAMPLE 90

2-Amino-2-(2-phenylpropyl)-1,3-propanediol

EXAMPLE 91

2-Amino-2-[8-(4-hexylphenyl)octyl]-1,3-propanediol

EXAMPLE 92

2-Amino-2-[4-(4-decylphenyl)butyl]-1,3-propanediol

EXAMPLE 93

2-Amino-2-[4-(4-pentyloxyphenyl)butyl]-1,3-propanediol

EXAMPLE 94

2-Amino-2-[4-(4-bromophenyl)butyl]-1,3-propanediol

EXAMPLE 95

2-Amino-2-[3-(2,4-dinitrophenyl)propyl]-1,3-propanediol

EXAMPLE 96

2-Amino-2-[3-(4-aminophenyl)propyl]-1,3-propanediol

EXAMPLE 97

2-Amino-2-[3-(4-decyloxyphenyl)-2-propenyl]-1,3-propanediol

EXAMPLE 98

2-Amino-2-(14-fluorotetradecyl)-1,3-propanediol hydrochloride, melting point=92°–94° C.

EXAMPLE 99

2-Acetamido-1,3-diacetoxy-2-(14-fluorotetradecyl) propane, melting point=82°–84° C.

EXAMPLE 100

2-Amino-2-(9-pentyloxynonyl)-1,3-propanediol ⅓ hydrate, melting point=32°–33° C.

EXAMPLE 101

2-Acetamido-1,3-diacetoxy-2-(9-pentyloxynonyl) propane, melting point=62°–64° C.

EXAMPLE 102

2-Amino-2-(8-hexyloxyoctyl)-1,3-propanediol hydrochloride, melting point=66°–67° C.

EXAMPLE 103

2-Acetamido-1,3-diacetoxy-2-(8-hexyloxyoctyl)propane, melting point=66°–69° C.

EXAMPLE 104

2-Amino-2-(7-heptyloxyheptyl)-1,3-propanediol hydrochloride, melting point=59°–61° C.

EXAMPLE 105

2-Acetamido-1,3-diacetoxy-2-(7-heptyloxyheptyl) propane, melting point=53°–55° C.

EXAMPLE 106

2-Amino-2-(6-octyloxyhexyl)-1,3-propanediol hydrochloride, melting point=58°–62° C.

EXAMPLE 107

2-Acetamido-1,3-diacetoxy-2-(6-octyloxyhexyl)propane, melting point=47°–50° C.

EXAMPLE 108

2-Amino-2-(2-phenylethyl)-1,3-propanediol hydrochloride, melting point=156°–157° C.

EXAMPLE 109

2-Acetamido-1,3-diacetoxy-2-(2-phenylethyl)propane, melting point=116°–117° C.

EXAMPLE 110

2-Amino-2-(3-phenylbutyl)-1,3-propanediol hydrochloride ⅕ hydrate, melting point=111°–118° C.

EXAMPLE 111

2-Acetamido-1,3-diacetoxy-2-(3-phenylbutyl)propane, melting point=98°–99° C.

EXAMPLE 112

2-Amino-2-(6-phenylhexyl)-1,3-propanediol, melting point=77°–79° C.

EXAMPLE 113

2-Acetamido-1,3-diacetoxy-2-(6-phenylhexyl)propane, melting point=58–59° C.

EXAMPLE 114

2-Amino-2-(10-phenyldecyl)-1,3-propanediol, melting point=87°–88.5° C.

EXAMPLE 115

2-Acetamido-1,3-diacetoxy-2-(10-phenyldecyl)propane,

IR; 3301, 2928, 2855, 1747, 1661, 1552 cm$^{-1}$

EXAMPLE 116

2-Amino-2-[6-(3-phenylpropyloxy)hexyl]-1,3-propanediol ¼ hydrate, melting point=66°–67° C.

EXAMPLE 117

2-Acetamido-1,3-diacetoxy-2-[6-(3-phenylpropyloxy)hexyl]propane,

IR; 3418, 1735, 1655, 1026 cm$^{-1}$

EXAMPLE 118

2-Amino-2-[8-(phenylmethyloxy)octyl]-1,3-propanediol hydrochloride, melting point= 87°–88° C.

EXAMPLE 119

2-Acetamido-1,3-diacetoxy-2-[8-(phenylmethyloxy)octyl]propane,

IR; 3308, 1740, 1660, 1240 cm$^{-1}$

EXAMPLE 120

2-Amino-2-[3-(4-heptylcyclohexyl)propyl]-1,3-propanediol, melting point=65°–66° C.

EXAMPLE 121

2-Acetamido-1,3-diacetoxy-2-[3-(4-heptylcyclohexyl)propyl]propane, melting point=53°–55° C.

EXAMPLE 122

2-Amino-2-[4-(4-butylcyclohexyl)butyl]-1,3-propanediol hydrochloride ⅕ hydrate, melting point=96°–99° C.

EXAMPLE 123

2-Acetamido-1,3-diacetoxy-2-[4-(4-butylcyclohexyl)butyl]propane, melting point=66°–69° C.

EXAMPLE 124

2-Amino-2-(4-nonylphenylmethyl)-1,3-propanediol, melting point=112°–113° C.

EXAMPLE 125

2-Acetamido-1,3-diacetoxy-2-(4-nonylphenylmethyl)propane, melting point=85°–89° C.

EXAMPLE 126

2-Amino-2-[3-(4-heptylphenyl)propyl]-1,3-propanediol ½ hydrate, melting point= 78°–80° C.

EXAMPLE 127

2-Acetamido-1,3-diacetoxy-2-[3-(4-heptylphenyl)propyl]propane, melting point=62°–64° C.

EXAMPLE 128

2-Amino-2-[3-(4-undecylphenyl)propyl]-1,3-propanediol, melting point=89°–91° C.

EXAMPLE 129

2-Acetamido-1,3-diacetoxy-2-[3-(4-undecylphenyl)propyl]propane, melting point=64°–67° C.

EXAMPLE 130

2-Amino-2-[4-(4-octylphenyl)butyl]-1,3-propanediol hydrochloride, melting point=108°–110° C.

EXAMPLE 131

2-Acetamido-1,3-diacetoxy-2-[4-(4-octylphenyl)butyl]propane, melting point=64°–67° C.

EXAMPLE 132

2-Amino-2-[6-(4-butylphenyl)hexyl]-1,3-propanediol, melting point=70°–71° C.

EXAMPLE 133

2-Acetamido-1,3-diacetoxy-2-[6-(4-butylphenyl)hexyl]propane,

IR; 3300, 2930, 2858, 1748, 1660 cm$^{-1}$

EXAMPLE 134

2-Amino-2-[8-(4-ethylphenyl)octyl]-1,3-propanediol hydrochloride 1 hydrate, melting point=47°–48° C.

EXAMPLE 135

2-Acetamido-1,3-diacetoxy-2-[8-(4-ethylphenyl)octyl]propane, melting point=58°–60° C.

EXAMPLE 136

2-Amino-2-(4-octyloxyphenylmethyl)-1,3-propanediol, melting point=119°–120° C.

EXAMPLE 137

2-Acetamido-1,3-diacetoxy-2-(4-octyloxyphenylmethyl)propane, melting point=77°–78° C.

EXAMPLE 138

2-Amino-2-(4-decyloxyphenylmethyl)-1,3-propanediol hydrochloride, melting point=100°–102° C.

EXAMPLE 139

2-Acetamido-1,3-diacetoxy-2-(4-decyloxyphenylmethyl)propane, melting point=74°–77° C.

EXAMPLE 140

2-Amino-2-[2-(4-pentyloxyphenyl)ethyl]-1,3-propanediol hydrochloride, melting point=134°–137° C.

EXAMPLE 141

2-Acetamido-1,3-diacetoxy-2-[2-(4-pentyloxyphenyl)ethyl]propane, melting point=93°–95° C.

EXAMPLE 142

2-Amino-2-[3-(4-hexyloxyphenyl)propyl]-1,3-propanediol, melting point=70°–71° C.

EXAMPLE 143

2-Acetamido-1,3-diacetoxy-2-[3-(4-hexyloxyphenyl)propyl]propane, melting point=70°–72.5° C.

EXAMPLE 144

2-Amino-2-[3-(4-heptyloxyphenyl)propyl]-1,3-propanediol hydrochloride ⅙ hydrate, melting point=111°–113° C.

EXAMPLE 145

2-Acetamido-2-[3-(4-heptyloxyphenyl)propyl]-1,3-propanediol, melting point=93°–95° C.

EXAMPLE 146

2-Amino-2-[3-(4-octyloxyphenyl)propyl]-1,3-propanediol, melting point=73°–75° C.

EXAMPLE 147

2-Acetamido-1,3-diacetoxy-2-[3-(4-octyloxyphenyl)propyl]propane, melting point=66°–69° C.

EXAMPLE 148

2-Amino-2-[4-(4-decyloxyphenyl)propyl]-1,3-propanediol, melting point=60°–62° C.

EXAMPLE 149

2-Acetamido-1,3-diacetoxy-2-[4-(4-decyloxyphenyl)propyl]propane, melting point=66°–67° C.

EXAMPLE 150

2-Amino-2-[3-(3-heptyloxyphenyl)propyl]-1,3-propanediol hydrochloride, melting point=102°–103° C.

EXAMPLE 151

2-Acetamido-2-[3-(3-heptyloxyphenyl)propyl]-1,3-propanediol,

IR; 3305, 2932, 1652, 1376 cm$^{-1}$

EXAMPLE 152

2-Amino-2-[4-(4-pentyloxyphenyl)butyl]-1,3-propanediol, melting point=79°–80° C.

EXAMPLE 153

2-Acetamido-1,3-diacetoxy-2-[4-(4-pentyloxyphenyl)butyl]propane, melting point=83°–84° C.

EXAMPLE 154

2-Amino-2-[4-(4-hexyloxyphenyl)butyl]-1,3-propanediol hydrochloride, melting point=99°–100° C.

EXAMPLE 155

2-Acetamido-1,3-diacetoxy-2-[4-(4-hexyloxyphenyl)butyl]propane, melting point=83°–87° C.

EXAMPLE 156

2-Amino-2-[5-(4-butoxyphenyl)pentyl]-1,3-propanediol hydrochloride, melting point=79°–80° C.

EXAMPLE 157

2-Acetamido-1,3-diacetoxy-2-[5-(4-butoxyphenyl)pentyl]propane, melting point=71°–73° C.

EXAMPLE 158

2-Amino-2-[8-(4-methoxyphenyl)octyl]-1,3-propanediol, melting point=69°–70° C.

EXAMPLE 159

2-Acetamido-1,3-diacetoxy-2-[8-(4-methoxyphenyl)octyl]propane,

IR; 3301, 1745, 1662, 1246 cm$^{-1}$

EXAMPLE 160

2-Amino-2-[4-(4-chlorophenyl)butyl]-1,3-propanediol, melting point=75°–79° C.

EXAMPLE 161

2-Acetamido-1,3-diacetoxy-2-[4-(4-chlorophenyl)butyl]propane, melting point=82°–84° C.

EXAMPLE 162

2-Amino-2-[3-(4-decanoylaminophenyl)propyl]-1,3-propanediol ¼ hydrate, melting point= 112°–113° C.

EXAMPLE 163

2-t-Butoxycarbonylamino-2-[3-(4-decanoylaminophenyl)propyl]propane, melting point= 93°–94° C.

EXAMPLE 164

2-Amino-2-[3-(4-decylaminophenyl)propyl]-1,3-propanediol ½ hydrate, melting point= 100°–102° C.

EXAMPLE 165

2-Amino-2-{7-[2-(4-hexylphenyl)-1,3-dioxolan-2-yl]heptyl}-1,3-propanediol ½ hydrate hydrochloride, IR; 3346, 1610, 1510, 1047 cm$^{-1}$

EXAMPLE 166

2-Acetamido-1,3-diacetoxy-2-{7-[2-(4-hexylphenyl)-1,3-dioxolan-2-yl]heptyl}propane, IR; 3308, 1745, 1660, 1238, 1043 cm$^{-1}$

EXAMPLE 167

2-Amino-2-[7-(4-hexylbenzoyl)heptyl]-1,3-propanediol hydrochloride, melting point= 114°–115° C.

EXAMPLE 168

2-Amino-2-[8-(4-hexylphenyl)octyl]-1,3-propanediol, melting point=71°–73° C.

EXAMPLE 169

2-Acetamido-1,3-diacetoxy-2-[8-(4-hexylphenyl)octyl]propane,

IR; 3306, 1745, 1660, 1240 cm$^{-1}$

EXAMPLE 170

2-Amino-2-{3-[4-(2-decyl-1,3-dioxolan-2-yl)phenyl]propyl}-1,3-propanediol ⅔ hydrate, IR; 3346, 1037 cm$^{-1}$

EXAMPLE 171

2-Acetamido-1,3-diacetoxy-2-{3-[4-(2-decyl-1,3-dioxolan-2-yl)phenyl]propyl}propane, melting point=45°–47° C.

EXAMPLE 172

2-Acetamido-1,3-diacetoxy-2-{3-[4-(2-hexyl-1,3-dioxolan-2-yl)phenyl]propyl}propane ⅗ hydrate, melting point=48°–50° C.

EXAMPLE 173

2-Amino-2-[3-(4-decanoylphenyl)propyl]-1,3-propanediol hydrochloride, melting point= 126°–127° C.

EXAMPLE 174

2-Amino-2-[3-(4-heptanoylphenyl)propyl]-1,3-propanediol hydrochloride, melting point= 129°–130° C.

EXAMPLE 175

2-Amino-2-{2-[4-(5-phenylpentyloxymethyl)phenyl]ethyl}-1,3-propanediol hydrochloride ½ hydrate, melting point=105°–108° C.

EXAMPLE 176

2-Acetamido-1,3-diacetoxy-2-{2-[4-(5-phenylpentyloxymethyl)phenyl]ethyl}propane, IR; 3308, 1738, 1651, 1226 cm$^{-1}$

EXAMPLE 177

2-Amino-2-[6-(4-hexyloxyphenyloxy)hexyl]-1,3-propanediol hydrochloride ⅝ hydrate, melting point=90°–95° C.

EXAMPLE 178

2-Acetamido-2-[6-(4-hexyloxyphenyloxy)hexyl]1,3-propanediol, melting point=81°–83° C.

EXAMPLE 179

2-Amino-2-[6-(2-phenyloxyethyloxy)hexyl]-1,3-propanediol, melting point=90°–93° C.

EXAMPLE 180

2-Acetamido-1,3-diacetoxy-2-[6-(2-phenyloxyethyloxy)hexyl]propane,

IR; 2935, 2864, 1744, 1660, 1245 cm$^{-1}$

EXAMPLE 181

2-Acetamido-2-(12-phenyloxydodecyl)-1,3-propanediol, melting point=76°–77° C.

EXAMPLE 182

2-Amino-2-(12-phenyloxydodecyl)-1,3-propanediol hydrochloride

EXAMPLE 183

2-(N,N-Dimethylamino)-2-[2-(4-octylphenyl)ethyl]-1,3-propanediol

EXAMPLE 184

2-Amino-2-[2-(4-hexyloxyphenyl)ethyl]-1,3-propanediol

EXAMPLE 185

2-Acetamido-1,3-diacetoxy-2-[2-(4-hexyloxyphenyl)ethyl]propane

EXAMPLE 186

2-Amino-2-{2-[4-(8-fluorooctyl)phenyl]ethyl}-1,3-propanediol

EXAMPLE 187

2-Acetamido-1,3-diacetoxy-2-{2-[4-(8-fluorooctyl)phenyl]ethyl}propane

EXAMPLE 188

2-Amino-2-{2-[4-(7-fluoroheptyloxy)phenyl]ethyl}-1,3-propanediol white amorphous-like solid Rf value=0.09 (chloroform:methanol=9:1) $^1$H-NMR (DMSO-d$_6$) δ; 1.26–1.64 (14H, m), 3.50 (4H, s), 3.90 (2H, t, J=6.3 Hz), 4.42 (2H, td, J=47.4 Hz, 6.3 Hz), 5.48 (2H, br.s), 6.83 (2H, d, J=8.8 Hz), 7.09 (2H, d, J=8.8 Hz), 7.86 (3H, br.s) IR(KBr) 3391, 1612, 1581, 1249, 831 cm$^{-1}$ elemental analysis: calculated C 56.61, H 8.71, N 3.67 found C 57.00, H 8.58, N 3.69

EXAMPLE 189

2-Acetamido-1,3-diacetoxy-2-{2-[4-(7-fluoroheptyloxy)phenyl]ethyl}propane, colorless liquid Rf value=0.70 (ethyl acetate) IR(neat) 3310, 1738, 1651, 1614, 1514, 1244, 815 cm$^{-1}$

EXAMPLE 190

2-Amino-2-{2-[4-(1,1-difluorooctyl)phenyl]ethyl}-1,3-propanediol

EXAMPLE 191

2-Acetamido-1,3-diacetoxy-2-{2-[4-(1,1-difluorooctyl)phenyl]ethyl}propane

EXAMPLE 192

2-Amino-2-{2-[4-(1,1-difluoroheptyloxy)phenyl]ethyl}-1,3-propanediol

EXAMPLE 193

2-Acetamido-1,3-diacetoxy-2-{2-[4-(1,1-difluoroheptyloxy)phenyl]ethyl}propane

EXAMPLE 194

2-Amino-2-{2-[4-(4-methylpentyl)phenyl]ethyl}1,3-propanediol

EXAMPLE 195

2-Acetamido-1,3-diacetoxy-2-{2-[4-(4-methylpentyl)phenyl]ethyl}propane

EXAMPLE 196

2-Amino-2-[2-(4-fluorophenyl)ethyl]-1,3-propanediol hydrochloride, melting point= 169°–170° C.

EXAMPLE 197

2-Acetamido-2-[2-(4-fluorophenyl)ethyl]-1,3propanediol, melting point=63°–65° C.

EXAMPLE 198

2-Acetamido-1,3-diacetoxy-2-[2-(4-fluorophenyl)ethyl]propane

EXAMPLE 199

2-Amino-2-[2-(3-fluoro-4-octylphenyl)ethyl]-1,3-propanediol

EXAMPLE 200

2-Acetamido-1,3-diacetoxy-2-[2-(3-fluoro-4-octylphenyl)ethyl]propane

EXAMPLE 201

2-Amino-2-[2-(2-ethyl-4-octylphenyl)ethyl]-1,3-propanediol

EXAMPLE 202

2-Acetamido-1,3-diacetoxy-2-[2-(2-ethyl-4-octylphenyl)ethyl]propane

EXAMPLE 203

2-Amino-2-[2-(3-methyl-4-octylphenyl)ethyl]-1,3-propanediol

EXAMPLE 204

2-Acetamido-1,3-diacetoxy-2-[2-(3-methyl-4-octylphenyl)ethyl]propane

EXAMPLE 205

2-Amino-2-[2-(4-heptyloxy-3-methoxyphenyl)ethyl]-1,3-propanediol ½ hydrate hydrochloride, melting point=126°–129° C.

$^1$H-NMR (CDCl$_3$) δ: 0.80 (3H, t, J=6 Hz), 1.22–1.36 (8H, m), 1.70–1.76 (2H, m), 1.83–1.91 (2H, m), 2.50–2.54 (2H, m), 3.30 (3H, s), 3.77 (4H, s), 3.89 (2H, t, J=8 Hz), 6.63–6.72 (3H, m) IRv 3179, 2931, 1617, 1518, 1240, 1036 cm$^{-1}$

EXAMPLE 206

2-Acetamido-1,3-diacetoxy-2-[2-(4-heptyloxy-3-methoxyphenyl)ethyl]propane, melting point= 138°–139° C.

$^1$H-NMR (CDCl$_3$) δ: 0.88 (3H, t, J=6 Hz), 1.30–1.56 (10H, m), 1.96 (3H, s), 2.09 (6H, s), 2.18–2.22 (2H, m), 2.53–2.57 (2H, m), 3.86 (3H, s), 3.97 (2H, t, J=6 Hz), 4.35 (4H, s), 5.65 (1H, s), 6.70–6.80 (3H, m)
IRv 3291, 2930, 1738, 1258 cm$^{-1}$ elemental analysis: calculated C 64.49, H 8.44, N 3.01 found C 64.32, H 8.33, N 3.03

EXAMPLE 207

2-Amino-2-[2-(4-heptyloxy-3-methylphenyl)ethyl]-1,3-propanediol

EXAMPLE 208

2-Acetamido-1,3-diacetoxy-2-[2-(4-heptyloxy-3-methylphenyl)ethyl]propane

EXAMPLE 209

2-Amino-2-[2-(4-phenylmethyloxyphenyl)ethyl]-1,3-propanediol ⅕ hydrate hydrochloride melting point=207°–210° C.

$^1$H-NMR (CDCl$_3$) δ: 1.90–1.95 (2H, m), 2.59–2.63 (2H, m), 3.71 (4H, q, J=12 Hz), 5.04 (2H, s), 6.91 (2H, d, J=8 Hz), 7.13 (2H, d, J=8 Hz), 7.37–7.44 (5H, m) IRv 3422, 1617, 1508, 1245 cm$^{-1}$

EXAMPLE 210

2-Acetamido-1,3-diacetoxy- 2-[2-(4-phenylmethyloxyphenyl)ethyl]propane, melting point=150°–153° C.

$^1$H-NMR (CDCl$_3$) δ: 1.95 (3H, s), 2.09 (6H, s), 2.15–2.20 (2H, m), 2.53–2.58 (2H, m), 4.34 (4H, s), 5.04 (2H, s), 5.64 (1H, s), 6.90 (2H, d, J=8 Hz), 7.10 (2H, d, J=8 Hz), 7.36–7.43 (5H, m) IRv 3318, 1763, 1736, 1654, 1250 cm$^{-1}$ elemental analysis: calculated C 67.43, H 6.84, N 3.28 found C 67.47, H 6.96, N 3.19

EXAMPLE 211

2-Amino-2-[2-(4-hydroxyphenyl)ethyl]-1,3-propanediol, melting point=180°–185° C.

$^1$H-NMR (CDCl$_3$) δ: 1.61–1.66 (2H, m), 2.52–2.57 (2H, m), 3.57 (4H, s), 6.74 (2H, d, J=8 Hz), 7.03 (2H, d, J=8 Hz) IRv 3355, 2923, 1602, 1474, 1232 cm$^{-1}$ elemental analysis: calculated C 62.54, H 8.11, N 6.63 found C 62.45, H 8.07, N 6.68

EXAMPLE 212

2-Acetamido-1,3-diacetoxy-2-[2-(4-hydroxyphenyl)ethyl]propane, melting point=100°–105° C.

$^1$H-NMR (CDCl$_3$) δ: 1.98 (3H, s), 2.10 (6H, s), 2.17–2.22 (2H, m), 2.52–2.56 (2H, m), 4.34 (4H, s), 5.73 (1H, s), 6.76 (2H, d, J=9 Hz), 7.03 (2H, d, J=9 Hz) IRv 3590, 1741, 1577, 1243 cm$^{-1}$

EXAMPLE 213

2-Amino-2-(9-phenyloxynonyl)-1,3-propanediol hydrochloride, melting point=103°–104° C.

elemental analysis: calculated C 62.50, H 9.32, N 4.05 found C 62.21, H 9.39, N 3.95

EXAMPLE 214

2-Acetamido-2-(9-phenyloxynonyl)-1,3-propanediol melting point=71°–73° C.

elemental analysis: calculated C 68.34, H 9.46, N 3.99 found C 68.34, H 9.44, N 3.01

EXAMPLE 215

2-Acetamido-1,3-diacetoxy-2-(9-phenyloxynonyl) propane

EXAMPLE 216

2-Amino-2-(12-fluorododecyl)-1,3-propanediol ⅒ hydrate hydrochloride, melting point=87°–89° C.

EXAMPLE 217

2-Acetamido-1,3-diacetoxy-2-(12-fluorododecyl) propane, melting point=57°–59° C.

EXAMPLE 218

2-Amino-2-(13-fluorotridecyl)-1,3-propanediol

EXAMPLE 219

2-Acetamido-1,3-diacetoxy-2-(13-fluorotridecyl) propane

EXAMPLE 220

2-Amino-2-{2-[4-(N-decyl-N-methylamino)phenyl] ethyl}-1,3-propanediol

EXAMPLE 221

2-Acetamido-1,3-diacetoxy-2-{2-[4-(N-decyl-N-methylamino)phenyl]ethyl}propane

EXAMPLE 222

2-Amino-2-[2-(4-heptylthiophenyl)ethyl]-1,3-propanediol

EXAMPLE 223

2-Acetamido-1,3-diacetoxy-2-[2-(4-heptylthiophenyl)ethyl]propane

EXAMPLE 224

2-Amino-2-[2-(4-heptylphenyl)ethyl]-1,3-propanediol

EXAMPLE 225

2-Acetamido-1,3-diacetoxy-2-[2-(4-heptylphenyl)ethyl]propane

EXAMPLE 226

2-Amino-2-[2-(4-heptylphenyl)-2-oxoethyl]-1,3-propanediol

EXAMPLE 227

2-Acetamido-1,3-diacetoxy-2-[2-(4-heptylphenyl)-2-oxoethyl]propane

EXAMPLE 228

2-Amino-2-[2-(4-heptylphenyl)-2-hydroxyethyl]-1,3-propanediol

EXAMPLE 229

2-Acetamido-1,3-diacetoxy-2-[2-(4-heptylphenyl)-2-hydroxyethyl]propane

EXAMPLE 230

2-Amino-2-{2-[2-(4-heptylphenyl)-1,3-dioxolan-2-yl]ethyl}-1,3-propanediol

EXAMPLE 231

2-Acetamido-1,3-diacetoxy-2-{2-[2-(4-heptylphenyl)-1,3-dioxolan-2-yl]ethyl}propane

EXAMPLE 232

2-Amino-2-[2-(4-octylphenyl)-2-oxoethyl]-1,3-propanediol

EXAMPLE 233

2-Acetamido-1,3-diacetoxy-2-[2-(4-octylphenyl)-2-oxoethyl]propane

EXAMPLE 234

2-Amino-2-[2-(4-octylphenyl)-2-hydroxyethyl]-1,3-propanediol

EXAMPLE 235

2-Acetamido-1,3-diacetoxy-2-[2-(4-octylphenyl)-2-hydroxyethyl]propane

EXAMPLE 236

2-Amino-2-{2-[2-(4-octylphenyl)-1,3-dioxolan-2-yl]ethyl}-1,3-propanediol

EXAMPLE 237

2-Acetamido-1,3-diacetoxy-2-{2-[2-(4-octylphenyl)-1,3-dioxolan-2-yl]ethyl}propane

EXAMPLE 261

2-Amino-2-(8-hydroxytetradecyl)-1,3-propanediol hydrochloride (1)  2-Acetamido-3-acetoxy-2-acetoxymethyl-14-oxoicosa-6-enoic acid-δ-lactone Acetic anhydride (200 ml) and pyridine (20 ml) were added to 2-amino-3,4-dihydroxy-2-dihydroxymethyl-14-oxoicosa-6-enoic acid (20 g) and the mixture was stirred at room temperature overnight. The reaction mixture was poured into ice water and extracted with ethyl acetate. The ethyl acetate layer was washed with 1N hydrochloric acid, a saturated aqueous sodium hydrogencarbonate solution and saturated brine in order. The resultant mixture was dried over magnesium sulfate and the solvent was distilled away to give the subject compound (22.9 g).

(2)  14-Hydroxy-2-acetamido-3-acetoxy-2-acetoxymethyl-14-oxoicosa-6-enoic acid-δ-lactone Deionized water (150 ml) was added to a solution of the above-mentioned compound (12.8 g) in dioxane. The mixture was stirred in an ice bath for about 30 minutes while bubbling carbon dioxide to saturation, thereby to make the solution weak acidic. Sodium borohydride (2.41 g) was added thereto and the mixture was stirred for 1 hour. The reaction mixture was acidified with 1N hydrochloric acid and made weak acidic with 1N sodium hydroxide. The resultant mixture was concentrated and extracted with ethyl acetate. The ethyl acetate layer was washed with a saturated sodium hydrogencarbonate solution and saturated brine in order and dried over magnesium sulfate. The solvent was distilled away and the residue obtained was purified by silica gel column chromatography (eluent; chloroform:methanol= 50:1) to give the subject compound (7.49 g).

IR: 3440, 2920, 2850, 1750, 1680 cm$^{-1}$ (3)  14-t-Butyldimethylsilyloxy-2-acetamido-3-acetoxy-2-acetoxymethyl-14-oxoicosa-6-enoic acid-δ-lactone Imidazole (4.97 g) and t-butyldimethylsilyl chloride (5.50 g) were added to a solution of the compound (7.49 g) as mentioned above in N,N-dimethylformamide (75 ml) and the mixture was stirred at 60° C. for 1 hour. Deionized water was added to the reaction mixture under ice-cooling and the mixture was stirred for 30 minutes and then at room temperature for 30 minutes. Deionized water was added thereto and the mixture was extracted with diethyl ether. The diethyl ether layer was concentrated and dried over magnesium sulfate. The solvent was distilled away and the residue obtained was purified by silica gel column chromatography (eluent; ethyl acetate:hexane=1:2) to give the subject compound (8.50 g).

IR: 3440, 2920, 2850, 1750, 1680, 830 cm$^{-1}$ (4)  5,6-Dihydroxy-14-t-butyldimethylsilyloxy-2-acetamido-3-acetoxy-2-acetoxymethyl-14-oxoicosa-6-enoic acid-δ-lactone N-Methylmorpholine-N-oxide (3.19 g) and a 1% aqueous osmium tetraoxide solution (34.5 ml) were added to a solution of the compound (8.50 g) as mentioned above in acetone (207 ml) and the mixture was stirred at room temperature for 2 hours. The reaction mixture was concentrated and extracted with ethyl acetate. The ethyl acetate layer was washed with a saturated sodium sulfite solution, 1N hydrochloric acid, a saturated sodium hydrogencarbonate solution and saturated brine in order and dried over magnesium sulfate. The solvent was distilled away to give the subject compound (8.05 g).

IR: 3440, 2920, 2850, 1750, 1680, 830 cm$^{-1}$ (5) 8-t-Butyldimethylsilyloxytetradecanal A 0.2N aqueous sodium periodate solution (183 ml) was added to a solution of the compound (8.05 g) as mentioned above in dioxane (610 ml) and the mixture was stirred at room temperature for 2 hours. The reaction mixture was concentrated and extracted with hexane. The hexane layer was dried over magnesium sulfate and the solvent was distilled away to give the subject compound (4.1 g, yield 98.4%).

IR: 2920, 2850, 1720, 830 cm$^{-1}$ (6) 8-t-Butyldimethylsilyloxytetradecanol

Deionized water (40 ml) was added to a solution of the compound (4.1 g) as mentioned above in dioxane (120 ml) and sodium borohydride (1.15 g) was added thereto under ice-cooling. The mixture was stirred at room temperature for 30 minutes. The reaction mixture was concentrated and extracted with ethyl acetate. The ethyl acetate layer was washed with 1N hydrochloric acid, a saturated sodium hydrogencarbonate solution and saturated brine in order, and dried over magnesium sulfate. The solvent was distilled away and the residue obtained was purified by silica gel column chromatography (eluent; ethyl acetate:hexane=1:10) to give the subject compound (3.74 g).

IR: 2920, 2850, 1710, 830 cm$^{-1}$ (7) 1-Iodo-8-t-butyldimethylsilyloxytetradecane Imidazole (1.85 g), triphenylphosphine (7.14 g) and iodine (5.53 g) were added to a solution of the compound (3.74 g) as mentioned above in benzene (200 ml) and the mixture was stirred at room temperature for 30 minutes. The reaction mixture was extracted with ethyl acetate and washed with a saturated sodium sulfite solution and saturated brine in order. The ethyl acetate layer was dried over magnesium sulfate and the solvent was distilled away. The residue obtained was purified by silica gel column chromatography (eluent; hexane) to give the subject compound (4.42 g).

IR: 2920, 2850, 830 cm$^{-1}$ (8) Diethyl 2-acetamido-2-(8-t-butyldimethylsilyloxytetradecyl)malonate Diethyl acetamidomalonate (2.54 g) and sodium ethoxide (0.80 g) were added to a solution of the compound (4.42 g) as mentioned above in dehydrated ethanol (200 ml) and the mixture was refluxed under heating in a stream of nitrogen overnight. The reaction mixture was concentrated and the residue obtained was purified by silica gel column chromatography (eluent; ethyl acetate:hexane=1:5→1:3) to give the subject compound (2.81 g).

$^1$H-NMR (CDCl$_3$) δ: 0.03 (6H, s), 0.84 (12H, m), 1.23 (18H, m), 1.23 (6H, t, J=7.0 Hz), 1.35 (4H, m), 2.01 (3H, s), 2.28 (2H, m), 3.57 (1H, q, J=6.0 Hz), 4.215 (4H, q, J=7 Hz), 6.74 (1H, s) IR: 3440, 2920, 2850, 1740, 1680, 830 cm$^{-1}$ (9) 2-Acetamido-1,3-diacetoxy-2-(8-t-butyldimethylsilyloxytetradecyl)propane Sodium borohydride (1.77 g) was added to a solution of the compound (3.38 g) as mentioned above in methanol (13 ml) and the mixture was allowed to stand at room temperature for 1 hour. The reaction mixture was extracted with ethyl acetate and washed with 1N hydrochloric acid, a saturated sodium hydrogencarbonate solution and saturated brine in order. The ethyl acetate layer was dried over magnesium sulfate and the solvent was distilled away. Acetic anhydride (19.6 ml) and pyridine (1.96 ml) were added to the residue obtained and the mixture was stirred at room temperature overnight. The reaction mixture was poured into ice water and extracted with ethyl acetate. The ethyl acetate layer was washed with 1N hydrochloric acid, a saturated sodium hydrogencarbonate solution and saturated brine in order and dried over magnesium sulfate. The solvent was distilled away and the residue obtained was purified by silica gel column chromatography (eluent; ethyl acetate:hexane=1:2) to give the subject compound (2.04 g).

$^1$H-NMR (CDCl$_2$) δ: 0.009 (6H, s), 0.86 (3H, t), 0.86 (9H, s), 1.24 (18H, m), 1.36 (4H, m), 1.82 (2H, m), 1.94 (3H, s), 2.06 (6H, s), 3.58 (1H, q, J=8 Hz), 4.26 (2H, d, J=11.2 Hz), 4.29 (2H, d, J=11.3 Hz), 5.59 (1H, s) IR: 3440, 2920, 2850, 1740, 1680, 830 cm$^{-1}$

(10) 2-Acetamido-1,3-diacetoxy-2-(8-hydroxytetradecyl)propane

A solution of the compound (2.04 g) as mentioned above in 0.01N hydrochloric acid-methanol (37.6 ml) was allowed to stand at room temperature for 3 hours. Deionized water was added thereto and the mixture was extracted with ethyl acetate. The ethyl acetate layer was washed with a saturated sodium hydrogencarbonate solution and a saturated sodium chloride solution in order and dried over magnesium sulfate. The solvent was distilled away and the residue obtained was purified by silica gel column chromatography (eluent; ethyl acetate:hexane=1:1) to give the subject compound (1.15 g).

melting point=82°–84° C. $^1$H-NMR (CDCl$_3$) δ: 0.85 (3H, t, J=6.9 Hz), 1.26 (18H, m), 1.40 (4H, m), 1.82 (2H, m), 1.93 (3H, s), 2.05 (6H, s), 3.55 (1H, m), 4.25 (2H, d, J=11.2 Hz), 4.28 (2H, d, J=11.7 Hz), 5.59 (1H, s) IR: 3440, 2920, 2850, 1720, 1680 cm$^{-1}$

(11) 2-Amino-2-(8-hydroxytetradecyl)-1,3-propanediol hydrochloride

1N Sodium hydroxide was added to a solution of the compound (300 mg) as mentioned above in methanol (12.6 ml) and the mixture was refluxed under heating in a stream of nitrogen for 6 hours. The reaction mixture was concentrated and extracted with ethyl acetate. The ethyl acetate layer was washed with saturated brine and dried over magnesium sulfate. The solvent was distilled away. 1N Hydrochloric acid-methanol (1.4 ml) was added to the residue obtained and the mixture was concentrated to give the subject compound (230 mg).

melting point=106°–108° C. $^1$H-NMR (CDCl$_3$) δ: 0.84 (3H, t, J=6.8 Hz), 1.22 (22H, m), 1.48 (2H, d, J=10.3 Hz), 3.40 (2H, d, J=10.3 Hz), 3.44 (2H, d, J=12.2 Hz), 4.21 (1H, m), 5.28 (2H, br.s), 7.74 (3H, br.s) IR: 3350, 2900, 2850 cm$^{-1}$

EXAMPLE 262

2-Amino-2-(8-oxotetradecyl)-1,3-propanediol hydrochloride (1) 2-Acetamido-1,3-diacetoxy-2-(8-oxotetradecyl)propane Pyridinium chlorochromate (301.5 mg) was added to a solution of 2-acetamido-1,3-diacetoxy-2-(8-hydroxytetradecyl)propane (300 mg) in dichloromethane (19 ml) and the mixture was stirred at room temperature for 2 hours in a stream of nitrogen. Ether (38 ml) and magnesium sulfate (appropriate amount) were added thereto and the mixture was stirred for 10 minutes. The reaction mixture was suction-filtered and the filtrate was concentrated. The concentrate was extracted with ethyl acetate and the ethyl acetate layer was washed with 1N hydrochloric acid, a saturated sodium hydrogencarbonate solution and saturated brine in order. The resultant mixture was dried over magnesium sulfate. The solvent was distilled away to give the subject compound (290 mg).

melting point=88°–89° C. $^1$H-NMR (CDCl$_3$) δ: 0.88 (3H, t, J=7.1 Hz), 1.27 (14H, m), 1.55 (4H, m), 1.84 (2H, dd, J=8.8, 15.6 Hz), 1.97 (3H, s), 2.08 (6H, s), 2.38 (4H, t, J=7.4 Hz), 4.28 (2H, d, J=11.3 Hz), 4.31 (2H, d, J=11.2 Hz), 5.63 (1H, s) IR: 2920, 2850, 1740–1680 cm$^{-1}$ (2) 2-Amino-2-(8-oxotetradecyl)-1,3-propanediol hydrochloride 1N Sodium hydroxide (4.1 ml) was added to a solution of the compound (290 mg) as mentioned above in methanol (12.2 ml) and the mixture was refluxed under heating in a nitrogen flow for 6 hours. The reaction mixture was concentrated and extracted with ethyl acetate. The ethyl acetate layer was washed with saturated brine and dried over magnesium sulfate. The solvent was distilled away and 1N hydrochloric acid-methanol (1.2 ml) was added to the residue obtained. The mixture was concentrated and the residue obtained was recrystallized from ethyl acetate to give the subject compound (176 mg).

melting point=121°–122° C. $^1$H-NMR (CDCl$_3$) δ: 0.614 (3H, t, J=6.3 Hz), 1.03 (18H, m), 1.28 (4H, m), 1.41 (2H, m), 2.12 (4H, t, J=7.3 Hz), 3.38 (2H, d, J=12.2 Hz), 3.48 (2H, d, J=12.2 Hz), 4.71 (2H, br.s), 7.65 (3H, br.s) IR: 3420–3340, 3030, 2920, 2850, 1700 cm$^{-1}$

EXAMPLE 263

2-Amino-2-(2-N-dodecylaminoethyl)-1,3-propanediol hydrochloride (1) Diethyl aminomalonate hydrochloride (10 g) was dissolved in 100 ml of N,N-dimethylformamide, and 6.3 g of triethylamine and 12.1 g of di-t-butyldicarbonate were added thereto. The mixture was stirred at 60° C. for 1 hour. Water was added to the reaction mixture under ice-cooling and the mixture was stirred at room temperature. The reaction mixture was extracted with ether, dried and concentrated. The resultant mixture was purified by silica gel column chromatography using hexane-ethyl acetate (10:1→5:1) as an eluent to give 13 g of colorless, oily diethyl N-t-butoxycarbonylaminomalonate.

IRν$_{max}$ (CHCl$_3$):3450, 2970, 1740(sh), 1710, 1490, 1375, 1340, 1160, 1060, 1020, 860 cm$^{-1}$ (2) Diethyl N-t-butoxycarbonylaminomalonate (5 g) was dissolved in 100 ml of dehydrated ethanol, and 1.53 g of sodium ethoxide and 2.7 g of aryl bromide were added thereto. The mixture was refluxed under a nitrogen atmosphere for 12 hours. The reaction mixture was concentrated and purified by silica gel column chromatography using hexane-ethyl acetate (20:1→10:1→8:1) to give 4.8 g of colorless, oily diethyl 2-aryl-N-t-butoxycarbonylaminomalonate.

IRν$_{max}$ (CHCl$_3$): 3450, 2980, 2860, 1740(sh), 1710, 1480, 1400, 1370, 1310, 1160, 1080, 1060, 1020, 915, 860 cm$^{-1}$ (3) Diethyl 2-aryl-N-t-butoxycarbonylaminomalonate (4.8 g) was dissolved in 30 ml of methanol and 4.34 g of sodium borohydride was added thereto. The mixture was allowed to stand at room temperature for 2 hours. Ethyl acetate was added to the reaction mixture and the mixture was washed with a 1N aqueous hydrochloric acid solution, a saturated aqueous sodium hydrogencarbonate solution and a saturated aqueous sodium chloride solution. The resultant mixture was dried and concentrated. The residue was dissolved in 32 ml of N,N-dimethylformamide, and 5.72 g of imidazole and 6.33 g of t-butyldimethylsilyl chloride were added thereto. The mixture was stirred at 60° C. for 1 hour.

Water was added to the reaction mixture under ice-cooling and the mixture was stirred at room temperature. The resultant mixture was extracted with ether, dried and concentrated. The concentrate was purified by silica gel column chromatography using hexane-ethyl acetate (10:1) as an eluent to give 3.8 g of colorless, oily 2-aryl-2-(N-t-butoxycarbonylamino)-1,3-propanediol bis-t-butyldimethylsilyl ether.

Rf value=0.7 (hexane-ethyl acetate=10:1)

(4) 2-Aryl-2-(N-t-butoxycarbonylamino)-1,3-propanediol bis-t-butyldimethylsilyl ether (3.8 g) was dissolved in 300 ml of acetone, and 2.45 g of N-methylmorpholine-N-oxide and 43 ml of a 1% aqueous osmium tetraoxide solution were added thereto. The mixture was stirred at room temperature for 4 hours. The reaction mixture was concentrated and ethyl acetate was added thereto. The mixture was washed with a saturated aqueous sodium sulfite solution, a 1N aqueous hydrochloric acid solution, a saturated aqueous sodium hydrogencarbonate solution and a saturated aqueous sodium chloride solution. After dehydration, the resultant mixture was concentrated to give 4.3 g of colorless, oily 2-(2,3-dihydroxypropyl)-2-(N-t-butoxycarbonylamino)-1,3-propanediol bis-t-butyldimethylsilyl ether.

IRν$_{max}$ (CHCl$_3$): 3450(br), 2940, 2850, 1710, 1500, 1470, 1400, 1370, 1260, 1160, 1080(br), 840 cm$^{-1}$ (5) 2-(2,3-Dihydroxypropyl)-2-(N-t-butoxycarbonylamino)-1,3-propanediol bis-t-butyldimethylsilyl ether (4.3 g) was dissolved in 600 ml of 1,4-dioxane and a solution of 3.8 g of meta-sodium periodate in 90 ml of water was added thereto. The mixture was stirred at room temperature for 3 hours. The reaction mixture was concentrated and hexane was added thereto. After washing with water, the resultant mixture was dried and concentrated to give 3.76 g of colorless, oily 2-(N-t-butoxycarbonylamino)-2-(2-formylethyl)-1,3-propanediol bis-t-butyldimethylsilyl ether.

Rf value=0.7 (hexane-ethyl acetate=5:1)

(6) 2-(N-t-Butoxycarbonylamino)-2-(2-formylethyl)-1,3-propanediol bis-t-butyldimethylsilyl ether (1.2 g) was dissolved in 20 ml of methanol and a solution of 2.89 g of dodecylamine in 5.2 ml of concentrated hydrochloric acid-methanol (1:11) and 245 mg of sodium cyanoborohydride were added thereto. The mixture was stirred at room temperature overnight. The reaction mixture was concentrated and ethyl acetate was added thereto. A 1N aqueous hydrochloric acid solution was added until the aqueous layer assumed acidity; a 1N aqueous sodium hydroxide solution was added until the aqueous layer assumed weak acidity; and the solution was partitioned. The ethyl acetate layer was washed with a saturated aqueous sodium chloride solution, dehydrated and concentrated. The resultant mixture was purified by silica gel column chromatography using hexane-ethyl acetate (3:1→2:1→1:1) as an eluent to give 956 mg of colorless, oily 2-(2-N-dodecylaminoethyl)-2-(butoxycarbonylamino)-1,3-propanediol bis-t-butyldimethylsilyl ether.

IRν$_{max}$ (CHCl$_3$): 3450, 2920, 2850, 1710, 1500, 1460, 1400, 1370, 1260, 1160, 1100(br), 840 cm$^{-1}$ $^1$H-NMR (CDCl$_3$) δ: 5.31 (1H, s, NHBoc), 3.69 (2H, d, J=8 Hz, OCH$_{2a}$×2), 3.61 (2H, d, J=8 Hz, OCH$_{2b}$×2), 2.66 (2H, t, J=8 Hz, H$_2$C—N), 2.55 (2H, t, J=8 Hz, N—CH$_2$), 1.85 (2H, t, J=8 Hz, —C—CH$_2$), 1.40 (9H, s, Boc.—t—Bu), 1.24 (20H, m, CH$_2$×10), 0.85 (21H, m, Si—tBu×2 and CH$_2$CH$_3$), 0.03 (12H, s, Si—CH$_3$×4)

(7) 2-(2-N-Dodecylaminoethyl)-2-(N-t-butoxycarbonylamino)-1,3-propanediol bis-t-butyldimethylsilyl ether (100 mg) was dissolved in 2 ml of methanol and 1.6 ml of concentrated hydrochloric acid-methanol (1:11) was added thereto. The mixture was warmed at 40° C. for 3 hours. The reaction mixture was concentrated to give 58 mg of pale yellow, oily 2-amino-2-(2-N-dodecylaminoethyl)-1,3-propanediol hydrochloride.

IRv$_{max}$ (KBr): 3350(br), 2920, 2850, 1600, 1460, 1060 cm$^{-1}$; $^1$H-NMR (DMSO-d$_6$) δ: 9.00 (2H, br.s, +NH$_2$Cl$^-$), 8.04 (3H, br.s, +NH$_3$Cl$^-$), 5.51 (2H, s, OH×2), 3.47 (2H, s, OCH$_2$), 3.45 (2H, s, OCH$_2$), 2.99 (2H, m, H$_2$CN), 2.81 (2H, m, NCH$_2$), 1.96 (2H, m, —C—CH$_2$), 1.23 (20H, m, CH$_2$× 10), 0.84 (3H, t, 6.8 Hz, CH$_3$).

EXAMPLE 264

2-Amino-2-(11-methoxycarbonylundecyl)-1,3-propanediol Hydrochloride

2-Acetamido-1,3-diacetoxy-2-(12-hydroxydodecyl)propane (426 mg) was dissolved in 2.7 ml of dry dimethylformamide and 1.345 g of pyridinium dichromate was added thereto. The mixture was stirred at room temperature day and night under a nitrogen atmosphere. The reaction mixture was poured into water and extracted twice with ether. The ether layer was washed with saturated brine and dried over anhydrous magnesium sulfate. The solvent was distilled away under reduced pressure and 17 ml of methanol and 4.23 ml of a 1N aqueous sodium hydroxide solution were added to the residue. The mixture was refluxed under heating under a nitrogen atmosphere for 6 hours. The reaction mixture was passed through a strongly acidic ion exchange resin, Amberlite IR-120B column, and the eluate was concentrated. The concentrate was dissolved in methanol and the mixture was acidified with hydrochloric acid. The solvent was distilled away under reduced pressure to give 122 mg of the subject compound.

melting point=100.0°–104.0° C. IR(cm$^{-1}$): 3370, 2920, 2850, 1740, 1500, 1470, 1170, 1080 NMR (DMSO) δ: 7.684 (3H, br.s), 5,275 (2H, br.s), 3.563 (3H, s), 3.441 (1H, d, J=11.2 Hz), 3.430 (1H, d, J=11.2 Hz), 3.402 (1H, d, J=11.7 Hz), 3.390 (1H, d, J=11.2 Hz), 2.272 (2H, t, J=7.3 Hz), 1.229 (2OH, s).

EXAMPLE 265

2-Amino-2-(11-carboxyundecyl)-1,3-propanediol Hydrochloride

2N Hydrochloric acid (0.5 ml) was added to 10 mg of 2-amino-2-(11-methoxycarbonylundecyl)-1,3-propanediol hydrochloride and the mixture was heated at 90° C. for 1 hour. The solvent was distilled away under reduced pressure to give 10 mg of the subject compound.

NMR (DMSO) δ: 11.992 (1H, br.s, COOH), 7.771 (3H, br.s, +NH$_3$), 5.292 (2H, t, J=4.9 Hz, OH×2), 3.417 (4H, ddd, J=16.5, 11.7, 5.0 Hz, CH$_2$O×2), 2.168 (2H, t, J=7.4 Hz, CH$_2$COO), 1.224 (2OH, s, CH$_2$×10).

EXAMPLE 266

2-Acetamido-1,3-diacetoxy-2-(8-acetoxytetradecyl)propane $^1$H-NMR (CDCl$_3$) δ: 0.85 (3H, t, J=6.8 Hz), 1.24 (18H, m), 1.47 (4H, m), 1.82 (2H, m), 1.94 (3H, s), 2.05–2.01 (9H, s), 4.25 (2H, d, J=11.7 Hz), 4.29 (2H, d, J=11.7 Hz), 4.83 (1H, q, J=6.3 Hz), 5.62 (1H, s); IR: 3400, 2920, 2850, 1720, 1680 cm$^{-1}$.

EXAMPLE 267

2-Acetamido-1,3-diacetoxy-2-(3,7,11-trimethyldodecyl)propane $^1$H-NMR (CDCl$_3$) δ: 5.589 (1H, br.s), 4.293 (4H, dd, J=13.7, 12.3 Hz), 2.073 (6H, s), 1.956 (3H, s), 1.857 (1H, qui, J=13.7 Hz), 1.844 (1H, qui, J=13.3 Hz), 1.513 (1H, septet, J=6.6 Hz), 1.345–1.040 (16H, m), 0.857 (6H, d, J=6.4 Hz), 0.848 (3H, d, J=6.4 Hz), 0.831 (3H, d, J=6.8 Hz)

EXAMPLE 268

2-Acetamido-1,3-diacetoxy-(3,7,11-trimethyl-2,6,10-tridecenyl)propane $^1$H-NMR (CDCl$_3$) δ: 5.57 (1H, br.s), 5.07 (3H, m), 4.28 (4H, s), 2.60 (2H, d, J=7.8 Hz), 2.01 (6H, s), 2.05–1.94 (8H, m), 1.94 (3H, s), 1.70–1.57 (12H, m).

EXAMPLE 269

2-Acetamido-1,3-diacetoxy-2-(11-methoxycarbonylundecyl)propane melting point=49.5°–51.5° C. IRv: 3300, 2930, 2850, 1740, 1655, 1580, 1475, 1390, 1240, 1060 cm$^{-1}$; $^1$H-NMR (CDCl$_3$) δ: 5.61 (1H, br.s), 4.265 (4H, dd, J=13.6 Hz, 11.2 Hz), 3.635 (3H, s), 2.272 (2H, t, J=7.6 Hz), 2.051 (6H, s), 1.934 (3H, s), 1.836–1.817 (2H, m), 1.225 (18H, br.s).

EXAMPLE 270

2-Acetamido-1,3-diacetoxy-(12-acetoxydodecyl)propane melting point=67.5°–69.0° C. $^1$H-NMR (CDCl$_3$) δ: 5.607 (1H, br.s), 4.267 (4H, dd, J=13.7, 11.3 Hz), 4.021 (2H, t, J=6.9 Hz), 2.052 (6H, s), 2.017 (3H, S), 1.934 (3H, s), 1.840–1.819 (2H, m), 1.225 (2OH, br.s).

EXAMPLE 271

2-Amino-2-(1,2,12-trihydroxyoctadecyl)-1,3-propanediol $^1$H-NMR (400 MHz, in CD$_3$OD) δ: 3.85–3.73 (7H, m), 1.60 (2H, m), 1.45–1.25 (26H, m), 0.90 (3H, t); IRv$_{max}$ (KBr): 3350(br), 2920, 2850, 1560, 1480, 1420, 1060 cm$^{-1}$.

EXAMPLE 272

2-Amino-2-(1,2-dihydroxy-12-oxooctadecyl)-1,3-propanediol $^1$H-NMR (400 MHz, in CD$_3$OD) δ: 5.48 (2H, m), 3.86–3.72 (6H, m), 2.44 (4H, t), 2.29 (2H, t), 2.02 (2H, t), 1.53 (4H, quintet), 1.29 (12H, br.s), 0.89 (3H, t); IRv$_{max}$ (CHCl$_3$): 3300, 2925, 2850, 1710, 1560, 1420, 1060, 980 cm$^{-1}$.

EXAMPLE 273

2-Amino-2-(1,2-dihydroxy-12-hydroxyimino-octadecyl)-1,3-propanediol $^1$H-NMR (400 MHz, in CD$_3$OD) δ: 3.85–3.73 (4H, m), 2.42 (2H, t), 2.15 (2H, t), 1.62–1.32 (24H, m), 0.89 (3H, t); IRv$_{max}$ (CHCl$_3$): 3300(br), 2920, 2850, 1560, 1420, 1050 cm$^{-1}$.

EXAMPLE 274

2-Amino-2-(1,2,12-trihydroxy-4-octadecenyl)-1,3-propanediol

A lactone compound (2.00 g) of 2-amino-3-hydroxy-2-(1,2-dihydro-12-oxo-4-octadecenyl)propionic acid was dissolved in 66 ml of dry tetrahydrofuran and 800 mg of lithium aluminum hydride was portionwise added thereto at room temperature with stirring. The mixture was stirred at room temperature for 40 minutes and 0.8 ml of water, 0.8 ml of a 15% aqueous sodium hydroxide solution and 2.4 ml of water were added thereto in order. The insoluble matters were filtered off. The filtrate obtained was concentrated under reduced pressure, and the residue was washed with water and dried under reduced pressure to give 408 mg of the subject compound.

IRv$_{max}$ (KBr): 3280, 2920, 2850, 1640, 1470, 1400, 1075, 970 cm$^{-1}$; $^1$H-NMR (300 MHz, in CD$_3$OD, Ref:TMS) δ: 5.57 (1H, dr, J=15.3 and 6.6 Hz), 5.43 (1H, dt, J=15.3 and 6.9 Hz), 3.85 (1H, dt, J=6.9 and 1.0 Hz), 3.84–3.73 (5H, m), 3.67 (1H, d, J=1.0 Hz), 2.31 (2H, br.t, J=6.7 Hz), 2.02 (2H, br.q, J=6.4 Hz), 1.42–1.31 (20H, m), 0.90 (3H, t, J=6.8 Hz).

EXAMPLE 275

2-Amino-2-(1,2-dihydroxy-4-octadecenyl)-1,3-propanediol

A lactone compound (978 mg) of 2-amino-3-hydroxy-2-(1,2-dihydroxy-4-octadecenyl)propionic acid and 403 mg of lithium aluminum hydride were reacted in 33 ml of dry tetrahydrofuran according to the method of Example 274 to give 222 mg of the subject compound.

IRv$_{max}$ (KBr) cm$^{-1}$: 3300, 2920, 2850, 1575, 1480, 1390, 1060, 1105, 975; $^1$H-NMR (200 MHz, in CD$_3$OD, Ref:TMS) δ: 5.57 (1H, dt, J=15.4 and 6.4 Hz), 5.42 (1H, dt, J=15.4 and 6.4 Hz), 3.88–3.66 (6H, m), 2.31 (2H, t, J=6.7 Hz), 2.04–1.93 (2H, m), 1.28 (22H, br.s), 0.90 (t, J=6.5 Hz).

EXAMPLE 276

2-Amino-2-(1,2-dihydroxyoctadeeyl)-1,3-propanediol

2-Amino-2-(1,2-dihydroxy-4-octadecenyl)-1,3-propanediol (68.0 mg) was dissolved in 14 ml of methanol and 6.8 mg of 5% palladium-carbon was added thereto. The catalytic reduction was conducted at ordinary temperature and at atmospheric pressure day and night. After the reaction, the catalyst was filtered off and the filtrate was concentrated under reduced pressure to give 34.3 mg of the subject compound.

IRv$_{max}$ (KBr) cm$^{-1}$: 3300, 2920, 2850, 1575, 1460, 1370, 1060; $^1$H-NMR (200 MHz, in CD$_3$OD, Ref:TMS) δ: 3.77 (6H, m), 1.65 (2H, m), 1.27 (28H, br.s), 0.89 (3H, t, J=6.5 Hz).

EXAMPLE 277

2-Amino-2-(1,12-dihydroxy-4-octadecenyl)-1,3-propanediol

According to the method of Example 274, 35.0 mg of 2-amino-3-hydroxy-2-(1-hydroxy-12-oxo-4-octadecenyl)propionic acid and 14.4 mg of lithium aluminum hydride were reacted in 2.0 ml of dry tetrahydrofuran to give 8.9 mg of the subject compound.

IRv$_{max}$ (KBr) cm$^{-1}$: 3300, 2920, 2850, 1640, 1400, 970; $^1$H-NMR (200 MHz, in CD$_3$OD, Ref:TMS) δ: 5.40 (2H, m), 3.97–3.70 (5H, m), 3.58 (1H, m), 1.94 (4H, m), 1.70–1.21 (22H, m), 0.88 (3H, t, J=6.5 Hz).

In the same manner as above, the following compounds are obtained.

EXAMPLE 278

2-Amino-2-(1,2,12-trihydroxyoctadecyl)-1,3-propanediol

EXAMPLE 279

2-Amino-2-(1,12-dihydroxyoctadecyl)-1,3-propanediol

EXAMPLE 280

2-Amino-2-[2-(4-heptyloxyphenyl)ethyl]-1,3-propanediol (1) 2-(4-Heptyloxyphenyl)ethanol 2-(4-Hydroxyphenyl)ethanol (10.0 g) and sodium methoxide (4.30 g) were added to methanol (120 ml) and the mixture was refluxed under heating for 30 minutes. A solution of heptyl bromide (14.2 g) in methanol (30 ml) was dropwise added thereto and the mixture was refluxed under heating for 6 hours with stirring. The reaction mixture was concentrated and the concentrate was poured into ice water. The mixture was extracted with ethyl acetate. The ethyl acetate layer was washed with saturated brine and dried over magnesium sulfate. The solvent was distilled away and the resultant residue was purified by silica gel column chromatography (eluent; ethyl acetate:hexane=1:2) to give the subject compound (10.81 g).

melting point=37°–39° C. Rf value: 0.44 (ethyl acetate:n-hexane=1:2); $^1$H-NMR (CDCl$_3$)δ: 0.89 (3H, t, J=6.0 Hz), 1.10–1.99 (11H, m), 2.81 (2H, t, J=6.25 Hz), 3.68–4.05 (4H, m), 6.85 (2H, d, J=8.7 Hz), 7.15 (2H, d, J=8.7 Hz); IR: 3312, 1610, 1514, 1249 cm$^{-1}$; MS(EI): 236(M$^+$).

(2) 2-(4-Heptyloxyphenyl)ethylmethanesulfonate

Triethylamine (4.2 g) was added to a solution of the above-mentioned compound (10.81 g) in tetrahydrofuran (300 ml) and the mixture was cooled with ice. Methanesulfonyl chloride (5.23 g) was dropwise added thereto and the mixture was stirred at room temperature for 2 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the resultant residue was purified by silica gel column chromatography (eluent; ethyl acetate:hexane=1:5) to give the subject compound (11.32 g).

melting point=35°–36° C. Rf value: 0.33 (ethyl acetate:n-hexane=1:2); $^1$H-NMR (CDCl$_3$)δ: 0.90 (3H, t, J=6.0 Hz), 1.10–1.95 (10H, m), 2.86 (3H, s), 3.00 (2H, t, J=7.5 Hz), 3.94 (2H, t, J=6.3 Hz), 4.39 (2H, t, J=7.0 Hz), 6.85 (2H, d, J=8.7 Hz), 7.15 (2H, d, J=8.7 Hz); IR: 1354, 1516, 1249cm$^{-1}$; MS(EI): 314(M$^+$)

(3) 2-(4-Heptyloxyphenyl)ethyl Iodide

Sodium iodide (10 g) was added to a solution of the above-mentioned compound (11.32 g) in 2-butanone (400 ml) and the mixture was refluxed under heating for 4 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane=1:5) to give the subject compound (9.07 g).

Rf value: 0.80 (ethyl acetate:n-hexane=1:2); $^1$H-NMR (CDCl$_3$)δ: 0.89 (3H, t, J=6.0 Hz), 1.10–1.96 (10H, m), 2.98–3.48 (4H, m), 3.94 (2H, t, J=6.3 Hz), 6.84 (2H, d, J=8.7 Hz), 7.11 (2H, d, J=8.7 Hz); IR: 1610, 1512, 1246 cm$^{-1}$; MS(EI): 346(M$^+$).

(4) Diethyl 2-Acetamido-2-(4-heptyloxyphenyl)ethylmalonate

A solution of sodium ethoxide (4.99 g) in absolute ethanol (60 ml) was dropwise added to diethyl acetamidomalonate (15 g) in a stream of nitrogen and the mixture was stirred at 65° C. for 30 minutes. A solution of the above-mentioned compound (8.0 g) in tetrahydrofuran (30 ml) was dropwise added thereto and the mixture was stirred at 65° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the resultant residue was purified by silica gel column chromatography (eluent; ethyl acetate:hexane=1:5) to give the subject compound (6.50 g).

melting point=77°–80° C. Rf value: 0.44 (chloroform-:methanol=9:1); $^1$H-NMR (CDCl$_3$)δ: 0.89 (3H, t, J=6.0 Hz), 1.05–1.90 (16H, m), 1.98 (3H, s), 2.10–2.85 (4H, m), 3.92 (2H, t, J=7.0 Hz), 4.21 (4H, q, J=7.5 Hz), 6.65 (1H, br.s), 6.79 (2H, d, J=8.7 Hz), 7.05 (2H, d, J=8.7 Hz); IR: 3242, 1745, 1641, 1614, 1512, 1296 cm$^{-1}$; MS(EI): 435(M$^+$).

(5) 1,3-Propanediyl-2-acetamido-2-[2-(4-heptyloxyphenyl)ethyl]ylidenediacetate A solution (50 ml) of the above-mentioned compound (6.50 g) in anhydrous tetrahydrofuran was dropwise added to a solution (150 ml) of lithium aluminum hydride (1.70 g) in anhydrous tetrahydrofuran under ice-cooling in a stream of nitrogen and the mixture was stirred at room temperature for 2 hours. A saturated aqueous sodium sulfate solution was added to the reaction mixture under ice-cooling and aluminum hydroxide produced was filtered off. The solvent was distilled away and pyridine (66 ml) was added to the residue. Acetic anhydride (14 ml) was added thereto under ice-cooling and the mixture was allowed to stand at room temperature overnight. The reaction mixture was poured into ice-cooled 5% hydrochloric acid and the mixture was extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (4.54 g) as white crystals.

melting point=89°–91° C. Rf value: 0.35 (chloroform-:methanol=9:1); $^1$H-NMR (CDCl$_3$)δ: 0.89 (3H, t, J=6.0 Hz), 1.05–2.72 (14H, m), 1.95 (3H, s), 2.08 (6H, s), 3.92 (2H, t, J=7.0 Hz), 4.34 (4H, s), 5.65 (1H, br.s), 6.80 (2H, d, J=8.7 Hz), 7.10 (2H, d, J=8.7 Hz); IR: 3308, 1739, 1651, 1614, 1514, 1246 cm$^{-1}$; MS(EI): 435(M$^+$).

(6) 2-Amino-2-[2-(4-heptyloxyphenyl)ethyl]-1,3-propanediol Hydrochloride

An aqueous solution (100 ml) of lithium hydroxide (3.93 g) was added to a solution of the above-mentioned compound (4.54 g) in methanol (70 ml)-tetrahydrofuran (70 ml) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the resultant mixture was recrystallized from ethyl acetate. A 1M hydrochloric acid-ether solution (43 ml) was added to a solution of the resultant crystals in tetrahydrofuran (28 ml)-methanol (28 ml). The solvent was distilled away and the crystals precipitated were recrystallized from ethyl acetate to give the subject compound (1.30 g).

melting point=111°–112° C. Rf value: 0.20 (chloroform-:methanol=5:1); $^1$H-NMR (CDCl$_3$)δ: 0.88 (3H, t, J=5.5 Hz), 1.10–1.91 (14H, m), 3.56 (4H, t, J=5.0 Hz), 5.36 (2H, t, J=4.5 Hz), 6.84 (2H, d, J=8.7 Hz), 7.13 (2H, d, J=8.7 Hz), 7.85 (2H, br.s); IR: 3279, 1610, 1514, 1246 cm$^{-1}$; MS(EI): 309(M$^+$); elemental analysis: calculated C 62.50, H 9.32, N 4.05, found C 62.06, H 9.11, N 4.13.

EXAMPLE 281

2-Amino-2-[2-(4-nonyloxyphenyl)ethyl]-1,3-propanediol

(1) 2-(4-Nonyloxyphenyl)ethanol 2-(4-Hydroxyphenyl)ethanol (10.0 g) and sodium methoxide (4.30 g) were added to methanol (120 ml) and the mixture was refluxed under heating for 30 minutes. A solution of nonyl bromide (33 g) in methanol (20 ml) was dropwise added thereto and the mixture was refluxed under heating for 6 hours. The reaction mixture was concentrated, poured into ice water and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane=1:3) to give the subject compound (20 g). Rf value: 0.46 (ethyl acetate:n-hexane=1:2)

(2) 2-(4-Nonyloxyphenyl)ethylmethanesulfonate

Triethylamine (8.8 g) was added to a solution of the above-mentioned compound (20 g) in tetrahydrofuran (500 ml) and the mixture was cooled with ice. Methanesulfonyl chloride (9.17 g) was dropwise added thereto and the mixture was stirred at room temperature for 4 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane= 1:3) to give the subject compound (19.6 g).

melting point=37°–42° C. Rf value: 0.45 (ethyl acetate:n-hexane=1:2); $^1$H-NMR (CDCl$_3$)δ: 0.89 (3H, t, J=6.9 Hz), 1.05–1.90 (16H, m), 2.82 (3H, s), 2.99 (2H, t, J=6.1 Hz), 3.90 (2H, t, J=6.9 Hz), 4.35 (2H, t, J=6.9 Hz), 6.78 (2H, d, J=8.3 Hz), 7.06 (2H, d, J=8.3 Hz); IR: 1354, 1251 cm$^{-1}$; MS(EI): 342(M$^+$).

(3) 2-(4-Nonyloxyphenyl)ethyl Iodide

Sodium iodide (17 g) was added to a solution of the above-mentioned compound (19.6 g) in 2-butanone (650 ml) and the mixture was refluxed under heating for 4 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane= 1:3) to give the subject compound (18.08 g) as an oily substance.

Rf value: 0.69 (ethyl acetate:n-hexane=1:2); $^1$H-NMR (CDCl$_3$)δ: 0.90 (3H, t, J=5.5 Hz), 1.05–1.90 (14H, m), 2.90–3.40 (4H, m), 3.90 (2H, t, J=6.9 Hz), 6.76 (2H, d, J=8.3 Hz), 7.02 (2H, d, J=8.3 Hz); IR: 1610, 1512, 1246 cm$^{-1}$; MS(EI): 374(M$^+$).

(4) Diethyl 2-Acetamido-2-(4-nonyloxyphenyl)ethylmalonate

A solution of sodium ethoxide (10.4 g) in absolute ethanol (135 ml) was dropwise added to diethyl acetamidomalonate (31 g) in a stream of nitrogen and the mixture was stirred at 65° C. for 30 minutes. A solution of the above-mentioned compound (18 g) in tetrahydrofuran (63 ml) was dropwise added thereto and the mixture was stirred at 65° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane=1:3) to give the subject compound (8.78 g).

melting point=76°–77° C. Rf value: 0.38 (ethyl acetate:n-hexane=1:2); $^1$H-NMR (CDCl$_3$) δ: 0.89 (3H, t, J=6.8 Hz), 1.05–1.80 (2OH, m), 1.99 (3H, s), 2.20–2.75 (4H, m), 3.88 (2H, t, J=6.2 Hz), 4.15 (4H, q, J=6.9 Hz), 6.70 (1H, br.s), 6.72 (2H, d, J=8.3 Hz), 6.99 (2H, d, J=8.3 Hz); IR: 3281, 1743, 1645, 1512, 1246 cm$^{-1}$; MS(EI): 463(M$^+$).

(5) 1,3-Propanediyl-2-acetamido-2-[2-(4-nonyloxyphenyl)ethyl]ylidenediacetate

A solution (50 ml) of the above-mentioned compound (8.78 g) in anhydrous tetrahydrofuran was dropwise added to a solution (150 ml) of lithium aluminum hydride (1.79 g) in anhydrous tetrahydrofuran under ice-cooling in a stream of nitrogen and the mixture was stirred at room temperature for 2 hours. A saturated aqueous sodium sulfate solution was added to the reaction mixture under ice-cooling and aluminum hydroxide produced was filtered off. The solvent was distilled away and pyridine (84 ml) was added to the residue. Acetic anhydride (18 ml) was added thereto under ice-cooling and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (5.62 g) as white crystals.

melting point=88°–94° C. Rf value: 0.50 (chloroform:methanol=9:1); $^1$H-NMR (CDCl$_3$)δ: 0.89 (3H, t, J=6.9 Hz), 1.05–2.30 (18H, m), 1.93 (3H, s), 2.06 (6H, s), 3.89 (2H, t, J=7.0 Hz), 4.30 (4H, s), 5.60 (1H, br.s), 6.72 (2H, d, J=8.2 Hz), 7.01 (2H, d, J=8.2 Hz); IR: 3308, 1738, 1651, 1614, 1514, 1246 cm$^{-1}$; MS(EI): 463(M$^+$); elemental analysis: calculated C 67.36, H 8.91, N 3.02, found C 67.35, H 8.77, N 3.05.

(6) 2-Amino-2-[2-(4-nonyloxyphenyl) ethyl]-1,3-propanediol Hydrochloride

An aqueous solution (54 ml) of lithium hydroxide (4.57 g) was added to a solution of the above-mentioned compound (5.62 g) in methanol (86 ml)-tetrahydrofuran (86 ml) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue was crystallized from ethyl acetate. A 1M hydrochloric acid/ether solution (20 ml) was added to a solution of the resultant crystals in tetrahydrofuran (40 ml)-methanol (40 ml). The solvent was distilled away and crystals precipitated were recrystallized from ethyl acetate to give the subject compound (2.10 g).

melting point=106°–108° C. Rf value: 0.14 (chloroform:methanol=5:1); $^1$H-NMR (CDCl$_3$)δ: 0.85 (3H, t, J=4.1 Hz), 1.10–1.90 (18H, m), 3.50 (4H, d, J=4.7 Hz), 3.88 (2H, t, J=5.4 Hz), 5.32 (2H, t, J=4.9 Hz), 6.75 (2H, d, J=8.2 Hz), 7.02 (2H, d, J=8.2 Hz), 7.81 (2H, br.s); IR: 3277, 1610, 1514, 1248 cm$^{-1}$; MS(EI): 337(M$^+$); elemental analysis: calculated C 64.24, H 9.70, N 3.75, found C 64.16, H 9.51, N 3.70.

EXAMPLE 282

2-Amino-2-[2-(4-(N-heptyl-N-methylamino)phenyl) ethyl]-1,3-propanediol (1) 2-(4-Heptanoylaminophenyl)ethanol 2-(p-Aminophenyl)ethyl alcohol (13.8 g) and triethylamine (10.8 g) were added to tetrahydrofuran (300 ml) and the mixture was stirred for 30 minutes under ice-cooling. Heptanoyl chloride (15 g) was dropwise added thereto, and the mixture was stirred for 30 minutes under ice-cooling and then at room temperature for 3 hours. The reaction mixture was poured into ice water and extracted with ethyl acetate. The ethyl acetate layer was washed with saturated brine and dried over magnesium sulfate. The solvent was distilled away and the residue obtained was recrystallized from ethyl acetate-isopropyl alcohol to give the subject compound (13.15 g).

melting point=105°–110° C. Rf value: 0.41 (ethyl acetate:n-hexane=1:2→1:1); $^1$H-NMR (CDCl$_3$)δ: 0.89 (3H, t, J=6.8 Hz), 1.31–1.42 (8H, m), 1.70 (2H, tt, J=7.3 Hz, J=7.8 Hz), 2.35 (2H, t, J=7.3 Hz), 2.83 (2H, t, J=6.4 Hz), 3.84 (2H, dd, J=6.3 Hz, J=5.8 Hz), 7.12 (1H, br.s), 7.18 (2H, d, J=8.3 Hz), 7.45 (2H, d, J=8.3 Hz); IR: 3302, 1660, 1593, 1412 cm$^{-1}$; MS(EI): 249(M$^+$); elemental analysis: calculated C 70.97, H 9.33, N 5.52, found C 71.30, H 9.26, N 5.66.

(2) 2-(4-Heptanoylaminophenyl) ethoxytetrahydropyran

The above-mentioned compound (7.0 g), 3,4-dihydro-2H-pyran (3.08 g) and p-toluenesulfonic acid (180 mg) were added to tetrahydrofuran (50 ml) and dichloromethane (50 ml), and the mixture was stirred at room temperature for 7 hours. Triethylamine (0.5 ml) was added thereto and the solvent was distilled away. The resultant residue was purified by silica gel column chromatography (eluent; ethyl acetate:hexane=1:1) to give the subject compound (11 g).

melting point=66°–68° C. Rf value: 0.72 (ethyl acetate:n-hexane=1:1); $^1$H-NMR (CDCl$_3$)δ: 0.89 (3H, t, J=6.4 Hz), 1.31–2.05 (14H, m), 2.34 (2H, t, J=7.3 Hz), 2.87 (2H, t, J=6.4 Hz), 3.47 (2H, t, J=6.4 Hz), 3.47 (2H, dr, J=7.3 Hz, J=9.7 Hz), 3.77 (1H, m), 3.92 (1H, dr, J=7.3 Hz, J=9.8 Hz), 4.58 (1H, t, J=3.9 Hz), 7.19 (2H, d, J=8.3 Hz), 7.42 (2H, d, J=8.3 Hz); IR: 3273, 1655, 1599, 1033 cm$^{-1}$; MS(EI): 333(M$^+$).

(3) 2-(4-(N-Heptanoyl-N-methylamino) phenyl)ethoxytetrahydropyran

The above-mentioned compound (7.0 g) and potassium-t-butoxide (5.18 g) were added to ethylene glycol dimethyl ether (120 ml) and the mixture was stirred at 60° C. for 30 minutes. A solution of methyl iodide (16.39 g) in ethylene glycol dimethyl ether (4 ml) was added thereto and the mixture was stirred at 60° C. for 1 hour. The solvent was distilled away and the residue obtained was purified by silica gel column chromatography (eluent; ethyl acetate:hexane=1:7) to give the subject compound (5.95 g).

Rf value: 0.23 (ethyl acetate:n-hexane=1:5); $^1$H-NMR (CDCl$_3$)δ: 0.83 (3H, t, J=6.8 Hz), 1.17–1.26 (6H, m), 1.42–1.60 (4H, m), 1.63–1.90 (4H, m), 2.04 (2H, t, J=6.4 Hz), 3.47 (2H, t, J=6.4 Hz ), 3.47 (2H, dt, J=7.3 Hz, J=9.7 Hz ), 3.77 (1H, m), 3.92 (1H, dt, J=7.3 Hz, J=9.8 Hz), 4.58 (1H, t, J=3.9 Hz), 7.19 (2tt, d, J=8.3 Hz), 7.42 (2H, d, J=8.3 Hz); IR: 3273, 1655, 1599, 1033 cm$^{-1}$; MS (EI): 333 (M$^+$).

(4) 2-(4-(N-Heptyl-N-methylamino)phenyl) ethoxytetrahydropyran

A solution of the above-mentioned compound (5.95 g) in tetrahydrofuran (90 ml) was cooled to 5° C. and a diborane-tetrahydrofuran complex (tetrahydrofuran 1M solution: 32.2 ml) was added thereto. The mixture was stirred at 5° C. for 3 hours and methanol (60 ml) was added thereto. The solvent was distilled away and the residue obtained was purified by silica gel column chromatography (eluent; ethyl acetate:hexane=1:7) to give the subject compound (3.6 g).

Rf value: 0.49 (ethyl acetate:n-hexane=1:2); $^1$H-NMR (CDCl$_3$)δ: 0.88 (3H, t, J=7.3 Hz), 1.22–1.40 (8H, m), 1.42–1.62 (8H, m), 1.68–1.84 (2H, m), 2.81 (2H, t, J=7.3 Hz), 2.89 (3H, s), 3.26 (2H, t, J=7.8 Hz), 3.46 (1H, m), 3.57 (1H, dt, J=7.4 Hz, J=7.8 Hz), 3.81 (1H, m), 3.89 (1H, dr, J=7.3 Hz, J=7.8 Hz), 4.60 (1H, t, J=3.0 Hz), 6.63 (2H, d, J=8.8 Hz), 7.08 (2H, d, J=8.8 Hz); IR: 1616, 1365, 1030 cm$^{-1}$; MS(EI): 333(M$^+$).

(5) 2-(4-(N-Heptyl-N-methylamino)phenyl)ethyl Alcohol p-Toluenesulfonic acid (3.10 g) was added to a solution of the above-mentioned compound (3.36 g) in methanol (60 ml) and the mixture was stirred at room temperature for 3 hours. Triethylamine (3 ml) was added thereto and the solvent was distilled away. The residue obtained was purified by silica gel column chromatography (eluent; ethyl acetate:hexane=1:12) to give the subject compound (3.22 g).

Rf value: 0.31 (methanol:chloroform=1:9); $^1$H-NMR (CDCl$_3$)δ: 0.88 (3H, t, J=6.9 Hz), 1.22–1.38 (10H, m), 2.77 (2H, t, J=6.4 Hz), 2.90 (3H, s), 3.27 (2H, t, J=7.4 Hz), 3.80 (1H, t, J=6.4 Hz), 6.66 (2H, d, J=8.7 Hz), 7.08 (2H, d, J=8.7 Hz); IR: 3368, 1369 cm$^{-1}$; MS(EI): 249(M$^+$).

(6) 2-(4-(N-Heptyl-N-methylamino)phenyl) ethylmethanesulfonate

Triethylamine (2.22 g) was added to a solution of the above-mentioned compound (3.65 g) in tetrahydrofuran (60 ml) and the mixture was cooled with ice. Methanesulfonyl chloride (3.01 g) was dropwise added thereto and the mixture was stirred at room temperature for 2 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane=1:5) to give the subject compound (4.02 g).

Rf value: 0.56 (ethyl acetate:n-hexane=1:5); $^1$H-NMR (CDCl$_3$)δ: 0.88 (3H, t, J=6.4 Hz), 1.24–1.29 (10H, m), 2.84 (3H, s), 2.90 (3H, s), 2.96 (2H, t, J=6.8 Hz), 3.27 (2H, t, J=7.3 Hz), 4.36 (2H, t, J=6.9 Hz), 6.64 (2H, d, J=8.3 Hz), 7.07 (2H, d, J=8.3 Hz).

(7) 2-(4-(N-heptyl-N-methylamino)phenyl)ethyl Iodide

Sodium iodide (3.66 g) was added to a solution of the above-mentioned compound (4.00 g) in 2-butanone (200 ml) and the mixture was refluxed under heating for 2 hours. The reaction mixture was concentrated and extracted with ethyl acetate. The ethyl acetate layer was washed with saturated brine and dried over magnesium sulfate. The solvent was distilled away and the resultant residue was purified by silica gel column chromatography (eluent; ethyl acetate:hexane=1:10) to give the subject compound (2.58 g) as an oily substance.

Rf value: 0.78 (ethyl acetate:n-hexane=1:10); $^1$H-NMR (CDCl$_3$) δ: 0.88 (3H, t, J=7.3 Hz), 1.22–1.40 (10H, m), 2.90 (2H, s), 3.07 (2H, t, J=7.8 Hz), 3.63 (2H, t, J=5.9 Hz), 3.65 (2H, t, J=7.3 Hz), 6.62 (2H, d, J=8.3 Hz), 7.04 (2H, d, J=8.3 Hz); IR: 1614, 1521, 1371, 804 cm$^{-1}$; MS(EI): 359(M$^+$).

(8) Diethyl 2-Acetamide-2-(4-(N-heptyl-N-methylamino)phenyl)ethylmalonate

A solution of sodium ethoxide (1.54 g) in absolute ethanol (18 ml) was dropwise added to diethyl acetamidomalonate (4.63 g) in a stream of nitrogen and the mixture was stirred at 60° C. for 30 minutes. A solution of the above-mentioned compound (18 g) in tetrahydrofuran (7 ml) was dropwise added thereto and the mixture was stirred at 60° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane=1:2) to give the subject compound (1.92 g) as an oily substance.

Rf value: 0.49 (ethyl acetate:n-hexane=1:2); $^1$H-NMR (CDCl$_3$) δ: 0.88 (3H, t, J=6.8 Hz), 1.23–1.29 (10H, m), 1.24 (6H, t, J=7.4 Hz), 1.99 (3H, s), 2.38 (2H, m), 2.63 (2H, m), 2.88 (3H, s), 3.25 (2H, t, J=7.3 Hz), 4.21 (4H, q, J=7.4 Hz), 6.60 (2H, d, J=8.3 Hz), 6.76 (1H, br.s), 6.99 (2H,d, J=8.3 Hz); IR: 3285, 1739, 1682, 1616, 1371 cm$^{-1}$; MS(EI): 448(M$^+$).

(9) 1,3-Propanediyl-2-acetamide-2-[2-(4-(N-heptyl-N-methylamino)phenyl)ethyl]ylidenediacetate A solution (20 ml) of the above-mentioned compound (1.92 g) in anhydrous tetrahydrofuran was added dropwise to a solution (35 ml) of lithium aluminum hydride (0.49 g) in anhydrous tetrahydrofuran under ice-cooling in a stream of nitrogen. The mixture was stirred at room temperature for 2 hours. A saturated aqueous sodium sulfate solution was added to the reaction mixture under ice-cooling and aluminum hydroxide produced was filtered off. The solvent was distilled away and pyridine (84 ml) was added to the residue. Acetic anhydride (19 ml) was added thereto under ice-cooling and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (1.2 g) as an oily substance.

melting point=88°–94° C. Rf value: 0.50 (chloroform:methanol=9:1); $^1$H-NMR (CDCl$_3$) δ: 0.88 (3H, t, J=6.9 Hz), 1.24–1.29 (10H, m), 1.94 (3H, s), 2.08 (6H, s), 2.15 (2H, m), 2.51 (2H, m), 2.89 (3H, s), 3.26 (2H, t, J=7.8 Hz), 4.36 (4H, s), 5.60 (1H, br.s), 6.63 (2H, d, J=8.3 Hz), 7.03 (2H, d, J=8.3 Hz); IR: 3314, 1739, 1651, 1616, 1386 cm$^{-1}$; MS(EI): 448(M$^+$).

(10) 2-Amino-2-[2-(4-(N-heptyl-N-methylamino)phenyl)ethyl]-1,3-propanediol Hydrochloride An aqueous solution (12 ml) of lithium hydroxide (1.01 g) was added to a solution of the above-mentioned compound (1.20 g) in methanol (18 ml)-tetrahydrofuran (18 ml) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue was recrystallized from ethyl acetate. A 1M hydrochloric acid/ether solution (14 ml) was added to a solution of the resultant crystals in tetrahydrofuran (7 ml)-methanol (7 ml). The solvent was distilled away and the crystals precipitated were recrystallized from ethyl acetate to give the subject compound (0.11 g).

melting point=128°–129° C. Rf value: 0.20 (chloroform:methanol=9:1); $^1$H-NMR (CDCl$_3$) δ: 0.84 (3H, t, J=6.8 Hz), 1.25–1.46 (10H, m), 1.70–1.74 (2H, m), 2.42–2.46 (2H, m), 2.81 (3H, s), 3.23 (2H, t, J=7.4 Hz), 3.49 (4H, d, J=5.3 Hz), 5.35 (2H, t, J=4.9 Hz), 6.59 (2H, d, J=8.3 Hz), 6.97 (2H, d, J=8.3 Hz); IR: 3277, 1610, 1514, 1248 cm$^{-1}$; MS(EI): 322(M$^+$); elemental analysis: calculated C 59.13, H 9.92, N 7.26 (1.5H$_2$O), found C 59.23, H 9.39, N 7.14.

EXAMPLE 283

2-Amino-2-[2-(4-heptanoylaminophenyl)ethyl]-1,3-propanediol (1) 2-(4-Heptanoylaminophenyl)ethanol 2-(p-Aminophenyl)ethyl alcohol (13.8 g) and triethylamine (10.8 g) were added to tetrahydrofuran (300 ml) and the mixture was stirred under ice-cooling for 30 minutes. Heptanoyl chloride (15 g) was dropwise added thereto and the mixture was stirred under ice-cooling for 30 minutes and then at room temperature for 3 hours. The reaction mixture was poured into ice water and extracted with ethyl acetate. The ethyl acetate layer was washed with saturated brine and dried over magnesium sulfate. The solvent was distilled away and the resultant residue was recrystallized from ethyl acetate-isopropyl alcohol to give the subject compound (13.15 g).

melting point=105°–110° C. Rf value: 0.41 (ethyl acetate:n-hexane=1:2→1:1); $^1$H-NMR (CDCl$_3$)δ: 0.89 (3H, t, J=6.8 Hz), 1.31–1.42 (8H, m), 1.70 (2H, tt, J=7.3 Hz, J=7.8 Hz), 2.35 (2H, t, J=7.3 Hz), 2.83 (2H, t, J=6.4 Hz), 3.84 (2H, dd, J=6.3 Hz, J=5.8 Hz), 7.12 (1H, br.s), 7.18 (2H, d, J=8.3 Hz), 7.45 (2H, d,J=8.3 Hz); IR: 3302, 1660, 1593, 1412 cm$^{-1}$; MS(EI): 249(M$^+$); elemental analysis: calculated C 70.97, H 9.33, N 5.52, found C 71.30, H 9.26, N 5.66.

(2) 2-(4-Heptanoylaminophenyl)ethylmethanesulfonate

Triethylamine (3.67 g) was added to the above-mentioned compound (6.00 g) in tetrahydrofuran (100 ml) and the mixture was cooled with ice. Methanesulfonyl chloride (5.00 g) was dropwise added thereto and the mixture was stirred at room temperature for 2 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane=1:1) to give the subject compound (6.02 g).

melting point=103°–105° C. Rf value: 0.56 (ethyl acetate:n-hexane=1:5); $^1$H-NMR (CDCl$_3$) δ: 0.89 (3H, t, J=6.4 Hz), 1.22–1.40 (6H, m), 1.72 (2H, t, J=7.3 Hz), 2.35 (2H, t, J=7.3 Hz), 2.87 (3H, s), 3.02 (2H, t, J=7.3 Hz), 4.39 (2H, t, J=6.4 Hz), 7.13 (1H, br.s), 7.19 (2H, d, J=8.3 Hz), 7.48 (2H, d, J=8.3 Hz); IR: 3307. 1659, 1337 cm$^{-1}$; MS(EI): 327(M$^+$); elemental analysis: calculated C 70.97, H 9.33, N 5.52, found C 71.30, H 9.26, N 5.66.

(3) 2-(4-Heptanoylaminophenyl)ethyl Iodide

Sodium iodide (5.51 g) was added to a solution of the above-mentioned compound (6.02 g) in 2-butanone (300 ml) and the mixture was refluxed under heating for 2 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane=1:5) to give the subject compound (5.31 g) as an oily substance.

melting point=82°–86° C. Rf value: 0.33 (ethyl acetate:n-hexane=1:5); $^1$H-NMR (CDCl$_3$) δ: 0.87 (3H, t, J=6.9 Hz), 1.21–1.40 (6H, m), 1.70 (2H, t, J=7.3 Hz), 2.32 (2H, t, J=7.3 Hz), 3.12 (2H, t, J=7.8 Hz), 3.30 (2H, t, J=7.4 Hz), 7.05 (1H, br.s), 7.12 (2H, d, J=8.3 Hz), 7.44 (2H, d, J=8.3 Hz); IR: 3450, 1660, 1595, 709 cm$^{-1}$; MS(EI): 359(M$^+$); elemental analysis: calculated C 50.15, H 6.17, N 3.96, found C 50.11, H 6.06, N 3.96.

(4) Diethyl-2-tert-butoxycarbonylamino-2-(4-heptanoylaminophenyl)ethyl Malonate

A solution of sodium ethoxide (3.19 g) in absolute ethanol (40 ml) was dropwise added to diethyl 2-tert-butoxycarbonyl-aminomalonate (12.12 g) in a stream of nitrogen and the mixture was stirred at 50° C. for 30 minutes. A solution of the above-mentioned compound (5.31 g) in tetrahydrofuran (20 ml) was dropwise added thereto and the mixture was stirred at 60° C. for 5 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane=1:7) to give the subject compound (4.29 g).

Rf value: 0.49 (ethyl acetate:n-hexane=1:2); $^1$H-NMR (CDCl$_3$) δ: 0.82 (3H, t, J=6.9 Hz), 1.18 (6H, t, J=6.8 Hz), 1.21–1.40 (6H, m), 1.37 (9H, s), 1.64 (2H, t, J=7.4 Hz), 2.27 (2H, t, J=7.3 Hz), 2.42 (2H, m), 2.51 (2H, m), 4.05–4.25 (4H, m), 5.92 (1H, br.s), 7.00 (1H, br.s), 7.03 (2H, d, J=8.3 Hz), 7.33 (2H, d, J=8.3 Hz); IR: 3319, 1772, 1739, 1666 cm$^{-1}$; MS(EI): 506(M$^+$).

2-tert-Butoxycarbonyl-amino-
2-[2-(4-heptanoylaminophenyl)ethyl]-1,3-propanediol Sodium borohydride (0.32 g) was added to a solution of the above-mentioned compound (4.29 g) in methanol in a stream of nitrogen. The residue was purified by silica gel column chromatography (eluent; ethyl acetate:hexane=2:1) to give the subject compound (0.56 g) as an oily substance.

Rf value: 0.31 (acetic acid:n-hexane=2:1); $^1$H-NMR (CDCl$_3$) δ: 0.89 (3H, t, J=6.8 Hz), 1.21–1.46 (10H, m), 1.45 (9H, s), 1.70–1.90 (4H, m), 2.34 (2H, t, J=7.3 Hz), 2.59 (2H, t, J=8.7 Hz), 3.61–3.64 (2H, m), 3.85–3.89 (2H, m), 5.03 (1H, br.s), 7.13 (2H, d, J=8.3 Hz), 7.42 (2H, d, J=8.3 Hz); IR: 3310, 1668, 1602 cm$^{-1}$; MS(EI): 422(M$^+$).

(6) 2-Amino-2-[2-(4-heptanoylaminophenyl)
ethyl]-1,3-propanediol

A solution of the above-mentioned compound (0.56 g) in trifluoroacetic acid (4 ml) was stirred under ice-cooling for 4 hours. The reaction mixture was concentrated and ethyl acetate (110 ml) was added thereto. The mixture was washed with a saturated aqueous sodium hydrogencarbonate solution and dried over anhydrous magnesium sulfate. The solvent was distilled away and the residue was recrystallized from methanol-ethyl acetate to give the subject compound (0.14 g) as white crystals.

melting point=133°–135° C. Rf value: 0.47 (chloroform:methanol=5:1); $^1$H-NMR (DMSO-d$_6$) δ: 0.85 (3H, t, J=6.4 Hz), 1.26–1.57 (12H, m), 2.25 (2H, t, J=3.9 Hz), 3.17–3.25 (4H, m), 4.43 (2H, t, J=4.9 Hz), 7.07 (2H, d, J=8.8 Hz), 7.45 (2H, d, J=8.7 Hz), 9.73 (1H, br.s); IR: 3317, 1653, 1601 cm$^{-1}$; MS(EI): 322(M$^+$); elemental analysis: calculated C 67.05, H 9.38, N 8.69 (1.5H$_2$O), found C 66.95, H 9.08, N 8.25.

EXAMPLE 284

2-Amino-2-[2-(4-octylphenyl)ethyl]-1,3-propanediol (1) Ethyl
2-Ethoxycarbonyl-4-(4-octylphenyl)butyrate Sodium (2.67 g) was dissolved in absolute ethanol (100 ml) and diethyl malonate (18.6 g) was dropwise added thereto at 27°–30° C. for 3 minutes. The mixture was stirred at 40° C. for 40 minutes and 2-(4-octylphenyl)ethyl iodide (40 g) was dropwise added to the reaction mixture at 44°–45° C. over 10 minutes. The mixture was refluxed at 50° C. for 1 hour and stirred under heating for 1.5 hours. The reaction mixture was cooled and the solvent was distilled away under reduced pressure. Water was added thereto and extracted with ethyl acetate. The extract was washed with water and dried over magnesium sulfate. The solvent was distilled away under reduced pressure and the residue obtained was subjected to silica gel column chromatography to give the subject compound (28.8 g).

IR: 2920, 2850, 1745, 1725, 1240, 1140, 1040 cm$^{-1}$.

(2) Ethyl
2-amino-2-ethoxycarbonyl-4-(4-octylphenyl)butyrate

60% Sodium hydride (0.38 g) was suspended in dry dimethylformamide (30 ml) and ethyl 2-ethoxycarbonyl-4-(4-octylphenyl)butyrate (3.0 g) was added thereto. The mixture was stirred at room temperature for 2 hours. O-(2,4-Dinitrophenyl)hydroxylamine (1.14 g) was added thereto and the mixture was stirred at room temperature for 5 hours. The reaction mixture was poured into cool water and extracted with toluene. The extract was washed with aqueous sodium chloride and dried over magnesium sulfate. The solvent was distilled away under reduced pressure to give 3 g of the subject compound.

IR: 3380, 3320, 2930, 2850, 1730, 1180 cm$^{-1}$.

(3) 2-Amino-2-[2-(4-octylphenyl)
ethyl]-1,3-propanediol

A suspension of sodium borohydride (0.60 g) and lithium bromide (1.66 g) in ethanol (17 ml) was stirred at room temperature for 25 minutes. Ethyl 2-amino-2-ethoxycarbonyl-4-(4-octylphenyl)butyrate (1.24 g) was dropwise added thereto over 3 minutes and the mixture was stirred at room temperature for 5 hours. Water (40 ml) was added to the reaction mixture and the mixture was stirred for 40 minutes. The crystals precipitated was collected by filtration and dried to give 0.68 g of the subject compound, melting point=125°–126° C. Treatment of the subject compound with hydrochloric acid-ethanol gives the corresponding hydrochloride.

EXAMPLE 285

2-Amino-2-{2-[4-(7-octenyloxy)phenyl]ethyl}-1,3-propanediol (1) 2-[4-(7-Octenyloxy)phenyl]ethyl Alcohol Sodium ethoxide (4.98 g) was added to a solution (240 ml) of 2-(4-hydroxyphenyl)ethyl alcohol (8.68 g) in absolute ethanol and the mixture was stirred at 50° C. for 30 minutes. A solution of 7-octenyl bromide (10 g) in anhydrous tetrahydrofuran was dropwise added thereto and the mixture was stirred at 50° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue was purified by silica gel chromatography (eluent; ethyl acetate:hexane=1:5) to give the subject compound (10.76 g) as an oily substance.

$^1$H-NMR (DMSO) δ: 1.35 (6H, s), 1.50–2.16 (4H, m), 2.62 (2H, t, J=6 Hz), 3.41–3.65 (2H, m), 3.88 (2H, t, J=6 Hz), 4.63 (1H, t, J=5 Hz), 4.95 (2H, txt, J=7 Hz, 2 Hz), 5.66–5.96 (1H, m), 6.74 (2H, d, J=9 Hz), 7.04 (2H, d, J=9 Hz); IRvNEAT$_{max}$: 3445, 2251, 1028, 823, 761 cm$^{-1}$; MS 248 (M$^+$).

(2) 2-[4-(7-Octenyloxy)phenyl]ethyl Iodide

Triethylamine (7.25 ml) was added to a solution (100 ml) of the above-mentioned compound (10.76 g) in dichloromethane and the mixture was cooled with ice. Methanesulfonyl chloride (3.69 ml) was dropwise added thereto and the mixture was stirred at room temperature for 1 hour. The reaction mixture was poured into ice water and extracted with chloroform. The chloroform layer was washed with saturated brine and dried over anhydrous magnesium sulfate. The solvent was distilled away and sodium iodide (7.78 g) was added to a solution (200 ml) of the residue in 2-butanone. The mixture was refluxed under heating for 5 hours. The reaction mixture was concentrated, poured into ice water and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:3) to give the subject compound (13.72 g) as an oily substance.

$^1$H-NMR (CDCl$_3$) δ: 1.53 (6H, s), 1.68–2.07 (4H, m), 2.96–3.18 (4H, m), 3.90 (2H, t, J=6 Hz), 4.92 (2H, m), 5.56–5.96 (1H, m), 6.76 (2H, d, J=9 Hz), 7.03 (2H, d, J=9 Hz); IRvNEAT$_{max}$: 2930, 1511, 1246cm$^{-1}$; MS 358 (M$^+$).

(3) Diethyl 2-Acetamido-2-[4-[7-octenyloxy]phenyl]ethylmalonate

Sodium ethoxide (5.72 g) was added to a solution (100 ml) of diethyl acetamidomalonate (16.60 g) in absolute ethanol and the mixture was stirred at 65° C. for 30 minutes. A solution (100 ml) of the above-mentioned compound (13.69 g) in absolute ethanol was dropwise added thereto and the mixture was stirred at 65° C. for 3 hours. The reaction mixture was concentrated, poured into ice water and extracted with ethyl acetate. The ethyl acetate layer was washed with saturated brine and dried over anhydrous magnesium sulfate. The solvent was distilled away and the residue was purified by silica gel chromatography (eluent; ethyl acetate:hexane=1:2) to give the subject compound (4.60 g).

melting point: 50°–53° C. $^1$H-NMR (CDCl$_3$)δ: 1.25 (8H, t), 1.30–1.49 (6H, m), 1.72–1.79 (2H, m), 2.00 (3H, s), 2.63–2.67 (2H, m), 3.91 (2H, t, J=6 Hz), 4.15–4.25 (4H, m), 4.92–5.03 (2H, m), 5.76–5.86 (1H, m), 6.79 (2H, d, J=8 Hz), 7.04 (2H, d, J=8 Hz); IRv$_{max}$: 3251, 2931, 1743, 1515, 1247, 1186cm$^{-1}$; MS 447 (M$^+$).

(4) 2-Acetamido-2-[2-{4-(7-octenyloxy)phenyl}ethyl]-1,3-propanediol Diacetate A solution (70 ml) of the above-mentioned compound (4.47 g) in anhydrous tetrahydrofuran was dropwise added to a solution (50 ml) of lithium aluminum hydride (1.52 g) in anhydrous tetrahydrofuran under ice-cooling. The mixture was heated to room temperature and stirred for 3 hours. A saturated aqueous sodium sulfate solution was dropwise added thereto under ice-cooling to decompose lithium aluminum hydride and the same was filtered off. The reaction mixture was dried over anhydrous sodium sulfate and the solvent was distilled away. Pyridine (19.8 ml) was added to the residue. Acetic anhydride (18.4 ml) was added thereto under ice-cooling and the mixture was allowed to stand at room temperature overnight. The reaction mixture was poured into ice water and extracted with ethyl acetate. The ethyl acetate layer was washed with 7% hydrochloric acid and saturated brine and dried over anhydrous magnesium sulfate. The solvent was distilled away and the residue was purified by silica gel chromatography (eluent; ethyl acetate:hexane=1:2) to give the subject compound (2.23 g) as white crystals.

melting point=88°–90° C. MS 447 (M$^+$); $^1$H-NMR (CDCl$_3$)δ: 1.54–1.57 (2H, m), 1.76 (2H, m), 1.96 (3H, s), 2.03–2.09 (8H, m), 2.52–2.57 (2H, m), 3.92 (2H, t, J=6 Hz), 4.34 (4H, s), 4.93–5.02 (2H, m), 5.64 (1H, s), 5.64–5.86 (1H, m), 6.81 (2H, d, J=4 Hz), 7.08 (2H, d, J=4 Hz) IRv: 3308, 1738, 1652, 1247, 1227 cm$^{-1}$.

(5) 2-Amino-2-{2-[4-(7-octenyloxy)phenyl]ethyl}-1,3-propanediol

An aqueous solution (20 ml) of lithium hydroxide (0.84 g) was added to a solution (20 ml) of the above-mentioned compound (1.01 g) in methanol and the mixture was refluxed under heating for 2 hours. The reaction mixture was concentrated and extracted with ethyl acetate. The ethyl acetate layer was washed with saturated brine and dried over anhydrous magnesium sulfate. The solvent was distilled away and the residue was recrystallized from ethyl acetate to give the subject compound (0.32 g), melting point 95°–98° C.

$^1$H-NMR (CDCl$_3$) δ: 1.36–1.48 (2H, m), 1.73–1.78 (2H, m), 2.06 (2H, q, J=8 Hz), 2.59 (2H, t, J=8 Hz), 3.56 (4H, q, J=12 Hz), 3.91 (2H, q, J=8 Hz), 4.93–5.02 (2H, m), 5.76–5.86 (1H, m), 6.82 (2H, d, J=10 Hz), 7.09 (2H, t, J=10 Hz); IRv: 3350, 2938, 1512, 1245, 1021 cm$^{-1}$.

EXAMPLE 286

2-Amino-2-[2-(4-octyloxyphenyl)ethyl]-1,3-propanediol Hydrochloride

(1) 2-Acetamido-2-[2-(4-octyloxyphenyl)ethyl]-1,3-propanediol Diacetate

10% Palladium carbon (0.1 g) was added to a solution (30 ml) of 2-acetamido-2-[2-{4-(7-octenyloxy)phenyl}ethyl]-1,3propanediol diacetate (1.27 g) in ethanol and the mixture was stirred at ordinary temperature and at atmospheric pressure for 6 hours under a hydrogen atmosphere. The catalyst was filtered off and the filtrate was concentrated. The residue was collected by filtration to give the subject compound (1.18 g).

melting point=99°–102° C. $^1$H-NMR (CDCl$_3$)δ: 0.86 (3H, t, J=8 Hz), 1.26–1.56 (12H, m), 1.94 (3H, s), 2.07 (6H, s), 2.12–2.17 (2H, m), 2.50–2.55 (2H, m), 3.89 (2H, t, J=6 Hz), 4.32 (4H, s), 5.62 (1H, s), 6.79 (2H, d, J=8 Hz), 7.06 (2H, d, J=8 Hz); IRv: 3311, 2917, 1738, 1651, 1247 cm$^{-1}$.

(2) 2-Amino-2-{2-(4-octyloxyphenyl)ethyl}-1,3-propanediol Hydrochloride

An aqueous solution (20 ml) of lithium hydroxide (0.94 g) was added to a solution (20 ml) of the above-mentioned compound (1.13 g) in ethanol and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue was dissolved in methanol (10 ml). A solution (10 ml) of 1M hydrochloric acid in ether was added thereto and the crystals precipitated were collected by filtration to give the subject compound (0.60 g, 65.2%).

melting point=59°–61° C. $^1$H-NMR (CDCl$_3$) δ: 0.88 (3H, t, J=4 Hz), 1.28–1.41 (12H, m), 1.73–1.75 (2H, m), 1.95(2H, m), 2.60 (2H, s), 3.78–3.92 (6H, m), 6.80 (2H, m), 7.10 (2H, m); IRv: 3354, 1609, 1513, 1247 cm$^{-1}$.

EXAMPLE 287

2-Amino-2-(13-phenyltridecyl)-1,3-propanediol (1) 12-(Tetrahydropyran-2-yloxy)dodecanol 1,12-Dodecanediol (25 g) was dissolved in dichloromethane (200 ml) and tetrahydrofuran (200 ml), and a catalytic amount of p-toluenesulfonic acid and 3,4-dihydro-2H-pyran (14 ml) were added thereto. The mixture was allowed to stand at room temperature for 2 hours and the reaction was stopped by triethylamine. The solvent was distilled away and the residue obtained was purified by silica gel column chromatography (eluent; ethyl acetate:hexane=1:2) to give the subject compound (15.46 g) as a colorless, oily substance.

Rf value: 0.39 (ethyl acetate:hexane=1:2); $^1$H-NMR (CDCl$_3$/TMS) δ: 1.28 (16H, m), 1.62 (10H, m), 3.65 (6H, m), 4.59 (1H, br.s); IR(neat): 3417, 2927, 2854, 1034 cm$^{-1}$; MS(EI): 285 (M$^+$–1).

(2) 12-(Tetrahydropyran-2-yloxy)dodecanal

Oxalyl chloride (6.9 ml) was slowly added dropwise to a solution (85 ml) of dimethyl sulfoxide (11.3 ml) in dichloromethane at −78° C. under a nitrogen atmosphere. The mixture was stirred at −78° C. for 20 minutes and a solution of the above-mentioned compound (15.25 g) in dichloromethane (130 ml) was gradually added thereto over 30 minutes. The mixture was stirred at −78° C. for 20 minutes and triethylamine (37 ml) was added thereto. The reaction was stopped with 150 ml of water and the reaction mixture was extracted twice with 150 ml of chloroform. The chloroform layer was dried and the solvent was distilled away. The residue obtained was purified by silica gel column chromatography (eluent; ethyl acetate:hexane=1:3) to give the subject compound (13.54 g) as a slightly yellow, oily substance.

Rf value: 0.63 (ethyl acetate:hexane=1:2); $^1$H-NMR (CDCl$_3$/TMS) δ: 1.29 (14H, m), 1.58 (10H, m), 2.43 (2H, dr, J=2 & 6 Hz), 3.26–4.20 (4H, m), 4.59 (1H, br.s), 9.79 (1H, t, J=2 Hz); IR (neat): 2929, 2855, 1727 cm$^{-1}$; MS (EI): 284 (M$^+$).

(3) 1-Phenyl-13-(tetrahydropyran-2-yloxy)-1-tridecene

A solution (31 ml) of 1.6M butyl lithium in hexane was added to a suspension of benzyltriphenylphosphonium chloride (19.44 g) in tetrahydrofuran (100 ml) under ice-cooling and a solution of the above-mentioned compound (13.54 g) in tetrahydrofuran (30 ml) was dropwise added thereto under ice-cooling. The mixture was stirred for 3 hours. The reaction mixture was concentrated and the concentrate was poured into 200 ml of ice water. The mixture was extracted twice with 150 ml of ethyl acetate and the extract was dried and concentrated. The residue obtained was purified by silica gel column chromatography (eluent; ethyl acetate:hexane=1:9) to give the subject compound (2.60 g).

Rf value: 0.66 (ethyl acetate:hexane=1:5); $^1$H-NMR (CDCl$_3$/TMS) δ: 1.30 (14H, m), 1.58 (10H, m), 2.22 (2H, m), 3.60 & 3.80 (4H, 2m), 4.59 (1H, br.s), 6.19–6.53 (2H, m), 7.30 (5H, m); IR(neat): 2927, 2854, 1466, 1034 cm$^{-1}$; MS(EI): 358 (M$^+$).

(4) 13-Phenyl-1-(tetrahydropyran-2-yloxy)tridecane

10% Palladium carbon (260 mg) was added to a solution of the above-mentioned compound (2.63 g) in ethanol (80 ml) and the mixture was stirred at room temperature for 3 hours under a hydrogen atmosphere. The catalyst was filtered through Celite and the filtrate was concentrated. The residue obtained was purified by silica gel column chromatography (eluent; ethyl acetate:hexane=1:9) to give the subject compound (2.67 g) as a colorless, oily substance.

Rf value: 0.60 (ethyl acetate:hexane=1:5); $^1$H-NMR (CDCl$_3$/TMS) δ: 1.27 (18H, m), 1.60 (10H, m), 2.62 (2H, t, J=7 Hz), 3.45 & 3.80 (4H, 2m), 4.59 (1H, br.s), 7.21 (5H, m); IR(neat): 2927, 2854, 1453 cm$^{-1}$; MS(EI): 360 (M$^+$).

(5) 13-Phenyltridecanol

A solution of the above-mentioned compound (2.63 g) and a catalytic amount of p-toluenesulfonic acid in methanol (30 ml) and tetrahydrofuran (8 ml) was allowed to stand at room temperature overnight. Triethylamine (0.5 ml) was added thereto and the mixture was concentrated. The residue obtained was purified by silica gel column chromatography (eluent; ethyl acetate:hexane=1:5) to give the subject compound (1.78 g) as white crystals.

melting point=34°–36° C. Rf value: 0.24 (ethyl acetate:hexane=1:5); $^1$H-NMR (CDCl$_3$/TMS) δ: 1.28 & 1.57 (23H, 2br.s), 2.62 (2H, t, J=7.5 Hz), 3.65 (2H, t, J=6 Hz), 7.23 (5H, m); IR(KBr): 3344, 3259, 2918, 2848, 1468 cm$^{-1}$; MS(EI): 276 (M$^+$).

(6) 13-Phenyltridecylmethanesulfonate

Triethylamine (1.2 ml) was added to a solution of the above-mentioned compound (1.73 g) in dichloromethane (30 ml) and the mixture was cooled with ice. Methanesulfonyl chloride (0.58 ml) was dropwise added thereto and the mixture was stirred at room temperature for 2 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane=1:5) to give the subject compound (2.12 g) as white crystals.

melting point=45°–47° C. Rf value: 0.39 (ethyl acetate:hexane=1:1); $^1$H-NMR (CDCl$_3$/TMS) δ: 1.28 & 1.70 (22H, 2m), 2.62 (2H, t, J=7.5 Hz), 3.01 (3H, s), 4.23 (2H, t, J=6 Hz), 7.22 (5H, m); IR(KBr): 2920, 2851, 1474, 1344 cm$^{-1}$; MS(EI): 354 (M$^+$); elemental analysis: calculated C 67.75, H 9.67, found C 67.70, H 9.48.

(7) 13-Phenyltridecyl Iodide

Sodium iodide (1.165 g) was added to a solution of the above-mentioned compound (2.12 g) in 2-butanone (60 ml) and the mixture was refluxed under heating for 2 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane=1:9) to give the subject compound (2.19 g) as white crystals.

melting point=19°–22° C. Rf value: 0.88 (ethyl acetate-:hexane=1:2); $^1$H-NMR (CDCl$_3$/TMS) δ: 1.27 & 1.70 (22H, 2m), 2.61 (2H, t, J=7.5 Hz), 3.19 (2H, t, J=6.5 Hz), 7.21 (5H, m); IR(KBr): 2917, 2851, 1472 cm$^{-1}$; MS(EI): 386 (M$^+$); elemental analysis: calculated C 75.63, H 9.91, found C 75.22, H 9.92.

(8) Diethyl 2-Acetamido-2-(13-phenyltridecyl)malonate

A solution of sodium ethoxide (0.764 g) in absolute ethanol (22 ml) was dropwise added to diethyl acetamidomalonate (2.38 g) in a stream of nitrogen and the mixture was stirred at 65° C. for 30 minutes. A solution of the above-mentioned compound (2.11 g) in tetrahydrofuran (5 ml) was dropwise added thereto and the mixture was stirred at 65° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane= 1:3) to give the subject compound (2.06 g) as a colorless, oily substance.

Rf value: 0.41 (ethyl acetate:hexane=1:2); $^1$H-NMR (CDCl$_3$/TMS) δ: 1.25 (20H, m), 1.58 (2H, m), 2.02 (3H, s), 2.30 (2H, m), 2.61 (2H, t, J=7.5 Hz), 4.23 (4H, q, J=6 Hz), 6.76 (1H, br.s), 7.21 (5H, m); IR(Neat): 3416, 3312, 2925, 2854, 1741, 1671 cm$^{-1}$; MS(EI): 475 (M$^+$).

(9) 2-Acetamido-1,3-diacetoxy-2-(13-phenyltridecyl)propane

A solution (20 ml) of the above-mentioned compound (1.90 g) in anhydrous tetrahydrofuran was added dropwise to a solution (40 ml) of lithium aluminum hydride (0.56 g) in anhydrous tetrahydrofuran under ice-cooling in a stream of nitrogen and the mixture was stirred at room temperature for 2 hours. A saturated aqueous sodium sulfate solution was added to the reaction mixture under ice-cooling and aluminum hydroxide produced was filtered off. The solvent was distilled away and pyridine (8 ml) was added to the residue. Acetic anhydride (5 ml) was added thereto under ice-cooling and the mixture was allowed to stand at room temperature overnight. The reaction mixture was poured into 5% hydrochloric acid under ice-cooling and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (1.01 g) as white crystals.

melting point=42°–45° C. Rf value: 0.24 (ethyl acetate-:hexane=1:1); $^1$H-NMR (CDCl$_3$/TMS) δ: 1.26 & 1.61 (22H, 2m), 1.96 (3H, s), 2.08 (6H, s), 2.62 (2H, t, J=7.5 Hz), 4.30 (4H, s), 5.61 (1H, br.s), 7.21 (5H, m); IR(KBr): 3295, 2926, 2854, 1748, 1660, 1553 cm$^{-1}$; MS(EI): 475 (M$^+$); elemental analysis: calculated C 70.70, H 9.54, N 2.94, found C 70.96, H 9.52, N 2.96.

(10) 2-Amino-2-(13-phenyltridecyl)-1,3-propanediol ¼ Hydrate

An aqueous solution (11.5 ml) of lithium hydroxide (0.88 g) was added to a solution of the above-mentioned compound (0.90 g) in methanol (11.5 ml) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue was recrystallized from ethyl acetate to give the subject compound (170 mg) as white crystals.

melting point=61°–64° C. $^1$H-NMR (CDCl$_3$/TMS) δ: 1.27 & 1.60 (24H, 2m), 2.00 (4H, m), 2.62 (2H, t, J=7.5 Hz), 3.50 (4H, m), 7.22 (5H, m); IR(KBr): 3342, 3290, 3157, 2916, 2849, 1581, 1472 cm$^{-1}$; MS(EI): 349 (M$^+$); elemental analysis: calculated C 74.63, H 11.24, N 3.96, found C 74.88, H 10.94, N 3.92.

EXAMPLE 288

2-Amino-2-{2-[4-(6-phenylhexyloxy) phenyl]ethyl}-1,3-propanediol (1) 6-Phenylhexylmethanesulfonate Triethylamine (5.09 ml) was added to a solution of 6-phenylhexanol (5.0 g) in dichloromethane (140 ml) and the mixture was cooled with ice. Methanesulfonyl chloride (2.50 ml) was dropwise added thereto and the mixture was stirred at room temperature for 2 hours. The reaction mixture was poured into ice water and extracted with chloroform. The chloroform layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane=1:2) to give the subject compound (8.08 g) as a colorless, oily substance.

Rf value: 0.45 (ethyl acetate:hexane=1:2); $^1$H-NMR (CDCl$_3$/TMS) δ: 1.15–1.95 (8H, m), 2.65 (2H, t, J=7.5 Hz), 2.99 (3H, s), 4.22 (2H, t, J=6 Hz), 7.22 (5H, m); IR(neat): 3027, 2937, 2858, 1497 cm$^{-1}$.

(2) 6-Phenylhexyl Iodide

Sodium iodide (5.33 g) was added to a solution of the above-mentioned compound (7.93 g) in 2-butanone (150 ml) and the mixture was refluxed under heating for 2 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane= 1:19) to give the subject compound (7.62 g) as a colorless, oily substance.

Rf value: 0.78 (ethyl acetate:hexane=1:5); $^1$H-NMR (CDCl$_3$/TMS) δ: 1.20–2.00 (8H, m), 2.60 (2H, t, J=7.5 Hz), 3.17 (2H, t, J=6.5 Hz), 7.15 (5H, m); IR(neat): 3026, 2930, 2855, 1496, 1453 cm$^{-1}$; MS(EI): 288 (M$^+$).

(3) 2-[4-(6-Phenylhexyloxy)phenyl]ethanol 2-(4-Hydroxyphenyl)ethanol (3.97 g) and sodium ethoxide (2.30 g) were added to ethanol (130 ml) and the mixture was refluxed under heating for 30 minutes. A solution of the above-mentioned compound (7.53 g) in tetrahydrofuran (30 ml) was dropwise added thereto and the mixture was stirred under reflux under heating for 6 hours. The reaction mixture was concentrated, poured into ice water and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane=1:3) to give the subject compound (5.49 g) as a colorless, oily substance.

Rf value: 0.50 (ethyl acetate:hexane=1:2); $^1$H-NMR (CDCl$_3$/TMS) δ: 1.24–1.89 (8H, m), 2.59 (2H, t, J=7.5 Hz), 2.76 (2H, t, J=5 Hz), 3.76 (2H, t, J=6.5 Hz), 3.89 (2H, t, J=5 Hz), 6.76 (2H, d, J=8.5 Hz), 7.06 (2H, d, J=8.5 Hz), 7.13 (5H, m); IR(neat): 3355, 2933, 2858, 1613, 1512 cm$^{-1}$; MS(EI): 298 (M$^+$).

(4) 2-[4-(6-Phenylhexyloxy)phenyl]ethylmethanesulfonate

Triethylamine (3.3 ml) was added to a solution of the above-mentioned compound (5.40 g) in dichloromethane (100 ml) and the mixture was cooled with ice. Methanesulfonyl chloride (1.7 ml) was dropwise added thereto and the mixture was stirred at room temperature for 2 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over magnesium sulfate. The solvent was distilled away and the residue obtained was purified by silica gel column chromatography (eluent; ethyl acetate:hexane= 1:2) to give the subject compound (6.99 g) as a colorless, oily substance.

Rf value: 0.39 (ethyl acetate:hexane=1:2); $^1$H-NMR (CDCl$_3$/TMS) δ: 1.30–1.92 (8H, m), 2.75 (2H, t, J=7.5 Hz), 2.81 (3H, s), 2.96 (2H, t, J=7 Hz), 3.89 (2H, t, J=6 Hz), 4.33 (2H, t, J=7 Hz), 6.80 (2H, d, J=8.5 Hz), 7.06 (2H, d, J=8.5 Hz), 7.15 (5H, m); IR(neat): 2936, 2858, 1513 cm$^{-1}$; MS(EI): 376 (M$^+$).

(5) 2-[4-(6-Phenylhexyloxy)phenyl]ethyl Iodide

Sodium iodide (3.29 g) was added to a solution of the above-mentioned compound (6.88 g) in 2-butanone (180 ml) and the mixture was refluxed under heating for 4 hours. The reaction mixture was concentrated and extracted with ethyl acetate. The ethyl acetate layer was washed with saturated brine and dried over magnesium sulfate. The solvent was distilled away and the residue obtained was purified by silica gel column chromatography (eluent; ethyl acetate:hexane= 1:9) to give the subject compound (6.25 g) as a colorless, oily substance.

Rf value: 0.81 (ethyl acetate:hexane=1:2); $^1$H-NMR (CDCl$_3$/TMS) δ: 1.18–1.92 (8H, m), 2.60 (2H, t, J=7.5 Hz), 3.18 (4H, m), 3.90 (2H, t, J=6 Hz), 6.75 (2H, d, J=8.5 Hz), 7.06 (2H, d, J=8.5 Hz), 7.10 (5H, m); IR(neat): 2932, 2856, 1611, 1511 cm$^{-1}$; MS(EI): 408 (M$^+$); elemental analysis: calculated C 58.83, H 6.17, found C 58.88, H 6.53.

(6) Diethyl 2-Acetamido-2-{2-[4-(6-phenylhexyl)phenyl]ethyl}malonate

A solution of sodium ethoxide (3.20 g) in absolute ethanol (40 ml) was dropwise added to diethyl acetamidomalonate (9.89 g) in a stream of nitrogen and the mixture was stirred at 65° C. for 30 minutes. A solution of the above-mentioned compound (6.20 g) in tetrahydrofuran (15 ml) was dropwise added thereto and the mixture was stirred at 65° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane=1:3) to give the subject compound (4.04 g) as white crystals.

melting point=53°–55° C. Rf value: 0.18 (ethyl acetate:hexane=1:2); $^1$H-NMR (CDCl$_3$/TMS) δ: 1.84 (6H, t, J=7 Hz), 1.11–1.88 (10H, m), 1.97 (3H, s), 2.24–2.76(6H, m), 3.87 (2H, t, J=6 Hz), 4.16 (4H, q, J=7 Hz), 6.70 (1H, s), 6.74 (2H, d, J=8.5 Hz), 6.97 (2H, d, J=8.5 Hz), 7.15 (5H, m); IR(neat): 3233, 2933, 1747, 1639, 1511 cm$^-$; MS(EI): 497 (M$^+$); elemental analysis: calculated C 70.00, H 7.90, N 2.81, found C 69.83, H 7.91, N 2.90.

(7) 2-Acetamido-1,3-diacetoxy-2-{2-[4-(6-phenylhexyloxy)phenyl]ethyl}propane A solution (10 ml) of the above-mentioned compound (3.79 g) in anhydrous tetrahydrofuran was dropwise added to a solution (60 ml) of lithium aluminum hydride (0.87 g) in anhydrous tetrahydrofuran under ice-cooling in a stream of nitrogen and the mixture was stirred at room temperature for 2 hours. A saturated aqueous sodium sulfate solution was added thereto under ice-cooling and aluminum hydroxide produced was filtered off. The solvent was distilled away and pyridine (15 ml) was added to the residue. Acetic anhydride (10 ml) was added thereto under ice-cooling and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (1.80 g) as white crystals.

melting point=68°–70° C. Rf value: 0.66 (ethyl acetate); $^1$H-NMR (CDCl$_3$/TMS) δ: 1.24–1.88 (8H, m), 1.94 (3H, s), 2.06 (6H, s), 2.10 (2H, m), 2.56 (4H, m), 3.88 (2H, t, J=7 Hz), 4.30 (4H, s), 5.60 (1H, s), 6.72 (2H, d, J=8.5 Hz), 7.02 (2H, d, J=8.5 Hz), 7.13 (5H, m); IR(KBr): 3319, 2934, 1739, 1652 cm$^{-1}$; MS(EI): 497 (M$^+$); elemental analysis: calculated C 70.00, H 7.90, N 2.81, found C 70.34, H 7.93, N 2.86.

(8) 2-Amino-2-{2-[4-(6-phenylhexyloxy)phenyl]ethyl}1,3-propanediol Hydrochloride An aqueous solution (17 ml) of lithium hydroxide (1.33 g) was added to a solution of the above-mentioned compound (1.75 g) in methanol (25 ml) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue obtained was recrystallized from ethyl acetate. A solution (10 ml) of 1M hydrochloric acid in ether was added to a solution of the resultant crystals in methanol (10 ml). The solvent was distilled away and the crystals precipitated were recrystallized from ethyl acetate to give the subject compound (0.90 g) as white crystals.

melting point: 89°–91° C. Rf value: 0.41 (chloroform:methanol:acetic acid:water=70:20:6:4); $^1$H-NMR (CDCl$_3$) δ: 1.33 (4H, m), 1.59 (6H, m), 1.91 (1H, br.s), 2.36 (1H, br.s), 2.55 (2H, t, J=7.8 Hz), 3.72 (4H, m), 4.98 (1H, br.s), 6.66 (2H, d, J=8.8 Hz), 7.03 (2H, d, J=8.8 Hz), 7.12 (3H, m), 7.22 (2H, m), 7.85 (1H, br.s); IR(KBr): 3275, 3028, 2934, 2858, 1513 cm$^{-1}$; MS(EI): 371 (M$^+$); elemental analysis: calculated C 67.71, H 8.40, N 3.43, found C 67.61, H 8.30, N 3.42.

EXAMPLE 289

2-Amino-2-[2-(4-undecyloxyphenyl)ethyl]-1,3-propanediol

(1) 2-(4-Undecyloxyphenyl)ethanol

A solution (300 ml) of 2-(4-hydroxyphenyl)ethanol (15.5 g), undecyl bromide (25 ml) and sodium ethoxide (8.40 g) in ethanol was refluxed under heating for 5 hours. The solvent was distilled away and water (200 ml) and ethyl acetate (200 ml) were added thereto. The aqueous layer was extracted with ethyl acetate (200 ml). The combined extract was dried and filtered. The solvent was distilled away and the residue obtained was purified by silica gel column chromatography (eluent; ethyl acetate:hexane=1:3) to give 23.37 g of the subject compound as white crystals.

melting point=47°–50° C. Rf value: 0.40 (ethyl acetate:hexane=1:2); $^1$H-NMR (CDCl$_3$) δ: 0.87 (3H, t, J=7.5 Hz), 1.10–1.58 (16H, m), 1.87 (2H, m), 2.78 (2H,t, J=7.5 Hz), 3.78 (2H, t, J=7 Hz), 3.89 (2H, t, J=7 Hz), 6.82 (2H, d, J=9 Hz), 7.09 (2H, d, J=9 Hz); IR(KBr): 3250, 2919, 2850, 1513, 1251 cm$^{-1}$; MS(EI): 292(M$^+$).

(2) 2-(4-Undecyloxyphenyl)ethyl Methanesulfonate

To a solution (400 ml) of the compound obtained above (23.24 g) in dichloromethane was added triethylamine (14.4 ml). Methanesulfonyl chloride (7.1 ml) was added to the mixture under ice-cooling and the mixture was stirred at room temperature for 2 hours. Then, the reaction mixture was poured into 200 ml of ice water and extracted twice with dichloromethane (200 ml). The extract was dried and concentrated, and the residue obtained was purified by silica gel column chromatography (eluent; ethyl acetate:hexane=1:3) to give the subject compound (28.07 g) as white crystals.

melting point=43°–44° C. Rf value: 0.51 (ethyl acetate:hexane=1:2); $^1$H-NMR (CDCl$_3$/TMS) δ: 0.88 (3H, t, J=7.5 Hz), 1.25 (16H, m), 1.75 (2H, m), 2.81 (3H, s), 2.96 (2H, t, J=7 Hz), 3.90 (2H, t, J=6 Hz), 4.35 (2H, t, J=7 Hz), 6.75 (2H, d, J=9 Hz), 7.05 (2H, d, J=9 Hz); IR(KBr): 2919, 2851, 1515, 1352 cm$^{-1}$; MS(EI): 370(M$^+$); elemental analysis: calculated C 64.83, H 9.25, found C 64.78, H 9.17.

(3) 2-(4-Undecyloxyphenyl)ethyl Iodide

A solution (350 ml) of the compound obtained above (27.95 g) and sodium iodide (13.00 g) in 2-butanone was refluxed under heating for 3 hours. The solvent was distilled away and water (200 ml) was added thereto. The mixture was extracted twice with ethyl acetate (200 ml) and dried. The solvent was distilled away and the residue obtained was purified by silica gel column chromatography (eluent; ethyl acetate:hexane=1:19) to give the subject compound (26.45 g) as white crystals.

melting point=22°–23° C. Rf value: 0.79 (ethyl acetate:hexane=1:5); $^1$H-NMR (CDCl$_3$/TMS)δ: 0.88 (3H, t, J=7 Hz), 1.30 (16H, m), 1.75 (2H, m), 2.90–3.40 (4H, m), 3.90 (2H, t, J=7 Hz), 6.76 (2H, d, J=9 Hz), 7.02 (2H, d, J=9 Hz); IR(KBr): 2920, 2852, 1609, 1509, 1247 cm$^{-1}$; MS(EI): 402(M$^+$).

(4) Diethyl 2-Acetamido-2-[2-(4-undecyloxyphenyl)ethyl]malonate

A solution of sodium ethoxide (13.37 g) in absolute ethanol (400 ml) was dropwise added to diethyl acetamidomalonate (42.68 g) in a stream of nitrogen and the mixture was stirred at 65° C. for 30 minutes. A solution of the compound obtained above (26.35 g) in tetrahydrofuran (50 ml) was dropwise added thereto and the mixture was stirred at 65° C. for 6 hours. The reaction mixture was concentrated, poured into ice water and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate:hexane=1:5) to give the subject compound (13.94 g).

melting point=63°–65° C. Rf value: 0.24 (ethyl acetate:hexane=1:2); $^1$H-NMR (CDCl$_3$/TMS) δ: 0.86 (3H, t, J=7.1 Hz), 1.24 (20H, m), 1.41 (2H, m), 1.73 (2H, m), 1.97 (3H, s), 2.39 (2H, m), 2.62 (2H, m), 3.89 (2H, t, J=6.3 Hz), 4.18 (4H, m), 6.74 (1H, s), 6.77 (2H, d, J=8.3 Hz), 7.02 (2H, d, J=8.3 Hz); IR(KBr): 3286, 2917, 2851, 1746, 1647, 1513 cm$^{-1}$; MS(EI): 491(M$^+$); elemental analysis: calculated C 68.40, H 9.22, N 2.85, found C 68.15, H 9.23, N 2.80.

(5) 2-Acetamido-1,3-diacetoxy-2-[2-(4-undecyloxyphenyl)ethyl]propane

A solution (60 ml) of the compound obtained above (13.02 g) in anhydrous tetrahydrofuran was dropwise added to a solution (200 ml) of lithium aluminum hydride (3.0 g) in anhydrous tetrahydrofuran in a stream of nitrogen under ice-cooling and the mixture was stirred at room temperature for 2 hours. A saturated aqueous sodium sulfate solution was added to the reaction mixture under ice-cooling and the resultant aluminum hydroxide was filtered off. The solvent was distilled away and pridine (40 ml) was added to the residue. Thereto was added acetic anhydride (30 ml) under ice-cooling and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue obtained was purified by silica gel column chromatography (eluent; ethyl acetate) to give the subject compound (7.18 g) as white crystals.

melting point=82°–85° C. Rf value: 0.6 (ethyl acetate); $^1$H-NMR (CDCl$_3$/TMS) δ: 0.86 (3H, t, J=6.4 Hz), 1.24 (14H, m), 1.41 (2H, m), 1.75 (2H, m), 1.94 (3H, s), 2.07 (6H, s), 2.14 (2H, m), 2.53 (2H, m), 3.89 (2H, t, J=6.6 Hz), 4.32 (4H, s), 5.62 (1H, s), 6.79 (2H, d, J=8.8 Hz), 7.06 (2H, d, J=8.8 Hz); IR(KBr): 3314, 2918, 2851, 1737, 1653 cm$^{-1}$; MS(EI): 491 (M$^+$); elemental analysis: calculated C 68.40, H 9.22, N 2.85, found C 68.36, H 9.19, N 2.85.

(6) 2-Amino-2-[2-(4-undecyloxyphenyl)ethyl]-1,3-propanediol Hydrochloride

To a solution of the compound obtained above (7.16 g) in methanol (70 ml) was added an aqueous solution (70 ml) of lithium hydroxide (5.50 g) and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and the residue was recrystallized from ethyl acetate. To a solution of the thus obtained crystals in tetrahydrofuran (20 ml)-methanol (20 ml), 1M hydrochloric acid in ether (30 ml) was added. The solvent was distilled away and the precipitated crystals were recrystallized from ethyl acetate to give the subject compound (1.90 g).

melting point=88°–91° C. ¹H-NMR (CDCl₃—CD₃OD/TMS) δ: 0.80 (3H, t, J=6.9 Hz), 1.19 (14H, m), 1.36 (2H, m), 1.68 (2H, m), 1.85 (2H, m), 2.53 (2H, m), 3.65 (4H, m), 3.84 (2H, t, J=6.4 Hz), 6.74 (2H, d, J=8.3 Hz), 7.04 (2H, d, J=8.3 Hz); IR(KBr): 3274, 2921, 2852, 1613, 1513, 1247 cm⁻¹; MS(EI): 365(M⁺); elemental analysis: calculated C 65.73, H 10.03, N 3.48, found C 65.53, H 9.82, N 3.42.

EXAMPLE 290

2-Amino-2-[2-(4-dodecylphenyl)ethyl]-1,3-propanediol (1) 2-(4-Dodecanoylphenyl)ethyl Acetate Aluminum chloride (48.2 g) was added to dichloroethane (400ml) in a stream of nitrogen and the mixture was stirred at room temperature. Then, phenethyl acetate (39.6 g) and undecanoyl chloride (52.7 g) were dropwise added thereto under ice-cooling and the mixture was stirred at room temperature overnight. The reaction mixture was poured into ice water and extracted with diethyl ether. The ether layer was washed with saturated brine and dried over anhydrous magnesium sulfate. The solvent was distilled away and the residue obtained was purified by silica gel column chromatography (eluent; ethyl acetate:hexane=1:20) to give the subject compound (34.5 g) as pale yellow crystals.

melting point=32°–33° C. IR(neat)$_{max}$: 2921, 2852, 1738, 1686, 1240 cm⁻¹;

(2) 2-(4-Dodecylphenyl)ethanol

To a solution (50 ml) of the compound obtained above (34.5 g) in trifluoroacetic acid was added triethylsilane (22.7 ml) under ice-cooling and the mixture was stirred at room temperature for 3 hours. The solvent was distilled away and ice water was poured to the residue. A cold, saturated aqueous sodium hydrogencarbonate solution was slowly added to the mixture. The mixture was extracted with ethyl acetate, and the ethyl acetate layer was washed and dried over magnesium sulfate. The solvent was distilled away and methanol (250 ml) was added to the residue to give a methanol solution. To the solution was added sodium methoxide (10.2 g) and the mixture was refluxed under heating for 4 hours. The reaction mixture was concentrated and ice water was poured to the residue. The mixture was extracted with ethyl acetate. The ethyl acetate layer was washed with a 5% aqueous hydrochloric acid solution and saturated brine and dried over anhydrous magnesium sulfate. The solvent was distilled away to give the subject compound (27.1 g) as an oily substance.

Rf: 0.21 (ethyl acetate:hexane=1:3).

(3) 2-(4-Dodecylphenyl)ethyl Iodide

To a solution (500 ml) of the compound obtained above (27.1 g) in dichloromethane was added triethylamine (14.4 ml) and the mixture was stirred at room temperature for 3 hours. The reaction mixture was poured into ice water and the mixture was extracted with dichloromethane. The dichloromethane layer was washed with a saturated aqueous potassium hydrogencarbonate solution, a 1% aqueous hydrochloric acid solution and saturated brine and dried over anhydrous magnesium sulfate. The solvent was distilled away and 2-butanone (500 ml) was added to the residue. Thereto was added sodium iodide (12.2 g) and the mixture was refluxed under heating for 3 hours. The reaction mixture was poured into ice water and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:20) to give the subject compound (18.6 g) as an oily substance.

¹H-NMR (CDCl₃) δ: 0.37 (3H, t, J=6 Hz), 0.66–0.86 (18H, m), 1.05–1.10 (2H, m), 2.06(2H, t, J=6 Hz), 2.63 (2H, t, J=4 Hz), 2.83 (2H, t, J=4 Hz), 6.60 (4H, dd, J=4 Hz, 8 Hz); IR(neat)$_{max}$: 2919, 1513, 1467, 1168 cm⁻¹.

(4) Diethyl 2-Acetamido-2-[2-(4-dodecylphenyl)ethyl]malonate

A solution (100 ml) of sodium ethoxide (6.3 g) in absolute ethanol was dropwise added to diethyl acetamidomalonate (20.2 g) in a stream of nitrogen and the mixture was stirred at 65° C. for 30 minutes. Then, a solution (50 ml) of the compound obtained above (18.6 g) in anhydrous tetrahydrofuran was dropwise added thereto and the mixture wad stirred at 65° C. for 3 hours. The reaction mixture was concentrated, poured into ice water and extracted with ethyl acetate. The extract was washed with saturated brine and dried over anhydrous magnesium sulfate. The solvent was distilled away and the residue was purified by silica gel column chromatography (eluent; ethyl acetate:hexane=1:3) to give the subject compound (8.9 g).

melting point=60°–62° C. ¹H-NMR (CDCl₃) δ: 0.86 (3H, t, J=6 Hz), 1.24 (6H, t, J=6 Hz), 1.23–1.59 (18H, m), 1.54–1.59 (2H, m), 1.97 (3H, s), 2.45 (3H, t, J=6 Hz), 2.54 (3H, t, J=6 Hz), 2.67 (3H, t, J=6 Hz), 4.15–4.24 (4H, m), 6.75 (1H, br.s), 7.06 (4H, dd, J=6 Hz, 6 Hz); IR(KBr)$_{max}$: 3253, 2920, 2850, 1747, 1644, 1517 cm⁻¹.

(5) 2-Acetamido-1,3-diacetoxy-2-[2-(4-dodecylphenyl)ethyl]propane

A solution (50 ml) of the compound obtained above (8.9 g) in anhydrous tetrahydrofuran was dropwise added to a solution (200 ml) of lithium aluminum hydride (1.38 g) in anhydrous tetrahydrofuran in a stream of nitrogen under ice-cooling, and the mixture was stirred at room temperature for 2 hours. A saturated aqueous sodium sulfate solution was added to the reaction mixture under ice-cooling and the resultant aluminum hydroxide was filtered off. The resultant mixture was dried over anhydrous sodium sulfate and the solvent was distilled away. Pyridine (28.7 ml) was added to the residue. Thereto was added acetic anhydride (18.5 ml) under ice-cooling and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:2) to give the subject compound (2.5 g) as white crystals.

melting point=111°–113° C. ¹H-NMR (CDCl₃) δ: 0.86 (3H, t, J=6 Hz), 1.24–1.31 (18H, m), 1.53–1.58 (4H, m), 1.95 (3H, s), 2.09 (6H, s), 2.56 (2H, t, J=6 Hz), 2.58 (2H, t, J=6 Hz), 4.35 (4H, s), 5.62 (1H, br.s), 7.09 (4H, s); IR(KBr): 3309, 2918, 2850, 1738, 1651 cm⁻¹.

(6) 2-Amino-2-[2-(4-dodecylphenyl)ethyl]-1,3-propanediol Hydrochloride

An aqueous solution (25 ml) of lithium hydroxide (1.7 g) was added to a solution (25 ml) of the compound obtained above (2.5 g) in methanol and the mixture was refluxed under heating for 3 hours. The reaction mixture was concentrated and extracted with ethyl acetate. The ethyl acetate layer was washed with saturated brine and dried over anhydrous magnesium sulfate. The solvent was distilled away and a 26% hydrochloric acid—ethanol solution was added thereto, followed by stirring. The solvent was distilled away and the residue was recrystallized from ethanol to give the subject compound (770 mg) as white crystals.

$^1$H-NMR (DMSO) δ: 0.88 (3H, t, J=6 Hz), 1.25–1.30 (18H, m), 1.52–1.58 (2H, m), 1.94–2.02 (2H, m), 2.56–2.60 (2H, m), 2.64–2.68 (2H, m), 3.81 (4H, dd, J=11, 26 Hz), 4.79 (2H, br.s), 7.09 (4H, dd, J=6, 26 Hz), 8.07 (3H, br.s); IR(KBr): 2921, 2852, 1738, 1686, 1240 cm$^{-1}$.

EXMAPLE 291

2-Amino-2-[2-(2-octylphenyl)ethyl]-1,3-propanediol (1) 1-(2-Bromophenyl)octanol

Magnesium pieces (6.56 g) were added to anhydrous tetrahydrofuran (10 ml) in a stream of nitrogen and the mixture was stirred at room temperature. A solution (200 ml) of 1bromoheptane (48.4 g) in anhydrous tetrahydrofuran was dropwise added thereto while heating gradually and the mixture was stirred at 40° C. for 1 hour. Thereto was dropwise added a solution (100 ml) of 2-bromobenzaldehyde (25 g) in anhydrous tetrahydrofuran at room temperature and the mixture was stirred for 1 hour. The reaction mixture was poured into a saturated, aqueous ammonium chloride solution and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:8) to give the subject compound (18.9 g) as an oily substance.

$^1$H-NMR (CDCl$_3$) δ: 0.85 (3H, t, J=6 Hz), 1.24–1.58 (10H, m), 1.61–1.79 (2H, m), 5.05(1H, m, J=4 Hz), 7.08–7.12 (1H, m, J=6 Hz), 7.29–7.31 (1H, m, J=6 Hz), 7.50–7.54 (2H, m, J=4 Hz); IRv(neat): 3350, 2927, 1466, 1023 cm$^{-1}$.

(2) trans-2-(1-Octenyl)bromobenzene

Diphosphorus pentaoxide (7.1 g) was added to a solution (200 ml) of the compound obtained above (2.85 g) in benzene and the mixture was refluxed under heating for 2 hours. The diphosphorus pentaoxide was filtered off and the solvent was distilled away. Ice water was added to the residue. The mixture was extracted with ethyl acetate, and the ethyl acetate layer was washed with saturated brine and dried over anhydrous magnesium sulfate. The solvent was distilled away and the residue was purified by silica gel column chromatography (eluent; ethyl acetate:hexane: 1:15) to give the subject compound (2.4 g) as an oily substance.

$^1$H-NMR (CDCl$_3$) δ: 0.86 (3H, t, J=7 Hz), 1.18–1.45 (6H, m), 1.46–1.55 (2H, m), 2.24 (2H, m, J=1 Hz, 7 Hz), 6.16 (1H, m, J=7 Hz), 6.72 (1H, d, J=16 Hz), 7.02–7.08 (1H, m), 7.19–7.33 (1H, m), 7.46–7.55 (2H, m); IRv(neat): 2957, 2855, 1466, 1023 cm$^{-1}$.

(3) trans-2-(1-Octenyl)-benzaldehyde

Magnesium pieces (3.74 g) were added to anhydrous tetrahydrofuran (10 ml) in a stream of nitrogen and the mixture was stirred at room temperature. A solution (100 ml) of the compound obtained above (37.4 g) in anhydrous tetrahydrofuran was dropwise added thereto while heating gradually and the reaction mixture was stirred at 60° C. for 1.5 hours. Thereto was dropwise added a solution (100 ml) of dimethylformamide (11.5 ml) in anhydrous tetrahydrofuran at room temperature and the mixture was stirred overnight. The reaction mixture was poured into a saturated aqueous ammonium chloride solution and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:15) to give the subject compound (26.7 g) as an oily substance.

$^1$H-NMR (CDCl$_3$) δ: 0.88 (3H, t, J=6 Hz), 1.22–1.38 (6H, m), 1.45–1.52 (2H, m), 2.24–2.36 (2H, m), 6.11–6.18 (1H, m), 7.15 (1H, d, J=18 Hz), 7.33–7.37 (1H, m), 7.48–7.53 (2H, m), 7.58 (1H, d, J=4 Hz), 10.31 (1H, s); IRv(neat): 2927, 2855, 1899, 1597 cm$^{-1}$;

(4) 2-Octylbenzaldehyde

To a solution (200 ml) of the compound obtained above (28.7 g) in methanol was added a solution (20 ml) of 10% palladium carbon (1 g) in methanol and the mixture was stirred at ordinary temperature and at atmospheric pressure in a stream of hydrogen for 14 hours for catalytic reduction. The 10% palladium carbon was filtered off and the solvent was distilled away. The residue was purified by silica gel column chromatography (eluent; ethyl acetate:hexane=1:20) to give the subject compound (22 g) as an oil.

$^1$H-NMR (CDCl$_3$) δ: 0.88 (3H, t, J=7 Hz), 1.25–1.38 (10H, m), 1.54–1.83 (2H, m), 3.00 (2H, t, J=7 Hz), 7.24–7.26 (1H, m), 7.31–7.35 (1H, m), 7.48–7.50 (1H, m), 7.80–7.83 (1H, m), 10.28 (1H, s); IRv(neat): 3335, 2928, 1701, 1801 cm$^{-1}$.

(5) Ethyl (2-octylphenyl)acetate

Methyl methylsulfinylmethyl sulfide (12.4 g) and Triton B (9.18 ml) were added to a solution (100 ml) of the compound obtained above (22 g) in dioxane at room temperature and the mixture was refluxed under heating for 2 hours. The solvent was distilled away and ethyl acetate was added to the residue. The ethyl acetate layer was washed with saturated brine and dried over anhydrous magnesium sulfate. The solvent was distilled away and ethanol (200 ml) was added to the residue. Thereto was added a 26% hydrochloric acid-ethanol solution and the mixture was stirred at room temperature for 30 minutes. The solvent was distilled away and ice water was poured to the residue. The mixture was extracted with ethyl acetate. The extract was washed with saturated brine and dried over anhydrous magnesium sulfate. The solvent was distilled away and the residue was purified by silica gel column chromatography (eluent; ethyl acetate:hexane=1:30) to give the subject compound (20.2 g) as an oily substance.

$^1$H-NMR (CDCl$_3$) δ: 0.86 (3H, t, J=5 Hz), 1.19–1.38 (10H, m), 1.24 (3H, t, J=5 Hz), 1.49–1.62 (2H, m), 2.59 (2H, t, J=6 Hz), 3.85 (2H, s), 4.13 (2H, q, J=5 Hz), 7.10–7.35 (4H, m).

(6) 2-(2-Octylphenyl)ethyl Alcohol

A solution (50 ml) of the compound obtained above (20.2 g) in anhydrous tetrahydrofuran was dropwise added to a solution (200 ml) of lithium aluminum hydride (3.04 g) in anhydrous tetrahydrofuran in stream of nitrogen under ice-cooling and the mixture was stirred at room temperature for 2 hours. A saturated aqueous sodium sulfate solution was added to the reaction mixture under ice-cooling and the resultant aluminum hydroxide was filtered off. The filtrate was dried over anhydrous sodium sulfate and the solvent was distilled away. The residue was purified by silica gel column chromatography (eluent; ethyl acetate:hexane=1:30) to give the subject compound (10.2 g) as an oily substance.

$^1$H-NMR (CDCl$_3$) δ: 0.87 (3H, t, J=6 Hz), 1.21–1.46 (10H, m), 1.47–1.62 (2H, m), 2.61(2H, t, J=6 Hz), 2.96 (3H, t, J=6 Hz), 3.82 (2H, dd, J=6 Hz, 12 Hz), 7.14–7.24 (4H, m) IRv(neat): 3335, 2926, 2854, 1467 cm$^{-1}$.

(7) 2-(2-Octylphenyl)ethyl Methanesulfonate

Triethylamine (7.37 ml) was added to a solution (250 ml) of the compound obtained above (10.2 g) in dichloromethane and the mixture was cooled with ice. Thereto was dropwise added methanesulfonyl chloride (6.04 g) and the mixture was stirred at room temperature for 2 hours. The reaction mixture was poured into ice water and extracted with dichloromethane. The dichloromethane layer was washed with a saturated aqueous potassium hydrogencarbonate solution, a 1% aqueous hydrochloric acid solution and saturated brine and dried over anhydrous magnesium sulfate. The solvent was distilled away and the residue was purified by silica gel column chromatography (eluent; ethyl acetate:hexane: 1:8) to give the subject compound (13.4 g) as an oily substance.

$^1$H-NMR (CDCl$_3$) δ: 0.86 (3H, t, J=6 Hz), 1.22–1.41 (10H, m), 1.51–1.59 (2H, m), 2.60 (2H, t, J=6 Hz), 2.84 (3H, s), 3.09 (2H, t, J=6 Hz), 4.38 (2H, t, J=6 Hz), 7.10–7.20 (4H, m); IR(neat): 2929, 1467, 1357, 1174 cm$^{-1}$.

(8) 2-(2-Octylphenyl)ethyl iodide

To a solution of the compound obtained above (13.4 g) in 2butanone (300 ml) was added sodium iodide (7.7 g) and the mixture was refluxed under heating for 2 hours. The reaction mixture was poured into ice water and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:30) to give the subject compound (11.9 g).

$^1$H-NMR (CDCl$_3$) δ: 0.87 (3H, t, J=6 Hz), 1.18–1.74 (10H, m), 1.50–1.59 (2H, m), 2.57 (2H, t, J=6 Hz), 3.18 (2H, t, J=6 Hz), 3.28 (2H, t, J=6 Hz), 7.10–7.25 (4H, m); IR(neat): 2923, 2854, 1490, 1468 cm$^{-1}$.

(9) Diethyl 2-Acetamido-2-[2-(2-octylphenyl)ethyl]malonate

A solution (50 ml) of sodium ethoxide (6.39 g) in anhydrous ethanol was dropwise added to diethyl acetamidomalonate (20.4 g) in a stream of nitrogen and the mixture was stirred at 65° C. for 1.5 hours. A solution of the compound obtained above (10.8 g) in tetrahydrofuran was dropwise added thereto and the mixture was refluxed under heating for 7 hours. The reaction mixture was concentrated, poured into ice water and extracted with ethyl acetate. The extract was washed with saturated brine and dried over anhydrous magnesium sulfate. The solvent was distilled away and the residue was purified by silica gel column chromatography (eluent; ethyl acetate:hexane=1:3) to give the subject compound (5.8 g) as white crystals.

melting point=37°–38° C. $^1$H-NMR (CDCl$_3$) δ: 0.86 (3H, t, J=6 Hz), 1.21–1.36 (10H, m), 1.25 (6H, t, J=6 Hz), 1.46–1.57 (2H, m), 2.03 (3H, s), 2.38–2.47 (2H, m), 2.51 (2H, t, J=6 Hz), 2.55–2.63 (2H, m, J=6 Hz), 4.16–4.41 (4H, m), 6.82 (2H, br.s), 7.05–7.15 (4H, m); IR(KBr): 3415, 2977, 2855, 1741, 1683, 1492 cm$^{-1}$.

(10) 2-Acetamido-1,3-diacetoxy-2-[2-(2-octylphenyl)ethyl]propane

A solution (50 ml) of the compound obtained above (4.3 g) in anhydrous tetrahydrofuran was dropwise added to a solution (200 ml) of lithium aluminum hydride (0.76 g) in anhydrous tetrahydrofuran in a stream of nitrogen under ice-cooling, and the mixture was stirred at room temperature for 2 hours. A saturated aqueous sodium sulfate solution was added to the reaction mixture under ice-cooling and the resultant aluminum hydroxide was filtered off. The filtrate was dried over anhydrous sodium sulfate and the solvent was distilled away. Pyridine (10 ml) was added to the residue and then, acetic anhydride (13 ml) was added thereto, and the mixture was allowed to stand at room temperature overnight. The reaction mixture was poured into ice-cooled 5% hydrochloric acid and extracted with ethyl acetate. The ethyl acetate layer was washed with saturated brine and dried over anhydrous magnesium sulfate. The solvent was distilled away and the residue was purified by silica gel column chromatography (eluent; ethyl acetate:hexane=1:3) to give the subject compound (2.2 g) as an oily substance.

$^1$H-NMR (CDCl$_3$) δ: 0.88 (3H, t, J=6 Hz), 1.21–1.38 (12H, m), 1.47–1.58 (2H, m), 1.97 (3H, s), 2.08 (6H, s), 2.56 (2H, t, J=6 Hz), 2.58 (2H, t, J=6 Hz), 4.35 (4H, s), 5.88 (1H, br.s), 7.09–7.13 (4H, m); IR(neat): 3295, 2927, 1747, 1880, 1258 cm$^{-1}$.

(11) 2-Amino-2-[2-(2-octylphenyl)ethyl]-1,3-propanediol Hydrochloride

An aqueous solution (20 ml) of lithium hydroxide (1.7 g) was added to a solution of the compound obtained above (2.2 g) in methanol (20 ml) and the mixture was refluxed under heating for 4 hours. The reaction mixture was concentrated and extracted with ethyl acetate. The extract was washed with saturated brine and dried over anhydrous magnesium sulfate. The solvent was distilled away and a 28% hydrochloric acid-ethanol solution was added to the residue. The solvent was distilled away and the residue was recrystallized from ethanol to give hydrochloride of the subject compound (800 mg).

melting point=188°–170° C. $^1$H-NMR (DMSO) δ: 0.85 (3H, t, J=7 Hz), 1.22–1.37 (10H, m), 1.43–1.54 (2H, m), 1.88–1.78 (2H, m), 2.52–2.83 (4H, m), 3.49–3.59 (4H, m), 5.40 (2H, t, J=4 Hz), 7.05–7.17 (4H, m), 7.89 (3H, br.s); IRv(KBr): 3385, 3272, 2925, 1519, 1069 cm$^{-1}$.

EXAMPLE 292

2-Amino-2-(4-octylthiobenzyl)-1,3-propanediol Hydrochloride ½ Hydrate (1) 4-(Methylthio)benzyl Alcohol Sodium borohydride (3.78 g) was added to isopropyl alcohol (50 ml) and the mixture was stirred under ice-cooling. Thereto was dropwise added 4-(methylthio)benzaldehyde (15 g) and the mixture was stirred at room temperature for 30 minutes. The solvent was distilled away and water was added to the residue. The mixture was extracted with ethyl acetate. The organic layer was washed with saturated brine and dried over anhydrous sodium sulfate. The solvent was distilled away and the residue obtained was recrystallized from hexane-ethyl acetate to give the subject compound (15 g) as white crystals.

melting point=41°–43° C. $^1$H-NMR (CDCl$_3$) δ: 2.40 (3H, s), 4.43 (2H, s), 7.10 (4H, s), 3.36 (1H, br.s); elemental analysis (C$_8$H$_{10}$OS): calculated C 62.30, H 6.54, found C 61.90, H 6.55; MS: 154 (M$^+$).

(2) 4-(Methylsulfinyl)benzyl Alcohol m-Chloroperbenzoic acid (content 50%, 35 g) was added to a solution (100 ml) of the compound obtained above (15 g) in chloroform under ice-cooling and the mixture was stirred for 1 hour. Thereto was added calcium hydroxide (37 g) and the mixture was stirred at room temperature for 1 hour. The insoluble matters were filtered off, and the filtrate was washed with saturated brine and dried over anhydrous sodium sulfate. The solvent was distilled away and the residue obtained was purified by silica gel column chromatography (eluent; chloroform:methanol=20:1) to give the subject compound (15.56 g) as an oily substance.

$^1$H-NMR (CDCl$_3$) δ: 2.73 (3H, s), 3.28 (1H, br.s), 4.45 (2H, s), 7.52 (4H, s); IR(neat): 3364, 1409, 1303, 1148, 1031 cm$^{-1}$; elemental analysis (C$_8$H$_{10}$O$_2$S): calculated C 56.45, H 5.92, found C 56.51, H 5.87; MS: 170 (M$^+$).

(3) 4-(Methylsulfinyl)benzyl Methanesulfonate

Triethylamine (14 ml) was added to a solution (100 ml) of the compound obtained above (13.88 g) in dichloromethane under ice-cooling. Thereto was dropwise added methanesulfonyl chloride (6.2 ml) and the mixture was stirred for 30 minutes. The reaction mixture was poured into ice water and extracted with dichloromethane. The organic layer was washed with a saturated aqueous sodium hydrogencarbonate solution, 0.1N hydrochloric acid and saturated brine and dried over anhydrous sodium sulfate. The solvent was distilled away and the residue obtained was purified by silica gel column chromatography (eluent; chloroform:methanol: 10:1) to give the subject compound (15.38 g) as white crystals.

melting point=63°–65° C. $^1$H-NMR (CDCl$_3$) δ: 2.74 (3H, s), 3.0 (3H, s), 5.22 (2H, s), 7.52 (2H, d, J=8 Hz), 7.63 (2H, d, J=8 Hz); IR(KBr): 3015, 1349, 1172, 1040, 951 cm$^{-1}$; elemental analysis (C$_9$H$_{12}$O$_4$S$_2$): calculated C 43.53, H 4.87, found C 43.51, H 4.82; MS: 248 (M$^+$).

(4) 4-(Methylsulfinyl)benzyl Iodide

To a solution (100 ml) of the compound obtained above (8.25 g) in 2=butanone was added sodium iodide (7.5 g) and the mixture was stirred at room temperature for 1 hour. The reaction mixture was concentrated, poured into ice water and extracted with ethyl acetate. The organic layer was washed with saturated brine and dried over anhydrous sodium sulfate. The solvent was distilled away and the residue was purified by silica gel column chromatography (eluent; chloroform:methanol =10:1) to give the subject compound (8.65 g) as yellow crystals.

melting point=80°–81° C. $^1$H-NMR (CDCl$_3$) δ: 2.70 (3H, s), 4.42 (3H, s), 7.50 (4H, s); IR(KBr): 1399, 1153, 1038, 837, 565 cm$^{-1}$; elemental analysis (C$_8$H$_9$OSI): calculated C 34.30, H 3.24, found C 34.17, H 3.21; MS: 280 (M$^+$).

(5) Diethyl 2-Acetamido-2-(4-methylsulfinylbenzyl)malonate

Sodium ethoxide (4 g) was added to a solution (200 ml) of diethyl acetamidomalonate (13 g) in absolute ethanol in a stream of nitrogen and the mixture was stirred at 65° C. for 1 hour. A solution of the compound obtained above (8.4 g) in absolute ethanol was dropwise added thereto and the mixture was stirred at 65° C. for 1 hour. The reaction mixture was concentrated, poured into ice water and extracted with ethyl acetate. The extract was washed with saturated brine and dried over anhydrous sodium sulfate. The solvent was distilled away and the residue was purified by silica gel column chromatography (eluent; chloroform:methanol=20:1) to give the subject compound (8.2 g) as crystals.

melting point=135°–136° C. 1H-NMR (CDCl$_3$) δ: 1.28 (6H, t, J=7 Hz), 2.02 (3H, s), 2.70 (3H, s), 3.70 (2H, s), 4.25 (4H, m), 6.52 (1H, s), 7.15 (2H, d, J=8 Hz), 7.53 (2H, d, J=8 Hz); IR(KBr): 3253, 2986, 1748, 1642, 1198, 1039 cm$^{-1}$; elemental analysis (C$_{17}$H$_{23}$NO$_{6S}$): calculated C 55.27, H 6.27, N 3.79, found C 55.09, H 6.25, N 3.78.

(6) Diethyl 2-Acetamido-2-(4-mercaptobenzyl)malonate

The compound obtained above (6.22 g) was added to trifluoroacetic anhydride (50 ml) under ice-cooling and the mixture was stirred for 1 hour. The trifluoroacetic anhydride was removed, and ethanol (100 ml) and triethylamine (100 ml) were added thereto. The mixture was stirred at room temperature for 1 hour. The reaction mixture was concentrated and chloroform (200 ml) was added thereto. Then, the mixture was washed with a saturated aqueous ammonium chloride solution and dried over anhydrous sodium sulfate. The solvent was distilled away and the residue was purified by silica gel column chromatography (eluent; chloroform:methanol=10:1) to give the subject compound (4.26 g) as crystals.

melting point=125°–128° C. $^1$H-NMR (CDCl$_3$) δ: 1.27 (6H, t, J=7 Hz), 2.00 (3H, s), 3.38 (1H, s), 3.57 (2H, s), 4.24 (4H, m), 6.50 (1H, s), 6.85 (2H, d, J=8 Hz), 7.14 (2H, d, J=8 Hz); IR(KBr): 3398, 2986, 2547, 1736, 1665, 1212, 1018 cm$^{-1}$; elemental analysis (C$_{16}$H$_{21}$NO$_5$S): calculated C 56.62, H 6.24, N 4.13, found C 56.61, H 6.20, N 4.09; MS: 339 (M$^+$).

(7) Diethyl 2-Acetamido-2-(4-octylthiobenzyl)malonate

1-Bromooctane (0.58 g) and potassium carbonate (0.5 g) were added to a solution (10 ml) of the compound obtained above (1 g) in dimethylformamide and the mixture was stirred at room temperature for 5 hours. The reaction mixture was poured into ice water and extracted with ethyl acetate. The organic layer was washed with a saturated aqueous ammonium chloride solution and dried over anhydrous sodium sulfate. The solvent was distilled away and the residue was purified by silica gel column chromatography (eluent; chLoroform:methanol: 25:1) to give the subjected compound (1.16 g) as crystals.

melting point: 82°–84° C. $^1$H-NMR (CDCl$_3$) δ: 0.85 (3H, t, J=7 Hz), 1.27 (14H, m), 1.40 (2H, quint, J=7 Hz), 1.61 (2H, quint, J=7 Hz), 2.01 (3H, s), 2.86 (2H, t, J=7 Hz), 3.58 (2H, s),4.25 (4H, m), 6.51 (1H, s), 6.89 (2H, d, J=8 Hz), 7.17 (2H, d, J=8 Hz); IR(KBr): 3255, 2952, 1747, 1644, 1298, 1274, 1220 cm$^{-1}$; elemental analysis (C$_{24}$H$_{37}$NO$_5$S): calculated C 63.83, H 8.26, N 3.10, found C 63.33, H 8.14, N 3.06; MS: 451 (M⁺).

(8) 2-Acetamido-2-(4-octylthiobenzyl)-1,3-propanediol

A solution (10 ml) of the compound obtained above (1 g) in anhydrous tetrahydrofuran was dropwise added to a solution of lithium aluminum hydride (0.26 g) in anhydrous tetrahydrofuran (10 ml) under ice-cooling. The mixture was stirred under ice-cooling for 1 hour and at room temperature for 1 hour. Then, thereto was dropwise added a saturated aqueous sodium sulfate solution to decompose the lithium aluminum hydride. The insoluble matters were filtered off and the filtrate was extracted with ethyl acetate. The organic layer was washed with saturated brine and dried over anhydrous sodium sulfate. The solvent was distilled away and the residue obtained was purified by silica gel column chromatography (eluent; chloroform:methanol=10:1) to give the subjected compound (0.6 g) as crystals.

melting point=76°–78° C. $^1$H-NMR (CDCl$_3$) δ: 0.86 (3H, t, J=7 Hz), 1.25 (8H, m), 1.40 (2H, quint, J=7 Hz), 1.61 (2H, quint, J=7 Hz), 1.99 (3H, s), 2.87 (2H, t, J=7 Hz), 2.89 (2H, s), 3.50 (2H, m), 3.70 (2H, m), 3.73 (2H, m, —OH×2), 5.79 (1H, s, —NH), 7.14 (2H, d, J=8 Hz), 7.25 (2H, d, J=8 Hz); IR(KBr): 3422, 3347, 3192, 2942, 1654, 1550, 1055 cm$^{-1}$; elemental analysis (C$_{20}$H$_{33}$NO$_S$): calculated C 65.36, H 9.05, N 3.81, found C 65.29, H 9.11, N 3.75; MS: 367 (M⁺).

(9) 2-Amino-2-(4-octylthiobenzyl)-1,3-propanediol Hydrochloride

An aqueous solution (5 ml) of lithium hydroxide (380 mg) was added to a solution (5ml) of the compound obtained above (400 mg) in methanol and the mixture was refluxed under heating for 4 hours. The reaction mixture was concentrated and extracted with ethyl acetate. The extract was washed with saturated brine and dried over anhydrous sodium sulfate. The solvent was distilled away to give white powder. The thus-obtained powder was dissolved in ethanol (2 ml) and thereto was added a 26% hydrochloric acid-ethanol solution(1 ml). The solvent was distilled away and the precipitated crystals were recrystallized from hexane-ethyl acetate to give the subjected compound (80 mg).

melting point=100°–102° C. $^1$H-NMR (CD$_3$OD) δ: 0.76 (3H, t, J=7 Hz), 1.16 (8H, m), 1.30 (2H, m), 1.53 (2H, quint, J=7 Hz), 2.79 (2H, t, J=7 Hz), 2.86 (2H, s), 3.43 (2H, m), 3.62 (3H, m), 7.06 (2H, d, J=8 Hz), 7.15 (2H, d, J=8 Hz); IR(KBr): 3363, 3286, 2924, 1516, 1494, 1072 cm$^{-1}$; elemental analysis (C$_{18}$H$_{31}$NO$_2$S HCl ½H$_2$O): calculated C 58.28, H 8.97, N 3.78, found C 58.44, H 9.02, N 3.68.

EXAMPLE 293

2-Amino-2-[2-(5-octyl-2-thienyl)ethyl]-1,3-propanediol Hydrochloride

(1) 2-(2-Thienylethyl)-2-tetrahydropyranyl Ether

To a solution (100 ml) of 2-(2-thienyl)ethanol (12.85 g) in dichloromethane, 3,4-dihydro-2H-pyran (9.25 g) and p-toluenesulfonic acid (2 g) were added. The mixture was stirred at room temperature for 4 hours. The solvent was distilled away and ethyl acetate was added thereto. The mixture was washed with saturated brine and dried over anhydrous sodium sulfate. The solvent was distilled away and the oily substance obtained was purified by distillation to give 13.52 g of the subject compound as an oily substance.

boiling point=107°–108° C./1 mmHg, $^1$H-NMR (CDCl$_3$) δ: 1.50 (4H, m), 1.70 (1H, m), 1.82 (1H, m), 3.11 (2H, t, J=7 Hz), 3.47 (1H, m), 3.60 (1H, dt, J=10, 7 Hz), 3.79 (1H, m), 3.95 (1H, dr, J=10,7 Hz), 4.61 (1H, t, J=3.5 Hz), 6.83 (1H, dd, J=1, 3.4 Hz), 6.90 (1H, dd, J=3.4, 5.4 Hz), 7.11 (1H, dd, J=1, 5.4 Hz); IR(neat): 2930, 1250, 1120, 1030, 870 cm$^{-1}$; elemental analysis C$_{11}$H$_{16}$O$_2$S: calculated C 62.23, H 7.60, found C 62.83, H 7.01; MS: 212 (M⁺).

(2) 2-(5-Octyl-2-thienyl)ethyl 2-Tetrahydropyranyl Ether

A solution (100 ml) of the above-mentioned compound (8.5 g) in anhydrous tetrahydrofuran was cooled to −78° C. and a solution (1.63 mol/l, 30 ml) of n-butyl lithium in hexane was dropwise added thereto. The mixture was stirred under ice-cooling for 30 minutes and then at room temperature for 30 minutes. A solution (15 ml) of 1-bromooctane (10 g) in anhydrous tetrahydrofuran was dropwise added thereto and the mixture was stirred at room temperature for 7 hours. The reaction mixture was poured into ice water and extracted with ethyl acetate. The organic layer was washed with a saturated aqueous ammonium chloride solution and dried over anhydrous sodium sulfate. The solvent was distilled away and the residue obtained was purified by silica gel column chromatography (eluent; hexane:ethyl acetate= 20:1) to give 6.6 g of the subject compound as an oily substance.

$^1$H-NMR (CDCl$_3$) δ: 0.85 (3H, t, 7 Hz), 1.25 (10H, m), 1.53 (4H, m), 1.62 (2H, m), 1.72 (1H, m), 1.83 (1H, m), 2.71 (2H, t, J=7 Hz), 3.02 (2H, t, J=7 Hz), 3.46 (1H, m), 3.60 (1H, dt, J=10, 7 Hz), 3.80 (1H, m), 3.92 (1H, dt, J=10, 7 Hz), 4.61 (1H, t, J=3.5 Hz), 6.54 (1H, d, J=3.4 Hz), 6.61 (1H, d, J=3.4 Hz); IR(neat): 2927, 2854, 1135, 1120, 1033 cm$^{-1}$; elemental analysis C$_{19}$H$_{32}$O$_2$S: calculated C 70.32, H 9.94, found C 70.12, H 10.03; MS: 324 (M⁺).

(3) 2-(5-Octyl-2-thienyl)ethanol

Tetrahydrofuran (20 ml) and p-toluenesulfonic acid (0.3 g) were added to a solution (80 ml) of the above-mentioned compound (6.5 g) in methanol and the mixture was stirred at room temperature for 1 hour. The solvent was distilled away and ethyl acetate was added to the resulting mixture. The mixture was washed with saturated brine and dried over anhydrous sodium sulfate. The solvent was distilled away and the residue obtained was purified by silica gel column chromatography (eluent; hexane:ethyl acetate=5:1) to give 4 g of the subject compound as an oil.

$^1$H-NMR (CDCl$_3$) δ: 0.86 (3H, t, J=7 Hz), 1.27 (10H, m), 1.62 (2H, quint, J=7 Hz), 2.73 (2H, t, J=7 Hz), 3.00 (2H, t, J=6 Hz), 3.80 (2H, t, J=6 Hz), 6.58 (1H, d, J=3.4 Hz), 6.64 (1H, d, J=3.4 Hz); IR(neat): 3348, 2927, 2854, 1466, 1047, 797; elemental analysis: calculated C 69.43, H 10.07, found C 69.34, H 10.17; MS: 240 (M⁺).

(4) 2-(5-Octyl-2-thienyl)ethyl Methanesulfonate

Triethylamine (3 ml) was added to a solution (50 ml) of the above-mentioned compound (4 g) in dichloromethane. Methanesulfonyl chloride (1.5 ml) was dropwise added thereto and the mixture was stirred for 30 minutes. The reaction mixture was poured into ice water and extracted with dichloromethane. The organic layer was washed with a saturated aqueous sodium hydrogencarbonate solution, 0.1N hydrochloric acid and saturated brine, and dried over anhydrous sodium sulfate. The solvent was distilled away and the residue obtained was purified by silica gel column chromatography (eluent; chloroform:methanol=20:1) to give 5 g of the subject compound as an oily substance.

$^1$H-NMR (CDCl$_3$) δ: 0.86 (3H, t, J=7 Hz), 1.27 (10H, m), 1.61 (2H, quint, J=7 Hz), 2.72 (2H, t, J=7.5 Hz), 2.91 (3H, s), 3.17 (2H, t, J=3.4 Hz), 4.37 (2H, t, J=6.5 Hz), 6.58 (1H, d, J=3.4 Hz), 6.67 (1H, d, J=3.4 Hz); IR(neat): 2927, 2854, 1357, 1176, 959, 802 cm$^{-1}$; elemental analysis: calculated C 56.57, H 8.23, found C 56.19, H 8.10; MS: 318 (M$^+$).

(5) 2-(5-Octyl-2-thienyl)ethyl Iodide

Sodium iodide (4.5 g) was added to a solution (50 ml) of the above-mentioned compound (4.8 g) in 2-butanone and the mixture was stirred at room temperature for 17 hours. The reaction mixture was concentrated, poured into ice water and extracted with ethyl acetate. The organic layer was washed with saturated brine and dried over anhydrous sodium sulfate. The solvent was distilled away and the residue was purified by silica gel column chromatography (eluent; hexane:ethyl acetate=20:1) to give 4.9 g of the subject compound as an oily substance.

$^1$H-NMR (CDCl$_3$) δ: 0.86 (3H, t, J=7 Hz), 1.28 (10H, m), 1.62 (2H, quint, J=7 Hz), 2.72 (2H, t, J=7.5 Hz), 3.30 (4H, m), 6.57 (1H, d, J=3.4 Hz), 6.63 (1H, d, J=3.4 Hz); IR(neat): 2926, 2853, 1466, 1168, 796 cm$^{-1}$; elemental analysis C$_{14}$H$_{23}$SI: calculated C 48.00, H 6.62, found C 48.29, H 6.99; MS: 350 (M$^+$).

(6) Diethyl 2-Acetamido-2-[2-(5-octyl-2-thienyl)ethyl]malonate

60% Oily sodium hydride (0.33 g) was suspended in anhydrous dimethylformamide (20 ml) and diethyl acetamidomalonate (1.82 g) was added thereto. The mixture was stirred at room temperature for 1 hour. Then, a solution (10 ml) of the above-mentioned compound (2.7 g) in anhydrous dimethylformamide was dropwise added thereto and the mixture was stirred at room temperature for 10 hours. The reaction mixture was poured into ice water and extracted with ethyl acetate. The extract was washed with a saturated aqueous ammonium chloride solution and dried over anhydrous sodium sulfate. The solvent was distilled away and the residue was purified by silica gel column chromatography (eluent; hexane:ethyl acetate=2:1) to give 1.4 g of the subject compound as crystals.

melting point=57°–58° C. $^1$H-NMR (CDCl$_3$) δ: 0.86 (3H, t, J=7 Hz), 1.25 (16H, m), 1.57 (2H, quint, J=7 Hz), 2.0 (3H, s), 2.61 (2H, m), 2.70 (4H, m), 4.20 (4H, m), 6.52 (1H, d, J=3.4 Hz), 6.53 (1H, d, J=3.4 Hz), 6.75 (1H, s); IR(neat): 3278, 2923, 2852, 1746, 1647, 1211, 1195 cm$^{-1}$; elemental analysis: calculated C 62.84, H 8.48, N 3.19; C$_{23}$H$_{37}$NO$_5$S found C 62.80, H 8.42, N 2.94; MS: 439 (M$^+$).

(7) 2-Acetamido-2-[2-(5-octyl-2-thienyl) ethyl]-1,3-propanediol

A solution (15 ml) of the above-mentioned compound (1.3 g) in anhydrous tetrahydrofuran was dropwise added to a solution (15 ml) of lithium aluminum hydride (0.38 g) in anhydrous tetrahydrofuran under ice-cooling. After stirring under ice-cooling for 1 hour, the mixture was stirred at room temperature for 1 hour. A saturated aqueous sodium sulfate solution was dropwise added under ice-cooling to decompose lithium aluminum hydride. The insoluble matters were filtered off and the filtrate was extracted with ethyl acetate. The organic layer was washed with saturated brine and dried over anhydrous sodium sulfate. The solvent was distilled away and the residue obtained was purified by silica gel column chromatography (eluent; chloroform:methanol=15:1) to give 0.5 g of the subject compound as crystals.

melting point=58°–60° C. $^1$H-NMR (CDCl$_3$) δ: 0.86 (3H, t, J=7 Hz), 1.27 (10H, m), 1.60 (2H, m), 1.94 (3H, s), 2.02 (2H, m), 2.71 (2H, t, J=7 Hz), 2.82 (2H, t, J=7 Hz), 3.57 (2H, dd, J=6, 12 Hz), 3.71 (2H, br.s, OH×2), 3.80 (2H, dd, J=6, 12 Hz), 5.88 (1H, s), 6.54 (1H, d, J=3.4 Hz), 6.58 (1H, d, J=3.4 Hz) IR(KBr): 3277, 2924, 2852, 1626, 1560, 1236, 1064, 1036 cm$^{-1}$; elemental analysis: calculated C 64.19, H 9.36, N 3.94, C$_{19}$H$_{33}$NO$_3$S found C 63.75, H 9.17, N 3.68; MS: 355 (M$^+$).

(8) 2-Amino-2-[2-(5-octyl-2-thienyl)ethyl]-1,3-propanediol Hydrochloride

A aqueous solution (5 ml) of lithium hydroxide (380 mg) was added to a solution (5 ml) of the above-mentioned compound (500 mg) in methanol and the mixture was refluxed under heating for 5 hours. The reaction mixture was concentrated and extracted with ethyl acetate. The extract was washed with saturated brine and dried over anhydrous sodium sulfate. The solvent was distilled away, whereby a powder was obtained. The powder was dissolved in ethanol (3 ml) and a 26% solution (2 ml) of hydrochloric acid in ethanol was added thereto. The solvent was distilled away and the precipitated crystals were recrystallized from hexane-ethyl acetate to give 150 mg of the subject compound.

melting point=63°–65° C. $^1$H-NMR (CD$_3$OD) δ: 0.79 (3H, t, J=7 Hz), 1.18 (10H, m), 1.53 (2H, m), 1.96 (2H, m), 2.63 (2H, t, J=7.5 Hz), 2.74 (2H, m), 3.61 (2H, d, J=12.2 Hz), 3.67 (2H, d, J=12.2 Hz), 6.47 (1H, d, J=3.4 Hz), 6.54 (1H, d, J=3.4 Hz); IR(KBr): 3482, 3265, 1631, 1530, 1468, 1059, 811 cm$^{-1}$; elemental analysis : calculated C 58.35, H 9.22, N 4.00, C$_{17}$H$_{31}$NO$_2$S HCl found C 58.12, H 9.25, N 4.03; MS: 313 (M$^+$).

EXAMPLE 294

2-Amino-2-(4-octylsulfinylbenzyl)-1,3-propanediol

(1) 2-Acetamido-1,3-diacetoxy-2-(4-octylthiobenzyl)propane

Acetic anhydride (0.67 ml) was added to a solution (30 ml) of 2-acetamido-2-(4-octylthiobenzyl)-1,3-propanediol (1.04 g) in pyridine and the mixture was stirred at room temperature for 4 hours. The reaction mixture was concentrated and a 5% aqueous ammonium chloride solution was added thereto. The mixture was extracted with ethyl acetate. The ethyl acetate layer was washed with water and dried over anhydrus magnesium sulfate. The solvent was distilled away and the residue was purified by silica gel column chromatography (eluent; ethyl acetate:hexane=4:1) to give 0.73 g of the subject compound.

melting point=71°–74° C. $^1$H-NMR (CDCl$_3$) δ: 0.85 (3H, t, J=6.9 Hz), 1.10–1.85 (12H, m), 1.94 (3H, s), 2.06 (6H, s), 2.28 (2H, t, J=7.8 Hz), 3.19 (2H, s), 4.26 (4H, dd, J=11.2, 17.6 Hz), 5.48 (1H, br.s), 7.03 (2H, d, J=8.3 Hz), 7.20 (2H, d, J=8.3 Hz); IR(KBr): 3295, 2924, 1739 cm$^{-1}$; MS: 451 (M$^+$); elemental analysis: calculated C 63.83, H 8.26, N 3.10, found C 64.00, H 8.32, N 3.12.

(2) 2-Acetamido-1,3-diacetoxy-2-(4-octylsulfinylbenzyl)propane

To a solution (15 ml) of the above-mentioned compound (0.73 g) in chloroform was added m-chloroperbenzoic acid (0.56 g) and the mixture was stirred for 40 minutes. Calcium hydroxide (0.23 g) was added to the reaction mixture and the mixture was stirred at room temperature for 1 hour. The insoluble matters were filtered off and the solvent was distilled away. The residue was purified by silica gel column chromatography (eluent; dichloromethane:methanol=30:1) to give 0.66 g of the subject compound.

melting point=70°–72° C. $^1$H-NMR (CDCl$_3$) δ: 0.85 (3H, t, J=7.3 Hz), 1.10–1.80 (12H, m), 1.95 (3H, s), 2.07 (6H,s), 2.76 (2H, m), 3.33 (2H, s), 4.09–4.16 (4H, m), 5.54 (1H, s), 7.29 (2H, d, J=8.3 Hz), 7.54 (2H, d, J=8.3 Hz); IR(KBr): 3278, 3081, 2928, 1746, 1672, 1218 cm$^{-1}$; MS: 467 (M$^+$); elemental analysis: calculated C 61.65, H 7.97, N 3.00, found C 61.36, H 7.90, N 2.93.

(3) 2-Amino-2-(4-octylsulfinylbenzyl)-1,3-propanediol

An aqueous solution (3 ml) of lithium hydroxide (242 mg) was added to a solution (3 ml) of the above-mentioned compound (300 mg) in methanol and the mixture was stirred at 50° C. for 5 hours. After concentration, the reaction mixture was extracted with ethyl acetate and washed with water. The mixture was dried over anhydrous magnesium sulfate and the solvent was distilled away. The residue was recrystallized from ethyl acetate-hexane to give 81.5 mg of the subject compound.

melting point: 80°–82° C. $^1$H-NMR (CDCl$_3$) δ: 0.85 (3H, t, J=6.8 Hz), 1.20–1.80 (16H, m), 2.70–2.90 (4H, m), 3.44 (4H, dd, J=10.3, 17.1 Hz), 7.38 (2H, d, J=7.8 Hz), 7.55 (2H, d, J=7.8 Hz); IR(KBr): 3339, 2915, 2758, 1033 cm$^{-1}$; MS: 342 (M$^+$); elemental analysis: calculated C 63.31, H 9.15, N 4.10, found C 62.62, H 9.04, N 3.91.

EXAMPLE 295

2-Amino-2-(4-octylsulfonylbenzyl)-1,3-propanediol

(1) 2-Acetamido-1,3-diacetoxy-2-(4-octylsulfonylbenzyl)propane

To a solution (10 ml) of 2-acetamido-1,3-diacetoxy-2-(4octylsulfinylbenzyl)propane (330 mg) in chloroform was added m-chloroperbenzoic acid (244 mg) under ice-cooling. The mixture was stirred for 2.5 hours and then at room temperature for 1.5 hours. Calcium hydroxide (0.1 g) was added to the reaction mixture and the mixture was stirred at room temperature for 45 minutes. The insoluble matters were filtered off and the filtrate was concentrated under reduced pressure. The residue was recrystallized from hexane-ethyl acetate to give 162 mg of the subject compound.

melting point=98°–100° C. $^1$H-NMR (CDCl$_3$) δ: 0.84 (3H, t, J=7.3 Hz), 1.10–1.80 (12H, m), 1.96 (3H, s), 2.07 (6H, s), 3.06 (2H, m), 3.38 (2H, s), 4.25 (4H, dd, J=11.7, 25.8 Hz), 5.54 (1H, s), 7.34 (2H, d, J=8.2 Hz), 7.81 (2H, d, J=8.2 Hz); IR(KBr): 3317, 2921, 2853, 1749, 1654, 1313, 1141 cm$^{-1}$; MS: 483 (M$^+$); elemental analysis: calculated C 59.61, H 7.71, N 2.90, found C 59.50, H 7.60, N 2.85.

(2) 2-Amino-2-(4-octylsulfonylbenzyl)-1,3-propanediol

An aquous solution (2.5 ml) of lithium hydroxide (109 mg) was added to a solution (2.5 ml) of the above-mentioned compound (140 mg) in methanol and the mixture was stirred at 50° C. for 4 hours. The reaction mixture was extracted with ethyl acetate and the extract was washed with water. The mixture was dried over anhydrous magnesium sulfate and the solvent was distilled away. The residue was recrystallized from hexane-ethyl acetate to give 45 mg of the subject compound.

melting point: 108°–109° C. $^1$H-NMR (CDCl$_3$) δ: 0.84 (3H, t, J=7.3 Hz), 1.10–1.86 (16H, m), 2.83 (2H, s), 3.06 (2H, m), 3.43 (2H, s), 3.44 (2H, s), 7.43 (2H, d, J=7.8 Hz), 7.82 (2H, d, J=7.8 Hz); IR(KBr): 3343, 2915, 1299, 1147 cm$^{-1}$; MS: 357 (M$^+$); elemental analysis: calculated (0.1H$_2$O) C 60.17, H 8.75, N 3.90, found C 59.89, H 8.79, N 3.91.

EXAMPLE 296

2-Amino-2-[2-(3-octylphenyl)ethyl]-1,3-propanediol and Hydrochloride Thereof

(1) 1-(3-Bromophenyl)octanol

A small amount of iodine was added to a solution (100 ml) of magnesium (9.8 g) in anhydrous tetrahydrofuran and the mixture was stirred at 50° C. until the color of the iodine disappeared. A solution of heptyl bromide in anhydrous tetrahydrofuran (200 ml) was dropwise added thereto over 1 hour. The mixture was stirred at 65° C. for 1 hour and a solution of m-bromobenzaldehyde in anhydrous tetrahydrofuran (200 ml) was dropwise added thereto under ice-cooling. The mixture was stirred at room temperature for 30 minutes. Under ice-cooling, a saturated aqueous ammonium chloride solution (7.3 ml) was added thereto and the mixture was stirred for 1 hour. The insoluble matters were filtered off and the filtrate was concentrated. The concentrate was dissolved in ethyl acetate and the mixture was washed with water. The mixture was dried over magnesium sulfate and the solvent was distilled away. The residue obtained was purified by silica gel column chromatography (eluent; hexane:ethyl acetate=10:1) to give 50.9 g of the subject compound as an oily substance.

$^1$H-NMR (CDCl$_3$) δ: 0.85 (3H, t, J=6.8 Hz), 1.20–1.90 (13H, m), 4.61 (1H, m), 7.1–7.3 (2H, m), 7.36 (1H, dt, J=1.5, 7.8 Hz), 7.49 (1H, m); IR(neat): 3346, 2922, 2853 cm$^{-1}$; MS: 285 (M$^+$); elemental analysis: calculated C 58.96, H 7.42, N 0.00, found C 58.92, H 7.36, N 0.00.

(2) trans-1-(3-Bromophenyl)-1-octene

Phosphorus pentaoxide (24.9 g) was added to a solution of the above-mentioned compound (10 g) in benzene (500 ml) and the mixture was refluxed under heating for 1.5 hours. The insoluble matters were filtered off, and the filtrate was washed with water and dried over anhydrous magnesium sulfate. The solvent was distilled away and the residue was purified by silica gel column chromatography (eluent; hexane:ethyl acetate=20:1) to give 9 g of the subject compound as an oily substance.

$^1$H-NMR (CDCl$_3$) δ: 0.88 (3H, t, J=6.9 Hz), 1.20–1.50 (8H, m), 2.19 (2H, dt, J=6.3, 6.5 Hz), 6.21 (1H, td, J=6.3, 16.1 Hz), 6.28 (1H, d, J=16.1 Hz), 7.13 (1H, t, J=7.9 Hz), 7.21 (1H, m), 7.28 (1H, m), 7.47 (1H, m); IR(neat): 3439, 3063 cm$^{-1}$; MS: 267 (M$^+$).

(3) trans-1-(3-Formylphenyl)-1-octene

A small amount of iodine was added to a solution of magnesium (1.38 g) in anhydrous tetrahydrofuran (30 ml) and the mixture was stirred at 50° C. until the color of the iodine disappeared. A solution of the above-mentioned compound (13.8 g) in anhydrous tetrahydrofuran (40 ml) was dropwise added thereto over 30 minutes. The mixture was stirred at 55° C. for 1 hour and a solution of dimethylformamide (4 ml) in anhydrous tetrahydrofuran (30 ml) was dropwise added thereto over 1 hour. The mixture was stirred at room temperature for 2 hours. Under ice-cooling, a saturated aqueous ammonium chloride solution was added thereto and the mixture was extracted with ethyl acetate. The ethyl acetate layer was washed with water and dried over magnesium sulfate. The solvent was distilled away and the residue obtained was purified by silica gel column chromatography (eluent; hexane:ethyl acetate=30:1) to give 7.12 g of the subject compound as an oily substance.

$^1$H-NMR (CDCl$_3$) δ: 0.86 (3H, t, J=6.8 Hz), 1.20–1.60 (8H, m), 2.22 (2H, dt, J=6.8, 6.9 Hz), 6.32 (1H, td, J=6.8, 15.7 Hz), 6.41 (1H, d, J=15.7 Hz), 7.43 (1H, t, J=7.8 Hz), 7.57 (1H, m), 7.68 (1H, m), 7.83 (1H, s), 9.99 (1H, s); IR(neat): 2956, 2927, 2855, 1699 cm$^{-1}$; MS: 216 (M$^+$); elemental analysis: calculated C 83.29, H 9.32, found C 83.50, H 9.29.

(4) 3-(trans-1-Octenyl)-β-methylsulfinyl-β-methylthiostyrene

Methyl methyl sulfinyl methyl sulfide (3 ml) and a solution (2.6 ml) of trimethylbenzyl ammonium hydroxide in methanol were added to a solution of the above-mentioned compound (6.17 g) in dioxane (30 ml) and the mixture was stirred at 80° C. for 2 hours. The reaction mixture was concentrated, dissolved in ethyl acetate and washed with water. The mixture was dried over anhydrous magnesium sulfate. The solvent was distilled away and the residue obtained was purified by silica gel column chromatography (eluent; hexane:ethyl acetate=4:1) to give 6.48 g of the subject compound as an oily substance. $^1$H-NMR (CDCl$_3$) δ: 0.87 (3H, t, J=6.8 Hz), 1.20–1.55 (8H, m), 2.12 (2H, dt, J=6.8, 6.9 Hz), 2.30 (3H, s), 2.75 (3H, s), 6.25 (1H, td, J=6.8, 16.1 Hz), 6.37 (3H, t, J=16.1 Hz), 7.30–7.40 (2H, m), 7.60 (1H, s), 7.72 (1H, m), 7.81 (1H, s); IR(neat): 2955, 2925, 1068 cm$^{-1}$; MS: 322 (M$^+$).

(5) Ethyl 3-(trans-1-octenyl)phenylacetate

A solution of 26% hydrogen chloride in ethanol (48 ml) was added to a solution of the above-mentioned compound (6.48 g) in ethanol (40 ml) and the mixture was stirred at room temperature for 1 hour. The reaction mixture was concentrated and the residue was purified by silica gel column chromatography (eluent; hexane:ethyl acetate=20:1) to give 5.11 g of the subject compound as an oily substance.

$^1$H-NMR (CDCl$_3$) δ: 0.87 (3H, t, J=6.8 Hz), 1.18–1.50 (11H, m), 2.19 (2H, dt, J=6.8, 6.9 Hz), 3.57 (2H, s), 4.13 (2H, q, J=7.3 Hz), 6.22 (1H, td, J=6.8, 16.1 Hz), 6.33 (1H, d, J=16.1 Hz), 7.10–7.25 (4H, m); IR(neat): 2957, 2927, 2855, 1737 cm$^{-1}$; MS: 274 (M$^+$).

(6) 2-[3-(trans-1-Octenyl)phenyl]ethanol

Lithium aluminum hydride (1.22 g) was suspended in anhydrous tetrahydrofuran (150 ml) and thereto was added the above-mentioned compound (5.89 g) under ice-cooling. The mixture was stirred for 1 hour. Under ice-cooling, ethanol and water were added thereto and the insoluble matters were filtered off. The filtrate was dried over anhydrous sodium sulfate and the solvent was distilled away. The residue was purified by silica gel column chromatography (eluent; hexane: ethyl acetate=5:1) to give 4.22 g of the subject compound as an oily substance. $^1$H-NMR (CDCl$_3$) δ: 0.87 (3H, t, J=6.8 Hz), 1.10–1.50 (8H, m), 2.19 (2H, dt, J=6.8, 6.9 Hz), 2.83 (2H, t, J=6.3 Hz), 3.85 (2H, dt, J=6.2, 6.3 Hz), 6.20 (1H, td, J=6.8, 16.1 Hz), 6.34 (1H, d, J=16.1 Hz), 7.03 (1H, m), 7.18–7.27(3H, m); IR(neat): 3348, 2956, 2926, 2854 cm$^{-1}$; MS: 232 (M$^+$).

(7) 2-[3-(trans-1-Octenyl)phenyl]ethylmethanesulfonate

Triethylamine (2.8 ml) was added to a solution (60 ml) of the above-mentioned compound (4.19 g) in dichloromethane and the mixture was ice-cooled. Thereto was dropwise added methanesulfonyl chloride (14 ml) and the mixture was stirred at room temperature for 1.5 hours. The reaction mixture was poured into ice water and extracted with dichloromethane. The dichloromethane layer was washed with a saturated potassium hydrogencarbonate solution, a 1% aqueous hydrochloric acid solution and saturated brine and dried over anhydrous magnesium sulfate. The solvent was distilled away and the residue was purified by silica gel column chromatography (eluent; hexane: ethyl acetate=5:1) to give 5.55 g of the subject compound as an oily substance.

$^1$H-NMR (CDCl$_3$) δ: 0.87 (3H, t, J=6.8 Hz), 1.20–1.50 (8H, m), 2.19 (2H, dr, J=6.8, 6.9 Hz), 2.83 (3H, s), 3.02 (2H, t, J=6.8 Hz), 4.40 (2H, t, J=6.8 Hz), 6.22 (1H, td, J=6.8, 15.6 Hz), 6.33 (1H, d, J=15.6 Hz), 7.03 (1H, m), 7.18–7.24 (3H, m); IR(neat): 2956, 2927, 2855 cm$^{-1}$; MS: 310 (M$^+$).

(8) 2-[3-(trans-1-Octenyl)phenyl]ethyl Iodide

Sodium iodide (3.99 g) was added to a solution of the above-mentioned compound (5.51 g) in 2-butanone (60 ml) and the mixture was stirred at 45° C. for 3 hours. The reaction mixture was concentrated, poured into ice water and extracted with ethyl acetate. The extract was washed with saturated brine and dried over anhydrous magnesium sulfate. The solvent was distilled away and the residue was purified by silica gel column chromatography (eluent; hexane:ethyl acetate=100:1) to give 4.75 g of the subject compound as an oily substance.

$^1$H-NMR (CDCl$_3$) δ: 0.87 (3H, t, J=6.8 Hz), 1.20–1.50 (8H, m), 2.19 (2H, dr, J=6.8, 6.9 Hz), 3.14 (2H, t, J=7.4 Hz), 3.34 (2H, t, J=7.4 Hz), 6.21 (1H, td, J=6.8, 18.1 Hz), 6.34 (1H, d, J=18.1 Hz), 7.00 (1H, m), 7.14–7.24 (3H, m); IR(neat): 2956, 2925, 2853 cm$^{-1}$; MS: 342 (M$^+$).

(9) Diethyl 2-Acetamido-2-[2-[3-(trans-1-octenyl)phenyl]ethyl]malonate

Sodium ethoxide (7.62 g) was added to a solution of diethyl acetamidomalonate (7.62 g) in ethanol (30 ml) and the mixture was stirred at 60° C. for 45 minutes. Thereto was dropwise added a solution of the above-mentioned compound (4 g) in ethanol (20 ml) and the mixture was refluxed under heating for 5 hours. The reaction mixture was concentrated, poured into ice water and extracted with ethyl acetate. The extract was washed with saturated brine and dried over anhydrous magnesium sulfate. The solvent was distilled away and the residue was purified by silica gel column chromatography (eluent; hexane:ethyl acetate=3:1) to give 2.46 g of the subject compound as an oily substance.

¹H-NMR (CDCl₃) δ: 0.87 (3H, t, J=6.9 Hz), 1.22 (6H, t, J=6.8 Hz), 1.22–1.50 (8H, m), 1.97 (3H, s), 2.17 (2H, dt, J=6.8, 6.9 Hz), 2.43 (2H, m), 2.67 (2H, m), 4.11–4.23 (4H, m), 6.18 (1H, td, J=6.8, 16.1 Hz), 6.31 (1H, d, J=16.1 Hz), 6.74 (1H, s), 6.94 (1H, d, J=6.8 Hz), 7.09–7.18 (3H, m); IR(neat): 3413, 2957, 2927, 1741, 1683 cm⁻¹; MS: 431 (M⁺); elemental analysis: calculated (¹/₁₀ H₂O) C 69.29, H 8.65, N 3.23, found C 69.04, H 8.75, N 3.26.

(10) 2-Acetamido-1,3-diacetoxy-2-[2-[3-(trans-1-octenyl)phenyl)ethyl]propane

The above-mentioned compound (2.8 g) in anhydrous tetrahydrofuran (20 ml) was dropwise added to a solution of lithium aluminum hydride (0.74 g) in anhydrous tetrahydrofuran (40 ml) in a stream of nitrogen under ice-cooling and the mixture was stirred at room temperature for 2 hours. Under ice-cooling, ethanol and water were added to the reaction mixture and the insoluble matters were filtered off. The filtrate was dried over anhydrous magnesium sulfate and the solvent was distilled away to give a yellow, oily substance (2.34 g). This substance was dissolved in pyridine (60 ml) and thereto was added acetic anhydride (1.6 ml) under ice-cooling. The mixture was stirred at room temperature for 2.5 hours. The reaction mixture was concentrated and the residue was dissolved in ethyl acetate. The mixture was washed with a saturated aqueous ammonium chloride and saturated brine and dried over anhydrous magnesium sulfate. The solvent was distilled away and the residue was purified by silica gel column chromatography (eluent; hexane:ethyl acetate=4:1) to give 1.8 g of the subject compound as white crystals.

melting point=84°–86° C. ¹H-NMR (CDCl₃) δ: 0.87 (3H, t, J=6.8 Hz), 1.10–1.50 (8H, m), 1.94 (3H, s), 2.07 (6H, s), 2.15–2.21 (4H, m), 2.57 (2H, m), 4.33 (4H, s), 5.62 (1H, s), 6.19 (1H, dr, J=6.8, 16.1 Hz), 6.33 (1H, d, J=16.1 Hz), 6.99 (1H, d, J=6.8 Hz), 7.13–7.21 (3H, m); IR(KBr): 3311, 2961, 2926, 1738, 1652 cm⁻¹; MS: 431 (M⁺); elemental analysis: calculated C 69.58, H 8.64, N 3.25, found C 69.85, H 8.74, N 3.35.

(11) 2-Acetamido-1,3-diacetoxy-2-[2-(3-(octylphenyl)ethyl]propane

A suspension of 10% palladium carbon (150 mg) in methanol (10 ml) was added to a solution of the above-mentioned compound (1.41 g) in methanol (10 ml) and the mixture was stirred under hydrogen pressurization (10 atm) for 2 hours. The inside of the reaction vessel was displaced with nitrogen and the insoluble matters were filtered off. The solvent was distilled away and the residue was purified by silica gel column chromatography (eluent; hexane:ethyl acetate=2:1) to give 1.05 g of the subject compound as white crystals.

melting point=86°–87° C. ¹H-NMR (CDCl₃) δ: 0.86 (3H, t, J=6.9 Hz), 1.10–1.60 (12H, m), 1.93 (3H, s), 2.07 (6H, s), 2.18 (2H, m), 2.52 (2H, t, J=6.8 Hz), 2.56 (2H, t, J=6.8 Hz), 4.33 (4H, s), 5.61 (1H, s), 6.95–7.05 (3H, m), 7.17 (1H, t, J=7.8 Hz); IR(KBr): 3313, 2960, 2925, 2854, 1738, 1651 cm⁻¹.

(12) 2-Amino-2-[2-(3-octylphenyl)ethyl]-1,3-propanediol

An aqueous solution (10 ml) of lithium hydroxide (1 g) was added to a solution of the above-mentioned compound (1.04 g) in methanol (10 ml) and the mixture was refluxed under heating for 5 hours. The reaction mixture was concentrated, exctracted with ethyl acetate and washed with saturated brine. The mixture was dried over anhydrous magnesium sulfate and the solvent was distilled away. The residue was purified by silica gel column chromatography (eluent; chloroform:methanol=5:1) to give 0.46 g of the subject compound as white crystals.

melting point=89°–92° C. ¹H-NMR (CDCl₃) δ: 0.85 (3H, t, J=6.4 Hz), 1.20–1.35 (12H, m), 1.55 (2H, m), 1.83 (2H, m), 2.51 (2H, t, J=7.2 Hz), 2.60 (2H, m), 2.98 (2H, br.s), 3.68 (2H, t, J=11.2 Hz), 3.71 (2H, t, J=11.2 Hz), 6.97 (3H, m), 7.12 (1H, t, J=7.3 Hz); IR(KBr): 3396, 3257, 2925, 2854 cm⁻¹.

(13) 2-Amino-2-[2-(3-octylphenyl)ethyl]-1,3-propanediol Hydrochloride

The above-mentioned compound (0.45 g) was dissolved in ethanol (20 ml) and thereto was added a 26% solution (1 ml) of hydrochloric acid in ethanol. The solvent was distilled away and the precipitated crystals were recrystallized from ethyl acetate:methanol: 30:1 to give 0.33 g of the subject compound.

melting point: 99°–101° C. ¹H-NMR (DMSO) δ: 0.84 (3H, t, J=6.8 Hz), 1.20–1.35 (12H, m), 1.53 (2H, m), 1.74 (2H, m), 2.40–2.60 (2H, m), 3.45 (4H, s), 5.33 (2H, br.s), 6.98–7.00 (3H, m), 7.18 (1H, t, J=7.3 Hz), 7.70 (3H, br.s); IR(KBr): 3178, 2924, 2853 cm⁻¹.

EXAMPLE 297

2-Amino-2-(4-decylphenyl)-1,3-propanediol (1) 4-Bromomethyldecylbenzene

4-Decylphenylmethanol (3.91 g) was dissolved in toluene (40 ml) and thereto was added 48% hydrobromic acid (40 ml). The mixture was refluxed under heating at 90° C. for 6 hours. After cooling, the organic layer was separated and washed with saturated brine and a sodium hydrogencarbonate solution. The mixture was dried over anhydrous sodium sulfate and the solvent was distilled away to give 4.9 g of the oily subject compound.

¹H-NMR (CDCl₃) δ: 0.86 (3H, t, J=6.6 Hz), 1.2–1.3 (14H, m), 1.5–1.6 (2H, m), 2.57 (2H, t, J=7.6 Hz), 4.47 (2H, s), 7.13 (2H, d, J=8.1 Hz), 7.28 (2H, d, J=8.0 Hz).

(2) 4-Decylphenylnitromethane

Silver nitrite (4.15 g) and dry ether (20 ml) were placed in a flask and cooled with ice. Thereto was dropwise added a solution of 4-bromomethyldecylbenzene (5.5 g) in ether (10 ml) with stirring. After the dropwise addition, the mixture was stirred under ice-cooling for 4 hours and the insoluble matters were filtered off. The solvent in the filtrate was distilled away and the residue was crystallized from pentane to give 1.44 g of the subject compound as pale yellow crystals.

melting point=50° C. ¹H-NMR (CDCl₃) δ: 0.88 (3H, t, J=6 Hz), 1.2–1.3 (14H, m), 1.5–1.6 (2H, m), 2.62 (2H, t, J=8 Hz), 5.41 (2H, s), 7.24 (2H, d, J=8 Hz), 7.28 (2H, d, J=8 Hz).

(3) 2-(4-Decylphenyl)-2-nitro-1,3-propanediol

4-Decylphenylnitromethane (555 mg) was dissolved in ethanol (5 ml) and thereto were added a 1N aqueous sodium hydroxide solution (0.02 ml) and 37% formalin (0.45 ml). The mixture was heated at 50° C. for 6 hours. The solvent was distilled away and the residue was extracted with ethyl acetate. The extract was washed with saturated brine and dried over anhydrous sodium sulfate. The solvent was distilled away and the residue was crystallized from hexane to give 1.75 g of the colorless, scale-like subject compound.

melting point: 80°–81° C. $^1$H-NMR (CDCl$_3$) δ: 0.88 (3H, t, J=6 Hz), 1.2–1.3 (14H, m), 1.5–1.6 (2H, m), 2.59 (2H, t, J=8 Hz), 2.77 (2H, m), 4.35 (2H, m), 4.60 (2H, m), 7.17 (2H, d, J=10 Hz), 7.21 (2H, d, J=10 Hz).

(4) 2-Amino-2-(4-decylphenyl)-1,3-propanediol 2-(4-Decylphenyl)-2-nitro-1,3-propanediol (170 mg) was dissolved in ethanol (30 ml) and the mixture was subjected to catalytic reduction in the presence of 5% palladium carbon (40 mg) under hydrogen pressure of 20 arm. After stirring the mixture for 8 hours, the insoluble matters were filtered off and the filtrate was concentrated. The residue was purified by preparative thin layer chromatography (silica gel) to give 8.9 mg of the subject compound.

melting point=136°–137° C. $^1$H-NMR (CDCl$_3$—CD$_3$OD) δ: 0.88 (3H, t, J=8 Hz), 1.1–1.4 (14H, m), 1.4–1.8 (2H, m), 2.3–2.7 (6H, m), 3.5–4.2 (4H, m), 7.2 (2H, d, J=10 Hz), 7.33 (2H, d, J=10 Hz); melting point of hydrochloride=113°–114° C. (recrystallized from isopropyl alcohol).

EXAMPLE 298

2-Acetylamino-2-(4-decylphenyl)-1,3-propanediol

2-Amino-2-(4-decylphenyl)-1,3-propanediol (313 mg) was dissolved in a mixed solvent of ethanol (20 ml) and chloroform (5 ml). Thereto was added triethylamine (0.4 ml) and the mixture was cooled to −60° C. with dry ice-methanol. Thereto was dropwise added a solution of acetyl chloride (0.12 ml) in dichloromethane (5 ml) under ice-cooling and the mixture was heated to room temperature. The solvent was distilled away and the residue was dissolved in ethyl acetate. The mixture was washed with brine, an aqueous dilute hydrochloric acid solution and an aqueous sodium hydrogencarbonate solution. The resultant mixture was dried over anhydrous sodium sulfate and the solvent was distilled away. The residue was purified by preparative thin layer chromatography (silica gel) and recrystallized from hexane to give 130 mg of the colorless, crystalline subject compound.

melting point=112°–113° C. $^1$H-NMR (CDCl$_3$) δ: 0.88 (3H, t, J=6.9 Hz), 1.2–1.4 (14H, m), 1.5–1.7 (2H, m), 2.17 (3H, s), 2.58 (2H, t, J=7.9 Hz), 3.66 (2H, dd, J=7.7 Hz, 6 Hz), 3.88 (2H, dd, J=12 Hz, 7.6 Hz), 4.05 (2H, dd, J=11.9 Hz, 6 Hz), 6.37 (1H, bs), 7.20 (2H, d, J=8.6 Hz), 7.25 (2H, d, J=8.6 Hz).

EXAMPLE 299

5-Acetamido-5-(4-decylphenyl)-2,2-dimethyl-1,3-dioxane

2-Acetylamino-2-(4-decylphenyl)-1,3-propanediol (224 mg) and 2,2-dimethoxypropane (0.3 ml) were dissolved in benzene (5 ml) and the mixture was refluxed under heating in the presence of a catalytic amount of toluenesulfonic acid. After cooling, the reaction mixture was washed with an aqueous sodium hydrogencarbonate solution and dried over sodium sulfate. The solvent was distilled away and the residue was purified by preparative thin layer chromatography (silica gel) to give 99 mg of the amorphous subject compound.

$^1$H-NMR (CDCl$_3$) δ: 0.88 (3H, t, J=6.6 Hz), 1.2–1.4 (14H, m), 1.48 (3H, s), 1.51 (3H, s), 1.5–1.7 (2H, m), 2.06 (3H, s), 2.56 (2H, t, J=7.8 Hz), 4.14 (4H, s), 6.23 (1H, bs), 7.15 (2H, d, J=8.3 Hz), 7.22 (2H, d, J=8.3 Hz).

EXAMPLE 300

2-Amino-2-(8-phenyloctyl)-1,3-propanediol

EXAMPLE 301

2-Amino-2-(9-phenylnonyl)-1,3-propanediol

EXAMPLE 302

2-Amino-2-(11-phenylundecyl)-1,3-propanediol

EXAMPLE 303

2-Amino-2-(12-phenyldodecyl)-1,3-propanediol

EXAMPLE 304

2-Amino-2-(14-phenyltetradecyl)-1,3-propanediol

EXAMPLE 305

2-Amino-2-(15-phenylpentadecyl)-1,3-propanediol

EXAMPLE 306

2-Amino-2-(16-phenylhexadecyl)-1,3-propanediol

EXAMPLE 307

2-Amino-2-[2-(4-tridecylphenyl)ethyl]-1,3-propanediol

EXAMPLE 308

2-Amino-2-[2-(4-tetradecylphenyl)ethyl]-1,3-propanediol

EXAMPLE 309

2-Amino-2-[2-(4-hexyloxyphenyl)ethyl]-1,3-propanediol

EXAMPLE 310

2-Amino-2-[2-(4-decyloxyphenyl)ethyl]-1,3-propanediol

EXAMPLE 311

2-Amino-2-[2-(4-dodecyloxyphenyl)ethyl]-1,3-propanediol

EXAMPLE 312

2-Amino-2-[2-(4-tridecyloxyphenyl)ethyl]-1,3-propanediol

EXAMPLE 313

2-Amino-2-[2-(4-(8-fluorooctyl)phenyl)ethyl]-1,3-propanediol

EXAMPLE 314

2-Amino-2-[2-(4-(12-fluorododecyl)phenyl)ethyl]-1,3-propanediol

EXAMPLE 315

2-Amino-2-[2-(4-(7-fluoroheptyloxy)phenyl)ethyl]-1,3-propanediol

EXAMPLE 316

2-Amino-2-[2-(4-(11-fluoroundecyloxy)phenyl)ethyl]-1,3-propanediol

EXAMPLE 317

2-Amino-2-[2-(4-phenylmethyloxyphenyl)ethyl]-1,3-propanediol

EXAMPLE 318

2-Amino-2-[2-(4-(2-phenylethyloxy)phenyl)ethyl]-1,3-propanediol

EXAMPLE 319

2-Amino-2-[2-(4-(3-phenylpropyloxy)phenyl)ethyl]-1,3-propanediol

EXAMPLE 320

2-Amino-2-[2-(4-(4-phenylbutyloxy)phenyl)ethyl]-1,3-propanediol

EXAMPLE 321

2-Amino-2-[2-(4-(5-phenylpentyloxy)phenyl)ethyl]-1,3-propanediol

EXAMPLE 322

2-Amino-2-[2-(4-(7-phenylheptyloxy)phenyl)ethyl]-1,3-propanediol

EXAMPLE 323

2-Amino-2-[2-(4-(8-phenyloctyloxy)phenyl)ethyl]-1,3-propanediol

EXAMPLE 324

2-Amino-2-[4-(6-(4-fluorophenyl)hexyloxy)phenyl)ethyl]-1,3-propanediol

EXAMPLE 325

2-Amino-2-[2-(4-(4-phenoxybutyloxy)phenyl)ethyl]-1,3-propanediol

EXAMPLE 326

2-Amino-2-[2-(4-(5-phenoxypentyloxy)phenyl)ethyl]-1,3-propanediol

EXAMPLE 327

2-Amino-2-[2-(4-(6-phenoxyhexyloxy)phenyl)ethyl]-1,3-propanediol

EXAMPLE 328

2-Amino-2-[2-(4-(7-phenoxyheptyloxy)phenyl)ethyl]-1,3-propanediol

EXAMPLE 329

2-Amino-2-[2-(4-(4-phenoxybutyl)phenyl)ethyl]-1,3-propanediol

EXAMPLE 330

2-Amino-2-[2-(4-(5-phenoxypentyl)phenyl)ethyl]-1,3-propanediol

EXAMPLE 331

2-Amino-2-[2-(4-(6-phenoxyhexyl)phenyl)ethyl]-1,3-propanediol

EXAMPLE 332

2-Amino-2-[2-(4-(7-phenoxyheptyl)phenyl)ethyl]-1,3-propanediol

EXAMPLE 333

2-Amino-2-[2-(4-octylcyclohexyl)ethyl]-1,3-propanediol

EXAMPLE 334

2-Amino-2-[2-(4-nonylcyclohexyl)ethyl]-1,3-propanediol

EXAMPLE 335

2-Amino-2-[2-(4-dodecylcyclohexyl)ethyl]-1,3-propanediol

EXAMPLE 336

2-Amino-2-[2-(1-octylpiperidin-4-yl)ethyl]-1,3-propanediol

EXAMPLE 337

2-Amino-2-[2-(1-dodecylpiperidin-4-yl)ethyl]-1,3-propanediol

EXAMPLE 338

2-Amino-2-[2-(5-nonyl-2-thienyl)ethyl]-1,3-propanediol

EXAMPLE 339

2-Amino-2-[2-(5-decyl-2-thienyl)ethyl]-1,3-propanediol

EXAMPLE 340

2-Amino-2-[2-(5-dodecyl-2-thienyl)ethyl]-1,3-propanediol

EXAMPLE 341

2-Amino-2-[13-(2-thienyl)tridecyl]-1,3-propanediol

EXAMPLE 342

2-Amino-2-[2-(5-octyl-2-pyridyl)ethyl]-1,3-propanediol

EXAMPLE 343

2-Amino-2-[2-(5-decyl-2-pyridyl)ethyl]-1,3-propanediol

EXAMPLE 344

2-Amino-2-[13-(2-pyridyl)tridecyl]-1,3-propanediol

EXAMPLE 345

2-Amino-2-[2-(2-octyl-5-pyridyl)ethyl]-1,3-propanediol

EXAMPLE 346

2-Amino-2-[2-(2-decyl-5-pyridyl)ethyl]-1,3-propanediol

EXAMPLE 347

2-Amino-2-[13-(3-pyridyl)tridecyl]-1,3-propanediol

EXAMPLE 348

2-Amino-2-(4-decylphenyl)-1,3-propanediol

EXAMPLE 349

2-Amino-2-(4-dodecylphenyl)-1,3-propanediol

EXAMPLE 350

2-Amino-2-(4-tetradecylphenyl)-1,3-propanediol

EXAMPLE 351

2-Amino-2-(4-hexadecylphenyl)-1,3-propanediol

EXAMPLE 352

2-Amino-2-[1-hydroxy-2-(4-octylphenyl)ethyl]-1,3-propanediol

EXAMPLE 353

2-Amino-2-[2-(4-dodecylphenyl)-1-hydroxyethyl]-1,3-propanediol

EXAMPLE 354

2-Amino-2-[2-(4-heptyloxyphenyl)-1-hydroxyethyl]-1,3-propanediol

EXAMPLE 355

2-Amino-2-[1-hydroxy-2-(4-undecyloxyphenyl)ethyl]-1,3-propanediol

EXAMPLE 356

2-Amino-2-[2-(4-(8-fluorooctyl)phenyl)-1-hydroxyethyl]-1,3-propanediol

EXAMPLE 357

2-Amino-2-[2-(4-(12-fluorododecyl)phenyl)-1-hydroxyethyl]-1,3-propanediol

EXAMPLE 358

2-Amino-2-[2-(4-(7-fluoroheptyloxy)phenyl)-1-hydroxyethyl]-1,3-propanediol

EXAMPLE 359

2-Amino-2-[1-hydroxy-2-(4-(11-fluoroundecyloxy)phenyl)ethyl]-1,3-propanediol

EXAMPLE 360

2-Amino-2-[2-(4-octylphenyl)ethenyl]-1,3-propanediol

EXAMPLE 361

2-Amino-2-[2-(4-decylphenyl)ethenyl]-1,3-propanediol

EXAMPLE 362

2-Amino-2-[2-(4-dodecylphenyl)ethenyl]-1,3-propanediol

EXAMPLE 363

2-Amino-2-[2-(4-tetradecylphenyl)ethenyl]-1,3-propanediol

EXAMPLE 364

2-Amino-2-(4-octylphenoxymethyl)-1,3-propanediol

EXAMPLE 365

2-Amino-2-(4-decylphenoxymethyl)-1,3-propanediol

EXAMPLE 366

2-Amino-2-(4-dodecylphenoxymethyl)-1,3-propanediol

EXAMPLE 367

2-Amino-2-(4-tetradecylphenoxymethyl)-1,3-propanediol

EXAMPLE 368

2-Amino-2-(1-hydroxy-2-phenylethyl)-1,3-propanediol Hydrochloride melting point=188°–190° C. $^1$H-NMR (DMSO-d$_6$) δ (ppm): 2.57 (1H, dd, J=10.7, 14.2 Hz), 2.88 (1H, d, J=14.2 Hz), 3.63 (4H, m), 3.85 (1H, d, J=10.7 Hz), 5.16 (1H, br.s), 5.28 (2H, br.s), 7.25 (5H, m), 7.77 (3H, br.s); IRv(KBr)$_{max}$: 3156. 2814, 1626, 1550, 1080, 1056, 743, 702 cm$^{-1}$.

EXAMPLE 369

2-Acetamido-1,3-diacetoxy-2-(1-acetoxy-2-phenylethyl)propane, Transparent Oil

¹H-NMR (CDCl₃) δ (ppm): 1.89 (3H,s), 1.94 (3H, s), 2.08 (3H, s), 2.13 (3H, S), 2.83 (1H, dd,J=10.3, 14.2 Hz), 3.05 (1H, dd, J=3.4, 14.2 Hz), 4.46 (1H, d, J=11.7 Hz), 4.48 (1H, d, J=11.7 Hz), 4.55 (1H, d, J=11.7 Hz), 4.71 (1H, d, J=11.7 Hz), 5.66 (1H, dd, J=3, 4, 10.3 Hz), 5.86 (1H, s, —NH), 7.22 (5H, m).

EXAMPLE 370

(Z)-2-Amino-2-styryl-1,3-propanediol

¹H-NMR (CDCl₃) δ (ppm): 2,62 (4H, br.s), 3.47 (2H, d, J=11 Hz), 3.55 (2H, d, J=11 Hz), 5.55 (1H, d, J=12.7 Hz), 6.74 (1H, d, J=12.7 Hz), 7.27 (5H, m).

EXAMPLE 371

(E)-2-Amino-2-styryl-1,3-propanediol

¹H-NMR (CD₃OD) δ (ppm): 3.51 (2H, d, J=11 Hz), 3.63 (2H, d, J=11 Hz), 6.10 (1H, d, J=16.4 Hz), 6.55 (1H, d, J=16.4 Hz), 7.23 (5H, m).

EXAMPLE 372

2-Acetamido-2-[2-(4-decylphenyl)ethyl]-1,3-propanediol Diacetate melting point=101°–104° C. ¹H-NMR (CDCl₃) δ (ppm): 0.88 (3H, t, J=6 Hz), 1.26–1.29 (16H, m), 1.95 (3H, s), 2.09 (6H, s), 2.17–2.21 (2H, m), 2.54–2.60 (4H, m), 4.35 (4H, s), 5.63 (1H, s), 7.09 (4H, s); IRv: 3310, 2919, 1735, 1654, 1231, 1058 cm⁻¹.

EXAMPLE 373

2-Amino-2-[2-(4-decylphenyl)ethyl]-1,3-propanediol Hydrochloride melting point=111°–115° C. ¹H-NMR (CDCl₃) δ (ppm): 0.88 (3H, t, J=6 Hz), 1.26–1.29 (16H, s), 1.92–1.96 (2H, m), 2.56 (2H, t, J=8 Hz), 2.61–2.65 (2H, m), 3.71 (4H, q, J=12 Hz), 7.11 (4H, s); IRv: 3373, 2923, 1603, 1518, 1070 cm⁻¹.

EXAMPLE 374

2-Acetamido-2-[2-(4-(4-methylpentyloxy)phenyl)ethyl]-1,3-propanediol Diacetate melting point=83°–87° C. ¹H-NMR (CDCl₃) δ (ppm): 0.91 (6H, d, J=6 Hz), 1.57 (4H, s), 1.96 (3H, s), 2.09 (6H, s), 2.15–2.19 (2H, m), 2.51–2.58 (2H, m), 3,91 (2H, t, J=6 Hz), 4.34 (4H, s), 6.81 (2H, d, J=4 Hz ), 7.08 (2H, d, J=4 Hz); IRv:3310, 2954, 1735, 1649 cm⁻¹; elemental analysis: calculated C 65.54, H 8.37, N 3.32, found C 65.60, H 8.40, N 3.43.

EXAMPLE 375

2-Amino-2-[2-(4-(4-methylpentyloxy)phenyl)ethyl]-1,3-propanediol ¹/₁₀ Hydrate melting point=125°–128° C. ¹H-NMR (CDCl₃) δ (ppm): 0.83 (6H, d, J=6 Hz), 1.25 (2H, t, J=6 Hz), 1.54–1.58 (3H, m), 1.66–1.72 (2H, m), 2.47–2.51 (2H, m), 3.39–3.50 (4H, m), 3.81–3.85 (2H, m), 6.73 (2H, d, J=12 Hz), 7.02 (2H, d, J=12 Hz); IRv: 3324, 2951, 1513, 1247, 1026 cm⁻¹.

EXAMPLE 376

2-Acetamido-2-(2-pyridylmethyl)-1,3-propanediol

¹H-NMR (400MHz, CDCl₃) δ (ppm): 1.66 (2H, br.s, OH), 1.94 (3H, s, CH₃), 3.26 (2H, s, CH₂), 3.56 (4H,dd, J=72, 12 Hz, CH₂×2), 6.97 (1H, br.s, NH), 7.23 (1H, dd, J=8.0, 4.0 Hz, ArH), 7.33 (1H, d, J=8.0 Hz, ArH), 7.69 (1H, dt, J=8.0, 4.0 Hz,ArH), 8.49 (1H, d, J=4.0 Hz, ArH).

EXAMPLE 377

2-Acetamido-2-(2-pyridylmethyl)-1,3-diacetoxypropane

¹H-NMR (400MHz, CDCl₃) δ (ppm): 1.96 (3H, s, CH₃), 2.05 (6H, s, CH₃×2), 3.13 (2H, s, CH₂), 4.47 (4H, dd, J=40, 12 Hz, CH₂×2), 7.15 (1H, d, J=8.0 Hz, ArH), 7.21 (1H, dd, J=8.0, 4.0 Hz, ArH), 7.48 (1H, s, NH), 7.65 (1H, dt, J=8.0, 4.0 Hz, ArH), 8.55 (1H, d, J=4.0 Hz, ArH); IRv(KBr)ₘₐₓ: 3320(NH), 1748 (CO), 1654, 1533, 1248 cm⁻¹; MS: 308 (M⁺); melting point=109°–110° C.

EXAMPLE 378

2-Amino-2-(2-pyridylmethyl)-1,3-propanediol ¾ Hydrate 2 Hydrochloride

¹H-NMR (400MHz, CD₃OD) δ (ppm): 3.53 (2H, s, ArCH₂), 3.65 (4H, ddd, J=24, 12, 4.0 Hz, CH₂×2), 4.88 (6H, br.s, OH×2, N⁺H₃, N⁺), 8.02 (1H, t, J=8.0 Hz, ArH), 8.09 (1H, d, J=8.0 Hz, ArH), 8.57–8.61 (1H, m, ArH), 8.81 (1H, d, J=4.0 Hz, ArH); IRv(KBr)ₘₐₓ: 3385, 3070, 3059, 2945, 2897, 1621, 1066 cm⁻¹; MS: 183 (M⁺); melting point= 165°–170° C.

EXAMPLE 379

2-Acetamido-2-[2-(5-butylpyridyl)methyl]-1,3-propanediol

¹H-NMR (400MHz, CDCl₃) δ (ppm): 0.94 (3H, t, d=8.0 Hz, CH₃), 1.26 (2H, t, J=8.0 Hz, CH₂ ), 1.36 (2H, m,CH₂), 1.59 (2H, br.s, OH×2), 1.93 (3H, s, CH₃), 2.58–2.62 (2H, m,CH₂), 3.21 (2H, s, CH₂), 3.55 (4H, dd, J=72, 12 Hz, CH₂×2), 6.97 (1H, br.s, NH), 7.22 (1H, d, J=8.0 Hz, ArH), 8.45–8.50 (1H, m, ArH), 8.31 (1H, br.s, ArH); IRv(neat)ₘₐₓ: 3378(H), 2958, 2933, 2862, 1738(CO), 1658 cm⁻¹ oil.

EXAMPLE 380

2-Acetamido-2-[2-(5-butylpyridyl)methyl]-1,3-diacetoxypropane

¹H-NMR (400MHz, CDCl₃) δ (ppm): 0.94 (3H, t, J=8.0 Hz, CH₃), 1.33–1.42 (2H, m, CH₂), 1.56–1.64 (2H, m, CH₂), 1.96 (3H, s, CH₃), 2.05 (6H, s, CH₃×2), 2.60 (2H, t, J=8.0 Hz, CH₂), 3.08 (2H, s, CH₂), 4.46 (4H, dd, J=40, 12 Hz, CH₂×2), 7.05 (1H, d, J=8.0 Hz, ArH), 7.44–7.46 (1H, m, ArH), 7.56 (1H, s, NH), 8.35–8.37 (1H, m, ArH); IRv(KBr)ₘₐₓ: 3371, 3290, 2959, 2934, 1745(CO), 1681, 1240 cm⁻¹ oil.

EXAMPLE 381

2-Amino-2-[2-(5-butylpyridyl)methyl]-1,3-propanediol

¹H-NMR (400MHz, CDCl₃) δ (ppm): 0.94 (3H, t, J=8.0 Hz, CH₃), 1.36 (2H, dt, J=16, 8.0 Hz, CH₂), 1.59 (2H, dr, J=16, 8.0 Hz, CH₂), 2.60 (2H, t, J=8.0 Hz, CH₂), 2.92 (2H, s, CH₂), 1.20–3.00 (4H, m, OH×2, NH₂), 3.39 (4H, dd, J=36, 12 Hz, CH₂×2), 7.13 (1H, d, J=8.0 Hz, ArH), 7.48 (1H, dd, J=8.0, 2.0 Hz, ArH), 8.33 (1H, d, J=2.0 Hz, ArH); IRv(KBr)$_{max}$: 3339, 3269, 2923, 2857, 1595, 1033 cm⁻¹; melting point: 63°–65° C.

EXAMPLE 382

2-Acetamido-1,3-diacetoxy-2-[2-(1-octylpiperidin-4-yl)ethyl]propane melting point=93°–95° C. ¹H-NMR (CDCl₃) δ (ppm): 0.85 (3H, t, J=6.4 Hz ), 1.19–1.36 (15H, m), 1.50 (2H, br.s), 1.64 (2H, d, J=11.8 Hz), 1.85–1.97 (3H, m), 1.93 (3H, s), 2.05 (6H, s), 2.33 (2H, br.s), 2.97 (2H, br.s), 4.25 (4H, s), 5.61 (1H, s); IRv(KBr)$_{max}$: 3302, 1739, 1654, 1560 cm⁻¹.

EXAMPLE 383

2-Acetamido-2-(2-propenyl)-1,3-propanediol Pale Yellow Liquid

Rf value: 0.55 (chloroform:methanol=5:1); ¹H-NMR (CDCl₃—CD₃OD) δ (ppm): 1.95 (3H, s), 2.33 (2H, d, J=7.33 Hz ), 3.49 (2H, d, J=11.7 Hz), 3.64 (2H, d, J=11.7 Hz), 5.07–5.10 (2H, m), 5.66–5.90 (1H, m); IRv(neat): 3310, 1641 cm⁻¹; MS(EI): 174 (M+1).

EXAMPLE 384

2-Amino-2-(2-propenyl)-1,3-propanediol ⅘ Hydrate Hydrochloride Brown Liquid

¹H-NMR (CDCl₃) δ (ppm): 2.33 (2H, d, J=10.7 Hz), 3.56 (4H, dd, J=3.0 Hz, J=19.0 Hz ), 3.39 (11H, br.s), 5.14–5.22 (2H, m), 5.62–5.23 (1H, m); IRv(neat): 3445, 1614, 1516 cm⁻¹; MS(EI): 132 (M+1); elemental analysis: calculated C 36.68, H 8.82, N 7.13, found C 36.27, H 8.47, N 7.26.

EXAMPLE 385

2-Amino-2-phenylmethyloxymethyl-1,3-propanediol ⅒ Hydrate Hydrochloride melting point=113°–114° C.

EXAMPLE 386

2-Acetamido-1,3-diacetoxy-2-phenylmethyloxymethylpropane

IRv(neat): 3307, 2934, 1743, 1662, 1549 cm⁻¹;

EXAMPLE 387

2-Amino-2-[2-(4-nonylphenyl)ethyl]-1,3-propanediol ⅓ Hydrate Hydrochloride melting point=95°–97° C. elemental analysis: calculated C 66.00, H 10.15, N 3.85, found C 66.19, H 10.24, N 3.86.

EXAMPLE 387

2-Acetamido-1,3-diacetoxy-2-[2-(4-nonylphenyl)ethyl]propane melting point=95°–98° C.

EXAMPLE 388

2-Acetamido-2-[2-(4-undecylphenyl)ethyl]-1,3-propanediol melting point=90°–91° C.

EXAMPLE 389

2-Amino-2-[2-(4-undecylphenyl)ethyl]-1,3-propanediol melting point=105°–107° C.
¹H-NMR (CDCl₃) δ (ppm): 0.88 (3H, t, J=6.8 Hz), 1.20–1.80 (24H, m), 2.56 (2H, t, J=7.8 Hz), 2.61 (2H, m), 3.51 (2H, d, J=10.8 Hz), 3.61 (2H, d, J=10.8 Hz), 7.10 (4H, s).

EXAMPLE 390

2-Acetamido-4-(4-heptylphenyl)-2-hydroxymethyl-1,4-butanediol melting point=117°–118° C.

EXAMPLE 391

2-Acetamido-4-(4-octylphenyl)-2-hydroxymethyl-1,4-butanediol melting point=118°–119° C.

EXAMPLE 392

2-Acetamido-2-[2-(4-heptylphenyl)ethyl]-1,3-propanediol melting point=89°–90° C.

EXAMPLE 393

2-Acetamido-2-1,3-propanediyl-[2-(4-heptylphenyl)ethyl]ylidene Diacetate melting point=108°–109° C.

EXAMPLE 394

2-Amino-2-[2-(4-heptylphenyl)ethyl]-1,3-propanediol Hydrochloride melting point=134°–135° C. ¹H-NMR (DMSO only) δ (ppm): 0.83 (3H, t, J=6 Hz), 1.17–2.33 (8H, m), 1.45–1.58 (2H, 1.69–1.79 (2H, m), 2.48–2.62 (4H, m), 3.34 (2H, br.s), 3.48 (4H, s), 7.08 (4H, s), 7.47 (3H, br.s); IRv(KBr)$_{max}$: 3369, 2926, 1515, 1467, 1059 cm⁻¹.

EXAMPLE 395

2-Acetamido-1,3-propanediyl-2-[2-(4-tetradecylphenyl)ethyl]ylidene Diacetate melting point=125°–126° C.

EXAMPLE 396

2-Amino-2-[2-(4-tetradecylphenyl)ethyl]-1,3-propanediol Hydrochloride melting point=123°–124° C. ¹H-NMR (DMSO-CDCl₃) δ (ppm): 0.80 (3H, t, J=6 Hz), 1.02–1.24 (22H, m), 1.45–1.53 (2H, m), 1.88 (2H, m, J=4 Hz), 2.46 (2H, t, J=6 Hz ), 2.56–2.62 (2H, m), 3.56 (2H, dd, J=12 Hz, 31 Hz), 3.57 (2H, dd, J=12 Hz, 31 Hz), 4.90 (2H, br.s), 7.01 (4H, dd, J=7 Hz, 12 Hz), 7.99 (3H, br.s); IRv(KBr)$_{max}$: 3374, 3268, 2922, 1516, 1469, 1069 cm$^{-1}$.

EXAMPLE 397

N-Methylamino-2-[2-(4-octylphenyl)ethyl]-1,3-propanediol $^1$H-NMR (CDCl$_3$) δ (ppm): 0.80 (3H, t, J=7 Hz), 1.09–1.39 (10H, m), 1.45–1.56 (2H, m), 1.56–1.76 (2H, m), 2.41 (3H, s), 2.44–2.61 (4H, m), 3.32 (3H, br.s), 3.47–3.81 (4H, m), 7.01 (4H, s); IRv(neat): 3386, 2927, 1467, 1058, 909 cm$^{-1}$.

EXAMPLE 398

2-Amino-4-(4-heptylphenyl)-2-hydroxymethyl-1,4-butanediol Hydrochloride melting point=105°–108° C. $^1$H-NMR (DMSO) δ (ppm): 0.86 (3H, t, J=7 Hz), 1.17–1.36 (8H, m), 1.46–1.63 (2H, m), 1.76 (2H, dd, J=7 Hz, 18 Hz), 2.54 (2H, t, J=7 Hz), 3.34 (3H, br.s), 3.58 (4H, dd, J=11 Hz, 35 Hz), 4.83–4.92 (1H, m), 6.99 (3H, br.s), 7.18 (4H, dd, J=7 Hz, 37 Hz); IRv(KBr)$_{max}$: 3388, 2928, 1610, 1511, 1063 cm$^{-1}$;

EXAMPLE 399

2-Amino-4-(4-octylphenyl)-2-hydroxymethyl-1,4-butanediol ¼ Hydrate $^1$H-NMR (CDCl$_3$) δ (ppm): 0.86 (3H, t, J=7 Hz), 1.22–1.38 (10H, m), 1.54–1.68 (3H, m), 1.68–1.79 (1H, m), 2.59 (2H, t, J=7 Hz), 3.40 (3H, br.s), 3.50 (4H, dd, J=8 Hz, 38 Hz), 3.63 (2H, br.s), 4.91 (1H, m), 7.20 (4H, dd, J=6 Hz, 30 Hz); IRv(neat): 3340, 3286, 2925, 1465, 1027 cm$^{-1}$.

The action and effect of the present invention are explained in detail by illustrating experimental examples in the following.

For determining the immunosuppressive activity, various immune reactions using lymphocytes of mouse, rat or human are usable. It may be determined with high sensitivity, for example, by an allogenic mixed lymphocyte reaction (allogenic MLR) of mouse, rat or human.

The allogenic MLR is a blastogenesis of lymphocytes induced by a mixed culture of lymphocytes derived from two kinds of cells which are allogenic but have different major histocompatibility antigens, such as spleen cells, lymph node cells and peripheral blood lymphocytes. The allogenic MLR is a phenomenon induced by and reflects the difference in major histocompatibility antigens of the donors of the lymphocytes, and a blastogenesis phenomenon of the lymphocytes is not developed by a mixed culture of the lymphocytes from monozygotic twins. Accordingly, allogenic MLR is widely used for the donor-recipient selection in organ transplantations.

When allogenic MLR is desired, one way-MLR, wherein the lymphocytes of one of them are used as stimulator cells upon X-ray irradiation or treatment with mitomycin C to inhibit proliferation and the blastogenesis of the other lymphocytes (responder cells) is determined, may be used.

Further, the immunosuppressive activity may be determined as an activity to inhibit induction of cytotoxic T cells having the major histocompatibility antigen restrictive property during allogenic MLR.

Also, the immunosuppressive activity may be determined, besides allogenic MLR, as an activity to inhibit the blastogenesis of the lymphocytes induced by the stimulation of of various mitogens such as concanavalin A, phytohemaggulutinin and pokeweed mitogen or as an activity to inhibit the proliferation of the lymphocytes induced by a cytokine (e.g. interleukin 1, 2, 3, 4, 5 or 6) having an activity to reinforce the proliferation or promote the differentiation of the lymphocytes such as T cells or B cells, or manifestation of such function. In addition, it is possible to evaluate the immunosuppressive activity according to the inhibition of the production of these cytokines from T cells or macrophages.

Alternatively, the activity may be evaluated as an activity to inhibit induction of allogenic cells-specific cytotoxic T cells induced in spleen cells of mouse previously immunized with, for example, allogenic cells by intraperitoneally, orally, intravenously, intradermally, subcutaneously or intramuscularly administering a compound to mice; as an activity to inhibit the production of an allogenic cells-specific antibody produced in the blood serum of mouse immunized with allogenic cells or the like; or as an activity to inhibit rejection on organ transplantation between allogenic mice, rats, dogs and so on, graft-versus-host reaction, or delayed type allergy and adjuvant arthritis.

Moreover, the immunosuppressive activity may be evaluated as an activity to inhibit, for example, production of an anti-DNA antiboty, production of a rheumatoid factor, nephritis, abnormal proliferation of lymphocytes or urinary protein; or a macrobiotic effect by the administration of the compound to MRL/1pr mouse, NZB/WF$_1$ mouse, BXSB mouse, NOD mouse and the like which are model animals with autoimmune diseases.

EXPERIMENTAL EXAMPLE 1 (Inhibition of Allogenic Mixed Lymphocyte Reaction in Mouse The mouse allogenic mixed lymphocyte reaction (hereinafter referred to as mouse allogenic MLR) is carried out by a mixed culture of spleen cells of BALB/c mouse as responder cells and spleen cells of C57BL/6 mouse treated with mitomycin C as stimulator cells at the same ratio.

The reaction cells are prepared as follows. A spleen is removed from a 5–6 weeks old BALB/c mouse and a single cell suspension of spleen cells is obtained by the use of an RPMI1640 medium (containing kanamycin sulfate 60 μg/ml, penicillin G potassium 100 units/ml, N-2-hydroxyethylpiperazine-N'-2ethanesulfonate 10 mM, 0.1% sodium hydrogencarbonate and L-glutamine 2 mM) supplemented with 5% heat-inactivated fetal calf serum (hereinafter referred to as FCS). After hemolysis treatment, the suspension is adjusted to a concentration of 10$^7$ cells/ml by the use of an RPMI1640 medium containing 10$^{-4}$M 2-mercaptoethanol and 10% FCS and used as a reaction cell suspension.

The stimulator cells are prepared as follows. A spleen is removed from a 5–6 weeks old C57BL/6 mouse and a single cell suspension of spleen cell is obtained by the use of an RPMI1640 medium. After hemolysis treatment, the suspension is treated with 40 μg/ml mitomycin C at 37° C. for 60 minutes. After washing three times, the suspension is adjusted to a concentration of 10$^7$ cells/ml by the use of an RPMI1640 medium containing 10$^{-4}$M 2-mercaptoethanol and 10% FCS and used as a stimulator cell suspension.

The responder cell suspension (50 μl) prepared by the method described above, the stimulator cell suspension (50 μl) prepared by the method described above and a test sample (100 μl) prepared by the use of an RPMI1640 medium containing 10% FCS are placed in a 96 well flat-bottomed micro testplate and cultured at 37° C. under 5% $CO_2$—95% air for 4 days.

The blastogenesis reaction of lymphocytes in mouse allogenic MLR is determined by a method using $^3$H-thymidine uptake as an index. Namely, after the culture, $^3$H-thymidine 18.5 KBq/well is added and the cells are cultured for 4 hours. The cells are collected by a cell harvester and the radioactivity incorporated into the cells is determined by a liquid scintillation counter and used as an index for the lymphocyte blastogenesis in mouse allogenic MLR. The inhibition of mouse allogenic MLR is calculated by the formula below and evaluated accordingly.

Of the compounds of the present invention, the preferred show an $IC_{50}$ value (a concentration to inhibit by 50%) of from about 1 nM to about 50 nM in a mouse allogenic mixed lymphocyte reaction.

Of the compounds of the present invention, the preferred show an $IC_{50}$ value (a concentration to inhibit by 50%) of from about 1 nM to about 50 nM in a mouse allogenic mixed lymphocyte reaction.

$$\text{Inhibition (\%)} = \left(1 - \frac{\left(\begin{array}{c}\text{cpm of MLR} \\ \text{with test sample}\end{array}\right) - \left(\begin{array}{c}\text{cpm of responder} \\ \text{cells alone}\end{array}\right)}{\left(\begin{array}{c}\text{cpm of MLR} \\ \text{without test sample}\end{array}\right) - \left(\begin{array}{c}\text{cpm of responder} \\ \text{cells alone}\end{array}\right)}\right) \times 100$$

EXPERIMENTAL EXAMPLE 2 [Inhibition of Proliferation of Interleukin 2 (IL-2)-dependent Mouse T Cell Line CTLL-2 Induced by IL-2]

An IL-2-dependent mouse T cell line CTLL-2 is prepared to a concentration of $2\times10^5$ cell/ml in an RPMI1640 medium containing 10% FCS. A cell suspension thereof (50 recombinant human IL-2 (rh-IL-2) 40 U/ml (50 μl) and a test sample (100 μl) prepared by the use of an RPMI1640 medium containing 10% FCS are placed in a 96 well flat-bottomed micro testplate and cultured at 37° C. under 5% $CO_2$—95% air for 68 hours. After the culture, 100 μl of the supernatant of each well is removed and a 5 mg/ml MTT [3-(4,5-dimethylthiazol-2-yl)-2,5-diphenyltetrazolium bromide] solution is added to each well by 20 μl and the cells are incubated at 37° C. for 4 hours. Then, 0.01N hydrochloric acid solution (100 μl) containing 10% sodium dodecyl sulfate is added thereto and the cells are incubated at 37° C. overnight. The purple formazan crystals produced are dissolved and the absorbance at 570 nm is measured using a microplate absorbance photometer and used as an index of the proliferation of the IL-2-dependent CTLL-2 cells. The inhibition (%) of the IL-2 dependent proliferation is calculated by the following formula.

Of the compounds of the present invention, the preferred show an IC50 value (a concentration to inhibit by 50%) of from about 1 nM to about 50 nM in the IL-2-dependent proliferation of mouse T cell line CTLL-2.

$$\text{Inhibition (\%)} = \left(1 - \frac{\left(\begin{array}{c}\text{absorbance when} \\ \text{test sample and} \\ \text{rh-IL-2 are added}\end{array}\right) - \left(\begin{array}{c}\text{absorbance when} \\ \text{rh-IL-2 is} \\ \text{not added}\end{array}\right)}{\left(\begin{array}{c}\text{absorbance when} \\ \text{rh-IL-2 alone} \\ \text{is added}\end{array}\right) - \left(\begin{array}{c}\text{absorbance when} \\ \text{rh-IL-2 is} \\ \text{not added}\end{array}\right)}\right)$$

EXPERIMENTAL EXAMPLE 3 (Take-prolonging Effect on Allogenic Skin Graft in Rat)

A full-thickness graft (1.5×1.5 cm) of a 4 weeks-old male WKAH rat or LEW rat is grafted to a graft floor on the back of a 4 weeks-old male F344 rat by suture. The graft is covered with a sterile gauze and bound. The bandage is removed 5 days after the grafting and the skin graft is observed daily until it is rejected. The skin graft is considered to be rejected when 90% or more of the epithelium of the skin graft showed necrosis and turned brown. The number of days from the grafting to rejection is taken as a graft taking days. A test compound is intraperitoneally, intravenously or orally administered once a day and 10 times from the grafting day to day 9.

When a test compound is not administered, an average taking days for grafting the skin of a WKAH rat to an F344 rat was 6.6±0.5 and that for grafting the skin of an LEW rat to an F344 rat was 8.2±0.4.

Of the compounds of the present invention, a preferred compound showed, when administered at 0.1–10 mg/kg, an average taking days of not less than 10 for grafting the skin of a WKAH rat to an F344 rat and not less than 20 for grafting the skin of an LEW rat to an F344 rat, thus showing a take-prolonging effect statistically significant as compared with the group without administration of the test compound.

EXPERIMENTAL EXAMPLE 4 (Inhibition of Adjuvant Arthritis in Rat)

Dead tuberclosis bacterium (R35H5v-1 strain, 0.5 mg) was suspended as an adjuvant in 1.0 ml of liquid paraffin and inoculated to the tail head of a 10 weeks-old male LEW rat to cause adjuvant arthritis. After the innoculation of the adjuvant, the rats are observed daily to determine the onset of arthritis, ratio of the onset cases and body weight changes. At day 21, swelling of the hind limbs and the weight of the organs are measured. A test compound is intravenously or orally administered from the adjuvant innoculation day once a day and 22 times up to day 21.

When the test compound was not administered, arthritis was found in all 7 rats innoculated with adjuvant at day 9.6±0.5, along with swelling and destruction of the bone of the hind limbs. Along with the onset of the adjuvant arthritis, decrease in body weight, increase in the weights of kidney and adrenal and decrease in the thymus weight were found.

Of the compounds of the present invention, a preferred compound delayed the onset of and decreased the ratio of the onset cases of the adjuvant arthritis to a statistically significant degree and significantly suppressed swelling and bone destruction of the hind limbs by the administration of 0.1–10 mg/kg thereof. In addition, decrease in body weight, increase in the weights of kidney and adrenal and decrease in the thymus weight, which accompany onset of adjuvant arthritis, were significantly reduced.

As is evident from the various experiments inclusive of phamacological experiments as noted above, the compounds of the present invention and salts thereof have superior immunosuppressive action and are useful as pharmaceuticals.

FORMULATION EXAMPLES

| (1) Soft capsules (per capsule) | |
| --- | --- |
| Compound of the invention | 30 mg |
| Polyethylene glycol 300 | 300 mg |
| Polysolbate 80 | 20 mg |
| Total | 350 mg |

Production Method

Polyethylene glycol 300 and Polysorbate 80 are added to a compound of the present invention and the mixture is packed in a soft capsule.

| (2) Injections (per 10 ml in one ampoule) | |
| --- | --- |
| Compound of the invention | 0.3% |
| Polyethylene glycol 300 | 20% |
| Ethanol | 60% |
| Injectable distilled water | amount to make the total 10 ml |

Production Method

Ethanol and polyethylene glycol 300 are added to a compound of the present invention and injectable distilled water is added to reach the total amount.

Injections containing 30 ml of the compound of the present invention in one ampoule (10 ml) are thus obtained.

While the present invention has been described in detail by the specification including examples, the present invention is subject to various modifications and changes insofar as they are within the spirit and scope of the present invention.

We claim:

1. A 2-amino-1,3-propanediol, having the formula

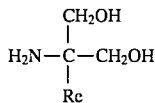
(I-8)

wherein

Re is a phenylalkyl wherein the alkyl moiety is a straight- or branched chain having 6 to 20 carbon atoms; a phenylalkyl which may be substituted by a straight- or branched chain C6–C20 alkyl optionally substituted by halogen, a straight- or branched chain C6–C20 alkoxy optionally substituted by halogen, a straight- or branched chain C6–C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms, or a heterocyclic alkyl substituted by a straight- or branched chain alkyl having 6 to 20 carbon atoms; wherein the alkyl moiety may have, in the carbon chain, a bond or a hereto atom selected from the group consisting of a double bond, a triple bond, oxygen, sulfur, sulfinyl, sulfonyl, —N(R⁶)— where R⁶ is hydrogen, alkyl, aralkyl, acyl or alkoxycarbonyl, and carbonyl, and may have, as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy; or a pharmaceutically acceptable salt thereof.

2. A 2-amino-1,3-propanediol compound of claim 1, having the formula

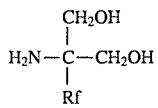
(I-9)

wherein

Rf is a phenylalkyl wherein the alkyl moiety is a straight- or branched chain having 6 to 20 carbon atoms which may have, in the carbon chain, one or two oxygen atoms; a phenylalkyl which may be substituted by a straight- or branched chain C6–C20 alkyl optionally substituted by halogen, a straight- or branched chain C6–C20 alkoxy optionally substituted by halogen, a straight- or branched chain C6–C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms which may have, in the carbon chain, one or two oxygen atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms which may have, in the carbon chain, one or two oxygen atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms which may have, in the carbon chain, one or two oxygen atoms, or a heterocyclic alkyl substituted by a straight- or branched chain alkyl having 6 to 20 carbon atoms;

wherein the alkyl moiety may have, in the carbon chain, a substituent selected from the group consisting of alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy and carboxy; or a pharmaceutically acceptable salt thereof.

3. A 2-amino-1,3-propanediol compound of any one of claims 1 or 2, having the formula

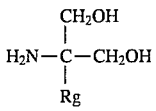
(I-10)

wherein

Rg is a phenylalkyl wherein the alkyl moiety is a straight- or branched chain having 6 to 20 carbon atoms which may have, in the carbon chain, one or two oxygen atoms; a phenylalkyl which may be substituted by a straight- or branched chain C6–C14 alkyl optionally substituted by halogen, a straight- or branched chain C6–C14 alkoxy optionally substituted by halogen, a straight- or branched chain C6–C14 alkenyloxy, phenylalkoxy, halophenylalkoxy, phenylalkoxyalkyl, phenoxyalkoxy or phenoxyalkyl; a cycloalkylalkyl wherein the alkyl moiety has 6 to 20 carbon atoms; a cycloalkylalkyl substituted by a straight- or branched chain alkyl having 6 to 14 carbon atoms; a heteroarylalkyl wherein the alkyl moiety has 6 to 20 carbon atoms; a heteroarylalkyl substituted by a straight- or branched chain alkyl having 6 to 14 carbon atoms; a heterocyclic alkyl wherein the alkyl moiety has 6 to 20 carbon atoms, or a heterocyclic alkyl substituted by a straight- or branched chain alkyl having 6 to 14 carbon atoms; or a pharmaceutically acceptable salt thereof.

4. A 2-amino-1,3-propanediol compound of claim 3, having the formula

(I-11)

wherein

Rh is a phenylalkyl wherein the alkyl moiety has 6 to 20 carbon atoms, a phenylalkoxyalkyl wherein the alkyl moiety and alkoxy moiety have 6 to 20 carbon atoms in total, a phenoxyalkyl wherein the alkyl moiety has 6 to 20 carbon atoms or a phenoxyalkoxyalkyl wherein the alkyl moiety and alkoxy moiety have 6 to 20 carbon atoms in total, or a pharmaceutically acceptable salt thereof.

5. A 2-amino-1,3-propanediol compound of claim 4, which is selected from the group consisting of
2-amino-2-(8-phenyloctyl)-1,3-propanediol,
2-amino-2-(9-phenylnonyl)-1,3-propanediol,
2-amino-2-(10-phenyldecyl)-1,3-propanediol,
2-amino-2-(11-phenylundecyl)-1,3-propanediol,
2-amino-2-(12-phenyldodecyl)-1,3-propanediol,
2-amino-2-(13-phenyltridecyl)-1,3-propanediol,
2-amino-2-(14-phenyltetradecyl)-1,3-propanediol,
2-amino-2-(15-phenylpentadecyl)-1,3-propanediol,
2-amino-2-(16-phenylhexadecyl)-1,3-propanediol,
2-amino-2-[6-(8-phenyloctyloxy)hexyl]-1,3-propanediol,
2-amino-2-(8-phenylmethyloxyoctyl)-1,3-propanediol,
2-amino-2-(9-phenoxynonyl)-1,3-propanediol,
2-amino-2-(12-phenoxydodecyl)-1,3-propanediol and
2-amino-2-[6-(2-phenoxyethyloxy)hexyl]-1,3-propanediol, or a pharmaceutically acceptable salt thereof.

6. A 2-amino-1,3-propanediol compound of claim 4, which is selected from the group consisting of
2-amino-2-(10-phenyldecyl)-1,3-propanediol,
2-amino-2-(13-phenyltridecyl)-1,3-propanediol,
2-amino-2-[6-(8-phenyloctyloxy)hexyl]-1,3-propanediol,
2-amino-2-(8-phenylmethyloxyoctyl)-1,3-propanediol,
2-amino-2-(9-phenoxynonyl)-1,3-propanediol,
2-amino-2-(12-phenoxydodecyl)-1,3-propanediol and
2-amino-2-[6-(2-phenoxyethyloxy)hexyl]-1,3-propanediol, or a pharmaceutically acceptable salt thereof.

7. A 2-amino-1,3-propanediol compound of claim 3, having the formula

(I-12)

wherein

Ri is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy, wherein the alkyl moiety of phenylalkyl may be substituted by hydroxy, or a pharmaceutically acceptable salt thereof.

8. A 2-amino-1,3-propanediol compound of claim 7, having the formula

(I-13)

wherein

Rj is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy, wherein the alkyl moiety is a C2–C6 alkyl optionally substituted by hydroxy, or a pharmaceutically acceptable salt thereof.

9. A 2-amino-1,3-propanediol compound of claim 7, which is selected from the group consisting of
2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-tridecylphenyl)ethyl]-1,3-propanediol,
2-amino-2-[2-(4-tetradecylphenyl)ethyl]-1,3-propanediol,
2-amino-2-[2-(4-hexyloxyphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-decyloxyphenyl)ethyl]-1,3-propanediol,
2-amino-2-[2-(4-undecyloxyphenyl)ethyl]-1,3-propanediol,
2-amino-2-[2-(4-dodecyloxyphenyl)ethyl]-1,3-propanediol,
2-amino-2-[2-(4-tridecyloxyphenyl)ethyl]-1,3-propanediol,
2-amino-2-[2-(4-(8-fluorooctyl)phenyl)ethyl]-1,3-propanediol,
2-amino-2-[2-(4-(12-fluorododecyl)phenyl)ethyl]-1,3-propanediol,
2-amino-2-[2-(4-(7-fluoroheptyloxy)phenyl)ethyl]-1,3-propanediol,
2-amino-2-[2-(4-(11-fluoroundecyloxy)phenyl)ethyl]-1,3propanediol and
2-amino-2-[2-(4-(7-octenyloxy)phenyl)ethyl]-1,3-propanediol, or a pharmaceutically acceptable salt thereof.

10. A 2-amino-1,3-propanediol compound of claim 7, which is selected from the group consisting of
2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-undecyloxyphenyl)ethyl]-1,3-propanediol and
2-amino-2-[2-(4-(7-octenyloxy)phenyl)ethyl]-1,3-propanediol, or a pharmaceutically acceptable salt thereof.

11. A 2-amino-1,3-propanediol compound of claim 3, having the formula

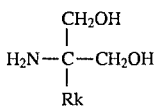 (I-14)

wherein

Rk is a phenylalkyl substituted by phenylalkoxy, halophenylalkoxy, phenylalkoxyalkyl, phenoxyalkoxy or phenoxyalkyl, or a pharmaceutically acceptable salt thereof.

12. A 2-amino-1,3-propanediol compound of claim 11, having the formula

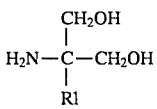 (I-15)

wherein

Rl is a phenylalkyl substituted by phenylalkoxy wherein the alkoxy moiety has 2 to 8 carbon atoms, halophenylalkoxy wherein the alkoxy moiety has 2 to 8 carbon atoms, phenylalkoxyalkyl wherein the alkoxy moiety and alkyl moiety have 2 to 8 carbon atoms in total, phenoxyalkoxy wherein the alkoxy moiety has 2 to 8 carbon atoms or phenoxyalkyl wherein the alkyl moiety has 2 to 8 carbon atoms, where the alkyl moiety has 2 to 6 carbon atoms, or a pharmaceutically acceptable salt thereof.

13. A 2-amino-1,3-propanediol compound of claim 11, which is selected from the group consisting of
2-amino-2-[2-(4-phenylmethyloxyphenyl)ethyl]-1,3-propanediol,
2-amino-2-[2-(4-(2-phenylethyloxy)phenyl)ethyl]-1,3-propanediol,
2-amino-2-[2-(4-(3-phenylpropyloxy)phenyl)ethyl]-1,3-propanediol,
2-amino-2-[2-(4-(4-phenylbutyloxy)phenyl)ethyl]-1,3-propanediol,
2-amino-2-[2-(4-(5-phenylpentyloxy)phenyl)ethyl]-1,3-propanediol,
2-amino-2-[2-(4-(6-phenylhexyloxy)phenyl)ethyl]-1,3-propanediol,
2-amino-2-[2-(4-(7-phenylheptyloxy)phenyl)ethyl]-1,3-propanediol,
2-amino-2-[2-(4-(8-phenyloctyloxy)phenyl)ethyl]-1,3-propanediol,
2-amino-2-[4-(6-(4-fluorophenyl)hexyloxy)phenyl)ethyl]-1,3propanediol,
2-amino-2-[2-(4-(5-phenylpentyloxymethyl)phenyl)ethyl]-1,3-propanediol,
2-amino-2-[2-(4-(4-phenoxybutyloxy)phenyl)ethyl]-1,3-propanediol,
2-amino-2-[2-(4-(5-phenoxypentyloxy)phenyl)ethyl]-1,3-propanediol,
2-amino-2-[2-(4-(6-phenoxyhexyloxy)phenyl) ethyl]-1,3-propanediol,
2-amino-2-[2-(4-(7-phenoxyheptyloxy)phenyl)ethyl]-1,3-propanediol,
2-amino-2-[2-(4-(4-phenoxybutyl)phenyl)ethyl]-1,3-propanediol,
2-amino-2-[2-(4-(5-phenoxypentyl)phenyl)ethyl]-1,3-propanediol,
2-amino-2-[2-(4-(6-phenoxyhexyl)phenyl)ethyl]-1,3-propanediol and
2-amino-2-[2-(4-(7-phenoxyheptyl)phenyl)ethyl]-1,3-propanediol, or a pharmaceutically acceptable salt thereof.

14. A 2-amino-1,3-propanediol compound of claim 11, which is selected from the group consisting of 2-amino-2-[2-(4-(6-phenylhexyloxy)phenyl)ethyl]-1,3-propanediol and 2-amino-2-[2(4-(5-phenylpentyloxymethyl)phenyl]ethyl]-1, 3-propanediol, or a pharmaceutically acceptable salt thereof.

15. A 2-amino-1,3-propanediol compound of claim 3, having the formula

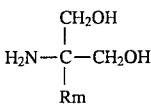 (I-16)

wherein

Rm is an alkyl-substituted cycloalkylalkyl wherein the alkyl moiety has 6 to 20 carbon atoms in total, or a pharmaceutically acceptable salt thereof.

16. A 2-amino-1,3-propanediol compound of claim 15, which selected from the group consisting of
2-amino-2-[3-(4-heptylcyclohexyl)propyl]-1,3-propanediol,
2-amino-2-[4-(4-butylcyclohexyl)butyl]-1,3-propanediol,
2-amino-2-[2-(4-octylcyclohexyl)ethyl]-1,3-propanediol,
2-amino-2-[2-(4-nonylcyclohexyl)ethyl]-1,3-propanediol and
2-amino-2-[2-(4-dodecylcyclohexyl)ethyl]-1,3-propanediol, or a pharmaceutically acceptable salt thereof.

17. A 2-amino-1,3-propanediol compound of claim 3, having the formula

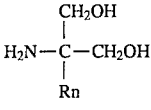 (I-17)

wherein

Rn is a 1-alkyl-substituted piperidin-4-ylalkyl wherein the alkyl moiety has 6 to 20 carbon atoms in total, or a pharmaceutically acceptable salt thereof.

18. A 2-amino-1,3-propanediol compound of claim 17, which is selected from the group consisting of 2-amino-2-[2-(1-octylpiperidin-4-yl)ethyl]-1,3-propanediol and 2-amino-2-[2-(1-dodecylpiperidin-4-yl)ethyl]-1,3-propanediol, or a pharmaceutically acceptable salt thereof.

19. A 2-amino-1,3-propanediol compound of claim 3, having the formula

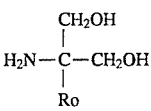 (I-18)

wherein

Ro is a thienylalkyl wherein the alkyl moiety has 6 to 20 carbon atoms, an alkyl-substituted thienylalkyl wherein the alkyl moiety has 6 to 20 carbon atoms in total, a pyridylalkyl wherein the alkyl moiety has 6 to 20 carbon atoms or an alkyl-substituted pyridylalkyl wherein the alkyl moiety has 6 to 20 carbon atoms in total, or a pharmaceutically acceptable salt thereof.

20. A 2-amino-1,3-propanediol compound of claim 19, which is selected from the group consisting of
2-amino-2-[2-(5-octyl-2-thienyl)ethyl]-1,3-propanediol,
2-amino-2-[2-(5-nonyl-2-thienyl)ethyl]-1,3-propanediol,
2-amino-2-[2-(5-decyl-2-thienyl)ethyl]-1,3-propanediol,
2-amino-2-[2-(5-dodecyl-2-thienyl)ethyl]-1,3-propanediol,
2-amino-2-[13-(2-thienyl)tridecyl]-1,3-propanediol,
2-amino-2-[2-(5-octyl-2-pyridyl)ethyl]-1,3-propanediol,
2-amino-2-[2-(5-decyl-2-pyridyl)ethyl]-1,3-propanediol,
2-amino-2-[13-(2-pyridyl)tridecyl]-1,3-propanediol,
2-amino-2-[2-(2-octyl-5-pyridyl)ethyl]-1,3-propanediol, 2-amino-2-[2-(2-decyl-5-pyridyl)ethyl]-1,3-propanediol and 2-amino-2-[13-(3-pyridyl)tridecyl]-1,3-propanediol, or a pharmaceutically acceptable salt thereof.

21. A 2-amino-1,3-propanediol compound, having the formula

(I-19)

wherein

Rp is a phenyl substituted by C6–C18 alkyl, a cycloalkyl, heteroaryl or a heterocycle, or a pharmaceutically acceptable salt thereof.

22. A 2-amino-1,3-propanediol compound of claim 21, having the formula

(I-20)

wherein

Rq is a phenyl substituted by C6–C18 alkyl, or a pharmaceutically acceptable salt thereof.

23. A 2-amino-1,3-propanediol compound of claim 21 or 22, which is selected from the group consisting of 2-amino-2-(4-decylphenyl)-1,3-propanediol, 2-amino-2-(4-dodecylphenyl)-1,3-propanediol, 2-amino-2-(4-tetradecylphenyl)-1,3-propanediol and 2-amino-2-(4-hexadecylphenyl)-1,3-propanediol, or a pharmaceutically acceptable salt thereof.

24. A 2-amino-1,3-propanediol compound, having the formula

(I-21)

wherein $R^1$ is an optionally substituted straight- or branched carbon chain which may have, in the chain, a bond, a hetero atom or a group selected from the group consisting of a double bond, a triple bond, oxygen, sulfur, sulfinyl, sulfonyl, —N($R^6$)— where $R^6$ is hydrogen, alkyl, aralkyl, acyl or alkoxycarbonyl, and carbonyl, optionally substituted arylene, optionally substituted cycloalkylene, optionally substituted heteroarylene and an alicycle thereof, and which may be substituted, at the chain end (ω-position) thereof, by a double bond, a triple bond, optionally substituted aryl, optionally substituted cycloalkyl, optionally substituted heteroaryl or an alicycle thereof, an optionally substituted aryl, an optionally substituted cycloalkyl, an optionally substituted heteroaryl or an alicycle thereof, and $R^2$a, $R^3$a, $R^4$a and $R^5$a are the same or different and each is a hydrogen, an alkyl, an acyl or an alkoxycarbonyl; wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxyimino, hydroxy, carboxy, optionally substituted aryl, optionally substituted aryloxy, optionally substituted cycloalkyl, optionally substituted heteroaryl and an alicycle thereof; and the aforementioned optionally substituted arylene, optionally substituted cycloalkylene, optionally substituted heteroarylene, an alicycle thereof, optionally substituted aryl, optionally substituted aryloxy, optionally substituted cycloalkyl, optionally substituted heteroaryl and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkyl carbamoyl, haloalkyl, haloalkoxy, nitro, halogen, amino, hydroxy and carboxy; or a pharmaceutically acceptable salt thereof.

25. A 2-amino-1,3-propanediol compound of claim 24, having the formula

(I-22)

wherein

Rr is an alkyl optionally substituted by hydroxy and/or hydroxyimino which may have, in the chain, a double bond or carbonyl, or a pharmaceutically acceptable salt thereof.

26. A 2-amino-1,3-propanediol compound of claim 24 or 25, which is selected from the group consisting of 2-amino-2-(1,2,12-trihydroxy-4-octadecenyl)-1,3-propanediol, 2-amino-2-(1,2-dihydroxy-4-octadecenyl)-1,3-propanediol, 2-amino-2-(1,2-dihydroxyoctadecyl)-1,3-propanediol, 2-amino-2-(1,12-dihydroxy-4-octadecenyl)-1,3-propanediol, 2-amino-2-(1,2,4-trihydroxybutyl)-1,3-propanediol, 2-amino-2-(1,2,12-trihydroxyoctadecyl)-1,3-propanediol and 2-amino-2-(1,12-dihydroxyoctadecyl)-1,3-propanediol, or a pharmaceutically acceptable salt thereof.

27. A 2-amino-1,3-propanediol compound of claim 24, having the formula

(I-23)

wherein

Rs is a phenylalkyl substituted by a straight- or branched chain C6–C14 alkyl optionally substituted by halogen, a straight- or branched chain C6–C14 alkoxy optionally substituted by halogen or a straight- or branched chain C6–C14 alkenyloxy, or a pharmaceutically acceptable salt thereof.

28. A 2-amino-1,3-propanediol compound of claim 27, which is selected from the group consisting of 2-amino-2-[1-hydroxy-2-(4-octylphenyl)ethyl]-1,3-propanediol, 2-amino-2-[2-(4-dodecylphenyl)-1-hydroxyethyl]-1,3-propanediol, 2-amino-2-[2-(4-heptyloxyphenyl)-1-hydroxyethyl]-1,3-propanediol, 2-amino-2-[1-hydroxy-2-(4-undecyloxyphenyl)ethyl]-1,3-propanediol, 2-amino-2-[2-(4-(8-fluorooctyl)phenyl)-1-hydroxyethyl]-1,3-propanediol, 2-amino-2-[2-(4-(12-fluorododecyl)phenyl)-1-hydroxyethyl]-1,3-propanediol, 2-amino-2-[2-(4-(7-fluoroheptyloxy)phenyl)-1-hydroxyethyl]-1,3-propanediol and 2-amino-2-[1-hydroxy-2-(4-(11-fluoroundecyloxy)phenyl)ethyl]-1,3-propanediol, or a pharmaceutically acceptable salt thereof.

29. A 2-amino-1,3-propanediol compound, having the formula

 (I-24)

wherein

Rt is an optionally substituted straight- or branched carbon chain which may have, in the chain, a bond, a hetero atom or a group selected from the group consisting of a double bond, a triple bond, oxygen, sulfur, sulfinyl, sulfonyl, —N($R^6$)— where $R^6$ is hydrogen, alkyl, aralkyl, acyl or alkoxycarbonyl, carbonyl, optionally substituted arylene, optionally substituted cycloalkylene, optionally substituted heteroarylene and an alicycle thereof, an optionally substituted aryl, an optionally substituted cycloalkyl, an optionally substituted heteroaryl or an alicycle thereof, and $R^2a$, $R^3a$, $R^4a$ and $R^5a$ are the same or different and each is a hydrogen, an alkyl, an acyl or an alkoxycarbonyl; wherein the optionally substituted straight- or branched carbon chain may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy, carboxy, optionally substituted aryl, optionally substituted aryloxy, optionally substituted cycloalkyl, optionally substituted heteroaryl and an alicycle thereof; and the aforementioned optionally substituted arylene, optionally substituted cycloalkylene, optionally substituted heteroarylene, an alicycle thereof, optionally substituted aryl, optionally substituted aryloxy, optionally substituted cycloalkyl, optionally substituted heteroaryl and an alicycle thereof may have a substituent selected from the group consisting of alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy; or a pharmaceutically acceptable salt thereof.

30. A 2-amino-1,3-propanediol compound of claim 29, having the formula

 (I-25)

wherein

Ru is a phenyl substituted by alkyl having 4 to 16 carbon atoms, or a pharmaceutically acceptable salt thereof.

31. A 2-amino-1,3-propanediol compound of claim 29 or 30, which is selected from the group consisting of
2-amino-2-[2-(4-octylphenyl)ethenyl]-1,3-propanediol,
2-amino-2-[2-(4-decylphenyl)ethenyl]-1,3-propanediol,
2-amino-2-[2-(4-dodecylphenyl)ethenyl]-1,3-propanediol and
2-amino-2-[2-(4-tetradecylphenyl)ethenyl]-1,3-propanediol, or a pharmaceutically acceptable salt thereof.

32. A 2-amino-1,3-propanediol compound, having the formula

 (I-26)

wherein

Rv is an optionally substituted aryl, an optionally substituted cycloalkyl, an optionally substituted heteroaryl or an alicycle thereof;

$R^2a$, $R^3a$, $R^4a$ and $R^5a$ are the same or different and each is a hydrogen, an alkyl, an acyl or an alkoxycarbonyl;

X is an oxygen, a sulfur, a sulfinyl, a sulfonyl, —N($R^6$)— where $R^6$ is hydrogen, alkyl, aralkyl, acyl or alkoxycarbonyl; and α and β are 0 or an integer of 1–20 provided that α+β=5–20, wherein the optionally substituted aryl, optionally substituted cycloalkyl, optionally substituted heteroaryl and an alicycle thereof may have a substituent selected from the group consisting of alkyl, alkoxy, alkenyloxy, alkynyloxy, aralkyloxy, alkylenedioxy, acyl, alkylamino, alkylthio, acylamino, alkoxycarbonyl, alkoxycarbonylamino, acyloxy, alkylcarbamoyl, haloalkyl, haloalkoxy, nitro, halogen, amino, hydroxy and carboxy; or a pharmaceutically acceptable salt thereof.

33. A 2-amino-1,3-propanediol compound of claim 32, having the formula

 (I-27)

wherein

Rw is a phenyl substituted by C4–C16 alkyl, or a pharmaceutically acceptable salt thereof.

34. A 2-amino-1,3-propanediol compound of claim 32 or 33, which is selected from the group consisting of
2-amino-2-(4-octylphenoxymethyl)-1,3-propanediol,
2-amino-2-(4-decylphenoxymethyl)-1,3-propanediol,
2-amino-2-(4-dodecylphenoxymethyl)-1,3-propanediol and
2-amino-2-(4-tetradecylphenoxymethyl)-1,3-propanediol, or a pharmaceutically acceptable salt thereof.

35. A 2-amino-1,3-propanediol compound of claim 8, which is selected from the group consisting of
2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-tridecylphenyl)ethyl]-1,3-propanediol,
2-amino-2-[2-(4-tetradecylphenyl)ethyl]-1,3-propanediol,
2-amino-2-[2-(4-hexyloxyphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-decyloxyphenyl)ethyl]-1,3-propanediol,
2-amino-2-[2-(4-undecyloxyphenyl)ethyl]-1,3-propanediol,
2-amino-2-[2-(4-dodecyloxyphenyl)ethyl]-1,3-propanediol,
2-amino-2-[2-(4-tridecyloxyphenyl)ethyl]-1,3-propanediol,
2-amino-2-[2-(4-(8-fluorooctyl)phenyl)ethyl]-1,3-propanediol,
2-amino-2-[2-(4-(12-fluorododecyl)phenyl)ethyl]-1,3-propanediol, 2-amino-2-[2-(4-(7-fluoroheptyloxy)phenyl)ethyl]-1,3-propanediol, 2-amino-2-[2-(4-(11-fluoroundecyloxy)phenyl)ethyl]-1,3propanediol and 2-amino-2-[2-(4-(7-octenyloxy)phenyl)ethyl]-1,3-propanediol, or a pharmaceutically acceptable salt thereof.

36. A 2-amino-1,3-propanediol compound of claim 8, which is selected from the group consisting of 2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-undecyloxyphenyl)ethyl]-1,3-propanediol and 2-amino-2-[2-(4-(7-octenyloxy)phenyl)ethyl]-1,3-propanediol, a pharmaceutically acceptable salt thereof.

37. A 2-amino-1,3-propanediol compound of claim 12, which is selected from the group consisting of 2-amino-2-[2-(4-phenylmethyloxyphenyl)ethyl]-1,3-propanediol,
2-amino-2-[2-(4-(2-phenylethyloxy)phenyl)ethyl]-1,3-propanediol,
2-amino-2-[2-(4-(3-phenylpropyloxy)phenyl)ethyl]-1,3-propanediol,
2-amino-2-[2-(4-(4-phenylbutyloxy)phenyl)ethyl]-1,3-propanediol,
2-amino-2-[2-(4-(5-phenylpentyloxy)phenyl)ethyl]-1,3-propanediol,
2-amino-2-[2-(4-(6-phenylhexyloxy)phenyl)ethyl]-1,3-propanediol,
2-amino-2-[2-(4-(7-phenylheptyloxy)phenyl)ethyl]-1,3-propanediol,
2-amino-2-[2-(4-(8-phenyloctyloxy)phenyl)ethyl]-1,3-propanediol,
2-amino-2-[4-(6-(4-fluorophenyl)hexyloxy)phenyl)ethyl]-1,3propanediol,
2-amino-2-[2-(4-(5-phenylpentyloxymethyl)phenyl)ethyl]-1,3-propanediol,
2-amino-2-[2-(4-(4-phenoxybutyloxy)phenyl)ethyl]-1,3-propanediol,
2-amino-2-[2-(4-(5-phenoxypentyloxy)phenyl)ethyl]-1,3-propanediol,
2-amino-2-[2-(4-(6-phenoxyhexyloxy)phenyl)ethyl]-1,3-propanediol,
2-amino-2-[2-(4-(7-phenoxyheptyloxy)phenyl)ethyl]-1,3-propanediol,
2-amino-2-[2-(4-(4-phenoxybutyl)phenyl)ethyl]-1,3-propanediol,
2-amino-2-[2-(4-(5-phenoxypentyl)phenyl)ethyl]-1,3-propanediol,
2-amino-2-[2-(4-(6-phenoxyhexyl)phenyl)ethyl]-1,3-propanediol and
2-amino-2-[2-(4-(7-phenoxyheptyl)phenyl)ethyl]-1,3-propanediol, or a pharmaceutically acceptable salt thereof.

38. A 2-amino-1,3-propanediol compound of claim 12, which is selected from the group consisting of 2-amino-2-[2-(4-(6-phenylhexyloxy)phenyl)ethyl]-1,3-propanediol and 2-amino-2-[2-(4-(5-phenylpentyloxymethyl)phenyl)ethyl]-1,3-propanediol, or pharmaceutically acceptable salt thereof.

39. A 2-amino-1,3-propanediol compound of the formula $$\begin{array}{c} CH_2OR^4b \\ | \\ R^2bR^3bN-C-CH_2OR^5b \\ | \\ CH_2R^1b \end{array} \quad (I\text{-}3)$$

wherein $R^1b$ is a substituted straight- or branched chain alkyl having 1 to 30 carbon atoms, a substituted straight- or branched chain alkenyl having 2 to 30 carbon atoms or a substituted straight- or branched chain alkynyl having 2 to 30 carbon atoms, and $R^2b$, $R^3b$, $R^4b$ and $R^5b$ are the same or different and each is a hydrogen, an alkyl or an acyl;

wherein the substituted straight- or branched chain alkyl having 1 to 30 carbon atoms, substituted straight- or branched chain alkenyl having 2 to 30 carbon atoms and substituted straight- or branched chain alkynyl having 2 to 30 carbon atoms have a substituent selected from the group consisting of alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy, carboxy, optionally substituted phenyl and optionally substituted cycloalkyl; and the aforementioned optionally substituted phenyl and optionally substituted cycloalkyl may have 1 to 3 substituents selected from the group consisting of alkyl, alkenyl, alkynyl, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, haloalkyl, nitro, halogen, amino, hydroxy and carboxy; or a pharmaceutically acceptable salt thereof.

40. A method for immunosuppression of an immune system of a mammal, which comprises administering to a mammal an immunosuppressing effective amount of any one of the compounds claimed in claims 1, 21, 24, 29 and 32.

41. A method for suppression of rejection in an organ or bone marrow transplantation in a mammal, which comprises administering to a mammal a rejection suppressing effective amount of any one of the compounds claimed in claims 1, 21, 24, 29 or 32.

42. A method for prevention or treatment of autoimmune disease, which comprises administering to a mammal a therapeutically effective amount of any one of the compounds claimed in claims 1, 21, 24, 29 or 32.

43. The method according to claim 42, wherein the autoimmune disease is rheumatoid arthritis.

44. A method for prevention or treatment of psoriasis or atopic dermatitis, which comprises administering to a mammal a therapeutically effective amount of any one of the compounds claimed in claims 1, 21, 24, 29 or 32.

45. A method for prevention or treatment of bronchial asthma or pollinosis, which comprises administering to a mammal a therapeutically effective amount of any one of the compounds claimed in claims 1, 21, 24, 29 or 32.

46. The method according to claim 40, wherein the compound is 2-amino-2-(2-(4-octylphenyl)ethyl)-1,3-propanediol or a pharmaceutically acceptable salt thereof.

47. The method according to claim 41, wherein the compound is 2-amino-2-(2-(4-octylphenyl)ethyl)-1,3-propanediol or a pharmaceutically acceptable salt thereof.

48. The method according to claim 42, wherein the compound is 2-amino-2-(2-(4-octylphenyl)ethyl)-1,3-propanediol or a pharmaceutically acceptable salt thereof.

49. The method according to claim 43, wherein the compound is 2-amino-2-(2-(4-octylphenyl)ethyl)-1,3-propanediol or a pharmaceutically acceptable salt thereof.

50. The method according to claim 44, wherein the compound is 2-amino-2-(2-(4-octylphenyl)ethyl)-1,3-propanediol or a pharmaceutically acceptable salt thereof.

51. The method according to claim 45, wherein the compound is 2-amino-2-(2-(4-octylphenyl)ethyl)-1,3-propanediol or a pharmaceutically acceptable salt thereof.

52. The method according to any one of claims 40, 41, 42, 43, 44 or 45, wherein the compound is 2-amino-2-(2-(4-octylphenyl)ethyl)-1,3-propanediol hydrochloride.

* * * * *

UNITED STATES PATENT AND TRADEMARK OFFICE
CERTIFICATE OF CORRECTION

Page 1 of 2

PATENT NO. : 5,604,229
APPLICATION NO. : 08/244942
DATED : February 18, 1997
INVENTOR(S) : Tetsuro Fujita et al.

It is certified that error appears in the above-identified patent and that said Letters Patent is hereby corrected as shown below:

In The Claims

Claim 36, replace
"36. A 2-amino-1,3-propanediol compound of claim 8, which is selected from the group consisting of
2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-undecyloxyphenyl)ethyl]-1,3-propanediol and
2-amino-2-[2-(4-(7-octenyloxy)phenyl)ethyl]-1,3-propanediol, a pharmaceutically acceptable salt thereof."

with

"36. A 2-amino-1,3-propanediol compound of claim 8, which is selected from the group consisting of 2-amino-2-[2-(4-heptylphenyl)ethyl]-1,3-propanediol,
2-amino-2-[2-(4-octylphenyl)ethyl]-1,3-propanediol,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol, Signed and Sealed this
Twenty-ninth Day of March, 2016

Michelle K. Lee
*Director of the United States Patent and Trademark Office*

CERTIFICATE OF CORRECTION (continued)
U.S. Pat. No. 5,604,229

2-amino-2-[2-(4-nonyloxyphenyl)ethyl]-1,3-propanediol,
2-amino-2-[2-(4-undecyloxyphenyl)ethyl]-1,3-propanediol and
2-amino-2-[2-(4-(7-octenyloxy)phenyl)ethyl]-1,3-propanediol, or a pharmaceutically acceptable salt thereof."

Claim 38, replace
"38. A 2-amino-1,3-propanediol compound of claim 12, which is selected from the group consisting of
2-amino-2-[2-(4-(6-phenylhexyloxy)phenyl)ethyl]-1,3-propanediol and
2-amino-2-[2-(4-(5-phenylpentyloxymethyl)phenyl)ethyl]-1,3-propanediol, or pharmaceutically acceptable salt thereof."

with

"38. A 2-amino-1,3-propanediol compound of claim 12, which is selected from the group consisting of
2-amino-2-[2-(4-(6-phenylhexyloxy)phenyl)ethyl]-1,3-propanediol and
2-amino-2-[2-(4-(5-phenylpentyloxymethyl)phenyl)ethyl]-1,3-propanediol, or a pharmaceutically acceptable salt thereof."